(12) United States Patent
Crowley et al.

(10) Patent No.: US 9,085,630 B2
(45) Date of Patent: Jul. 21, 2015

(54) COMPOSITIONS AND METHODS FOR THE TREATMENT OF TUMOR OF HEMATOPOIETIC ORIGIN

(75) Inventors: Craig Crowley, Portola Valley, CA (US); Frederic J. de Sauvage, Foster City, CA (US); Dan L. Eaton, San Rafael, CA (US); Allen Ebens, Jr., San Carlos, CA (US); Andrew Poison, San Francisco, CA (US); Victoria Smith, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 939 days.

(21) Appl. No.: 13/154,076

(22) Filed: Jun. 6, 2011

(65) Prior Publication Data
US 2013/0149298 A1 Jun. 13, 2013

Related U.S. Application Data

(63) Continuation of application No. 12/756,149, filed on Apr. 7, 2010, now abandoned, which is a continuation of application No. 12/079,893, filed on Mar. 27, 2008, now abandoned, which is a continuation of application No. 10/989,826, filed on Nov. 16, 2004, now abandoned, which is a continuation-in-part of application No. PCT/US03/36298, filed on Nov. 13, 2003, and a continuation-in-part of application No. 10/712,892, filed on Nov. 12, 2003, now abandoned.

(60) Provisional application No. 60/426,847, filed on Nov. 15, 2002.

(51) Int. Cl.
| A61K 39/00 | (2006.01) |
| C07K 16/30 | (2006.01) |
| A61K 31/713 | (2006.01) |
| A61K 47/48 | (2006.01) |
| A61K 39/395 | (2006.01) |
| A61K 45/06 | (2006.01) |
| A61N 5/10 | (2006.01) |

(52) U.S. Cl.
CPC ............ *C07K 16/3061* (2013.01); *A61K 31/713* (2013.01); *A61K 39/39558* (2013.01); *A61K 45/06* (2013.01); *A61K 47/4863* (2013.01); *A61K 47/48384* (2013.01); *A61N 5/10* (2013.01); *C07K 2317/73* (2013.01); *C07K 2317/77* (2013.01); *C07K 2319/55* (2013.01)

(58) Field of Classification Search
None
See application file for complete search history.

(56) References Cited

U.S. PATENT DOCUMENTS

| 4,137,230 A | 1/1979 | Hashimoto et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 4,816,567 A | 3/1989 | Cabilly et al. |
| 4,970,198 A | 11/1990 | Lee et al. |
| 4,975,278 A | 12/1990 | Senter et al. |
| 5,079,233 A | 1/1992 | Lee |
| 5,208,020 A | 5/1993 | Chari et al. |
| 5,416,064 A | 5/1995 | Chari et al. |
| 5,530,101 A | 6/1996 | Queen et al. |
| 5,585,089 A | 12/1996 | Queen et al. |
| 5,606,040 A | 2/1997 | McGahren et al. |
| 5,644,033 A | 7/1997 | Seon |
| 5,655,033 A | 8/1997 | Inoguchi et al. |
| 5,693,762 A | 12/1997 | Queen et al. |
| 5,739,116 A | 4/1998 | Hamann et al. |
| 5,767,237 A | 6/1998 | Sakakibara et al. |
| 5,767,285 A | 6/1998 | Hamann et al. |
| 5,773,001 A | 6/1998 | Hamann et al. |
| 5,869,045 A | 2/1999 | Hellstrom et al. |

(Continued)

FOREIGN PATENT DOCUMENTS

| EP | 0425235 | 9/1996 |
| EP | 1013761 A2 | 6/2000 |

(Continued)

OTHER PUBLICATIONS

Kaiser, Science, 2006, 313, 1370.*

(Continued)

*Primary Examiner* — Mark Halvorson
(74) *Attorney, Agent, or Firm* — Stephanie Yonker; Christopher De Vry; Arnold & Porter, LLP

(57) ABSTRACT

The present invention is directed to compositions of matter useful for the treatment of hematopoietic tumor in mammals and to methods of using those compositions of matter for the same.

39 Claims, 185 Drawing Sheets

(56) References Cited

U.S. PATENT DOCUMENTS

| | | | |
|---|---|---|---|
| 6,075,181 | A | 6/2000 | Kucherlapati et al. |
| 6,124,431 | A | 9/2000 | Sakakibara et al. |
| 6,150,584 | A | 11/2000 | Kucherlapati et al. |
| 6,172,213 | B1 | 1/2001 | Lowman et al. |
| 6,194,551 | B1 | 2/2001 | Idusogie et al. |
| 6,248,564 | B1 | 6/2001 | Walter et al. |
| 6,441,163 | B1 | 8/2002 | Chari et al. |
| 7,084,257 | B2 | 8/2006 | Deshpande et al. |
| 8,088,378 | B2 | 1/2012 | Chen et al. |
| 8,545,850 | B2 | 10/2013 | Chen et al. |
| 8,691,531 | B2 | 4/2014 | Chen et al. |
| 8,722,857 | B2 | 5/2014 | Chen et al. |
| 2002/0012665 | A1 | 1/2002 | Hanna |
| 2002/0150573 | A1 | 10/2002 | Nussenzweig |
| 2004/0001827 | A1 | 1/2004 | Dennis |
| 2004/0018194 | A1 | 1/2004 | Francisco et al. |
| 2005/0123925 | A1 | 6/2005 | Ashkenazi et al. |
| 2005/0169933 | A1 | 8/2005 | Steeves et al. |
| 2005/0238649 | A1 | 10/2005 | Doronina et al. |
| 2005/0238650 | A1 | 10/2005 | Crowley et al. |
| 2005/0244828 | A1 | 11/2005 | Kreitman et al. |
| 2005/0256030 | A1 | 11/2005 | Feng |
| 2005/0276812 | A1 | 12/2005 | Ebens et al. |
| 2007/0020714 | A1 | 1/2007 | Lee et al. |
| 2007/0092940 | A1 | 4/2007 | Eigenbrot et al. |
| 2007/0207142 | A1 | 9/2007 | Crowley et al. |
| 2009/0028856 | A1 | 1/2009 | Chen et al. |
| 2009/0053226 | A1 | 2/2009 | Crowley et al. |
| 2009/0068178 | A1 | 3/2009 | Crowley et al. |
| 2009/0068202 | A1 | 3/2009 | Chen et al. |
| 2010/0215669 | A1 | 8/2010 | Chen et al. |
| 2011/0042260 | A1 | 2/2011 | Crowley et al. |
| 2011/0045005 | A1 | 2/2011 | Crowley et al. |
| 2011/0070243 | A1 | 3/2011 | Crowley et al. |
| 2011/0206658 | A1 | 8/2011 | Crowley et al. |

FOREIGN PATENT DOCUMENTS

| | | |
|---|---|---|
| EP | 1391213 | 2/2004 |
| EP | 1689432 B1 | 12/2009 |
| EP | 2161283 A1 | 3/2010 |
| EP | 2295073 A1 | 3/2011 |
| EP | 2301568 A1 | 3/2011 |
| WO | WO 99/51642 | 10/1999 |
| WO | WO 00/12130 | 3/2000 |
| WO | WO 00/42072 | 7/2000 |
| WO | WO 01/31065 | 5/2001 |
| WO | WO 01/45746 A2 | 6/2001 |
| WO | WO 2004/054615 A1 | 7/2001 |
| WO | WO 01/71500 | 9/2001 |
| WO | WO 01/74388 | 10/2001 |
| WO | WO 02/088172 A2 | 11/2002 |
| WO | WO 02/098883 | 12/2002 |
| WO | WO 03/043583 A2 | 5/2003 |
| WO | WO 03/062401 | 7/2003 |
| WO | WO 03/072036 A2 | 9/2003 |
| WO | WO 03/072736 | 9/2003 |
| WO | WO 03/074567 | 9/2003 |
| WO | WO 03/093320 | 11/2003 |
| WO | WO 2004/032828 A2 | 4/2004 |
| WO | WO 2005/037992 A2 | 4/2005 |
| WO | WO 2005/049075 | 6/2005 |
| WO | WO 2005/081711 A2 | 9/2005 |
| WO | WO 2005/113003 | 12/2005 |
| WO | WO 2005/117986 | 12/2005 |
| WO | WO 2006/017173 A1 | 2/2006 |
| WO | WO 2006/034488 A2 | 3/2006 |
| WO | WO 2006/042240 | 4/2006 |
| WO | WO 2007/008603 A1 | 1/2007 |
| WO | WO 2007/008848 A2 | 1/2007 |
| WO | WO 2009/012256 | 1/2009 |
| WO | WO 2009/012268 | 1/2009 |
| WO | WO 2009/099719 | 8/2009 |
| WO | WO 2009/099728 | 8/2009 |

OTHER PUBLICATIONS

Granziero et al, Eur. J. Immunol. 1999, 29:1127-1138.*
Byers, T, CA Journal, vol. 49, No. 6, Nov./Dec. 1999.*
Ghetie, et al., "Immunotoxins in the therapy of cancer: from bench to Clinic", Pharmac. Ther. vol. 63, pp. 209-234, (1994).
Kunkel, et al., "Rapid and efficient site-specific mutagenesis without phenotypic selection", Methods in Enzymology, vol. 154, pp. 367-382, (1987).
Miyake, et al., "RP105, A novel B cell surface molecule implicated in B cell activation, is a member of the Leucine-Rich repeat protein family", The Journal of Immunology, 154: 3333-3340, (1995).
Miura, et al., "Molecular cloning of a human RP105 homologue and chromosomal localization of the mouse and human RP105 genes (Ly64 and LY64)", Genomics, 38: 299-304, (1996).
Szatrowski, et al., "Lineage specific treatment of adult patients with acute lymphoblastic leukemia in first remission with anti-B4-blicked Ricin or high-dose cytarabine. Cancer and leukemia group B study 9311", Cancer, 97(6): 1471-1480, (2003).
Alfarano et al., "An alternatively spliced form of CD79b gene may account for altered B-cell receptor expression in B-chronic lymphocytic leukemia" Blood 93(7): 2327-2335, (1999).
Amlot et al., "A phase I study of an anti-CD22-deglycosylated ricin a chain immunotoxin in the treatment of B-cell lymphomas resistant to conventional therapy" Blood 82(9): 2624-2633, (1993).
Baldwin ct al., "Monoclonal Antibodies in Cancer Treatment" Lancet, the pp. 603-605, (1986).
Barbas et al., "In Vitro Evolution of a Neutralizing Human Antibody to Human Immunodeficiency Virus Type 1 to Enhance Affinity and Broaden Strain Cross-Reactivity" Proc Natl Acad Sci U S A 91(9): 3809-3813 (1994).
Bernhard et al, "Cysteine analogs of recombinant barley ribosome inactivating protein form antibody conjugates with enhanced stability and potency in vitro" Bioconjug Chem. 5(2): 126-132.
Better et al., "Gelonin analogs J with engineered cysteine residues form antibody immunoconjugates with unique properties", Biol Chem. 269(13): 9644-9650, (1994).
Bhaskar et al., "E-Selectin Up-Regulation Allows for Targeted Drug Delivery in Prostate Cancer" Cancer Research 63: 6387-6394, (2003).
Boerner et al., "Production of Antigen-Specific Human Monoclonal Antibodies From in Vitro-Primed Human Splenocytes" J Immunol 147(1): 86-95, (1991).
Boring et al., "Cancer Statistics, 1993" CA: A Cancer Journal for Clinicians 43(1): 7-26, (Jan.-Feb. 1993).
Cabezudo et al., "Quantitative analysis of CD79b, CD5 and CD19 in mature B-cell lymphoproliferative disorders" Haematologica 84(5): 413-418, (1999).
Carter et al., "Humanization of an Anti-p185-iihx2 Antibody for Human Cancer Therapy" Proc Natl Acad Sci USA. 89(10):4285-4289, (May 1992).
Cesano et al., "Differential Expression of CD22 in Indolent and Aggresive Non-Hodgkin's Lymphoma (NHL): Implications for Targeted Immunotherapy" Blood (Abstract #1358) 100:350a (2002).
Chari et al., "Immunoconjugates Containing Novel Maytansinoids: Promising Anticancer Drugs" Cancer Research 52:127-131, (Jan. 1992).
Chen et al., "Selection and analysis of an optimized anti-VEGF antibody: crystal structure of an affinity-matured Fab in complex with antigen" J Mol Biol. 293(4): 865-881, (Nov. 5, 1999).
Chen et al., "A useful marker to distinguish florid follicular hyperplasia from follicular lymphoma by flow cytometry", Am J Clin Pathol, Jun. 2003, 119:842-851.
Chen et al., "Regulated expression of human histocompatibility leukocyte antigen (HLA)-DO during antigen-dependent and antigen-independent phases of B cell development", J Exp Med, Jul. 2002, 195:1053-1062.
Chmura et al., "Antibodies with infinite affinity" Proc Natl Acad Sci U S A. 98(15): 8480-8484, (Jul. 17, 2001).
Chothia and Lesk, "Canonical Structures for the Hypervariable Regions of Immunoglobulins" J Mol Biol. 196(4):901-917, (Aug. 20, 1987).

(56) References Cited

OTHER PUBLICATIONS

Cole et al., "The EBV-Hybridoma Technique and its Application to Human Lung Cancer" Monoclonal Antibodies and Cancer :Therapy, New York:Alan R. Liss, Inc. pp. 77-96, (1985).
Cragg, "The alternative transcript of CD79b is overexpressed in B-Cll and inhibits signaling for apoptosis" Blood 100(9): 3068-3076, (Nov. 1, 2002).
D'Arena et al., "Quantitative flow cytometry for the diagnosis of leukemic B-cell chronic lymphoproliferative differential disorders" Am J Hematol., (64(4):275-281, (2000.
De Pascalis, et al., "Grafting of "Abbreviated" complementarity-determining regions containing specificity-determining residues essential for ligand contact to engineer a less immunogenic humanized monoclonal antibody", The Journal of Immunology, 169: 3076-3084, (2002).
Dennis et al., "Albumin binding as a general strategy for improving the pharmacokinetics of proteins" Journal of Biological Chemistry 277(38): 35035-35043, (Sep. 20, 2002).
DiJoseph et al., "Antibody-targeted chemotherapy with CMC-544: a CD22-targeted immunoconjugate of calicheamicin for the treatment of B-lymphoid malignancies", Blood 103 : 1807-1814, (2004).
Dorken et al., "HD39 (33), a B lineage-restricted antigen whose cell surface expression is limited to resting and activated human B lymphocytes" J. Immunol 136(12):4470-4479, (Jun. 15, 1986).
Doronina et al., "Development of potent monoclonal antibody auristatin conjugates for cancer therapy" Nature Biotechnology 21:778-784, (2003).
Doronina et al., "Enhanced activity of monomethylauristatin F through monoclonal antibody delivery: effects of linker technology on efficacy and toxicity" Bioconjuq Chem. 17(1):114-124, (2006).
Erickson et al., "Antibody-maytansinoid conjugates are activated in targeted cancer cells by lysosomal degradation and linker-dependent intracellular processing" Cancer Research 66(8):4426-4433, (2006).
Fisher et al., "Current therapeutic paradigm for the treatment of non-Hodgkin's lymphoma" Semin Oncol. 27(6 Suppl. 12): 2-8,(2000).
Francisco et al., "cAC10-vcMMAE, an anti-CD30 monomethyl auristatin E conjugate with potent and selective antitumor activity" Blood 102:1458-1465, (2003).
Garman, Non-Radioactive Labelling: A Practical Approach, London:Academic Press pp. 55 (1997).
Gemtuzumab Ozogamicin, "Treatment of acute myreloid leukemia", Drugs of the Future 25(7): 686-692,(2000).
Ghetie et al., "Evaluation of ricin a chain-containing immunotoxins directed against CD19 and CD22 antigens on normal and malignant human B-cells as potential reagents for in vivo therapy" Cancer Research 48(9): 2610-2617, (May 1, 1988).
Graham et al., "Characteristics of a Human Cell Line Transformed by DNA from Human Adenovirus Type 5", J. Gen. Virol. 36(1):59-72, (1977).
Greenwood et al., "Engineering multiple-domain forms of the therapeutic antibody CAMPATH-1H: effects on complement lysis" Therapeutic Immunology 1(5): 247-255 (Oct. 1994).
Griffiths et al., "90Y-DOTA-hLL2: an agent for radioimmunotherapy of non-Hodgkin's lymphoma" J Nucl Med. 44(1): 77-84, (Jan. 2003).
Grillo-Lopez et al., "Monoclonal antibodies: a new era in the treatment of non-Hodgkin's lymphoma" Current Pharmaceutical Biotechnology 2: 301-311,(2001).
Gura, "Systems for identifying new drugs are often faulty", Science, 1997, 278: 1041-1042.
Harris et al., "The World Health Organization classification of neoplasms of the hematopoietic and lymphoid tissues: report of the Clinical Advisory Committee meeting—Airlie House, Virginia, Nov. 1997", Hematol J. 1: 53-66, (2000).
Hashimoto et al., "Alternative splicing of CD79a (Ig-alpha/mb-1) and CD79b (Ig-beta/B29) RNA transcripts in human B cells", Mol. Immunol , 32(9): 651-659, (Jun. 1995).
Hawkins et al., "Selection of Phage Antibodies by Binding Affinity Mimicking Affinity Maturation" J Mol Biol. 226: 889-896, (1992).

Hinman, et al., "Preparation and Characterization of Monoclonal Antibody conjugates of the Calicheamicins: A Novel and Potent Family of Antitumor Antibiotics", Cancer Research 53:3336-3342, (Jul. 15, 1993).
Holm, et al., "Functional mapping and single chain construction of the anti-cytokeratin 8 monoclonal antibody TS1", Molecular Immunology, 44: 1075-1084, (2007).
Hongo et al., "Development and Characterization of Murine Monoclonal Antibodies to the Latency-Associated Peptide of Transforming Growth Factor 131", Hybridoma 14: 253-260, (1995).
Hoogenboom and Winter, "By-passing immunisation. Human antibodies from synthetic repertoires of germline VH gene segments rearranged in vitro" J Mol Biol. 227(2): 381-388 (Sep. 20, 1992).
Tdusogie et al., Mapping of the Clq Binding Site on Rituxan, A Chimeric Antibody with a Human IgG1 FF. J. Immunol. 164(8): 4178-4184, (2000).
Schier et al., "Identification of functional and structural amino-acid residues by parsimonious mutagenesis" Gene 169(2):147-155, (Mar. 9, 1996).
Senter et al., "Immunoconjugates comprised of drugs with impaired cellular permeability: a new approach to targeted therapy, Abstract No. 623, presented on Mar. 28, 2004, Proceedings of The American Association for Cancer Research" 45:36, (2004).
Shalaby, et al., "Development of Humanized Bispecific Antibodies Reactive with Cytotoxic Lymphocytes and Tumor Cells Overexpressing the HER2 Protooncogene" Journal of Experimental Medicine 175:217-225, (1992).
Shields et al., "High Resolution Mapping of the Binding Site on Human IgG1 for FcγRI, FcγRII, FcγRIII, and FcRn and Design of IgG1 Variants with Improved Binding to the FcγR*" Journal of Biological Chemistry 276(9):6591-6604, (2001).
Sone et al., "Dolabellin, a Cytotoxic Bisthiazole Metabolite from the Sea Hare *Dolabella auricularia*: Structural Determination and Synthesis" Journal Org. Chem. 60:4474-4781, (1995).
Stancovski, et al., "Mechanistic aspects of the opposing effects of monoclonal antibodies to the ERBB2 receptor on tumor growth", PNAS, vol. 88, pp. 8691-8696, (1991).
Stein et al., "Epitope specificity of the anti-(B cell lymphoma) monoclonal antibody, LL2" Cancer Immunol Immunother. 37(5):293-298, (Oct. 1993).
Syrigos et al., "Antibody Directed Enzyme Prodrug Therapy (ADEPT): A Review of the Experimental and Clinical Considerations" Anticancer Research 19: 605-614, (1999).
Thorpe, "Antibody Carriers of Cytotoxic Agents in Cancer Therapy: A Review" Monoclonal Antibodies 84: Biological and Clinical Applications, A. Pinchera, G. Doria, Dammacco & Bargellesi, Editrice Kurtis s.r.l. pp. 475-506, (1985).
Tobinai kensei, "Rituximab and other emerging antibodies as molecular target-based therapy of lympoma", Int. J. Clin. Oncol., 8(4): 212-223, (2003).
Tu et al., "Protein footprinting at cysteines: probing ATP-modulated contacts in cysteine-substitution mutants of yeast DNA topoisomerase II" Proc Natl Acad Sci U S A. 96(9): 4862-4867 (Apr. 27, 1999).
Tur, et al., "Recombinant Cd64-specific single chain immunotoxin exibits specific cytotoxicity against acute myeloid leukemia cells", Cancer Research, 63(23): 8414-8419, (2003).
Vajdos, et al., "Comprehensive functional maps of the antigen-binding site of an Anti-ErbB2 antibody obtained with shotgun scanning mutagenesis", J. Mol. Biol., 320: 415-428, (2002).
Van Dijk and van de Winkel, "Human antibodies as next generation therapeutics" Curr Opin Chem Biol. 5(4):368-374, (Aug. 2001).
Vasile et al, "Isolation and chemical characterization of the human B29 and mb-1 proteins of the B cell antigen receptor complex", Mol. Immunol, 1994, 31: 419-427.
Verhoeyen et al., "Reshaping Human Antibodies: Grafting an Antilysozyme Activity" Science 239:1534-1536 (Mar. 1988).
White et al., "Antibody-targeted immunotherapy for treatment of malignancy", Annu Rev Med 52:125-145, 2001.
Winter et al., "Making antibodies by phage display technology" Annu Rev Immunol 12:433-455.
Wiseman et al, "Ibritumomab tiuxetan radioimmunotherapy for patients with relapsed or refractory non-Hodgkin lymphoma and

(56) References Cited

OTHER PUBLICATIONS mild thrombocytopenia: a phase II multicenter trial" Blood 99(12):4336-4342, (Jun. 15, 2002).
Wiseman et al., "Phase I/II 90Y-Zevalin (yttrium-90 ibritumomab tiuxetan, IDEC-Y2B8) radioimmunotherapy dosimetry results in relapsed or refractory non-Hodgkin's lymphoma" European Journal of Nuclear Medicine 27(7):766-777, (Jul. 2000).
Witzig et al, "Randomized Controlled Trial of Yttrium-90—Labeled Ibritumomab Tiuxetan Radioimmunotherapy Versus Rituximab Immunotherapy for Patients With Relapsed or Refractory Low-Grade, Follicular, or Transformed B-Cell Non-Hodgkin's Lymphoma" Journal of Clinical Oncology 20(10):2453-2463.
Witzig et al, "Treatment With Ibritumomab Tiuxetan Radioimmunotherapy in Patients With Rituximab-Refractory Follicular Non-Hodgkin's Lymphoma" Journal of Clinical Oncology 20(15):3262-3269, (Aug. 1, 2002).
Wu et al., "Arming antibodies: prospects and challenges for immunoconjugates" Nat Biotechnol 23(9): 1137-1146, (Sep. 23, 2005).
Wu, et al., "Humanization of a Murine monoclonal antibody by simultaneous optimization of framework and CDR residues", J. Mol. Biol., 294: 151-162, (1999).
Yamashita, et al., "Activation mediated by RP105 but not CD40 makes normal B cells susceptible to anti-IgM-induced apoptosis: a role for Fc receptor coligation", J. Exp. Med., 184(1): 113-120, (1996).
Yelton et al., "Affinity Maturation of the BR96 Anti-Carcinoma Antibody by Codon-Based Mutagenesis" The Journal of Immunology 155: 1994-2004, (1995).
Zhang et al., "Complete disulfide bond assignment of a recombinant immunoglobulin G4 monoclonal antibody" Analytical Biochemistry 311(1): 1-9, (2002).
Coleman, P.M., "Effects of amino acid sequence changes on antibody-antigen interactions" Resimmunol. 145: 33-36 ( 1994).
Herrera et al. et al., "Treatment of SCID/human B cell precursor ALL with anti-CD19 and anti-CD22 immunotoxins", Leukemia 17(2): 334-338 (2003).
Winter, et al., "Humanized antibodies", Immunology Today, 14(6): 243-246, (1993).
Jackson et al., "In vitro antibody maturation. Improvement of a high affinity, neutralizing antibody against IL-10" J Immunol 154(7): 3310-3319, (1995).
Jemal et al., "Cancer Statistics, 2002" CA-A Cancer Journal for Physicians 52: 23-47, (2002).
Jones et al., "Replacing the Complementarity-Determining Regions in a Human Antibody with Those From a Mouse" Nature 321(6069): 522-525, (May 29, 1986).
Junutula et al., "Rapid identification of reactive cysteine residues for site-specific labeling of antibody-Fabs" J Immunol Methods 332: 41-52, (2008).
Kabat et al., "Sequences of Proteins of Immunological Interest" U.S. Dept. of Health and Human Services (Publication No. 91-3242), Fifth edition (1991).
Kanno et al., "Assembling of engineered IgG-binding protein on gold surface for highly oriented antibody immobilization" J Biotechnol. 76(2-3): 207-214, (Jan. 21, 2000).
Kerr et al., "Listeriolysin 0 Potentiates Immunotoxin and Bleomycin Cytotoxicity" Bioconjugate Chem 8(6): 781-784, (Nov. 1997).
Kleijmeer et al., "Major histocompatibility complex class II. compartments in human and mouse B lymphoblasts represent conventional endocytic compartments", J. Cell Biol.,39(3): 639-649, (1997).
Klussman et al., "Secondary mAb-vcMMAE Conjugates Are Highly Sensitive Reporters of Antibody Internalization via the Lysosome Pathway" Bioconjugate Chemistry 15: 765-773, (2004).
Kohler et al., "Continuous cultures of fused cells secreting antibody of predefined specificity" Nature 256: 495-497, (1975).
Kropshofer, et al., "A role for HLA-DO as a co-chaperone of HLA-DM in peptide loading of MHC class II molecules", The EMBO Journal., 17: 2971-2981, (1998).

Lambert, J, "Drug-conjugated monoclonal antibodies for the treatment of cancer" Curr Opin Pharmacol. 5(5): 543-549, (Oct. 2005).
Law et al., "CD70 is expressed on renal cell carcinoma and is a potential target for tumor cell elimination by antibody-drug conjugates" Proceedings of the American Association for Cancer Research 45 (2004).
Li et al., "Human antibodies for immunotherapy development generated via a human B cell hybridoma technology" Proc Natl Acad Sci USA. 103(10):3557-62,(Mar. 2006).
Liu et al., "Eradication of Large Colon Tumor Xenografts by Targeted Delivery of Maytansinoids." Proc. Natl. Acad. Sci USA 93: 8618-8623, (1996).
Lode et al., "Targeted Therapy with a Novel Enediyene Antibiotic Calicheamicin d I1 Effectively Suppresses Growth and Dissemination of Liver Metastases in a Syngeneic Model of Murine Neuroblastoma" Cancer Research 58: 2925-2928, (Jul. 15, 1998).
MacCallum, et al., "Antibody-antigen interactions: Contact analysis and binding site topography", J. Mol. Biol., 262: 732-745, (1996).
Mandler et al., "Immunoconjugates of Geldanamycin and Anti-HER2 Monoclonal Antibodies: Antiproliferative Activity on Human Breast Carcinoma Cell Lines" Journal of the National Cancer Institute 92(19):1573-1581, (Oct. 4, 2000).
Mandler et al., "Synthesis and Evaluation of Antiproliferative Activity of a Geldanamycin-Herceptin(tm) Immunoconjugate" Bioorganic & Medicinal Chemistry Letters 10:1025-1028 (2000).
Mandler, et al., "Modifications in synthesis strategy improve the yield and efficacy of Geldanamycin-Herceptin immunoconjugates", Bioconjugate Chem., 13: 786-791, (2002).
Mao et al., "EphB2 as a Therapeutic Antibody Drug Target for the Treatment of Colorectal Cancer" Cancer Research 64:781-788, (2004).
Marks et al., "By-Passing Immunization: Building High Affinity Human Antibodies by Chain Shuffling" Bio/Technology 10:779-783, (Jul. 1992).
Marks et al., "By-Passing Immunization: Human Antibodies From V-gene Libraries Displayed on Phage" J Mol Biol. 222(3):581-597, (Dec. 5, 1991).
Matsuuchi et al., "New views of BCR structure and organization", Curr. Opin. Immunol 13(3): 270-277, (2001).
Meyer et al., "Recent Advances in Antibody Drug Conjugates for Cancer Therapy" Annual Reports in Medicinal Chemistry, Chapter 23, 38:229-237, (2003).
Nakamura et al., "Stereochemistry and Total Synthesis of Dolastatin E" Tetrahedron Letters 36(28):5059-5062, (1995).
Niculescu-Duvaz and Springer, "Antibody-Directed Enzyme prodrug Therapy (ADEPT): A Review" Adv. Drg. Del. Rev. 26: 151-172,(1997).
Okazaki et al.,"Three new monoclonal antibodies that define a unique antigen associated with prolymphocytic leukemia/non-Hodgkin's lymphoma and are effectively internalized after binding to the cell surface antigen" Blood 81(1):84-94, (Jan. 1, 1993).
Olejniczak et al., "A quantitative exploration of surface antigen expression in common B-cell malignancies using flow cytometry", Tmmunol. Invest. 35(1):93-114, (2006).
Paul, Fundamental Immunology, 3rd Edition, 1993, pp. 292-295, under the heading Fv Structure and Diversity in Three Dimensions.
Pawlak-Byczkowska et al., "Two new monoclonal antibodies, EPB-1 and EPB-2, reactive with human lymphoma" Cancer Research 49(16):4568-4577, (Aug. 15, 1989).
Payne, Gillian, "Progress in Immunoconjugate Cancer Therapeutics" Cancer Cell 3: 207-212, (2003).
Pettit et al., "Antineoplastic agents 365. Dolastatin 10 SAR probes" Anti-Cancer Drug Design 13:243-277, (1998).
Pettit et al., Isolation of dolastatins 10 15 from the marine mollusc, *Dolabella auricularia* Tetrahedron Letters 49(41):9151-9170, (1993).
Pettit, "The Dolastatins" Progress in the Chemistry of Organic Natural Products, W. Hertz et al., SpringerWienNewYork vol. 70:1-79,(1997).

(56) References Cited

OTHER PUBLICATIONS

Polson, et al., "Antibody-drug conjugates targeted to CD79 for the treatment of non-Hodgkin lymphoma", Blood, vol. 110, No. 2, pp. 616-623, (2007).

Riechmann et al., "Reshaping Human Antibodies for Therapy" Nature 332:323-327 (Mar. 24, 1988).

Riemer, et al., "Matching of trastuzumab (Herceptin) epitope mimics onto the surface of Her-2/neu—a new method of epitope definition", Molecular Immunology, 42: 1121-1124, (2005).

Roitt, et al., "Molecules which recognize antigen", Immunology, 5.7-5.11, (1989).

Rowland et al., "Drug Localisation and Growth Inhibition Studies of Vindesine-Monoclonal anti-CEA Conjugates in a Human Tumour Xenograft" Cancer Immunol Immunother. 21:183-187.

Rudikoff, et al., "Single amino acid substitution altering antigen-binding specificity", PNAS, vol.79, pp. 1979-1983, (1982).

Zhang et al. "The development of anti-CD79 monoclonal antibodies for treatment of B-cell neoplastic disease", Therapeutic Immunology vol. 2:191-2002, 1995.

Carnahan et al. "Epratuzumab, a humanized monoclonal antibody targeting CD22", Clinical Cancer Research 2003, vol. 9, p. 3982s.

U.S. Appl. No. 14/181,529, filed May 13, 2014, Chen et al.

* cited by examiner

FIGURE 1

DNA105250

AGTGTGATGGATATCTGCAGAATTCGCCCTT<u>ATG</u>GCGTTTGACGTCAGCTGCTTCTTTTG
GGTGGTGCTGTTTTCTGCCGGCTGTAAAGTCATCACCTCCTGGGATCAGATGTGCATTGA
GAAAGAAGCCAACAAAACATATAACTGTGAAAATTTAGGTCTCAGTGAAATCCCTGACAC
TCTACCAAACACAACAGAATTTTTGGAATTCAGCTTTAATTTTTTGCCTACAATTCACAA
TAGAACCTTCAGCAGACTCATGAATCTTACCTTTTTGGATTTAACTAGGTGCCAGATTAA
CTGGATACATGAAGACACTTTTCAAAGCCATCATCAATTAAGCACACTTGTGTTAACTGG
AAATCCCCTGATATTCATGGCAGAAACATCGCTTAATGGGCCCAAGTCACTGAAGCATCT
TTTCTTAATCCAAACGGGAATATCCAATCTCGAGTTTATTCCAGTGCACAATCTGGAAAA
CTTGGAAAGCTTGTATCTTGGAAGCAACCATATTTCCTCCATTAAGTTCCCCAAAGACTT
CCCAGCACGGAATCTGAAAGTACTGGATTTTCAGAATAATGCTATACACTACATCTCTAG
AGAAGACATGAGGTCTCTGGAGCAGGCCATCAACCTAAGCCTGAACTTCAATGGCAATAA
TGTTAAAGGTATTGAGCTTGGGGCTTTTGATTCAACGGTCTTCCAAAGTTTGAACTTTGG
AGGAACTCCAAATTTGTCTGTTATATTCAATGGTCTGCAGAACTCTACTACTCAGTCTCT
CTGGCTGGGAACATTTGAGGACATTGATGACGAAGATATTAGTTCAGCCATGCTCAAGGG
ACTCTGTGAAATGTCTGTTGAGAGCCTCAACCTGCAGGAACACCGCTTCTCTGACATCTC
ATCCACCACATTTCAGTGCTTCACCCAACTCCAAGAATTGGATCTGACAGCAACTCACTT
GAAAGGGTTACCCTCTGGGATGAAGGGTCTGAACTTGCTCAAGAAATTAGTTCTCAGTGT
AAATCATTTCGATCAATTGTGTCAAATCAGTGCTGCCAATTTCCCCTCCCTTACACACCT
CTACATCAGAGGCAACGTGAAGAAACTTCACCTTGGTGTTGGCTGCTTGGAGAAACTAGG
AAACCTTCAGACACTTGATTTAAGCCATAATGACATAGAGGCTTCTGACTGCTGCAGTCT
GCAACTCAAAAACCTGTCCCACTTGCAAACCTTAAACCTGAGCCACAATGAGCCTCTTGG
TCTCCAGAGTCAGGCATTCAAAGAATGTCCTCAGCTAGAACTCCTCGATTTGGCATTTAC
CCGCTTACACATTAATGCTCCACAAAGTCCCTTCCAAAACCTCCATTTCCTTCAGGTTCT
GAATCTCACTTACTGCTTCCTTGATACCAGCAATCAGCATCTTCTAGCAGGCCTACCAGT
TCTCCGGCATCTCAACTTAAAAGGGAATCACTTTCAAGATGGGACTATCACGAAGACCAA
CCTACTTCAGACCGTGGGCAGCTTGGAGGTTCTGATTTTGTCCTCTTGTGGTCTCCTCTC
TATAGACCAGCAAGCATTCCACAGCTTGGGAAAAATGAGCCATGTAGACTTAAGCCACAA
CAGCCTGACATGCGACAGCATTGATTCTCTTAGCCATCTTAAGGGAATCTACCTCAATCT
GGCTGCCAACAGCATTAACATCATCTCACCCCGTCTCCTCCCTATCTTGTCCCAGCAGAG
CACCATTAATTTAAGTCATAACCCCCTGGACTGCACTTGCTCGAATATTCATTTCTTAAC
ATGGTACAAAGAAAACCTGCACAAACTTGAAGGCTCGGAGGAGACCACGTGTGCAAACCC
GCCATCTCTAAGGGGAGTTAAGCTATCTGATGTCAAGCTTTCCTGTGGGATTACAGCCAT
AGGCATTTTCTTTCTCATAGTATTTCTATTATTGTTGGCTATTCTGCTATTTTTTGCAGT
TAAATACCTTCTCAGGTGGAAATACCAACACATTTAGTGCTGAAGGTTTCCAGAGAA

FIGURE 2A

DNA105250
></usr/seqdb2/sst/DNA/Dnaseqs.min/ss.DNA105250
><subunit 1 of 1, 661 aa, 1 stop
><MW: 74165, 'pI: 6.34, NX(S/T): 11

MAFDVSCFFWVVLFSAGCKVITSWDQMCIEKEANKTYNCENLGLSEIPDTLPNTTEFLEF
SFNFLPTIHNRTFSRLMNLTFLDLTRCQINWIHEDTFQSHHQLSTLVLTGNPLIFMAETS
LNGPKSLKHLFLIQTGISNLEFIPVHNLENLESLYLGSNHISSIKFPKDFPARNLKVLDF
QNNAIHYISREDMRSLEQAINLSLNFNGNNVKGIELGAFDSTVFQSLNFGGTPNLSVIFN
GLQNSTTQSLWLGTFEDIDDEDISSAMLKGLCEMSVESLNLQEHRFSDISSTTFQCFTQL
QELDLTATHLKGLPSGMKGLNLLKKLVLSVNHFDQLCQISAANFPSLTHLYIRGNVKKLH
LGVGCLEKLGNLQTLDLSHNDIEASDCCSLQLKNLSHLQTLNLSHNEPLGLQSQAFKECP
QLELLDLAFTRLHINAPQSPFQNLHFLQVLNLTYCFLDTSNQHLLAGLPVLRHLNLKGNH
FQDGTITKTNLLQTVGSLEVLILSSCGLLSIDQQAFHSLGKMSHVDLSHNSLTCDSIDSL
SHLKGIYLNLAANSINIISPRLLPILSQQSTINLSHNPLDCTCSNIHFLTWYKENLHKLE
GSEETTCANPPSLRGVKLSDVKLSCGITAIGIFFLIVFLLLLAILLFFAVKYLLRWKYQH
I

Signal sequence.
amino acids 1-18

Transmembrane domain.
amino acids 489-509, 628-648

Leucine Rich Repeat.
amino acids 54-77, 78-101, 102-125, 126-149, 150-171, 174-197, 275-298, 299-
321, 322-348, 371-396, 397-420, 421-445, 446-469, 470-493, 497-520, 521-544

Leucine Rich Repeat C-terminal Domain.
amino acids 577-626

N-glycosylation site.
amino acids 34-37, 53-56, 70-73, 78-81, 201-204, 234-237, 244-247, 394-397,
401-405, 451-454, 573-576

Protein kinase C phosphorylation site.
amino acids 126-128, 163-165, 559-561, 612-614

Casein kinase II phosphorylation site.
amino acids 22-25, 80-83, 138-141, 189-192, 254-257, 378-381, 404-407, 523-
526

N-myristoylation site.
amino acids 213-218, 217-222, 230-235, 241-246, 312-317, 370-375, 545-560,
601-606, 615-620

FIGURE 2B

Prokaryotic membrane lipoprotein lipid attachment site.
amino acids 8-18

Leucine zipper pattern.
amino acids 44-65, 450-471

FIGURE 3

DNA150004

CAGCAGTAGGCCTTGCCTCAGATCCAAGGTCACTCGGAAGAGGCCATGTCTACCCTCAAT
GACACTCATGGAGGAAATGCTGAGAGAAGCATTCAGATGCATGACACAAGGTAAGACTGC
CAAAAATCTTGTTCTTGCTCTCCTCATTTTGTTATTTGTTTTATTTTAGGAGTTTTGAG
AGCAAA<u>ATG</u>ACAACACCCAGAAATTCAGTAAATGGGACTTTCCCGGCAGAGCCAATGAAA
GGCCCTATTGCTATGCAATCTGGTCCAAAACCACTCTTCAGGAGGATGTCTTCACTGGTG
GGCCCCACGCAAAGCTTCTTCATGAGGGAATCTAAGACTTTGGGGGCTGTCCAGATTATG
AATGGGCTCTTCCACATTGCCCTGGGGGGTCTTCTGATGATCCCAGCAGGGATCTATGCA
CCCATCTGTGTGACTGTGTGGTACCCTCTCTGGGGAGGCATTATGTATATTATTTCCGGA
TCACTCCTGGCAGCAACGGAGAAAAACTCCAGGAAGTGTTTGGTCAAAGGAAAAATGATA
ATGAATTCATTGAGCCTCTTTGCTGCCATTTCTGGAATGATTCTTTCAATCATGGACATA
CTTAATATTAAAATTTCCCATTTTTTAAAAATGGAGAGTCTGAATTTTATTAGAGCTCAC
ACACCATATATTAACATATACAACTGTGAACCAGCTAATCCCTCTGAGAAAAACTCCCCA
TCTACCCAATACTGTTACAGCATACAATCTCTGTTCTTGGGCATTTGTCAGTGATGCTG
ATCTTTGCCTTCTTCCAGGAACTTGTAATAGCTGGCATCGTTGAGAATGAATGGAAAAGA
ACGTGCTCCAGACCCAAATCTAACATAGTTCTCCTGTCAGCAGAAGAAAAAAAGAACAG
ACTATTGAAATAAAAGAAGAAGTGGTTGGGCTAACTGAAACATCTTCCCAACCAAAGAAT
GAAGAAGACATTGAAATTATTCCAATCCAAGAAGAGGAAGAAGAAGAAACAGAGACGAAC
TTTCCAGAACCTCCCCAAGATCAGGAATCCTCACCAATAGAAAATGACAGCTCTCCT <u>TAA</u>
GTGATTTCTTCTGTTTTCTGTTTCCTTTTTTAAACATTAGTGTTCATAGCTTCCAAGAGA
CATGCTGACTTTCATTTCTTGAGGTACTCTGCACATACGCACCACATCTCTATCTGGCCT
TTGCATGGAGTGACCATAGCTCCTTCTCTCTTACATTGAATGTAGAGAATGTAGCCATTG
TAGCAGCTTGTGTTGTCACGCTTCTTCTTTTGAGCAACTTTCTTACACTGAAGAAAGGCA
GAATGAGTGCTTCAGAATGTGATTTCCTACTAACCTGTTCCTTGGATAGGCTTTTTAGTA
TAGTATTTTTTTTGTCATTTTCTCCATCAACAACCAGGGAGACTGCACCTGATGGAAAA
GATATATGACTGCTTCATGACATTCCTAAACTATCTTTTTTTATTCCACATCTACGTTT
TTGGTGGAGTCCCTTTTGCATCATTGTTTAAGGATGATAAAAAAAAAATAACAACTAGGG
ACAATACAGAACCCATTCCATTTATCTTTCTACAGGGCTGACATTGTGGCACATTCTTAG
AGTTACCACACCCCATGAGGGAAGCTCTAAATAGCCAACACCCATCTGTTTTTTGTAAAA
ACAGCATAGCTTATACATGGACATGTCTCTGCCTTAACTTTTCCTAACTCCCACTCTAGG
CTATTGTTTGCATGTCTACCTACTTTTAGCCATTATGCGAGAAAAGAAAAAAATGACCAT
AGAAAATGCCACCATGAGGTGCCCAAATTTCAAATAATAATTAACATTTAGTTATATTTA
TAATTTCCAGATGACAAAGTATTTCATCAAATAACTTCATTTGATGTTCCATGATCAAGA
AAGAATCCCTATCTCTATTTTACAAGTAATTCAAAGAGGCCAAATAACTTGTAAACAAGA
AAAGGTAACTTGTCAACAGTCATAACTAGTAATTATGAGAGCCTTGTTTCATAACCAGGT
CTTCTTACTCAAATCCTGTGATGTTTGAAATAACCAAATTGTCTCTCCAATGTCTGCATA
AACTGTGAGAGCCAAGTCAACAGCTTTTATCAAGAATTTACTCTCTGACCAGCAATAAAC
AAGCACTGAGAGACACAGAGAGCCAGATTCAGATTTTACCCATGGGGATAAAAAGACTCA
GACTTTCACCACATTTGGAAAACTACTTGCATCATAAATATATAATAACTGGTAGTTTAT
ATGAAGCAGACACTAAGTGCTATAGACACTCTCAGAATATCATACTTGGAAACAATGTAA
TTAAAATGCCGAATCTGAGTCAACAGCTGCCCTACTTTTCAATTCAGATATACTAGTACC
TTACCTAGAAATAATGTTAACCTAGGGTGAAGTCACTATAATCTGTAGTCTATTATTTGG
GCATTTGCTACATGATGAGTGCTGCCAGATTGTGGCAGGTAAAGAGACAATGTAATTTGC
ACTCCCTATGATATTTCTACATTTTTAGCGACCACTAGTGGAAGACATTCCCCAAAATTA
GAAAAAAGGAGATAGAAGATTTCTGTCTATGTAAAGTTCTCAAAATTTGTTCTAAATTA
ATAAAACTATCTTTGTGTTCA

FIGURE 4

DNA150004

></usr/seqdb2/sst/DNA/Dnaseqs.min/ss.DNA150004
><subunit 1 of 1, 297 aa, 1 stop
><MW: 33077, pI: 5.10, NX(S/T): 3

MTTPRNSVNGTFPAEPMKGPIAMQSGPKPLFRRMSSLVGPTQSFFMRESKTLGAVQIMNG
LFHIALGGLLMIPAGIYAPICVTVWYPLWGGIMYIISGSLLAATEKNSRKCLVKGKMIMN
SLSLFAAISGMILSIMDILNIKISHFLKMESLNFIRAHTPYINIYNCEPANPSEKNSPST
QYCYSIQSLFLGILSVMLIFAFFQELVIAGIVENEWKRTCSRPKSNIVLLSAEEKKEQTI
EIKEEVVGLTETSSQPKNEEDIEIIPIQEEEEEETETNFPEPPQDQESSPIENDSSP

Transmembrane domain.
amino acids 56-76, 82-102, 118-138, 187-207

CD 20/IgE Fc Receptor Beta Subunit Family.
amino acids 58-224.

N-glycosylation site.
amino acids 9-12, 293-296 cAMP- and cGMP-dependent protein kinase phosphorylation site.
amino acids 32-35

Protein kinase C phosphorylation site.
amino acids 3-5, 104-106, 108-110, 173-175

Casein kinase II phosphorylation site.
amino acids 134-137, 231-234, 289-292

N-myristoylation site.
amino acids 10-15, 98-103, 130-135, 210-215, 248-253

FIGURE 5

DNA 182432

GTTGGTGACCAAGAGTACATCTCTTTTCAAATAGCTGGATTAGGTCCTC ATGCTGCTGTG
GTCATTGCTGGTCATCTTTGATGCAGTCACTGAACAGGCAGATTCGCTGACCCTTGTGGC
GCCCTCTTCTGTCTTCGAAGGAGACAGCATCGTTCTGAAATGCCAGGGAGAACAGAACTG
GAAAATTCAGAAGATGGCTTACCATAAGGATAACAAAGAGTTATCTGTTTTCAAAAAATT
CTCAGATTTCCTTATCCAAAGTGCAGTTTTAAGTGACAGTGGTAACTATTTCTGTAGTAC
CAAAGGACAACTCTTTCTCTGGGATAAAACTTCAAATATAGTAAAGATAAAAGTCCAAGA
GCTCTTTCAACGTCCTGTGCTGACTGCCAGCTCCTTCCAGCCCATCGAAGGGGGTCCAGT
GAGCCTGAAATGTGAGACCCGGCTCTCTCCACAGAGGTTGGATGTTCAACTCCAGTTCTG
CTTCTTCAGAGAAAACCAGGTCCTGGGGTCAGGCTGGAGCAGCTCTCCGGAGCTCCAGAT
TTCTGCCGTGTGGAGTGAAGACACAGGGTCTTACTGGTGCAAGGCAGAAACGGTGACTCA
CAGGATCAGAAAACAGAGCCTCCAATCCCAGATTCACGTGCAGAGAATCCCCATCTCTAA
TGTAAGCTTGGAGATCCGGGCCCCCGGGGACAGGTGACTGAAGGACAAAAACTGATCCT
GCTCTGCTCAGTGGCTGGGGGTACAGGAAATGTCACATTCTCCTGGTACAGAGAGGCCAC
AGGAACCAGTATGGGAAAGAAAACCCAGCGTTCCCTGTCAGCAGAGCTGGAGATCCCAGC
TGTGAAAGAGAGTGATGCCGGCAAATATTACTGTAGAGCTGACAACGGCCATGTGCCTAT
CCAGAGCAAGGTGGTGAATATCCCTGTGAGAATTCCAGTGTCTCGCCCTGTCCTCACCCT
CAGGTCTCCTGGGGCCCAGGCTGCAGTGGGGACCTGCTGGAGCTTCACTGTGAGGCCCT
GAGAGGCTCTCCCCCAATCTTGTACCAATTTTATCATGAGGATGTCACCCTTGGGAACAG
CTCGGCCCCCTCTGGAGGAGGGGCCTCCTTCAACCTCTCTTTGACTGCAGAACATTCTGG
AAACTACTCCTGTGAGGCCAACAACGGCCTGGGGCCCAGTGCAGTGAGGCAGTGCCAGT
CTCCATCTCAGGACCTGATGGCTATAGAAGAGACCTCATGACAGCTGGAGTTCTCTGGGG
ACTGTTTGGTGTCCTTGGTTTCACTGGTGTTGCTTTGCTGTTGTATGCCTTGTTCCACAA
GATATCAGGAGAAAGTTCTGCCACTAATGAACCCAGAGGGGCTTCCAGGCCAAATCCTCA
AGAGTTCACCTATTCAAGCCCAACCCCAGACATGGAGGAGCTGCAGCCAGTGTATGTCAA
TGTGGGCTCTGTAGATGTGGATGTGGTTTATTCTCAGGTCTGGAGCATGCAGCAGCCAGA
AAGCTCAGCAAACATCAGGACACTTCTGGAGAACAAGGACTCCCAAGTCATCTACTCTTC
TGTGAAGAAATCA TAACACTTGGAGGAATCAGAAGGGAAGATCAACAGCAAGGATGGGGC
ATCATTAAGACTTGCTATAAAACCTTATGAAAATGCTTGAGGCTTATCACCTGCCACAGC
CAGAACGTGCCTCAGGAGGCACCTCCTGTCATTTTTGTCCTGATGATGTTTCTTCTCCAA
TATCTTCTTTTACCTATCAATATTCATTGAACTGCTGCTACATCCAGACACTGTGCAAAT
AAATTATTTCTGCTACCTTCAAAAAAAAAAAAAAAAAAAAATGCAG

FIGURE 6A

DNA 182432

></usr/seqdb2/sst/DNA/Dnaseqs.min/ss.DNA182432
><subunit 1 of 1, 508 aa, 1 stop
><MW: 55542, pI: 6.30, NX(S/T): 5

MLLWSLLVIFDAVTEQADSLTLVAPSSVFEGDSIVLKCQGEQNWKIQKMAYHKDNKELSV
FKKFSDFLIQSAVLSDSGNYFCSTKGQLFLWDKTSNIVKIKVQELFQRPVLTASSFQPIE
GGPVSLKCETRLSPQRLDVQLQFCFFRENQVLGSGWSSSPELQISAVWSEDTGSYWCKAE
TVTHRIRKQSLQSQIHVQRIPISNVSLEIRAPGGQVTEGQKLILLCSVAGGTGNVTFSWY
REATGTSMGKKTQRSLSAELEIPAVKESDAGKYYCRADNGHVPIQSKVVNIPVRIPVSRP
VLTLRSPGAQAAVGDLLELHCEALRGSPPILYQFYHEDVTLGNSSAPSGGGASFNLSLTA
EHSGNYSCEANNGLGAQCSRAVPVSISGPDGYRRDLMTAGVLWGLFGVLGFTGVALLLYA
LFHKISGESSATNEPRGASRPNPQEFTYSSPTPDMEELQPVYVNVGSVDVDVVYSQVWSM
QQPESSANIRTLLENKDSQVIYSSVKKS

Signal sequence.
amino acids 1-14.

Transmembrane domain.
amino acids 400-420.

Immunoglobulin domain.
amino acids 17-84, 121-179, 219-277, 314-370.

N-glycosylation site.
amino acids 204-207, 234-237, 343-346, 355-358, 365-368

Glycosaminoglycan attachment site.
amino acids 348-351 cAMP- and cGMP-dependent protein kinase phosphorylation site.
amino acids 62-65, 187-190

Protein kinase C phosphorylation site.
amino acids 83-85, 125-127, 183-185, 252-254, 303-305, 504-506

Casein kinase II phosphorylation site.
amino acids 27-30, 158-161, 387-390, 491-494

Tyrosine kinase phosphorylation site.
amino acids 266-273

N-myristoylation site.
amino acids 78-83, 121-126, 153-158, 173-178, 213-218, 230-235, 245-250, 308-313, 349-354, 351-356, 364-369, 375-380, 400-405

FIGURE 6B

Amidation site.
amino acids 248-251

FIGURE 7

DNA225785

TGCTGCAACTCAAACTAACCAACCCACTGGGAGAAG<u>ATG</u>CCTGGGGGTCCAGGAGTCCTC
CAAGCTCTGCCTGCCACCATCTTCCTCCTCTTCCTGCTGTCTGCTGTCTACCTGGGCCCT
GGGTGCCAGGCCCTGTGGATGCACAAGGTCCCAGCATCATTGATGGTGAGCCTGGGGGAA
GACGCCCACTTCCAATGCCCGCACAATAGCAGCAACAACGCCAACGTCACCTGGTGGCGC
GTCCTCCATGGCAACTACACGTGGCCCCCTGAGTTCTTGGGCCCGGGCGAGGACCCCAAT
GGTACGCTGATCATCCAGAATGTGAACAAGAGCCATGGGGGCATATACGTGTGCCGGGTC
CAGGAGGGCAACGAGTCATACCAGCAGTCCTGCGGCACCTACCTCCGCGTGCGCCAGCCG
CCCCCCAGGCCCTTCCTGGACATGGGGGAGGGCACCAAGAACCGAATCATCACAGCCGAG
GGGATCATCCTCCTGTTCTGCGCGGTGGTGCCTGGGACGCTGCTGCTGTTCAGGAAACGA
TGGCAGAACGAGAAGCTCGGGTTGGATGCCGGGGATGAATATGAAGATGAAAACCTTTAT
GAAGGCCTGAACCTGGACGACTGCTCCATGTATGAGGACATCTCCCGGGGCCTCCAGGGC
ACCTACCAGGATGTGGGCAGCCTCAACATAGGAGATGTCCAGCTGGAGAAGCCG<u>TGA</u>CAC
CCCTACTCCTGCCAGGCTGCCCCCGCCTGCTGTGCACCCAGCTCCAGTGTCTCAGCTCAC
TTCCCTGGGACATTCTCCTTTCAGCCCTTCTGGGGCTTCCTTAGTCATATTCCCCCAGT
GGGGGGTGGGAGGGTAACCTCACTCTTCTCCAGGCCAGGCCTCCTTGGACTCCCCTGGGG
GTGTCCCACTCTTCTTCCCTCTAAACTGCCCCACCTCCTAACCTAATCCCCACGCCCCGC
TGCCTTTCCCAGGCTCCCCTCACCCAGCGGGTAATGAGCCCTTAATCGCTGCCTCTAGGG
GAGCTGATTGTAGCAGCCTCGTTAGTGTCACCCCCTCCTCCCTGATCTGTCAGGGCCACT
TAGTGATAATAAATTCTTCCCAACTGC

FIGURE 8

DNA225785

></usr/seqdb2/sst/DNA/Dnaseqs.min/ss.DNA225785
><subunit 1 of 1, 226 aa, 1 stop
><MW: 25038, pI: 4.91, NX(S/T): 6

MPGGPGVLQALPATIFLLFLLSAVYLGPGCQALWMHKVPASLMVSLGEDAHFQCPHNSSN
NANVTWWRVLHGNYTWPPEFLGPGEDPNGTLIIQNVNKSHGGIYVCRVQEGNESYQQSCG
TYLRVRQPPPRPFLDMGEGTKNRIITAEGIILLFCAVVPGTLLLFRKRWQNEKLGLDAGD
EYEDENLYEGLNLDDCSMYEDISRGLQGTYQDVGSLNIGDVQLEKP

Signal sequence.
amino acids 1-29.

Transmembrane domain.
amino acids 143-163.

Immunoreceptor tyrosine-based activation motif.
amino acids 185-205.

N-glycosylation site.
amino acids 57-60, 63-66, 73-76, 88-91, 97-100, 112-115

Casein kinase II phosphorylation site.
amino acids 45-48, 197-200, 209-212.

N-myristoylation site.
amino acids 6-11, 102-107, 175-180, 205-210.

Ribosomal protein S2 signature 1.
amino acids 16-27.

FIGURE 9

DNA225786

CAGGGGACAGGCTGCAGCCGGTGCAGTTACACGTTTTCCTCCAAGGAGCCTCGGACGTTG
TCACGGGTTTGGGGTCGGGGACAGAGCAGTGACC<u>ATG</u>GCCAGGCTGGCGTTGTCTCCTGT
GCCCAGCCACTGGATGGTGGCGTTGCTGCTGCTGCTCTCAGCTGAGCCAGTACCAGCAGC
CAGATCGGAGGACCGGTACCGGAATCCCAAAGGTAGTGCTTGTTCGCGGATCTGGCAGAG
CCCACGTTTCATAGCCAGGAAACGGGGCTTCACGGTGAAAATGCACTGCTACATGAACAG
CGCCTCCGGCAATGTGAGCTGGCTCTGGAAGCAGGAGATGGACGAGAATCCCCAGCAGCT
GAAGCTGGAAAAGGGCCGCATGGAAGAGTCCCAGAACGAATCTCTCGCCACCCTCACCAT
CCAAGGCATCCGGTTTGAGGACAATGGCATCTACTTCTGTCAGCAGAAGTGCAACAACAC
CTCGGAGGTCTACCAGGGCTGCGGCACAGAGCTGCGAGTCATGGGATTCAGCACCTTGGC
ACAGCTGAAGCAGAGGAACACGCTGAAGGATGGTATCATCATGATCCAGACGCTGCTGAT
CATCCTCTTCATCATCGTGCCTATCTTCCTGCTGCTGGACAAGGATGACAGCAAGGCTGG
CATGGAGGAAGATCACACCTACGAGGGCCTGGACATTGACCAGACAGCCACCTATGAGGA
CATAGTGACGCTGCGGACAGGGGAAGTGAAGTGGTCTGTAGGTGAGCACCCAGGCCAGGA
<u>GTGA</u>GAGCCAGGTCGCCCCATGACCTGGGTGCAGGCTCCCTGGCCTCAGTGACTGCTTCG
GAGCTGCCTGGCTCATGGCCCAACCCCTTTCCTGGACCCCCAGCTGGCCTCTGAAGCTG
GCCCACCAGAGCTGCCATTTGTCTCCAGCCCCTGGTCCCCAGCTCTTGCCAAAGGGCCTG
GAGTAGAAGGACAACAGGGCAGCAACTTGGAGGGAGTTCTCTGGGGATGGACGGGACCCA
GCCTTCTGGGGGTGCTATGAGGTGATCCGTCCCCACACATGGGATGGGGAGGCAGAGAC
TGGTCCAGAGCCCGCAAATGGACTCGGAGCCGAGGGCCTCCCAGCAGAGCTTGGGAAGGG
CCATGGACCCAACTGGGCCCCAGAAGAGCCACAGGAACATCATTCCTCTCCCGCAACCAC
TCCCACCCCAGGGAGGCCCTGGCCTCCAGTGCCTTCCCCCGTGGAATAAACGGTGTGTCC
TGAGAAACCA

FIGURE 10

DNA225786

></usr/seqdb2/sst/DNA/Dnaseqs.min/ss.DNA225786
><subunit 1 of 1, 229 aa, 1 stop
><MW: 26048, pI: 5.86, NX(S/T): 4

MARLALSPVPSHWMVALLLLLSAEPVPAARSEDRYRNPKGSACSRIWQSPRFIARKRGFT
VKMHCYMNSASGNVSWLWKQEMDENPQQLKLEKGRMEESQNESLATLTIQGIRFEDNGIY
FCQQKCNNTSEVYQGCGTELRVMGFSTLAQLKQRNTLKDGIIMIQTLLIILFIIVPIFLL
LDKDDSKAGMEEDHTYEGLDIDQTATYEDIVTLRTGEVKWSVGEHPGQE

Signal sequence.
amino acids 1-28.

Transmembrane domain.
amino acids 5-25, 159-179.

Immunoglobulin domain.
amino acids 58-124.

Immunoreceptor tyrosine-based activation motif.
amino acids 193-213.

N-glycosylation site.
amino acids 73-76, 101-104, 127-130, 128-131.

Protein kinase C phosphorylation site.
amino acids 49-51, 60-62, 156-158, 212-214.

Casein kinase II phosphorylation site.
amino acids 99-102, 156-159, 206-209, 221-224.

Tyrosine kinase phosphorylation site.
amino acids 113-120.

N-myristoylation site.
amino acids 40-45, 118-123.

FIGURE 11A

DNA225875

```
GCCCTCCCAGAGCTGCCGGACGCTCGCGGGTCTCGGAACGCATCCCGCCGCGGGGGCTTC
GGCCGTGGCATGGGCGCCGCGGGCCTGCTCGGGGTTTTCTTGGCTCTCGTCGCACCGGGG
GTCCTCGGGATTTCTTGTGGCTCTCCTCCGCCTATCCTAAATGGCCGGATTAGTTATTAT
TCTACCCCATTGCTGTTGGTACCGTGATAAGGTACAGTTGTTCAGGTACCTTCCGCCTC
ATTGGAGAAAAAAGTCTATTATGCATAACTAAAGACAAAGTGGATGGAACCTGGGATAAA
CCTGCTCCTAAATGTGAATATTTCAATAAATATTCTTCTTGCCCTGAGCCCATAGTACCA
GGAGGATACAAAATTAGAGGCTCTACACCCTACAGACATGGTGATTCTGTGACATTTGCC
TGTAAAACCAACTTCTCCATGAACGGAAACAAGTCTGTTTGGTGTCAAGCAAATAATATG
TGGGGGCCGACACGACTACCAACCTGTGTAAGTGTTTTCCCTCTCGAGTGTCCAGCACTT
CCTATGATCCACAATGGACATCACACAAGTGAGAATGTTGGCTCCATTGCTCCAGGATTG
TCTGTGACTTACAGCTGTGAATCTGGTTACTTGCTTGTTGGAGAAAAGATCATTAACTGT
TTGTCTTCGGGAAAATGGAGTGCTGTCCCCCCCACATGTGAAGAGGCACGCTGTAAATCT
CTAGGACGATTTCCCAATGGGAAGGTAAAGGAGCCTCCAATTCTCCGGGTTGGTGTAACT
GCAAACTTTTTCTGTGATGAAGGGTATCGACTGCAAGGCCCACCTTCTAGTCGGTGTGTA
ATTGCTGGACAGGGAGTTGCTTGGACCAAAATGCCAGTATGTGAAGAAATTTTTTGCCCA
TCACCTCCCCCTATTCTCAATGGAAGACATATAGGCAACTCACTAGCAAATGTCTCATAT
GGAAGCATAGTCACTTACACTTGTGACCCGGACCCAGAGGAAGGAGTGAACTTCATCCTT
ATTGGAGAGAGCACTCTCCGTTGTACAGTTGATAGTCAGAAGACTGGGACCTGGAGTGGC
CCTGCCCCACGCTGTGAACTTTCTACTTCTGCGGTTCAGTGTCCACATCCCCAGATCCTA
AGAGGCCGAATGGTATCTGGGCAGAAAGATCGATATACCTATAACGACACTGTGATATTT
GCTTGCATGTTTGGCTTCACCTTGAAGGGCAGCAAGCAAATCCGATGCAATGCCCAAGGC
ACATGGGAGCCATCTGCACCAGTCTGTGAAAAGGAATGCCAGGCCCCTCCTAACATCCTC
AATGGGCAAAAGGAAGATAGACACATGGTCCGCTTTGACCCTGGAACATCTATAAAATAT
AGCTGTAACCCTGGCTATGTGCTGGTGGGAGAAGAATCCATACAGTGTACCTCTGAGGGG
GTGTGGACACCCCCTGTACCCCAATGCAAAGTGGCAGCGTGTGAAGCTACAGGAAGGCAA
CTCTTGACAAAACCCCAGCACCAATTTGTTAGACCAGATGTCAACTCTTCTTGTGGTGAA
GGGTACAAGTTAAGTGGGAGTGTTTATCAGGAGTGTCAAGGCACAATTCCTTGGTTTATG
GAGATTCGTCTTTGTAAAGAAATCACCTGCCCACCACCCCCTGTTATCTACAATGGGGCA
CACACCGGGAGTTCCTTAGAAGATTTTCCATATGGAACCACGGTCACTTACACATGTAAC
CCTGGGCCAGAAAGAGGAGTGGAATTCAGCCTCATTGGAGAGAGCACCATCCGTTGTACA
AGCAATGATCAAGAAAGAGGCACCTGGAGTGGCCCTGCTCCCCTATGTAAACTTTCCCTC
CTTGCTGTCCAGTGCTCACATGTCCATATTGCAAATGGATACAAGATATCTGGCAAGGAA
GCCCCATATTTCTACAATGACACTGTGACATTCAAGTGTTATAGTGGATTTACTTTGAAG
GGCAGTAGTCAGATTCGTTGCAAAGCTGATAACACCTGGGATCCTGAAATACCAGTTTGT
GAAAAAGAAACATGCCAGCATGTGAGACAGAGTCTTCAAGAACTTCCAGCTGGTTCACGT
GTGGAGCTAGTTAATACGTCCTGCCAAGATGGGTACCAGTTGACTGGACATGCTTATCAG
ATGTGTCAAGATGCTGAAAATGGAATTTGGTTCAAAAAGATTCCACTTTGTAAAGTTATT
CACTGTCACCCTCCACCAGTGATTGTCAATGGGAAGCACACAGGGATGATGGCAGAAAAC
TTTCTATATGGAAATGAAGTCTCTTATGAATGTGACCAAGGATTCTATCTCCTGGGAGAG
AAAAAATTGCAGTGCAGAAGTGATTCTAAAGGACATGGATCTTGGAGCGGGCCTTCCCCA
CAGTGCTTACGATCTCCTCCTGTGACTCGCTGCCCTAATCCAGAAGTCAAACATGGGTAC
AAGCTCAATAAAACACATTCTGCATATTCCCACAATGACATAGTGTATGTTGACTGCAAT
CCTGGCTTCATCATGAATGGTAGTCGCGTGATTAGGTGTCATACTGATAACACATGGGTG
```

FIGURE 11B

```
CCAGGTGTGCCAACTTGTATGAAAAAAGCCTTCATAGGGTGTCCACCTCCGCCTAAGACC
CCTAACGGGAACCATACTGGTGGAAACATAGCTCGATTTTCTCCTGGAATGTCAATCCTG
TACAGCTGTGACCAAGGCTACCTGCTGGTGGGAGAGGCACTCCTTCTTTGCACACATGAG
GGAACCTGGAGCCAACCTGCCCCTCATTGTAAAGAGGTAAACTGTAGCTCACCAGCAGAT
ATGGATGGAATCCAGAAAGGGCTGGAACCAAGGAAAATGTATCAGTATGGAGCTGTTGTA
ACTCTGGAGTGTGAAGATGGGTATATGCTGGAAGGCAGTCCCCAGAGCCAGTGCCAATCG
GATCACCAATGGAACCCTCCCCTGGCGGTTTGCAGATCCCGTTCACTTGCTCCTGTCCTT
TGTGGTATTGCTGCAGGTTTGATACTTCTTACCTTCTTGATTGTCATTACCTTATACGTG
ATATCAAAACACAGAGAACGCAATTATTATACAGATACAAGCCAGAAAGAAGCTTTTCAT
TTAGAAGCACGAGAAGTATATTCTGTTGATCCATACAACCCAGCCAGC<u>TGA</u>TCAGAAGAC
AAACTGGTGTGTGCCTCATTGCTTGGAATTCAGCGGAATATTGATTAGAAAGAAACTGCT
CTAATATCAGCAAGTCTCTTTATATGGCCTCAAGATCAATGAAATGATGTCATAAGCGAT
CACTTCCTATATGCACTTATTCTCAAGAAGAACATCTTTATGGTAAAGATGGGAGCCCAG
TTTCACTGCCATATACTCTTCAAGGACTTTCTGAAGCCTCACTTATGAGATGCCTGAAGC
CAGGCCATGGCTATAAACAATTACATGGCTCTAAAAAGTTTTGCCCTTTTTAAGGAAGGC
ACTAAAAAGAGCTGTCCTGGTATCTAGACCCATCTTCTTTTTGAAATCAGCATACTCAAT
GTTACTATCTGCTTTTGGTTATAATGTGTTTTTAATTATCTAAAGTATGAAGCATTTTCT
GGGGTTATGATGGCCTTACCTTTATTAGGAAGTATGGTTTTATTTTGATAGTAGCTTCCT
CCTCTGGTGGTGTTAATCATTTCATTTTTACCCTTACTGTTTGAGTTTCTCTCACATTAC
TGTATATACTTTGCCTTTCCATAATCACTCAGTGATTGCAATTTGCACAAGTTTTTTTAA
ATTATGGGAATCAAGATTTAATCCTAGAGATTTGGTGTACAATTCAGGCTTTGGATGTTT
CTTTAGCAGTTTTGTGATAAGTTCTAGTTGCTTGTAAAATTTCACTTAATAATGTGTACA
TTAGTCATTCAATAAATTGTAATTGTAAAGAAAA
```

FIGURE 12A

DNA225875

```
></usr/seqdb2/sst/DNA/Dnaseqs.min/ss.DNA225875
><subunit 1 of 1, 1033 aa, 1 stop
><MW: 112992, pI: 7.78, NX(S/T): 11
```

MGAAGLLGVFLALVAPGVLGISCGSPPPILNGRISYYSTPIAVGTVIRYSCSGTFRLIGE
KSLLCITKDKVDGTWDKPAPKCEYFNKYSSCPEPIVPGGYKIRGSTPYRHGDSVTFACKT
NFSMNGNKSVWCQANNMWGPTRLPTCVSVFPLECPALPMIHNGHHTSENVGSIAPGLSVT
YSCESGYLLVGEKIINCLSSGKWSAVPPTCEEARCKSLGRFPNGKVKEPPILRVGVTANF
FCDEGYRLQGPPSSRCVIAGQGVAWTKMPVCEEIFCPSPPPILNGRHIGNSLANVSYGSI
VTYTCDPDPEEGVNFILIGESTLRCTVDSQKTGTWSGPAPRCELSTSAVQCPHPQILRGR
MVSGQKDRYTYNDTVIFACMFGFTLKGSKQIRCNAQGTWEPSAPVCEKECQAPPNILNGQ
KEDRHMVRFDPGTSIKYSCNPGYVLVGEESIQCTSEGVWTPPVPQCKVAACEATGRQLLT
KPQHQFVRPDVNSSCGEGYKLSGSVYQECQGTIPWFMEIRLCKEITCPPPPVIYNGAHTG
SSLEDFPYGTTVTYTCNPGPERGVEFSLIGESTIRCTSNDQERGTWSGPAPLCKLSLLAV
QCSHVHIANGYKISGKEAPYFYNDTVTFKCYSGFTLKGSSQIRCKADNTWDPEIPVCEKE
TCQHVRQSLQELPAGSRVELVNTSCQDGYQLTGHAYQMCQDAENGIWFKKIPLCKVIHCH
PPPVIVNGKHTGMMAENFLYGNEVSYECDQGFYLLGEKKLQCRSDSKGHGSWSGPSPQCL
RSPPVTRCPNPEVKHGYKLNKTHSAYSHNDIVYVDCNPGFIMNGSRVIRCHTDNTWVPGV
PTCMKKAFIGCPPPPKTPNGNHTGGNIARFSPGMSILYSCDQGYLLVGEALLLCTHEGTW
SQPAPHCKEVNCSSPADMDGIQKGLEPRKMYQYGAVVTLECEDGYMLEGSPQSQCQSDHQ
WNPPLAVCRSRSLAPVLCGIAAGLILLTFLIVITLYVISKHRERNYYTDTSQKEAFHLEA
REVYSVDPYNPAS

Signal sequence.
amino acids 1-20.

Transmembrane domain.
amino acids 973-993.

Sushi domain (SCR repeat).
amino acids 23-82, 91-146, 154-210, 215-271, 276-342, 351-406, 410-466, 471-
522, 527-593, 602-657, 662-714, 719-779, 788-843, 851-907, 912-968.

N-glycosylation site.
amino acids 121-124, 127-130, 294-297, 372-375, 492-495, 623-626, 682-685,
800-803, 823-826, 861-864, 911-914.

Protein kinase C phosphorylation site.
amino acids 54-56, 200-202, 253-255, 322-324, 329-331, 384-386, 434-436, 474-
476, 573-575, 614-616, 627-629, 635-637, 1011-1013.

FIGURE 12B

Casein kinase II phosphorylation site.

amino acids 90-93, 209-212, 370-373, 494-497, 541-544, 542-545, 577-560, 614-617, 668-671, 676-679, 684-687, 807-810, 914-917, 1011-1014.

Tyrosine kinase phosphorylation site.

amino acids 1000-1006, 1000-1007.

N-myristoylation site.

amino acids 8-13, 20-25, 176-181, 235-240, 260-265, 262-267, 289-294, 298-303, 536-541, 549-554, 563-568, 741-746, 839-844, 860-865, 864-869, 920-925, 934-939, 949-954, 979-984.

Prokaryotic membrane lipoprotein lipid attachment site.

amino acids 13-23, 173-183, 870-880.

Zinc carboxypeptidases, zinc-binding region 2 signature.

amino acids 538-548.

Cereal trypsin/alpha-amylase inhibitors family signature.

amino acids 132-154.

FIGURE 13A

DNA226179
CAAACGTTCCCAAATCTTCCCAGTCGGCTTGCAGAGACTCCTTGCTCCCAGGAGATAACC
AGAAGCTGCATCTTATTGACAGATGGTCATCACATTGGTGAGCTGGAGTCATCAGATTGT
GGGGCCCGGAGTGAGGCTGAAGGGAGTGGATCAGAGCACTGCCTGAGAGTCACCTCTACT
TTCCTGCTACCGCTGCCTGTGAGCTGAAGGGGCTGAACCATACACTCCTTTTTCTACAAC
CAGCTTGCATTTTTTCTGCCCACAATGAGCGGGGAATCAATGAATTTCAGCGATGTTTTC
GACTCCAGTGAAGATTATTTTGTGTCAGTCAATACTTCATATTACTCAGTTGATTCTGAG
ATGTTACTGTGCTCCTTGCAGGAGGTCAGGCAGTTCTCCAGGCTATTTGTACCGATTGCC
TACTCCTTGATCTGTGTCTTTGGCCTCCTGGGGAATATTCTGGTGGTGATCACCTTTGCT
TTTTATAAGAAGGCCAGGTCTATGACAGACGTCTATCTCTTGAACATGGCCATTGCAGAC
ATCCTCTTTGTTCTTACTCTCCCATTCTGGGCAGTGAGTCATGCCACTGGTGCGTGGGTT
TTCAGCAATGCCACGTGCAAGTTGCTAAAAGGCATCTATGCCATCAACTTTAACTGCGGG
ATGCTGCTCCTGACTTGCATTAGCATGGACCGGTACATCGCCATTGTACAGGCGACTAAG
TCATTCCGGCTCCGATCCAGAACACTACCGCGCACGAAAATCATCTGCCTTGTTGTGTGG
GGGCTGTCAGTCATCATCTCCAGCTCAACTTTTGTCTTCAACCAAAAATACAACACCCAA
GGCAGCGATGTCTGTGAACCCAAGTACCAGACTGTCTCGGAGCCCATCAGGTGGAAGCTG
CTGATGTTGGGGCTTGAGCTACTCTTTGGTTTCTTTATCCCTTTGATGTTCATGATATTT
TGTTACACGTTCATTGTCAAAACCTTGGTGCAAGCTCAGAATTCTAAAAGGCACAAAGCC
ATCCGTGTAATCATAGCTGTGGTGCTTGTGTTTCTGGCTTGTCAGATTCCTCATAACATG
GTCCTGCTTGTGACGGCTGCAAATTTGGGTAAAATGAACCGATCCTGCCAGAGCGAAAAG
CTAATTGGCTATACGAAAACTGTCACAGAAGTCCTGGCTTTCCTGCACTGCTGCCTGAAC
CCTGTGCTCTACGCTTTTATTGGGCAGAAGTTCAGAAACTACTTTCTGAAGATCTTGAAG
GACCTGTGGTGTGAGAAGGAAGTACAAGTCCTCAGGCTTCTCCTGTGCCGGGAGGTAC
TCAGAAAACATTTCTCGGCAGACCAGTGAGACCGCAGATAACGACAATGCGTCGTCCTTC
ACTATGTGATAGAAAGCTGAGTCTCCCTAAGGCATGTGTGAAACATACTCATAGATGTTA
TGCAAAAAAAGTCTATGGCCAGGTATGCATGGAAAATGTGGGAATTAAGCAAAATCAAG
CAAGCCTCTCTCCTGCGGGACTTAACGTGCTCATGGGCTGTGTGATCTCTTCAGGGTGGG
GTGGTCTCTGATAGGTAGCATTTTCCAGCACTTTGCAAGGAATGTTTTGTAGCTCTAGGG
TATATATCCGCCTGGCATTTCACAAAACAGCCTTTGGGAAATGCTGAATTAAAGTGAATT
GTTGACAAATGTAAACATTTTCAGAAATATTCATGAAGCGGTCACAGATCACAGTGTCTT
TTGGTTACAGCACAAAATGATGGCAGTGGTTTGAAAAACTAAAACAGAAAAAAAAATGGA
AGCCAACACATCACTCATTTTAGGCAAATGTTTAAACATTTTTATCTATCAGAATGTTTA
TTGTTGCTGGTTATAAGCAGCAGGATTGGCCGGCTAGTGTTTCCTCTCATTTCCCTTTGA
TACAGTCAACAAGCCTGACCCTGTAAAATGGAGGTGGAAAGACAAGCTCAAGTGTTCACA
ACCTGGAAGTGCTTCGGGAAGAAGGGGACAATGGCAGAACAGGTGTTGGTGACAATTGTC
ACCAATTGGATAAAGCAGCTCAGGTTGTAGTGGGCCATTAGGAAACTGTCGGTTTGCTTT
GATTTCCCTGGGAGCTGTTCTCTGTCGTGAGTGTCTCTTGTCTAAACGTCCATTAAGCTG
AGAGTGCTATGAAGACAGGATCTAGAATAATCTTGCTCACAGCTGTGCTCTGAGTGCCTA
GCGGAGTTCCAGCAAACAAAATGGACTCAAGAGAGATTTGATTAATGAATCGTAATGAAG
TTGGGGTTTATTGTACAGTTTAAAATGTTAGATGTTTTTAATTTTTTAAATAAATGGAAT
ACTTTTTTTTTTTTAAAGAAAGCAACTTTACTGAGACAATGTAGAAAGAAGTTTTGTTC
CGTTTCTTTAATGTGGTTGAAGAGCAATGTGTGGCTGAAGACTTTTGTTATGAGGAGCTG
CAGATTAGCTAGGGGACAGCTGGAATTATGCTGGCTTCTGATAATTATTTTAAAGGGGTC
TGAAATTTGTGATGGAATCAGATTTTAACAGCTCTCTTCAATGACATAGAAAGTTCATGG
AACTCATGTTTTTAAAGGGCTATGTAAATATATGAACATTAGAAAAATAGCAACTTGTGT

FIGURE 13B

TACAAAAATACAAACACATGTTAGGAAGGTACTGTCATGGGCTAGGCATGGTGGCTCACA
CCTGTAATCCCAGCATTTTGGGAAGCTAAGATGGGTGGATCACTTGAGGTCAGGAGTTTG
AGACCAGCCTGGCCAACATGGCGAAACCCCTCTCTACTAAAAATACAAAAATTTGCCAGG
CGTGGTGGCGGGTGCCTGTAATCCCAGCTACTTGGGAGGCTGAGGCAAGAGAATCGCTTG
AACCCAGGAGGCAGAGGTTGCAGTGAGCCGAGATCGTGCCATTGCACTCCAGCCTGGGTG
ACAGAGCGAGACTCCATCTCAAAAAAAAAAAAAAAAAA

FIGURE 14

DNA226179

```
></usr/seqdb2/sst/DNA/Dnaseqs.min/ss,DNA226179
><subunit 1 of 1, 374 aa, 1 stop
><MW: 42508, pI: 9.34, NX(S/T): 6
```

MSGESMNFSDVFDSSEDYFVSVNTSYYSVDSEMLLCSLQEVRQFSRLFVPIAYSLICVFG
LLGNILVVITFAFYKKARSMTDVYLLNMAIADILFVLTLPFWAVSHATGAWVFSNATCKL
LKGIYAINFNCGMLLLTCISMDRYIAIVQATKSFRLRSRTLPRTKIICLVVWGLSVIISS
STFVFNQKYNTQGSDVCEPKYQTVSEPIRWKLLMLGLELLFGFFIPLMFMIFCYTFIVKT
LVQAQNSKRHKAIRVIIAVVLVFLACQIPHNMVLLVTAANLGKMNRSCQSEKLIGYTKTV
TEVLAFLHCCLNPVLYAFIGQKFRNYFLKILKDLWCVRRKYKSSGFSCAGRYSENISRQT
SETADNDNASSFTM

Signal sequence.
amino acids 1-43.

Transmembrane domain.
amino acids 48-68, 84-104, 123-143, 164-184, 204-224, 220-240, 245-265, 261-281, 298-318.

N-glycosylation site.
amino acids 7-10, 23-26, 115-118, 285-288, 355-358, 368-371.

Protein kinase C phosphorylation site.
amino acids 117-119, 153-155, 247-249, 290-292.

Casein kinase II phosphorylation site.
amino acids 14-17, 37-40, 79-82, 203-206, 299-302.

N-myristoylation site.
amino acids 60-65, 193-198.

Prokaryotic membrane lipoprotein lipid attachment site.
amino acids 256-266.

7 transmembrane receptor (rhodopsin family).
amino acids 63-316.

FIGURE 15

DNA226239

AGTCACAGAGGGAACACAGAGCCTAGTTGTAAACGGACAGAGACGAGAGGGGCAAGGGAG
GACAGTGGATGACAGGGAAGACGAGTGGGGGCAGAGCTGCTCAGGACC<u>ATG</u>GCTGAGGCC
ATCACCTATGCAGATCTGAGGTTTGTGAAGGCTCCCCTGAAGAAGAGCATCTCCAGCCGG
TTAGGACAGGACCCAGGGGCTGATGATGATGGGGAAATCACCTACGAGAATGTTCAAGTG
CCCGCAGTCCTAGGGGTGCCCTCAAGCTTGGCTTCTTCTGTACTAGGGGACAAAGCAGCG
GTCAAGTCGGAGCAGCCAACTGCGTCCTGGAGAGCCGTGACGTCACCAGCTGTCGGGCGG
ATTCTCCCCTGCCGCACAACCTGCCTGCGATACCTCCTGCTCGGCCTGCTCCTCACCTGC
CTGCTGTTAGGAGTGACCGCCATCTGCCTGGGAGTGCGCTATCTGCAGGTGTCTCAGCAG
CTCCAGCAGACGAACAGGGTTCTGGAAGTCACTAACAGCAGCCTGAGGCAGCAGCTCCGC
CTCAAGATAACGCAGCTGGGACAGAGTGCAGAGGATCTGCAGGGGTCCAGGAGAGAGCTG
GCGCAGAGTCAGGAAGCACTACAGGTGGAACAGAGGGCTCATCAGGCGGCCGAAGGGCAG
CTACAGGCCTGCCAGGCAGACAGACAGAAGACGAAGGAGACCTTGCAAAGTGAGGAGCAA
CAGAGGAGGGCCTTGGAGCAGAAGCTGAGCAACATGGAGAACAGACTGAAGCCCTTCTTC
ACATGCGGCTCAGCAGACACCTGCTGTCCGTCGGGATGGATAATGCATCAGAAAAGCTGC
TTTTACATCTCACTTACTTCAAAAAATTGGCAGGAGAGCCAAAAACAATGTGAAACTCTG
TCTTCCAAGCTGGCCACATTCAGTGAAATTTATCCACAATCACACTCTTACTACTTCTTA
AATTCACTGTTGCCAAATGGTGGTTCAGGGAATTCATATTGGACTGGCCTCAGCTCTAAC
AAGGATTGGAAGTTGACTGATGATACACAACGCACTAGGACTTATGCTCAAAGCTCAAAA
TGTAACAAGGTACATAAAACTTGGTCATGGTGGACACTGGAGTCAGAGTCATGTAGAAGT
TCTCTTCCCTACATCTGTGAGATGACAGCTTTCAGGTTTCCAGAT<u>TAG</u>GACAGTCCTTTG
CACTGAGTTGACACTCATGCCAACAAGAACCTGTGCCCCTCCTTCCTAACCTGAGGCCTG
GGGTTCCTCAGACCATCTCCTTCATTCTGGGCAGTGCCAGCCACCGGCTGACCCACACCT
GACACTTCCAGCCAGTCTGCTGCCTGCTCCCTCTTCCTGAAACTGGACTGTTCCTGGGAA
AAGGGTGAAGCCACCTCTAGAAGGGACTTTGGCCTCCCCCCAAGAACTTCCCATGGTAGA
ATGGGGTGGGGAGGAGGGCGCACGGGCTGAGCGGATAGGGGCGGCCCGGAGCCAGCCAG
GCAGTTTTATTGAAATCTTTTTAAATAATTG

FIGURE 16

DNA226239

><subunit 1 of 1, 359 aa, 1 stop
><MW: 40220, pI: 8.70, NX(S/T): 1

MAEAITYADLRFVKAPLKKSISSRLGQDPGADDDGEITYENVQVPAVLGVPSSLASSVLG
DKAAVKSEQPTASWRAVTSPAVGRILPCRTTCLRYLLLGLLLTCLLLGVTAICLGVRYLQ
VSQQLQQTNRVLEVTNSSLRQQLRLKITQLGQSAEDLQGSRRELAQSQEALQVEQRAHQA
AEGQLQACQADRQKTKETLQSEEQQRRALEQKLSNMENRLKPFFTCGSADTCCPSGWIMH
QKSCFYISLTSKNWQESQKQCETLSSKLATFSEIYPQSHSYYFLNSLLPNGGSGNSYWTG
LSSNKDWKLTDDTQRTRTYAQSSKCNKVHKTWSWWTLESESCRSSLPYICEMTAFRFPD

Signal sequence.
amino acids 1-22.

Transmembrane domain.
amino acids 91-111.

N-glycosylation site.
amino acids 136-139.

Protein kinase C phosphorylation site.
amino acids 22-24, 73-75, 128-130, 138-140, 160-162, 250-252, 257-259, 265-267, 303-305, 313-315, 322-324, 341-343.

Casein kinase II phosphorylation site.
amino acids 6-9, 153-156, 160-163, 214-217, 270-273, 303-306.

N-myristoylation site.
amino acids 26-31, 49-54, 99-104, 183-188, 227-232, 291-296, 292-297, 300-305.

Leucine zipper pattern.
amino acids 86-107, 93-114, 143-164, 150-171.

Lectin C-type domain.
amino acids 250-352.

FIGURE 17

DNA226394

GGCACGAGGGTCCGCAAGCCCGGCTGAGAGCGCGCC<u>ATG</u>GGGCAGGCGGGCTGCAAGGGG
CTCTGCCTGTCGCTGTTCGACTACAAGACCGAGAAGTATGTCATCGCCAAGAACAAGAAG
GTGGGCCTGCTGTACCGGCTGCTGCAGGCCTCCATCCTGGCGTACCTGGTCGTATGGGTG
TTCCTGATAAAGAAGGGTTACCAAGACGTCGACACGTCCCTGCAGAGTGCTGTCATCACC
AAAGTCAAGGGCGTGGCCTTCACCAACACCTCGGATCTTGGGCAGCGGATCTGGGATGTC
GCCGACTACGTCATTCCAGCCCAGGGAGAGAACGTCTTTTTTGTGGTCACCAACCTGATT
GTGACCCCCAACCAGCGGCAGAACGTCTGTGCTGAGAATGAAGGCATTCCTGATGGCGCG
TGCTCCAAGGACAGCGACTGCCACGCTGGGGAAGCGGTTACAGCTGGAAACGGAGTGAAG
ACCGGCCGCTGCCTGCGGAGAGGGAACTTGGCCAGGGGCACCTGTGAGATCTTTGCCTGG
TGCCCGTTGGAGACAAGCTCCAGGCCGGAGGAGCCATTCCTGAAGGAGGCCGAAGACTTC
ACCATTTTCATAAAGAACCACATCCGTTTCCCCAAATTCAACTTCTCCAAAAACAATGTG
ATGGACGTCAAGGACAGATCTTTCCTGAAATCATGCCACTTTGGCCCCAAGAACCACTAC
TGCCCCATCTTCCGACTGGGCTCCATCGTCCGCTGGGCCGGGAGCGACTTCCAGGATATA
GCCCTGCGAGGTGGCGTGATAGGAATTAATATTGAATGGAACTGTGATCTTGATAAAGCT
GCCTCTGAGTGCCACCCTCACTATTCTTTTAGCCGTCTGGACAATAAACTTTCAAAGTCT
GTCTCCTCCGGGTACAACTTCAGATTTGCCAGATATTACCGAGACGCAGCCGGGGTGGAG
TTCCGCACCCTGATGAAAGCCTACGGGATCCGCTTTGACGTGATGGTGAACGGCAAGGGT
GCTTTCTTCTGCGACCTGGTACTCATCTACCTCATCAAAAAGAGAGAGTTTTACCGTGAC
AAGAAGTACGAGGAAGTGAGGGGCCTAGAAGACAGTTCCCAGGAGGCCGAGGACGAGGCA
TCGGGGCTGGGGCTATCTGAGCAGCTCACATCTGGGCCAGGGCTGCTGGGGATGCCGGAG
CAGCAGGAGCTGCAGGAGCCACCCGAGGCGAAGCGTGGAAGCAGCAGTCAGAAGGGGAAC
GGATCTGTGTGCCCACAGCTCCTGGAGCCCCACAGGAGCACG<u>TGA</u>ATTGCCTCTGCTTAC
GTTCAGGCCCTGTCCTAAACCCAGCCGTCTAGCACCCAGTGATCCCATGCCTTTGGGAAT
CCCAGGATGCTGCCCAACGGGAAATTTGTACATTGGGTGCTATCAATGCCACATCACAGG
GACCAGCCATCACAGAGCAAAGTGACCTCCACGTCTGATGCTGGGGTCATCAGGACGGAC
CCATCATGGCTGTCTTTTTGCCCCACCCCCTGCCGTCAGTTCTTCCTTTCTCCGTGGCTG
GCTTCCCGCACTAGGGAACGGGTTGTAAATGGGGAACATGACTTCCTTCCGGAGTCCTTG
AGCACCTCAGCTAAGGACCGCAGTGCCCTGTAGAGTTCCTAGATTACCTCACTGGGAATA
GCATTGTGCGTGTCCGGAAAAGGGCTCCATTTGGTTCCAGCCCACTCCCCTCTGCAAGTG
CCACAGCTTCCCTCAGAGCATACTCTCCAGTGGATCCAAGTACTCTCTCTCCTAAAGACA
CCACCTTCCTGCCAGCTGTTTGCCCTTAGGCCAGTACACAGAATTAAAGTGGGGGAGATG
GCAGACGCTTTCTGGGACCTGCCCAAGATATGTATTCTCTGACACTCTTATTTGGTCATA
AAACAATAAATGGTGTCAATTTCAAAAAAAAAAAAAAAAAAAAAAAAAAAAAAAAAAAAA

FIGURE 18

DNA226394

><subunit 1 of 1, 422 aa, 1 stop
><MW: 47187, pI: 8.40, NX(S/T): 3

MGQAGCKGLCLSLFDYKTEKYVIAKNKKVGLLYRLLQASILAYLVVWVFLIKKGYQDVDT
SLQSAVITKVKGVAFTNTSDLGQRIWDVADYVIPAQGENVFFVVTNLIVTPNQRQNVCAE
NEGIPDGACSKDSDCHAGEAVTAGNGVKTGRCLRRGNLARGTCEIFAWCPLETSSRPEEP
FLKEAEDFTIFIKNHIRFPKFNFSKNNVMDVKDRSFLKSCHFGPKNHYCPIFRLGSIVRW
AGSDFQDIALRGGVIGINIEWNCDLDKAASECHPHYSFSRLDNKLSKSVSSGYNFRFARY
YRDAAGVEFRTLMKAYGIRFDVMVNGKGAFFCDLVLIYLIKKREFYRDKKYEEVRGLEDS
SQEAEDEASGLGLSEQLTSGPGLLGMPEQQELQEPPEAKRGSSSQKGNGSVCPQLLEPHR
ST

N-glycosylation site.
amino acids 77-80, 202-205, 408-411.

Glycosaminoglycan attachment site.
amino acids 369-372, 379-382.

cAMP- and cGMP-dependent protein kinase phosphorylation site.
amino acids 399-402.

Protein kinase C phosphorylation site.
amino acids 18-20, 149-151, 174-176, 404-406.

Casein kinase II phosphorylation site.
amino acids 12-15, 175-178, 279-282, 360-363.

Tyrosine kinase phosphorylation site.
amino acids 84-91.

N-myristoylation site.
amino acids 2-7, 8-13, 72-77, 123-128, 146-151, 252-257, 328-333, 356-361, 370-375.

ATP P2X receptor.
amino acids 14-364.

FIGURE 19

DNA226423

AACTCATTCTGAAGAGGCTGACGATTTTACTGTCTCATTTTTTTCCTTTCTCCAGAATGG
GTTCTGGGTGGGTCCCCTGGGTGGTGGCTCTGCTAGTGAATCTGACCCGACTGGATTCCT
CCATGACTCAAGGCACAGACTCTCCAGAAGATTTTGTGATTCAGGCAAAGGCTGACTGTT
ACTTCACCAACGGGACAGAAAAGGTGCAGTTTGTGGTCAGATTCATCTTTAACTTGGAGG
AGTATGTACGTTTCGACAGTGATGTGGGGATGTTTGTGGCATTGACCAAGCTGGGGCAGC
CAGATGCTGAGCAGTGGAACAGCCGGCTGGATCTCTTGGAGAGGAGCAGACAGGCCGTGG
ATGGGGTCTGTAGACACAACTACAGGCTGGGCGCACCCTTCACTGTGGGGAGAAAAGTGC
AACCAGAGGTGACAGTGTACCCAGAGAGGACCCCACTCCTGCACCAGCATAATCTGCTGC
ACTGCTCTGTGACAGGCTTCTATCCAGGGGATATCAAGATCAAGTGGTTCCTGAATGGGC
AGGAGGAGAGAGCTGGGGTCATGTCCACTGGCCCTATCAGGAATGGAGACTGGACCTTTC
AGACTGTGGTGATGCTAGAAATGACTCCTGAACTTGGACATGTCTACACCTGCCTTGTCG
ATCACTCCAGCCTGCTGAGCCCTGTTTCTGTGGAGTGGAGAGCTCAGTCTGAATATTCTT
GGAGAAAGATGCTGAGTGGCATTGCAGCCTTCCTACTTGGGCTAATCTTCCTTCTGGTGG
GAATCGTCATCCAGCTAAGGGCTCAGAAAGGATATGTGAGGACGCAGATGTCTGGTAATG
AGGTCTCAAGAGCTGTTCTGCTCCCTCAGTCATGCTAAGGTCCTCACTAAGCTTGCTCTC
TCTGGAGCCTGAAGTAGTGATGAGTAGTCTGGGCCCTGGGTGAGGTAAAGGACATTCATG
AGGTCAATGTTCTGGGAATAACTCTCTTCCCTGATCCTTGGAGGAGCCCGAACTGATTCT
GGAGCTCTGTGTTCTGAGATCATGCATCTCCCACCCATCTGCCCTTCTCCCTTCTACGTG
TACATCATTAATCCCCATTGCCAAGGGCATTGTCCAGAAACTCCCCTGAGACCTTACTCC
TTCCAGCCCCAAATCATTTACTTTTCTGTGGTCCAGCCCTACTCCTATAAGTCATGATCT
CCAAAGCTTTCTGTCTTCCAACTGCAGTCTCCACAGTCTTCAGAAGACAAATGCTCAGGT
AGTCACTGTTTCCTTTTCACTGTTTTTAAAAACCTTTTATTGTCAAATAAAATGGAGATA
CA

FIGURE 20

DNA226423

><subunit 1 of 1, 273 aa, 1 stop
><MW: 30822, pI: 6.72, NX(S/T): 2
MGSGWVPWVVALLVNLTRLDSSMTQGTDSPEDFVIQAKADCYFTNGTEKVQFVVRFIFNL
EEYVRFDSDVGMFVALTKLGQPDAEQWNSRLDLLERSRQAVDGVCRHNYRLGAPFTVGRK
VQPEVTVYPERTPLLHQHNLLHCSVTGFYPGDIKIKWFLNGQEERAGVMSTGPIRNGDWT
FQTVVMLEMTPELGHVYTCLVDHSSLLSPVSVEWRAQSEYSWRKMLSGIAAFLLGLIFLL
VGIVIQLRAQKGYVRTQMSGNEVSRAVLLPQSC Signal sequence.
amino acids 1-21.

Transmembrane domain.
amino acids 225-245.

N-glycosylation site.
amino acids 15-18, 45-48.

Protein kinase C phosphorylation site.
amino acids 47-49, 221-223.

Casein kinase II phosphorylation site.
amino acids 17-20, 29-32, 89-92, 259-262.

Tyrosine kinase phosphorylation site.
amino acids 120-128.

N-myristoylation site.
amino acids 71-76, 80-85, 112-117, 167-172, 260-265.

Amidation site.
amino acids 117-120.

Leucine zipper pattern.
amino acids 226-247.

Immunoglobulins and major histocompatibility complex proteins signature.
amino acids 197-203.

Class II histocompatibility antigen, beta.
amino acids 39-116.

Immunoglobulin domain.
amino acids 136-201.

FIGURE 21A

DNA227781

GCTGCCACCTCTCTAGAGGCACCTGGCGGGGAGCCTCTCAACATAAGACAGTGACCAGTC
TGGTGACTCACAGCCGGCACAGCC<u>ATG</u>AACTACCCGCTAACGCTGGAAATGGACCTCGAG
AACCTGGAGGACCTGTTCTGGGAACTGGACAGATTGGACAACTATAACGACACCTCCCTG
GTGGAAAATCATCTCTGCCCTGCCACAGAGGGTCCCCTCATGGCCTCCTTCAAGGCCGTG
TTCGTGCCCGTGGCCTACAGCCTCATCTTCCTCCTGGGCGTGATCGGCAACGTCCTGGTG
CTGGTGATCCTGGAGCGGCACCGGCAGACACGCAGTTCCACGGAGACCTTCCTGTTCCAC
CTGGCCGTGGCCGACCTCCTGCTGGTCTTCATCTTGCCCTTTGCCGTGGCCGAGGGCTCT
GTGGGCTGGGTCCTGGGGACCTTCCTCTGCAAAACTGTGATTGCCCTGCACAAAGTCAAC
TTCTACTGCAGCAGCCTGCTCCTGGCCTGCATCGCCGTGGACCGCTACCTGGCCATTGTC
CACGCCGTCCATGCCTACCGCCACCGCCGCCTCCTCTCCATCCACATCACCTGTGGGACC
ATCTGGCTGGTGGGCTTCCTCCTTGCCTTGCCAGAGATTCTCTTCGCCAAAGTCAGCCAA
GGCCATCACAACAACTCCCTGCCACGTTGCACCTTCTCCCAAGAGAACCAAGCAGAAACG
CATGCCTGGTTCACCTCCCGATTCCTCTACCATGTGGCGGGATTCCTGCTGCCCATGCTG
GTGATGGGCTGGTGCTACGTGGGGGTAGTGCACAGGTTGCGCCAGGCCCAGCGGCGCCCT
CAGCGGCAGAAGGCAGTCAGGGTGGCCATCCTGGTGACAAGCATCTTCTTCCTCTGCTGG
TCACCCTACCACATCGTCATCTTCCTGGACACCCTGGCGAGGCTGAAGGCCGTGGACAAT
ACCTGCAAGCTGAATGGCTCTCTCCCCGTGGCCATCACCATGTGTGAGTTCCTGGGCCTG
GCCCACTGCTGCCTCAACCCCATGCTCTACACTTTCGCCGGCGTGAAGTTCCGCAGTGAC
CTGTCGCGGCTCCTGACCAAGCTGGGCTGTACCGGCCCTGCCTCCCTGTGCCAGCTCTTC
CCTAGCTGGCGCAGGAGCAGTCTCTCTGAGTCAGAGAATGCCACCTCTCTCACCACGTTC
<u>TAG</u>GTCCCAGTGTCCCCTTTTATTGCTGCTTTTCCTTGGGGCAGGCAGTGATGCTGGATG
CTCCTTCCAACAGGAGCTGGGATCCTAAGGGCTCACCGTGGCTAAGAGTGTCCTAGGAGT
ATCCTCATTTGGGGTAGCTAGAGGAACCAACCCCATTTCTAGAACATCCCTGCCAGCTCT
TCTGCCGGCCCTGGGGCTAGGCTGGAGCCCAGGGAGCGGAAAGCAGCTCGAAGGCACAGT
GAAGGCTGTCCTTACCCATCTGCACCCCCCTGGGCTGAGAGAACCTCACGCACCTCCCAT
CCTAATCATCCAATGCTCAAGAAACAACTTCTACTTCTGCCCCTTGCCAACGGAGAGCGCC
TGCCCCTCCCAGAACACACTCCATCAGCTTAGGGGCTGCTGACCTCCACAGCTTCCCCTC
TCTCCTCCTGCCCACCTGTCAAACAAAGCCAGAAGCTGAGCACCAGGGGATGAGTGGAGG
TTAAGGCTGAGGAAAGGCCAGCTGGCAGCAGAGTGTGGCTTCGGACAACTCAGTCCCTAA
AAACACAGACATTCTGCCAGGCCCCAAGCCTGCAGTCATCTTGACCAAGCAGGAAGCTC
AGACTGGTTGAGTTCAGGTAGCTGCCCCTGGCTCTGACCGAAACAGCGCTGGGTCCACCC
CATGTCACCGGATCCTGGGTGGTCTGCAGGCAGGGCTGACTCTAGGTGCCCTTGGAGGCC
AGCCAGTGACCTGAGGAAGCGTGAAGGCCGAGAAGCAAGAAAGAAACCCGACAGAGGGAA
GAAAAGAGCTTTCTTCCCGAACCCCAAGGAGGGAGATGGATCAATCAAACCCGGCTGTCC
CCTCCGCCCAGGCGAGATGGGGTGGGGGGAGAACTCCTAGGGTGGCTGGGTCCAGGGGAT
GGGAGGTTGTGGGCATTGATGGGAAGGAGGCTGGCTTGTCCCCTCCTCACTCCCTTCCC
ATAAGCTATAGACCCGAGGAAACTCAGAGTCGGAACGGAGAAAGGTGGACTGGAAGGGGC
CCGTGGGAGTCATCTCAACCATCCCCTCCGTTGGCATCACCTTAGGCAGGGAAGTGTAAG
AAACACACTGAGGCAGGAACTCCCAGGCCCAGGAAGCCGTGCCCTGCCCCCGTGAGGATG
TCACTCAGATGGAACCGCAGGAAGCTGCTCCGTGCTTGTTTGCTCACCTGGGGTGTGGGA
GGCCCGTCCGGCAGTTCTGGGTGCTCCCTACCACCTCCCCAGCCTTTGATCAGGTGGGGA
GTCAGGGACCCCTGCCCTTGTCCCACTCAAGCCAAGCAGCCAAGCTCCTTGGGAGGCCCC
ACTGGGGAAATAACAGCTGTGGCTCACGTGAGAGTGTCTTCACGGCAGGACAACGAGAAA
GCCCTAAGACGTCCCTTTTTTCTCTGAGTATCTCCTCGCAAGCTGGGTAATCGATGGGGA
GTCTGAAGCAGATGCAAAGAGGCAGAGGATGGATTTTGAATTTTCTTTTTAATAAAAAGG

FIGURE 21B

CACCTATAAAACAGGTCAATACAGTACAGGCAGCACAGAGACCCCCGGAACAAGCCTAAA
AATTGTTTCAAAATAAAAACCAAGAAGATGTCTTCAAAAAAAAAAAAAAAAAAAAAAAA

FIGURE 22

DNA227781
><subunit 1 of 1, 372 aa, 1 stop
><MW: 41955, pI: 8.58, NX(S/T): 4
MNYPLTLEMDLENLEDLFWELDRLDNYNDTSLVENHLCPATEGPLMASFKAVFVPVAYSL
IFLLGVIGNVLVLVILERHRQTRSSTETFLFHLAVADLLLVFILPFAVAEGSVGWVLGTF
LCKTVIALHKVNFYCSSLLLACIAVDRYLAIVHAVHAYRHRRLLSIHITCGTIWLVGFLL
ALPEILFAKVSQGHHNNSLPRCTFSQENQAETHAWFTSRFLYHVAGFLLPMLVMGWCYVG
VVHRLRQAQRRPQRQKAVRVAILVTSIFFLCWSPYHIVIFLDTLARLKAVDNTCKLNGSL
PVAITMCEFLGLAHCCLNPMLYTFAGVKFRSDLSRLLTKLGCTGPASLCQLFPSWRRSSL
SESENATSLTTF Transmembrane domain.
amino acids 52-72, 90-110, 129-149, 166-186, 219-239, 259-279, 299-319.

N-glycosylation site.
amino acids 28-31, 196-199, 297-300, 365-368.

cAMP- and cGMP-dependent protein kinase.
amino acids 356-359.

Protein kinase C phosphorylation site.
amino acids 48-50, 217-219, 293-295, 354-356.

Casein kinase II phosphorylation site.
amino acids 31-34, 84-87, 305-308, 359-362, 361-364.

N-myristoylation site.
amino acids 65-70, 118-123, 311-316.

Prokaryotic membrane lipoprotein lipid attachment site.
amino acids 132-142.

FIGURE 23

DNA 227879
AGTGGCTCTACTTTCAGAAGAAAGTGTCTCTCTTCCTGCTTAAACCTCTGTCTCTGACGG
TCCCTGCCAATCGCTCTGGTCGACCCCAACACACTAGGAGGACAGACACAGGCTCCAAAC
TCCACTAACCAGAGCTGTGATTGTGCCCGCTGAGTGGACTGCGTTGTCAGGGAGTGAGTG
CTCCATCATCGGGAGAATCCAAGCAGGACCGCCATGGAGGAAGGTCAATATTCAGAGATC
GAGGAGCTTCCCAGGAGGCGGTGTTGCAGGCGTGGGACTCAGATCGTGCTGCTGGGGCTG
GTGACCGCCGCTCTGTGGGCTGGGCTGCTGACTCTGCTTCTCCTGTGGCACTGGGACACC
ACACAGAGTCTAAAACAGCTGGAAGAGAGGGCTGCCCGGAACGTCTCTCAAGTTTCCAAG
AACTTGGAAAGCCACCACGGTGACCAGATGGCGCAGAAATCCCAGTCCACGCAGATTTCA
CAGGAACTGGAGGAACTTCGAGCTGAACAGCAGAGATTGAAATCTCAGGACTTGGAGCTG
TCCTGGAACCTGAACGGGCTTCAAGCAGATCTGAGCAGCTTCAAGTCCCAGGAATTGAAC
GAGAGGAACGAAGCTTCAGATTTGCTGGAAAGACTCCGGGAGGAGGTGACAAAGCTAAGG
ATGGAGTTGCAGGTGTCCAGCGGCTTTGTGTGCAACACGTGCCCTGAAAAGTGGATCAAC
TTCCAACGGAAGTGCTACTACTTCGGCAAGGGCACCAAGCAGTGGGTCCACGCCCGGTAT
GCCTGTGACGACATGGAAGGGCAGCTGGTCAGCATCCACAGCCCGGAGGAGCAGGACTTC
CTGACCAAGCATGCCAGCCACACCGGCTCCTGGATTGGCCTTCGGAACTTGGACCTGAAG
GGAGAGTTTATCTGGGTGGATGGGAGCCATGTGGACTACAGCAACTGGGCTCCAGGGGAG
CCCACCAGCCGGAGCCAGGGCGAGGACTGCGTGATGATGCGGGGCTCCGGTCGCTGGACC
GACGCCTTCTGCGACCGTAAGCTGGGCGCCTGGGTGTGCGACCGGCTGGCCACATGCACG
CCGCCAGCCAGCGAAGGTTCCGCGGAGTCCATGGGACCTGATTCAAGACCAGACCCTGAC
GGCCGCCTGCCCACCCCCTCTGCCCCTCTCCACTCTTGAGCATGGATACAGCCAGGCCCA
GAGCAAGACCCTGAAGACCCCCAACCACGGCCTAAAAGCCTCTTTGTGGCTGAAAGGTCC
CTGTGACATTTTCTGCCACCCAAACGGAGGCAGCTGACACATCTCCCGCTCCTCTATGGC
CCCTGCCTTCCCAGGAGTACACCCCAACAGCACCCTCTCCAGATGGGAGTGCCCCAACA
GCACCCTCTCCAGATGAGAGTTACACCCCAACAGCACCCTCTCCAGATGCAGCCCCATCT
CCTCAGCACCCCAGGACCTGAGTATCCCCAGCTCAGGGTGGTGAGTCCTCCTGTCCAGCC
TGCATCAATAAAATGGGGCAGTGATGGCC

FIGURE 24

DNA 227879

><subunit 1 of 1, 321 aa, 1 stop
><MW: 36456, pI: 5.52, NX(S/T): 1
MEEGQYSEIEELPRRRCCRRGTQIVLLGLVTAALWAGLLTLLLLWHWDTTQSLKQLEERA
ARNVSQVSKNLESHHGDQMAQKSQSTQISQELEELRAEQQRLKSQDLELSWNLNGLQADL
SSFKSQELNERNEASDLLERLREEVTKLRMELQVSSGFVCNTCPEKWINFQRKCYYFGKG
TKQWVHARYACDDMEGQLVSIHSPEEQDFLTKHASHTGSWIGLRNLDLKGEFIWVDGSHV
DYSNWAPGEPTSRSQGEDCVMMRGSGRWTDAFCDRKLGAWVCDRLATCTPPASEGSAESM
GPDSRPDPDGRLPTPSAPLHS Signal sequence.
amino acids 1-36.

Transmembrane domain.
amino acids 23-43.

N-glycosylation site.
amino acids 63-66.

cAMP- and cGMP-dependent protein kinase phosphorylation site.
amino acids 19-22.

Protein kinase C phosphorylation site.
amino acids 52-54, 122-124, 251-253, 265-267.

Casein kinase II phosphorylation site.
amino acids 7-10, 162-165, 203-206, 238-241, 254-257, 304-307.

FIGURE 25 getseq sst.DNA256363

AGAGATGGGGACGGAGGCCACAGAGCAGGTTTCCTGGGGCCATTACTCTGGGGATGAAGA
GGACGCATACTCGGCTGAGCCACTGCCGGAGCTTTGCTACAAGGCCGATGTCCAGGCCTT
CAGCCGGGCCTTCCAACCCAGTGTCTCCCTGACCGTGGCTGCGCTGGGTCTGGCCGGCAA
TGGCCTGGTCCTGGCCACCCACCTGGCAGCCCGACGCGCAGCGCGCTCGCCCACCTCTGC
CCACCTGCTCCAGCTGGCCCTGGCCGACCTCTTGCTGGCCCTGACTCTGCCCTTCGCGGC
AGCAGGGGCTCTTCAGGGCTGGAGTCTGGGAAGTGCCACCTGCCGCACCATCTCTGGCCT
CTACTCGGCCTCCTTCCACGCCGGCTTCCTCTTCCTGGCCTGTATCAGCGCCGACCGCTA
CGTGGCCATCGCGCGAGCGCTCCCAGCCGGGCCGCGGCCCTCCACTCCCGGCCGCGCACA
CTTGGTCTCCGTCATCGTGTGGCTGCTGTCACTGCTCCTGGCGCTGCCTGCGCTGCTCTT
CAGCCAGGATGGGCAGCGGGAAGGCCAACGACGCTGTCGCCTCATCTTCCCCGAGGGCCT
CACGCAGACGGTGAAGGGGGCGAGCGCCGTGGCGCAGGTGGCCCTGGGCTTCGCGCTGCC
GCTGGGCGTCATGGTAGCCTGCTACGCGCTTCTGGGCCGCACGCTGCTGGCCGCCAGGGG
GCCCGAGCGCCGGCGTGCGCTGCGCGTCGTGGTGGCTCTGGTGGCGGCCTTCGTGGTGCT
GCAGCTGCCCTACAGCCTCGCCCTGCTGCTGGATACTGCCGATCTACTGGCTGCGCGCGA
GCGGAGCTGCCCTGCCAGCAAACGCAAGGATGTCGCACTGCTGGTGACCAGCGGCTTGGC
CCTCGCCCGCTGTGGCCTCAATCCCGTTCTCTACGCCTTCCTGGGCCTGCGCTTCCGCCA
GGACCTGCGGAGGCTGCTACGGGGTGGGAGCTCGCCCTCAGGGCCTCAACCCCGCCGCGG
CTGCCCCCGCCGGCCCCGCCTTTCTTCCTGCTCAGCTCCCACGGAGACCCACAGTCTCTC
CTGGGACAACTAGGGCTGCGAATCTAGAGGAGGGGGCAGGCTGAGGGTCGTGGGAAAGGG
GAGTAGGTGGGGAACACTGAGAAAGAGGCAGGGACCTAAAGGGACTACCTCTGTGCCTT
GCCACATTAAATTGATAACATGGAAATGAAAAAAAAAAAAAAA

FIGURE 26

></usr/seqdb2/sst/DNA/Dnaseqs.min/ss.DNA256363
><subunit 1 of 1, 362 aa, 1 stop
><MW: 38400, pI: 10.04, NX(S/T): 0
MGTEATEQVSWGHYSGDEEDAYSAEPLPELCYKADVQAFSRAFQPSVSLTVAALGLAGNG
LVLATHLAARRAARSPTSAHLLQLALADLLLALTLPFAAAGALQGWSLGSATCRTISGLY
SASFHAGFLFLACISADRYVAIARALPAGPRPSTPGRAHLVSVIVWLLSLLLALPALLFS
QDGQREGQRRCRLIFPEGLTQTVKGASAVAQVALGFALPLGVMVACYALLGRTLLAARGP
ERRRALRVVVALVAAFVVLQLPYSLALLLDTADLLAARERSCPASKRKDVALLVTSGLAL
ARCGLNPVLYAFLGLRFRQDLRRLLRGGSSPSGPQPRRGCPRRPRLSSCSAPTETHSLSW
DN Transmembrane domain.
Amino acids 43-63, 80-100, 119-139, 158-178, 209-229, 249-269, 291-311.

Seven-transmembrane receptor domain.
Amino acids 58-310.

Protein kinase C phosporylation site.
Amino acids 112-114, 202-204, 285-287.

Casein kinase II phosphorylation site.
Amino acids 15-18.

N-myristoylation site.
Amino acids 2-7, 55-60, 60-65, 101-106, 109-114, 118-123, 183-188, 187-192, 198-203, 221-226, 297-302, 328-333.

Prokaryotic membrane lipoprotein lipid attachment site.
Amino acids 123-133, 216-226.

FIGURE 27

DNA332467

CCTCGGTTCTATCGATTGAATTC<u>ATG</u>AAGACATTGCCTGCCATGCTTGGAACTGGGAAAT
TATTTTGGGTCTTCTTCTTAATCCCATATCTGGACATCTGGAACATCCATGGGAAAGAAT
CATGTGATGTACAGCTTTATATAAAGAGACAATCTGAACACTCCATCTTAGCAGGAGATC
CCTTTGAACTAGAATGCCCTGTGAAATACTGTGCTAACAGGCCTCATGTGACTTGGTGCA
AGCTCAATGGAACAACATGTGTAAAACTTGAAGATAGACAAACAAGTTGGAAGGAAGAGA
AGAACATTTCATTTTTCATTCTACATTTTGAACCAGTGCTTCCTAATGACAATGGGTCAT
ACCGCTGTTCTGCAAATTTTCAGTCTAATCTCATTGAAAGCCACTCAACAACTCTTTATG
TGACAGATGTAAAAAGTGCTTCAGAACGACCCTCCAAGGACGAAATGGCAAGCAGACCCT
GGCTCCTGTATAGTTTACTTCCTTTGGGGGATTGCCTCTACTCATCACTACCTGTTTCT
GCCTGTTCTGCTGCCTGAGAAGGCACCAAGGAAAGCAAAATGAACTCTCTGACACAGCAG
GAAGGGAAATTAACCTGGTTGATGCTCACCTTAAGAGTGAGCAAACAGAAGCAAGCACCA
GGCAAAATTCCCAAGTACTGCTATCAGAAACTGGAATTTATGATAATGACCCTGACCTTT
GTTTCAGAATGCAGGAAGGGTCTGAAGTTTATTCTAATCCATGCCTGGAAGAAAACAAAC
CAGGCATTGTTTATGCTTCCCTGAACCATTCTGTCATTGGACTGAACTCAAGACTGGCAA
GAAATGTAAAAGAAGCACCAACAGAATATGCATCCATATGTGTGAGGAGT<u>TAA</u>GGATCCT
CTAGAGTCGACCTGCAGAAGCTTGGCCGCCATGGCCCAACTTGTTTATTGCAGCTTATAA
GTGTTACAAATAAACAAATAATATTTCTCAATTTGAGAATTTTTACTTTAGAAATGTTCA
TGTTAGTGCTTGGGTCTGAAGGGTCCATAGGACAAATGATTAAAAT

FIGURE 28

DNA332467

><subunit 1 of 1, 289 aa, 1 stop
><MW: 32781, pI: 6.27, NX(S/T): 4
MKTLPAMLGTGKLFWVFFLIPYLDIWNIHGKESCDVQLYIKRQSEHSILAGDPFELECPV
KYCANRPHVTWCKLNGTTCVKLEDRQTSWKEEKNISFFILHFEPVLPNDNGSYRCSANFQ
SNLIESHSTTLYVTDVKSASERPSKDEMASRPWLLYSLLPLGGLPLLITTCFCLFCCLRR
HQGKQNELSDTAGREINLVDAHLKSEQTEASTRQNSQVLLSBTGIYDNDPDLCFRMQEGS
EVYSNPCLEENKPGIVYASLNHSVIGLNSRLARNVKEAPTEYASICVRS Transmembrane domain.
amino acids 153-173.

N-glycosylation site.
amino acids 75-78, 94-97, 110-113, 261-264.

cAMP- and cGMP-dependent protein kinase phosphorylation site.
amino acids 41-44.

Protein kinase C phosphorylation site.
amino acids 10-12, 88-90, 112-114, 140-142, 211-213.

Casein kinase II phosphorylation site.
amino acids 88-91, 138-141, 144-147.

Tyrosine kinase phosphorylation site.
amino acids 31-39.

N-myristoylation site.
amino acids 111-116, 224-229, 254-259.

Immunoglobulin domain.
amino acids 51-117.

FIGURE 29

DNA335922

```
GTTCTCCTTTCCGAGCCAAAATCCCAGGCGATGGTGAATTATGAACGTGCCACACC ATGA
AGCTCTTGTGGCAGGTAACTGTGCACCACCACACCTGGAATGCCATCCTGCTCCCGTTCG
TCTACCTCACGGCGCAAGTGTGGATTCTGTGTGCAGCCATCGCTGCTGCCGCCTCAGCCG
GGCCCCAGAACTGCCCCTCCGTTTGCTCGTGCAGTAACCAGTTCAGCAAGGTGGTGTGCA
CGCGCCGGGGCCTCTCCGAGGTCCCGCAGGGTATTCCCTCGAACACCCGGTACCTCAACC
TCATGGAGAACAACATCCAGATGATCCAGGCCGACACCTTCCGCCACCTCCACCACCTGG
AGGTCCTGCAGTTGGGCAGGAACTCCATCCGGCAGATTGAGGTGGGGGCCTTCAACGGCC
TGGCCAGCCTCAACACCCTGGAGCTGTTCGACAACTGGCTGACAGTCATCCCTAGCGGGG
CCTTTGAATACCTGTCCAAGCTGCGGGAGCTCTGGCTTCGCAACAACCCCATCGAAAGCA
TCCCCTCTTACGCCTTCAACCGGGTGCCCTCCCTCATGCGCCTGGACTTGGGGGAGCTCA
AGAAGCTGGAGTATATCTCTGAGGGAGCTTTTGAGGGGCTGTTCAACCTCAAGTATCTGA
ACTTGGGCATGTGCAACATTAAAGACATGCCCAATCTCACCCCCCTGGTGGGGCTGGAGG
AGCTGGAGATGTCAGGGAACCACTTCCCTGAGATCAGGCCTGGCTCCTTCCATGGCCTGA
GCTCCCTCAAGAAGCTCTGGGTCATGAACTCACAGGTCAGCCTGATTGAGCGGAATGCTT
TTGACGGGCTGGCTTCACTTGTGGAACTCAACTTGGCCCACAATAACCTCTCTTCTTTGC
CCCATGACCTCTTTACCCCGCTGAGGTACCTGGTGGAGTTGCATCTACACCACAACCCTT
GGAACTGTGATTGTGACATTCTGTGGCTAGCCTGGTGGCTTCGAGAGTATATACCCACCA
ATTCCACCTGCTGTGGCCGCTGTCATGCTCCCATGCACATGCGAGGCCGCTACCTCGTGG
AGGTGGACCAGGCCTCCTTCCAGTGCTCTGCCCCCTTCATCATGGACGCACCTCGAGACC
TCAACATTTCTGAGGGTCGGATGGCAGAACTTAAGTGTCGGACTCCCCCTATGTCCTCCG
TGAAGTGGTTGCTGCCCAATGGGACAGTGCTCAGCCACGCCTCCCGCCACCCAAGGATCT
CTGTCCTCAACGACGGCACCTTGAACTTTTCCCACGTGCTGCTTTCAGACACTGGGGTGT
ACACATGCATGGTGACCAATGTTGCAGGCAACTCCAACGCCTCGGCCTACCTCAATGTGA
GCACGGCTGAGCTTAACACCTCCAACTACAGCTTCTTCACCACAGTAACAGTGGAGACCA
CGGAGATCTCGCCTGAGGACACAACGCGAAAGTACAAGCCTGTTCCTACCACGTCCACTG
GTTACCAGCCGGCATATACCACCTCTACCACGGTGCTCATTCAGACTACCCGTGTGCCCA
AGCAGGTGGCAGTACCCGCGACAGACACCACTGACAAGATGCAGACCAGCCTGGATGAAG
TCATGAAGACCACCAAGATCATCATTGGCTGCTTTGTGGCAGTGACTCTGCTAGCTGCCG
CCATGTTGATTGTCTTCTATAAACTTCGTAAGCGGCACCAGCAGCGGAGTACAGTCACAG
CCGCCCGGACTGTTGAGATAATCCAGGTGGACGAAGACATCCCAGCAGCAACATCCGCAG
CAGCAACAGCAGCTCCGTCCGGTGTATCAGGTGAGGGGGCAGTAGTGCTGCCCACAATTC
ATGACCATATTAACTACAACACCTACAAACCAGCACATGGGGCCCACTGGACAGAAAACA
GCCTGGGGAACTCTCTGCACCCCACAGTCACCACTATCTCTGAACCTTATATAATTCAGA
CCCATACCAAGGACAAGGTACAGGAAACTCAAATA TGACTCCCCTCCCCCAAAAAACTTA
TAAAATGCAATAGAATGCACACAAAGACAGCAACTTTTGTACAGAGTGGGGAGAGACTTT
TTCTTGTATATGCTTATATATTAAGTCTATGGGCTGGTTAAAAAAAAACAGATTATATTAA
AATTTAAAGACAAAAAGTCAAAACA
```

FIGURE 30A

DNA58721

></usr/seqdb2/sst/DNA/Dnaseqs.min/ss.DNA58721
><subunit 1 of 1, 653 aa, 1 stop
><MW: 72717, pI: 6.99, NX(S/T): 10
MKLLWQVTVHHHTWNAILLPFVYLTAQVWILCAAIAAAASAGPQNCPSVCSCSNQFSKVV
CTRRGLSEVPQGIPSNTRYLNLMENNIQMIQADTFRHLHHLEVLQLGRNSIRQIEVGAFN
GLASLNTLELFDNWLTVIPSGAFEYLSKLRELWLRNNPIESIPSYAFNRVPSLMRLDLGE
LKKLEYISEGAFEGLFNLKYLNLGMCNIKDMPNLTPLVGLEELEMSGNHFPEIRPGSFHG
LSSLKKLWVMNSQVSLIERNAFDGLASLVELNLAHNNLSSLPHDLFTPLRYLVELHLHHN
PWNCDCDILWLAWWLREYIPTNSTCCGRCHAPMHMRGRYLVEVDQASFQCSAPFIMDAPR
DLNISEGRMAELKCRTPPMSSVKWLLPNGTVLSHASRHPRISVLNDGTLNFSHVLLSDTG
VYTCMVTNVAGNSNASAYLNVSTAELNTSNYSFFTTVTVETTEISPEDTTRKYKPVPTTS
TGYQPAYTTSTTVLIQTTRVPKQVAVPATDTTDKMQTSLDEVMKTTKIIIGCFVAVTLLA
AAMLIVFYKLRKRHQQRSTVTAARTVEIIQVDEDIPAATSAAATAAPSGVSGEGAVVLPT
IHDHINYNTYKPAHGAHWTENSLGNSLHPTVTTISEPYIIQTHTKDKVQETQI Signal sequence.
amino acids 1-41.

Transmembrane domain.
amino acids 12-32, 526-546.

N-glycosylation site.
amino acids 277-280, 322-325, 363-366, 388-391, 410-413, 434-437, 440-443, 447-450, 450-453.

Glycosaminoglycan attachment site.
amino acids 591-594.

Protein kinase C phosphorylation site.
amino acids 62-63, 94-96, 110-112, 243-245, 381-383, 469-471, 470-472, 497-499, 512-514, 525-527, 609-611.

Casein kinase II phosphorylation site.
amino acids 255-258, 267-270, 442-445, 465-468, 517-520, 518-521, 600-603, 633-636.

N-myristoylation site.
amino acids 72-77, 117-122, 190-195, 236-241, 389-394, 420-425, 431-436, 531-536, 615-620.

Prokaryotic membrane lipoprotein lipid attachment site.
amino acids 42-52.

FIGURE 30B

Leucine zipper pattern.
amino acids 271-292.

Leucine Rich Repeat.
amino acids 76-99, 100-123, 124-147, 148-171, 172-196, 197-218, 219-242, 243-266, 267-290.

Leucine rich repeat C-terminal domain.
amino acids 300-351.

Leucine rich repeat N-terminal domain.
amino acids 45-74.

FIGURE 31

DNA335924

GCTGAAAGGGCCACGTTTGTTTTCATTACAAATAAGACCACCGAGTGGGCTCCTGGCGTG
GGGGCGGGAGCAGCCGCGCGCAGTCTTCAGAGGCAGCCCCCAGGCTGTCTCTGGAGGGT
GTGTCTCTGCTTCCCTTTCCCCGTGTTTATTTTCAGACGAAGCCAAGTGGCCCGGGGGA
CCCTCCGGACTCCCAGCCTTCAGAGAGGAGGGCAGCTCGGGCTTTCGCCGCAGTGCTTCC
TGCCCGTCACGTGTGTGCTCCTAGCCGGGGTCGGGGGAGCTGGTATCTTGGCCCTTCTGG
GAGGACGCGCACAGCCCGAGGAGGCAGAGCCCAGACGGGAATGGGCTTTTCAGAGGTGG
GGTGCGGGCGAGGGGACGATGCATTATTTTTAATATTTGATTTATTTTTCCAACTGGACT
TCTTCCCGGGGCTCTTTCTGGGCCAGCTGCCTTTGTGATCCCGCGCCCCGGTCCTCGGC
CTCTCACCTCCAGCGCCGGGGCGCCCCTGCTGTCGGAAGCGGCTGTGACCGGGCAGAGG
TGCTATCTGGACTCTGGGTTCTCAGCCCGGGGACAGCGAACCGAGGGGCAGATGATCCA
TCAGAAAAGAGCCGGCACTGCCCAGCCCCGCGCCCTGCCCCTGCCTTTTTCCGGGAGCG
CGCCGCGCCGCACCCGCTACGGCCGCTTGACCCCATCTTTGAGCCCGGCCCCAAGCTCTG
GGACCGTCGTGCCCCTCATCAAGGAAGAGCCAAGGACCCCAAGGAGAAGGTCAGGAGCGG
CGGTGTGGATGTCCCTTGGCTGCAGGCCCCGCCGCGCACTCCCTTCAGTCCTTCCCTTCT
CTAGGGACCAGGTAGCATCAGTGCCTGGATCTCGGCCTTGTGTGCCCTGCTCCCTGCCCC
ACCTACTAAGAACCAAGTCTGGTTCACCGGCTCCCAAGAGCTGGAACCCATTCTCAGCTA
GCTGGGGGCCCAGGCCACCCCTTCCCTCCAGACCTGTGTGCCTTCTGCCCTGGCTCCAGG
GCCCCCACACCGTGACCAGGGCGGGATCCCTATGGGGCTGGCCAGTCGGCACCGTGCCA
GGCCCACAGTGCCCTGGGCGTCCATGGAAGTCGTTCTGTGTCTTTAAAATCAGAAGGAAG
ACATTAACCTTTAGGCTGAAGAAAATGTTTTAGTACACAGCAATAACTTATTTGTCTTTA
TCCAACAGCCATAAAATATAACTTTAAATATTCTATTGATAGAGAAAGGAGTTCATGAAG
GCAGAAATGCCTGGGGCCCACGAACATCCCAGTGTGGCCCTGGACGGGACATCATGCTGG
GCAACACAGCTAAAATGCGGGTGAAGACCAGATTTCTTGCACATGGCGGTGACGGGATGC
TCCCTAGAGAGCTTCAAGTGGATTCTTTGCTTTTATTTTCTCTCTTAATAAAAATGTAT
GATGTTTACATTGTCAGAGAACAAACAGAAAAAAAAAAAAAAAAAAAA

FIGURE 32

DNA335924

><subunit 1 of 1, 112 aa, 1 stop
><MW: 12158, pI: 11.55, NX(S/T): 0
MSLGCRPRRALPSVLPFSRDQVASVPGSRPCVPCSLPHLLRTKSGSPAPKSWNPFSASWG
PRPPLPSRPVCLLPWLQGPPHRDQGGIPMGLASRHRARPTVPWASMEVVLCL N-myristoylation site.
amino acids 27-32, 86-91.

FIGURE 33

DNA340394

ATATATCGAT<u>ATG</u>CTGCCGAGGCTGTTGCTGTTGATCTGTGCTCCACTCTGTGAACCTGC
CGAGCTGTTTTTGATAGCCAGCCCCTCCCATCCCACAGAGGGGAGCCCAGTGACCCTGAC
GTGTAAGATGCCCTTTCTACAGAGTTCAGATGCCCAGTTCCAGTTCTGCTTTTTCAGAGA
CACCCGGGCCTTGGGCCCAGGCTGGAGCAGCTCCCCAAGCTCCAGATCGCTGCCATGTG
GAAAGAAGACACAGGGTCATACTGGTGCGAGGCACAGACAATGGCGTCCAAAGTCTTGAG
GAGCAGGAGATCCCAGATAAATGTGCACAGGGTCCCTGTCGCTGATGTGAGCTTGGAGAC
TCAGCCCCAGGAGGACAGGTGATGGAGGGAGACAGGCTGGTCCTCATCTGCTCAGTTGC
TATGGGCACAGGAGACATCACCTTCCTTTGGTACAAAGGGGCTGTAGGTTTAAACCTTCA
GTCAAAGACCCAGCGTTCACTGACAGCAGAGTATGAGATTCCTTCAGTGAGGGAGAGTGA
TGCTGAGCAATATTACTGTGTAGCTGAAAATGGCTATGGTCCCAGCCCCAGTGGGCTGGT
GAGCATCACTGTCAGAATCCCGGTGTCTCGCCCAATCCTCATGCTCAGGGCTCCCAGGGC
CCAGGCTGCAGTGGAGGATGTGCTGGAGCTTCACTGTGAGGCCCTGAGAGGCTCTCCTCC
GATCCTGTACTGGTTTTATCACGAGGATATCACCCTGGGGAGCAGGTCGGCCCCCTCTGG
AGGAGGAGCCTCCTTCAACCTTTCCCTGACTGAAGAACATTCTGGAAACTACTCCTGTGA
GGCCAACAATGGCCTGGGGGCCCAGCGCAGTGAGGCGGTGACACTCAACTTCACAGTGCC
TACTGGGGCCAGAAGCAATCATCTTACCTCAGGAGTCATTGAGGGGCTGCTCAGCACCCT
TGGTCCAGCCACCGTGGCCTTATTATTTTGCTACGGCCTCAAAAGAAAAATAGGAAGACG
TTCAGCCAGGGATCCACTCAGGAGCCTTCCCAGCCCTCTACCCCAAGAGTTCACGTACCT
CAACTCACCTACCCCAGGGCAGCTACAGCCTATATATGAAAATGTGAATGTTGTAAGTGG
GGATGAGGTTTATTCACTGGCGTACTATAACCAGCCGGAGCAGGAATCAGTAGCAGCAGA
AACCCTGGGGACACATATGGAGGACAAGGTTTCCTTAGACATCTATTCCAGGCTGAGGAA
AGCAAACATTACAGATGTGGACTATGAAGATGCTATG<u>TAA</u>GGTTATGGAAGATTCTGCTC
TT

FIGURE 34

DNA340394

><subunit 1 of 1, 429 aa, 1 stop
><MW: 46936, pI: 5.42, NX(S/T): 4
MLPRLLLLICAPLCEPAELFLIASPSHPTEGSPVTLTCKMPFLQSSDAQFQFCFFRDTRA
LGPGWSSSPKLQIAAMWKEDTGSYWCEAQTMASKVLRSRRSQINVHRVPVADVSLETQPP
GGQVMEGDRLVLICSVAMGTGDITFLWYKGAVGLNLQSKTQRSLTAEYEIPSVRESDAEQ
YYCVAENGYGPSPSGLVSITVRIPVSRPILMLRAPRAQAAVEDVLELHCEALRGSPPILY
WFYHEDITLGSRSAPSGGGASFNLSLTEEHSGNYSCEANNGLGAQRSEAVTLNFTVPTGA
RSNHLTSGVIEGLLSTLGPATVALLFCYGLKRKIGRRSARDPLRSLPSPLPQEFTYLNSP
TPGQLQPIYENVNVVSGDEVYSLAYYNQPEQESVAAETLGTHMEDKVSLDIYSRLRKANI
TDVDYEDAM Signal sequence.
amino acids 1-16.

N-glycosylation site.
amino acids 263-266, 273-276, 293-296, 419-422.

Glycosaminoglycan attachment site.
amino acids 256-259.

Protein kinase C phosphorylation site.
amino acids 37-39, 68-70, 98-100, 160-162, 172-174, 200-202, 338-340.

Casein kinase II phosphorylation site.
amino acids 172-175, 176-179, 265-268, 338-341, 376-379, 401-404, 421-424.

Tyrosine kinase phosphorylation site.
amino acids 174-181.

N-myristoylation site.
amino acids 31-36, 82-87, 257-262, 259-264, 272-277, 283-288, 299-304, 308-313, 312-317.

Amidation site.
amino acids 334-337.

Immunoglobulin.
amino acids 31-88, 127-185, 222-278.

FIGURE 35

DNA56041

GATGTGCTCCTTGGAGCTGGTGTGCAGTGTCCTGACTGTAAGATCAAGTCCAAACCTGTT
TTGGAATTGAGGAAACTTCTCTTTTGATCTCAGCCCTTGGTGGTCCAGGTCTTC<u>ATG</u>CTG
CTGTGGGTGATATTACTGGTCCTGGCTCCTGTCAGTGGACAGTTTGCAAGGACACCCAGG
CCCATTATTTTCCTCCAGCCTCCATGGACCACAGTCTTCCAAGGAGAGAGAGTGACCCTC
ACTTGCAAGGGATTTCGCTTCTACTCACCACAGAAAACAAAATGGTACCATCGGTACCTT
GGGAAAGAAATACTAAGAGAAACCCCAGACAATATCCTTGAGGTTCAGGAATCTGGAGAG
TACAGATGCCAGGCCCAGGGCTCCCCTCTCAGTAGCCCTGTGCACTTGGATTTTTCTTCA
GAGATGGGATTTCCTCATGCTGCCCAGGCTAATGTTGAACTCCTGGGCTCAAGTGATCTG
CTCACC<u>TAG</u>GCCTCTCAAAGCGCTGGGATTACAGCTTCGCTGATCCTGCAAGCTCCACTT
TCTGTGTTTGAAGGAGACTCTGTGGTTCTGAGGTGCCGGGCAAAGGCGGAAGTAACACTG
AATAATACTATTTACAAGAATGATAATGTCCTGGCATTCCTTAATAAAAGAACTGACTTC
CAAAAAAAAAAAAAAAAAAAAAAAA

FIGURE 36

DNA56041

><subunit 1 of 1, 124 aa, 1 stop
><MW: 14080, pI: 7.48, NX(S/T): 0
MLLWVILLVLAPVSGQFARTPRPIIFLQPPWTTVFQGERVTLTCKGFRFYSPQKTKWYHR
YLGKEILRETPDNILEVQESGEYRCQAQGSPLSSPVHLDFSSEMGFPHAAQANVELLGSS
DLLT Signal sequence.
amino acids 1-15.

Protein kinase C phosphorylation site.
amino acids 20-22, 43-45.

N-myristoylation site.
amino acids 89-94.

FIGURE 37

DNA59607

GGATTTTTGTGATCCGCGATTCGCTCCCACGGGCGGGACCTTTGTAACTGCGGGAGGCCC
AGGACAGGCCCACCCTGCGGGGCGGGAGGCAGCCGGGGTGAGGGAGGTGAAGAAACCAAG
ACGCAGAGAGGCCAAGCCCCTTGCCTTGGGTCACACAGCCAAAGGAGGCAGAGCCAGAAC
TCACAACCAGATCCAGAGGCAACAGGGACATGGCCACCTGGGACGAAAAGGCAGTCACCC
GCAGGGCCAAGGTGGCTCCCGCTGAGAGGATGAGCAAGTTCTTAAGGCACTTCACGGTCG
TGGGAGACGACTACCATGCCTGGAACATCAACTACAAGAAATGGGAGAATGAAGAGGAGG
AGGAGGAGGAGGAGCAGCCACCACCCACACCAGTCTCAGGCGAGGAAGGCAGAGCTGCAG
CCCCTGACGTTGCCCCTGCCCCTGGCCCCGCACCCAGGGCCCCCCTTGACTTCAGGGGCA
TGTTGAGGAAACTGTTCAGCTCCCACAGGTTTCAGGTCATCATCATCTGCTTGGTGGTTC
TGGATGCCCTCCTGGTGCTTGCTGAGCTCATCCTGGACCTGAAGATCATCCAGCCCGACA
AGAATAACTATGCTGCCATGGTATTCCACTACATGAGCATCACCATCTTGGTCTTTTTTA
TGATGGAGATCATCTTTAAATTATTTGTCTTCCGCCTGAGTTCTTTCACCACAAGTTTGA
GATCCTGGATGCCCGTCGTGGTGGTGGTCTCATTCATCCTGGACATTGTCCTCCTGTTCC
AGGAGCACCAGTTTGAGGCTCTGGGCCTGCTGATTCTGCTCCGGCTGTGGCGGGTGGCCC
GGATCATCAATGGGATTATCATCTCAGTTAAGACACGTTCAGAACGGCAACTCTTAAGGT
TAAAACAGATGAATGTACAATTGGCCGCCAAGATTCAACACCTTGAGTTCAGCTGCTCTG
AGAAGCCCCTGGACTGATGAGTTTGCTGTATCAACCTGTAAGGAGAAGCTCTCTCCGGAT
GGCTATGGGAATGAAAGAATCCGACTTCTACTCTCACACAGCCACCGTGAAAGTCCTGGA
GTAAAATGTGCTGTGTACAGAAGAGAGAGAAGGAAGCAGGCTGGCATGTTCACTGGGCTG
GTGTTACGACAGAGAACCTGACAGTCACTGGCCAGTTATCACTTCAGATTACAAATCACA
CAGAGCATCTGCCTGTTTTCAATCACAAGAGAACAAAACCAAAATCTATAAAGATATTCT
GAAAATATGACAGAATTTGACAAATAAAAGCATAAACGTGTAAAAAAAAAAAAAAAAAAA
AAAAAAAAAAAAAAAAA

FIGURE 38

DNA59607

></usr/seqdb2/sst/DNA/Dnaseqs.min/ss.DNA59607
><subunit 1 of 1, 255 aa, 1 stop
><MW: 29405, pI: 7.64, NX(S/T): 0
MATWDEKAVTRRAKVAPAERMSKFLRHFTVVGDDYHAWNINYKKWENEEEEEEEQPPPT
PVSGEEGRAAAPDVAPAPGPAPRAPLDFRGMLRKLFSSHRFQVIIICLVVLDALLVLAEL
ILDLKIIQPDKNNYAAMVFHYMSITILVFFMMEIIFKLFVFRLSSFTTSLRSWMPVVVVV
SFILDIVLLFQEHQFEALGLLILLRLWRVARIINGIISVKTRSERQLLRLKQMNVQLAA
KIQHLEFSCSEKPLD Transmembrane domain.
amino acids 101-121, 141-161, 168-188, 195-215.

Protein kinase C phosphorylation site.
amino acids 20-22, 43-45.

N-myristoylation site.
amino acids 89-94.

FIGURE 39A

DNA257955

AGTGAAGGGGTTTCCCATATGAAAAATACAGAAAGAATTATTTGAATACTAGCAAATACA
CAACTTGATATTTCTAGAGAACCCAGGCACAGTCTTGGAGACATTACTCCTGAGAGACTG
CAGCTGATGGAAGATGAGCCCCAACTTCTAAAAATGTATCACTACCGGGATTGAGATACA
AACAGCATTTAGGAAGGTCTCATCTGAGTAGCAGCTTCCTGCCCTCCTTCTTGGAGATAA
GTCGGGCTTTTGGTGAGACAGACTTTCCCAACCCTCTGCCCGGCCGGTGCCCATGCTTCT
GTGGCTGCTGCTGCTGATCCTGACTCCTGGAAGAGAACAATCAGGGGTGGCCCCAAAAGC
TGTACTTCTCCTCAATCCTCCATGGTCCACAGCCTTCAAAGGAGAAAAAGTGGCTCTCAT
ATGCAGCAGCATATCACATTCCCTAGCCCAGGGAGACACATATTGGTATCACGATGAGAA
GTTGTTGAAAATAAAACATGACAAGATCCAAATTACAGAGCCTGGAAATTACCAATGTAA
GACCCGAGGATCCTCCCTCAGTGATGCCGTGCATGTGGAATTTTCACCTGACTGGCTGAT
CCTGCAGGCTTTACATCCTGTCTTTGAAGGAGACAATGTCATTCTGAGATGTCAGGGGAA
AGACAACAAAAACACTCATCAAAAGGTTTACTACAAGGATGGAAAACAGCTTCCTAATAG
TTATAATTTAGAGAAGATCACAGTGAATTCAGTCTCCAGGGATAATAGCAAATATCATTG
TACTGCTTATAGGAAGTTTTACATACTTGACATTGAAGTAACTTCAAAACCCCTAAATAT
CCAAGTTCAAGAGCTGTTTCTACATCCTGTGCTGAGAGCCAGCTCTTCCACGCCCATAGA
GGGGAGTCCCATGACCCTGACCTGTGAGACCCAGCTCTCTCCACAGAGGCCAGATGTCCA
GCTGCAATTCTCCCTCTTCAGAGATAGCCAGACCCTCGGATTGGGCTGGAGCAGGTCCCC
CAGACTCCAGATCCCTGCCATGTGGACTGAAGACTCAGGGTCTTACTGGTGTGAGGTGGA
GACAGTGACTCACAGCATCAAAAAAGGAGCCTGAGATCTCAGATACGTGTACAGAGAGT
CCCTGTGTCTAATGTGAATCTAGAGATCCGGCCCACCGGAGGGCAGCTGATTGAAGGAGA
AAATATGGTCCTTATTTGCTCAGTAGCCCAGGGTTCAGGGACTGTCACATTCTCCTGGCA
CAAAGAAGGAAGAGTAAGAAGCCTGGGTAGAAAGACCCAGCGTTCCCTGTTGGCAGAGCT
GCATGTTCTCACCGTGAAGGAGAGTGATGCAGGGAGATACTACTGTGCAGCTGATAACGT
TCACAGCCCCATCCTCAGCACGTGGATTCGAGTCACCGTGAGAATTCCGGTATCTCACCC
TGTCCTCACCTTCAGGGCTCCCAGGGCCCACACTGTGGTGGGGGACCTGCTGGAGCTTCA
CTGTGAGTCCCTGAGAGGCTCTCCCCCGATCCTGTACCGATTTTATCATGAGGATGTCAC
CCTGGGGAACAGCTCAGCCCCCTCTGGAGGAGGAGCCTCCTTCAACCTCTCTCTGACTGC
AGAACATTCTGGAAACTACTCCTGTGATGCAGACAATGGCCTGGGGGCCCAGCACAGTCA
TGGAGTGAGTCTCAGGGTCACAGTTCCGGTGTCTCGCCCCGTCCTCACCCTCAGGGCTCC
CGGGGCCCAGGCTGTGGTGGGGGACCTGCTGGAGCTTCACTGTGAGTCCCTGAGAGGCTC
CTTCCCGATCCTGTACTGGTTTTATCACGAGGATGACACCTTGGGGAACATCTCGGCCCA
CTCTGGAGGAGGGGCATCCTTCAACCTCTCTCTGACTACAGAACATTCTGGAAACTACTC
ATGTGAGGCTGACAATGGCCTGGGGGCCCAGCACAGTAAAGTGGTGACACTCAATGTTAC
AGGAACTTCCAGGAACAGAACAGGCCTTACCGCTGCGGGAATCACGGGGCTGGTGCTCAG
CATCCTCGTCCTTGCTGCTGCTGCTGCTCTGCTGCATTACGCCAGGGCCCGAAGGAAACC
AGGAGGACTTTCTGCCACTGGAACATCTAGTCACAGTCCTAGTGAGTGTCAGGAGCCTTC
CTCGTCCAGGCCTTCCAGGATAGACCCTCAAGAGCCCACTCACTCTAAACCACTAGCCCC
AATGGAGCTGGAGCCAATGTACAGCAATGTAAATCCTGGAGATAGCAACCCGATTTATTC
CCAGATCTGGAGCATCCAGCATACAAAAGAAAACTCAGCTAATTGTCCAATGATGCATCA
AGAGCATGAGGAACTTACAGTCCTCTATTCAGAACTGAAGAAGACACACCCAGACGACTC
TGCAGGGGAGGCTAGCAGCAGAGGCAGGGCCCATGAAGAAGATGATGAAGAAAACTATGA
GAATGTACCACGTGTATTACTGGCCTCAGACCACTAGCCCCTTACCCAGAGTGGCCCACA
GGAAACAGCCTGCACCATTTTTTTTTCTGTTCTCTCCAACCACACATCATCCATCTCTCC
AGACTCTGCCTCCTACGAGGCTGGGCTGCAGGGTATGTGAGGCTGAGCAAAAGGTCTGCA

FIGURE 39B

AATCTCCCCTGTGCCTGATCTGTGTGTTCCCCAGGAAGAGAGCAGGCAGCCTCTGAGCAA
GCACTGTGTTATTTTCACAGTGGAGACACGTGGCAAGGCAGGAGGGCCCTCAGCTCCTAG
GGCTGTCGAATAGAGGAGGAGAGAGAAATGGTCTAGCCAGGGTTACAAGGGCACAATCAT
GACCATTTGATCCAAGTGTGATCGAAAGCTGTTAATGTGCTCTCTGTATAAACAATTTGC
TCCAAATATTTTGTTTCCCTTTTTTGTGTGGCTGGTAGTGGCATTGCTGATGTTTTGGTG
TATATGCTGTATCCTTGCTACCATATTGGG

FIGURE 40A

DNA257955

><subunit 1 of 1, 734 aa, 1 stop
><MW: 80856, pI: 6.97, NX(S/T): 8
MLLWLLLLILTPGREQSGVAPKAVLLLNPPWSTAFKGEKVALICSSISHSLAQGDTYWYH
DEKLLKIKHDKIQITEPGNYQCKTRGSSLSDAVHVEFSPDWLILQALHPVFEGDNVILRC
QGKDNKNTHQKVYYKDGKQLPNSYNLEKITVNSVSRDNSKYHCTAYRKFYILDIEVTSKP
LNIQVQELFLHPVLRASSSTPIEGSPMTLTCETQLSPQRPDVQLQFSLFRDSQTLGLGWS
RSPRLQIPAMWTEDSGSYWCEVETVTHSIKKRSLRSQIRVQRVPVSNVNLEIRPTGGQLI
EGENMVLICSVAQGSGTVTFSWHKEGRVRSLGRKTQRSLLAELHVLTVKESDAGRYYCAA
DNVHSPILSTWIRVTVRIPVSHPVLTFRAPRAHTVVGDLLELHCESLRGSPPILYRFYHE
DVTLGNSSAPSGGGASFNLSLTAEHSGNYSCDADNGLGAQHSHGVSLRVTVPVSRPVLTL
RAPGAQAVVGDLLELHCESLRGSFPILYWFYHEDDTLGNISAHSGGGASFNLSLTTEHSG
NYSCEADNGLGAQHSKVVTLNVTGTSRNRTGLTAAGITGLVLSILVLAAAAALLHYARAR
RKPGGLSATGTSSHSPSECQEPSSSRPSRIDPQEPTHSKPLAPMELEPMYSNVNPGDSNP
IYSQIWSIQHTKENSANCPMMHQEHEELTVLYSELKKTHPDDSAGEASSRGRAHEEDDEE
NYENVPRVLLASDH Signal sequence.
amino acids 1-13.

Transmembrane domain.
amino acids 574-594.

N-glycosylation site.
amino acids 426-429, 438-441, 448-451, 519-522, 531-534, 541-544, 561-564, 568-571.

Glycosaminoglycan attachment site.
amino acids 431-434, 524-527.

cAMP- and cGMP-dependent protein kinase phosphorylation site.
amino acids 270-273.

Protein kinase C phosphorylation site.
amino acids 177-179, 242-244, 268-270, 273-275, 335-337, 347-349, 375-377, 386-388, 406-408, 466-468, 479-481, 499-501, 565-567, 624-626, 708-710.

Casein kinase II phosphorylation site.
amino acids 88-91, 200-203, 347-350, 615-618, 628-631, 698-701, 703-706.

Tyrosine kinase phosphorylation site.
amino acids 349-356.

FIGURE 40B

N-myristoylation site.
amino acids 78-83, 86-91, 204-209, 236-241, 256-261, 432-437, 434-439, 447-452, 458-463, 518-523, 525-530, 527-532, 540-545, 551-556, 564-569, 571-576, 579-584, 604-609, 605-610.

Amidation site.
amino acids 331-334.

N-6 Adenine-specific DNA methylases signature.
amino acids 25-31.

Immunoglobulin domain.
amino acids 37-84, 113-165, 204-262, 302-360, 397-453, 490-546.

FIGURE 41A

DNA329863

CTCAATCAGCTTTATGCAGAGAAGAAGCTTACTGAGCTCACTGCTGGTGCTGGTGTAGGC
AAGTGCTGCTTTGGCAATCTGGGCTGACCTGGCTTGTCTCCTCAGAACTCCTTCTCCAAC
CCTGGAGCAGGCTTCC<u>ATG</u>CTGCTGTGGGCGTCCTTGCTGGCCTTTGCTCCAGTCTGTGG
ACAATCTGCAGCTGCACACAAACCTGTGATTTCCGTCCATCCTCCATGGACCACATTCTT
CAAAGGAGAGAGAGTGACTCTGACTTGCAATGGATTTCAGTTCTATGCAACAGAGAAAAC
AACATGGTATCATCGGCACTACTGGGGAGAAAAGTTGACCCTGACCCCAGGAAACACCCT
CGAGGTTCGGGAATCTGGACTGTACAGATGCCAGGCCCGGGGCTCCCCACGAAGTAACCC
TGTGCGCTTGCTCTTTTCTTCAGACTCCTTAATCCTGCAGGCACCATATTCTGTGTTTGA
AGGTGACACATTGGTTCTGAGATGCCACAGAAGAAGGAAAGAGAAATTGACTGCTGTGAA
ATATACTTGGAATGGAAACATTCTTTCCATTTCTAATAAAAGCTGGGATCTTCTTATCCC
ACAAGCAAGTTCAAATAACAATGGCAATTATCGATGCATTGGATATGGAGATGAGAATGA
TGTATTTAGATCAAATTTCAAAATAATTAAAATTCAAGAACTATTTCCACATCCAGAGCT
GAAAGCTACAGACTCTCAGCCTACAGAGGGGAATTCTGTAAACCTGAGCTGTGAAACACA
GCTTCCTCCAGAGCGGTCAGACACCCCACTTCACTTCAACTTCTTCAGAGATGGCGAGGT
CATCCTGTCAGACTGGAGCACGTACCCGGAACTCCAGCTCCCAACCGTCTGGAGAGAAAA
CTCAGGATCCTATTGGTGTGGTGCTGAAACAGTGAGGGGTAACATCCACAAGCACAGTCC
CTCGCTACAGATCCATGTGCAGCGGATCCCTGTGTCTGGGGTGCTCCTGGAGACCCAGCC
CTCAGGGGCCAGGCTGTTGAAGGGGAGATGCTGGTCCTTGTCTGCTCCGTGGCTGAAGG
CACAGGGGATACCACATTCTCCTGGCACCGAGAGGACATGCAGGAGAGTCTGGGGAGGAA
AACTCAGCGTTCCCTGAGAGCAGAGCTGGAGCTCCCTGCCATCAGACAGAGCCATGCAGG
GGGATACTACTGTACAGCAGACAACAGCTACGGCCCTGTCCAGAGCATGGTGCTGAATGT
CACTGTGAGAGAGACCCCAGGCAACAGAGATGGCCTTGTCGCCGCGGGAGCCACTGGAGG
GCTGCTCAGTGCTCTTCTCCTGGCTGTGGCCCTGCTGTTTCACTGCTGGCGTCGGAGGAA
GTCAGGAGTTGGTTTCTTGGGAGACGAAACCAGGCTCCCTCCCGCTCCAGGCCCAGGAGA
GTCCTCCCATTCCATCTGCCCTGCCCAGGTGGAGCTTCAGTCGTTGTATGTTGATGTACA
CCCCAAAAAGGGAGATTTGGTATACTCTGAGATCCAGACTACTCAGCTGGGAGAAGAAGA
GGAAGCTAATACCTCCAGGACACTTCTAGAGGATAAGGATGTCTCAGTTGTCTACTCTGA
GGTAAAGACACAACACCCAGATAACTCAGCTGGAAAGATCAGCTCTAAGGATGAAGAAAG
T<u>TAA</u>GAGAATGAAAAGTTACGGGAACGTCCTACTCATGTGATTTCTCCCTTGTCCAAAGT
CCCAGGCCCAGTGCAGTCCTTGCGGCACCTGGAATGATCAACTCATTCCAGCTTTCTAAT
TCTTCTCATGCATATGCATTCACTCCCAGGAATACTCATTCGTCTACTCTGATGTTGGGA
TGGAATGGCCTCTGAAAGACTTCACTAAAATGACCAGGATCCACAGTTAAGAGAAGACCC
TGTAGTATTTGCTGTGGGCCTGACCTAATGCATTCCCTAGGGTCTGCTTTAGAGAAGGGG
GATAAAGAGAGAGAAGGACTGTTATGAAAAACAGAAGCACAAATTTTGGTGAATTGGGAT
TTGCAGAGATGAAAAGACTGGGTGACCTGGATCTCTGCTTAATACATCTACAACCATTG
TCTCACTGGAGACTCACTTGCATCAGTTTGTTTAACTGTGAGTGGCTGCACAGGCACTGT
GCAAACAATGAAAAGCCCCTTCACTTCTGCCTGCACAGCTTACACTGTCAGGATTCAGTT
GCAGATTAAAGAACCCATCTGGAATGGTTTACAGAGAGAGGAATTTAAAAGAGGACATCA
GAAGAGCTGGAGATGCAAGCTCTAGGCTGCGCTTCCAAAAGCAAATGATAATTATGTTAA
TGTCATTAGTGACAAAGATTTGCAACATTAGAGAAAAGAGACACAAATATAAAATTAAAA
ACTTAAGTACCAACTCTCCAAAACTAAATTTGAACTTAAAATATTAGTATAAACTCATAA
TAAACTCTGCCTTTAAAAAAAGATAAATATTTCCTACGTCTGTTCACTGAAATAATTACC
AACCCCTTAGCAATAAGCACTCCTTGCAGAGAGGTTTTATTCTCTAAATACCATTCCCTT

FIGURE 41B

```
CTCAAAGGAAATAAGGTTGCTTTTCTTGTAGGAACTGTGTCTTTGAGTTACTAATTAGTT
TATATGAGAATAATTCTTGCAATAAATGAAGAAGGAATAAAAGAAATAGGAAGCCACAAA
TTTGTATGGATATTTCATGATACACCTACTGGTTAAATAATTGACAAAAACCAGCAGCCA
AATATTAGAGGTCTCCTGATGGAAGTGTACAATACCACCTACAAATTATCCATGCCCCAA
GTGTTAAAACTGAATCCATTCAAGTCTTTCTAACTGAATACTTGTTTTATAGAAAATGCA
TGGAGAAAAGGAATTTGTTTAAATAACATTATGGATTGCAACCAGCAAAACATAAACTG
AGAAAAAGTTCTATAGGGCAAATCACCTGGCTTCTATAACAAATAAATGGGAAAAAAATG
AAATAAAAGAAGAGAGGGAGGAAGAAAGGGAGAGAGAAGAAAAGAAAAATGAAGAAAAG
TAATTAGAATATTTTCAACATAAAGAAAAGACGAATATTTAAGGTGACAGATATCCCAAC
TACGCTGATTTGATCTTTACAAATTATATGAGTGTATGAATTTGTCACATGTATCACCCC
CAAAAAAAGAGAAAAAGAAAAATAGAAGACATATAAATTAAATGAGACGAGACATGTCGA
CCAAAAGGAATGTGTGGGTCTTGTTTGGATCCTGACTCAAATTAAGAAAAAATAAAACTA
CCTACGAAATACTAAGAAAAATTTGTATACTAATATTAAGAAATTGTTGTGTGTTTTGGA
TATAAGTGATAGTTTATTGTAGTGATGTTTTTATAAAAGCAAAAGGATATTCACTTTCAG
CGCTTATACTGAAGTATTAGATTAAAGCTTATTAACGTA
```

FIGURE 42A

DNA329863

><subunit 1 of 1, 515 aa, 1 stop
><MW: 57224, pI: 6.45, NX(S/T): 4
MLLWASLLAFAPVCGQSAAAHKPVISVHPPWTTFFKGERVTLTCNGFQFYATEKTTWYHR
HYWGEKLTLTPGNTLEVRESGLYRCQARGSPRSNPVRLLFSSDSLILQAPYSVFEGDTLV
LRCHRRRKEKLTAVKYTWNGNILSISNKSWDLLIPQASSNNNGNYRCIGYGDENDVFRSN
FKIIKIQELFPHPELKATDSQPTEGNSVNLSCETQLPPERSDTPLHPNFFRDGEVILSDW
STYPELQLPTVWRENSGSYWCGAETVRGNIHKHSPSLQIHVQRIPVSGVLLETQPSGGQA
VEGEMLVLVCSVAEGTGDTTFSWHREDMQESLGRKTQRSLRAELELPAIRQSHAGGYYCT
ADNSYGPVQSMVLNVTVRETPGNRDGLVAAGATGGLLSALLLAVALLFHCWRRRKSGVGF
LGDETRLPPAPGPGESSHSICPAQVELQSLYVDVHPKKGDLVYSEIQTTQLGEEEEANTS
RTLLEDKDVSVVYSEVKTQHPDNSAGKISSKDEES Signal Sequence.
amino acids 1-16.

Transmembrane domain.
amino acids 387-407.

N-glycosylation site.
amino acids 147-150, 209-212, 374-377, 478-481.

Glycosaminoglycan attachment site.
amino acids 416-419.

cAMP- and cGMP-dependent protein kinase phosphorylation site.
amino acids 413-416.

Protein kinase C phosphorylation site.
amino acids 52-54, 90-92, 146-148, 265-267, 336-338, 339-341, 376-378, 479-481, 509-511.

Casein kinase II phosphorylation site.
amino acids 112-115, 242-245, 311-314, 376-379, 482-485, 509-512, 510-513.

Tyrosine kinase phosphorylation site.
amino acids 457-463.

N-myristoylation site.
amino acids 15-20, 81-86, 89-94, 140-145, 163-168, 205-210, 257-262, 315-320, 355-360, 382-387, 386-391, 391-396, 394-399, 395-400.

Amidation site.
amino acids 332-335.

FIGURE 42B

Immunoglobulin domain.
amino acids 37-87, 116-169, 205-263, 303-361.

FIGURE 43

DNA346528

ACACACCCACAGGACCTGCAGCTGAACGAAGTTGAAGACAACTCAGGAGATCTGTTGGAA
AGAGAACGATAGAGGAAAATATATGA<u>ATG</u>TTGCCATCTTTAGTTCCCTGTGTTGGGAAAA
CTGTCTGGCTGTACCTCCAAGCCTGGCCAAACCCTGTGTTTGAAGGAGATGCCCTGACTC
TGCGATGTCAGGGATGGAAGAATACACCACTGTCTCAGGTGAAGTTCTACAGAGATGGAA
AATTCCTTCATTTCTCTAAGGAAAACCAGACTCTGTCCATGGGAGCAGCAACAGTGCAGA
GCCGTGGCCAGTACAGCTGCTCTGGGCAGGTGATGTATATTCCACAGACATTCACACAAA
CTTCAGAGACTGCCATGGTTCAAGTCCAAGAGCTGTTTCCACCTCCTGTGCTGAGTGCCA
TCCCCTCTCCTGAGCCCCGAGAGGGTAGCCTGGTGACCCTGAGATGTCAGACAAAGCTGC
ACCCCCTGAGGTCAGCCTTGAGGCTCCTTTTCTCCTTCCACAAGGACGGCCACACCTTGC
AGGACAGGGGCCCTCACCCAGAACTCTGCATCCCGGGAGCCAAGGAGGGAGACTCTGGGC
TTTACTGGTGTGAGGTGGCCCCTGAGGGTGGCCAGGTCCAGAAGCAGAGCCCCCAGCTGG
AGGTCAGAGTGCAGGCTCCTGTATCCCGTCCTGTGCTCACTCTGCACCACGGGCCTGCTG
ACCCTGCTGTGGGGACATGGTGCAGCTCCTCTGTGAGGCACAGAGGGGCTCCCCTCCGA
TCCTGTATTCCTTCTACCTTGATGAGAAGATTGTGGGGAACCACTCAGCTCCCTGTGGTG
GAACCACCTCCCTCCTCTTCCCAGTGAAGTCAGAACAGGATGCTGGGAACTACTCCTGCG
AGGCTGAGAACAGTGTCTCCAGAGAGAGGAGTGAGCCCAAGAAGCTGTCTCTGAAGGGTT
CTCAAGTCTTGTTCACTCCCGCCAGCAACTGGCTGGTTCCTTGGCTTCCTGCGAGCCTGC
TTGGCCTGATGGTTATTGCTGCTGCACTTCTGGTTTATGTGAGATCCTGGAGAAAAGCTG
GGCCCCTTCCATCCCAGATACCACCCACAGCTCCAGGTGGAGAGCAGTGCCCACTATATG
CCAACGTGCATCACCAGAAAGGGAAAGATGAAGGTGTTGTCTACTCTGTGGTGCATAGAA
CCTCAAAGAGGAGTGAAGGACAGTTCTATCATCTGTGCGGAGGTGAGATGCCTGCAGCCC
AG<u>TGA</u>GGTTTCATCCACGGAGGTGAATATGAGAAGCAGGACTCTCCAAGAACCCCTTAGC
GACTGTGAGGAGGTTCTCTGCTAGTGATGGTGTTCTCCTATCAACACACGCCCACCCCCA
GTCTCCAGTGCTCCTCAGGAAGACAGTGGGGTCCTCAACTCTTTCTGTGGGTCCTTCAGT
TCCCAAGCCCAGCATCACAGAGCCCCCTGAGCCCTTGTCCTGGTCAGGAGCACCTGAACC
CTGGGTTCTTTTCTTAGCAGAAGACCAACCAATGGAATGGGAAGGGAGATGCTCCCACCA
ACACACACACTTAGGTTCAATCAGTGACACTGGACACATAAGCCACAGATGTCTTCTTTC
CATACAAGCATGTTAGTTCGCCCCAATATACATATATATATGAAATAGTCATGTGCCGCA
TAACAACATTTCAGTCAGTGATAGACTGCATACACAACAGTGGTCCCATAAGACTGTAAT
GGAGTTTAAAAATTCCTACTGCCTAGTGATATCATAGTTGCCTTAACATCATAACACAAC
ACATTTCTCACGCGTTTGTGGTGATGCTGGTACAAACAAGCTACAGCGCCGCTAGTCATA
TACAAATATAGCACATACAATTATGTACAGTACACTATACTTGATAATGATAATAAACAA
CTATGTTACTGGT

FIGURE 44

DNA346528

><subunit 1 of 1, 392 aa, 1 stop
><MW: 42948, pI: 8.37, NX(S/T): 3
MLPSLVPCVGKTVWLYLQAWPNPVFEGDALTLRCQGWKNTPLSQVKFYRDGKFLHFSKEN
QTLSMGAATVQSRGQYSCSGQVMYIPQTFTQTSETAMVQVQELFPPPVLSAIPSPEPREG
SLVTLRCQTKLHPLRSALRLLFSFHKDGHTLQDRGPHPELCIPGAKEGDSGLYWCEVAPE
GGQVQKQSPQLEVRVQAPVSRPVLTLHHGPADPAVGDMVQLLCEAQRGSPPILYSFYLDE
KIVGNHSAPCGGTTSLLFPVKSEQDAGNYSCEAENSVSRERSEPKKLSLKGSQVLFTPAS
NWLVPWLPASLLGLMVIAAALLVYVRSWRKAGPLPSQIPPTAPGGEQCPLYANVHHQKGK
DEGVVYSVVHRTSKRSEGQFYHLCGGEMPAAQ Transmembrane domain.
amino acids 302-322.

N-glycosylation site.
amino acids 60-63, 245-248, 268-271.

cAMP- and cGMP-dependent protein kinase phosphorylation site.
amino acids 285-288.

Protein kinase C phosphorylation site.
amino acids 31-33, 124-126, 288-290, 327-329, 372-374, 373-375.

Casein kinase II phosphorylation site.
amino acids 150-153, 262-265.

Tyrosine kinase phosphorylation site.
amino acids 166-173, 261-269, 358-366, 374-381.

N-myristoylation site.
amino acids 74-79, 120-125, 164-169, 171-176, 251-256, 267-272, 363-368.

Immunoglobulin domain.
amino acids 27-80, 120-177, 216-273.

FIGURE 45

DNA212930

CCATTGTTCTCAACATTCTAGCTGCTCTTGCTGCATTTGCTCTGGAATTCTTGTAGAGAT
ATTACTTGTCCTTCCAGGCTGTTCTTTCTGTAGCTCCCTTGTTTTCTTTTTGTGATCATG
TTGCAGATGGCTGGGCAGTGCTCCCAAAATGAATATTTTGACAGTTTGTTGCATGCTTGC
ATACCTTGTCAACTTCGATGTTCTTCTAATACTCCTCCTCTAACATGTCAGCGTTATTGT
AATGCAAGTGTGACCAATTCAGTGAAAGGAACGAATGCGATTCTCTGGACCTGTTTGGGA
CTGAGCTTAATAATTTCTTTGGCAGTTTTCGTGCTAATGTTTTGCTAAGGAAGATAAGC
TCTGAACCATTAAAGGACGAGTTTAAAAACACAGGATCAGGTCTCCTGGGCATGGCTAAC
ATTGACCTGGAAAAGAGCAGGACTGGTGATGAAATTATTCTTCCGAGAGGCCTCGAGTAC
ACGGTGGAAGAATGCACCTGTGAAGACTGCATCAAGAGCAAACCGAAGGTCGACTCTGAC
CATTGCTTTCCACTCCCAGCTATGGAGGAAGGCGCAACCATTCTTGTCACCACGAAAACG
AATGACTATTGCAAGAGCCTGCCAGCTGCTTTGAGTGCTACGGAGATAGAGAAATCAATT
TCTGCTAGGTAATTAACCATTTCGACTCGAGCAGTGCCACTTTAAAAATCTTTTGTCAGA
ATAGATGATGTGTCAGATCTCTTTAGGATGACTGTATTTTTCAGTTGCCGATACAGCTTT
TTGTCCTCTAACTGTGGAAACTCTTTATGTTAGATATATTTCTCTAGGTTACTGTTGGGA
GCTTAATGGTAGAAACTTCCTTGGTTTCATGATTAAAGTCTTTTTTTTTCCTGAAAAAAA

FIGURE 46

DNA212930

></usr/seqdb2/sst/DNA/Dnaseqs.min/ss.DNA212930
><subunit 1 of 1, 184 aa, 1 stop
><MW: 20138, pI: 5.30, NX(S/T): 1
MLQMAGQCSQNEYFDSLLHACIPCQLRCSSNTPPLTCQRYCNASVTNSVKGTNAILWTCL
GLSLIISLAVFVLMFLLRKISSEPLKDEFKNTGSGLLGMANIDLEKSRTGDEIILPRGLE
YTVEECTCEDCIKSKPKVDSDHCFPLPAMEEGATILVTTKTNDYCKSLPAALSATEIEKS
ISAR Signal sequence.
amino acids 1-28.

Transmembrane domain.
amino acids 55-75.

N-glycosylation site.
amino acids 42-45.

cAMP- and cGMP-dependent protein kinase phosphorylation site.
amino acids 78-81.

Protein kinase C phosphorylation site.
amino acids 48-50, 158-160, 182-184.

Casein kinase II phosphorylation site.
 amino acids 9-12, 109-112, 122-125, 127-130, 173-176, 175-178.

N-myristoylation site.
amino acids 118-123.

FIGURE 47

DNA335918

CTTCCCAGCCTTCGGAACTATGGAGCCCGCACTCTCCAGTTCATCACCACCCCAGCATCC
CTACTCTTGCATCTAACAGTTTCCGCTATTTTGCACCACCTGCCTNGNCCTTATGGGCAA
CTCAAGGAAGAAAGGAAAGAAGAGATAGAGGAAAAATGGATTCAACANATGAAAGTGTTC
TTTCTGACTACTGCTGTGTTTACAAACATTTTAATCATCAAAACATGCTTTATTTGATAG
AAAGATCAAATCTGCCTTTGTAAAACAAGAGACTATTTTAATCATTAAGACAACACANAT
GTTTGATTTGGAGGCGTGTTCTCATTCAAAACCTTGC

FIGURE 48

DNA225820

GGAGAGTCTGACCACCATGCCACCTCCTCGCCTCCTCTTCTTCCTCCTCTTCCTCACCCC
CATGGAAGTCAGGCCCGAGGAACCTCTAGTGGTGAAGGTGGAAGAGGGAGATAACGCTGT
GCTGCAGTGCCTCAAGGGGACCTCAGATGGCCCCACTCAGCAGCTGACCTGGTCTCGGGA
GTCCCCGCTTAAACCCTTCTTAAAACTCAGCCTGGGGCTGCCAGGCCTGGGAATCCACAT
GAGGCCCCTGGCCATCTGGCTTTTCATCTTCAACGTCTCTCAACAGATGGGGGCTTCTA
CCTGTGCCAGCCGGGGCCCCCCTCTGAGAAGGCCTGGCAGCCTGGCTGGACAGTCAATGT
GGAGGGCAGCGGGGAGCTGTTCCGGTGGAATGTTTCGGACCTAGGTGGCCTGGGCTGTGG
CCTGAAGAACAGGTCCTCAGAGGGCCCCAGCTCCCCTTCCGGGAAGCTCATGAGCCCCAA
GCTGTATGTGTGGGCCAAAGACCGCCCTGAGATCTGGGAGGGAGAGCCTCCGTGTGTCCC
ACCGAGGGACAGCCTGAACCAGAGCCTCAGCCAGGACCTCACCATGGCCCCTGGCTCCAC
ACTCTGGCTGTCCTGTGGGGTACCCCCTGACTCTGTGTCCAGGGGCCCCCTCTCCTGGAC
CCATGTGCACCCCAAGGGGCCTAAGTCATTGCTGAGCCTAGAGCTGAAGGACGATCGCCC
GGCCAGAGATATGTGGGTAATGGAGACGGGTCTGTTGTTGCCCCGGGCCACAGCTCAAGA
CGCTGGAAAGTATTATTGTCACCGTGGCAACCTGACCATGTCATTCCACCTGGAGATCAC
TGCTCGGCCAGTACTATGGCACTGGCTGCTGAGGACTGGTGGCTGGAAGGTCTCAGCTGT
GACTTTGGCTTATCTGATCTTCTGCCTGTGTTCCCTTGTGGGCATTCTTCATCTTCAAAG
AGCCCTGGTCCTGAGGAGGAAAAGAAAGCGAATGACTGACCCCACCAGGAGATTCTTCAA
AGTGACGCCTCCCCCAGGAAGCGGGCCCCAGAACCAGTACGGGAACGTGCTGTCTCTCCC
CACACCCACCTCAGGCCTCGGACGCGCCCAGCGTTGGGCCGCAGGCCTGGGGGCACTGC
CCCGTCTTATGGAAACCCGAGCAGCGACGTCCAGGCGGATGGAGCCTTGGGGTCCCGGAG
CCGCCGGGAGTGGGCCCAGAAGAAGAGGAAGGGAGGGCTATGAGGAACCTGACAGTGAG
GAGGACTCCGAGTTCTATGAGAACGACTCCAACCTTGGGCAGGACCAGCTCTCCCAGGAT
GGCAGCGGCTACGAGAACCCTGAGGATGAGCCCCTGGGTCCTGAGGATGAAGACTCCTTC
TCCAACGCTGAGTCTTATGAGAACGAGGATGAAGAGCTGACCCAGCCGGTCGCCAGGACA
ATGGACTTCCTGAGCCCTCATGGGTCAGCCTGGGACCCCAGCCGGGAAGCAACCTCCCTG
GGGTCCCAGTCCTATGAGGATATGAGAGGAATCCTGTATGCAGCCCCCAGCTCCGCTCC
ATTCGGGGCCAGCCTGGACCCAATCATGAGGAAGATGCAGACTCTTATGAGAACATGGAT
AATCCCGATGGGCCAGACCCAGCCTGGGGAGGAGGGGCCGCATGGGCACCTGGAGCACC
AGGTGATCCTCAGGTGGCCAGCCTGGATCTCCTCAAGTCCCAAGATTCACACCTGACTC
TGAAATCTGAAGACCTCGAGCAGATGATGCCAACCTCTGGAGCAATGTTGCTTAGGATGT
GTGCATGTGTGTAAGTGTGTGTGTGTGTGTGTGTGTGTGTGTGTATACATGCCAGT
GACACTTCCAGTCCCCTTTGTATTCCTTAAATAAACTCAATGAGCTCTTCCAAAAAAAAA
AA

FIGURE 49A

DNA225820

```
></usr/seqdb2/sst/DNA/Dnaseqs.min/ss.DNA225820
><subunit 1 of 1, 467 aa, 1 stop
><MW: 51818, pI: 10.69, NX(S/T): 7
```

MPPPRLLFFLLFLTPMEVRPEEPLVVKVEEGDNAVLQCLKGTSDGPTQQLTWSRESPLKP
FLKLSLGLPGLGIHMRPLAIWLFIFNVSQQMGGFYLCQPGPPSEKAWQPGWTVNVEGSGE
LFRWNVSDLGGLGCGLKNRSSEGPSSPSGKLMSPKLYVWAKDRPEIWEGEPPCVPPRDSL
NQSLSQDLTMAPGSTLWLSCGVPPDSVSRGPLSWTHVHPKGPKSLLSLELKDDRPARDMW
VMETGLLLPRATAQDAGKYYCHRGNLTMSFHLEITARPVLWHWLLRTGGWKVSAVTLAYL
IFCLCSLVGILHLQRALVLRRKRKRMTDPTRRFFKVTPPPGSGPQNQYGNVLSLPTPTSG
LGRAQRWAAGLGGTAPSYGNPSSDVQADGALGSRSRREWAQKKRKGRAMRNLTVRRTPSS
MRTTPTLGRTSSPRMAAATRTLRMSPWVLRMKTPSPTLSLMRTRMKS

Signal Sequence.
Amino acids 1-20.

Transmembrane Domain.
Amino acids 294-314.

Immunoglobulin Domain.
Amino acids 31-99, 193-263.

N-glycosylation Site.
Amino acids 86-89, 125-128, 138-141, 181-184, 265-268, 411-414.

Glycosaminoglycan attachment site.
Amino acids 359-362.

cAMP- and cGMP-dependent protein kinase phosphorylation site.
Amino acids 324-327.

Protein kinase C phosphorylation site.
Amino acids 103-105, 148-150, 153-155, 275-277, 330-332, 395-397, 413-415, 420-422, 432-434, 441-443.

Casein kinase II phosphorylation site.
Amino acids 14-17, 252-255, 395-398.

Figure 49B

N-myristoylation Site.
Amino acids 130-135, 131-136, 349-354, 360-365, 370-375, 373-378, 379-384, 389-394.

Prokaryotic membrane lipoprotein lipid attachment site.
Amino aicds 190-200.

FIGURE 50A

DNA88116

CCATCCCATAGTGAGGGAAGACACGCGGAAACAGGCTTGCACCCAGACACGACACC<u>ATG</u>C
ATCTCCTCGGCCCCTGGCTCCTGCTCCTGGTTCTAGAATACTTGGCTTTCTCTGACTCAA
GTAAATGGGTTTTTGAGCACCCTGAAACCCTCTACGCCTGGGAGGGGGCCTGCGTCTGGA
TCCCCTGCACCTACAGAGCCCTAGATGGTGACCTGGAAAGCTTCATCCTGTTCCACAATC
CTGAGTATAACAAGAACACCTCGAAGTTTGATGGGACAAGACTCTATGAAAGCACAAAGG
ATGGGAAGGTTCCTTCTGAGCAGAAAAGGGTGCAATTCCTGGGAGACAAGAATAAGAACT
GCACACTGAGTATCCACCCGGTGCACCTCAATGACAGTGGTCAGCTGGGGCTGAGGATGG
AGTCCAAGACTGAGAAATGGATGGAACGAATACACCTCAATGTCTCTGAAAGGCCTTTTC
CACCTCATATCCAGCTCCCTCCAGAAATTCAAGAGTCCCAGGAAGTCACTCTGACCTGCT
TGCTGAATTTCTCCTGCTATGGGTATCCGATCCAATTGCAGTGGCTCCTAGAGGGGGTTC
CAATGAGGCAGGCTGCTGTCACCTCGACCTCCTTGACCATCAAGTCTGTCTTCACCCGGA
GCGAGCTCAAGTTCTCCCCACAGTGGAGTCACCATGGGAAGATTGTGACCTGCCAGCTTC
AGGATGCAGATGGGAAGTTCCTCTCCAATGACACGGTGCAGCTGAACGTGAAGCACACCC
CGAAGTTGGAGATCAAGGTCACTCCCAGTGATGCCATAGTGAGGGAGGGGGACTCTGTGA
CCATGACCTGCGAGGTCAGCAGCAGCAACCCGGAGTACACGACGGTATCCTGGCTCAAGG
ATGGGACCTCGCTGAAGAAGCAGAATACATTCACGCTAAACCTGCGCAAGTGACCAAGG
ACCAGAGTGGGAAGTACTGCTGTCAGGTCTCCAATGACGTGGGCCCGGGAAGGTCGGAAG
AAGTGTTCCTGCAAGTGCAGTATGCCCCGGAACCTTCCACGGTTCAGATCCTCCACTCAC
CGGCTGTGGAGGGAAGTCAAGTCGAGTTTCTTTGCATGTCACTGGCCAATCCTCTTCCAA
CAAATTACACGTGGTACCACAATGGGAAAGAAATGCAGGGAAGGACAGAGGAGAAAGTCC
ACATCCCAAAGATCCTCCCCTGGCACGCTGGGACTTATTCCTGTGTGGCAGAAAACATTC
TTGGTACTGGACAGAGGGGCCCGGGAGCTGAGCTGGATGTCCAGTATCCTCCCAAGAAGG
TGACCACAGTGATTCAAAACCCCATGCCGATTCGAGAAGGAGACACAGTGACCCTTTCCT
GTAACTACAATTCCAGTAACCCCAGTGTTACCCGGTATGAATGGAAACCCCATGGCGCCT
GGGAGGAGCCATCGCTTGGGGTGCTGAAGATCCAAAACGTTGGCTGGGACAACACAACCA
TCGCCTGCGCACGTTGTAATAGTTGGTGCTCGTGGGCCTCCCCTGTCGCCCTGAATGTCC
AGTATGCCCCCCGAGACGTGAGGGTCCGGAAAATCAAGCCCCTTTCCGAGATTCACTCTG
GAAACTCGGTCAGCCTCCAATGTGACTTCTCAAGCAGCCACCCCAAAGAAGTCCAGTTCT
TCTGGGAGAAAAATGGCAGGCTTCTGGGGAAAGAAAGCCAGCTGAATTTTGACTCCATCT
CCCCAGAAGATGCTGGGAGTTACAGCTGCTGGGTGAACAACTCCATAGGACAGACAGCGT
CCAAGGCCTGGACACTTGAAGTGCTGTATGCACCCAGGAGGCTGCGTGTGTCCATGAGCC
CGGGGGACCAAGTGATGGAGGGGAAGAGTGCAACCCTGACCTGTGAGAGTGACGCCAACC
CTCCCGTCTCCCACTACACCTGGTTTGACTGGAATAACCAAAGCCTCCCCCACCACAGCC
AGAAGCTGAGATTGGAGCCGGTGAAGGTCCAGCACTCGGGTGCCTACTGGTGCCAGGGGA
CCAACAGTGTGGGCAAGGGCCGTTCGCCTCTCAGCACCCTTACTGTCTACTATAGCCCGG
AGACCATCGGCAGGCGAGTGGCTGTGGGACTCGGGTCCTGCCTCGCCATCCTCATCCTGG
CAATCTGTGGGCTCAAGCTCCAGCGACGTTGGAAGAGGACACAGAGCCAGCAGGGCTTC
AGGAGAATTCCAGCGGCCAGAGCTTCTTTGTGAGGAATAAAAAGGTTAGAAGGGCCCCCC
TCTCTGAAGGCCCCCACTCCCTGGGATGCTACAATCCAATGATGGAAGATGGCATTAGCT
ACACCACCCTGCGCTTTCCCGAGATGAACATACCACGAACTGGAGATGCAGAGTCCTCAG
AGATGCAGAGACCTCCCCGGACCTGCGATGACACGGTCACTTATTCAGCATTGCACAAGC

FIGURE 50B

GCCAAGTGGGCGACTATGAGAACGTCATTCCAGATTTTCCAGAAGATGAGGGGATTCATT
ACTCAGAGCTGATCCAGTTTGGGGTCGGGGAGCGGCCTCAGGCACAAGAAAATGTGGACT
ATGTGATCCTCAAACAT<u>TGA</u>CACTGGATGGGCTGCAGCAGAGGCACTGGGGGCAGCGGGG
GCCAGGGAAGTCCCCGAGTTTCCCCAGACACCGCCACATGGCTTCCTCCTGCGTGCATGT
GCGCACACACACACACACGCACACACACACACACACTCACTGCGGAGAACCTTGTG
CCTGGCTCAGAGCCAGTCTTTTTGGTGAGGGTAACCCCAAACCTCCAAAACTCCTGCCCC
TGTTCTCTTCCACTCTCCTTGCTACCCAGAAATCATCTAAATACCTGCCCTGACATGCAC
ACCTCCCCTGCCCCACCAGCCCACTGGCCATCTCCACCCGGAGCTGCTGTGTCCTCTGGA
TCTGCTCGTCATTTTCCTTCCCTTCTCCATCTCTCTGGCCCTCTACCCCTGATCTGACAT
CCCCACTCACGAATATTATGCCCAGTTTCTGCCTCTGAGGGAAAGCCCAGAAAAGGACAG
AAACGAAGTAGAAAGGGGCCCAGTCCTGGCCTGGCTTCTCCTTTGGAAGTGAGGCATTGC
ACGGGGAGACGTACGTATCAGCGGCCCCTTGACTCTGGGGACTCCGGGTTTGAGATGGAC
ACACTGGTGTGGATTAACCTGCCAGGGAGACAGAGCTCACAATAAAAATGGCTCAGATGC
CACTTCAAAGAAAAAAAAAA

FIGURE 51A

></usr/seqdb2/sst/DNA/Dnaseqs.min/ss.DNA88116
><subunit 1 of 1, 847 aa, 1 stop
><MW: 95452, pI: 6.82, NX(S/T): 13

MHLLGPWLLLLVLEYLAFSDSSKWVFEHPETLYAWEGACVWIPCTYRALDGDLESFILFH
NPEYNKNTSKFDGTRLYESTKDGKVPSEQKRVQFLGDKNKNCTLSIHPVHLNDSGQLGLR
MESKTEKWMERIHLNVSERPFPPHIQLPPEIQESQEVTLTCLLNFSCYGYPIQLQWLLEG
VPMRQAAVTSTSLTIKSVFTRSELKFSPQWSHHGKIVTCQLQDADGKFLSNDTVQLNVKH
TPKLEIKVTPSDAIVREGDSVTMTCEVSSSNPEYTTVSWLKDGTSLKKQNTFTLNLREVT
KDQSGKYCCQVSNDVGPGRSEEVFLQVQYAPEPSTVQILHSPAVEGSQVEFLCMSLANPL
PTNYTWYHNGKEMQGRTEEKVHIPKILPWHAGTYSCVAENILGTGQRGPGAELDVQYPPK
KVTTVIQNPMPIREGDTVTLSCNYNSSNPSVTRYEWKPHGAWEEPSLGVLKIQNVGWDNT
TIACARCNSWCSWASPVALNVQYAPRDVRVRKIKPLSEIHSGNSVSLQCDFSSSHPKEVQ
FFWEKNGRLLGKESQLNFDSISPEDAGSYSCWVNNSIGQTASKAWTLEVLYAPRRLRVSM
SPGDQVMEGKSATLTCESDANPPVSHYTWFDWNNQSLPHHSQKLRLEPVKVQHSGAYWCQ
GTNSVGKGRSPLSTLTVYYSPETIGRRVAVGLGSCLAILILAICGLKLQRRWKRTQSQQG
LQENSSGQSFFVRNKKVRRAPLSEGPHSLGCYNPMMEDGISYTTLRFPEMNIPRTGDAES
SEMQRPPRTCDDTVTYSALHKRQVGDYENVIPDFPEDEGIHYSELIQFGVGERPQAQENV
DYVILKH

Signal sequence.
Amino acids 1-19.

Transmembrane domain.
Amino acids 685-705.

Immunoglobulin domain.
Amino acids 154-221, 258-311, 346-398, 435-486, 522-573, 609-611.

N-glycosylation site.
Amino acids 67-70, 101-104, 112-115, 135-138, 164-167, 231-234, 363-366, 445-448, 479-482, 574-577, 634-637, 724-727.

cAMP- and cGMP-dependent protein kinase phosphorylation site.
Amino aicds 420-423.

Protein kinase C phosphorylatioon site.
Amino acids 21-23, 45-47, 68-70, 79-81, 125-127, 137-139, 194-196, 241-243, 285-287, 304-306, 641-643, 764-766.

FIGURE 51B

Casein kinase II phosporylation site.
Amino acids 69-72, 79-82, 123-126, 200-203, 249-252, 270-273, 347-350, 452-455, 562-565, 601-604, 628-631, 789-792.

Tyrosine kinase phosphorylation site.
Amino acids 788-796.

N-myristoylation site.
Amino acids 392-397, 522-527, 567-572, 578-583, 655-660, 691-696, 693-698, 720725, 759-764, 819-824.

Amidation site.
Amino acids 684-687.

Prokaryotic membrane lipoprotein lipid attachment site.
Amino acids 386-396.

FIGURE 52

DNA227752

CCAACCACAAGCACCAAAGCAGAGGGGCAGGCAGCACACCACCCAGCAGCCAGAGCACCA
GCCCAGCC<u>ATG</u>GTCCTTGAGGTGAGTGACCACCAAGTGCTAAATGACGCCGAGGTTGCCG
CCCTCCTGGAGAACTTCAGCTCTTCCTATGACTATGGAGAAAACGAGAGTGACTCGTGCT
GTACCTCCCCGCCCTGCCCACAGGACTTCAGCCTGAACTTCGACCGGGCCTTCCTGCCAG
CCCTCTACAGCCTCCTCTTTCTGCTGGGGCTGCTGGGCAACGGCGCGGTGGCAGCCGTGC
TGCTGAGCCGGCGGACAGCCCTGAGCAGCACCGACACCTTCCTGCTCCACCTAGCTGTAG
CAGACACGCTGCTGGTGCTGACACTGCCGCTCTGGGCAGTGGACGCTGCCGTCCAGTGGG
TCTTTGGCTCTGGCCTCTGCAAAGTGGCAGGTGCCCTCTTCAACATCAACTTCTACGCAG
GAGCCCTCCTGCTGGCCTGCATCAGCTTTGACCGCTACCTGAACATAGTTCATGCCACCC
AGCTCTACCGCCGGGGGCCCCGGCCCGCGTGACCCTCACCTGCCTGGCTGTCTGGGGGC
TCTGCCTGCTTTTCGCCCTCCCAGACTTCATCTTCCTGTCGGCCCACCACGACGAGCGCC
TCAACGCCACCCACTGCCAATACAACTTCCCACAGGTGGGCCGCACGGCTCTGCGGGTGC
TGCAGCTGGTGGCTGGCTTTCTGCTGCCCCTGCTGGTCATGGCCTACTGCTATGCCCACA
TCCTGGCCGTGCTGCTGGTTTCCAGGGGCCAGCGGCGCCTGCGGGCCATGCGGCTGGTGG
TGGTGGTCGTGGTGGCCTTTGCCCTCTGCTGGACCCCCTATCACCTGGTGGTGCTGGTGG
ACATCCTCATGGACCTGGGCGCTTTGGCCCGCAACTGTGGCCGAGAAAGCAGGGTAGACG
TGGCCAAGTCGGTCACCTCAGGCCTGGGCTACATGCACTGCTGCCTCAACCCGCTGCTCT
ATGCCTTTGTAGGGGTCAAGTTCCGGGAGCGGATGTGGATGCTGCTCTTGCGCCTGGGCT
GCCCCAACCAGAGAGGGCTCCAGAGGCAGCCATCGTCTTCCCGCCGGGATTCATCCTGGT
CTGAGACCTCAGAGGCCTCCTACTCGGGCTTG<u>TGA</u>GGCCGGAATCCGGGCTCCCCTTTCG
CCCACAGTCTGACTTCCCCGCATTCCAGGCTCCTCCCTCCTCTGCCGGCTCTGGCTCTC
CCCAATATCCTCGCTCCCGGGACTCACTGGCAGCCCAGCACCACCAGGTCTCCCGGGAA
GCCACCCTCCCAGCTCTGAGGACTGCACCATTGCTGCTCCTTAGCTGCCAAGCCCCATCC
TGCCGCCCGAGGTGGCTGCCTGGAGCCCACTGCCCTTCTCATTTGGAAACTAAAACTTC
ATCTTCCCCAAGTGCGGGGAGTACAAGGCATGGCGTAGAGGGTGCTGCCCCATGAAGCCA
CAGCCCAGGCCTCCAGCTCAGCAGTGACTGTGGCCATGGTCCCCAAGACCTCTATATTTG
CTCTTTTATTTTTATGTCTAAAATCCTGCTTAAAACTTTTCAATAAACAAGATCGTCAGG
ACCAAAAAAAAAAAAAAAAAAAAAAAAAAAAAAAAAAAAAAAAAAAAAAA

FIGURE 53

></usr/seqdb2/sst/DNA/Dnaseqs.min/ss.DNA227752
><subunit 1 of 1, 368 aa, 1 stop
><MW: 40660, pI: 8.10, NX(S/T): 3

```
MVLEVSDHQVLNDAEVAALLENFSSSYDYGENESDSCCTSPPCPQDFSLNFDRAFLPALY
SLLFLLGLLGNGAVAAVLLSRRTALSSTDTFLLHLAVADTLLVLTLPLWAVDAAVQWVFG
SGLCKVAGALFNINFYAGALLLACISFDRYLNIVHATQLYRRGPPARVTLTCLAVWGLCL
LFALPDFIFLSAHHDERLNATHCQYNFPQVGRTALRVLQLVAGFLLPLLVMAYCYAHILA
VLLVSRGQRRLRAMRLVVVVVVAFALCWTPYHLVVLVDILMDLGALARNCGRESRVDVAK
SVTSGLGYMHCCLNPLLYAFVGVKFRERMWMLLLRLGCPNQRGLQRQPSSSRRDSSWSET
SEASYSGL
```

Transmembrane domain.
Amino acids 54-74, 90-110, 129-149, 168-188, 216-236, 260-280, 303-323.

Seven transmembrane receptor domain.
Amino acids 70-318.

N-glycosylation site.
Amino acids 22-25, 32-35, 199-202.

Glycosaminoglycan attachment site.
Amino acids 304-307.

cAMP- and cGMP-dependent protein kinase phosphorylation site.
Amino acids 352-355.

Protein kinase C phosphorylation site.
Amino acids 80-82, 350-352, 351-353.

Casein kinase II phosphorylation site.
Amino acids 25-28, 86-89, 294-297, 351-354, 356-359.

N-myristoylation site.
Amino acids 67-72, 72-77, 120-125, 128-133.

Prokaryotic membrane lipoprotein lipid attachment site.
Amino acids 134-144.

FIGURE 54

DNA119476

GAGGGAAGAACACAATGGATCTGGTGCTAAAAAGATGCCTTCTTCATTTGGCTGTGATAG
GTGCTTTGCTGGCTGTGGGGCTACAAAAGTACCCAGAAACCAGGACTGGCTTGGTGTCT
CAAGGCAACTCAGAACCAAAGCCTGGAACAGGCAGCTGTATCCAGAGTGGACAGAAGCCC
AGAGACTTGACTGCTGGAGAGGTGGTCAAGTGTCCCTCAAGGTCAGTAATGATGGGCCTA
CACTGATTGGTGCAAATGCCTCCTTCTCTATTGCCTTGAACTTCCCTGGAAGCCAAAAGG
TATTGCCAGATGGGCAGGTTATCTGGGTCAACAATACCATCATCAATGGGAGCCAGGTGT
GGGGAGGACAGCCAGTGTATCCCCAGGAAACTGACGATGCCTGCATCTTCCCTGATGGTG
GACCTTGCCCATCTGGCTCTTGGTCTCAGAAGAGAAGCTTTGTTTATGTCTGGAAGACCT
GGGGCCAATACTGGCAAGTTCTAGGGGGCCCAGTGTCTGGGCTGAGCATTGGGACAGGCA
GGGCAATGCTGGGCACACACACCATGGAAGTGACTGTCTACCATCGCCGGGGATCCCGGA
GCTATGTGCCTCTTGCTCATTCCAGCTCAGCCTTCACCATTACTGACCAGGTGCCTTTCT
CCGTGAGCGTGTCCCAGTTGCGGGCCTTGGATGGAGGGAACAAGCACTTCCTGAGAAATC
AGCCTCTGACCTTTGCCCTCCAGCTCCATGACCCAGTGGCTATCTGGCTGAAGCTGACC
TCTCCTACACCTGGGACTTTGGAGACAGTAGTGGAACCCTGATCTCTCGGGCACTTGTGG
TCACTCATACTTACCTGGAGCCTGGCCCAGTCACTGCCCAGGTGGTCCTGCAGGCTGCCA
TTCCTCTCACCTCCTGTGGCTCCTCCCCAGTTCCAGGCACCACAGATGGGCACAGGCCAA
CTGCAGAGGCCCCTAACACCACAGCTGGCCAAGTGCCTACTACAGAAGTTGTGGGTACTA
CACCTGGTCAGGCGCCAACTGCAGAGCCCTCTGGAACCACATCTGTGCAGGTGCCAACCA
CTGAAGTCATAAGCACTGCACCTGTGCAGATGCCAACTGCAGAGAGCACAGGTATGACAC
CTGAGAAGGTGCCAGTTTCAGAGGTCATGGGTACCACACTGGCAGAGATGTCAACTCCAG
AGGCTACAGGTATGACACCTGCAGAGGTATCAATTGTGGTGCTTTCTGGAACCACAGCTG
CACAGGTAACAACTACAGAGTGGGTGGAGACCACAGCTAGAGAGCTACCTATCCCTGAGC
CTGAAGGTCCAGATGCCAGCTCAATCATGTCTACGGAAAGTATTACAGGTTCCCTGGGCC
CCCTGCTGGATGGTACAGCCACCTTAAGGCTGGTGAAGAGACAAGTCCCCCTGGATTGTG
TTCTGTATCGATATGGTTCCTTTTCCGTCACCCTGGACATTGTCCAGGGTATTGAAAGTG
CCGAGATCCTGCAGGCTGTGCCGTCCGGTGAGGGGGATGCATTTGAGCTGACTGTGTCCT
GCCAAGGCGGGCTGCCCAAGGAAGCCTGCATGGAGATCTCATCGCCAGGGTGCCAGCCCC
CTGCCCAGCGGCTGTGCCAGCCTGTGCTACCCAGCCCAGCCTGCCAGCTGGTTCTGCACC
AGATACTGAAGGGTGGCTCGGGGACATACTGCCTCAATGTGTCTCTGGCTGATACCAACA
GCCTGGCAGTGGTCAGCACCCAGCTTATCATGCCTGGTCAAGAAGCAGGCCTTGGGCAGG
TTCCGCTGATCGTGGGCATCTTGCTGGTGTTGATGGCTGTGGTCCTTGCATCTCTGATAT
ATAGGCGCAGACTTATGAAGCAAGACTTCTCCGTACCCAGTTGCCACATAGCAGCAGTC
ACTGGCTGCGTCTACCCCGCATCTTCTGCTCTTGTCCCATTGGTGAGAACAGCCCCCTCC
TCAGTGGGCAGCAGGTCTGAGTACTCTCATATGATGCTGTGATTTTCCTGGAGTTGACAG
AAACACCTATATTTCCCCCAGTCTTCCCTGGGAGACTACTATTAACTGAAATAAATACTC
AGAGCCTGA

FIGURE 55A

```
><Thu Jul 20 10:27:08 2000 DNA119476 [min]
></usr/seqdb2/sst/DNA/Dnaseqs.min/ss.DNA119476
><subunit 1 of 1, 661 aa, 1 stop
><MW: 70255, pI: 5.52, NX(S/T): 5
```

MDLVLKRCLLHLAVIGALLAVGATKVPRNQDWLGVSRQLRTKAWNRQLYPEWTEAQRLDC
WRGGQVSLKVSNDGPTLIGANASFSIALNFPGSQKVLPDGQVIWVNNTIINGSQVWGGQP
VYPQETDDACIFPDGGPCPSGSWSQKRSFVYVWKTWGQYWQVLGGPVSGLSIGTGRAMLG
THTMEVTVYHRRGSRSYVPLAHSSSAFTITDQVPFSVSVSQLRALDGGNKHFLRNQPLTF
ALQLHDPSGYLAEADLSYTWDFGDSSGTLISRALVVTHTYLEPGPVTAQVVLQAAIPLTS
CGSSPVPGTTDGHRPTAEAPNTTAGQVPTTEVVGTTPGQAPTAEPSGTTSVQVPTTEVIS
TAPVQMPTAESTGMTPEKVPVSEVMGTTLAEMSTPEATGMTPAEVSIVVLSGTTAAQVTT
TEWVETTARELPIPEPEGPDASSIMSTESITGSLGPLLDGTATLRLVKRQVPLDCVLYRY
GSFSVTLDIVQGIESAEILQAVPSGEGDAFELTVSCQGGLPKEACMEISSPGCQPPAQRL
CQPVLPSPACQLVLHQILKGGSGTYCLNVSLADTNSLAVVSTQLIMPGQEAGLGQVPLIV
GILLVLMAVVLASLIYRRRLMKQDFSVPQLPHSSSHWLRLPRIFCSCPIGENSPLLSGQQ
V

Signal Sequence.
Amino acids 1-20.

Transmembrane Domain.
Amino acids 594-614.

N-glycosylation site.
Amino acids 81-84, 106-109, 111-114, 321-324, 568-571.

Glycosaminoglycan attachment site.
Amino acids 504-507.

cAMP- and cGMP-dependent protein kinase phosphorylation site.
Amino aicds 191-194.

Protein kinase C phosphorylation site.
Amino acids 67-69, 93-95, 144-146, 174-176, 427-429, 463-465.

Casein kinase II phosphorylation site.
Amino acids 208-211, 279-282, 388-391, 401-404, 419-422, 427-430, 570-573.

FIGURE 55B

N-myristoylation site.

Amino acids 16-21, 63-68, 79-84, 164-169, 173-178, 267-272, 308-313, 325-330, 334-339, 338-343, 386-391, 399-404, 412-417, 492-497, 560-565, 588-593.

FIGURE 56A

DNA254890

CAGTCGGCACCGGCGAGGCCGTGCTGGAACCCGGGCCTCAGCCGCAGCCGCAGCGGGGCC
GACATGACGACAGCTCCCCAGGAGCCCCCGCCCGGCCCCTCCAGGCGGGCAGTGGAGCT
GGCCCGGCGCCTGGGCGCGCCATGCGCAGCACCACGCTCCTGGCCCTGCTGGCGCTGGTC
TTGCTTTACTTGGTGTCTGGTGCCCTGGTGTTCCGGGCCCTGGAGCAGCCCCACGAGCAG
CAGGCCCAGAGGGAGCTGGGGAGGTCCGAGAGAAGTTCCTGAGGGCCCATCCGTGTGTG
AGCGACCAGGAGCTGGGCCTCCTCATCAAGGAGGTGGCTGATGCCCTGGGAGGGGGTGCG
GACCCAGAAACCAACTCGACCAGCAACAGCAGCCACTCAGCCTGGGACCTGGGCAGCGCC
TTCTTTTTCTCAGGGACCATCATCACCACCATCGGCTATGGCAATGTGGCCCTGCGCACA
GATGCCGGGCGCCTCTTCTGCATCTTCTATGCGCTGGTGGGGATTCCGCTGTTTGGGATC
CTACTGGCAGGGGTCGGGGACCGGCTGGGCTCCTCCCTGCGCCATGGCATCGGTCACATT
GAAGCCATCTTCTTGAAGTGGCACGTGCCACCGGAGCTAGTAAGAGTGCTGTCGGCGATG
CTTTTCCTGCTGATCGGCTGCCTGCTCTTTGTCCTCACGCCCACGTTCGTGTTCTGCTAT
ATGGAGGACTGGAGCAAGCTGGAGGCCATCTACTTTGTCATAGTGACGCTTACCACCGTG
GGCTTTGGCGACTATGTGGCCGGCGCGGACCCCAGGCAGGACTCCCCGGCCTATCAGCCG
CTGGTGTGGTTCTGGATCCTGCTCGGCCTGGCTTACTTCGCCTCAGTGCTCACCACCATC
GGGAACTGGCTGCAGTAGTGTCCCGCCGCACTCGGGCAGAGATGGGCGGCCTCACGGCT
CAGGCTGCCAGCTGGACTGGCACAGTGACAGCGCGCGTGACCCAGCGAGCCGGGCCCGCC
GCCCCGCCGCCGGAGAAGGAGCAGCCACTGCTGCCTCCACCGCCCTGTCCAGCGCAGCCG
CTGGGCAGGCCCCGATCCCCTTCGCCCCCCGAGAAGGCTCAGCTGCCTTCCCCGCCCACG
GCCTCGGCCCTGGATTATCCCAGCGAGAACCTGGCCTTCATCGACGAGTCCTCGGATACG
CAGAGCGAGCGCGGCTGCCCGCTGCCCCGCGCGCCGAGAGGTCGCCGCCGCCCAAATCCC
CCCAGGAAGCCCGTGCGGCCCCGCGGCCCCGGGCGTCCCCGAGACAAAGGCGTGCCGGTG
TAGGGGCAGGATCCCTGGCCGGGCCTCTCAAGGGCTTCGTTTCTGCTCTCCCGGCATGC
CTGGCTTGTTTGACCAAAGAGCCCTCTTTCCACGAGACTGAAGTCTGGGGAGGAGGCTAC
AGTTGCCTCTCCGCCTCCTCCCTGGCCCCGGCCCTTCCCTCACTTCCATCCATCTCTAGA
CCCCCCCAAGGCTTTCTGTGTCGCTGCCCCGGGCGGGTGTATCCCTCACAGCACCTCACG
ACTGTGCCTCAAAGCCTGCATCAATAAATGAAAACGGTCTGCACCGCTGCGGGCGTGACG
CTCCCGGACGCGAGTGGGTGTGGAATTGCTTTCCTCGGGCCACCGTGGGGGCACCTCTGG
CCTCCCGTGACCCCAGGCCGAGGGTCCCCGGGCACCCAGGTCGGTCAAGTCTCGGCCCT
CTCAGGCCCGCGTCTCTGCCTGGAGGAGACTGTGTAGGGTCCGGCGTGGGGATCAGCCGG
GATGGGCTGCGCGTCTCCAGCCTCTGCACACACATTGGCGGGTGGGGTGCAGGGAGGGAG
AGGCAGGGGAGAGAGAATGGCATCTCGCGTGGAGGGCTGTCGTTTGAACTCTCCCAGCGC
GAGAGACCCTGCCCCGCCCCCTTCCTGGAGCGTTGACTCCCTTCTCGTCTCGAGGCCTGT
GGCGTCTGGGTCCGTTGGGGCAGAACCATGGAGGAAAAGCCTTCGAAAGTGTCGCTCAAG
TCTTCCGACCGCCAAGGCTCGGACGAGGAGAGCGTGCATAGCGACACTCGGGACCTGTGG
ACCACGACCACGCTGTCCCAGGCACAGCTGAACATGCCGCTGTCCGAGGTCTGCGAGGGC
TTCGACGAGGAGGCCGCAACATTAGCAAGACCCGCGGGTGGCACAGCCCGGGCGGGGC
TCGTTGGACGAGGGGTACAAGGCCAGCCACAAGCCGGAGGAACTGGACGAGCACGCGCTG
GTGGAGCTGGAGTTGCACCGCGGCAGCTCCATGGAAATCAATCTGGGGGAGAAGGACACT
GCATCCCAGATCGAGGCCGAAAAGTCTTCCTCAATGTCATCACTCAATATTGCGAAGCAC
ATGCCCCATCGAGCCTACTGGGCAGAGCAGCAGAGCAGGCTGCCACTGCCCCTGATGGAA
CTCATGGAGAATGAAGCTCTGGAAATCCTCACCAAAGCCCTCCGGAGCTACCAGTTAGGG
ATCGGCAGGGACCACTTCCTGACTAAGGAGCTGCAGCGATACATCGAAGGGCTCAAGAAG

FIGURE 56B

CGCCGGAGCAAGAGGCTGTACGTGAATTAAAAACGCCACCTTGGGCTCGAGCAGCGACCC
GAACCAGCCCCGTGCCAGCCCGGTCCCCAGACCCAAGCCTGACCCCATCCGAGTGGAATT
TGAGTCCTAAAGAAATAAAAGAGTCGATGCATGAAAAAAAAAAAAAAAAAAAAAAAAAAA
AAAAAAAAAAA

FIGURE 57

></usr/seqdb2/sst/DNA/Dnaseqs.min/ss.DNA254890
><subunit 1 of 1, 419 aa, 1 stop
><MW: 45189, pI: 9.15, NX(S/T): 2

MTTAPQEPPARPLQAGSGAGPAPGRAMRSTTLLALLALVLLYLVSGALVFRALEQPHEQQ
AQRELGEVREKFLRAHPCVSDQELGLLIKEVADALGGGADPETNSTSNSSHSAWDLGSAF
FFSGTIITTIGYGNVALRTDAGRLFCIFYALVGIPLFGILLAGVGDRLGSSLRHGIGHIE
AIFLKWHVPPELVRVLSAMLFLLIGCLLFVLTPTFVFCYMEDWSKLEAIYFVIVTLTTVG
FGDYVAGADPRQDSPAYQPLVWFWILLGLAYFASVLTTIGNWLRVVSRRTRAEMGGLTAQ
AASWTGTVTARVTQRAGPAAPPPEKEQPLLPPPPCPAQPLGRPRSPSPPEKAQLPSPPTA
SALDYPSENLAFIDESSDTQSERGCPLPRAPRGRRRPNPPRKPVRPRGPGRPRDKGVPV

Signal sequence.
Amino acids 1-46.

Transmembrane domain.
Amino acids 114-134, 145-165, 190-210, 224-244, 259-279.

N-glycosylation site.
Amino acids 104-107, 108-111.

Glycosaminoglycan attachment site.
Amino acids 17-20.

Protein kinase C phosphorylation site.
Amino acids 171-173, 287-289, 309-311, 313-315, 381-383.

Casein kinase II phosphorylation site.
Amino acids 80-83, 112-115, 224-227, 290-293, 347-351, 361-364, 379-382.

N-myristoylation site.
Amino acids 124-129, 158-163, 295-300, 306-311.

Amidation site.
Amino acids 392-395.

Prokaryotic membrane lipoprotein, lipid attachment site.
Amino acids 196-206.

FIGURE 58A getseq sst.DNA219240
GCCAACACTGGCCAAACAGAAGCCTCCGGTCGGCCTGCAGTGCCCAAGTCCCATGGCGAG
GGCAGCCCGAGTGGCCGTCGCGGCTGTAGGTCCGCATGCCGGGCACCGCACCAGGCGTCT
AGCAGATGGACACAGGAAGATCCAGAAGCTAGTGGCACATCTAGCAACAGAGCCAGATCA
GAACCCAGATGCTAAACTCCTGGTGGACTGCAGAGGAGAGGGATTCAGTCTTCTCCTGAT
GTCGATTGCGATTTCTGCTGGGAGCTCAAGACGGGCGAGCTGCCCGAGATCTCTTCGAGA
TACCCCAGGGGAGGAGGAGATGGGCAGGATTTAGTAGGACAACTCGGTTACTAATGACTT
GGCGGCTGGCTGCGACCCCCGGGAAATCAGGTGCAAGCATGTTTGCCTGTAGGTACCTG
AGTTGACACCGAAGGTGCCTAAAGATGCTGAGCGGCGTTTGGTTCCTCAGTGTGTTAACC
GTGGCCGGGATCTTACAGACAGAGAGTCGCAAAACTGCCAAAGACATTTGCAAGATCCGC
TGTCTGTGCGAAGAAAAGGAAAACGTACTGAATATCAACTGTGAGAACAAAGGATTTACA
ACAGTTAGCCTGCTCCAGCCCCCCAGTATCGAATCTATCAGCTTTTTCTCAATGGAAAC
CTCTTGACAAGACTGTATCCAAACGAATTTGTCAATTACTCCAACGCGGTGACTCTTCAC
CTAGGTAACAACGGGTTACAGGAGATCCGAACGGGGCATTCAGTGGCCTGAAAACTCTC
AAAAGACTGCATCTCAACAACAACAAGCTTGAGATATTGAGGGAGGACACCTTCCTAGGC
CTGGAGAGCCTGGAGTATCTCCAGGCCGACTACAATTACATCAGTGCCATCGAGGCTGGG
GCATTCAGCAAACTTAACAAGCTCAAAGTGCTCATCCTGAATGACAACCTTCTGCTTTCA
CTGCCCAGCAATGTGTTCCGCTTTGTCCTGCTGACCCACTTAGACCTCAGGGGGAATAGG
CTAAAAGTAATGCCTTTTGCTGGCGTCCTTGAACATATTGGAGGGATCATGGAGATTCAG
CTGGAGGAAAATCCATGGAATTGCACTTGTGACTTACTTCCTCTCAAGGCCTGGCTAGAC
ACCATAACTGTTTTTGTGGGAGAGATTGTCTGTGAGACTCCCTTTAGGTTGCATGGGAAA
GACGTGACCCAGCTGACCAGGCAAGACCTCTGTCCCAGAAAAGTGCCAGTGATTCCAGT
CAGAGGGGCAGCCATGCTGACACCCACGTCCAAAGGCTGTCACCTACAATGAATCCTGCT
CTCAACCCAACCAGGGCTCCGAAAGCCAGCCGGCCGCCCAAAATGAGAAATCGTCCAACT
CCCCGAGTGACTGTGTCAAAGGACAGGCAAAGTTTTGGACCCATCATGGTGTACCAGACC
AAGTCTCCTGTGCCTCTCACCTGTCCCAGCAGCTGTGTCTGCACCTCTCAGAGCTCAGAC
AATGGTCTGAATGTAAACTGCCAAGAAAGGAAGTTCACTAATATCTCTGACCTGCAGCCC
AAACCGACCAGTCCAAAGAAACTCTACCTAACAGGGAACTATCTTCAAACTGTCTATAAG
AATGACCTCTTAGAATACAGTTCTTTGGACTTACTGCACTTAGGAAACAACAGGATTGCA
GTCATTCAGGAAGGTGCCTTTACAAACCTGACCAGTTTACGCAGACTTTATCTGAATGGC
AATTACCTTGAAGTGCTGTACCCTTCTATGTTTGATGGACTGCAGAGCTTGCAATATCTC
TATTTAGAGTATAATGTCATTAAGGAAATTAAGCCTCTGACCTTTGATGCTTTGATTAAC
CTACAGCTACTGTTTCTGAACAACAACCTTCTTCGGTCCTTACCTGATAATATATTTGGG
GGGACGGCCCTAACCAGGCTGAATCTGAGAAACAACCATTTTTCTCACCTGCCCGTGAAA
GGGGTTCTGGATCAGCTCCCGGCTTTCATCCAGATAGATCTGCAGGAGAACCCCTGGGAC
TGTACCTGTGACATCATGGGGCTGAAAGACTGGACAGAACATGCCAATTCCCCTGTCATC
ATTAATGAGGTGACTTGCGAATCTCCTGCTAAGCATGCAGGGGAGATACTAAAATTTCTG
GGGAGGGAGGCTATCTGTCCAGACAGCCCAAACTTGTCAGATGGAACCGTCTTGTCAATG
AATCACAATACAGACACACCTCGGTCGCTTAGTGTGTCTCCTAGTTCCTATCCTGAACTA
CACACTGAAGTTCCACTGTCTGTCTTAATTCTGGGATTGCTTGTTGTTTTCATCTTATCT
GTCTGTTTTGGGGCTGGTTATTCGTCTTTGTCTTGAAACGCCGAAAGGGAGTGCCGAGC
GTTCCCAGGAATACCAACAACTTAGACGTAAGCTCCTTTCAATTACAGTATGGGTCTTAC
AACACTGAGACTCACGATAAAACAGACGGCCATGTCTACAACTATATCCCCCCACCTGTG
GGTCAGATGTGCCAAAACCCCATCTACATGCAGAAGGAAGGAGACCCAGTAGCCTATTAC
CGAAACCTGCAGGAGTTCAAGACCAGCCTAGAGAACATATGGAGACCCTGTCTTCACAAA

FIGURE 58B

AAA<u>TAA</u>AAAAGTCAGCCAAGCGTGGTGGTGTGTGCCTGTAGTTACTTAGGAGGCTGAGGC
AGGACGATCGCTTAAGCCCAGGAGTTTGAGGCTGTGGTGAGCTACAATTGCGCCACTGCA
CGCCAGCCTGGCTACAGAACGAGACCCTGCCTCTCTAAAAAAAAAAAAAAAAAAA

FIGURE 59A

```
></usr/seqdb2/sst/DNA/Dnaseqs.min/ss.DNA219240
><subunit 1 of 1, 733 aa, 1 stop
><MW: 82695, pI: 8.37, NX(S/T): 6

MLSGVWFLSVLTVAGILQTESRKTAKDICKIRCLCEEKENVLNINCENKGFTTVSLLQPP
QYRIYQLFLNGNLLTRLYPNEFVNYSNAVTLHLGNNGLQEIRTGAFSGLKTLKRLHLNNN
KLEILREDTFLGLESLEYLQADYNYISAIEAGAFSKLNKLKVLILNDNLLLSLPSNVFRF
VLLTHLDLRGNRLKVMPFAGVLEHIGGIMEIQLEENPWNCTCDLLPLKAWLDTITVFVGE
IVCETPFRLHGKDVTQLTRQDLCPRKSASDSSQRGSHADTHVQRLSPTMNPALNPTRAPK
ASRPPKMRNRPTPRVTVSKDRQSFGPIMVYQTKSPVPLTCPSSCVCTSQSSDNGLNVNCQ
ERKFTNISDLQPKPTSPKKLYLTGNYLQTVYKNDLLEYSSLDLLHLGNNRIAVIQEGAFT
NLTSLRRLYLNGNYLEVLYPSMFDGLQSLQYLYLEYNVIKEIKPLTFDALINLQLLFLNN
NLLRSLPDNIFGGTALTRLNLRNNHFSHLPVKGVLDQLPAFIQIDLQENPWDCTCDIMGL
KDWTEHANSPVIINEVTCESPAKHAGEILKFLGREAICPDSPNLSDGTVLSMNHNTDTPR
SLSVSPSSYPELHTEVPLSVLILGLLVVFILSVCFGAGLFVFVLKRRKGVPSVPRNTNNL
DVSSFQLQYGSYNTETHDKTDGHVYNYIPPPVGQMCQNPIYMQKEGDPVAYYRNLQEFKT
SLENIWRPCLHKK
```

Signal sequence.
Amino acids 1-18.

Transmembrane domain.
Amino acids 161-181, 466-486, 616-636.

N-glycosylation site.
Amino acids 84-87, 219-222, 366-369, 421-424, 583-586.

cAMP- and cGMP-dependent protein kinase phosphorylation site.
Amino acids 362-365.

Protein kinase C phosphorylation site.
Amino acids 21-23, 24-26, 111-113, 272-274, 312-314, 376-378, 424-426, 598-600.

Casein kinase II phosphorylation site.
Amino acids 24-27, 147-150, 184-187, 258-261, 267-270, 276-279, 399-402, 441-444, 485-488, 608-611, 720-723.

Tyrosine kinase phosphorylation site.
Amino acids 704-711.

FIGURE 59B

N-myristoylation site.
Amino acids 15-20, 71-76, 104-109, 354-359, 417-422, 493-498, 587-592, 670-675.

FIGURE 60A getseq sst.DNA37151

```
AAGGAGGCTGGGAGGAAAGAGGTAAGAAAGGTTAGAGAACCTACCTCACATCTCTCTGGG
CTCAGAAGGACTCTGAAGATAACAATAATTTCAGCCCATCCACTCTCCTTCCCTCCCAAA
CACACATGTGCATGTACACACACACATACACACATACACCTTCCTCTCCTTCACTGAA
GACTCACAGTCACTCACTCTGTGAGCAGGTCATAGAAAAGGACACTAAAGCCTTAAGGAC
AGGCCTGGCCATTACCTCTGCAGCTCCTTTGGCTTGTTGAGTCAAAAAACATGGGAGGGG
CCAGGCACGGTGACTCACACCTGTAATCCCAGCATTTTGGGAGACCGAGGTGAGCAGATC
ACTTGAGGTCAGGAGTTCGAGACCAGCCTGGCCAACATGGAGAAACCCCCATCTCTACTA
AAAATACAAAAATTAGCCAGGAGTGGTGGCAGGTGCCTGTAATCCCAGCTACTCAGGTGG
CTGAGCCAGGAGAATCGCTTGAATCCAGGAGGCGGAGGATGCAGTCAGCTGAGTGCACCG
CTGCACTCCAGCCTGGGTGACAGAATGAGACTCTGTCTCAAACAAACAAACACGGGAGGA
GGGGTAGATACTGCTTCTCTGCAACCTCCTTAACTCTGCATCCTCTTCTTCCAGGGCTGC
CCCTGATGGGGCCTGGCAATGACTGAGCAGGCCCAGCCCCAGAGGACAAGGAAGAGAAGG
CATATTGAGGAGGGCAAGAAGTGACGCCCGGTGTAGAATGACTGCCCTGGGAGGGTGGTT
CCTTGGGCCCTGGCAGGGTTGCTGACCCTTACCCTGCAAAACACAAAGAGCAGGACTCCA
GACTCTCCTTGTGAATGGTCCCCTGCCCTGCAGCTCCACCATGAGGCTTCTCGTGGCCCC
ACTCTTGCTAGCTTGGGTGGCTGGTGCCACTGCCACTGTGCCCGTGGTACCCTGGCATGT
TCCCTGCCCCCCTCAGTGTGCCTGCCAGATCCGGCCCTGGTATACGCCCCGCTCGTCCTA
CCGCGAGGCTACCACTGTGGACTGCAATGACCTATTCCTGACGGCAGTCCCCCCGGCACT
CCCCGCAGGCACACAGACCCTGCTCCTGCAGAGCAACAGCATTGTCCGTGTGGACCAGAG
TGAGCTGGGCTACCTGGCCAATCTCACAGAGCTGGACCTGTCCCAGAACAGCTTTTCGGA
TGCCCGAGACTGTGATTTCCATGCCCTGCCCCAGCTGCTGAGCCTGCACCTAGAGGAGAA
CCAGCTGACCCGGCTGGAGGACCACAGCTTTGCAGGGCTGGCCAGCCTACAGGAACTCTA
TCTCAACCACAACCAGCTCTACCGCATCGCCCCCAGGGCCTTTTCTGGCCTCAGCAACTT
GCTGCGGCTGCACCTCAACTCCAACCTCCTGAGGGCCATTGACAGCCGCTGGTTTGAAAT
GCTGCCCAACTTGGAGATACTCATGATTGGCGGCAACAAGGTAGATGCCATCCTGGACAT
GAACTTCCGGCCCCTGGCCAACCTGCGTAGCCTGGTGCTAGCAGGCATGAACCTGCGGGA
GATCTCCGACTATGCCCTGGAGGGGCTGCAAAGCCTGGAGAGCCTCTCCTTCTATGACAA
CCAGCTGGCCCGGGTGCCCAGGCGGGCACTGGAACAGGTGCCCGGGCTCAAGTTCCTAGA
CCTCAACAAGAACCCGCTCCAGCGGGTAGGGCCGGGGACTTTGCCAACATGCTGCACCT
TAAGGAGCTGGGACTGAACAACATGGAGGAGCTGGTCTCCATCGACAAGTTTGCCCTGGT
GAACCTCCCCGAGCTGACCAAGCTGGACATCACCAATAACCCACGGCTGTCCTTCATCCA
CCCCCGCGCCTTCCACCACCTGCCCCAGATGGAGACCCTCATGCTCAACAACAACGCTCT
CAGTGCCTTGCACCAGCAGACGGTGGAGTCCCTGCCCAACCTGCAGGAGGTAGGTCTCCA
CGGCAACCCCATCCGCTGTGACTGTGTCATCCGCTGGGCCAATGCCACGGGCACCCGTGT
CCGCTTCATCGAGCCGCAATCCACCCTGTGTGCGGAGCCTCCGGACCTCCAGCGCCTCCC
GGTCCGTGAGGTGCCCTTCCGGAGATGACGGACCACTGTTTGCCCCTCATCTCCCCACG
AAGCTTCCCCCCAAGCCTCCAGGTAGCCAGTGGAGAGAGCATGGTGCTGCATTGCCGGGC
ACTGGCCGAACCCGAACCCGAGATCTACTGGGTCACTCCAGCTGGGCTTCGACTGACACC
TGCCCATGCAGGCAGGAGGTACCGGGTGTACCCCGAGGGGACCCTGGAGCTGCGGAGGGT
GACAGCAGAAGAGGCAGGGCTATACACCTGTGTGGCCCAGAACCTGGTGGGGCTGACAC
TAAGACGGTTAGTGTGGTTGTGGGCCGTGCTCTCCTCCAGCCAGGCAGGGACGAAGGACA
GGGGCTGGAGCTCCGGGTGCAGGAGACCCACCCCTATCACATCCTGCTATCTTGGGTCAC
CCCACCCAACACAGTGTCCACCAACCTCACCTGGTCCAGTGCCTCCTCCCTCCGGGGCCA
```

FIGURE 60B

GGGGGCCACAGCTCTGGCCCGCCTGCCTCGGGGAACCCACAGCTACAACATTACCCGCCT
CCTTCAGGCCACGGAGTACTGGGCCTGCCTGCAAGTGGCCTTTGCTGATGCCCACACCCA
GTTGGCTTGTGTATGGGCCAGGACCAAAGAGGCCACTTCTTGCCACAGAGCCTTAGGGGA
TCGTCCTGGGCTCATTGCCATCCTGGCTCTCGCTGTCCTTCTCCTGGCAGCTGGGCTAGC
GGCCCACCTTGGCACAGGCCAACCCAGGAAGGGTGTGGGTGGGAGGCGGCCTCTCCCTCC
AGCCTGGGCTTTCTGGGGCTGGAGTGCCCCTTCTGTCCGGGTTGTGTCTGCTCCCCTCGT
CCTGCCCTGGAATCCAGGGAGGAAGCTGCCCAGATCCTCAGAAGGGGAGACACTGTTGCC
ACCATTGTCTCAAAATTCT<u>TGA</u>AGCTCAGCCTGTTCTCAGCAGTAGAGAAATCACTAGGA
CTACTTTTTACCAAAAGAGAAGCAGTCTGGGCCAGATGCCCTGCCAGGAAAGGGACATGG
ACCCACGTGCTTGAGGCCTGGCAGCTGGGCCAAGACAGATGGGGCTTTGTGGCCCTGGGG
GTGCTTCTGCAGCCTTGAAAAAGTTGCCCTTACCTCCTAGGGTCACCTCTGCTGCCATTC
TGAGGAACATCTCCAAGGAACAGGAGGGACTTTGGCTAGAGCCTCCTGCCTCCCCATCTT
CTCTCTGCCCAGAGGCTCCTGGGCCTGGCTTGGCTGTCCCCTACCTGTGTCCCCGGGCTG
CACCCCTTCCTCTTCTCTTTCTCTGTACAGTCTCAGTTGCTTGCTCTTGTGCCTCCTGGG
CAAGGGCTGAAGGAGGCCACTCCATCTCACCTCGGGGGGCTGCCCTCAATGTGGGAGTGA
CCCCAGCCAGATCTGAAGGACATTTGGGAGAGGGATGCCCAGGAACGCCTCATCTCAGCA
GCCTGGGCTCGGCATTCCGAAGCTGACTTTCTATAGGCAATTTTGTACCTTTGTGGAGAA
ATGTGTCACCTCCCCCAACCCGATTCACTCTTTTCTCCTGTTTTGTAAAAAATAAAAATA
AATAATAACAATAAAAAAA

FIGURE 61A

```
></usr/seqdb2/sst/DNA/Dnaseqs.min/ss.DNA37151
><subunit 1 of 1, 713 aa, 1 stop
><MW: 78889, pI: 7.49, NX(S/T): 4
MRLLVAPLLLAWVAGATATVPVVPWHVPCPPQCACQIRPWYTPRSSYREATTVDCNDLFL
TAVPPALPAGTQTLLLQSNSIVRVDQSELGYLANLTELDLSQNSFSDARDCDFHALPQLL
SLHLEENQLTRLEDHSFAGLASLQELYLNHNQLYRIAPRAFSGLSNLLRLHLNSNLLRAI
DSRWFEMLPNLEILMIGGNKVDAILDMNFRPLANLRSLVLAGMNLREISDYALEGLQSLE
SLSFYDNQLARVPRRALEQVPGLKFLDLNKNPLQRVGPGDFANMLHLKELGLNNMEELVS
IDKFALVNLPELTKLDITNNPRLSFIHPRAFHHLPQMETLMLNNNALSALHQQTVESLPN
LQEVGLHGNPIRCDCVIRWANATGTRVRFIEPQSTLCAEPPDLQRLPVREVPFREMTDHC
LPLISPRSFPPSLQVASGESMVLHCRALAEPEPEIYWVTPAGLRLTPAHAGRRYRVYPEG
TLELRRVTAEEAGLYTCVAQNLVGADTKTVSVVVGRALLQPGRDEGQGLELRVQETHPYH
ILLSWVTPPNTVSTNLTWSSASSLRGQGATALARLPRGTHSYNITRLLQATEYWACLQVA
FADAHTQLACVWARTKEATSCHRALGDRPGLIAILALAVLLLAAGLAAHLGTGQPRKGVG
GRRPLPPAWAFWGWSAPSVRVVSAPLVLPWNPGRKLPRSSEGETLLPPLSQNS
```

Signal sequence.
Amino acids 1-18.

Transmembrane domain.
Amino acids 628-648, 667-687.

Leucine rich repeat domain.
Amino acids 94-117, 118-141, 142-165, 166-189, 190-213, 214-237, 238-261, 262-285, 286-310, 311-335, 336-359, 360-407.

Immunoglobulin domain.
Amino acids 438-499.

N-glycosylation site.
Amino acids 94-97, 381-834, 555-558, 583-586.

cAMP- and cGMP-dependent protein kinase phosphorylation site.
Amino acids 485-488.

Protein kinase C phosporylation site.
Amino acids 42-44, 46-48, 425-427, 563-565, 678-680.

Casein kinase II phosphorylation site.
Amino acids 46-49, 51-54, 96-99, 104-107, 130-133, 142-145, 243-246, 313-316, 488-491, 700-703.

FIGURE 61B

Tyrosine kinase phosphorylation site.
Amino acids 532-539.

N-myristoylation site.
Amino acids 15-20, 493-498, 566-571.

Amidation site.
Amino acids 470-473, 660-663, 692-695.

FIGURE 62 getseq sst.DNA210233

GGCACGAGCCGGCAAGCCGAGCTAGGGTGAAAACTGGGGGCGCACCAGGATGTXXGACAG
AAAAGCAGAAGATGAGACTCTGTTCATTCACTTTTCCTAGGCCCATCCTGTGGTCATCTT
TCCCCCTCCCATCATACCTCCTCCTTCCTGGAGCCTCTGCCGGCTTGGCTGTAATGGTGG
CACTTACCTGGATATTTCAGTGGGAGGATGAAAGGCGAGACTCACCCTACGCGGTGGGAC
AGATGGGGAGAGGAAAAAGGCAGAGATGGCCAGGAGAGGGGTGCAGGACAAACCAGAGAG
GTTGGGTCAGGGGAAAAGGGTGGGGAGAAAGAGGGGTGCAGGCCCTGCAGGCCGGTTAGC
CAGCAGCTGCGGCCTCCCCGGGCCCTTGGCATCCAACTTCGCAGACAGGGTACCAGCCTC
CTGGTGTGTATCATAGGATTTGTTCACATAGTGTTATGCATGATCTTCGTAAGGTTAAGA
AGCCGTGGTGGTGCACCATGACATCCAACCCGTATATATAAAGATAAATATATATATATA
TGTATGTAAATTATGGCACGAGAAATTATAGCACTGAGGGCCCTGCTGCCCTGCTGGACC
AAGCAAAACTAAGCCTTTTGGTTTGGGTATTATGTTTCGTTTTGTTATTTGTTTGTTTTT
GTGGCTTGTCTTATGTCGTGATAGCACAAGTGCCAGTCGGATTGCTCTGTATTACAGAAT
AGTGTTTTTAATTCATCAATGTTCTAGTTAATGTCTACCTCAGCACCTCCTCTTAGCCTA
ATTTTAGGAGGTTGCCCAATTTTGTTTCTTCAATTTTACTGGTTACTTTTTGTACAAAT
CAATCTCTTTCTCTCTTTCTCTCCTCCCCACCTCTCACCCTTGCCCTCTCCATCTCCCTC
TCCCGCCCTCCCCTCCTCCCTCTGGCTCCCCGTCTCATTTCTGTCCACTCCATTCTCTCT
CCCTCTCTCCTGCCTCCTGCTGCCCCCTCCCCAGCCCACTTCCCCGAGTTGTGCTTGCCG
CTCCTTATCTGTTCTAGTTCCGAAGCAGTTTCACTCGAAGTTGTGCAGTCCTGGTTGCAG
CTTTCCGCATCTGCCTTCGTTTCGTGTAGATTGACGCGTTTCTTTGTAATTTCAGTGTTT
CTGACAAGATTTAAAAAAAAAAAAAAGGAAAAAAAAAAAAAAAAAAAA

FIGURE 63

></usr/seqdb2/sst/DNA/Dnaseqs.min/ss.DNA210233
><subunit 1 of 1, 145 aa, 0 stop
><MW: 15963, pI: 10.59, NX(S/T): 1
MSTSAPPLSLILGGCPILFLQFYWLLFCTNQSLSLFLSSPPLTLALSISLSRPPLLPLAP
RLISVHSILSPSLLPPAAPSPAHFPELCLPLLICSSSEAVSLEVVQSWLQLSASAFVSCR
LTRFFVISVFLTRFKKKKRKKKKK Signal sequence.
Amino acids 1-45.

Transmembrane domain.
Amino acids 54-74, 108-128.

N-glycosylation site.
Amino acids 30-33.

Protein kinase C phosphorylation site.
Amino acids 118-120.

Casein kinase II phosphorylation site.
Amino acids 95-98.

Prokaryotic membrane lipoprotein lipid attachment site.
Amino acids 5-15, 109-119.

FIGURE 64 getseq sst.DNA35918

CCCACGCGTCCGCACCTCGGCCCCGGGCTCCGAAGCGGCTCGGGGGCGCCCTTTCGGTCA
ACATCGTAGTCCACCCCCTCCCCATCCCCAGCCCCGGGGATTCAGGCTCGCCAGCGCCC
AGCCAGGGAGCCGGCCGGGAAGCGCG<u>ATG</u>GGGGCCCCAGCCGCCTCGCTCCTGCTCCTGC
TCCTGCTGTTCGCCTGCTGCTGGGCGCCCGGCGGGGCCAACCTCTCCCAGGACGACAGCC
AGCCCTGGACATCTGATGAAACAGTGGTGGCTGGTGGCACCGTGGTGCTCAAGTGCCAAG
TGAAAGATCACGAGGACTCATCCCTGCAATGGTCTAACCCTGCTCAGCAGACTCTCTACT
TTGGGGAGAAGAGAGCCCTTCGAGATAATCGAATTCAGCTGGTTACCTCTACGCCCCACG
AGCTCAGCATCAGCATCAGCAATGTGGCCCTGGCAGACGAGGGCGAGTACACCTGCTCAA
TCTTCACTATGCCTGTGCGAACTGCCAAGTCCCTCGTCACTGTGCTAGGAATTCCACAGA
AGCCCATCATCACTGGTTATAAATCTTCATTACGGGAAAAAGACACAGCCACCCTAAACT
GTCAGTCTTCTGGGAGCAAGCCTGCAGCCCGGCTCACCTGGAGAAAGGGTGACCAAGAAC
TCCACGGAGAACCAACCCGCATACAGGAAGATCCCAATGGTAAAACCTTCACTGTCAGCA
GCTCGGTGACATTCCAGGTTACCCGGGAGGATGATGGGGCGAGCATCGTGTGCTCTGTGA
ACCATGAATCTCTAAAGGGAGCTGACAGATCCACCTCTCAACGCATTGAAGTTTTATACA
CACCAACTGCGATGATTAGGCCAGACCCTCCCCATCCTCGTGAGGGCCAGAAGCTGTTGC
TACACTGTGAGGGTCGCGGCAATCCAGTCCCCCAGCAGTACCTATGGGAGAAGGAGGGCA
GTGTGCCACCCCTGAAGATGACCCAGGAGAGTGCCCTGATCTTCCCTTTCCTCAACAAGA
GTGACAGTGGCACCTACGGCTGCACAGCCACCAGCAACATGGGCAGCTACAAGGCCTACT
ACACCCTCAATGTTAATGACCCCAGTCCGGTGCCCTCCTCCTCCAGCACCTACCACGCCA
TCATCGGTGGGATCGTGGCTTTCATTGTCTTCCTGCTGCTCATCATGCTCATCTTCCTTG
GCCACTACTTGATCCGGCACAAAGGAACCTACCTGACACATGAGGCAAAAGGCTCCGACG
ATGCTCCAGACGCGGACACGGCCATCATCAATGCAGAAGGCGGGCAGTCAGGAGGGGACG
ACAAGAAGGAATATTTCATC<u>TAG</u>AGGCGCCTGCCCACTTCCTGCGCCCCCAGGGGCCCT
GTGGGGACTGCTGGGGCCGTCACCAACCCGGACTTGTACAGAGCAACCGCAGGGCCGCCC
CTCCCGCTTGCTCCCCAGCCCACCCACCCCCCTGTACAGAATGTCTGCTTTGGGTGCGGT
TTTGTACTCGGTTTGGAATGGGGAGGGAGGAGGGCGGGGGAGGGGAGGGTTGCCCTCAG
CCCTTTCCGTGGCTTCTCTGCATTTGGGTTATTATTATTTTTGTAACAATCCCAAATCAA
ATCTGTCTCCAGGCTGGAGAGGCAGGAGCCCTGGGGTGAGAAAAGCAAAAAACAAACAAA
AAACA

FIGURE 65

><Tue Nov 11 14:57:29 PST 1997 DNA35918 [min]
></usr/seqdb2/sst/DNA/Dnaseqs.min/ss.DNA35918
><subunit 1 of 1, 398 aa, 1 stop
><MW: 43300, pI: 6.00, NX(S/T): 2
MGAPAASLLLLLLLLFACCWAPGGANLSQDDSQPWTSDETVVAGGTVVLKCQVKDHEDSSL
QWSNPAQQTLYFGEKRALRDNRIQLVTSTPHELSISISNVALADEGEYTCSIFTMPVRTA
KSLVTVLGIPQKPIITGYKSSLREKDTATLNCQSSGSKPAARLTWRKGDQELHGEPTRIQ
EDPNGKTFTVSSSVTFQVTREDDGASIVCSVNHESLKGADRSTSQRIEVLYTPTAMIRPD
PPHPREGQKLLLHCEGRGNPVPQQYLWEKEGSVPPLKMTQESALIFPFLNKSDSGTYGCT
ATSNMGSYKAYYTLNVNDPSPVPSSSSTYHAIIGGIVAFIVFLLLIMLIFLGHYLIRHKG
TYLTHEAKGSDDAPDADTAIINAEGGQSGGDDKKEYFI Signal Sequence
Amino acids 1-20.

Transmembrane domain.
Amino acids 332-352.

Immunoglobulin domain.
Amino acids 43-112, 145-211, 247-301.

N-glycosylation site.
Amino acids 25-28, 290-293, 119-121, 141-143, 164-166, 215-217, 224-226, 307-309.

Casein kinase II phosphorylation site.
Amino acids 27-30, 35-38, 89-92, 141-144, 199-202, 388-391.

N-myristoylation site.
Amino acids 2-7, 23-28, 156-161, 218-223, 295-300, 298-303, 306-311, 334-339, 360-365, 385-390, 386-391.

Prokaryotic membrane lipoprotein lipid attachment site.
Amino acids 7-17.

FIGURE 66 getseq sst.DNA260038

CTTGGATCTGCCTGCCAGGCCATCCTGGGCGCTGCAGGAAGCAACATGACTTAGGTAACT
GCCCAGAGGTGCACCAGACATGATGCAGCAGCCGCGAGTGGAGACAGATACCATCGGGGC
TGGCGAGGGGCCACAGCAGGCAGTGCCTGGTCAGCCTGGGTCACGAGGCATGGCTGGGTG
CGCTGGTGGGTGAGCCACATGCCCCGAGCTGGATCCAGTGGTGGAGCACCTCGAACTGG
CGGCAACGGCTGCAGCGCCTGCTGTGGGTCTGGAGGGGATACTCTACCTGCTGCTGGCA
CTGATGTTGTGCCATGCACTCTTCACCACTGGCTCCCACCTGCTGAGCTCCTTGTGGCCT
GTCGTGGCCGCGGTGTGGCGCCACCTGCTACCGGCTCTCCTGCTGCTGGTGCTCAGTGCT
CTGCCTGCCCTCCTCTTCACGGCCTCCTTCCTGCTGCTCTTCTCCACACTGCTGAGCCTT
GTGGGCCTCCTCACCTCCATGACTCACCCAGGCGACACTCAGGATTTGGATCAATAGAAG
GGCAACCCCATCCCACTGCCTGTGTTTGTTGAGCCCTGGCCTAGGGCCTGAGACCCCACG
GGGAGAGGGAGGGCAATGGGATCAGGGCTCCCTGCCTTGGCAGGGCCCAGACCCCTAGTC
CCTAACAGGTAGGCTGGCCTG

FIGURE 67

></usr/seqdb2/sst/DNA/Dnaseqs.min/ss.DNA260038
><subunit 1 of 1, 112 aa, 1 stop
><MW: 12573, pI: 6.85, NX(S/T): 0
MPPSWIQWWSTSNWRQPLQRLLWGLEGILYLLLALMLCHALFTTGSHLLSSLWPVVAAVW
RHLLPALLLLVLSALPALLFTASFLLLFSTLLSLVGLLTSMTHPGDTQDLDQ Signal sequence.
Amino acids 1-40.

Transmembrane domain.
Amino acids 54-74, 70-90.

N-myristoylation site.
Amino acids 96-101.

Eukaryotic thiol (cysteine) proteases histidine active site.
Amino acids 37-47.

FIGURE 68 getseq sst.DNA334818

AC<u>ATG</u>CGCCCTGACAGCCCAACAATGGCGGCGCCCGCGGAGTCGCTGAGGAGGCGGAAGA
CTGGGTACTCGGATCCGGAGCCTGAGTCGCCGCCCGCGCCGGGGCGTGGCCCCGCAGGCT
CTCCGGCCCATCTTCACACGGGCACCTTCTGGCTGACCCGGATCGTGCTCCTGAAGGCCC
TAGCCTTCGTGTACTTCGTGGCATTCCTGGTGGCTTTCCATCAGAACAAGCAGCTCATCG
GTGACAGGGGGCTGCTTCCCTGCAGAGTGTTCCTGAAGGACTTCCAGCAGTACTTCCAGG
ACAGGACAAGCTGGGAAGTCTTCAGCTACATGCCCACCATCCTCTGGCTGATGGACTGGT
CAGACATGAACTCCAACCTGGACTTGCTGGCTCTTCTCGGACTGGGCATCTCGTCTTTCG
TACTGATCACGGGTTGCGCCAACATGCTTCTCATGGCTGCCCTGTGGGCCTCTACATGT
CCCTGGTTAATGTGGGCCATGTCTGGTACTCTTTCGGATGGGAGTCCCAGCTTCTGGAGA
CGGGATTCCTGGGGATCTTCCTGTGCCCTCTGTGGACGCTGTCAAGGCTGCCCCAGCATA
CCCCCACATCCCGGATTGTCCTGTGGGCTTCCGGTGGCTGATCTTCAGGATCATGCTTG
GAGCAGGCCTGATCAAGATCCGGGGGGACCGGTGCTGGCGAGACCTCACCTGCATGGACT
TCCACTATGAGACCCAGCCGATGCCCAATCCTGTGGCATACTACCTGCACCACTCACCCT
GGTGGTTCCATCGCTTCGAGACGCTCAGCAACCACTTCATCGAGCTCCTGGTGCCCTTCT
TCCTCTTCCTCGGCCGGCGGGCGTGCATCATCCACGGGGTGCTGCAGATCCTGTTCCAGG
CCGTCCTCATCGTCAGCGGGAACCTCAGCTTCCTGAACTGGCTGACTATGGTGCCCAGCC
TGGCCTGCTTTGATGACGCCACCCTGGGATTCTTGTTCCCCTCTGGGCCAGGCAGCCTGA
AGGACCGAGTTCTGCAGATGCAGAGGGACATCCGAGGGGCCCGGCCCGAGCCCAGATTCG
GCTCCGTGGTGCGGCGTGCAGCCAACGTCTCGCTGGGCGTCCTGCTGGCCTGGCTCAGCG
TGCCCGTGGTCCTCAACTTGCTGAGCTCCAGGCAGGTCATGAACACCCACTTCAACTCTC
TTCACATCGTCAACACTTACGGGGCCTTCGGAAGCATCACCAAGGAGCGGGCGGAGGTGA
TCCTGCAGGGCACAGCCAGCTCCAACGCCAGCGCCCCGATGCCATGTGGGAGGACTACG
AGTTCAAGTGCAAGCCAGGTGACCCCAGCAGACGGCCCTGCCTCATCTCCCCGTACCACT
ACCGCCTGGACTGGCTGATGTGGTTCGCGGCCTTCCAGACCTACGAGCACAACGACTGGA
TCATCCACCTGGCTGGCAAGCTCCTGGCCAGCGACGCCGAGGCCTTGTCCCTGCTGGCAC
ACAACCCCTTCGCGGGCAGGCCCCGCCCAGGTGGGTCCGAGGAGAGCACTACAGGTACA
AGTTCAGCCGTCCTGGGGGCAGGCACGCCGCCGAGGGCAAGTGGTGGGTGCGGAAGAGGA
TCGGAGCCTACTTCCCTCCGCTCAGCCTGGAGGAGCTGAGGCCCTACTTCAGGGACCGTG
GGTGGCCTCTGCCCGGGCCCCTC<u>TAG</u>ACGTGCACCAGAAATAAAGGCGAAGACCCAGCCC
CTCGGCGGCTCAGCAACGTTTGCCCTTCCCTGCGCCCAGCCCAAGCTGGGCATCGCCAAG
AGAGACGTGGAGAGGAGAGCGGTGGGACCCAGCCCCAGCACGGGGGTCCAGGGTGGGGT
CTGTTGTCACATACTGTGGCGGCTCCCAGGCCCTGCCCACCTGGGGCCCCACATCCAGGC
CAACCCTTGTCCCAGGCGCCAGGGGCTCTGATCTCCCATCCATCCCACCCTCCTCCCAGA
GGCCCAGCCTGGGGCTGTGCCGCCCACAGGAGTTGAGACAATGGCAATCCTGACACCTTC
CTCCACTACAGCCCTGACCATAGACCCAGCCAGGTAGCTCTTGGGGTCTCTAGCGTCCCA
GGGCCTGGTTTCTGTTCCCTCTTCAATGGTGTGTTCCCAGCCAGGTCCTGACCCTCAGAG
CCAAGTCCCTGTCACGTCTGGGGCAGCCAAACCCTCGCCCCACAGGGACCTGGACACGCC
CGGCCAGGATGTGGGGTTGGATGGGCCATTTTCTGTCCTATCCCTCATCTCCACCCCCGC
CACAGCCTACACGCATCCCACACATGCAGGCACACACAGCCTGTGCACACATGTGTTCTT
GGCCCGGTTTCATCCCCCCATGACTGGTGTCTGTGAGGTGCAGATGGACACAGCGCACAC
CCAGACCCTCCACCAGGCTGTGACCTCGCTGCCTCTGAGGCCTTGACAAGGCCCCTCAAT
CGGAGGACAGCCGGCCGTGCACACTTTCATCATCGTCGGACAAACAGCGTCTACTGCACA
TTTTTCTTATTCCTATTCTTGAGCCATAGCTATGGCATATTCTTCTACTATTCCTATTAT
ACCACTTACCAGCTTACTCG

FIGURE 69A

```
></usr/seqdb2/sst/DNA/Dnaseqs.min/ss.DNA334818
><subunit 1 of 1, 567 aa, 1 stop
><MW: 64874, pI: 9.45, NX(S/T): 3

MRPDSPTMAAPAESLRRRKTGYSDPEPESPPAPGRGPAGSPAHLHTGTFWLTRIVLLKAL
AFVYFVAFLVAFHQNKQLIGDRGLLPCRVFLKDFQQYFQDRTSWEVFSYMPTILWLMDWS
DMNSNLDLLALLGLGISSFVLITGCANMLLMAALWGLYMSLVNVGHVWYSFGWESQLLET
GFLGIFLCPLWTLSRLPQHTPTSRIVLWGFRWLIFRIMLGAGLIKIRGDRCWRDLTCMDF
HYETQPMPNPVAYYLHHSPWWFHRFETLSNHFIELLVPFFLFLGRRACIIHGVLQILFQA
VLIVSGNLSFLNWLTMVPSLACFDDATLGFLFPSGPGSLKDRVLQMQRDIRGARPEPRFG
SVVRRAANVSLGVLLAWLSVPVVLNLLSSRQVMNTHFNSLHIVNTYGAFGSITKERAEVI
LQGTASSNASAPDAMWEDYEFKCKPGDPSRRPCLISPYHYRLDWLMWFAAFQTYEHNDWI
IHLAGKLLASDAEALSLLAHNPFAGRPPPRWVRGEHYRYKFSRPGGRHAAEGKWWVRKRI
GAYFPPLSLEELRPYFRDRGWPLPGPL
```

Transmembrane domain.
Amino acids 51-71, 124-144, 175-195, 205-225, 272-292, 295-315, 320-340, 365-385.

Protein of unknown function (DUF1222) domain.
Amino acids 362-549.

N-glycosylation site.
Amino acids 307-310, 368-371, 428-431.

Glycosaminoglycan attachment site.
Amino acids 334-337.

cAMP- and cGMP-dependent protein kinase phosphorylation site.
Amino acids 17-20.

Protein kinase C phosphorylation site.
Amino acids 14-16, 202-204, 338-340, 388-390, 449-451.

Casein kinase II phosphorylation site.
Amino acids 23-26, 102-105, 124-127, 236-239, 338-341, 430-433, 490-493, 548-551.

Tyrosine kianse phosphorylation site.
Amino acids 101-109.

FIGURE 69B

N-myristoylation site.
Amino acids 83-88, 133-138, 156-161, 372-377, 407-412, 423-428, 525-530.

Amidation site.
Amino acids 283-286.

Prokaryotic membrane lipoprotein lipid attachment site.
Amino acids 135-145.

Cell attachment sequence.
Amino acids 227-229.

FIGURE 70 getseq sst.DNA257501

GGCACGAGGAGAAGACTTTGGTGGGGTAGTCTCGGGGCAGCTCAGCGGCCCGCTGTGCCC
GTTTCTGGCCTCGCTCGCAGCTTGCACGTCGAGACTCGTAGGCCGCACCGTAGGGCGAGC
GTGCGGGTCGCCGCCGCGGCCGCCTCGGGGTCTGGGCCCAGCCGCAGCCTCTTCTACCGC
GGCCGGTTGGGAGTCGCCGCGAG<u>ATG</u>CAGCCTCCGGGCCCGCCCCGGCCTATGCCCCA
CTAACGGGACTTCACCTTTGTCTCCTCAGCAGACGCGGAAGATCTCAGTGGTTCAATAG
CATCCCCAGATGTCAAATTAAATCTTGGTGGAGATTTTATCAAAGAATCTACAGCTACTA
CATTTCTGAGACAAAGAGGTTATGGCTGGCTTCTGGAAGTTGAAGATGATGATCCTGAAG
ATAACAAGCCACTCTTGGAAGAATTGGACATTGATCTAAAGGATATTTACTACAAAATCC
GATGTGTTTTGATGCCAATGCCATCACTTGGTTTTAATAGACAAGTGGTGAGAGACAATC
CTGACTTTTGGGGTCCTCTGGCTGTTGTTCTTTTCTTTTCCATGATATCATTATATGGAC
AGTTTAGGGTGGTCTCATGGATTATAACCATTTGGATATTTGGTTCACTAACAATTTTCT
TACTGGCCAGAGTTCTTGGTGGAGAAGTTGCATATGGCCAAGTCCTTGGAGTTATAGGAT
ATTCATTACTTCCTCTCATTGTAATAGCCCCTGTACTTTTGGTGGTTGGATCATTTGAAG
TGGTGTCTACACTTATAAAACTGTTTGGTGTGTTTTGGGCTGCCTACAGTGCTGCTTCAT
TGTTAGTGGGTGAAGAATTCAAGACCAAAAAGCCTCTTCTGATTTATCCAATCTTTTTAT
TATACATTTATTTTTTGTCGTTATATACTGGTGTG<u>TGA</u>TCCAAGTTATACATGAATAGAA
AAAGATGGTGTTAAATTTGTGTGTAGGCTGGGAATTCTTGCTGAAGGAATTGGAGAAAAC
CTGTTGCTGCAAAATTTTACATGTTCCAGATGGAAAGGGAAGTCTAAGCGCTTTTTAAAA
CAATTTTTTTTTGTATTTAATTAAGCAATTGCAGTTATCTGGGATTTTTGGGTCAGAATT
TTAAATTCTGTTTGATTCTCCATATTCCAGTGAATAAAATACAAAAGCATTGTGTTTTTA
AGATTGTGTCGATATTCACCTAAAAACTTGTGCCAAAAGCACCTGGATTGGTAATTATAT
TTCACTTAAAGGGTAAATTTGACAATATCTTGATAATCAAAAGTGCAATTTTTTTCTTCA
AAATGTTTTCTCCAGCATCACAGATCCTGCAGATATATATTTATATTTATACATATATAT
TTATGAAATAATTCTTACTCACAAAATATATTTCTGATAAACATTAAGATATTAAATCTG
ATGCACAAACTTTAATTTGGCCATTAATCTTTTTATTTAAAAATTTAAATTTGTTTTTA
AAATTGTATATAGTTTTTAAAATCTCACACATGCTTCGATACTTCCTTGTTAAGAATTCT
TAATAACTACTAAAACTGATTTTTAATAGTTGCTGATATATATTTGGTTTGTTTGGGTAT
ACTTTTCAAAACCATTTTTGAATGTCCAAACATCTGATTTAAAGTTTCTGTTTATCTTTC
TGACCAAAGGAGCAAGAGGTATAATGGATATGGCATTCATTAAAATCTTTACTATGTACA
AAAACAGTAATATTTACAGCATCAGTAAATATTTTTAAGTGGTACTTCTAAATCATAAAA
GTTGGGGAAAGAGACCTTTAAAATCTTGTGGTGTTGAACAATGTTATATGAAGTAGAAAA
AATAAAATACTTCCCAGTTGTGAAAAAAAAAAAAAAAAAA

FIGURE 71

></usr/seqdb2/sst/DNA/Dnaseqs.min/ss.DNA257501
><subunit 1 of 1, 244 aa, 1 stop
><MW: 27083, pI: 4.49, NX(S/T): 0
MQPPGPPPAYAPTNGDFTFVSSADAEDLSGSIASPDVKLNLGGDFIKESTATTFLRQRGY
GWLLEVEDDDPEDNKPLLEELDIDLKDIYYKIRCVLMPMPSLGFNRQVVRDNPDFWGPLA
VVLFFSMISLYGQFRVVSWIITIWIFGSLTIFLLARVLGGEVAYGQVLGVIGYSLLPLIV
IAPVLLVVGSFEVVSTLIKLFGVFWAAYSAASLLVGEBFKTKKPLLIYPIFLLYIYFLSL Transmembrane domain.
Amino acids 115-135, 136-156, 170-190, 186-206, 224-243.

Yip1 domain.
Amino acids 81-226.

Protein kinase C phosphorylation site.
Amino acids 221-223.

Casein kinase II phosphorylation site.
Amino acids 13-16, 21-24.

N-myristoylation site.
Amino acids 159-164, 165-170, 202-207.

SEQUENCE LISTING

```
<160> NUMBER OF SEQ ID NOS: 75

<210> SEQ ID NO 1
<211> LENGTH: 2037
<212> TYPE: DNA
<213> ORGANISM: Homo sapiens
```

```
<400> SEQUENCE: 1
agtgtgatgg atatctgcag aattcgccct tatggcgttt gacgtcagct        50
gcttcttttg ggtggtgctg ttttctgccg gctgtaaagt catcacctcc       100
tgggatcaga tgtgcattga gaaagaagcc aacaaaacat ataactgtga       150
aaatttaggt ctcagtgaaa tccctgacac tctaccaaac acaacagaat       200
ttttggaatt cagctttaat tttttgccta caattcacaa tagaaccttc       250
agcagactca tgaatcttac cttttttggat ttaactaggt gccagattaa      300
ctggatacat gaagacactt ttcaaagcca tcatcaatta agcacacttg       350
tgttaactgg aaatcccctg atattcatgg cagaaacatc gcttaatggg       400
cccaagtcac tgaagcatct tttcttaatc caaacgggaa tatccaatct       450
cgagtttatt ccagtgcaca atctggaaaa cttggaaagc ttgtatcttg       500
gaagcaacca tatttcctcc attaagttcc caaagactt cccagcacgg        550 aatctgaaag tactggattt tcagaataat gctatacact acatctctag       600
agaagacatg aggtctctgg agcaggccat caacctaagc ctgaacttca       650
atggcaataa tgttaaaggt attgagcttg gggcttttga ttcaacggtc       700
ttccaaagtt tgaactttgg aggaactcca aatttgtctg ttatattcaa       750
tggtctgcag aactctacta ctcagtctct ctggctggga acatttgagg       800
acattgatga cgaagatatt agttcagcca tgctcaaggg actctgtgaa       850
atgtctgttg agagcctcaa cctgcaggaa caccgcttct ctgacatctc       900
atccaccaca tttcagtgct tcacccaact ccaagaattg gatctgacag       950
caactcactt gaaagggtta ccctctggga tgaagggtct gaacttgctc      1000
aagaaattag ttctcagtgt aaatcatttc gatcaattgt gtcaaatcag      1050
tgctgccaat ttcccctccc ttacacacct ctacatcaga ggcaacgtga      1100
agaaacttca ccttggtgtt ggctgcttgg agaaactagg aaaccttcag      1150
acacttgatt taagccataa tgacatagag gcttctgact gctgcagtct      1200
gcaactcaaa aacctgtccc acttgcaaac cttaaacctg agccacaatg      1250
agcctcttgg tctccagagt caggcattca agaatgtcc tcagctagaa       1300 ctcctcgatt tggcatttac ccgcttacac attaatgctc cacaaagtcc      1350
cttccaaaac ctccatttcc ttcaggttct gaatctcact tactgcttcc      1400
ttgataccag caatcagcat cttctagcag gcctaccagt tctccggcat      1450
ctcaacttaa aagggaatca ctttcaagat gggactatca cgaagaccaa      1500
cctacttcag accgtgggca gcttggaggt tctgattttg tcctcttgtg      1550
gtctcctctc tatagaccag caagcattcc acagcttggg aaaaatgagc      1600
catgtagact taagccacaa cagcctgaca tgcgacagca ttgattctct      1650
tagccatctt aagggaatct acctcaatct ggctgccaac agcattaaca      1700
tcatctcacc ccgtctcctc cctatcttgt cccagcagag caccattaat      1750
ttaagtcata accccctgga ctgcacttgc tcgaatattc atttcttaac      1800
atggtacaaa gaaaacctgc acaaacttga aggctcggag gagaccacgt      1850
gtgcaaaccc gccatctcta aggggagtta agctatctga tgtcaagctt      1900
tcctgtggga ttacagccat aggcatttc tttctcatag tatttctatt        1950
```

-continued

```
attgttggct attctgctat tttttgcagt taaataccct tctcaggtgga        2000 aataccaaca catttagtgc tgaaggtttc cagagaa                       2037
```

<210> SEQ ID NO 2
<211> LENGTH: 660
<212> TYPE: PRT
<213> ORGANISM: Homo sapiens

<400> SEQUENCE: 2

```
Met Ala Phe Asp Val Ser Cys Phe Phe Trp Val Val Leu Phe Ser
 1               5                  10                  15

Ala Gly Cys Lys Val Ile Thr Ser Trp Asp Gln Met Cys Ile Glu
                20                  25                  30

Lys Glu Ala Asn Lys Thr Tyr Asn Cys Glu Asn Leu Gly Leu Ser
                35                  40                  45

Glu Ile Pro Asp Thr Leu Pro Asn Thr Thr Glu Phe Leu Glu Phe
                50                  55                  60

Ser Phe Asn Phe Leu Pro Thr Ile His Asn Arg Thr Phe Ser Arg
                65                  70                  75

Leu Met Asn Leu Thr Phe Leu Asp Leu Thr Arg Cys Gln Ile Asn
                80                  85                  90

Trp Ile His Glu Asp Thr Phe Gln Ser His His Gln Leu Ser Thr
                95                 100                 105

Leu Val Leu Thr Gly Asn Pro Leu Ile Phe Met Ala Glu Thr Ser
               110                 115                 120

Leu Asn Gly Pro Lys Ser Leu Lys His Leu Phe Leu Ile Gln Thr
               125                 130                 135

Gly Ile Ser Asn Leu Glu Phe Ile Pro Val His Asn Leu Glu Asn
               140                 145                 150

Leu Glu Ser Leu Tyr Leu Gly Ser Asn His Ile Ser Ser Ile Lys
               155                 160                 165

Phe Pro Lys Asp Phe Pro Ala Arg Asn Leu Lys Val Leu Asp Phe
               170                 175                 180

Gln Asn Asn Ala Ile His Tyr Ile Ser Arg Glu Asp Met Arg Ser
               185                 190                 195

Leu Glu Gln Ala Ile Asn Leu Ser Leu Asn Phe Asn Gly Asn Asn
               200                 205                 210

Val Lys Gly Ile Glu Leu Gly Ala Phe Asp Ser Thr Val Phe Gln
               215                 220                 225

Ser Leu Asn Phe Gly Gly Thr Pro Asn Leu Ser Val Ile Phe Asn
               230                 235                 240

Gly Leu Gln Asn Ser Thr Thr Gln Ser Leu Trp Leu Gly Thr Phe
               245                 250                 255

Glu Asp Ile Asp Asp Glu Asp Ile Ser Ser Ala Met Leu Lys Gly
               260                 265                 270

Leu Cys Glu Met Ser Val Glu Ser Leu Asn Leu Gln Glu His Arg
               275                 280                 285

Phe Ser Asp Ile Ser Ser Thr Thr Phe Gln Cys Phe Thr Gln Leu
               290                 295                 300

Gln Glu Leu Asp Leu Thr Ala Thr His Leu Lys Gly Leu Pro Ser
               305                 310                 315

Gly Met Lys Gly Leu Asn Leu Leu Lys Lys Leu Val Leu Ser Val
               320                 325                 330
```

-continued

Asn His Phe Asp Gln Leu Cys Gln Ile Ser Ala Ala Asn Phe Pro
            335                 340                 345

Ser Leu Thr His Leu Tyr Ile Arg Gly Asn Val Lys Lys Leu His
            350                 355                 360

Leu Gly Val Gly Cys Leu Glu Lys Leu Gly Asn Leu Gln Thr Leu
            365                 370                 375

Asp Leu Ser His Asn Asp Ile Glu Ala Ser Asp Cys Cys Ser Leu
            380                 385                 390

Gln Leu Lys Asn Leu Ser His Leu Gln Thr Leu Asn Leu Ser His
            395                 400                 405

Asn Glu Pro Leu Gly Leu Gln Ser Gln Ala Phe Lys Glu Cys Pro
            410                 415                 420

Gln Leu Glu Leu Leu Asp Leu Ala Phe Thr Arg Leu His Ile Asn
            425                 430                 435

Ala Pro Gln Ser Pro Phe Gln Asn Leu His Phe Leu Gln Val Leu
            440                 445                 450

Asn Leu Thr Tyr Cys Phe Leu Asp Thr Ser Asn Gln His Leu Leu
            455                 460                 465

Ala Gly Leu Pro Val Leu Arg His Leu Asn Leu Lys Gly Asn His
            470                 475                 480

Phe Gln Asp Gly Thr Ile Thr Lys Thr Asn Leu Leu Gln Thr Val
            485                 490                 495

Gly Ser Leu Glu Val Leu Ile Leu Ser Ser Cys Gly Leu Leu Ser
            500                 505                 510

Ile Asp Gln Gln Ala Phe His Ser Leu Gly Lys Met Ser His Val
            515                 520                 525

Asp Leu Ser His Asn Ser Leu Thr Cys Asp Ser Ile Asp Ser Leu
            530                 535                 540

Ser His Leu Lys Gly Ile Tyr Leu Asn Leu Ala Ala Asn Ser Ile
            545                 550                 555

Asn Ile Ile Ser Pro Arg Leu Leu Pro Ile Leu Ser Gln Gln Ser
            560                 565                 570

Thr Ile Asn Leu Ser His Asn Pro Leu Asp Cys Thr Cys Ser Asn
            575                 580                 585

Ile His Phe Leu Thr Trp Tyr Lys Glu Asn Leu His Lys Leu Glu
            590                 595                 600

Gly Ser Glu Glu Thr Thr Cys Ala Asn Pro Pro Ser Leu Arg Gly
            605                 610                 615

Val Lys Leu Ser Asp Val Lys Leu Ser Cys Gly Ile Thr Ala Ile
            620                 625                 630

Gly Ile Phe Phe Leu Ile Val Phe Leu Leu Leu Ala Ile Leu
            635                 640                 645

Leu Phe Phe Ala Val Lys Tyr Leu Leu Arg Trp Lys Tyr Gln His
            650                 655                 660

<210> SEQ ID NO 3
<211> LENGTH: 2661
<212> TYPE: DNA
<213> ORGANISM: Homo sapiens

<400> SEQUENCE: 3
cagcagtagg ccttgcctca gatccaaggt cactcggaag aggccatgtc        50
taccctcaat gacactcatg gaggaaatgc tgagagaagc attcagatgc       100
atgacacaag gtaagactgc caaaaatctt gttcttgctc tcctcatttt       150

```
gttatttgtt ttattttttag gagttttgag agcaaaatga caacacccag      200
aaattcagta aatgggactt tcccggcaga gccaatgaaa ggccctattg      250
ctatgcaatc tggtccaaaa ccactcttca ggaggatgtc ttcactggtg      300
ggccccacgc aaagcttctt catgagggaa tctaagactt tggggggctgt     350 ccagattatg aatgggctct tccacattgc cctgggggt cttctgatga       400 tcccagcagg gatctatgca cccatctgtg tgactgtgtg gtaccctctc      450
tggggaggca ttatgtatat tatttccgga tcactcctgg cagcaacgga      500
gaaaaactcc aggaagtgtt tggtcaaagg aaaaatgata atgaattcat      550
tgagcctctt tgctgccatt tctggaatga ttctttcaat catggacata      600
cttaatatta aaatttccca tttttttaaaa atggagagtc tgaattttat     650
tagagctcac acaccatata ttaacatata caactgtgaa ccagctaatc      700
cctctgagaa aaactcccca tctacccaat actgttacag catacaatct      750
ctgttcttgg gcattttgtc agtgatgctg atctttgcct tcttccagga      800
acttgtaata gctggcatcg ttgagaatga atggaaaaga acgtgctcca      850
gacccaaatc taacatagtt ctcctgtcag cagaagaaaa aaagaacag       900 actattgaaa taaagaagaa agtggttggg ctaactgaaa catcttccca      950
accaaagaat gaagaagaca ttgaaattat tccaatccaa gaagaggaag      1000
aagaagaaac agagacgaac tttccagaac ctccccaaga tcaggaatcc      1050
tcaccaatag aaaatgacag ctctccttaa gtgatttctt ctgttttctg      1100
tttccttttt taaacattag tgttcatagc ttccaagaga catgctgact      1150
ttcatttctt gaggtactct gcacatacgc accacatctc tatctggcct      1200
ttgcatggag tgaccatagc tccttctctc ttacattgaa tgtagagaat      1250
gtagccattg tagcagcttg tgttgtcacg cttcttcttt tgagcaactt      1300
tcttacactg aagaaaggca gaatgagtgc ttcagaatgt gatttcctac      1350
taacctgttc cttggatagg ctttttagta tagtattttt ttttgtcatt      1400
ttctccatca acaaccaggg agactgcacc tgatggaaaa gatatatgac      1450
tgcttcatga cattcctaaa ctatcttttt tttattccac atctacgttt      1500
ttggtggagt cccttttgca tcattgtttt aaggatgata aaaaaaaata      1550
acaactaggg acaatacaga acccattcca tttatctttc tacagggctg      1600
acattgtggc acattcttag agttaccaca ccccatgagg gaagctctaa      1650
atagccaaca cccatctgtt ttttgtaaaa acagcatagc ttatacatgg      1700
acatgtctct gccttaactt ttcctaactc ccactctagg ctattgtttg      1750
catgtctacc tactttttagc cattatgcga gaaaagaaaa aaatgaccat      1800
agaaaatgcc accatgaggt gcccaaattt caaataataa ttaacattta      1850 gttatatttta taatttccag atgacaaagt atttcatcaa ataacttcat     1900
ttgatgttcc atgatcaaga aagaatccct atctctattt tacaagtaat      1950
tcaaagaggc caaataactt gtaaacaaga aaaggtaact tgtcaacagt      2000
cataactagt aattatgaga gccttgtttc ataaccaggg cttcttactc      2050
aaatcctgtg atgtttgaaa taaccaaatt gtctctccaa tgtctgcata      2100
```

```
aactgtgaga gccaagtcaa cagctttat caagaattta ctctctgacc         2150
agcaataaac aagcactgag agacacagag agccagattc agattttacc         2200
catggggata aaaagactca gactttcacc acatttggaa aactacttgc         2250
atcataaata tataataact ggtagtttat atgaagcaga cactaagtgc         2300
tatagacact ctcagaatat catacttgga aacaatgtaa ttaaaatgcc         2350
gaatctgagt caacagctgc cctacttttc aattcagata tactagtacc         2400
ttacctagaa ataatgttaa cctagggtga agtcactata atctgtagtc         2450
tattatttgg gcatttgcta catgatgagt gctgccagat tgtggcaggt         2500
aaagagacaa tgtaatttgc actccctatg atatttctac atttttagcg         2550
accactagtg gaagacattc cccaaaatta gaaaaaaagg agatagaaga         2600
tttctgtcta tgtaaagttc tcaaaatttg ttctaaatta ataaaactat         2650
ctttgtgttc a                                                   2661
```

<210> SEQ ID NO 4
<211> LENGTH: 297
<212> TYPE: PRT
<213> ORGANISM: Homo sapiens

<400> SEQUENCE: 4

```
Met Thr Thr Pro Arg Asn Ser Val Asn Gly Thr Phe Pro Ala Glu
 1               5                  10                  15

Pro Met Lys Gly Pro Ile Ala Met Gln Ser Gly Pro Lys Pro Leu
                20                  25                  30

Phe Arg Arg Met Ser Ser Leu Val Gly Pro Thr Gln Ser Phe Phe
                35                  40                  45

Met Arg Glu Ser Lys Thr Leu Gly Ala Val Gln Ile Met Asn Gly
                50                  55                  60

Leu Phe His Ile Ala Leu Gly Gly Leu Leu Met Ile Pro Ala Gly
                65                  70                  75

Ile Tyr Ala Pro Ile Cys Val Thr Val Trp Tyr Pro Leu Trp Gly
                80                  85                  90

Gly Ile Met Tyr Ile Ile Ser Gly Ser Leu Leu Ala Ala Thr Glu
                95                 100                 105

Lys Asn Ser Arg Lys Cys Leu Val Lys Gly Lys Met Ile Met Asn
               110                 115                 120

Ser Leu Ser Leu Phe Ala Ala Ile Ser Gly Met Ile Leu Ser Ile
               125                 130                 135

Met Asp Ile Leu Asn Ile Lys Ile Ser His Phe Leu Lys Met Glu
               140                 145                 150

Ser Leu Asn Phe Ile Arg Ala His Thr Pro Tyr Ile Asn Ile Tyr
               155                 160                 165

Asn Cys Glu Pro Ala Asn Pro Ser Glu Lys Asn Ser Pro Ser Thr
               170                 175                 180

Gln Tyr Cys Tyr Ser Ile Gln Ser Leu Phe Leu Gly Ile Leu Ser
               185                 190                 195

Val Met Leu Ile Phe Ala Phe Phe Gln Glu Leu Val Ile Ala Gly
               200                 205                 210

Ile Val Glu Asn Glu Trp Lys Arg Thr Cys Ser Arg Pro Lys Ser
               215                 220                 225

Asn Ile Val Leu Leu Ser Ala Glu Glu Lys Lys Glu Gln Thr Ile
               230                 235                 240
```

```
Glu Ile Lys Glu Glu Val Val Gly Leu Thr Glu Thr Ser Ser Gln
            245                 250                 255

Pro Lys Asn Glu Glu Asp Ile Glu Ile Ile Pro Ile Gln Glu Glu
        260                 265                 270

Glu Glu Glu Glu Thr Glu Thr Asn Phe Pro Glu Pro Pro Gln Asp
        275                 280                 285

Gln Glu Ser Ser Pro Ile Glu Asn Asp Ser Ser Pro
        290                 295

<210> SEQ ID NO 5
<211> LENGTH: 1846
<212> TYPE: DNA
<213> ORGANISM: Homo sapiens

<400> SEQUENCE: 5
```

| | | |
|---|---|---|
| gttggtgacc aagagtacat ctcttttcaa atagctggat taggtcctca | 50 |
| tgctgctgtg gtcattgctg gtcatctttg atgcagtcac tgaacaggca | 100 |
| gattcgctga cccttgtggc gccctcttct gtcttcgaag agacagcat | 150 |
| cgttctgaaa tgccagggag aacagaactg gaaaattcag aagatggctt | 200 |
| accataagga taacaaagag ttatctgttt tcaaaaaatt ctcagatttc | 250 |
| cttatccaaa gtgcagtttt aagtgacagt ggtaactatt tctgtagtac | 300 |
| caaaggacaa ctctttctct gggataaaac ttcaaatata gtaaagataa | 350 |
| aagtccaaga gctctttcaa cgtcctgtgc tgactgccag ctccttccag | 400 |
| cccatcgaag ggggtccagt gagcctgaaa tgtgagaccc ggctctctcc | 450 |
| acagaggttg gatgttcaac tccagttctg cttcttcaga gaaaaccagg | 500 |
| tcctggggtc aggctggagc agctctccgg agctccagat ttctgccgtg | 550 |
| tggagtgaag acacagggtc ttactggtgc aaggcagaaa cggtgactca | 600 |
| caggatcaga aaacagagcc tccaatccca gattcacgtg cagagaatcc | 650 |
| ccatctctaa tgtaagcttg gagatccggg cccccggggg acaggtgact | 700 |
| gaaggacaaa aactgatcct gctctgctca gtggctgggg gtacaggaaa | 750 |
| tgtcacattc tcctggtaca gagaggccac aggaaccagt atgggaaaga | 800 |
| aaacccagcg ttccctgtca gcagagctgg agatcccagc tgtgaaagag | 850 |
| agtgatgccg gcaaatatta ctgtagagct gacaacggcc atgtgcctat | 900 |
| ccagagcaag gtggtgaata tccctgtgag aattccagtg tctcgccctg | 950 |
| tcctcaccct caggtctcct ggggcccagg ctgcagtggg ggacctgctg | 1000 |
| gagcttcact gtgaggccct gagaggctct cccccaatct tgtaccaatt | 1050 |
| ttatcatgag gatgtcaccc ttgggaacag ctcggccccc tctggaggag | 1100 |
| gggcctcctt caacctctct ttgactgcag aacattctgg aaactactcc | 1150 |
| tgtgaggcca acaacggcct gggggcccag tgcagtgagg cagtgccagt | 1200 |
| ctccatctca ggacctgatg gctatagaag agacctcatg acagctggag | 1250 |
| ttctctgggg actgtttggt gtccttggtt tcactggtgt gctttgctg | 1300 |
| ttgtatgcct tgttccacaa gatatcagga gaaagttctg ccactaatga | 1350 |
| acccagaggg gcttccaggc caaatcctca agagttcacc tattcaagcc | 1400 |
| caaccccaga catggaggag ctgcagccag tgtatgtcaa tgtgggctct | 1450 |

```
gtagatgtgg atgtggttta ttctcaggtc tggagcatgc agcagccaga      1500
aagctcagca acatcagga cacttctgga gaacaaggac tcccaagtca       1550
tctactcttc tgtgaagaaa tcataacact tggaggaatc agaagggaag      1600
atcaacagca aggatggggc atcattaaga cttgctataa aaccttatga      1650
aaatgcttga ggcttatcac ctgccacagc cagaacgtgc ctcaggaggc      1700
acctcctgtc attttgtcc tgatgatgtt tcttctccaa tatcttcttt       1750
tacctatcaa tattcattga actgctgcta catccagaca ctgtgcaaat      1800
aaattatttc tgctaccttc aaaaaaaaaa aaaaaaaaa atgcag           1846
```

<210> SEQ ID NO 6
<211> LENGTH: 508
<212> TYPE: PRT
<213> ORGANISM: Homo sapiens

<400> SEQUENCE: 6

```
Met Leu Leu Trp Ser Leu Leu Val Ile Phe Asp Ala Val Thr Glu
 1               5                  10                  15

Gln Ala Asp Ser Leu Thr Leu Val Ala Pro Ser Ser Val Phe Glu
                20                  25                  30

Gly Asp Ser Ile Val Leu Lys Cys Gln Gly Glu Gln Asn Trp Lys
                35                  40                  45

Ile Gln Lys Met Ala Tyr His Lys Asp Asn Lys Glu Leu Ser Val
                50                  55                  60

Phe Lys Lys Phe Ser Asp Phe Leu Ile Gln Ser Ala Val Leu Ser
            65                      70                  75

Asp Ser Gly Asn Tyr Phe Cys Ser Thr Lys Gly Gln Leu Phe Leu
                80                  85                  90

Trp Asp Lys Thr Ser Asn Ile Val Lys Ile Lys Val Gln Glu Leu
                95                 100                 105

Phe Gln Arg Pro Val Leu Thr Ala Ser Ser Phe Gln Pro Ile Glu
               110                 115                 120

Gly Gly Pro Val Ser Leu Lys Cys Glu Thr Arg Leu Ser Pro Gln
               125                 130                 135

Arg Leu Asp Val Gln Leu Gln Phe Cys Phe Phe Arg Glu Asn Gln
               140                 145                 150

Val Leu Gly Ser Gly Trp Ser Ser Ser Pro Glu Leu Gln Ile Ser
               155                 160                 165

Ala Val Trp Ser Glu Asp Thr Gly Ser Tyr Trp Cys Lys Ala Glu
               170                 175                 180

Thr Val Thr His Arg Ile Arg Lys Gln Ser Leu Gln Ser Gln Ile
               185                 190                 195

His Val Gln Arg Ile Pro Ile Ser Asn Val Ser Leu Glu Ile Arg
               200                 205                 210

Ala Pro Gly Gly Gln Val Thr Glu Gly Gln Lys Leu Ile Leu Leu
               215                 220                 225

Cys Ser Val Ala Gly Gly Thr Gly Asn Val Thr Phe Ser Trp Tyr
               230                 235                 240

Arg Glu Ala Thr Gly Thr Ser Met Gly Lys Lys Thr Gln Arg Ser
               245                 250                 255

Leu Ser Ala Glu Leu Glu Ile Pro Ala Val Lys Glu Ser Asp Ala
               260                 265                 270

Gly Lys Tyr Tyr Cys Arg Ala Asp Asn Gly His Val Pro Ile Gln
```

```
                    275                 280                 285
Ser Lys Val Val Asn Ile Pro Val Arg Ile Pro Val Ser Arg Pro
                290                 295                 300
Val Leu Thr Leu Arg Ser Pro Gly Ala Gln Ala Val Gly Asp
                305                 310                 315
Leu Leu Glu Leu His Cys Glu Ala Leu Arg Gly Ser Pro Ile
                320                 325                 330
Leu Tyr Gln Phe Tyr His Glu Asp Val Thr Leu Gly Asn Ser Ser
                335                 340                 345
Ala Pro Ser Gly Gly Gly Ala Ser Phe Asn Leu Ser Leu Thr Ala
                350                 355                 360
Glu His Ser Gly Asn Tyr Ser Cys Glu Ala Asn Asn Gly Leu Gly
                365                 370                 375
Ala Gln Cys Ser Glu Ala Val Pro Val Ser Ile Ser Gly Pro Asp
                380                 385                 390
Gly Tyr Arg Arg Asp Leu Met Thr Ala Gly Val Leu Trp Gly Leu
                395                 400                 405
Phe Gly Val Leu Gly Phe Thr Gly Val Ala Leu Leu Leu Tyr Ala
                410                 415                 420
Leu Phe His Lys Ile Ser Gly Glu Ser Ser Ala Thr Asn Glu Pro
                425                 430                 435
Arg Gly Ala Ser Arg Pro Asn Pro Gln Glu Phe Thr Tyr Ser Ser
                440                 445                 450
Pro Thr Pro Asp Met Glu Glu Leu Gln Pro Val Tyr Val Asn Val
                455                 460                 465
Gly Ser Val Asp Val Asp Val Val Tyr Ser Gln Val Trp Ser Met
                470                 475                 480
Gln Gln Pro Glu Ser Ser Ala Asn Ile Arg Thr Leu Leu Glu Asn
                485                 490                 495
Lys Asp Ser Gln Val Ile Tyr Ser Ser Val Lys Lys Ser
                500                 505

<210> SEQ ID NO 7
<211> LENGTH: 1107
<212> TYPE: DNA
<213> ORGANISM: Homo sapiens

<400> SEQUENCE: 7
tgctgcaact caaactaacc aacccactgg gagaagatgc ctgggggtcc        50
aggagtcctc caagctctgc ctgccaccat cttcctcctc ttcctgctgt       100
ctgctgtcta cctgggccct gggtgccagg ccctgtggat gcacaaggtc       150
ccagcatcat tgatggtgag cctggggaa gacgcccact ccaatgccc         200 gcacaatagc agcaacaacg ccaacgtcac ctggtggcgc gtcctccatg       250
gcaactacac gtggccccct gagttcttgg gcccgggcga ggaccccaat       300
ggtacgctga tcatccagaa tgtgaacaag agccatgggg gcatatacgt       350
gtgccgggtc caggagggca acgagtcata ccagcagtcc tgcggcacct       400
acctccgcgt gcgccagccg cccccaggc ccttcctgga catggggag         450 ggcaccaaga accgaatcat cacagccgag gggatcatcc tcctgttctg       500
cgcggtggtg cctgggacgc tgctgctgtt caggaaacga tggcagaacg       550
agaagctcgg gttggatgcc ggggatgaat atgaagatga aaaccttat        600
```

-continued

```
gaaggcctga acctggacga ctgctccatg tatgaggaca tctcccgggg      650
cctccagggc acctaccagg atgtgggcag cctcaacata ggagatgtcc      700
agctggagaa gccgtgacac ccctactcct gccaggctgc ccccgcctgc      750
tgtgcaccca gctccagtgt ctcagctcac ttccctggga cattctcctt      800
tcagccette tgggggcttc cttagtcata ttcccccagt gggggggtggg     850
agggtaacct cactcttctc caggccaggc ctccttggac tcccctgggg      900
gtgtcccact cttcttccct ctaaactgcc ccacctccta acctaatccc      950
cacgccccgc tgcctttccc aggctcccct cacccagcgg gtaatgagcc      1000
cttaatcgct gcctctaggg gagctgattg tagcagcctc gttagtgtca      1050
cccccctcctc cctgatctgt cagggccact tagtgataat aaattcttcc    1100
caactgc                                                     1107
```

<210> SEQ ID NO 8
<211> LENGTH: 226
<212> TYPE: PRT
<213> ORGANISM: Homo sapiens

<400> SEQUENCE: 8

```
Met Pro Gly Gly Pro Gly Val Leu Gln Ala Leu Pro Ala Thr Ile
 1               5                  10                  15

Phe Leu Leu Phe Leu Leu Ser Ala Val Tyr Leu Gly Pro Gly Cys
                20                  25                  30

Gln Ala Leu Trp Met His Lys Val Pro Ala Ser Leu Met Val Ser
                35                  40                  45

Leu Gly Glu Asp Ala His Phe Gln Cys Pro His Asn Ser Ser Asn
                50                  55                  60

Asn Ala Asn Val Thr Trp Trp Arg Val Leu His Gly Asn Tyr Thr
                65                  70                  75

Trp Pro Pro Glu Phe Leu Gly Pro Gly Glu Asp Pro Asn Gly Thr
                80                  85                  90

Leu Ile Ile Gln Asn Val Asn Lys Ser His Gly Gly Ile Tyr Val
                95                 100                 105

Cys Arg Val Gln Glu Gly Asn Glu Ser Tyr Gln Gln Ser Cys Gly
               110                 115                 120

Thr Tyr Leu Arg Val Arg Gln Pro Pro Arg Pro Phe Leu Asp
               125                 130                 135

Met Gly Glu Gly Thr Lys Asn Arg Ile Ile Thr Ala Glu Gly Ile
               140                 145                 150

Ile Leu Leu Phe Cys Ala Val Val Pro Gly Thr Leu Leu Phe
               155                 160                 165

Arg Lys Arg Trp Gln Asn Glu Lys Leu Gly Leu Asp Ala Gly Asp
               170                 175                 180

Glu Tyr Glu Asp Glu Asn Leu Tyr Glu Gly Leu Asn Leu Asp Asp
               185                 190                 195

Cys Ser Met Tyr Glu Asp Ile Ser Arg Gly Leu Gln Gly Thr Tyr
               200                 205                 210

Gln Asp Val Gly Ser Leu Asn Ile Gly Asp Val Gln Leu Glu Lys
               215                 220                 225

Pro
```

<210> SEQ ID NO 9

```
<211> LENGTH: 1270
<212> TYPE: DNA
<213> ORGANISM: Homo sapiens

<400> SEQUENCE: 9
caggggacag gctgcagccg gtgcagttac acgttttcct ccaaggagcc         50
tcggacgttg tcacgggttt ggggtcgggg acagagcagt gaccatggcc        100
aggctggcgt tgtctcctgt gcccagccac tggatggtgg cgttgctgct        150
gctgctctca gctgagccag taccagcagc cagatcggag gaccggtacc        200
ggaatcccaa aggtagtgct tgttcgcgga tctggcagag cccacgtttc        250
atagccagga aacggggctt cacggtgaaa atgcactgct acatgaacag        300
cgcctccggc aatgtgagct ggctctggaa gcaggagatg gacgagaatc        350
cccagcagct gaagctggaa aagggccgca tggaagagtc ccagaacgaa        400
tctctcgcca ccctcaccat ccaaggcatc cggtttgagg acaatggcat        450
ctacttctgt cagcagaagt gcaacaacac ctcggaggtc taccagggct        500
gcggcacaga gctgcgagtc atgggattca gcaccttggc acagctgaag        550
cagaggaaca cgctgaagga tggtatcatc atgatccaga cgctgctgat        600
catcctcttc atcatcgtgc ctatcttcct gctgctggac aaggatgaca        650
gcaaggctgg catggaggaa gatcacacct acgagggcct ggacattgac        700
cagacagcca cctatgagga catagtgacg ctgcggacag ggaagtgaa         750
gtggtctgta ggtgagcacc caggccagga gtgagagcca ggtcgcccca        800
tgacctgggt gcaggctccc tggcctcagt gactgcttcg gagctgcctg        850
gctcatggcc caacccctt cctggacccc ccagctggcc tctgaagctg         900
gcccaccaga gctgccattt gtctccagcc cctggtcccc agctcttgcc        950
aaagggcctg gagtagaagg acaacagggc agcaacttgg agggagttct       1000
ctggggatgg acgggaccca gccttctggg ggtgctatga ggtgatccgt       1050
ccccacacat gggatggggg aggcagagac tggtccagag cccgcaaatg       1100
gactcggagc cgagggcctc ccagcagagc ttgggaaggg ccatggaccc       1150
aactgggccc cagaagagcc acaggaacat cattcctctc ccgcaaccac       1200
tcccacccca gggaggccct ggcctccagt gccttccccc gtggaataaa       1250
cggtgtgtcc tgagaaacca                                        1270

<210> SEQ ID NO 10
<211> LENGTH: 229
<212> TYPE: PRT
<213> ORGANISM: Homo sapiens

<400> SEQUENCE: 10

Met Ala Arg Leu Ala Leu Ser Pro Val Pro Ser His Trp Met Val
  1               5                  10                  15

Ala Leu Leu Leu Leu Leu Ser Ala Glu Pro Val Pro Ala Ala Arg
                 20                  25                  30

Ser Glu Asp Arg Tyr Arg Asn Pro Lys Gly Ser Ala Cys Ser Arg
                 35                  40                  45

Ile Trp Gln Ser Pro Arg Phe Ile Ala Arg Lys Arg Gly Phe Thr
                 50                  55                  60

Val Lys Met His Cys Tyr Met Asn Ser Ala Ser Gly Asn Val Ser
```

```
                 65                  70                  75
Trp Leu Trp Lys Gln Glu Met Asp Glu Asn Pro Gln Gln Leu Lys
             80                  85                  90

Leu Glu Lys Gly Arg Met Glu Ser Gln Asn Glu Ser Leu Ala
             95                 100                 105

Thr Leu Thr Ile Gln Gly Ile Arg Phe Glu Asp Asn Gly Ile Tyr
            110                 115                 120

Phe Cys Gln Gln Lys Cys Asn Asn Thr Ser Glu Val Tyr Gln Gly
            125                 130                 135

Cys Gly Thr Glu Leu Arg Val Met Gly Phe Ser Thr Leu Ala Gln
            140                 145                 150

Leu Lys Gln Arg Asn Thr Leu Lys Asp Gly Ile Ile Met Ile Gln
            155                 160                 165

Thr Leu Leu Ile Ile Leu Phe Ile Ile Val Pro Ile Phe Leu Leu
            170                 175                 180

Leu Asp Lys Asp Asp Ser Lys Ala Gly Met Glu Glu Asp His Thr
            185                 190                 195

Tyr Glu Gly Leu Asp Ile Asp Gln Thr Ala Thr Tyr Glu Asp Ile
            200                 205                 210

Val Thr Leu Arg Thr Gly Glu Val Lys Trp Ser Val Gly Glu His
            215                 220                 225

Pro Gly Gln Glu

<210> SEQ ID NO 11
<211> LENGTH: 3934
<212> TYPE: DNA
<213> ORGANISM: Homo sapiens

<400> SEQUENCE: 11
gccctcccag agctgccgga cgctcgcggg tctcggaacg catcccgccg         50
cgggggcttc ggccgtggca tgggcgccgc gggcctgctc ggggttttct        100
tggctctcgt cgcaccgggg gtcctcggga tttcttgtgg ctctcctccg        150
cctatcctaa atggccggat tagttattat tctaccccca ttgctgttgg        200
taccgtgata aggtacagtt gttcaggtac cttccgcctc attggagaaa        250
aaagtctatt atgcataact aaagacaaag tggatggaac tgggataaa         300 cctgctccta atgtgaata tttcaataaa tattcttctt gccctgagcc         350
catagtacca ggaggataca aaattagagg ctctacaccc tacagacatg        400
gtgattctgt gacatttgcc tgtaaaacca acttctccat gaacggaaac        450
aagtctgttt ggtgtcaagc aaataatatg tggggccga cacgactacc         500 aacctgtgta agtgttttcc ctctcgagtg tccagcactt cctatgatcc        550
acaatggaca tcacacaagt gagaatgttg gctccattgc tccaggattg        600
tctgtgactt acagctgtga atctggttac ttgcttgttg gagaaaagat        650
cattaactgt ttgtcttcgg aaaatggag tgctgtcccc cccacatgtg         700
aagaggcacg ctgtaaatct ctaggacgat ttcccaatgg aaggtaaag         750 gagcctccaa ttctccgggt tggtgtaact gcaaactttt tctgtgatga        800
agggtatcga ctgcaaggcc caccttctag tcggtgtgta attgctggac        850
agggagttgc ttgaccaaa atgccagtat gtgaagaaat tttttgccca         900
tcacctcccc ctattctcaa tggaagacat ataggcaact cactagcaaa        950
```

```
tgtctcatat ggaagcatag tcacttacac ttgtgacccg gacccagagg        1000
aaggagtgaa cttcatcctt attggagaga gcactctccg ttgtacagtt        1050
gatagtcaga agactgggac ctggagtggc cctgccccac gctgtgaact        1100
ttctacttct gcggttcagt gtccacatcc ccagatccta agaggccgaa        1150
tggtatctgg gcagaaagat cgatatacct ataacgacac tgtgatattt        1200
gcttgcatgt ttggcttcac cttgaagggc agcaagcaaa tccgatgcaa        1250
tgcccaaggc acatgggagc catctgcacc agtctgtgaa aaggaatgcc        1300
aggcccctcc taacatcctc aatgggcaaa aggaagatag acacatggtc        1350
cgctttgacc ctggaacatc tataaaatat agctgtaacc ctggctatgt        1400
gctggtggga gaagaatcca tacagtgtac ctctgagggg gtgtggacac        1450
cccctgtacc ccaatgcaaa gtggcagcgt gtgaagctac aggaaggcaa        1500
ctcttgacaa aaccccagca ccaatttgtt agaccagatg tcaactcttc        1550
ttgtggtgaa gggtacaagt taagtgggag tgtttatcag gagtgtcaag        1600
gcacaattcc ttggtttatg gagattcgtc tttgtaaaga aatcacctgc        1650
ccaccacccc ctgttatcta caatggggca cacaccggga gttccttaga        1700
agattttcca tatggaacca cggtcactta cacatgtaac cctgggccag        1750
aaagaggagt ggaattcagc ctcattggag agagcaccat ccgttgtaca        1800
agcaatgatc aagaaagagg cacctggagt ggccctgctc ccctatgtaa        1850
actttccctc cttgctgtcc agtgctcaca tgtccatatt gcaaatggat        1900
acaagatatc tggcaaggaa gccccatatt tctacaatga cactgtgaca        1950
ttcaagtgtt atagtggatt tactttgaag ggcagtagtc agattcgttg        2000
caaagctgat aacacctggg atcctgaaat accagtttgt gaaaaagaaa        2050
catgccagca tgtgagacag agtcttcaag aacttccagc tggttcacgt        2100
gtggagctag ttaatacgtc ctgccaagat gggtaccagt tgactggaca        2150
tgcttatcag atgtgtcaag atgctgaaaa tggaatttgg ttcaaaaaga        2200
ttccactttg taaagttatt cactgtcacc ctccaccagt gattgtcaat        2250
gggaagcaca cagggatgat ggcagaaaac tttctatatg gaaatgaagt        2300
ctcttatgaa tgtgaccaag gattctatct cctgggagag aaaaaattgc        2350
agtgcagaag tgattctaaa ggacatggat cttggagcgg gccttcccca        2400
cagtgcttac gatctcctcc tgtgactcgc tgccctaatc agaagtcaa         2450 acatgggtac aagctcaata aaacacattc tgcatattcc cacaatgaca        2500
tagtgtatgt tgactgcaat cctggcttca tcatgaatgg tagtcgcgtg        2550
attaggtgtc atactgataa cacatgggtg ccaggtgtgc caacttgtat        2600
gaaaaaagcc ttcataggdgt gtccacctcc gcctaagacc cctaacggga        2650
accatactgg tggaaacata gctcgatttt ctcctggaat gtcaatcctg        2700
tacagctgtg accaaggcta cctgctggtg ggagaggcac tccttctttg        2750
cacacatgag ggaacctgga gccaacctgc ccctcattgt aaagaggtaa        2800
actgtagctc accagcagat atggatggaa tccagaaagg gctggaacca        2850
aggaaaatgt atcagtatgg agctgttgta actctggagt gtgaagatgg        2900
```

| | |
|---|---|
| gtatatgctg gaaggcagtc cccagagcca gtgccaatcg gatcaccaat | 2950 |
| ggaaccctcc cctggcggtt tgcagatccc gttcacttgc tcctgtcctt | 3000 |
| tgtggtattg ctgcaggttt gatacttctt accttcttga ttgtcattac | 3050 |
| cttatacgtg atatcaaaac acagagaacg caattattat acagatacaa | 3100 |
| gccagaaaga agcttttcat ttagaagcac gagaagtata ttctgttgat | 3150 |
| ccatacaacc cagccagctg atcagaagac aaactggtgt gtgcctcatt | 3200 |
| gcttggaatt cagcggaata ttgattagaa agaaactgct ctaatatcag | 3250 |
| caagtctctt tatatggcct caagatcaat gaaatgatgt cataagcgat | 3300 |
| cacttcctat atgcacttat tctcaagaag aacatcttta tggtaaagat | 3350 |
| gggagcccag tttcactgcc atatactctt caaggacttt ctgaagcctc | 3400 |
| acttatgaga tgcctgaagc caggccatgg ctataaacaa ttacatggct | 3450 |
| ctaaaaagtt ttgcccttt taaggaaggc actaaaaaga gctgtcctgg | 3500 |
| tatctagacc catcttcttt ttgaaatcag catactcaat gttactatct | 3550 |
| gcttttggtt ataatgtgtt tttaattatc taaagtatga agcattttct | 3600 |
| ggggttatga tggccttacc tttattagga agtatggttt tattttgata | 3650 |
| gtagcttcct cctctggtgg tgttaatcat ttcatttta cccttactgt | 3700 |
| ttgagtttct ctcacattac tgtatatact ttgcctttcc ataatcactc | 3750 |
| agtgattgca atttgcacaa gttttttaa attatgggaa tcaagattta | 3800 |
| atcctagaga tttggtgtac aattcaggct ttggatgttt ctttagcagt | 3850 |
| tttgtgataa gttctagttg cttgtaaaat ttcacttaat aatgtgtaca | 3900 |
| ttagtcattc ataaattgt aattgtaaag aaaa | 3934 |

<210> SEQ ID NO 12
<211> LENGTH: 1033
<212> TYPE: PRT
<213> ORGANISM: Homo sapiens

<400> SEQUENCE: 12

Met Gly Ala Ala Gly Leu Leu Gly Val Phe Leu Ala Leu Val Ala
1               5                   10                  15

Pro Gly Val Leu Gly Ile Ser Cys Gly Ser Pro Pro Ile Leu
            20                  25                  30

Asn Gly Arg Ile Ser Tyr Tyr Ser Thr Pro Ile Ala Val Gly Thr
        35                  40                  45

Val Ile Arg Tyr Ser Cys Ser Gly Thr Phe Arg Leu Ile Gly Glu
    50                  55                  60

Lys Ser Leu Leu Cys Ile Thr Lys Asp Lys Val Asp Gly Thr Trp
65                  70                  75

Asp Lys Pro Ala Pro Lys Cys Glu Tyr Phe Asn Lys Tyr Ser Ser
            80                  85                  90

Cys Pro Glu Pro Ile Val Pro Gly Gly Tyr Lys Ile Arg Gly Ser
        95                  100                 105

Thr Pro Tyr Arg His Gly Asp Ser Val Thr Phe Ala Cys Lys Thr
    110                 115                 120

Asn Phe Ser Met Asn Gly Asn Lys Ser Val Trp Cys Gln Ala Asn
            125                 130                 135

Asn Met Trp Gly Pro Thr Arg Leu Pro Thr Cys Val Ser Val Phe
        140                 145                 150

```
Pro Leu Glu Cys Pro Ala Leu Pro Met Ile His Asn Gly His His
                155                 160                 165

Thr Ser Glu Asn Val Gly Ser Ile Ala Pro Gly Leu Ser Val Thr
                170                 175                 180

Tyr Ser Cys Glu Ser Gly Tyr Leu Leu Val Gly Glu Lys Ile Ile
                185                 190                 195

Asn Cys Leu Ser Ser Gly Lys Trp Ser Ala Val Pro Pro Thr Cys
                200                 205                 210

Glu Glu Ala Arg Cys Lys Ser Leu Gly Arg Phe Pro Asn Gly Lys
                215                 220                 225

Val Lys Glu Pro Pro Ile Leu Arg Val Gly Val Thr Ala Asn Phe
                230                 235                 240

Phe Cys Asp Glu Gly Tyr Arg Leu Gln Gly Pro Pro Ser Ser Arg
                245                 250                 255

Cys Val Ile Ala Gly Gln Gly Val Ala Trp Thr Lys Met Pro Val
                260                 265                 270

Cys Glu Glu Ile Phe Cys Pro Ser Pro Pro Ile Leu Asn Gly
                275                 280                 285

Arg His Ile Gly Asn Ser Leu Ala Asn Val Ser Tyr Gly Ser Ile
                290                 295                 300

Val Thr Tyr Thr Cys Asp Pro Asp Pro Glu Glu Gly Val Asn Phe
                305                 310                 315

Ile Leu Ile Gly Glu Ser Thr Leu Arg Cys Thr Val Asp Ser Gln
                320                 325                 330

Lys Thr Gly Thr Trp Ser Gly Pro Ala Pro Arg Cys Glu Leu Ser
                335                 340                 345

Thr Ser Ala Val Gln Cys Pro His Pro Gln Ile Leu Arg Gly Arg
                350                 355                 360

Met Val Ser Gly Gln Lys Asp Arg Tyr Thr Tyr Asn Asp Thr Val
                365                 370                 375

Ile Phe Ala Cys Met Phe Gly Phe Thr Leu Lys Gly Ser Lys Gln
                380                 385                 390

Ile Arg Cys Asn Ala Gln Gly Thr Trp Glu Pro Ser Ala Pro Val
                395                 400                 405

Cys Glu Lys Glu Cys Gln Ala Pro Pro Asn Ile Leu Asn Gly Gln
                410                 415                 420

Lys Glu Asp Arg His Met Val Arg Phe Asp Pro Gly Thr Ser Ile
                425                 430                 435

Lys Tyr Ser Cys Asn Pro Gly Tyr Val Leu Val Gly Glu Glu Ser
                440                 445                 450

Ile Gln Cys Thr Ser Glu Gly Val Trp Thr Pro Pro Val Pro Gln
                455                 460                 465

Cys Lys Val Ala Ala Cys Glu Ala Thr Gly Arg Gln Leu Leu Thr
                470                 475                 480

Lys Pro Gln His Gln Phe Val Arg Pro Asp Val Asn Ser Ser Cys
                485                 490                 495

Gly Glu Gly Tyr Lys Leu Ser Gly Ser Val Tyr Gln Glu Cys Gln
                500                 505                 510

Gly Thr Ile Pro Trp Phe Met Glu Ile Arg Leu Cys Lys Glu Ile
                515                 520                 525

Thr Cys Pro Pro Pro Val Ile Tyr Asn Gly Ala His Thr Gly
                530                 535                 540
```

```
Ser Ser Leu Glu Asp Phe Pro Tyr Gly Thr Val Thr Tyr Thr
                545                 550                 555

Cys Asn Pro Gly Pro Glu Arg Gly Val Glu Phe Ser Leu Ile Gly
            560                 565                 570

Glu Ser Thr Ile Arg Cys Thr Ser Asn Asp Gln Glu Arg Gly Thr
            575                 580                 585

Trp Ser Gly Pro Ala Pro Leu Cys Lys Leu Ser Leu Leu Ala Val
            590                 595                 600

Gln Cys Ser His Val His Ile Ala Asn Gly Tyr Lys Ile Ser Gly
            605                 610                 615

Lys Glu Ala Pro Tyr Phe Tyr Asn Asp Thr Val Thr Phe Lys Cys
            620                 625                 630

Tyr Ser Gly Phe Thr Leu Lys Gly Ser Ser Gln Ile Arg Cys Lys
            635                 640                 645

Ala Asp Asn Thr Trp Asp Pro Glu Ile Pro Val Cys Glu Lys Glu
            650                 655                 660

Thr Cys Gln His Val Arg Gln Ser Leu Gln Glu Leu Pro Ala Gly
            665                 670                 675

Ser Arg Val Glu Leu Val Asn Thr Ser Cys Gln Asp Gly Tyr Gln
            680                 685                 690

Leu Thr Gly His Ala Tyr Gln Met Cys Gln Asp Ala Glu Asn Gly
            695                 700                 705

Ile Trp Phe Lys Lys Ile Pro Leu Cys Lys Val Ile His Cys His
            710                 715                 720

Pro Pro Pro Val Ile Val Asn Gly Lys His Thr Gly Met Met Ala
            725                 730                 735

Glu Asn Phe Leu Tyr Gly Asn Glu Val Ser Tyr Glu Cys Asp Gln
            740                 745                 750

Gly Phe Tyr Leu Leu Gly Glu Lys Lys Leu Gln Cys Arg Ser Asp
            755                 760                 765

Ser Lys Gly His Gly Ser Trp Ser Gly Pro Ser Pro Gln Cys Leu
            770                 775                 780

Arg Ser Pro Pro Val Thr Arg Cys Pro Asn Pro Glu Val Lys His
            785                 790                 795

Gly Tyr Lys Leu Asn Lys Thr His Ser Ala Tyr Ser His Asn Asp
            800                 805                 810

Ile Val Tyr Val Asp Cys Asn Pro Gly Phe Ile Met Asn Gly Ser
            815                 820                 825

Arg Val Ile Arg Cys His Thr Asp Asn Thr Trp Val Pro Gly Val
            830                 835                 840

Pro Thr Cys Met Lys Lys Ala Phe Ile Gly Cys Pro Pro Pro
            845                 850                 855

Lys Thr Pro Asn Gly Asn His Thr Gly Gly Asn Ile Ala Arg Phe
            860                 865                 870

Ser Pro Gly Met Ser Ile Leu Tyr Ser Cys Asp Gln Gly Tyr Leu
            875                 880                 885

Leu Val Gly Glu Ala Leu Leu Leu Cys Thr His Glu Gly Thr Trp
            890                 895                 900

Ser Gln Pro Ala Pro His Cys Lys Glu Val Asn Cys Ser Ser Pro
            905                 910                 915

Ala Asp Met Asp Gly Ile Gln Lys Gly Leu Glu Pro Arg Lys Met
            920                 925                 930

Tyr Gln Tyr Gly Ala Val Val Thr Leu Glu Cys Glu Asp Gly Tyr
```

```
                935                 940                 945
Met Leu Glu Gly Ser Pro Gln Ser Gln Cys Gln Ser Asp His Gln
            950                 955                 960
Trp Asn Pro Pro Leu Ala Val Cys Arg Ser Arg Ser Leu Ala Pro
            965                 970                 975
Val Leu Cys Gly Ile Ala Ala Gly Leu Ile Leu Leu Thr Phe Leu
            980                 985                 990
Ile Val Ile Thr Leu Tyr Val Ile Ser Lys His Arg Glu Arg Asn
            995                 1000                1005
Tyr Tyr Thr Asp Thr Ser Gln Lys Glu Ala Phe His Leu Glu Ala
            1010                1015                1020
Arg Glu Val Tyr Ser Val Asp Pro Tyr Asn Pro Ala Ser
            1025                1030

<210> SEQ ID NO 13
<211> LENGTH: 2978
<212> TYPE: DNA
<213> ORGANISM: Homo sapiens

<400> SEQUENCE: 13
caaacgttcc caaatcttcc cagtcggctt gcagagactc cttgctccca        50
ggagataacc agaagctgca tcttattgac agatggtcat cacattggtg       100
agctggagtc atcagattgt ggggcccgga gtgaggctga agggagtgga       150
tcagagcact gcctgagagt cacctctact ttcctgctac cgctgcctgt       200
gagctgaagg ggctgaacca tacactcctt tttctacaac cagcttgcat       250
tttttctgcc cacaatgagc ggggaatcaa tgaatttcag cgatgttttc       300
gactccagtg aagattattt tgtgtcagtc aatacttcat attactcagt       350
tgattctgag atgttactgt gctccttgca ggaggtcagg cagttctcca       400
ggctatttgt accgattgcc tactccttga tctgtgtctt tggcctcctg       450
gggaatattc tggtggtgat cacctttgct ttttataaga aggccaggtc       500
tatgacagac gtctatctct tgaacatggc cattgcagac atcctctttg       550
ttcttactct cccattctgg gcagtgagtc atgccactgg tgcgtgggtt       600
ttcagcaatg ccacgtgcaa gttgctaaaa ggcatctatg ccatcaactt       650
taactgcggg atgctgctcc tgacttgcat tagcatggac cggtacatcg       700
ccattgtaca ggcgactaag tcattccggc tccgatccag aacactaccg       750
cgcacgaaaa tcatctgcct tgttgtgtgg gggctgtcag tcatcatctc       800
cagctcaact tttgtcttca accaaaaata caacacccaa ggcagcgatg       850
tctgtgaacc caagtaccag actgtctcgg agcccatcag gtggaagctg       900
ctgatgttgg ggcttgagct actctttggt ttctttatcc ctttgatgtt       950
catgatattt tgttacacgt tcattgtcaa aaccttggtg caagctcaga      1000
attctaaaag gcacaaagcc atccgtgtaa tcatagctgt ggtgcttgtg      1050
tttctggctt gtcagattcc tcataacatg gtcctgcttg tgacggctgc      1100
aaatttgggt aaaatgaacc gatcctgcca gagcgaaaag ctaattggct      1150
atacgaaaac tgtcacagaa gtcctggctt cctgcactg ctgcctgaac      1200 cctgtgctct acgcttttat tgggcagaag ttcagaaact actttctgaa      1250
gatcttgaag gacctgtggt gtgtgagaag gaagtacaag tcctcaggct      1300
```

| | |
|---|---|
| tctcctgtgc cgggaggtac tcagaaaaca tttctcggca gaccagtgag | 1350 |
| accgcagata acgacaatgc gtcgtccttc actatgtgat agaaagctga | 1400 |
| gtctccctaa ggcatgtgtg aaacatactc atagatgtta tgcaaaaaaa | 1450 |
| agtctatggc caggtatgca tggaaaatgt gggaattaag caaaatcaag | 1500 |
| caagcctctc tcctgcggga cttaacgtgc tcatgggctg tgtgatctct | 1550 |
| tcagggtggg gtggtctctg ataggtagca ttttccagca ctttgcaagg | 1600 |
| aatgttttgt agctctaggg tatatatccg cctggcattt cacaaaacag | 1650 |
| cctttgggaa atgctgaatt aaagtgaatt gttgacaaat gtaaacattt | 1700 |
| tcagaaatat tcatgaagcg gtcacagatc acagtgtctt ttggttacag | 1750 |
| cacaaaatga tggcagtggt ttgaaaaact aaaacagaaa aaaaaatgga | 1800 |
| agccaacaca tcactcattt taggcaaatg tttaaacatt tttatctatc | 1850 |
| agaatgttta ttgttgctgg ttataagcag caggattggc cggctagtgt | 1900 |
| ttcctctcat ttcccttga tacagtcaac aagcctgacc ctgtaaaatg | 1950 |
| gaggtggaaa gacaagctca agtgttcaca acctggaagt gcttcgggaa | 2000 |
| gaaggggaca atggcagaac aggtgttggt gacaattgtc accaattgga | 2050 |
| taaagcagct caggttgtag tgggccatta ggaaactgtc ggtttgcttt | 2100 |
| gatttccctg ggagctgttc tctgtcgtga gtgtctcttg tctaaacgtc | 2150 |
| cattaagctg agagtgctat gaagacagga tctagaataa tcttgctcac | 2200 |
| agctgtgctc tgagtgccta gcggagttcc agcaaacaaa atggactcaa | 2250 |
| gagagatttg attaatgaat cgtaatgaag ttggggttta ttgtacagtt | 2300 |
| taaaatgtta gatgttttta atttttttaaa taaatggaat actttttttt | 2350 |
| tttttaaaga aagcaacttt actgagacaa tgtagaaaga agttttgttc | 2400 |
| cgtttctttta atgtggttga agagcaatgt gtggctgaag acttttgtta | 2450 |
| tgaggagctg cagattagct aggggacagc tggaattatg ctggcttctg | 2500 |
| ataattattt taaaggggtc tgaaatttgt gatggaatca gattttaaca | 2550 |
| gctctcttca atgacataga aagttcatgg aactcatgtt tttaaagggc | 2600 |
| tatgtaaata tatgaacatt agaaaatag caacttgtgt tacaaaaata | 2650 |
| caaacacatg ttaggaaggt actgtcatgg gctaggcatg gtggctcaca | 2700 |
| cctgtaatcc cagcattttg ggaagctaag atgggtggat cacttgaggt | 2750 |
| caggagtttg agaccagcct ggccaacatg gcgaaacccc tctctactaa | 2800 |
| aaatacaaaa atttgccagg cgtggtggcg ggtgcctgta atcccagcta | 2850 |
| cttgggaggc tgaggcaaga gaatcgcttg aacccaggag gcagaggttg | 2900 |
| cagtgagccg agatcgtgcc attgcactcc agcctgggtg acagagcgag | 2950 |
| actccatctc aaaaaaaaaa aaaaaaa | 2978 |

<210> SEQ ID NO 14
<211> LENGTH: 374
<212> TYPE: PRT
<213> ORGANISM: Homo sapiens

<400> SEQUENCE: 14

Met Ser Gly Glu Ser Met Asn Phe Ser Asp Val Phe Asp Ser Ser
1               5                   10                  15

```
Glu Asp Tyr Phe Val Ser Val Asn Thr Ser Tyr Tyr Ser Val Asp
             20                  25                  30

Ser Glu Met Leu Leu Cys Ser Leu Gln Val Arg Gln Phe Ser
         35                  40                  45

Arg Leu Phe Val Pro Ile Ala Tyr Ser Leu Ile Cys Val Phe Gly
             50                  55                  60

Leu Leu Gly Asn Ile Leu Val Val Ile Thr Phe Ala Phe Tyr Lys
             65                  70                  75

Lys Ala Arg Ser Met Thr Asp Val Tyr Leu Leu Asn Met Ala Ile
             80                  85                  90

Ala Asp Ile Leu Phe Val Leu Thr Leu Pro Phe Trp Ala Val Ser
             95                  100                 105

His Ala Thr Gly Ala Trp Val Phe Ser Asn Ala Thr Cys Lys Leu
             110                 115                 120

Leu Lys Gly Ile Tyr Ala Ile Asn Phe Asn Cys Gly Met Leu Leu
             125                 130                 135

Leu Thr Cys Ile Ser Met Asp Arg Tyr Ile Ala Ile Val Gln Ala
             140                 145                 150

Thr Lys Ser Phe Arg Leu Arg Ser Arg Thr Leu Pro Arg Thr Lys
             155                 160                 165

Ile Ile Cys Leu Val Val Trp Gly Leu Ser Val Ile Ile Ser Ser
             170                 175                 180

Ser Thr Phe Val Phe Asn Gln Lys Tyr Asn Thr Gln Gly Ser Asp
             185                 190                 195

Val Cys Glu Pro Lys Tyr Gln Thr Val Ser Glu Pro Ile Arg Trp
             200                 205                 210

Lys Leu Leu Met Leu Gly Leu Glu Leu Leu Phe Gly Phe Phe Ile
             215                 220                 225

Pro Leu Met Phe Met Ile Phe Cys Tyr Thr Phe Ile Val Lys Thr
             230                 235                 240

Leu Val Gln Ala Gln Asn Ser Lys Arg His Lys Ala Ile Arg Val
             245                 250                 255

Ile Ile Ala Val Val Leu Val Phe Leu Ala Cys Gln Ile Pro His
             260                 265                 270

Asn Met Val Leu Leu Val Thr Ala Ala Asn Leu Gly Lys Met Asn
             275                 280                 285

Arg Ser Cys Gln Ser Glu Lys Leu Ile Gly Tyr Thr Lys Thr Val
             290                 295                 300

Thr Glu Val Leu Ala Phe Leu His Cys Cys Leu Asn Pro Val Leu
             305                 310                 315

Tyr Ala Phe Ile Gly Gln Lys Phe Arg Asn Tyr Phe Leu Lys Ile
             320                 325                 330

Leu Lys Asp Leu Trp Cys Val Arg Arg Lys Tyr Lys Ser Ser Gly
             335                 340                 345

Phe Ser Cys Ala Gly Arg Tyr Ser Glu Asn Ile Ser Arg Gln Thr
             350                 355                 360

Ser Glu Thr Ala Asp Asn Asp Asn Ala Ser Ser Phe Thr Met
             365                 370

<210> SEQ ID NO 15
<211> LENGTH: 1531
<212> TYPE: DNA
<213> ORGANISM: Homo sapiens
```

<400> SEQUENCE: 15

| | | |
|---|---|---|
| agtcacagag ggaacacaga gcctagttgt aaacggacag agacgagagg | 50 |
| ggcaagggag gacagtggat gacagggaag acgagtgggg gcagagctgc | 100 |
| tcaggaccat ggctgaggcc atcacctatg cagatctgag gtttgtgaag | 150 |
| gctcccctga agaagagcat ctccagccgg ttaggacagg acccaggggc | 200 |
| tgatgatgat ggggaaatca cctacgagaa tgttcaagtg cccgcagtcc | 250 |
| taggggtgcc ctcaagcttg gcttcttctg tactagggga caaagcagcg | 300 |
| gtcaagtcgg agcagccaac tgcgtcctgg agagccgtga cgtcaccagc | 350 |
| tgtcgggcgg attctcccct gccgcacaac ctgcctgcga tacctcctgc | 400 |
| tcggcctgct cctcacctgc ctgctgttag gagtgaccgc catctgcctg | 450 |
| ggagtgcgct atctgcaggt gtctcagcag ctccagcaga cgaacagggt | 500 |
| tctggaagtc actaacagca gcctgaggca gcagctccgc ctcaagataa | 550 |
| cgcagctggg acagagtgca gaggatctgc aggggtccag gagagagctg | 600 |
| gcgcagagtc aggaagcact acaggtggaa cagagggctc atcaggcggc | 650 |
| cgaagggcag ctacaggcct gccaggcaga cagacagaag acgaaggaga | 700 |
| ccttgcaaag tgaggagcaa cagaggaggg ccttggagca gaagctgagc | 750 |
| aacatggaga acagactgaa gcccttcttc acatgcggct cagcagacac | 800 |
| ctgctgtccg tcgggatgga taatgcatca gaaaagctgc ttttacatct | 850 |
| cacttacttc aaaaaattgg caggagagcc aaaaacaatg tgaaactctg | 900 |
| tcttccaagc tggccacatt cagtgaaatt tatccacaat cacactctta | 950 |
| ctacttctta aattcactgt tgccaaatgg tggttcaggg aattcatatt | 1000 |
| ggactggcct cagctctaac aaggattgga agttgactga tgatacacaa | 1050 |
| cgcactagga cttatgctca aagctcaaaa tgtaacaagg tacataaaac | 1100 |
| ttggtcatgg tggacactgg agtcagagtc atgtagaagt tctcttccct | 1150 |
| acatctgtga gatgacagct ttcaggtttc cagattagga cagtcctttg | 1200 |
| cactgagttg acactcatgc caacaagaac ctgtgcccct ccttcctaac | 1250 |
| ctgaggcctg gggttcctca gaccatctcc ttcattctgg gcagtgccag | 1300 |
| ccaccggctg acccacacct gacacttcca gccagtctgc tgcctgctcc | 1350 |
| ctcttcctga aactggactg ttcctgggaa aagggtgaag ccacctctag | 1400 |
| aagggacttt ggcctccccc caagaacttc ccatggtaga atggggtggg | 1450 |
| ggaggagggc gcacgggctg agcggatagg ggcggcccgg agccagccag | 1500 |
| gcagttttat tgaaatcttt ttaaataatt g | 1531 |

<210> SEQ ID NO 16
<211> LENGTH: 359
<212> TYPE: PRT
<213> ORGANISM: Homo sapiens

<400> SEQUENCE: 16

Met Ala Glu Ala Ile Thr Tyr Ala Asp Leu Arg Phe Val Lys Ala
1               5                   10                  15

Pro Leu Lys Lys Ser Ile Ser Ser Arg Leu Gly Gln Asp Pro Gly
                20                  25                  30

Ala Asp Asp Asp Gly Glu Ile Thr Tyr Glu Asn Val Gln Val Pro

|  |  |  |  | 35 |  |  |  |  | 40 |  |  |  |  | 45 |
| --- | --- | --- | --- | --- | --- | --- | --- | --- | --- | --- | --- | --- | --- | --- |
| Ala | Val | Leu | Gly | Val | Pro | Ser | Ser | Leu | Ala | Ser | Ser | Val | Leu | Gly |
|  |  |  |  | 50 |  |  |  |  | 55 |  |  |  |  | 60 |
| Asp | Lys | Ala | Ala | Val | Lys | Ser | Glu | Gln | Pro | Thr | Ala | Ser | Trp | Arg |
|  |  |  |  | 65 |  |  |  |  | 70 |  |  |  |  | 75 |
| Ala | Val | Thr | Ser | Pro | Ala | Val | Gly | Arg | Ile | Leu | Pro | Cys | Arg | Thr |
|  |  |  |  | 80 |  |  |  |  | 85 |  |  |  |  | 90 |
| Thr | Cys | Leu | Arg | Tyr | Leu | Leu | Leu | Gly | Leu | Leu | Leu | Thr | Cys | Leu |
|  |  |  |  | 95 |  |  |  |  | 100 |  |  |  |  | 105 |
| Leu | Leu | Gly | Val | Thr | Ala | Ile | Cys | Leu | Gly | Val | Arg | Tyr | Leu | Gln |
|  |  |  |  | 110 |  |  |  |  | 115 |  |  |  |  | 120 |
| Val | Ser | Gln | Gln | Leu | Gln | Gln | Thr | Asn | Arg | Val | Leu | Glu | Val | Thr |
|  |  |  |  | 125 |  |  |  |  | 130 |  |  |  |  | 135 |
| Asn | Ser | Ser | Leu | Arg | Gln | Gln | Leu | Arg | Leu | Lys | Ile | Thr | Gln | Leu |
|  |  |  |  | 140 |  |  |  |  | 145 |  |  |  |  | 150 |
| Gly | Gln | Ser | Ala | Glu | Asp | Leu | Gln | Gly | Ser | Arg | Arg | Glu | Leu | Ala |
|  |  |  |  | 155 |  |  |  |  | 160 |  |  |  |  | 165 |
| Gln | Ser | Gln | Glu | Ala | Leu | Gln | Val | Glu | Gln | Arg | Ala | His | Gln | Ala |
|  |  |  |  | 170 |  |  |  |  | 175 |  |  |  |  | 180 |
| Ala | Glu | Gly | Gln | Leu | Gln | Ala | Cys | Gln | Ala | Asp | Arg | Gln | Lys | Thr |
|  |  |  |  | 185 |  |  |  |  | 190 |  |  |  |  | 195 |
| Lys | Glu | Thr | Leu | Gln | Ser | Glu | Glu | Gln | Arg | Arg | Ala | Leu | Glu |
|  |  |  |  | 200 |  |  |  |  | 205 |  |  |  |  | 210 |
| Gln | Lys | Leu | Ser | Asn | Met | Glu | Asn | Arg | Leu | Lys | Pro | Phe | Phe | Thr |
|  |  |  |  | 215 |  |  |  |  | 220 |  |  |  |  | 225 |
| Cys | Gly | Ser | Ala | Asp | Thr | Cys | Cys | Pro | Ser | Gly | Trp | Ile | Met | His |
|  |  |  |  | 230 |  |  |  |  | 235 |  |  |  |  | 240 |
| Gln | Lys | Ser | Cys | Phe | Tyr | Ile | Ser | Leu | Thr | Ser | Lys | Asn | Trp | Gln |
|  |  |  |  | 245 |  |  |  |  | 250 |  |  |  |  | 255 |
| Glu | Ser | Gln | Lys | Gln | Cys | Glu | Thr | Leu | Ser | Ser | Lys | Leu | Ala | Thr |
|  |  |  |  | 260 |  |  |  |  | 265 |  |  |  |  | 270 |
| Phe | Ser | Glu | Ile | Tyr | Pro | Gln | Ser | His | Ser | Tyr | Tyr | Phe | Leu | Asn |
|  |  |  |  | 275 |  |  |  |  | 280 |  |  |  |  | 285 |
| Ser | Leu | Leu | Pro | Asn | Gly | Gly | Ser | Gly | Asn | Ser | Tyr | Trp | Thr | Gly |
|  |  |  |  | 290 |  |  |  |  | 295 |  |  |  |  | 300 |
| Leu | Ser | Ser | Asn | Lys | Asp | Trp | Lys | Leu | Thr | Asp | Asp | Thr | Gln | Arg |
|  |  |  |  | 305 |  |  |  |  | 310 |  |  |  |  | 315 |
| Thr | Arg | Thr | Tyr | Ala | Gln | Ser | Ser | Lys | Cys | Asn | Lys | Val | His | Lys |
|  |  |  |  | 320 |  |  |  |  | 325 |  |  |  |  | 330 |
| Thr | Trp | Ser | Trp | Trp | Thr | Leu | Glu | Ser | Glu | Ser | Cys | Arg | Ser | Ser |
|  |  |  |  | 335 |  |  |  |  | 340 |  |  |  |  | 345 |
| Leu | Pro | Tyr | Ile | Cys | Glu | Met | Thr | Ala | Phe | Arg | Phe | Pro | Asp |
|  |  |  |  | 350 |  |  |  |  | 355 |  |  |  |  |  |

<210> SEQ ID NO 17
<211> LENGTH: 1978
<212> TYPE: DNA
<213> ORGANISM: Homo sapiens

<400> SEQUENCE: 17

| ggcacgaggg tccgcaagcc cggctgagag cgcgccatgg ggcaggcggg | 50 |
| --- | --- |
| ctgcaagggg ctctgcctgt cgctgttcga ctacaagacc gagaagtatg | 100 |
| tcatcgccaa gaacaagaag gtgggcctgc tgtaccggct gctgcaggcc | 150 |

-continued

```
tccatcctgg cgtacctggt cgtatgggtg ttcctgataa agaagggtta        200
ccaagacgtc gacacctccc tgcagagtgc tgtcatcacc aaagtcaagg        250
gcgtggcctt caccaacacc tcggatcttg gcagcggat  ctgggatgtc        300 gccgactacg tcattccagc ccaggggagag aacgtctttt ttgtggtcac       350
caacctgatt gtgaccccca accagcggca gaacgtctgt gctgagaatg        400
aaggcattcc tgatggcgcg tgctccaagg acagcgactg ccacgctggg        450
gaagcggtta cagctggaaa cggagtgaag accggccgct gcctgcggag        500
agggaacttg gccaggggca cctgtgagat ctttgcctgg tgcccgttgg        550
agacaagctc caggccggag gagccattcc tgaaggaggc cgaagacttc        600
accattttca taaagaacca catccgtttc cccaaattca acttctccaa        650
aaacaatgtg atggacgtca aggacagatc tttcctgaaa tcatgccact        700
ttggccccaa gaaccactac tgccccatct tccgactggg ctccatcgtc        750
cgctgggccg ggagcgactt ccaggatata gccctgcgag gtggcgtgat        800
aggaattaat attgaatgga actgtgatct tgataaagct gcctctgagt        850
gccaccctca ctattctttt agccgtctgg acaataaact ttcaaagtct        900
gtctcctccg ggtacaactt cagatttgcc agatattacc gagacgcagc        950
cggggtggag ttccgcaccc tgatgaaagc ctacgggatc cgctttgacg        1000
tgatggtgaa cggcaagggt gctttcttct gcgacctggt actcatctac        1050
ctcatcaaaa agagagagtt ttaccgtgac aagaagtacg aggaagtgag        1100
gggcctagaa gacagttccc aggaggccga ggacgaggca tcggggctgg        1150
ggctatctga gcagctcaca tctgggccag ggctgctggg gatgccggag        1200
cagcaggagc tgcaggagcc acccgaggcg aagcgtggaa gcagcagtca        1250
gaaggggaac ggatctgtgt gcccacagct cctggagccc cacaggagca        1300
cgtgaattgc ctctgcttac gttcaggccc tgtcctaaac ccagccgtct        1350
agcacccagt gatcccatgc ctttgggaat cccaggatgc tgcccaacgg        1400
gaaatttgta cattgggtgc tatcaatgcc acatcacagg gaccagccat        1450
cacagagcaa agtgacctcc acgtctgatg ctggggtcat caggacggac        1500
ccatcatggc tgtcttttg  ccccacccc  tgccgtcagt tcttcctttc        1550
tccgtggctg gcttcccgca ctagggaacg ggttgtaaat ggggaacatg        1600
acttccttcc ggagtccttg agcacctcag ctaaggaccg cagtgccctg        1650
tagagttcct agattacctc actgggaata gcattgtgcg tgtccggaaa        1700
agggctccat ttggttccag cccactcccc tctgcaagtg ccacagcttc        1750
cctcagagca tactctccag tggatccaag tactctctct cctaaagaca        1800
ccaccttcct gccagctgtt tgcccttagg ccagtacaca gaattaaagt        1850
gggggagatg gcagacgctt tctgggacct gcccaagata tgtattctct        1900
gacactctta tttggtcata aaacaataaa tggtgtcaat ttcaaaaaaa        1950
aaaaaaaaaa aaaaaaaaa  aaaaaaa                                 1978
```

<210> SEQ ID NO 18
<211> LENGTH: 422
<212> TYPE: PRT
<213> ORGANISM: Homo sapiens

<400> SEQUENCE: 18

```
Met Gly Gln Ala Gly Cys Lys Gly Leu Cys Leu Ser Leu Phe Asp
  1               5                  10                  15

Tyr Lys Thr Glu Lys Tyr Val Ile Ala Lys Asn Lys Lys Val Gly
                 20                  25                  30

Leu Leu Tyr Arg Leu Leu Gln Ala Ser Ile Leu Ala Tyr Leu Val
                 35                  40                  45

Val Trp Val Phe Leu Ile Lys Lys Gly Tyr Gln Asp Val Asp Thr
                 50                  55                  60

Ser Leu Gln Ser Ala Val Ile Thr Lys Val Lys Gly Val Ala Phe
                 65                  70                  75

Thr Asn Thr Ser Asp Leu Gly Gln Arg Ile Trp Asp Val Ala Asp
                 80                  85                  90

Tyr Val Ile Pro Ala Gln Gly Glu Asn Val Phe Phe Val Val Thr
                 95                 100                 105

Asn Leu Ile Val Thr Pro Asn Gln Arg Gln Asn Val Cys Ala Glu
                110                 115                 120

Asn Glu Gly Ile Pro Asp Gly Ala Cys Ser Lys Asp Ser Asp Cys
                125                 130                 135

His Ala Gly Glu Ala Val Thr Ala Gly Asn Gly Val Lys Thr Gly
                140                 145                 150

Arg Cys Leu Arg Arg Gly Asn Leu Ala Arg Gly Thr Cys Glu Ile
                155                 160                 165

Phe Ala Trp Cys Pro Leu Glu Thr Ser Ser Arg Pro Glu Glu Pro
                170                 175                 180

Phe Leu Lys Glu Ala Glu Asp Phe Thr Ile Phe Ile Lys Asn His
                185                 190                 195

Ile Arg Phe Pro Lys Phe Asn Phe Ser Lys Asn Asn Val Met Asp
                200                 205                 210

Val Lys Asp Arg Ser Phe Leu Lys Ser Cys His Phe Gly Pro Lys
                215                 220                 225

Asn His Tyr Cys Pro Ile Phe Arg Leu Gly Ser Ile Val Arg Trp
                230                 235                 240

Ala Gly Ser Asp Phe Gln Asp Ile Ala Leu Arg Gly Gly Val Ile
                245                 250                 255

Gly Ile Asn Ile Glu Trp Asn Cys Asp Leu Asp Lys Ala Ala Ser
                260                 265                 270

Glu Cys His Pro His Tyr Ser Phe Ser Arg Leu Asp Asn Lys Leu
                275                 280                 285

Ser Lys Ser Val Ser Ser Gly Tyr Asn Phe Arg Phe Ala Arg Tyr
                290                 295                 300

Tyr Arg Asp Ala Ala Gly Val Glu Phe Arg Thr Leu Met Lys Ala
                305                 310                 315

Tyr Gly Ile Arg Phe Asp Val Met Val Asn Gly Lys Gly Ala Phe
                320                 325                 330

Phe Cys Asp Leu Val Leu Ile Tyr Leu Ile Lys Lys Arg Glu Phe
                335                 340                 345

Tyr Arg Asp Lys Lys Tyr Glu Glu Val Arg Gly Leu Glu Asp Ser
                350                 355                 360

Ser Gln Glu Ala Glu Asp Glu Ala Ser Gly Leu Gly Leu Ser Glu
                365                 370                 375

Gln Leu Thr Ser Gly Pro Gly Leu Leu Gly Met Pro Glu Gln Gln
```

```
            380                 385                 390
Glu Leu Gln Glu Pro Pro Glu Ala Lys Arg Gly Ser Ser Ser Gln
            395                 400                 405
Lys Gly Asn Gly Ser Val Cys Pro Gln Leu Leu Glu Pro His Arg
            410                 415                 420
Ser Thr

<210> SEQ ID NO 19
<211> LENGTH: 1322
<212> TYPE: DNA
<213> ORGANISM: Homo sapiens

<400> SEQUENCE: 19
aactcattct gaagaggctg acgattttac tgtctcattt ttttcctttc          50
tccagaatgg gttctgggtg ggtccctgg gtggtggctc tgctagtgaa          100
tctgacccga ctggattcct ccatgactca aggcacagac tctccagaag          150
attttgtgat tcaggcaaag gctgactgtt acttcaccaa cgggacagaa          200
aaggtgcagt ttgtggtcag attcatcttt aacttggagg agtatgtacg          250
tttcgacagt gatgtgggga tgtttgtggc attgaccaag ctggggcagc          300
cagatgctga gcagtggaac agccggctgg atctcttgga gaggagcaga          350
caggccgtgg atggggtctg tagacacaac tacaggctgg gcgcacccct          400
cactgtgggg agaaaagtgc aaccagaggt gacagtgtac ccagagagga          450
ccccactcct gcaccagcat aatctgctgc actgctctgt gacaggcttc          500
tatccagggg atatcaagat caagtggttc ctgaatgggc aggaggagag          550
agctggggtc atgtccactg gccctatcag gaatggagac tggaccttc          600 agactgtggt gatgctagaa atgactcctg aacttggaca tgtctacacc          650
tgccttgtcg atcactccag cctgctgagc cctgtttctg tggagtggag          700
agctcagtct gaatattctt ggagaaagat gctgagtggc attgcagcct          750
tcctacttgg gctaatcttc cttctggtgg gaatcgtcat ccagctaagg          800
gctcagaaag gatatgtgag gacgcagatg tctggtaatg aggtctcaag          850
agctgttctg ctccctcagt catgctaagg tcctcactaa gcttgctctc          900
tctggagcct gaagtagtga tgagtagtct gggccctggg tgaggtaaag          950
gacattcatg aggtcaatgt tctgggaata actctcttcc ctgatccttg          1000
gaggagcccg aactgattct ggagctctgt gttctgagat catgcatctc          1050
ccacccatct gcccttctcc cttctacgtg tacatcatta atccccattg          1100
ccaagggcat tgtccagaaa ctcccctgag accttactcc ttccagcccc          1150
aaatcattta cttttctgtg gtccagcccct actcctataa gtcatgatct          1200
ccaaagcttt ctgtcttcca actgcagtct ccacagtctt cagaagacaa          1250
atgctcaggt agtcactgtt tccttttcac tgtttttaaa aaccttttat          1300
tgtcaaataa aatggagata ca                                       1322

<210> SEQ ID NO 20
<211> LENGTH: 273
<212> TYPE: PRT
<213> ORGANISM: Homo sapiens

<400> SEQUENCE: 20
```

Met Gly Ser Gly Trp Val Pro Trp Val Ala Leu Leu Val Asn
1               5                   10                  15

Leu Thr Arg Leu Asp Ser Ser Met Thr Gln Gly Thr Asp Ser Pro
            20                  25                  30

Glu Asp Phe Val Ile Gln Ala Lys Ala Asp Cys Tyr Phe Thr Asn
            35                  40                  45

Gly Thr Glu Lys Val Gln Phe Val Val Arg Phe Ile Phe Asn Leu
            50                  55                  60

Glu Glu Tyr Val Arg Phe Asp Ser Asp Val Gly Met Phe Val Ala
            65                  70                  75

Leu Thr Lys Leu Gly Gln Pro Asp Ala Glu Gln Trp Asn Ser Arg
            80                  85                  90

Leu Asp Leu Leu Glu Arg Ser Arg Gln Ala Val Asp Gly Val Cys
            95                  100                 105

Arg His Asn Tyr Arg Leu Gly Ala Pro Phe Thr Val Gly Arg Lys
            110                 115                 120

Val Gln Pro Glu Val Thr Val Tyr Pro Glu Arg Thr Pro Leu Leu
            125                 130                 135

His Gln His Asn Leu Leu His Cys Ser Val Thr Gly Phe Tyr Pro
            140                 145                 150

Gly Asp Ile Lys Ile Lys Trp Phe Leu Asn Gly Gln Glu Glu Arg
            155                 160                 165

Ala Gly Val Met Ser Thr Gly Pro Ile Arg Asn Gly Asp Trp Thr
            170                 175                 180

Phe Gln Thr Val Val Met Leu Glu Met Thr Pro Glu Leu Gly His
            185                 190                 195

Val Tyr Thr Cys Leu Val Asp His Ser Ser Leu Leu Ser Pro Val
            200                 205                 210

Ser Val Glu Trp Arg Ala Gln Ser Glu Tyr Ser Trp Arg Lys Met
            215                 220                 225

Leu Ser Gly Ile Ala Ala Phe Leu Leu Gly Leu Ile Phe Leu Leu
            230                 235                 240

Val Gly Ile Val Ile Gln Leu Arg Ala Gln Lys Gly Tyr Val Arg
            245                 250                 255

Thr Gln Met Ser Gly Asn Glu Val Ser Arg Ala Val Leu Leu Pro
            260                 265                 270

Gln Ser Cys

<210> SEQ ID NO 21
<211> LENGTH: 2818
<212> TYPE: DNA
<213> ORGANISM: Homo sapiens

<400> SEQUENCE: 21
gctgccacct ctctagaggc acctggcggg gagcctctca acataagaca         50
gtgaccagtc tggtgactca cagccggcac agccatgaac tacccgctaa        100
cgctggaaat ggacctcgag aacctggagg acctgttctg ggaactggac        150
agattggaca actataacga cacctccctg gtggaaaatc atctctgccc        200
tgccacagag ggtcccctca tggcctcctt caaggccgtg ttcgtgcccg        250
tggcctacag cctcatcttc ctcctgggcg tgatcggcaa cgtcctggtg        300
ctggtgatcc tggagcggca ccggcagaca cgcagttcca cggagacctt        350

```
cctgttccac ctggccgtgg ccgacctcct gctggtcttc atcttgccct        400
ttgccgtggc cgagggctct gtgggctggg tcctggggac cttcctctgc        450
aaaactgtga ttgccctgca caaagtcaac ttctactgca gcagcctgct        500
cctggcctgc atcgccgtgg accgctacct ggccattgtc cacgccgtcc        550
atgcctaccg ccaccgccgc ctcctctcca tccacatcac ctgtgggacc        600
atctggctgg tgggcttcct ccttgccttg ccagagattc tcttcgccaa        650
agtcagccaa ggccatcaca caactccct gccacgttgc accttctccc         700
aagagaacca agcagaaacg catgcctggt tcacctcccg attcctctac        750
catgtggcgg gattcctgct gcccatgctg gtgatgggct ggtgctacgt        800
gggggtagtg cacaggttgc gccaggccca gcggcgccct cagcggcaga        850
aggcagtcag ggtggccatc ctggtgacaa gcatcttctt cctctgctgg        900
tcaccctacc acatcgtcat cttcctggac accctggcga ggctgaaggc        950
cgtggacaat acctgcaagc tgaatggctc tctcccgtg ccatcacca         1000 tgtgtgagtt cctgggcctg gcccactgct gcctcaaccc catgctctac       1050
actttcgccg gcgtgaagtt ccgcagtgac ctgtcgcggc tcctgaccaa       1100
gctgggctgt accggccctg cctccctgtg ccagctcttc cctagctggc       1150
gcaggagcag tctctctgag tcagagaatg ccacctctct caccacgttc       1200
taggtcccag tgtccccttt tattgctgct tttccttggg gcaggcagtg       1250
atgctggatg ctccttccaa caggagctgg gatcctaagg gctcaccgtg       1300
gctaagagtg tcctaggagt atcctcattt ggggtagcta gaggaaccaa       1350
ccccatttct agaacatccc tgccagctct tctgccggcc ctggggctag       1400
gctggagccc agggagcgga aagcagctcg aaggcacagt gaaggctgtc       1450
cttacccatc tgcaccccc tgggctgaga gaacctcacg cacctcccat        1500
cctaatcatc caatgctcaa gaaacaactt ctacttctgc ccttgccaac       1550
ggagagcgcc tgccctccc agaacacact ccatcagctt aggggctgct        1600
gacctccaca gcttcccctc tctcctcctg cccacctgtc aaacaaagcc       1650
agaagctgag caccagggga tgagtggagg ttaaggctga ggaaaggcca       1700
gctggcagca gagtgtggct tcggacaact cagtccctaa aaacacagac       1750
attctgccag gccccaagc ctgcagtcat cttgaccaag caggaagctc         1800
agactggttg agttcaggta gctgccctg gctctgaccg aaacagcgct         1850
gggtccaccc catgtcaccg gatcctgggt ggtctgcagg cagggctgac       1900
tctaggtgcc cttggaggcc agccagtgac ctgaggaagc gtgaaggccg       1950
agaagcaaga aagaaacccg acagagggaa gaaaagagct ttcttcccga       2000
accccaagga gggagatgga tcaatcaaac ccggctgtcc cctccgccca       2050
ggcgagatgg ggtgggggga gaactcctag ggtggctggg tccaggggat       2100
gggaggttgt gggcattgat ggggaaggag gctggcttgt cccctcctca       2150
ctcccttccc ataagctata gacccgagga aactcagagt cggaacggag       2200
aaaggtggac tggaaggggc ccgtgggagt catctcaacc atcccctccg       2250
ttggcatcac cttaggcagg gaagtgtaag aaacacactg aggcaggaac       2300
tcccaggccc aggaagccgt gccctgcccc cgtgaggatg tcactcagat       2350
```

-continued

```
ggaaccgcag gaagctgctc cgtgcttgtt tgctcacctg gggtgtggga      2400
ggcccgtccg gcagttctgg gtgctcccta ccacctcccc agcctttgat      2450
caggtgggga gtcagggacc cctgcccttg tcccactcaa gccaagcagc      2500
caagctcctt gggaggcccc actggggaaa taacagctgt ggctcacgtg      2550
agagtgtctt cacggcagga caacgagaaa gccctaagac gtccctttt       2600 tctctgagta tctcctcgca agctgggtaa tcgatgggga gtctgaagca      2650
gatgcaaaga ggcagaggat ggattttgaa ttttcttttt aataaaaagg      2700
cacctataaa acaggtcaat acagtacagg cagcacagag accccggaa       2750 caagcctaaa aattgtttca aaataaaaac caagaagatg tcttcaaaaa      2800
aaaaaaaaaa aaaaaaaa                                         2818

<210> SEQ ID NO 22
<211> LENGTH: 372
<212> TYPE: PRT
<213> ORGANISM: Homo sapiens

<400> SEQUENCE: 22

Met Asn Tyr Pro Leu Thr Leu Glu Met Asp Leu Glu Asn Leu Glu
1               5                   10                  15

Asp Leu Phe Trp Glu Leu Asp Arg Leu Asp Asn Tyr Asn Asp Thr
            20                  25                  30

Ser Leu Val Glu Asn His Leu Cys Pro Ala Thr Glu Gly Pro Leu
            35                  40                  45

Met Ala Ser Phe Lys Ala Val Phe Val Pro Val Ala Tyr Ser Leu
            50                  55                  60

Ile Phe Leu Leu Gly Val Ile Gly Asn Val Leu Val Leu Val Ile
            65                  70                  75

Leu Glu Arg His Arg Gln Thr Arg Ser Ser Thr Glu Thr Phe Leu
            80                  85                  90

Phe His Leu Ala Val Ala Asp Leu Leu Leu Val Phe Ile Leu Pro
            95                  100                 105

Phe Ala Val Ala Glu Gly Ser Val Gly Trp Val Leu Gly Thr Phe
            110                 115                 120

Leu Cys Lys Thr Val Ile Ala Leu His Lys Val Asn Phe Tyr Cys
            125                 130                 135

Ser Ser Leu Leu Leu Ala Cys Ile Ala Val Asp Arg Tyr Leu Ala
            140                 145                 150

Ile Val His Ala Val His Ala Tyr Arg His Arg Arg Leu Leu Ser
            155                 160                 165

Ile His Ile Thr Cys Gly Thr Ile Trp Leu Val Gly Phe Leu Leu
            170                 175                 180

Ala Leu Pro Glu Ile Leu Phe Ala Lys Val Ser Gln Gly His His
            185                 190                 195

Asn Asn Ser Leu Pro Arg Cys Thr Phe Ser Gln Glu Asn Gln Ala
            200                 205                 210

Glu Thr His Ala Trp Phe Thr Ser Arg Phe Leu Tyr His Val Ala
            215                 220                 225

Gly Phe Leu Leu Pro Met Leu Val Met Gly Trp Cys Tyr Val Gly
            230                 235                 240

Val Val His Arg Leu Arg Gln Ala Gln Arg Arg Pro Gln Arg Gln
            245                 250                 255
```

```
Lys Ala Val Arg Val Ala Ile Leu Val Thr Ser Ile Phe Phe Leu
                260                 265                 270

Cys Trp Ser Pro Tyr His Ile Val Ile Phe Leu Asp Thr Leu Ala
            275                 280                 285

Arg Leu Lys Ala Val Asp Asn Thr Cys Lys Leu Asn Gly Ser Leu
        290                 295                 300

Pro Val Ala Ile Thr Met Cys Glu Phe Leu Gly Leu Ala His Cys
    305                 310                 315

Cys Leu Asn Pro Met Leu Tyr Thr Phe Ala Gly Val Lys Phe Arg
320                 325                 330

Ser Asp Leu Ser Arg Leu Leu Thr Lys Leu Gly Cys Thr Gly Pro
                335                 340                 345

Ala Ser Leu Cys Gln Leu Phe Pro Ser Trp Arg Arg Ser Ser Leu
            350                 355                 360

Ser Glu Ser Glu Asn Ala Thr Ser Leu Thr Thr Phe
        365                 370

<210> SEQ ID NO 23
<211> LENGTH: 1529
<212> TYPE: DNA
<213> ORGANISM: Homo sapiens

<400> SEQUENCE: 23
agtggctcta ctttcagaag aaagtgtctc tcttcctgct taaacctctg          50
tctctgacgg tccctgccaa tcgctctggt cgaccccaac acactaggag          100
gacagacaca ggctccaaac tccactaacc agagctgtga ttgtgcccgc          150
tgagtggact gcgttgtcag ggagtgagtg ctccatcatc gggagaatcc          200
aagcaggacc gccatggagg aaggtcaata ttcagagatc gaggagcttc          250
ccaggaggcg tgttgcagg cgtgggactc agatcgtgct gctggggctg          300
gtgaccgccg ctctgtgggc tgggctgctg actctgcttc cctgtggca           350 ctgggacacc acacagagtc taaaacagct ggaagagagg gctgcccgga          400
acgtctctca gtttccaag aacttggaaa gccaccacgg tgaccagatg           450
gcgcagaaat cccagtccac gcagatttca caggaactgg aggaacttcg          500
agctgaacag cagagattga atctcaggac cttggagctg tcctggaacc          550
tgaacgggct tcaagcagat ctgagcagct tcaagtccca ggaattgaac          600
gagaggaacg aagcttcaga tttgctggaa agactccggg aggaggtgac          650
aaagctaagg atggagttgc aggtgtccag cggctttgtg tgcaacacgt          700 gcccctgaaaa gtgatcaac ttccaacgga agtgctacta cttcggcaag          750
ggcaccaagc agtgggtcca cgcccggtat gcctgtgacg acatggaagg          800
gcagctggtc agcatccaca gcccggagga gcaggacttc ctgaccaagc          850
atgccagcca caccggctcc tggattggcc ttcggaactt ggacctgaag          900
ggagagttta tctgggtgga tgggagccat gtggactaca gcaactgggc          950
tccaggggag cccaccagcc ggagccaggg cgaggactgc gtgatgatgc          1000
ggggctccgg tcgctggacc gacgccttct gcgaccgtaa gctgggcgcc          1050
tgggtgtgcg accggctggc cacatgcacg ccgccagcca gcgaaggttc          1100
cgcggagtcc atgggacctg attcaagacc agaccctgac ggccgcctgc          1150
```

-continued

```
ccacccccctc tgcccctctc cactcttgag catggataca gccaggccca      1200
gagcaagacc ctgaagaccc ccaaccacgg cctaaaagcc tctttgtggc      1250
tgaaaggtcc ctgtgacatt ttctgccacc caaacggagg cagctgacac      1300
atctcccgct cctctatggc ccctgccttc ccaggagtac accccaacag      1350
caccctctcc agatgggagt gcccccaaca gcaccctctc cagatgagag      1400
ttacacccca acagcaccct ctccagatgc agccccatct cctcagcacc      1450
ccaggacctg agtatcccca gctcagggtg gtgagtcctc ctgtccagcc      1500
tgcatcaata aatgggggca gtgatggcc                              1529
```

<210> SEQ ID NO 24
<211> LENGTH: 321
<212> TYPE: PRT
<213> ORGANISM: Homo sapiens

<400> SEQUENCE: 24

```
Met Glu Glu Gly Gln Tyr Ser Glu Ile Glu Glu Leu Pro Arg Arg
 1               5                  10                  15

Arg Cys Cys Arg Arg Gly Thr Gln Ile Val Leu Leu Gly Leu Val
                20                  25                  30

Thr Ala Ala Leu Trp Ala Gly Leu Leu Thr Leu Leu Leu Leu Trp
                35                  40                  45

His Trp Asp Thr Thr Gln Ser Leu Lys Gln Leu Glu Glu Arg Ala
                50                  55                  60

Ala Arg Asn Val Ser Gln Val Ser Lys Asn Leu Glu Ser His His
                65                  70                  75

Gly Asp Gln Met Ala Gln Lys Ser Gln Ser Thr Gln Ile Ser Gln
                80                  85                  90

Glu Leu Glu Glu Leu Arg Ala Glu Gln Gln Arg Leu Lys Ser Gln
                95                 100                 105

Asp Leu Glu Leu Ser Trp Asn Leu Asn Gly Leu Gln Ala Asp Leu
               110                 115                 120

Ser Ser Phe Lys Ser Gln Glu Leu Asn Glu Arg Asn Glu Ala Ser
               125                 130                 135

Asp Leu Leu Glu Arg Leu Arg Glu Glu Val Thr Lys Leu Arg Met
               140                 145                 150

Glu Leu Gln Val Ser Ser Gly Phe Val Cys Asn Thr Cys Pro Glu
               155                 160                 165

Lys Trp Ile Asn Phe Gln Arg Lys Cys Tyr Tyr Phe Gly Lys Gly
               170                 175                 180

Thr Lys Gln Trp Val His Ala Arg Tyr Ala Cys Asp Asp Met Glu
               185                 190                 195

Gly Gln Leu Val Ser Ile His Ser Pro Glu Glu Gln Asp Phe Leu
               200                 205                 210

Thr Lys His Ala Ser His Thr Gly Ser Trp Ile Gly Leu Arg Asn
               215                 220                 225

Leu Asp Leu Lys Gly Glu Phe Ile Trp Val Asp Gly Ser His Val
               230                 235                 240

Asp Tyr Ser Asn Trp Ala Pro Gly Glu Pro Thr Ser Arg Ser Gln
               245                 250                 255

Gly Glu Asp Cys Val Met Met Arg Gly Ser Gly Arg Trp Thr Asp
               260                 265                 270

Ala Phe Cys Asp Arg Lys Leu Gly Ala Trp Val Cys Asp Arg Leu
```

```
                    275                 280                 285
Ala Thr Cys Thr Pro Pro Ala Ser Glu Gly Ser Ala Glu Ser Met
                290                 295                 300

Gly Pro Asp Ser Arg Pro Asp Pro Asp Gly Arg Leu Pro Thr Pro
                305                 310                 315

Ser Ala Pro Leu His Ser
                320

<210> SEQ ID NO 25
<211> LENGTH: 1244
<212> TYPE: DNA
<213> ORGANISM: Homo sapiens

<400> SEQUENCE: 25
agagatgggg acggaggcca cagagcaggt ttcctggggc cattactctg           50
gggatgaaga ggacgcatac tcggctgagc cactgccgga gctttgctac          100
aaggccgatg tccaggcctt cagccgggcc ttccaaccca gtgtctccct          150
gaccgtggct gcgctgggtc tggccggcaa tggcctggtc ctggccaccc          200
acctggcagc ccgacgcgca gcgcgctcgc ccacctctgc ccacctgctc          250
cagctggccc tggccgacct cttgctggcc ctgactctgc ccttcgcggc          300
agcaggggct cttcagggct ggagtctggg aagtgccacc tgccgcacca          350
tctctggcct ctactcggcc tccttccacg ccggcttcct cttcctggcc          400
tgtatcagcg ccgaccgcta cgtggccatc gcgcgagcgc tcccagccgg          450
gccgcggccc tccactcccg gccgcgcaca cttggtctcc gtcatcgtgt          500
ggctgctgtc actgctcctg gcgctgcctg cgctgctctt cagccaggat          550
gggcagcggg aaggccaacg acgctgtcgc ctcatcttcc ccgagggcct          600
cacgcagacg gtgaaggggg cgagcgccgt ggcgcaggtg gccctgggct          650
tcgcgctgcc gctgggcgtc atggtagcct gctacgcgct tctgggccgc          700
acgctgctgg ccgccagggg gcccgagcgc cggcgtgcgc tgcgcgtcgt          750
ggtggctctg gtggcggcct tcgtggtgct gcagctgccc tacagcctcg          800
ccctgctgct ggatactgcc gatctactgg ctgcgcgcga gcggagctgc          850
cctgccagca aacgcaagga tgtcgcactg ctggtgacca gcggcttggc          900
cctcgcccgc tgtggcctca atcccgttct ctacgccttc ctgggcctgc          950
gcttccgcca ggacctgcgg aggctgctac ggggtgggag ctcgccctca         1000
gggcctcaac cccgccgcgg ctgcccccgc cggccccgcc tttcttcctg         1050
ctcagctccc acgagaccc acagtctctc ctgggacaac tagggctgcg          1100
aatctagagg aggggggcagg ctgagggtcg tgggaaaggg gagtaggtgg        1150
gggaacactg agaaagaggc agggacctaa agggactacc tctgtgcctt         1200
gccacattaa attgataaca tggaaatgaa aaaaaaaaaa aaaa              1244

<210> SEQ ID NO 26
<211> LENGTH: 362
<212> TYPE: PRT
<213> ORGANISM: Homo sapiens

<400> SEQUENCE: 26

Met Gly Thr Glu Ala Thr Glu Gln Val Ser Trp Gly His Tyr Ser
 1               5                  10                  15
```

-continued

Gly Asp Glu Glu Asp Ala Tyr Ser Ala Glu Pro Leu Pro Glu Leu
            20                  25                  30

Cys Tyr Lys Ala Asp Val Gln Ala Phe Ser Arg Ala Phe Gln Pro
            35                  40                  45

Ser Val Ser Leu Thr Val Ala Ala Leu Gly Leu Ala Gly Asn Gly
            50                  55                  60

Leu Val Leu Ala Thr His Leu Ala Ala Arg Arg Ala Ala Arg Ser
            65                  70                  75

Pro Thr Ser Ala His Leu Leu Gln Leu Ala Leu Ala Asp Leu Leu
            80                  85                  90

Leu Ala Leu Thr Leu Pro Phe Ala Ala Gly Ala Leu Gln Gly
            95                  100                 105

Trp Ser Leu Gly Ser Ala Thr Cys Arg Thr Ile Ser Gly Leu Tyr
            110                 115                 120

Ser Ala Ser Phe His Ala Gly Phe Leu Phe Leu Ala Cys Ile Ser
            125                 130                 135

Ala Asp Arg Tyr Val Ala Ile Ala Arg Ala Leu Pro Ala Gly Pro
            140                 145                 150

Arg Pro Ser Thr Pro Gly Arg Ala His Leu Val Ser Val Ile Val
            155                 160                 165

Trp Leu Leu Ser Leu Leu Leu Ala Leu Pro Ala Leu Leu Phe Ser
            170                 175                 180

Gln Asp Gly Gln Arg Glu Gly Gln Arg Arg Cys Arg Leu Ile Phe
            185                 190                 195

Pro Glu Gly Leu Thr Gln Thr Val Lys Gly Ala Ser Ala Val Ala
            200                 205                 210

Gln Val Ala Leu Gly Phe Ala Leu Pro Leu Gly Val Met Val Ala
            215                 220                 225

Cys Tyr Ala Leu Gly Arg Thr Leu Ala Ala Arg Gly Pro
            230                 235                 240

Glu Arg Arg Arg Ala Leu Arg Val Val Ala Leu Val Ala Ala
            245                 250                 255

Phe Val Val Leu Gln Leu Pro Tyr Ser Leu Ala Leu Leu Leu Asp
            260                 265                 270

Thr Ala Asp Leu Leu Ala Ala Arg Glu Arg Ser Cys Pro Ala Ser
            275                 280                 285

Lys Arg Lys Asp Val Ala Leu Leu Val Thr Ser Gly Leu Ala Leu
            290                 295                 300

Ala Arg Cys Gly Leu Asn Pro Val Leu Tyr Ala Phe Leu Gly Leu
            305                 310                 315

Arg Phe Arg Gln Asp Leu Arg Arg Leu Leu Arg Gly Gly Ser Ser
            320                 325                 330

Pro Ser Gly Pro Gln Pro Arg Arg Gly Cys Pro Arg Arg Pro Arg
            335                 340                 345

Leu Ser Ser Cys Ser Ala Pro Thr Glu Thr His Ser Leu Ser Trp
            350                 355                 360

Asp Asn

<210> SEQ ID NO 27
<211> LENGTH: 1066
<212> TYPE: DNA
<213> ORGANISM: Homo sapiens

<400> SEQUENCE: 27

```
cctcggttct atcgattgaa ttcatgaaga cattgcctgc catgcttgga         50
actgggaaat tattttgggt cttcttctta atcccatatc tggacatctg        100
gaacatccat gggaaagaat catgtgatgt acagctttat ataaagagac        150
aatctgaaca ctccatctta gcaggagatc cctttgaact agaatgccct        200
gtgaaatact gtgctaacag gcctcatgtg acttggtgca agctcaatgg        250
aacaacatgt gtaaaacttg aagatagaca acaagttgg aaggaagaga         300 agaacatttc attttcatt ctacattttg aaccagtgct tcctaatgac         350
aatgggtcat accgctgttc tgcaaatttt cagtctaatc tcattgaaag        400
ccactcaaca actctttatg tgacagatgt aaaaagtgct tcagaacgac        450
cctccaagga cgaaatggca agcagaccct ggctcctgta tagtttactt        500
cctttggggg gattgcctct actcatcact acctgtttct gcctgttctg        550
ctgcctgaga aggcaccaag gaaagcaaaa tgaactctct gacacagcag        600
gaagggaaat taacctggtt gatgctcacc ttaagagtga gcaaacagaa        650
gcaagcacca ggcaaaattc ccaagtactg ctatcagaaa ctggaattta        700
tgataatgac cctgaccttt gtttcagaat gcaggaaggg tctgaagttt        750
attctaatcc atgcctggaa gaaacaaac caggcattgt ttatgcttcc         800
ctgaaccatt ctgtcattgg actgaactca agactggcaa gaaatgtaaa        850
agaagcacca acagaaatatg catccatatg tgtgaggagt taaggatcct       900
ctagagtcga cctgcagaag cttggccgcc atggcccaac ttgtttattg        950
cagcttataa gtgttacaaa taaacaaata atatttctca atttgagaat       1000
ttttacttta gaaatgttca tgttagtgct tgggtctgaa gggtccatag       1050
gacaaatgat taaaat                                            1066
```

<210> SEQ ID NO 28
<211> LENGTH: 289
<212> TYPE: PRT
<213> ORGANISM: Homo sapiens

<400> SEQUENCE: 28

```
Met Lys Thr Leu Pro Ala Met Leu Gly Thr Gly Lys Leu Phe Trp
 1               5                  10                  15

Val Phe Phe Leu Ile Pro Tyr Leu Asp Ile Trp Asn Ile His Gly
                20                  25                  30

Lys Glu Ser Cys Asp Val Gln Leu Tyr Ile Lys Arg Gln Ser Glu
                35                  40                  45

His Ser Ile Leu Ala Gly Asp Pro Phe Glu Leu Glu Cys Pro Val
                50                  55                  60

Lys Tyr Cys Ala Asn Arg Pro His Val Thr Trp Cys Lys Leu Asn
                65                  70                  75

Gly Thr Thr Cys Val Lys Leu Glu Asp Arg Gln Thr Ser Trp Lys
                80                  85                  90

Glu Glu Lys Asn Ile Ser Phe Phe Ile Leu His Phe Glu Pro Val
                95                 100                 105

Leu Pro Asn Asp Asn Gly Ser Tyr Arg Cys Ser Ala Asn Phe Gln
               110                 115                 120

Ser Asn Leu Ile Glu Ser His Ser Thr Thr Leu Tyr Val Thr Asp
               125                 130                 135
```

```
Val Lys Ser Ala Ser Glu Arg Pro Ser Lys Asp Glu Met Ala Ser
            140                 145                 150

Arg Pro Trp Leu Leu Tyr Ser Leu Leu Pro Leu Gly Gly Leu Pro
            155                 160                 165

Leu Leu Ile Thr Thr Cys Phe Cys Leu Phe Cys Cys Leu Arg Arg
            170                 175                 180

His Gln Gly Lys Gln Asn Glu Leu Ser Asp Thr Ala Gly Arg Glu
            185                 190                 195

Ile Asn Leu Val Asp Ala His Leu Lys Ser Glu Gln Thr Glu Ala
            200                 205                 210

Ser Thr Arg Gln Asn Ser Gln Val Leu Leu Ser Glu Thr Gly Ile
            215                 220                 225

Tyr Asp Asn Asp Pro Asp Leu Cys Phe Arg Met Gln Glu Gly Ser
            230                 235                 240

Glu Val Tyr Ser Asn Pro Cys Leu Glu Glu Asn Lys Pro Gly Ile
            245                 250                 255

Val Tyr Ala Ser Leu Asn His Ser Val Ile Gly Leu Asn Ser Arg
            260                 265                 270

Leu Ala Arg Asn Val Lys Glu Ala Pro Thr Glu Tyr Ala Ser Ile
            275                 280                 285

Cys Val Arg Ser

<210> SEQ ID NO 29
<211> LENGTH: 2185
<212> TYPE: DNA
<213> ORGANISM: Homo sapiens

<400> SEQUENCE: 29
gttctccttt ccgagccaaa atcccaggcg atggtgaatt atgaacgtgc        50
cacaccatga agctcttgtg gcaggtaact gtgcaccacc acacctggaa       100
tgccatcctg ctcccgttcg tctacctcac ggcgcaagtg tggattctgt       150
gtgcagccat cgctgctgcc gcctcagccg gccccagaa ctgccccctcc       200 gtttgctcgt gcagtaacca gttcagcaag gtggtgtgca cgcgccgggg       250
cctctccgag gtcccgcagg gtattccctc gaacacccgg tacctcaacc       300
tcatggagaa caacatccag atgatccagg ccgacacctt ccgccacctc       350
caccacctgg aggtcctgca gttgggcagg aactccatcc ggcagattga       400 ggtggggggcc ttcaacggcc tggccagcct caacaccctg agctgttcg       450 acaactggct gacagtcatc cctagcgggg cctttgaata cctgtccaag       500
ctgcgggagc tctggcttcg caacaacccc atcgaaagca tccctctta       550 cgccttcaac cgggtgccct cctcatgcg cctggacttg ggggagctca       600
agaagctgga gtatatctct gagggagctt ttgagggct gttcaaccte       650 aagtatctga acttgggcat gtgcaacatt aaagacatgc caatctcac       700 cccctggtg gggctggagg agctggagat gtcagggaac cacttccctg       750
agatcaggcc tggctccttc catggcctga gctccctcaa gaagctctgg       800
gtcatgaact cacaggtcag cctgattgag cggaatgctt ttgacgggct       850
ggcttcactt gtggaactca acttggccca caataacctc tcttctttgc       900
cccatgacct ctttaccccg ctgaggtacc tggtggagtt gcatctacac       950
```

| | |
|---|---|
| cacaacccttt ggaactgtga ttgtgacatt ctgtggctag cctggtggct | 1000 |
| tcgagagtat atacccacca attccacctg ctgtggccgc tgtcatgctc | 1050 |
| ccatgcacat gcgaggccgc tacctcgtgg aggtggacca ggcctccttc | 1100 |
| cagtgctctg ccccctccat catggacgca cctcgagacc tcaacatttc | 1150 |
| tgagggtcgg atggcagaac ttaagtgtcg gactcccct atgtcctccg | 1200 |
| tgaagtggtt gctgcccaat gggacagtgc tcagccacgc ctcccgccac | 1250 |
| ccaaggatct ctgtcctcaa cgacggcacc ttgaactttt ccacgtgct | 1300 |
| gctttcagac actggggtgt acacatgcat ggtgaccaat gttgcaggca | 1350 |
| actccaacgc ctcggcctac ctcaatgtga gcacggctga gcttaacacc | 1400 |
| tccaactaca gcttcttcac cacagtaaca gtggagacca cggagatctc | 1450 |
| gcctgaggac acaacgcgaa agtacaagcc tgttcctacc acgtccactg | 1500 |
| gttaccagcc ggcatatacc acctctacca cggtgctcat tcagactacc | 1550 |
| cgtgtgccca agcaggtggc agtacccgcg acagacacca ctgacaagat | 1600 |
| gcagaccagc ctggatgaag tcatgaagac caccaagatc atcattggct | 1650 |
| gctttgtggc agtgactctg ctagctgccg ccatgttgat tgtcttctat | 1700 |
| aaacttcgta agcggcacca gcagcggagt acagtcacag ccgcccggac | 1750 |
| tgttgagata atccaggtgg acgaagacat cccagcagca catccgcag | 1800 |
| cagcaacagc agctccgtcc ggtgtatcag gtgagggggc agtagtgctg | 1850 |
| cccacaattc atgaccatat taactacaac acctacaaac cagcacatgg | 1900 |
| ggcccactgg acagaaaaca gcctggggaa ctctctgcac cccacagtca | 1950 |
| ccactatctc tgaaccttat ataattcaga cccataccaa ggacaaggta | 2000 |
| caggaaactc aaatatgact cccctcccc aaaaaactta taaatgcaa | 2050 |
| tagaatgcac acaaagacag caacttttgt acagagtggg gagagacttt | 2100 |
| ttccttgtata tgcttatata ttaagtctat gggctggtta aaaaaaacag | 2150 |
| attatattaa aatttaaaga caaaaagtca aaaca | 2185 |

<210> SEQ ID NO 30
<211> LENGTH: 653
<212> TYPE: PRT
<213> ORGANISM: Homo sapiens

<400> SEQUENCE: 30

Met Lys Leu Leu Trp Gln Val Thr Val His His Thr Trp Asn
 1               5                  10                  15

Ala Ile Leu Leu Pro Phe Val Tyr Leu Thr Ala Gln Val Trp Ile
                20                  25                  30

Leu Cys Ala Ala Ile Ala Ala Ala Ala Ser Ala Gly Pro Gln Asn
                35                  40                  45

Cys Pro Ser Val Cys Ser Cys Ser Asn Gln Phe Ser Lys Val Val
                50                  55                  60

Cys Thr Arg Arg Gly Leu Ser Glu Val Pro Gln Gly Ile Pro Ser
                65                  70                  75

Asn Thr Arg Tyr Leu Asn Leu Met Glu Asn Asn Ile Gln Met Ile
                80                  85                  90

Gln Ala Asp Thr Phe Arg His Leu His His Leu Glu Val Leu Gln
                95                  100                 105

```
Leu Gly Arg Asn Ser Ile Arg Gln Ile Glu Val Gly Ala Phe Asn
            110                 115                 120

Gly Leu Ala Ser Leu Asn Thr Leu Glu Leu Phe Asp Asn Trp Leu
            125                 130                 135

Thr Val Ile Pro Ser Gly Ala Phe Glu Tyr Leu Ser Lys Leu Arg
            140                 145                 150

Glu Leu Trp Leu Arg Asn Asn Pro Ile Glu Ser Ile Pro Ser Tyr
            155                 160                 165

Ala Phe Asn Arg Val Pro Ser Leu Met Arg Leu Asp Leu Gly Glu
            170                 175                 180

Leu Lys Lys Leu Glu Tyr Ile Ser Glu Gly Ala Phe Glu Gly Leu
            185                 190                 195

Phe Asn Leu Lys Tyr Leu Asn Leu Gly Met Cys Asn Ile Lys Asp
            200                 205                 210

Met Pro Asn Leu Thr Pro Leu Val Gly Leu Glu Glu Leu Glu Met
            215                 220                 225

Ser Gly Asn His Phe Pro Glu Ile Arg Pro Gly Ser Phe His Gly
            230                 235                 240

Leu Ser Ser Leu Lys Lys Leu Trp Val Met Asn Ser Gln Val Ser
            245                 250                 255

Leu Ile Glu Arg Asn Ala Phe Asp Gly Leu Ala Ser Leu Val Glu
            260                 265                 270

Leu Asn Leu Ala His Asn Asn Leu Ser Ser Leu Pro His Asp Leu
            275                 280                 285

Phe Thr Pro Leu Arg Tyr Leu Val Glu Leu His Leu His His Asn
            290                 295                 300

Pro Trp Asn Cys Asp Cys Asp Ile Leu Trp Leu Ala Trp Trp Leu
            305                 310                 315

Arg Glu Tyr Ile Pro Thr Asn Ser Thr Cys Cys Gly Arg Cys His
            320                 325                 330

Ala Pro Met His Met Arg Gly Arg Tyr Leu Val Glu Val Asp Gln
            335                 340                 345

Ala Ser Phe Gln Cys Ser Ala Pro Phe Ile Met Asp Ala Pro Arg
            350                 355                 360

Asp Leu Asn Ile Ser Glu Gly Arg Met Ala Glu Leu Lys Cys Arg
            365                 370                 375

Thr Pro Pro Met Ser Ser Val Lys Trp Leu Leu Pro Asn Gly Thr
            380                 385                 390

Val Leu Ser His Ala Ser Arg His Pro Arg Ile Ser Val Leu Asn
            395                 400                 405

Asp Gly Thr Leu Asn Phe Ser His Val Leu Leu Ser Asp Thr Gly
            410                 415                 420

Val Tyr Thr Cys Met Val Thr Asn Val Ala Gly Asn Ser Asn Ala
            425                 430                 435

Ser Ala Tyr Leu Asn Val Ser Thr Ala Glu Leu Asn Thr Ser Asn
            440                 445                 450

Tyr Ser Phe Phe Thr Thr Val Thr Val Glu Thr Thr Glu Ile Ser
            455                 460                 465

Pro Glu Asp Thr Thr Arg Lys Tyr Lys Pro Val Pro Thr Thr Ser
            470                 475                 480

Thr Gly Tyr Gln Pro Ala Tyr Thr Thr Ser Thr Thr Val Leu Ile
            485                 490                 495

Gln Thr Thr Arg Val Pro Lys Gln Val Ala Val Pro Ala Thr Asp
```

```
                        500                 505                 510
Thr Thr Asp Lys Met Gln Thr Ser Leu Asp Glu Val Met Lys Thr
                515                 520                 525
Thr Lys Ile Ile Ile Gly Cys Phe Val Ala Val Thr Leu Leu Ala
                530                 535                 540
Ala Ala Met Leu Ile Val Phe Tyr Lys Leu Arg Lys Arg His Gln
                545                 550                 555
Gln Arg Ser Thr Val Thr Ala Ala Arg Thr Val Glu Ile Ile Gln
                560                 565                 570
Val Asp Glu Asp Ile Pro Ala Ala Thr Ser Ala Ala Ala Thr Ala
                575                 580                 585
Ala Pro Ser Gly Val Ser Gly Glu Gly Ala Val Val Leu Pro Thr
                590                 595                 600
Ile His Asp His Ile Asn Tyr Asn Thr Tyr Lys Pro Ala His Gly
                605                 610                 615
Ala His Trp Thr Glu Asn Ser Leu Gly Asn Ser Leu His Pro Thr
                620                 625                 630
Val Thr Thr Ile Ser Glu Pro Tyr Ile Ile Gln Thr His Thr Lys
                635                 640                 645
Asp Lys Val Gln Glu Thr Gln Ile
                650

<210> SEQ ID NO 31
<211> LENGTH: 1488
<212> TYPE: DNA
<213> ORGANISM: Homo sapiens

<400> SEQUENCE: 31
gctgaaaggg ccacgtttgt tttcattaca aataagacca ccgagtgggc         50
tcctggcgtg ggggcgggag cagccgcgcg cagtcttcag aggcagcccc        100
ccaggctgtc tctggagggt gtgtctctgc ttccctttcc ccgtgtttat        150
tttcagacga agccaagtgg cccgggggga ccctccggac tcccagcctt        200
cagagaggag ggcagctcgg gctttcgccg cagtgcttcc tgcccgtcac        250
gtgtgtgctc ctagccgggg tcgggggagc tggtatcttg gcccttctgg        300
gaggacgcgc acagcccgag gaggcagagc cccagacggg aatgggcttt        350
tcagaggtgg ggtgcgggcg aggggacgat gcattatttt taatatttga        400
tttatttttc caactggact tcttcccggg gctctttctg ggcccagctg        450
cctttgtgat cccgcgcccc ggtcctcggc ctctcacctc cagcgccggg        500 gcgcccctg ctgtcggaag cggctgtgac cgggcagagg tgctatctgg         550
gactctgggt tctcagcccg ggacagcga accgaggggc agatgatcca         600
tcagaaaaga gccggcactg cccagccccg cgccctgcc cctgccttt          650 tccgggagcg cgccgcgccg cacccgctac ggccgcttga ccccatcttt        700
gagcccggcc ccaagctctg ggaccgtcgt gcccctcatc aaggaagagc        750
caaggacccc aaggagaagg tcaggagcgg cggtgtggat gtcccttggc        800
tgcaggcccc gccgcgcact cccttcagtc cttcccttct ctagggacca        850
ggtagcatca gtgcctggat ctcggccttg tgtgccctgc tccctgcccc        900
acctactaag aaccaagtct ggttcaccgg ctcccaagag ctggaaccca        950
ttctcagcta gctgggggcc caggccaccc cttccctcca gacctgtgtg       1000
```

| | |
|---|---|
| ccttctgccc tggctccagg gccccccaca ccgtgaccag ggcgggatcc | 1050 |
| ctatggggct ggccagtcgg caccgtgcca ggcccacagt gccctgggcg | 1100 |
| tccatggaag tcgttctgtg tctttaaaat cagaaggaag acattaacct | 1150 |
| ttaggctgaa gaaaatgttt tagtacacag caataactta tttgtcttta | 1200 |
| tccaacagcc ataaaatata actttaaata ttctattgat agagaaagga | 1250 |
| gttcatgaag gcagaaatgc ctggggccca cgaacatccc agtgtggccc | 1300 |
| tggacgggac atcatgctgg gcaacacagc taaaatgcgg gtgaagacca | 1350 |
| gatttcttgc acatggcggt gacgggatgc tccctagaga gcttcaagtg | 1400 |
| gattctttgc ttttatttt ctctcttaat aaaaatgtat gatgtttaca | 1450 |
| ttgtcagaga acaaacagaa aaaaaaaaaa aaaaaaa | 1488 |

<210> SEQ ID NO 32
<211> LENGTH: 112
<212> TYPE: PRT
<213> ORGANISM: Homo sapiens

<400> SEQUENCE: 32

Met Ser Leu Gly Cys Arg Pro Arg Arg Ala Leu Pro Ser Val Leu
1               5                   10                  15
Pro Phe Ser Arg Asp Gln Val Ala Ser Val Pro Gly Ser Arg Pro
                20                  25                  30
Cys Val Pro Cys Ser Leu Pro His Leu Leu Arg Thr Lys Ser Gly
                35                  40                  45
Ser Pro Ala Pro Lys Ser Trp Asn Pro Phe Ser Ala Ser Trp Gly
                50                  55                  60
Pro Arg Pro Pro Leu Pro Ser Arg Pro Val Cys Leu Leu Pro Trp
                65                  70                  75
Leu Gln Gly Pro Pro His Arg Asp Gln Gly Gly Ile Pro Met Gly
                80                  85                  90
Leu Ala Ser Arg His Arg Ala Arg Pro Thr Val Pro Trp Ala Ser
                95                  100                 105
Met Glu Val Val Leu Cys Leu
                110

<210> SEQ ID NO 33
<211> LENGTH: 1322
<212> TYPE: DNA
<213> ORGANISM: Homo sapiens

<400> SEQUENCE: 33

| | |
|---|---|
| atatatcgat atgctgccga ggctgttgct gttgatctgt gctccactct | 50 |
| gtgaacctgc cgagctgttt ttgatagcca gcccctccca tcccacagag | 100 |
| gggagcccag tgaccctgac gtgtaagatg ccctttctac agagttcaga | 150 |
| tgcccagttc cagttctgct ttttcagaga cacccgggcc ttgggcccag | 200 |
| gctggagcag ctcccccaag ctccagatcg ctgccatgtg gaaagaagac | 250 |
| acagggtcat actggtgcga ggcacagaca atggcgtcca aagtcttgag | 300 |
| gagcaggaga tcccagataa atgtgcacag gtccctgtc gctgatgtga | 350 |
| gcttggagac tcagccccca ggaggacagg tgatggaggg agacaggctg | 400 |
| gtcctcatct gctcagttgc tatgggcaca ggagacatca ccttcctttg | 450 |

| | |
|---|---|
| gtacaaaggg gctgtaggtt taaaccttca gtcaaagacc cagcgttcac | 500 |
| tgacagcaga gtatgagatt ccttcagtga gggagagtga tgctgagcaa | 550 |
| tattactgtg tagctgaaaa tggctatggt cccagcccca gtgggctggt | 600 |
| gagcatcact gtcagaatcc cggtgtctcg cccaatcctc atgctcaggg | 650 |
| ctcccagggc ccaggctgca gtggaggatg tgctggagct tcactgtgag | 700 |
| gccctgagag gctctcctcc gatcctgtac tggttttatc acgaggatat | 750 |
| cacccctgggg agcaggtcgg ccccctctgg aggaggagcc tccttcaacc | 800 |
| tttccctgac tgaagaacat tctggaaact actcctgtga ggccaacaat | 850 |
| ggcctggggg cccagcgcag tgaggcggtg acactcaact tcacagtgcc | 900 |
| tactggggcc agaagcaatc atcttacctc aggagtcatt gaggggctgc | 950 |
| tcagcaccct tggtccagcc accgtggcct tattattttg ctacggcctc | 1000 |
| aaaagaaaaa taggaagacg ttcagccagg gatccactca ggagccttcc | 1050 |
| cagccctcta ccccaagagt tcacgtacct caactcacct accccagggc | 1100 |
| agctacagcc tatatatgaa aatgtgaatg ttgtaagtgg ggatgaggtt | 1150 |
| tattcactgg cgtactataa ccagccggag caggaatcag tagcagcaga | 1200 |
| aaccctgggg acacatatgg aggacaaggt ttccttagac atctattcca | 1250 |
| ggctgaggaa agcaaacatt acagatgtgg actatgaaga tgctatgtaa | 1300 |
| ggttatggaa gattctgctc tt | 1322 |

<210> SEQ ID NO 34
<211> LENGTH: 429
<212> TYPE: PRT
<213> ORGANISM: Homo sapiens

<400> SEQUENCE: 34

Met Leu Pro Arg Leu Leu Leu Ile Cys Ala Pro Leu Cys Glu
1               5                   10                  15

Pro Ala Glu Leu Phe Leu Ile Ala Ser Pro Ser His Pro Thr Glu
                20                  25                  30

Gly Ser Pro Val Thr Leu Thr Cys Lys Met Pro Phe Leu Gln Ser
            35                  40                  45

Ser Asp Ala Gln Phe Gln Phe Cys Phe Phe Arg Asp Thr Arg Ala
        50                  55                  60

Leu Gly Pro Gly Trp Ser Ser Pro Lys Leu Gln Ile Ala Ala
            65                  70                  75

Met Trp Lys Glu Asp Thr Gly Ser Tyr Trp Cys Glu Ala Gln Thr
        80                  85                  90

Met Ala Ser Lys Val Leu Arg Ser Arg Ser Gln Ile Asn Val
            95                  100                 105

His Arg Val Pro Val Ala Asp Val Ser Leu Glu Thr Gln Pro Pro
        110                 115                 120

Gly Gly Gln Val Met Glu Gly Asp Arg Leu Val Leu Ile Cys Ser
            125                 130                 135

Val Ala Met Gly Thr Gly Asp Ile Thr Phe Leu Trp Tyr Lys Gly
        140                 145                 150

Ala Val Gly Leu Asn Leu Gln Ser Lys Thr Gln Arg Ser Leu Thr
            155                 160                 165

Ala Glu Tyr Glu Ile Pro Ser Val Arg Glu Ser Asp Ala Glu Gln
        170                 175                 180

```
Tyr Tyr Cys Val Ala Glu Asn Gly Tyr Gly Pro Ser Pro Ser Gly
            185                 190                 195

Leu Val Ser Ile Thr Val Arg Ile Pro Val Ser Arg Pro Ile Leu
            200                 205                 210

Met Leu Arg Ala Pro Arg Ala Gln Ala Ala Val Glu Asp Val Leu
            215                 220                 225

Glu Leu His Cys Glu Ala Leu Arg Gly Ser Pro Pro Ile Leu Tyr
            230                 235                 240

Trp Phe Tyr His Glu Asp Ile Thr Leu Gly Ser Arg Ser Ala Pro
            245                 250                 255

Ser Gly Gly Gly Ala Ser Phe Asn Leu Ser Leu Thr Glu Glu His
            260                 265                 270

Ser Gly Asn Tyr Ser Cys Glu Ala Asn Asn Gly Leu Gly Ala Gln
            275                 280                 285

Arg Ser Glu Ala Val Thr Leu Asn Phe Thr Val Pro Thr Gly Ala
            290                 295                 300

Arg Ser Asn His Leu Thr Ser Gly Val Ile Glu Gly Leu Leu Ser
            305                 310                 315

Thr Leu Gly Pro Ala Thr Val Ala Leu Leu Phe Cys Tyr Gly Leu
            320                 325                 330

Lys Arg Lys Ile Gly Arg Arg Ser Ala Arg Asp Pro Leu Arg Ser
            335                 340                 345

Leu Pro Ser Pro Leu Pro Gln Glu Phe Thr Tyr Leu Asn Ser Pro
            350                 355                 360

Thr Pro Gly Gln Leu Gln Pro Ile Tyr Glu Asn Val Asn Val Val
            365                 370                 375

Ser Gly Asp Glu Val Tyr Ser Leu Ala Tyr Tyr Asn Gln Pro Glu
            380                 385                 390

Gln Glu Ser Val Ala Ala Glu Thr Leu Gly Thr His Met Glu Asp
            395                 400                 405

Lys Val Ser Leu Asp Ile Tyr Ser Arg Leu Arg Lys Ala Asn Ile
            410                 415                 420

Thr Asp Val Asp Tyr Glu Asp Ala Met
            425
```

<210> SEQ ID NO 35
<211> LENGTH: 685
<212> TYPE: DNA
<213> ORGANISM: Homo sapiens

<400> SEQUENCE: 35

| | | |
|---|---|---|
| gatgtgctcc ttggagctgg tgtgcagtgt cctgactgta agatcaagtc | 50 |
| caaacctgtt ttgaattga ggaaacttct cttttgatct cagcccttgg | 100 |
| tggtccaggt cttcatgctg ctgtgggtga tattactggt cctggctcct | 150 |
| gtcagtggac agtttgcaag gacacccagg cccattattt tcctccagcc | 200 |
| tccatggacc acagtcttcc aaggagagag agtgaccctc acttgcaagg | 250 |
| gatttcgctt ctactcacca cagaaaacaa aatggtacca tcggtacctt | 300 |
| gggaagaaa tactaagaga aaccccagac aatatccttg aggttcagga | 350 |
| atctggagag tacagatgcc aggcccaggg ctcccctctc agtagccctg | 400 |
| tgcacttgga ttttttcttca gagatgggat ttcctcatgc tgcccaggct | 450 |
| aatgttgaac tcctgggctc aagtgatctg ctcacctagg cctctcaaag | 500 |

-continued

```
cgctgggatt acagcttcgc tgatcctgca agctccactt tctgtgtttg        550
aaggagactc tgtggttctg aggtgccggg caaaggcgga agtaacactg        600
aataatacta tttacaagaa tgataatgtc ctggcattcc ttaataaaag        650
aactgacttc caaaaaaaaa aaaaaaaaaa aaaaa                         685
```

<210> SEQ ID NO 36
<211> LENGTH: 124
<212> TYPE: PRT
<213> ORGANISM: Homo sapiens

<400> SEQUENCE: 36

```
Met Leu Leu Trp Val Ile Leu Val Leu Ala Pro Val Ser Gly
 1               5                  10                  15

Gln Phe Ala Arg Thr Pro Arg Pro Ile Ile Phe Leu Gln Pro Pro
            20                  25                  30

Trp Thr Thr Val Phe Gln Gly Glu Arg Val Thr Leu Thr Cys Lys
            35                  40                  45

Gly Phe Arg Phe Tyr Ser Pro Gln Lys Thr Lys Trp Tyr His Arg
            50                  55                  60

Tyr Leu Gly Lys Glu Ile Leu Arg Glu Thr Pro Asp Asn Ile Leu
            65                  70                  75

Glu Val Gln Glu Ser Gly Glu Tyr Arg Cys Gln Ala Gln Gly Ser
            80                  85                  90

Pro Leu Ser Ser Pro Val His Leu Asp Phe Ser Ser Glu Met Gly
            95                  100                 105

Phe Pro His Ala Ala Gln Ala Asn Val Glu Leu Leu Gly Ser Ser
            110                 115                 120

Asp Leu Leu Thr
```

<210> SEQ ID NO 37
<211> LENGTH: 1337
<212> TYPE: DNA
<213> ORGANISM: Homo sapiens

<400> SEQUENCE: 37

```
ggattttttgt gatccgcgat tcgctcccac gggcgggacc tttgtaactg         50
cgggaggccc aggacaggcc caccctgcgg ggcgggaggc agccggggtg        100
agggaggtga agaaaccaag acgcagagag gccaagcccc ttgccttggg        150
tcacacagcc aaaggaggca gagccagaac tcacaaccag atccagaggc        200
aacagggaca tggccaccctg ggacgaaaag gcagtcaccc gcagggccaa       250
ggtggctccc gctgagagga tgagcaagtt cttaaggcac ttcacggtcg        300
tgggagacga ctaccatgcc tggaacatca actacaagaa atgggagaat        350
gaagaggagg aggaggagga ggagcagcca ccacccacac cagtctcagg        400
cgaggaaggc agagctgcag cccctgacgt tgcccctgcc cctggccccg        450
cacccagggc ccccttgac ttcaggggca tgttgaggaa actgttcagc         500
tcccacaggt ttcaggtcat catcatctgc ttggtggttc tggatgccct        550
cctggtgctt gctgagctca tcctggacct gaagatcatc cagcccgaca        600
agaataacta tgctgccatg gtattccact acatgacgat caccatcttg        650 gtcttttttta tgatggagat catctttaaa ttatttgtct tccgcctgag        700
```

```
ttctttcacc acaagtttga gatcctggat gcccgtcgtg gtggtggtct      750
cattcatcct ggacattgtc ctcctgttcc aggagcacca gtttgaggct      800
ctgggcctgc tgattctgct ccggctgtgg cgggtggccc ggatcatcaa      850
tgggattatc atctcagtta agacacgttc agaacggcaa ctcttaaggt      900
taaaacagat gaatgtacaa ttggccgcca agattcaaca ccttgagttc      950
agctgctctg agaagcccct ggactgatga gtttgctgta tcaacctgta     1000
aggagaagct ctctccggat ggctatggga atgaaagaat ccgacttcta     1050
ctctcacaca gccaccgtga aagtcctgga gtaaaatgtg ctgtgtacag     1100
aagagagaga aggaagcagg ctggcatgtt cactgggctg gtgttacgac     1150
agagaacctg acagtcactg gccagttatc acttcagatt acaaatcaca     1200
cagagcatct gcctgttttc aatcacaaga gaacaaaacc aaaatctata     1250
aagatattct gaaatatga cagaatttga caaataaaag cataaacgtg     1300
taaaaaaaaa aaaaaaaaa aaaaaaaaaa aaaaaaa                   1337
```

<210> SEQ ID NO 38
<211> LENGTH: 255
<212> TYPE: PRT
<213> ORGANISM: Homo sapiens

<400> SEQUENCE: 38

```
Met Ala Thr Trp Asp Glu Lys Ala Val Thr Arg Arg Ala Lys Val
  1               5                  10                  15

Ala Pro Ala Glu Arg Met Ser Lys Phe Leu Arg His Phe Thr Val
                 20                  25                  30

Val Gly Asp Asp Tyr His Ala Trp Asn Ile Asn Tyr Lys Lys Trp
                 35                  40                  45

Glu Asn Glu Glu Glu Glu Glu Glu Glu Gln Pro Pro Pro Thr
                 50                  55                  60

Pro Val Ser Gly Glu Glu Gly Arg Ala Ala Ala Pro Asp Val Ala
                 65                  70                  75

Pro Ala Pro Gly Pro Ala Pro Arg Ala Pro Leu Asp Phe Arg Gly
                 80                  85                  90

Met Leu Arg Lys Leu Phe Ser Ser His Arg Phe Gln Val Ile Ile
                 95                 100                 105

Ile Cys Leu Val Val Leu Asp Ala Leu Leu Val Leu Ala Glu Leu
                110                 115                 120

Ile Leu Asp Leu Lys Ile Ile Gln Pro Asp Lys Asn Asn Tyr Ala
                125                 130                 135

Ala Met Val Phe His Tyr Met Ser Ile Thr Ile Leu Val Phe Phe
                140                 145                 150

Met Met Glu Ile Ile Phe Lys Leu Phe Val Phe Arg Leu Ser Ser
                155                 160                 165

Phe Thr Thr Ser Leu Arg Ser Trp Met Pro Val Val Val Val
                170                 175                 180

Ser Phe Ile Leu Asp Ile Val Leu Leu Phe Gln Glu His Gln Phe
                185                 190                 195

Glu Ala Leu Gly Leu Leu Ile Leu Leu Arg Leu Trp Arg Val Ala
                200                 205                 210

Arg Ile Ile Asn Gly Ile Ile Ile Ser Val Lys Thr Arg Ser Glu
                215                 220                 225
```

```
Arg Gln Leu Leu Arg Leu Lys Gln Met Asn Val Gln Leu Ala Ala
                230                 235                 240
Lys Ile Gln His Leu Glu Phe Ser Cys Ser Glu Lys Pro Leu Asp
                245                 250                 255

<210> SEQ ID NO 39
<211> LENGTH: 2970
<212> TYPE: DNA
<213> ORGANISM: Homo sapiens

<400> SEQUENCE: 39
```

| | | | | |
|---|---|---|---|---|
| agtgaagggg | tttcccatat | gaaaaataca | gaaagaatta | tttgaatact | 50 |
| agcaaataca | caacttgata | tttctagaga | acccaggcac | agtcttggag | 100 |
| acattactcc | tgagagactg | cagctgatgg | aagatgagcc | ccaacttcta | 150 |
| aaaatgtatc | actaccggga | ttgagataca | aacagcattt | aggaaggtct | 200 |
| catctgagta | gcagcttcct | gccctccttc | ttggagataa | gtcgggcttt | 250 |
| tggtgagaca | gactttccca | accctctgcc | cggccggtgc | ccatgcttct | 300 |
| gtggctgctg | ctgctgatcc | tgactcctgg | aagagaacaa | tcaggggtgg | 350 |
| ccccaaaagc | tgtacttctc | ctcaatcctc | catggtccac | agccttcaaa | 400 |
| ggagaaaaag | tggctctcat | atgcagcagc | atatcacatt | ccctagccca | 450 |
| gggagacaca | tattggtatc | acgatgagaa | gttgttgaaa | ataaaacatg | 500 |
| acaagatcca | aattacagag | cctggaaatt | accaatgtaa | gacccgagga | 550 |
| tcctccctca | gtgatgccgt | gcatgtgaaa | ttttcacctg | actggctgat | 600 |
| cctgcaggct | ttacatcctg | tctttgaagg | agacaatgtc | attctgagat | 650 |
| gtcaggggaa | agacaacaaa | aacactcatc | aaaaggttta | ctacaaggat | 700 |
| ggaaaacagc | ttcctaatag | ttataattta | gagaagatca | cagtgaattc | 750 |
| agtctccagg | gataatagca | aatatcattg | tactgcttat | aggaagtttt | 800 |
| acatacttga | cattgaagta | acttcaaaac | ccctaaatat | ccaagttcaa | 850 |
| gagctgtttc | tacatcctgt | gctgagagcc | agctcttcca | cgcccataga | 900 |
| ggggagtccc | atgaccctga | cctgtgagac | ccagctctct | ccacagaggc | 950 |
| cagatgtcca | gctgcaattc | tccctcttca | gagatagcca | gaccctcgga | 1000 |
| ttgggctgga | gcaggtcccc | cagactccag | atccctgcca | tgtggactga | 1050 |
| agactcaggg | tcttactggt | gtgaggtgga | gacagtgact | cacagcatca | 1100 |
| aaaaaaggag | cctgagatct | cagatacgtg | tacagagagt | ccctgtgtct | 1150 |
| aatgtgaatc | tagagatccg | gcccaccgga | gggcagctga | ttgaaggaga | 1200 |
| aaatatggtc | cttatttgct | cagtagccca | gggttcaggg | actgtcacat | 1250 |
| tctcctggca | caaagaagga | agagtaagaa | gcctgggtag | aaagacccag | 1300 |
| cgttccctgt | tggcagagct | gcatgttctc | accgtgaagg | agagtgatgc | 1350 |
| agggagatac | tactgtgcag | ctgataacgt | tcacagcccc | atcctcagca | 1400 |
| cgtggattcg | agtcaccgtg | agaattccgg | tatctcaccc | tgtcctcacc | 1450 |
| ttcagggctc | ccagggccca | cactgtggtg | ggggacctgc | tggagcttca | 1500 |
| ctgtgagtcc | ctgagaggct | ctcccccgat | cctgtaccga | ttttatcatg | 1550 |
| aggatgtcac | cctggggaac | agctcagccc | cctctgagg | aggagcctcc | 1600 |
| ttcaacctct | ctctgactgc | agaacattct | ggaaactact | cctgtgatgc | 1650 |

```
agacaatggc ctgggggccc agcacagtca tggagtgagt ctcagggtca      1700
cagttccggt gtctcgcccc gtcctcaccc tcagggctcc cggggcccag      1750
gctgtggtgg gggacctgct ggagcttcac tgtgagtccc tgagaggctc      1800
cttcccgatc ctgtactggt tttatcacga ggatgacacc ttggggaaca      1850
tctcggccca ctctggagga ggggcatcct tcaacctctc tctgactaca      1900
gaacattctg gaaactactc atgtgaggct gacaatggcc tggggccca       1950
gcacagtaaa gtggtgacac tcaatgttac aggaacttcc aggaacagaa      2000
caggccttac cgctgcggga atcacggggc tggtgctcag catcctcgtc      2050
cttgctgctg ctgctgctct gctgcattac gccagggccc gaaggaaacc      2100
aggaggactt ctgccactg gaacatctag tcacagtcct agtgagtgtc       2150
aggagccttc ctcgtccagg ccttccagga tagaccctca agagcccact      2200
cactctaaac cactagcccc aatggagctg gagccaatgt acagcaatgt      2250
aaatcctgga gatagcaacc cgatttattc ccagatctgg agcatccagc      2300
atacaaaaga aaactcagct aattgtccaa tgatgcatca agagcatgag      2350
gaacttacag tcctctattc agaactgaag aagacacacc cagacgactc      2400
tgcaggggag gctagcagca gaggcagggc ccatgaagaa gatgatgaag      2450
aaaactatga gaatgtacca cgtgtattac tggcctcaga ccactagccc      2500
cttacccaga gtggcccaca ggaaacagcc tgcaccattt ttttttctgt      2550
tctctccaac cacacatcat ccatctctcc agactctgcc tcctacgagg      2600
ctgggctgca gggtatgtga ggctgagcaa aaggtctgca aatctcccct      2650
gtgcctgatc tgtgtgttcc ccaggaagag agcaggcagc ctctgagcaa      2700
gcactgtgtt attttcacag tggagacacg tggcaaggca ggagggccct      2750
cagctcctag ggctgtcgaa tagaggagga gagagaaatg gtctagccag      2800
ggttacaagg gcacaatcat gaccatttga tccaagtgtg atcgaaagct      2850
gttaatgtgc tctctgtata aacaatttgc tccaaatatt ttgtttccct      2900
tttttgtgtg gctggtagtg gcattgctga tgttttggtg tatatgctgt      2950
atccttgcta ccatattggg                                      2970
```

<210> SEQ ID NO 40
<211> LENGTH: 734
<212> TYPE: PRT
<213> ORGANISM: Homo sapiens

<400> SEQUENCE: 40

Met Leu Leu Trp Leu Leu Leu Ile Leu Thr Pro Gly Arg Glu
 1               5                  10                  15

Gln Ser Gly Val Ala Pro Lys Ala Val Leu Leu Asn Pro Pro
            20                  25                  30

Trp Ser Thr Ala Phe Lys Gly Glu Lys Val Ala Leu Ile Cys Ser
            35                  40                  45

Ser Ile Ser His Ser Leu Ala Gln Gly Asp Thr Tyr Trp Tyr His
            50                  55                  60

Asp Glu Lys Leu Leu Lys Ile Lys His Asp Lys Ile Gln Ile Thr
            65                  70                  75

Glu Pro Gly Asn Tyr Gln Cys Lys Thr Arg Gly Ser Ser Leu Ser

-continued

```
                80                  85                  90
Asp Ala Val His Val Glu Phe Ser Pro Asp Trp Leu Ile Leu Gln
                95                 100                 105
Ala Leu His Pro Val Phe Glu Gly Asp Asn Val Ile Leu Arg Cys
               110                 115                 120
Gln Gly Lys Asp Asn Lys Asn Thr His Gln Lys Val Tyr Tyr Lys
               125                 130                 135
Asp Gly Lys Gln Leu Pro Asn Ser Tyr Asn Leu Glu Lys Ile Thr
               140                 145                 150
Val Asn Ser Val Ser Arg Asp Asn Ser Lys Tyr His Cys Thr Ala
               155                 160                 165
Tyr Arg Lys Phe Tyr Ile Leu Asp Ile Glu Val Thr Ser Lys Pro
               170                 175                 180
Leu Asn Ile Gln Val Gln Glu Leu Phe Leu His Pro Val Leu Arg
               185                 190                 195
Ala Ser Ser Ser Thr Pro Ile Glu Gly Ser Pro Met Thr Leu Thr
               200                 205                 210
Cys Glu Thr Gln Leu Ser Pro Gln Arg Pro Asp Val Gln Leu Gln
               215                 220                 225
Phe Ser Leu Phe Arg Asp Ser Gln Thr Leu Gly Leu Gly Trp Ser
               230                 235                 240
Arg Ser Pro Arg Leu Gln Ile Pro Ala Met Trp Thr Glu Asp Ser
               245                 250                 255
Gly Ser Tyr Trp Cys Glu Val Glu Thr Val Thr His Ser Ile Lys
               260                 265                 270
Lys Arg Ser Leu Arg Ser Gln Ile Arg Val Gln Arg Val Pro Val
               275                 280                 285
Ser Asn Val Asn Leu Glu Ile Arg Pro Thr Gly Gly Gln Leu Ile
               290                 295                 300
Glu Gly Glu Asn Met Val Leu Ile Cys Ser Val Ala Gln Gly Ser
               305                 310                 315
Gly Thr Val Thr Phe Ser Trp His Lys Glu Gly Arg Val Arg Ser
               320                 325                 330
Leu Gly Arg Lys Thr Gln Arg Ser Leu Leu Ala Glu Leu His Val
               335                 340                 345
Leu Thr Val Lys Glu Ser Asp Ala Gly Arg Tyr Tyr Cys Ala Ala
               350                 355                 360
Asp Asn Val His Ser Pro Ile Leu Ser Thr Trp Ile Arg Val Thr
               365                 370                 375
Val Arg Ile Pro Val Ser His Pro Val Leu Thr Phe Arg Ala Pro
               380                 385                 390
Arg Ala His Thr Val Val Gly Asp Leu Leu Glu Leu His Cys Glu
               395                 400                 405
Ser Leu Arg Gly Ser Pro Pro Ile Leu Tyr Arg Phe Tyr His Glu
               410                 415                 420
Asp Val Thr Leu Gly Asn Ser Ser Ala Pro Ser Gly Gly Gly Ala
               425                 430                 435
Ser Phe Asn Leu Ser Leu Thr Ala Glu His Ser Gly Asn Tyr Ser
               440                 445                 450
Cys Asp Ala Asp Asn Gly Leu Gly Ala Gln His Ser His Gly Val
               455                 460                 465
Ser Leu Arg Val Thr Val Pro Val Ser Arg Pro Val Leu Thr Leu
               470                 475                 480
```

```
Arg Ala Pro Gly Ala Gln Ala Val Val Gly Asp Leu Leu Glu Leu
            485                 490                 495

His Cys Glu Ser Leu Arg Gly Ser Phe Pro Ile Leu Tyr Trp Phe
            500                 505                 510

Tyr His Glu Asp Asp Thr Leu Gly Asn Ile Ser Ala His Ser Gly
            515                 520                 525

Gly Gly Ala Ser Phe Asn Leu Ser Leu Thr Thr Glu His Ser Gly
            530                 535                 540

Asn Tyr Ser Cys Glu Ala Asp Asn Gly Leu Gly Ala Gln His Ser
            545                 550                 555

Lys Val Thr Leu Asn Val Thr Gly Thr Ser Arg Asn Arg Thr
            560                 565                 570

Gly Leu Thr Ala Ala Gly Ile Thr Gly Leu Val Leu Ser Ile Leu
            575                 580                 585

Val Leu Ala Ala Ala Ala Leu Leu His Tyr Ala Arg Ala Arg
            590                 595                 600

Arg Lys Pro Gly Gly Leu Ser Ala Thr Gly Thr Ser His Ser
            605                 610                 615

Pro Ser Glu Cys Gln Glu Pro Ser Ser Arg Pro Ser Arg Ile
            620                 625                 630

Asp Pro Gln Glu Pro Thr His Ser Lys Pro Leu Ala Pro Met Glu
            635                 640                 645

Leu Glu Pro Met Tyr Ser Asn Val Asn Pro Gly Asp Ser Asn Pro
            650                 655                 660

Ile Tyr Ser Gln Ile Trp Ser Ile Gln His Thr Lys Glu Asn Ser
            665                 670                 675

Ala Asn Cys Pro Met Met His Gln Glu His Glu Glu Leu Thr Val
            680                 685                 690

Leu Tyr Ser Glu Leu Lys Lys Thr His Pro Asp Asp Ser Ala Gly
            695                 700                 705

Glu Ala Ser Ser Arg Gly Arg Ala His Glu Glu Asp Asp Glu Glu
            710                 715                 720

Asn Tyr Glu Asn Val Pro Arg Val Leu Leu Ala Ser Asp His
            725                 730

<210> SEQ ID NO 41
<211> LENGTH: 3459
<212> TYPE: DNA
<213> ORGANISM: Homo sapiens

<400> SEQUENCE: 41
ctcaatcagc tttatgcaga gaagaagctt actgagctca ctgctggtgc        50
tggtgtaggc aagtgctgct ttggcaatct gggctgacct ggcttgtctc        100
ctcagaactc cttctccaac cctggagcag gcttccatgc tgctgtgggc        150
gtccttgctg gcctttgctc cagtctgtgg acaatctgca gctgcacaca        200
aacctgtgat ttccgtccat cctccatgga ccacattctt caaaggagag        250
agagtgactc tgacttgcaa tggatttcag ttctatgcaa cagagaaaac        300
aacatggtat catcggcact actggggaga aaagttgacc ctgacccag         350 gaaacaccct cgaggttcgg gaatctggac tgtacagatg ccaggccgg         400 ggctccccac gaagtaaccc tgtgcgcttg ctcttttctt cagactcctt        450
aatcctgcag gcaccatatt ctgtgtttga aggtgacaca ttggttctga        500
```

-continued

```
gatgccacag aagaaggaaa gagaaattga ctgctgtgaa atatacttgg      550
aatggaaaca ttctttccat ttctaataaa agctgggatc ttcttatccc      600
acaagcaagt tcaaataaca atggcaatta tcgatgcatt ggatatggag      650
atgagaatga tgtatttaga tcaaatttca aaataattaa aattcaagaa      700
ctatttccac atccagagct gaaagctaca gactctcagc ctacagaggg      750
gaattctgta aacctgagct gtgaaacaca gcttcctcca gagcggtcag      800
acaccccact tcacttcaac ttcttcagag atggcgaggt catcctgtca      850
gactggagca cgtacccgga actccagctc ccaaccgtct ggagagaaaa      900
ctcaggatcc tattggtgtg gtgctgaaac agtgaggggt aacatccaca      950
agcacagtcc ctcgctacag atccatgtgc agcggatccc tgtgtctggg     1000
gtgctcctgg agacccagcc ctcaggggc caggctgttg aagggagat      1050 gctggtcctt gtctgctccg tggctgaagg cacaggggat accacattct     1100
cctggcaccg agaggacatg caggagagtc tggggaggaa aactcagcgt     1150
tccctgagag cagagctgga gctccctgcc atcagacaga gccatgcagg     1200
gggatactac tgtacagcag acaacagcta cggccctgtc cagagcatgg     1250
tgctgaatgt cactgtgaga gagacccag gcaacagaga tggccttgtc      1300
gccgcgggag ccactggagg gctgctcagt gctcttctcc tggctgtggc     1350
cctgctgttt cactgctggc gtcggaggaa gtcaggagtt ggtttcttgg     1400
gagacgaaac caggctccct cccgctccag gcccaggaga gtcctcccat     1450
tccatctgcc ctgcccaggt ggagcttcag tcgttgtatg ttgatgtaca     1500
ccccaaaaag ggagatttgg tatactctga gatccagact actcagctgg     1550
gagaagaaga ggaagctaat acctccagga cacttctaga ggataaggat     1600
gtctcagttg tctactctga ggtaaagaca caacacccag ataactcagc     1650
tggaaagatc agctctaagg atgaagaaag ttaagagaat gaaaagttac     1700
gggaacgtcc tactcatgtg atttctccct tgtccaaagt cccaggccca     1750
gtgcagtcct tgcggcacct ggaatgatca actcattcca gctttctaat     1800
tcttctcatg catatgcatt cactcccagg aatactcatt cgtctactct     1850
gatgttggga tggaatggcc tctgaaagac ttcactaaaa tgaccaggat     1900
ccacagttaa gagaagaccc tgtagtattt gctgtgggcc tgacctaatg     1950
cattccctag ggtctgcttt agagaagggg gataaagaga gagaaggact     2000
gttatgaaaa acagaagcac aaatttggt gaattggat ttgcagagat      2050 gaaaaagact gggtgacctg gatctctgct taatacatct acaaccattg     2100
tctcactgga gactcacttg catcagtttg tttaactgtg agtggctgca     2150
caggcactgt gcaaacaatg aaaagcccct tcacttctgc ctgcacagct     2200
tacactgtca ggattcagtt gcagattaaa gaacccatct ggaatggttt     2250
acagagagag gaatttaaaa gaggcacatca gaagagctgg agatgcaagc     2300
tctaggctgc gcttccaaaa gcaaatgata attatgttaa tgtcattagt     2350
gacaaagatt tgcaacatta gagaaaagag acacaaatat aaaattaaaa     2400
acttaagtac caactctcca aaactaaatt tgaacttaaa atattagtat     2450
```

|                                                      |      |
|------------------------------------------------------|------|
| aaactcataa taaactctgc cttttaaaaaa agataaatat ttcctacgtc | 2500 |
| tgttcactga ataattacc aacccttag caataagcac tccttgcaga   | 2550 |
| gaggttttat tctctaaata ccattccctt ctcaaaggaa ataaggttgc | 2600 |
| ttttcttgta ggaactgtgt ctttgagtta ctaattagtt tatatgagaa | 2650 |
| taattcttgc aataaatgaa gaaggaataa aagaaatagg aagccacaaa | 2700 |
| tttgtatgga tatttcatga tacacctact ggttaaataa ttgacaaaaa | 2750 |
| ccagcagcca aatattagag gtctcctgat ggaagtgtac aataccacct | 2800 |
| acaaattatc catgccccaa gtgttaaaac tgaatccatt caagtctttc | 2850 |
| taactgaata cttgttttat agaaaatgca tggagaaaag gaatttgttt | 2900 |
| aaataacatt atgggattgc aaccagcaaa acataaactg agaaaaagtt | 2950 |
| ctatagggca aatcacctgg cttctataac aaataaatgg gaaaaaaatg | 3000 |
| aaataaaaag aagagaggga ggaagaaagg gagagagaag aaaagaaaaa | 3050 |
| tgaagaaaag taattagaat attttcaaca taaagaaaag acgaatattt | 3100 |
| aaggtgacag atatcccaac tacgctgatt tgatctttac aaattatatg | 3150 |
| agtgtatgaa tttgtcacat gtatcacccc caaaaaaaga gaaaaagaaa | 3200 |
| aatagaagac atataaatta aatgagacga gacatgtcga ccaaaaggaa | 3250 |
| tgtgtgggtc ttgtttggat cctgactcaa attaagaaaa aataaaacta | 3300 |
| cctacgaaat actaagaaaa atttgtatac taatattaag aaattgttgt | 3350 |
| gtgtttggga tataagtgat agtttattgt agtgatgttt ttataaaagc | 3400 |
| aaaaggatat tcactttcag cgcttatact gaagtattag attaaagctt | 3450 |
| attaacgta                                            | 3459 |

<210> SEQ ID NO 42
<211> LENGTH: 515
<212> TYPE: PRT
<213> ORGANISM: Homo sapiens

<400> SEQUENCE: 42

```
Met Leu Leu Trp Ala Ser Leu Ala Phe Ala Pro Val Cys Gly
  1               5                  10                  15

Gln Ser Ala Ala Ala His Lys Pro Val Ile Ser Val His Pro Pro
             20                  25                  30

Trp Thr Thr Phe Phe Lys Gly Glu Arg Val Thr Leu Thr Cys Asn
             35                  40                  45

Gly Phe Gln Phe Tyr Ala Thr Glu Lys Thr Thr Trp Tyr His Arg
             50                  55                  60

His Tyr Trp Gly Glu Lys Leu Thr Leu Thr Pro Gly Asn Thr Leu
             65                  70                  75

Glu Val Arg Glu Ser Gly Leu Tyr Arg Cys Gln Ala Arg Gly Ser
             80                  85                  90

Pro Arg Ser Asn Pro Val Arg Leu Leu Phe Ser Ser Asp Ser Leu
             95                 100                 105

Ile Leu Gln Ala Pro Tyr Ser Val Phe Glu Gly Asp Thr Leu Val
            110                 115                 120

Leu Arg Cys His Arg Arg Arg Lys Glu Lys Leu Thr Ala Val Lys
            125                 130                 135

Tyr Thr Trp Asn Gly Asn Ile Leu Ser Ile Ser Asn Lys Ser Trp
            140                 145                 150
```

-continued

Asp Leu Leu Ile Pro Gln Ala Ser Ser Asn Asn Asn Gly Asn Tyr
                 155                 160                 165

Arg Cys Ile Gly Tyr Gly Asp Glu Asn Asp Val Phe Arg Ser Asn
                 170                 175                 180

Phe Lys Ile Ile Lys Ile Gln Glu Leu Phe Pro His Pro Glu Leu
                 185                 190                 195

Lys Ala Thr Asp Ser Gln Pro Thr Gly Asn Ser Val Asn Leu
                 200                 205                 210

Ser Cys Glu Thr Gln Leu Pro Pro Glu Arg Ser Asp Thr Pro Leu
                 215                 220                 225

His Phe Asn Phe Phe Arg Asp Gly Glu Val Ile Leu Ser Asp Trp
                 230                 235                 240

Ser Thr Tyr Pro Glu Leu Gln Leu Pro Thr Val Trp Arg Glu Asn
                 245                 250                 255

Ser Gly Ser Tyr Trp Cys Gly Ala Glu Thr Val Arg Gly Asn Ile
                 260                 265                 270

His Lys His Ser Pro Ser Leu Gln Ile His Val Gln Arg Ile Pro
                 275                 280                 285

Val Ser Gly Val Leu Leu Glu Thr Gln Pro Ser Gly Gly Gln Ala
                 290                 295                 300

Val Glu Gly Glu Met Leu Val Leu Val Cys Ser Val Ala Glu Gly
                 305                 310                 315

Thr Gly Asp Thr Thr Phe Ser Trp His Arg Glu Asp Met Gln Glu
                 320                 325                 330

Ser Leu Gly Arg Lys Thr Gln Arg Ser Leu Arg Ala Glu Leu Glu
                 335                 340                 345

Leu Pro Ala Ile Arg Gln Ser His Ala Gly Gly Tyr Tyr Cys Thr
                 350                 355                 360

Ala Asp Asn Ser Tyr Gly Pro Val Gln Ser Met Val Leu Asn Val
                 365                 370                 375

Thr Val Arg Glu Thr Pro Gly Asn Arg Asp Gly Leu Val Ala Ala
                 380                 385                 390

Gly Ala Thr Gly Gly Leu Leu Ser Ala Leu Leu Leu Ala Val Ala
                 395                 400                 405

Leu Leu Phe His Cys Trp Arg Arg Arg Lys Ser Gly Val Gly Phe
                 410                 415                 420

Leu Gly Asp Glu Thr Arg Leu Pro Pro Ala Pro Gly Pro Gly Glu
                 425                 430                 435

Ser Ser His Ser Ile Cys Pro Ala Gln Val Glu Leu Gln Ser Leu
                 440                 445                 450

Tyr Val Asp Val His Pro Lys Lys Gly Asp Leu Val Tyr Ser Glu
                 455                 460                 465

Ile Gln Thr Thr Gln Leu Gly Glu Glu Glu Ala Asn Thr Ser
                 470                 475                 480

Arg Thr Leu Leu Glu Asp Lys Asp Val Ser Val Val Tyr Ser Glu
                 485                 490                 495

Val Lys Thr Gln His Pro Asp Asn Ser Ala Gly Lys Ile Ser Ser
                 500                 505                 510

Lys Asp Glu Glu Ser
                 515

<210> SEQ ID NO 43
<211> LENGTH: 1933

```
<212> TYPE: DNA
<213> ORGANISM: Homo sapiens

<400> SEQUENCE: 43
acacacccac aggacctgca gctgaacgaa gttgaagaca actcaggaga        50
tctgttggaa agagaacgat agaggaaaat atatgaatgt tgccatcttt       100
agttccctgt gttgggaaaa ctgtctggct gtacctccaa gcctggccaa       150
accctgtgtt tgaaggagat gccctgactc tgcgatgtca gggatggaag       200
aatacaccac tgtctcaggt gaagttctac agagatggaa aattccttca       250
tttctctaag gaaaaccaga ctctgtccat gggagcagca acagtgcaga       300
gccgtggcca gtacagctgc tctgggcagg tgatgtatat tccacagaca       350
ttcacacaaa cttcagagac tgccatggtt caagtccaag agctgtttcc       400
acctcctgtg ctgagtgcca tcccctctcc tgagcccga gagggtagcc       450 tggtgaccct gagatgtcag acaaagctgc accccctgag gtcagccttg       500
aggctccttt tctccttcca caaggacggc cacaccttgc aggacagggg       550
ccctcaccca gaactctgca tcccgggagc caaggaggga gactctgggc       600
tttactggtg tgaggtggcc cctgagggtg gccaggtcca gaagcagagc       650
ccccagctgg aggtcagagt gcaggctcct gtatcccgtc ctgtgctcac       700
tctgcaccac gggcctgctg accctgctgt ggggacatg gtgcagctcc       750 tctgtgaggc acagggggc tcccctccga tcctgtattc cttctaccct       800
gatgagaaga ttgtggggaa ccactcagct ccctgtggtg gaaccacctc       850
cctcctcttc ccagtgaagt cagaacagga tgctgggaac tactcctgcg       900
aggctgagaa cagtgtctcc agagagagga gtgagcccaa gaagctgtct       950
ctgaagggtt ctcaagtctt gttcactccc gccagcaact ggctggttcc      1000
ttggcttcct gcgagcctgc ttggcctgat ggttattgct gctgcacttc      1050
tggtttatgt gagatcctgg agaaaagctg ggccccttcc atcccagata      1100
ccacccacag ctccaggtgg agagcagtgc ccactatatg ccaacgtgca      1150
tcaccagaaa gggaaagatg aaggtgttgt ctactctgtg gtgcatagaa      1200
cctcaaagag gagtgaagga cagttctatc atctgtgcgg aggtgagatg      1250
cctgcagccc agtgaggttt catccacgga ggtgaatatg agaagcagga      1300
ctctccaaga accccttagc gactgtgagg aggttctctg ctagtgatgg      1350
tgttctccta tcaacacacg cccaccccca gtctccagtg ctcctcagga      1400
agacagtggg gtcctcaact ctttctgtgg gtccttcagt tcccaagccc      1450
agcatcacag agcccctga gcccttgtcc tggtcaggag cacctgaacc      1500
ctgggttctt ttcttagcag aagaccaacc aatggaatgg aagggagat       1550 gctcccacca acacacacac ttaggttcaa tcagtgacac tggacacata      1600
agccacagat gtcttctttc catacaagca tgttagttcg ccccaatata      1650
catatatata tgaaatagtc atgtgccgca taacaacatt tcagtcagtg      1700
atagactgca tacacaacag tggtcccata agactgtaat ggagtttaaa      1750
aattcctact gcctagtgat atcatagttg ccttaacatc ataacacaac      1800
acatttctca cgcgtttgtg gtgatgctgg tacaaacaag ctacagcgcc      1850
```

```
gctagtcata tacaaatata gcacatacaa ttatgtacag tacactatac        1900
ttgataatga aataaacaa ctatgttact ggt                           1933
```

<210> SEQ ID NO 44
<211> LENGTH: 392
<212> TYPE: PRT
<213> ORGANISM: Homo sapiens

<400> SEQUENCE: 44

```
Met Leu Pro Ser Leu Val Pro Cys Val Gly Lys Thr Val Trp Leu
 1               5                  10                  15

Tyr Leu Gln Ala Trp Pro Asn Pro Val Phe Glu Gly Asp Ala Leu
             20                  25                  30

Thr Leu Arg Cys Gln Gly Trp Lys Asn Thr Pro Leu Ser Gln Val
         35                  40                  45

Lys Phe Tyr Arg Asp Gly Lys Phe Leu His Phe Ser Lys Glu Asn
     50                  55                  60

Gln Thr Leu Ser Met Gly Ala Ala Thr Val Gln Ser Arg Gly Gln
 65                  70                  75

Tyr Ser Cys Ser Gly Gln Val Met Tyr Ile Pro Gln Thr Phe Thr
             80                  85                  90

Gln Thr Ser Glu Thr Ala Met Val Gln Val Gln Glu Leu Phe Pro
         95                 100                 105

Pro Pro Val Leu Ser Ala Ile Pro Ser Pro Glu Pro Arg Glu Gly
    110                 115                 120

Ser Leu Val Thr Leu Arg Cys Gln Thr Lys Leu His Pro Leu Arg
125                 130                 135

Ser Ala Leu Arg Leu Leu Phe Ser Phe His Lys Asp Gly His Thr
            140                 145                 150

Leu Gln Asp Arg Gly Pro His Pro Glu Leu Cys Ile Pro Gly Ala
        155                 160                 165

Lys Glu Gly Asp Ser Gly Leu Tyr Trp Cys Glu Val Ala Pro Glu
    170                 175                 180

Gly Gly Gln Val Gln Lys Gln Ser Pro Gln Leu Glu Val Arg Val
185                 190                 195

Gln Ala Pro Val Ser Arg Pro Val Leu Thr Leu His His Gly Pro
            200                 205                 210

Ala Asp Pro Ala Val Gly Asp Met Val Gln Leu Leu Cys Glu Ala
        215                 220                 225

Gln Arg Gly Ser Pro Pro Ile Leu Tyr Ser Phe Tyr Leu Asp Glu
    230                 235                 240

Lys Ile Val Gly Asn His Ser Ala Pro Cys Gly Gly Thr Thr Ser
245                 250                 255

Leu Leu Phe Pro Val Lys Ser Glu Gln Asp Ala Gly Asn Tyr Ser
            260                 265                 270

Cys Glu Ala Glu Asn Ser Val Ser Arg Glu Arg Ser Glu Pro Lys
        275                 280                 285

Lys Leu Ser Leu Lys Gly Ser Gln Val Leu Phe Thr Pro Ala Ser
    290                 295                 300

Asn Trp Leu Val Pro Trp Leu Pro Ala Ser Leu Leu Gly Leu Met
305                 310                 315

Val Ile Ala Ala Ala Leu Leu Val Tyr Val Arg Ser Trp Arg Lys
            320                 325                 330

Ala Gly Pro Leu Pro Ser Gln Ile Pro Pro Thr Ala Pro Gly Gly
```

```
                    335                 340                 345
Glu Gln Cys Pro Leu Tyr Ala Asn Val His His Gln Lys Gly Lys
                350                 355                 360

Asp Glu Gly Val Val Tyr Ser Val Val His Arg Thr Ser Lys Arg
                365                 370                 375

Ser Glu Gly Gln Phe Tyr His Leu Cys Gly Gly Glu Met Pro Ala
                380                 385                 390

Ala Gln

<210> SEQ ID NO 45
<211> LENGTH: 900
<212> TYPE: DNA
<213> ORGANISM: Homo sapiens

<400> SEQUENCE: 45
ccattgttct caacattcta gctgctcttg ctgcatttgc tctggaattc           50
ttgtagagat attacttgtc cttccaggct gttctttctg tagctccctt          100
gttttctttt tgtgatcatg ttgcagatgg ctgggcagtg ctcccaaaat          150
gaatattttg acagtttgtt gcatgcttgc ataccttgtc aacttcgatg          200
ttcttctaat actcctcctc taacatgtca gcgttattgt aatgcaagtg          250
tgaccaattc agtgaaagga acgaatgcga ttctctggac ctgtttggga          300
ctgagcttaa taatttcttt ggcagttttc gtgctaatgt ttttgctaag          350
gaagataagc tctgaaccat taaggacga gtttaaaaac acaggatcag           400
gtctcctggg catggctaac attgacctgg aaaagagcag gactggtgat          450
gaaattattc ttccgagagg cctcgagtac acggtggaag aatgcacctg          500
tgaagactgc atcaagagca aaccgaaggt cgactctgac cattgctttc          550
cactcccagc tatggaggaa ggcgcaacca ttccttgtca cacgaaaacg          600
aatgactatt gcaagagcct gccagctgct ttgagtgcta cggagataga          650
gaaatcaatt tctgctaggt aattaaccat ttcgactcga gcagtgccac          700
tttaaaaatc ttttgtcaga atagatgatg tgtcagatct ctttaggatg          750
actgtatttt tcagttgccg atacagcttt ttgtcctcta actgtggaaa          800
ctctttatgt tagatatatt tctctaggtt actgttggga gcttaatggt          850
agaaacttcc ttggtttcat gattaaagtc tttttttttc ctgaaaaaaa          900

<210> SEQ ID NO 46
<211> LENGTH: 184
<212> TYPE: PRT
<213> ORGANISM: Homo sapiens

<400> SEQUENCE: 46

Met Leu Gln Met Ala Gly Gln Cys Ser Gln Asn Glu Tyr Phe Asp
  1               5                  10                  15

Ser Leu Leu His Ala Cys Ile Pro Cys Gln Leu Arg Cys Ser Ser
                 20                  25                  30

Asn Thr Pro Pro Leu Thr Cys Gln Arg Tyr Cys Asn Ala Ser Val
                 35                  40                  45

Thr Asn Ser Val Lys Gly Thr Asn Ala Ile Leu Trp Thr Cys Leu
                 50                  55                  60

Gly Leu Ser Leu Ile Ile Ser Leu Ala Val Phe Val Leu Met Phe
 65                  70                  75
```

```
Leu Leu Arg Lys Ile Ser Ser Glu Pro Leu Lys Asp Glu Phe Lys
                80                  85                  90

Asn Thr Gly Ser Gly Leu Leu Gly Met Ala Asn Ile Asp Leu Glu
            95                  100                 105

Lys Ser Arg Thr Gly Asp Glu Ile Ile Leu Pro Arg Gly Leu Glu
        110                 115                 120

Tyr Thr Val Glu Glu Cys Thr Cys Glu Asp Cys Ile Lys Ser Lys
    125                 130                 135

Pro Lys Val Asp Ser Asp His Cys Phe Pro Leu Pro Ala Met Glu
140                 145                 150

Glu Gly Ala Thr Ile Leu Val Thr Thr Lys Thr Asn Asp Tyr Cys
                155                 160                 165

Lys Ser Leu Pro Ala Ala Leu Ser Ala Thr Glu Ile Glu Lys Ser
            170                 175                 180

Ile Ser Ala Arg
```

<210> SEQ ID NO 47
<211> LENGTH: 337
<212> TYPE: DNA
<213> ORGANISM: Homo sapiens
<220> FEATURE:
<221> NAME/KEY: Unsure
<222> LOCATION: 106, 108, 168, 298
<223> OTHER INFORMATION: Unknown base

<400> SEQUENCE: 47

| | |
|---|---|
| cttcccagcc ttcggaacta tgagcccgc actctccagt tcatcaccac | 50 |
| cccagcatcc ctactcttgc atctaacagt ttccgctatt ttgcaccacc | 100 |
| tgcctngncc ttatgggcaa ctcaaggaag aaaggaaaga agagatagag | 150 |
| gaaaaatgga ttcaacanat gaaagtgttc tttctgacta ctgctgtgtt | 200 |
| tacaaacatt ttaatcatca aaacatgctt tatttgatag aaagatcaaa | 250 |
| tctgcctttg taaaacaaga gactatttta atcattaaga caacacanat | 300 |
| gtttgatttg gaggcgtgtt ctcattcaaa accttgc | 337 |

<210> SEQ ID NO 48
<211> LENGTH: 1922
<212> TYPE: DNA
<213> ORGANISM: Homo sapiens

<400> SEQUENCE: 48

| | |
|---|---|
| ggagagtctg accaccatgc cacctcctcg cctcctcttc ttcctcctct | 50 |
| tcctcacccc catggaagtc aggcccgagg aacctctagt ggtgaaggtg | 100 |
| gaagagggag ataacgctgt gctgcagtgc ctcaagggga cctcagatgg | 150 |
| ccccactcag cagctgacct ggtctcggga gtccccgctt aaaccccttct | 200 |
| taaaactcag cctggggctg ccaggcctgg gaatccacat gaggcccctg | 250 |
| gccatctggc ttttcatctt caacgtctct caacagatgg ggggcttcta | 300 |
| cctgtgccag ccggggcccc cctctgagaa ggcctggcag cctggctgga | 350 |
| cagtcaatgt ggagggcagc ggggagctgt tccggtggaa tgtttcggac | 400 |
| ctaggtggcc tgggctgtgg cctgaagaac aggtcctcag agggccccag | 450 |
| ctccccttcc gggaagctca tgagcccaa gctgtatgtg tgggcaaag | 500 |
| accgccctga gatctgggag ggagagcctc cgtgtgtccc accgagggac | 550 |

```
agcctgaacc agagcctcag ccaggacctc accatggccc ctggctccac      600
actctggctg tcctgtgggg tacccctga  ctctgtgtcc aggggccccc      650
tctcctggac ccatgtgcac cccaagggc  ctaagtcatt gctgagccta      700
gagctgaagg acgatcgccc ggccagagat atgtgggtaa tggagacggg      750
tctgttgttg ccccgggcca cagctcaaga cgctggaaag tattattgtc      800
accgtggcaa cctgaccatg tcattccacc tggagatcac tgctcggcca      850
gtactatggc actggctgct gaggactggt ggctggaagg tctcagctgt      900
gactttggct tatctgatct tctgcctgtg ttcccttgtg ggcattcttc      950
atcttcaaag agccctggtc ctgaggagga aagaaagcg  aatgactgac     1000
cccaccagga gattcttcaa agtgacgcct ccccaggaa  gcgggcccca     1050
gaaccagtac gggaacgtgc tgtctctccc cacacccacc tcaggcctcg     1100
gacgcgccca gcgttgggcc gcaggcctgg ggggcactgc cccgtcttat     1150
ggaaacccga gcagcgacgt ccaggcggat ggagccttgg ggtcccggag     1200
ccgccgggag tgggcccaga agaagaggaa ggggagggct atgaggaacc     1250
tgacagtgag gaggactccg agttctatga gaacgactcc aaccttgggc     1300
aggaccagct ctcccaggat ggcagcggct acgagaaccc tgaggatgag     1350
cccctgggtc ctgaggatga agactccttc tccaacgctg agtcttatga     1400
gaacgaggat gaagagctga cccagccggt cgccaggaca atggacttcc     1450
tgagccctca tgggtcagcc tgggacccca gccgggaagc aacctccctg     1500
gggtcccagt cctatgagga tatgagagga atcctgtatg cagcccccca     1550
gctccgctcc attcggggcc agcctggacc caatcatgag gaagatgcag     1600
actcttatga gaacatggat aatcccgatg ggccagaccc agcctgggga     1650
ggaggggcc  gcatgggcac ctggagcacc aggtgatcct caggtggcca     1700
gcctggatct cctcaagtcc ccaagattca cacctgactc tgaaatctga     1750
agacctcgag cagatgatgc caacctctgg agcaatgttg cttaggatgt     1800
gtgcatgtgt gtaagtgtgt gtgtgtgtgt gtgtgtgtgt gtgtgtgtat     1850
acatgccagt gacacttcca gtccccttgg tattccttaa ataaactcaa     1900
tgagctcttc caaaaaaaaa aa                                   1922
```

<210> SEQ ID NO 49
<211> LENGTH: 467
<212> TYPE: PRT
<213> ORGANISM: Homo sapiens

<400> SEQUENCE: 49

```
Met Pro Pro Pro Arg Leu Leu Phe Phe Leu Leu Phe Leu Thr Pro
  1               5                  10                  15

Met Glu Val Arg Pro Glu Glu Pro Leu Val Val Lys Val Glu Glu
                 20                  25                  30

Gly Asp Asn Ala Val Leu Gln Cys Leu Lys Gly Thr Ser Asp Gly
                 35                  40                  45

Pro Thr Gln Gln Leu Thr Trp Ser Arg Glu Ser Pro Leu Lys Pro
                 50                  55                  60

Phe Leu Lys Leu Ser Leu Gly Leu Pro Gly Leu Gly Ile His Met
 65                  70                  75
```

```
Arg Pro Leu Ala Ile Trp Leu Phe Ile Phe Asn Val Ser Gln Gln
                80                  85                  90

Met Gly Gly Phe Tyr Leu Cys Gln Pro Gly Pro Ser Glu Lys
            95                 100                 105

Ala Trp Gln Pro Gly Trp Thr Val Asn Val Glu Gly Ser Gly Glu
               110                 115                 120

Leu Phe Arg Trp Asn Val Ser Asp Leu Gly Gly Leu Gly Cys Gly
               125                 130                 135

Leu Lys Asn Arg Ser Ser Glu Gly Pro Ser Ser Pro Ser Gly Lys
               140                 145                 150

Leu Met Ser Pro Lys Leu Tyr Val Trp Ala Lys Asp Arg Pro Glu
               155                 160                 165

Ile Trp Glu Gly Glu Pro Pro Cys Val Pro Pro Arg Asp Ser Leu
               170                 175                 180

Asn Gln Ser Leu Ser Gln Asp Leu Thr Met Ala Pro Gly Ser Thr
               185                 190                 195

Leu Trp Leu Ser Cys Gly Val Pro Pro Asp Ser Val Ser Arg Gly
               200                 205                 210

Pro Leu Ser Trp Thr His Val His Pro Lys Gly Pro Lys Ser Leu
               215                 220                 225

Leu Ser Leu Glu Leu Lys Asp Asp Arg Pro Ala Arg Asp Met Trp
               230                 235                 240

Val Met Glu Thr Gly Leu Leu Leu Pro Arg Ala Thr Ala Gln Asp
               245                 250                 255

Ala Gly Lys Tyr Tyr Cys His Arg Gly Asn Leu Thr Met Ser Phe
               260                 265                 270

His Leu Glu Ile Thr Ala Arg Pro Val Leu Trp His Trp Leu Leu
               275                 280                 285

Arg Thr Gly Gly Trp Lys Val Ser Ala Val Thr Leu Ala Tyr Leu
               290                 295                 300

Ile Phe Cys Leu Cys Ser Leu Val Gly Ile Leu His Leu Gln Arg
               305                 310                 315

Ala Leu Val Leu Arg Arg Lys Arg Lys Arg Met Thr Asp Pro Thr
               320                 325                 330

Arg Arg Phe Phe Lys Val Thr Pro Pro Gly Ser Gly Pro Gln
               335                 340                 345

Asn Gln Tyr Gly Asn Val Leu Ser Leu Pro Thr Pro Thr Ser Gly
               350                 355                 360

Leu Gly Arg Ala Gln Arg Trp Ala Ala Gly Leu Gly Gly Thr Ala
               365                 370                 375

Pro Ser Tyr Gly Asn Pro Ser Ser Asp Val Gln Ala Asp Gly Ala
               380                 385                 390

Leu Gly Ser Arg Ser Arg Glu Trp Ala Gln Lys Lys Arg Lys
               395                 400                 405

Gly Arg Ala Met Arg Asn Leu Thr Val Arg Arg Thr Pro Ser Ser
               410                 415                 420

Met Arg Thr Thr Pro Thr Leu Gly Arg Thr Ser Ser Pro Arg Met
               425                 430                 435

Ala Ala Ala Thr Arg Thr Leu Arg Met Ser Pro Trp Val Leu Arg
               440                 445                 450

Met Lys Thr Pro Ser Pro Thr Leu Ser Leu Met Arg Thr Arg Met
               455                 460                 465
```

Lys Ser

<210> SEQ ID NO 50
<211> LENGTH: 3260
<212> TYPE: DNA
<213> ORGANISM: Homo sapiens

<400> SEQUENCE: 50

| | | | | | |
|---|---|---|---|---|---|
| ccatcccata | gtgagggaag | acacgcggaa | acaggcttgc | acccagacac | 50 |
| gacaccatgc | atctcctcgg | cccctggctc | ctgctcctgg | ttctagaata | 100 |
| cttggctttc | tctgactcaa | gtaaatgggt | ttttgagcac | cctgaaaccc | 150 |
| tctacgcctg | ggagggggcc | tgcgtctgga | tcccctgcac | ctacagagcc | 200 |
| ctagatggtg | acctgaaaag | cttcatcctg | ttccacaatc | ctgagtataa | 250 |
| caagaacacc | tcgaagtttg | atgggacaag | actctatgaa | agcacaaagg | 300 |
| atgggaaggt | tccttctgag | cagaaaaggg | tgcaattcct | gggagacaag | 350 |
| aataagaact | gcacactgag | tatccacccg | gtgcacctca | atgacagtgg | 400 |
| tcagctgggg | ctgaggatgg | agtccaagac | tgagaaatgg | atggaacgaa | 450 |
| tacacctcaa | tgtctctgaa | aggccttttc | cacctctat | ccagctccct | 500 |
| ccagaaattc | aagagtccca | ggaagtcact | ctgacctgct | tgctgaattt | 550 |
| ctcctgctat | gggtatccga | tccaattgca | gtggctccta | gagggggttc | 600 |
| caatgaggca | ggctgctgtc | acctcgacct | ccttgaccat | caagtctgtc | 650 |
| ttcacccgga | gcgagctcaa | gttctcccca | cagtggagtc | accatgggaa | 700 |
| gattgtgacc | tgccagcttc | aggatgcaga | tgggaagttc | ctctccaatg | 750 |
| acacggtgca | gctgaacgtg | aagcacaccc | gaagttgga | gatcaaggtc | 800 |
| actcccagtg | atgccatagt | gagggagggg | gactctgtga | ccatgacctg | 850 |
| cgaggtcagc | agcagcaacc | ggagtacac | gacggtatcc | tggctcaagg | 900 |
| atgggaccctc | gctgaagaag | cagaatacat | tcacgctaaa | cctgcgcgaa | 950 |
| gtgaccaagg | accagagtgg | gaagtactgc | tgtcaggtct | ccaatgacgt | 1000 |
| gggcccggga | aggtcggaag | aagtgttcct | gcaagtgcag | tatgccccgg | 1050 |
| aaccttccac | ggttcagatc | ctccactcac | cggctgtgga | gggaagtcaa | 1100 |
| gtcgagtttc | tttgcatgtc | actggccaat | cctcttccaa | caaattacac | 1150 |
| gtggtaccac | aatgggaaag | aaatgcaggg | aaggacagag | gagaaagtcc | 1200 |
| acatcccaaa | gatcctcccc | tggcacgctg | ggacttattc | ctgtgtggca | 1250 |
| gaaacattc | ttggtactgg | acagagggc | ccgggagctg | agctggatgt | 1300 |
| ccagtatcct | cccaagaagg | tgaccacagt | gattcaaaac | cccatgccga | 1350 |
| ttcgagaagg | agacacagtg | acccttcct | gtaactacaa | ttccagtaac | 1400 |
| cccagtgtta | cccggtatga | atggaaaccc | catggcgcct | gggaggagcc | 1450 |
| atcgcttggg | gtgctgaaga | tccaaaacgt | tggctgggac | aacacaacca | 1500 |
| tcgcctgcgc | acgttgtaat | agttggtgct | cgtgggcctc | cctgtcgcc | 1550 |
| ctgaatgtcc | agtatgcccc | ccgagacgtg | agggtccgga | aaatcaagcc | 1600 |
| cctttccgag | attcactctg | gaaactcggt | cagcctccaa | tgtgacttct | 1650 |
| caagcagcca | ccccaaagaa | gtccagttct | tctgggagaa | aaatgcagg | 1700 |
| cttctgggga | agaaaagcca | gctgaatttt | gactccatct | ccccagaaga | 1750 |

| | |
|---|---|
| tgctgggagt tacagctgct gggtgaacaa ctccatagga cagacagcgt | 1800 |
| ccaaggcctg gacacttgaa gtgctgtatg cacccaggag gctgcgtgtg | 1850 |
| tccatgagcc cggggdacca agtgatggag gggaagagtg caaccctgac | 1900 |
| ctgtgagagt gacgccaacc ctcccgtctc ccactacacc tggtttgact | 1950 |
| ggaataacca aagcctcccc caccacagcc agaagctgag attggagccg | 2000 |
| gtgaaggtcc agcactcggg tgcctactgg tgccagggga ccaacagtgt | 2050 |
| gggcaagggc cgttcgcctc tcagcaccct tactgtctac tatagcccgg | 2100 |
| agaccatcgg caggcgagtg gctgtgggac tcgggtcctg cctcgccatc | 2150 |
| ctcatcctgg caatctgtgg gctcaagctc cagcgacgtt ggaagaggac | 2200 |
| acagagccag caggggcttc aggagaattc cagcggccag agcttctttg | 2250 |
| tgaggaataa aaaggttaga agggcccccc tctctgaagg cccccactcc | 2300 |
| ctgggatgct acaatccaat gatggaagat ggcattagct acaccaccct | 2350 |
| gcgctttccc gagatgaaca taccacgaac tggagatgca gagtcctcag | 2400 |
| agatgcagag acctccccgg acctgcgatg acacggtcac ttattcagca | 2450 |
| ttgcacaagc gccaagtggg cgactatgag aacgtcattc cagattttcc | 2500 |
| agaagatgag gggattcatt actcagagct gatccagttt ggggtcgggg | 2550 |
| agcggcctca ggcacaagaa aatgtggact atgtgatcct caaacattga | 2600 |
| cactggatgg gctgcagcag aggcactggg ggcagcgggg gccagggaag | 2650 |
| tccccgagtt tccccagaca ccgccacatg gcttcctcct gcgtgcatgt | 2700 |
| gcgcacacac acacacacac gcacacacac acacacacac tcactgcgga | 2750 |
| gaaccttgtg cctggctcag agccagtctt tttggtgagg gtaaccccaa | 2800 |
| acctccaaaa ctcctgcccc tgttctcttc cactctcctt gctacccaga | 2850 |
| aatcatctaa atacctgccc tgacatgcac acctcccctg ccccaccagc | 2900 |
| ccactggcca tctccacccg gagctgctgt gtcctctgga tctgctcgtc | 2950 |
| attttccttc ccttctccat ctctctggcc ctctacccct gatctgacat | 3000 |
| ccccactcac gaatattatg cccagtttct gcctctgagg gaaagcccag | 3050 |
| aaaaggacag aaacgaagta gaaagggggcc cagtcctggc ctggcttctc | 3100 |
| ctttggaagt gaggcattgc acggggagac gtacgtatca gcggcccctt | 3150 |
| gactctgggg actccgggtt tgagatggac acactggtgt ggattaacct | 3200 |
| gccagggaga cagagctcac aataaaaatg gctcagatgc cacttcaaag | 3250 |
| aaaaaaaaaa | 3260 |

<210> SEQ ID NO 51
<211> LENGTH: 847
<212> TYPE: PRT
<213> ORGANISM: Homo sapiens

<400> SEQUENCE: 51

Met His Leu Leu Gly Pro Trp Leu Leu Leu Val Leu Glu Tyr
1               5                   10                  15

Leu Ala Phe Ser Asp Ser Ser Lys Trp Val Phe Glu His Pro Glu
            20                  25                  30

Thr Leu Tyr Ala Trp Glu Gly Ala Cys Val Trp Ile Pro Cys Thr
            35                  40                  45

```
Tyr Arg Ala Leu Asp Gly Asp Leu Glu Ser Phe Ile Leu Phe His
            50                  55                  60

Asn Pro Glu Tyr Asn Lys Asn Thr Ser Lys Phe Asp Gly Thr Arg
            65                  70                  75

Leu Tyr Glu Ser Thr Lys Asp Gly Lys Val Pro Ser Glu Gln Lys
            80                  85                  90

Arg Val Gln Phe Leu Gly Asp Lys Asn Lys Asn Cys Thr Leu Ser
            95                 100                 105

Ile His Pro Val His Leu Asn Asp Ser Gly Gln Leu Gly Leu Arg
           110                 115                 120

Met Glu Ser Lys Thr Glu Lys Trp Met Glu Arg Ile His Leu Asn
           125                 130                 135

Val Ser Glu Arg Pro Phe Pro Pro His Ile Gln Leu Pro Pro Glu
           140                 145                 150

Ile Gln Glu Ser Gln Glu Val Thr Leu Thr Cys Leu Leu Asn Phe
           155                 160                 165

Ser Cys Tyr Gly Tyr Pro Ile Gln Leu Gln Trp Leu Leu Glu Gly
           170                 175                 180

Val Pro Met Arg Gln Ala Ala Val Thr Ser Thr Ser Leu Thr Ile
           185                 190                 195

Lys Ser Val Phe Thr Arg Ser Glu Leu Lys Phe Ser Pro Gln Trp
           200                 205                 210

Ser His His Gly Lys Ile Val Thr Cys Gln Leu Gln Asp Ala Asp
           215                 220                 225

Gly Lys Phe Leu Ser Asn Asp Thr Val Gln Leu Asn Val Lys His
           230                 235                 240

Thr Pro Lys Leu Glu Ile Lys Val Thr Pro Ser Asp Ala Ile Val
           245                 250                 255

Arg Glu Gly Asp Ser Val Thr Met Thr Cys Glu Val Ser Ser Ser
           260                 265                 270

Asn Pro Glu Tyr Thr Thr Val Ser Trp Leu Lys Asp Gly Thr Ser
           275                 280                 285

Leu Lys Lys Gln Asn Thr Phe Thr Leu Asn Leu Arg Glu Val Thr
           290                 295                 300

Lys Asp Gln Ser Gly Lys Tyr Cys Cys Gln Val Ser Asn Asp Val
           305                 310                 315

Gly Pro Gly Arg Ser Glu Val Phe Leu Gln Val Gln Tyr Ala
           320                 325                 330

Pro Glu Pro Ser Thr Val Gln Ile Leu His Ser Pro Ala Val Glu
           335                 340                 345

Gly Ser Gln Val Glu Phe Leu Cys Met Ser Leu Ala Asn Pro Leu
           350                 355                 360

Pro Thr Asn Tyr Thr Trp Tyr His Asn Gly Lys Glu Met Gln Gly
           365                 370                 375

Arg Thr Glu Glu Lys Val His Ile Pro Lys Ile Leu Pro Trp His
           380                 385                 390

Ala Gly Thr Tyr Ser Cys Val Ala Glu Asn Ile Leu Gly Thr Gly
           395                 400                 405

Gln Arg Gly Pro Gly Ala Glu Leu Asp Val Gln Tyr Pro Pro Lys
           410                 415                 420

Lys Val Thr Thr Val Ile Gln Asn Pro Met Pro Ile Arg Glu Gly
           425                 430                 435
```

-continued

Asp Thr Val Thr Leu Ser Cys Asn Tyr Asn Ser Ser Asn Pro Ser
                440                 445                 450

Val Thr Arg Tyr Glu Trp Lys Pro His Gly Ala Trp Glu Glu Pro
                455                 460                 465

Ser Leu Gly Val Leu Lys Ile Gln Asn Val Gly Trp Asp Asn Thr
                470                 475                 480

Thr Ile Ala Cys Ala Arg Cys Asn Ser Trp Cys Ser Trp Ala Ser
                485                 490                 495

Pro Val Ala Leu Asn Val Gln Tyr Ala Pro Arg Asp Val Arg Val
                500                 505                 510

Arg Lys Ile Lys Pro Leu Ser Glu Ile His Ser Gly Asn Ser Val
                515                 520                 525

Ser Leu Gln Cys Asp Phe Ser Ser His Pro Lys Glu Val Gln
                530                 535                 540

Phe Phe Trp Glu Lys Asn Gly Arg Leu Leu Gly Lys Glu Ser Gln
                545                 550                 555

Leu Asn Phe Asp Ser Ile Ser Pro Glu Asp Ala Gly Ser Tyr Ser
                560                 565                 570

Cys Trp Val Asn Asn Ser Ile Gly Gln Thr Ala Ser Lys Ala Trp
                575                 580                 585

Thr Leu Glu Val Leu Tyr Ala Pro Arg Arg Leu Arg Val Ser Met
                590                 595                 600

Ser Pro Gly Asp Gln Val Met Glu Gly Lys Ser Ala Thr Leu Thr
                605                 610                 615

Cys Glu Ser Asp Ala Asn Pro Pro Val Ser His Tyr Thr Trp Phe
                620                 625                 630

Asp Trp Asn Asn Gln Ser Leu Pro His His Ser Gln Lys Leu Arg
                635                 640                 645

Leu Glu Pro Val Lys Val Gln His Ser Gly Ala Tyr Trp Cys Gln
                650                 655                 660

Gly Thr Asn Ser Val Gly Lys Gly Arg Ser Pro Leu Ser Thr Leu
                665                 670                 675

Thr Val Tyr Tyr Ser Pro Glu Thr Ile Gly Arg Arg Val Ala Val
                680                 685                 690

Gly Leu Gly Ser Cys Leu Ala Ile Leu Ile Leu Ala Ile Cys Gly
                695                 700                 705

Leu Lys Leu Gln Arg Arg Trp Lys Arg Thr Gln Ser Gln Gln Gly
                710                 715                 720

Leu Gln Glu Asn Ser Ser Gly Gln Ser Phe Phe Val Arg Asn Lys
                725                 730                 735

Lys Val Arg Arg Ala Pro Leu Ser Glu Gly Pro His Ser Leu Gly
                740                 745                 750

Cys Tyr Asn Pro Met Met Glu Asp Gly Ile Ser Tyr Thr Thr Leu
                755                 760                 765

Arg Phe Pro Glu Met Asn Ile Pro Arg Thr Gly Asp Ala Glu Ser
                770                 775                 780

Ser Glu Met Gln Arg Pro Pro Arg Thr Cys Asp Asp Thr Val Thr
                785                 790                 795

Tyr Ser Ala Leu His Lys Arg Gln Val Gly Asp Tyr Glu Asn Val
                800                 805                 810

Ile Pro Asp Phe Pro Glu Asp Glu Gly Ile His Tyr Ser Glu Leu
                815                 820                 825

Ile Gln Phe Gly Val Gly Glu Arg Pro Gln Ala Gln Glu Asn Val

Asp Tyr Val Ile Leu Lys His
                845

<210> SEQ ID NO 52
<211> LENGTH: 1670
<212> TYPE: DNA
<213> ORGANISM: Homo sapiens

<400> SEQUENCE: 52

| | | | | |
|---|---|---|---|---|
| ccaaccacaa | gcaccaaagc | agaggggcag | gcagcacacc | acccagcagc | 50 |
| cagagcacca | gcccagccat | ggtccttgag | gtgagtgacc | accaagtgct | 100 |
| aaatgacgcc | gaggttgccg | ccctcctgga | gaacttcagc | tcttcctatg | 150 |
| actatggaga | aaacgagagt | gactcgtgct | gtacctcccc | gccctgccca | 200 |
| caggacttca | gcctgaactt | cgaccgggcc | ttcctgccag | ccctctacag | 250 |
| cctcctcttt | ctgctggggc | tgctgggcaa | cggcgcggtg | gcagccgtgc | 300 |
| tgctgagccg | gcggacagcc | ctgagcagca | ccgacacctt | cctgctccac | 350 |
| ctagctgtag | cagacacgct | gctggtgctg | acactgccgc | tctgggcagt | 400 |
| ggacgctgcc | gtccagtggg | tctttggctc | tggcctctgc | aaagtggcag | 450 |
| gtgccctctt | caacatcaac | ttctacgcag | gagccctcct | gctggcctgc | 500 |
| atcagctttg | accgctacct | gaacatagtt | catgccaccc | agctctaccg | 550 |
| ccggggccc | ccggcccgcg | tgaccctcac | ctgcctggct | gtctggggc | 600 |
| tctgcctgct | tttcgccctc | ccagacttca | tcttcctgtc | ggcccaccac | 650 |
| gacgagcgcc | tcaacgccac | ccactgccaa | tacaacttcc | cacaggtggg | 700 |
| ccgcacggct | ctgcgggtgc | tgcagctggt | ggctggcttt | ctgctgcccc | 750 |
| tgctggtcat | ggcctactgc | tatgcccaca | tcctggccgt | gctgctggtt | 800 |
| tccagggggcc | agcggcgcct | gcgggccatg | cggctggtgg | tggtggtcgt | 850 |
| ggtggccttt | gccctctgct | ggaccccta | tcacctggtg | gtgctggtgg | 900 |
| acatcctcat | ggacctgggc | gctttggccc | gcaactgtgg | ccgagaaagc | 950 |
| agggtagacg | tggccaagtc | ggtcacctca | ggcctgggct | acatgcactg | 1000 |
| ctgcctcaac | ccgctgctct | atgccttttgt | aggggtcaag | ttccgggagc | 1050 |
| ggatgtggat | gctgctcttg | cgcctgggct | gccccaacca | gagagggctc | 1100 |
| cagaggcagc | atcgtcttc | ccgccgggat | tcatcctggt | ctgagacctc | 1150 |
| agaggcctcc | tactcgggct | tgtgaggccg | gaatccgggc | tccccttcg | 1200 |
| cccacagtct | gacttccccg | cattccaggc | tcctccctcc | ctctgccggc | 1250 |
| tctggctctc | cccaatatcc | tcgctcccgg | gactcactgg | cagccccagc | 1300 |
| accaccaggt | ctcccgggaa | gccaccctcc | cagctctgag | gactgcacca | 1350 |
| ttgctgctcc | ttagctgcca | agcccatcc | tgccgcccga | ggtggctgcc | 1400 |
| tggagcccca | ctgcccttct | catttggaaa | ctaaaacttc | atcttcccca | 1450 |
| agtgcgggga | gtacaaggca | tggcgtagag | ggtgctgccc | catgaagcca | 1500 |
| cagcccaggc | ctccagctca | gcagtgactg | tggccatggt | ccccaagacc | 1550 |
| tctatatttg | ctcttttatt | tttatgtcta | aaatcctgct | taaaacttttt | 1600 |
| caataaacaa | gatcgtcagg | accaaaaaaa | aaaaaaaaa | aaaaaaaaa | 1650 | aaaaaaaaaa aaaaaaaaa                                                1670

<210> SEQ ID NO 53
<211> LENGTH: 368
<212> TYPE: PRT
<213> ORGANISM: Homo sapiens

<400> SEQUENCE: 53

Met Val Leu Glu Val Ser Asp His Gln Val Leu Asn Asp Ala Glu
 1               5                  10                  15

Val Ala Ala Leu Leu Glu Asn Phe Ser Ser Tyr Asp Tyr Gly
            20                  25                  30

Glu Asn Glu Ser Asp Ser Cys Cys Thr Ser Pro Pro Cys Pro Gln
                35                  40                  45

Asp Phe Ser Leu Asn Phe Asp Arg Ala Phe Leu Pro Ala Leu Tyr
            50                  55                  60

Ser Leu Leu Phe Leu Leu Gly Leu Leu Gly Asn Gly Ala Val Ala
            65                  70                  75

Ala Val Leu Leu Ser Arg Arg Thr Ala Leu Ser Ser Thr Asp Thr
            80                  85                  90

Phe Leu Leu His Leu Ala Val Ala Asp Thr Leu Leu Val Leu Thr
            95                  100                 105

Leu Pro Leu Trp Ala Val Asp Ala Ala Val Gln Trp Val Phe Gly
            110                 115                 120

Ser Gly Leu Cys Lys Val Ala Gly Ala Leu Phe Asn Ile Asn Phe
            125                 130                 135

Tyr Ala Gly Ala Leu Leu Leu Ala Cys Ile Ser Phe Asp Arg Tyr
            140                 145                 150

Leu Asn Ile Val His Ala Thr Gln Leu Tyr Arg Arg Gly Pro Pro
            155                 160                 165

Ala Arg Val Thr Leu Thr Cys Leu Ala Val Trp Gly Leu Cys Leu
            170                 175                 180

Leu Phe Ala Leu Pro Asp Phe Ile Phe Leu Ser Ala His His Asp
            185                 190                 195

Glu Arg Leu Asn Ala Thr His Cys Gln Tyr Asn Phe Pro Gln Val
            200                 205                 210

Gly Arg Thr Ala Leu Arg Val Leu Gln Leu Val Ala Gly Phe Leu
            215                 220                 225

Leu Pro Leu Leu Val Met Ala Tyr Cys Tyr Ala His Ile Leu Ala
            230                 235                 240

Val Leu Leu Val Ser Arg Gly Gln Arg Arg Leu Arg Ala Met Arg
            245                 250                 255

Leu Val Val Val Val Val Ala Phe Ala Leu Cys Trp Thr Pro
            260                 265                 270

Tyr His Leu Val Val Leu Val Asp Ile Leu Met Asp Leu Gly Ala
            275                 280                 285

Leu Ala Arg Asn Cys Gly Arg Glu Ser Arg Val Asp Val Ala Lys
            290                 295                 300

Ser Val Thr Ser Gly Leu Gly Tyr Met His Cys Cys Leu Asn Pro
            305                 310                 315

Leu Leu Tyr Ala Phe Val Gly Val Lys Phe Arg Glu Arg Met Trp
            320                 325                 330

Met Leu Leu Leu Arg Leu Gly Cys Pro Asn Gln Arg Gly Leu Gln
            335                 340                 345

Arg Gln Pro Ser Ser Ser Arg Arg Asp Ser Ser Trp Ser Glu Thr
            350                 355             360
Ser Glu Ala Ser Tyr Ser Gly Leu
            365

<210> SEQ ID NO 54
<211> LENGTH: 2109
<212> TYPE: DNA
<213> ORGANISM: Homo sapiens

<400> SEQUENCE: 54

| | |
|---|---:|
| gagggaagaa cacaatggat ctggtgctaa aaagatgcct tcttcatttg | 50 |
| gctgtgatag gtgctttgct ggctgtgggg gctacaaaag tacccagaaa | 100 |
| ccaggactgg cttggtgtct caaggcaact cagaaccaaa gcctggaaca | 150 |
| ggcagctgta tccagagtgg acagaagccc agagacttga ctgctggaga | 200 |
| ggtggtcaag tgtccctcaa ggtcagtaat gatgggccta cactgattgg | 250 |
| tgcaaatgcc tccttctcta ttgccttgaa cttccctgga agccaaaagg | 300 |
| tattgccaga tgggcaggtt atctgggtca acaataccat catcaatggg | 350 |
| agccaggtgt ggggaggaca gccagtgtat ccccaggaaa ctgacgatgc | 400 |
| ctgcatcttc cctgatggtg accttgccc atctggctct tggtctcaga | 450 |
| agagaagctt tgtttatgtc tggaagacct ggggccaata ctggcaagtt | 500 |
| ctaggggggcc cagtgtctgg gctgagcatt gggacaggca gggcaatgct | 550 |
| gggcacacac accatggaag tgactgtcta ccatcgccgg ggatcccgga | 600 |
| gctatgtgcc tcttgctcat tccagctcag ccttcaccat tactgaccag | 650 |
| gtgccttcct ccgtgagcgt gtcccagttg cgggccttgg atggagggaa | 700 |
| caagcacttc ctgagaaatc agcctctgac cttgtgccct cagctccatg | 750 |
| accccagtgg ctatctggct gaagctgacc tctcctacac ctgggacttt | 800 |
| ggagacagta gtgaacccct gatctctcgg gcacttgtgg tcactcatac | 850 |
| ttacctggag cctggcccag tcactgccca gtggtcctg caggctgcca | 900 |
| ttcctctcac ctcctgtggc tcctccccag ttccaggcac acagatgggg | 950 |
| cacaggccaa ctgcagaggc ccctaacacc acagctggcc aagtgcctac | 1000 |
| tacagaagtt gtgggtacta cacctggtca ggcgccaact gcagagccct | 1050 |
| ctggaaccac atctgtgcag gtgccaacca ctgaagtcat aagcactgca | 1100 |
| cctgtgcaga tgccaactgc agagagcaca ggtatgacac ctgagaaggt | 1150 |
| gccagtttca gaggtcatgg gtaccacact ggcagagatg tcaactccag | 1200 |
| aggctacagg tatgacacct gcagaggtat caattgtggt gctttctgga | 1250 |
| accacagctg cacaggtaac aactacagag tgggtggaga ccacagctag | 1300 |
| agagctacct atccctgagc ctgaaggtcc agatgccagc tcaatcatgt | 1350 |
| ctacggaaag tattacaggt tccctgggcc cctgctgga tggtacagcc | 1400 |
| accttaaggc tggtgaagag acaagtcccc ctggattgtg ttctgtatcg | 1450 |
| atatggttcc ttttccgtca ccctggacat tgtccagggt attgaaagtg | 1500 |
| ccgagatcct gcaggctgtg ccgtccggtg agggggatgc atttgagctg | 1550 |
| actgtgtcct gccaaggcgg gctgcccaag gaagcctgca tggagatctc | 1600 |
| atcgccaggg tgccagcccc ctgcccagcg gctgtgccag cctgtgctac | 1650 |

```
ccagcccagc ctgccagctg gttctgcacc agatactgaa gggtggctcg      1700
gggacatact gcctcaatgt gtctctggct gataccaaca gcctggcagt      1750
ggtcagcacc cagcttatca tgcctggtca agaagcaggc cttgggcagg      1800
ttccgctgat cgtgggcatc ttgctggtgt tgatggctgt ggtccttgca      1850
tctctgatat ataggcgcag acttatgaag caagacttct ccgtacccca      1900
gttgccacat agcagcagtc actggctgcg tctaccccgc atcttctgct      1950
cttgtcccat tggtgagaac agccccctcc tcagtgggca gcaggtctga      2000
gtactctcat atgatgctgt gattttcctg gagttgacag aaacacctat      2050
atttccccca gtcttccctg ggagactact attaactgaa ataaatactc      2100
agagcctga                                                   2109
```

<210> SEQ ID NO 55
<211> LENGTH: 661
<212> TYPE: PRT
<213> ORGANISM: Homo sapiens

<400> SEQUENCE: 55

```
Met Asp Leu Val Leu Lys Arg Cys Leu Leu His Leu Ala Val Ile
 1               5                  10                  15

Gly Ala Leu Leu Ala Val Gly Ala Thr Lys Val Pro Arg Asn Gln
                20                  25                  30

Asp Trp Leu Gly Val Ser Arg Gln Leu Arg Thr Lys Ala Trp Asn
                35                  40                  45

Arg Gln Leu Tyr Pro Glu Trp Thr Glu Ala Gln Arg Leu Asp Cys
                50                  55                  60

Trp Arg Gly Gly Gln Val Ser Leu Lys Val Ser Asn Asp Gly Pro
 65                  70                  75

Thr Leu Ile Gly Ala Asn Ala Ser Phe Ser Ile Ala Leu Asn Phe
                80                  85                  90

Pro Gly Ser Gln Lys Val Leu Pro Asp Gly Gln Val Ile Trp Val
                95                  100                 105

Asn Asn Thr Ile Ile Asn Gly Ser Gln Val Trp Gly Gly Gln Pro
                110                 115                 120

Val Tyr Pro Gln Glu Thr Asp Asp Ala Cys Ile Phe Pro Asp Gly
                125                 130                 135

Gly Pro Cys Pro Ser Gly Ser Trp Ser Gln Lys Arg Ser Phe Val
                140                 145                 150

Tyr Val Trp Lys Thr Trp Gly Gln Tyr Trp Gln Val Leu Gly Gly
                155                 160                 165

Pro Val Ser Gly Leu Ser Ile Gly Thr Gly Arg Ala Met Leu Gly
                170                 175                 180

Thr His Thr Met Glu Val Thr Val Tyr His Arg Arg Gly Ser Arg
                185                 190                 195

Ser Tyr Val Pro Leu Ala His Ser Ser Ala Phe Thr Ile Thr
                200                 205                 210

Asp Gln Val Pro Phe Ser Val Ser Val Ser Gln Leu Arg Ala Leu
                215                 220                 225

Asp Gly Gly Asn Lys His Phe Leu Arg Asn Gln Pro Leu Thr Phe
                230                 235                 240

Ala Leu Gln Leu His Asp Pro Ser Gly Tyr Leu Ala Glu Ala Asp
                245                 250                 255
```

```
Leu Ser Tyr Thr Trp Asp Phe Gly Asp Ser Ser Gly Thr Leu Ile
            260                 265                 270

Ser Arg Ala Leu Val Val Thr His Thr Tyr Leu Glu Pro Gly Pro
            275                 280                 285

Val Thr Ala Gln Val Val Leu Gln Ala Ala Ile Pro Leu Thr Ser
            290                 295                 300

Cys Gly Ser Ser Pro Val Pro Gly Thr Thr Asp Gly His Arg Pro
            305                 310                 315

Thr Ala Glu Ala Pro Asn Thr Thr Ala Gly Gln Val Pro Thr Thr
            320                 325                 330

Glu Val Val Gly Thr Thr Pro Gly Gln Ala Pro Thr Ala Glu Pro
            335                 340                 345

Ser Gly Thr Thr Ser Val Gln Val Pro Thr Thr Glu Val Ile Ser
            350                 355                 360

Thr Ala Pro Val Gln Met Pro Thr Ala Glu Ser Thr Gly Met Thr
            365                 370                 375

Pro Glu Lys Val Pro Val Ser Glu Val Met Gly Thr Thr Leu Ala
            380                 385                 390

Glu Met Ser Thr Pro Glu Ala Thr Gly Met Thr Pro Ala Glu Val
            395                 400                 405

Ser Ile Val Val Leu Ser Gly Thr Thr Ala Ala Gln Val Thr Thr
            410                 415                 420

Thr Glu Trp Val Glu Thr Thr Ala Arg Glu Leu Pro Ile Pro Glu
            425                 430                 435

Pro Glu Gly Pro Asp Ala Ser Ser Ile Met Ser Thr Glu Ser Ile
            440                 445                 450

Thr Gly Ser Leu Gly Pro Leu Leu Asp Gly Thr Ala Thr Leu Arg
            455                 460                 465

Leu Val Lys Arg Gln Val Pro Leu Asp Cys Val Leu Tyr Arg Tyr
            470                 475                 480

Gly Ser Phe Ser Val Thr Leu Asp Ile Val Gln Gly Ile Glu Ser
            485                 490                 495

Ala Glu Ile Leu Gln Ala Val Pro Ser Gly Glu Gly Asp Ala Phe
            500                 505                 510

Glu Leu Thr Val Ser Cys Gln Gly Gly Leu Pro Lys Glu Ala Cys
            515                 520                 525

Met Glu Ile Ser Ser Pro Gly Cys Gln Pro Pro Ala Gln Arg Leu
            530                 535                 540

Cys Gln Pro Val Leu Pro Ser Pro Ala Cys Gln Leu Val Leu His
            545                 550                 555

Gln Ile Leu Lys Gly Gly Ser Gly Thr Tyr Cys Leu Asn Val Ser
            560                 565                 570

Leu Ala Asp Thr Asn Ser Leu Ala Val Val Ser Thr Gln Leu Ile
            575                 580                 585

Met Pro Gly Gln Glu Ala Gly Leu Gly Gln Val Pro Leu Ile Val
            590                 595                 600

Gly Ile Leu Leu Val Leu Met Ala Val Val Leu Ala Ser Leu Ile
            605                 610                 615

Tyr Arg Arg Arg Leu Met Lys Gln Asp Phe Ser Val Pro Gln Leu
            620                 625                 630

Pro His Ser Ser Ser His Trp Leu Arg Leu Pro Arg Ile Phe Cys
            635                 640                 645
```

Ser Cys Pro Ile Gly Glu Asn Ser Pro Leu Leu Ser Gly Gln Gln
            650                 655                 660

Val

<210> SEQ ID NO 56
<211> LENGTH: 2772
<212> TYPE: DNA
<213> ORGANISM: Homo sapiens

<400> SEQUENCE: 56

| | |
|---|---:|
| cagtcggcac cggcgaggcc gtgctggaac ccgggcctca gccgcagccg | 50 |
| cagcggggcc gacatgacga cagctcccca ggagcccccc gcccggcccc | 100 |
| tccaggcggg cagtggagct ggcccggcgc ctgggcgcgc catgcgcagc | 150 |
| accacgctcc tggccctgct ggcgctggtc ttgctttact tggtgtctgg | 200 |
| tgccctggtg ttccgggccc tggagcagcc ccacgagcag caggcccaga | 250 |
| gggagctggg ggaggtccga gagaagttcc tgagggccca tccgtgtgtg | 300 |
| agcgaccagg agctgggcct cctcatcaag gaggtggctg atgccctggg | 350 |
| aggggggtgcg gacccagaaa ccaactcgac cagcaacagc agccactcag | 400 |
| cctgggacct gggcagcgcc ttctttttct cagggaccat catcaccacc | 450 |
| atcggctatg caatgtggcc ctgcgcaca gatgccgggc gcctcttctg | 500 |
| catcttctat gcgctggtgg ggattccgct gtttgggatc ctactggcag | 550 |
| gggtcgggga ccggctgggc tcctccctgc gccatggcat cggtcacatt | 600 |
| gaagccatct tcttgaagtg gcacgtgcca ccggagctag taagagtgct | 650 |
| gtcggcgatg cttttcctgc tgatcggctg cctgctcttt gtcctcacgc | 700 |
| ccacgttcgt gttctgctat atggaggact ggagcaagct ggaggccatc | 750 |
| tactttgtca tagtgacgct taccaccgtg ggctttggcg actatgtggc | 800 |
| cggcgcggac cccaggcagg actccccggc ctatcagccg ctggtgtggt | 850 |
| tctggatcct gctcggcctg gcttacttcg cctcagtgct caccaccatc | 900 |
| gggaactggc tgcgagtagt gtcccgccgc actcgggcag agatgggcgg | 950 |
| cctcacggct caggctgcca gctggactgg cacagtgaca gcgcgcgtga | 1000 |
| cccagcgagc cgggccccgcc gccccgcgc cggagaagga gcagccactg | 1050 |
| ctgcctccac cgcccctgtcc agcgcagccg ctgggcaggc ccgatcccc | 1100 |
| ttcgccccccc gagaaggctc agctgccttc cccgcccacg gcctcggccc | 1150 |
| tggattatcc cagcgagaac ctggccttca tcgacgagtc ctcggatacg | 1200 |
| cagagcgagc gcggctgccc gctgcccgc gcgccgagag tcgccgccg | 1250 |
| cccaaatccc cccaggaagc ccgtgcggcc ccgcggcccc gggcgtcccc | 1300 |
| gagacaaagg cgtgccggtg taggggcagg atccctggcc gggcctctca | 1350 |
| agggcttcgt ttctgctctc cccggcatgc ctggcttgtt tgaccaaaga | 1400 |
| gccctctttc cacgagactg aagtctgggg aggaggctac agttgcctct | 1450 |
| ccgcctcctc cctggccccg ccccttccct cacttccatc catctctaga | 1500 |
| ccccccaag gctttctgtg tcgctgcccc gggcgggtgt atccctcaca | 1550 |
| gcacctcacg actgtgcctc aaagcctgca tcaataaatg aaaacggtct | 1600 |
| gcaccgctgc gggcgtgacg ctcccggacg cgagtggtg tggaattgct | 1650 |

-continued

```
ttcctcgggc caccgtgggg gcacctctgg cctcccgtga cccccaggcc      1700
gagggtcccc gggcacccag gtcggtcaag tctcggccct ctcaggcccg      1750
cgtctctgcc tggaggagac tgtgtagggt ccggcgtggg gatcagccgg      1800
gatgggctgc gcgtctccag cctctgcaca cacattggcg ggtggggtgc      1850
agggagggag aggcagggga gagagaatgg catctcgcgt ggagggctgt      1900
cgtttgaact ctcccagcgc gagagaccct gccccgcccc cttcctggag      1950
cgttgactcc cttctcgtct cgaggcctgt ggcgtctggg tccgttgggg      2000
cagaaccatg gaggaaaagc cttcgaaagt gtcgctcaag tcttccgacc      2050
gccaaggctc ggacgaggag agcgtgcata gcgacactcg ggacctgtgg      2100
accacgacca cgctgtccca ggcacagctg aacatgccgc tgtccgaggt      2150
ctgcgagggc ttcgacgagg agggccgcaa cattagcaag acccgcgggt      2200
ggcacagccc ggggcgggc tcgttggacg aggggtacaa ggccagccac      2250
aagccggagg aactggacga gcacgcgctg gtggagctgg agttgcaccg      2300
cggcagctcc atggaaatca atctgggga aaggacact gcatcccaga      2350
tcgaggccga aaagtcttcc tcaatgtcat cactcaatat gcgaagcac      2400
atgccccatc gagcctactg ggcagagcag cagagcaggc tgccactgcc      2450
cctgatggaa ctcatggaga atgaagctct ggaaatcctc accaaagccc      2500
tccggagcta ccagttaggg atcggcaggg accacttcct gactaaggag      2550
ctgcagcgat acatcgaagg gctcaagaag cgccggagca agaggctgta      2600
cgtgaattaa aaacgccacc ttgggctcga gcagcgaccc gaaccagccc      2650
cgtgccagcc cggtccccag acccaagcct gaccccatcc gagtggaatt      2700
tgagtcctaa agaaataaaa gagtcgatgc atgaaaaaaa aaaaaaaaaa      2750
aaaaaaaaaa aaaaaaaaaa aa                                   2772
```

<210> SEQ ID NO 57
<211> LENGTH: 419
<212> TYPE: PRT
<213> ORGANISM: Homo sapiens

<400> SEQUENCE: 57

```
Met Thr Thr Ala Pro Gln Glu Pro Pro Ala Arg Pro Leu Gln Ala
  1               5                  10                  15

Gly Ser Gly Ala Gly Pro Ala Pro Gly Arg Ala Met Arg Ser Thr
                 20                  25                  30

Thr Leu Leu Ala Leu Leu Ala Leu Val Leu Leu Tyr Leu Val Ser
                 35                  40                  45

Gly Ala Leu Val Phe Arg Ala Leu Glu Gln Pro His Glu Gln Gln
                 50                  55                  60

Ala Gln Arg Glu Leu Gly Glu Val Arg Glu Lys Phe Leu Arg Ala
                 65                  70                  75

His Pro Cys Val Ser Asp Gln Glu Leu Gly Leu Leu Ile Lys Glu
                 80                  85                  90

Val Ala Asp Ala Leu Gly Gly Gly Ala Asp Pro Glu Thr Asn Ser
                 95                 100                 105

Thr Ser Asn Ser Ser His Ser Ala Trp Asp Leu Gly Ser Ala Phe
                110                 115                 120

Phe Phe Ser Gly Thr Ile Ile Thr Thr Ile Gly Tyr Gly Asn Val
```

```
                    125                 130                 135
Ala Leu Arg Thr Asp Ala Gly Arg Leu Phe Cys Ile Phe Tyr Ala
                140                 145                 150
Leu Val Gly Ile Pro Leu Phe Gly Ile Leu Ala Gly Val Gly
            155                 160                 165
Asp Arg Leu Gly Ser Ser Leu Arg His Gly Ile Gly His Ile Glu
                170                 175                 180
Ala Ile Phe Leu Lys Trp His Val Pro Glu Leu Val Arg Val
            185                 190                 195
Leu Ser Ala Met Leu Phe Leu Leu Ile Gly Cys Leu Leu Phe Val
                200                 205                 210
Leu Thr Pro Thr Phe Val Phe Cys Tyr Met Glu Asp Trp Ser Lys
                215                 220                 225
Leu Glu Ala Ile Tyr Phe Val Ile Val Thr Leu Thr Thr Val Gly
                230                 235                 240
Phe Gly Asp Tyr Val Ala Gly Ala Asp Pro Arg Gln Asp Ser Pro
                245                 250                 255
Ala Tyr Gln Pro Leu Val Trp Phe Trp Ile Leu Leu Gly Leu Ala
                260                 265                 270
Tyr Phe Ala Ser Val Leu Thr Thr Ile Gly Asn Trp Leu Arg Val
                275                 280                 285
Val Ser Arg Arg Thr Arg Ala Glu Met Gly Gly Leu Thr Ala Gln
                290                 295                 300
Ala Ala Ser Trp Thr Gly Thr Val Thr Ala Arg Val Thr Gln Arg
                305                 310                 315
Ala Gly Pro Ala Ala Pro Pro Glu Lys Glu Gln Pro Leu Leu
            320                 325                 330
Pro Pro Pro Pro Cys Pro Ala Gln Pro Leu Gly Arg Pro Arg Ser
                335                 340                 345
Pro Ser Pro Pro Glu Lys Ala Gln Leu Pro Ser Pro Pro Thr Ala
                350                 355                 360
Ser Ala Leu Asp Tyr Pro Ser Glu Asn Leu Ala Phe Ile Asp Glu
                365                 370                 375
Ser Ser Asp Thr Gln Ser Glu Arg Gly Cys Pro Leu Pro Arg Ala
                380                 385                 390
Pro Arg Gly Arg Arg Arg Pro Asn Pro Pro Arg Lys Pro Val Arg
                395                 400                 405
Pro Arg Gly Pro Gly Arg Pro Arg Asp Lys Gly Val Pro Val
            410                 415

<210> SEQ ID NO 58
<211> LENGTH: 2814
<212> TYPE: DNA
<213> ORGANISM: Homo sapiens

<400> SEQUENCE: 58
gccaacactg gccaaacaga agcctccggt cggcctgcag tgcccaagtc          50
ccatggcgag ggcagcccga gtggccgtcg cggctgtagg tccgcatgcc         100
gggcaccgca ccaggcgtct agcagatgga cacaggaaga tccagaagct         150
agtggcacat ctagcaacag agccagatca gaacccagat gctaaactcc         200
tggtggactg cagaggagag ggattcagtc ttctcctgat gtcgattgcg         250
atttctgctg ggagctcaag acgggcgagc tgcccgagat ctcttcgaga         300
```

```
taccccaggg gaggaggaga tgggcaggat ttagtaggac aactcggtta      350
ctaatgactt ggcggctggc tgcgaccccc cgggaaatca ggtgcaagca      400
tgtttgcctg taggtacctg agttgacacc gaaggtgcct aaagatgctg      450
agcggcgttt ggttcctcag tgtgttaacc gtggccggga tcttacagac      500
agagagtcgc aaaactgcca agacatttg caagatccgc tgtctgtgcg       550
aagaaaagga aaacgtactg aatatcaact gtgagaacaa aggatttaca      600
acagttagcc tgctccagcc ccccagtat cgaatctatc agcttttct        650
caatggaaac ctcttgacaa gactgtatcc aaacgaattt gtcaattact      700
ccaacgcggt gactcttcac ctaggtaaca acgggttaca ggagatccga      750
acggggcat tcagtggcct gaaaactctc aaaagactgc atctcaacaa       800
caacaagctt gagatattga gggaggacac cttcctaggc ctggagagcc      850
tggagtatct ccaggccgac tacaattaca tcagtgccat cgaggctggg      900
gcattcagca aacttaacaa gctcaaagtg ctcatcctga atgacaacct      950
tctgctttca ctgcccagca atgtgttccg cttgtcctg ctgacccact       1000
tagacctcag ggggaatagg ctaaaagtaa tgccttttgc tggcgtcctt      1050
gaacatattg gagggatcat ggagattcag ctggaggaaa atccatggaa      1100
ttgcacttgt gacttacttc ctctcaaggc ctggctagac accataactg      1150
tttttgtggg agagattgtc tgtgagactc cctttaggtt gcatgggaaa      1200
gacgtgaccc agctgaccag gcaagacctc tgtcccagaa aaagtgccag      1250
tgattccagt cagaggggca gccatgctga cacccacgtc caaggctgt       1300
cacctacaat gaatcctgct ctcaacccaa ccagggctcc gaaagccagc      1350
cggccgccca aaatgagaaa tcgtccaact ccccgagtga ctgtgtcaaa      1400
ggacaggcaa agttttggac ccatcatggt gtaccgacc aagtctcctg       1450
tgcctctcac ctgtcccagc agctgtgtct gcacctctca gagctcagac      1500
aatggtctga atgtaaactg ccaagaaagg aagttcacta atatctctga      1550
cctgcagccc aaaccgacca gtccaaagaa actctaccta acagggaact      1600
atcttcaaac tgtctataag aatgacctct tagaatacag ttctttggac      1650
ttactgcact taggaaacaa caggattgca gtcattcagg aaggtgcctt      1700
tacaaacctg accagtttac gcagacttta tctgaatggc aattaccttg      1750
aagtgctgta cccttctatg tttgatggac tgcagagctt gcaatatctc      1800
tatttagagt ataatgtcat taaggaaatt aagcctctga cctttgatgc      1850
tttgattaac ctacagctac tgtttctgaa caacaaccct cttcggtcct      1900
tacctgataa tatatttggg gggacggccc taaccaggct gaatctgaga      1950
aacaaccatt tttctcacct gcccgtgaaa ggggttctgg atcagctccc      2000
ggctttcatc cagatagatc tgcaggagaa cccctgggac tgtacctgtg      2050
acatcatggg gctgaaagac tggacagaac atgccaattc ccctgtcatc      2100
attaatgagg tgacttgcga atctcctgct aagcatcag gggagatact       2150
aaaatttctg gggagggagg ctatctgtcc agacagccca aacttgtcag      2200
atggaaccgt cttgtcaatg aatcacaata cagacacacc tcggtcgctt      2250
agtgtgtctc ctagttccta tcctgaacta cacactgaag ttccactgtc      2300
```

-continued

```
tgtcttaatt ctgggattgc ttgttgtttt catcttatct gtctgttttg      2350
gggctggttt attcgtcttt gtcttgaaac gccgaaaggg agtgccgagc      2400
gttcccagga ataccaacaa cttagacgta agctcctttc aattacagta      2450
tgggtcttac aacactgaga ctcacgataa aacagacggc catgtctaca      2500
actatatccc cccacctgtg ggtcagatgt gccaaaaccc catctacatg      2550
cagaaggaag agacccagt agcctattac cgaaacctgc aggagttcaa       2600
gaccagccta gagaacatat ggagaccctg tcttcacaaa aaataaaaaa      2650
gtcagccaag cgtggtggtg tgtgcctgta gttacttagg aggctgaggc      2700
aggacgatcg cttaagccca ggagtttgag gctgtggtga gctacaattg      2750
cgccactgca cgccagcctg gctacagaac gagaccctgc ctctctaaaa      2800
aaaaaaaaaa aaaa                                            2814
```

<210> SEQ ID NO 59
<211> LENGTH: 733
<212> TYPE: PRT
<213> ORGANISM: Homo sapiens

<400> SEQUENCE: 59

```
Met Leu Ser Gly Val Trp Phe Leu Ser Val Leu Thr Val Ala Gly
  1               5                  10                  15

Ile Leu Gln Thr Glu Ser Arg Lys Thr Ala Lys Asp Ile Cys Lys
                 20                  25                  30

Ile Arg Cys Leu Cys Glu Glu Lys Glu Asn Val Leu Asn Ile Asn
                 35                  40                  45

Cys Glu Asn Lys Gly Phe Thr Thr Val Ser Leu Leu Gln Pro Pro
                 50                  55                  60

Gln Tyr Arg Ile Tyr Gln Leu Phe Leu Asn Gly Asn Leu Leu Thr
                 65                  70                  75

Arg Leu Tyr Pro Asn Glu Phe Val Asn Tyr Ser Asn Ala Val Thr
                 80                  85                  90

Leu His Leu Gly Asn Asn Gly Leu Gln Glu Ile Arg Thr Gly Ala
                 95                 100                 105

Phe Ser Gly Leu Lys Thr Leu Lys Arg Leu His Leu Asn Asn Asn
                110                 115                 120

Lys Leu Glu Ile Leu Arg Glu Asp Thr Phe Leu Gly Leu Glu Ser
                125                 130                 135

Leu Glu Tyr Leu Gln Ala Asp Tyr Asn Tyr Ile Ser Ala Ile Glu
                140                 145                 150

Ala Gly Ala Phe Ser Lys Leu Asn Lys Leu Lys Val Leu Ile Leu
                155                 160                 165

Asn Asp Asn Leu Leu Ser Leu Pro Ser Asn Val Phe Arg Phe
                170                 175                 180

Val Leu Leu Thr His Leu Asp Leu Arg Gly Asn Arg Leu Lys Val
                185                 190                 195

Met Pro Phe Ala Gly Val Leu Glu His Ile Gly Gly Ile Met Glu
                200                 205                 210

Ile Gln Leu Glu Glu Asn Pro Trp Asn Cys Thr Cys Asp Leu Leu
                215                 220                 225

Pro Leu Lys Ala Trp Leu Asp Thr Ile Thr Val Phe Val Gly Glu
                230                 235                 240
```

```
Ile Val Cys Glu Thr Pro Phe Arg Leu His Gly Lys Asp Val Thr
                245                 250                 255

Gln Leu Thr Arg Gln Asp Leu Cys Pro Arg Lys Ser Ala Ser Asp
                260                 265                 270

Ser Ser Gln Arg Gly Ser His Ala Asp Thr His Val Gln Arg Leu
                275                 280                 285

Ser Pro Thr Met Asn Pro Ala Leu Asn Pro Thr Arg Ala Pro Lys
                290                 295                 300

Ala Ser Arg Pro Pro Lys Met Arg Asn Arg Pro Thr Pro Arg Val
                305                 310                 315

Thr Val Ser Lys Asp Arg Gln Ser Phe Gly Pro Ile Met Val Tyr
                320                 325                 330

Gln Thr Lys Ser Pro Val Pro Leu Thr Cys Pro Ser Ser Cys Val
                335                 340                 345

Cys Thr Ser Gln Ser Ser Asp Asn Gly Leu Asn Val Asn Cys Gln
                350                 355                 360

Glu Arg Lys Phe Thr Asn Ile Ser Asp Leu Gln Pro Lys Pro Thr
                365                 370                 375

Ser Pro Lys Lys Leu Tyr Leu Thr Gly Asn Tyr Leu Gln Thr Val
                380                 385                 390

Tyr Lys Asn Asp Leu Leu Glu Tyr Ser Ser Leu Asp Leu Leu His
                395                 400                 405

Leu Gly Asn Asn Arg Ile Ala Val Ile Gln Glu Gly Ala Phe Thr
                410                 415                 420

Asn Leu Thr Ser Leu Arg Arg Leu Tyr Leu Asn Gly Asn Tyr Leu
                425                 430                 435

Glu Val Leu Tyr Pro Ser Met Phe Asp Gly Leu Gln Ser Leu Gln
                440                 445                 450

Tyr Leu Tyr Leu Glu Tyr Asn Val Ile Lys Glu Ile Lys Pro Leu
                455                 460                 465

Thr Phe Asp Ala Leu Ile Asn Leu Gln Leu Leu Phe Leu Asn Asn
                470                 475                 480

Asn Leu Leu Arg Ser Leu Pro Asp Asn Ile Phe Gly Gly Thr Ala
                485                 490                 495

Leu Thr Arg Leu Asn Leu Arg Asn Asn His Phe Ser His Leu Pro
                500                 505                 510

Val Lys Gly Val Leu Asp Gln Leu Pro Ala Phe Ile Gln Ile Asp
                515                 520                 525

Leu Gln Glu Asn Pro Trp Asp Cys Thr Cys Asp Ile Met Gly Leu
                530                 535                 540

Lys Asp Trp Thr Glu His Ala Asn Ser Pro Val Ile Ile Asn Glu
                545                 550                 555

Val Thr Cys Glu Ser Pro Ala Lys His Ala Gly Glu Ile Leu Lys
                560                 565                 570

Phe Leu Gly Arg Glu Ala Ile Cys Pro Asp Ser Pro Asn Leu Ser
                575                 580                 585

Asp Gly Thr Val Leu Ser Met Asn His Asn Thr Asp Thr Pro Arg
                590                 595                 600

Ser Leu Ser Val Ser Pro Ser Ser Tyr Pro Glu Leu His Thr Glu
                605                 610                 615

Val Pro Leu Ser Val Leu Ile Leu Gly Leu Leu Val Val Phe Ile
                620                 625                 630

Leu Ser Val Cys Phe Gly Ala Gly Leu Phe Val Phe Val Leu Lys
```

```
                    635                 640                 645
Arg Arg Lys Gly Val Pro Ser Val Pro Arg Asn Thr Asn Leu
                650                 655                 660
Asp Val Ser Ser Phe Gln Leu Gln Tyr Gly Ser Tyr Asn Thr Glu
                665                 670                 675
Thr His Asp Lys Thr Asp Gly His Val Tyr Asn Tyr Ile Pro Pro
                680                 685                 690
Pro Val Gly Gln Met Cys Gln Asn Pro Ile Tyr Met Gln Lys Glu
                695                 700                 705
Gly Asp Pro Val Ala Tyr Tyr Arg Asn Leu Gln Glu Phe Lys Thr
                710                 715                 720
Ser Leu Glu Asn Ile Trp Arg Pro Cys Leu His Lys Lys
                725                 730

<210> SEQ ID NO 60
<211> LENGTH: 3679
<212> TYPE: DNA
<213> ORGANISM: Homo sapiens

<400> SEQUENCE: 60
aaggaggctg ggaggaaaga ggtaagaaag gttagagaac ctacctcaca        50
tctctctggg ctcagaagga ctctgaagat aacaataatt tcagcccatc        100
cactctcctt ccctcccaaa cacacatgtg catgtacaca cacacataca        150
cacacataca ccttcctctc cttcactgaa gactcacagt cactcactct        200
gtgagcaggt catagaaaag gacactaaag ccttaaggac aggcctggcc        250
attacctctg cagctccttt ggcttgttga gtcaaaaaac atgggagggg        300
ccaggcacgg tgactcacac ctgtaatccc agcattttgg gagaccgagg        350
tgagcagatc acttgaggtc aggagttcga gaccagcctg gccaacatgg        400
agaaaccccc atctctacta aaaatacaaa aattagccag gagtggtggc        450
aggtgcctgt aatcccagct actcaggtgg ctgagccagg agaatcgctt        500
gaatccagga ggcggaggat gcagtcagct gagtgcaccg ctgcactcca        550
gcctgggtga cagaatgaga ctctgtctca aacaaacaaa cacgggagga        600
ggggtagata ctgcttctct gcaacctcct taactctgca tcctcttctt        650
ccagggctgc ccctgatggg gcctggcaat gactgagcag gcccagcccc        700
agaggacaag gaagagaagg catattgagg agggcaagaa gtgacgcccg        750
gtgtagaatg actgccctgg gagggtggtt ccttgggccc tggcagggtt        800
gctgaccctt accctgcaaa acacaaagag caggactcca gactctcctt        850
gtgaatggtc ccctgccctg cagctccacc atgaggcttc tcgtggcccc        900
actcttgcta gctgggtgg ctggtgccac tgccactgtg cccgtggtac        950
cctggcatgt tccctgcccc cctcagtgtg cctgccagat ccggccctgg       1000
tatacgcccc gctcgtccta ccgcgaggct accactgtgg actgcaatga       1050
cctattcctg acggcagtcc ccccggcact ccccgcaggc acacagaccc       1100
tgctcctgca gagcaacagc attgtccgtg tggaccagag tgagctgggc       1150
tacctggcca atctcacaga gctggacctg tcccagaaca gcttttcgga       1200
tgcccgagac tgtgatttcc atgccctgcc ccagctgctg agcctgcacc       1250
tagaggagaa ccagctgacc cggctggagg accacagctt tgcagggctg       1300
```

-continued

```
gccagcctac aggaactcta tctcaaccac aaccagctct accgcatcgc      1350
ccccagggcc ttttctggcc tcagcaactt gctgcggctg cacctcaact      1400
ccaacctcct gagggccatt gacagccgct ggtttgaaat gctgcccaac      1450
ttggagatac tcatgattgg cggcaacaag gtagatgcca tcctggacat      1500
gaacttccgg cccctggcca acctgcgtag cctggtgcta gcaggcatga      1550
acctgcggga gatctccgac tatgccctgg aggggctgca aagcctggag      1600
agcctctcct tctatgacaa ccagctggcc cgggtgccca ggcgggcact      1650
ggaacaggtg cccgggctca agttcctaga cctcaacaag aacccgctcc      1700
agcgggtagg gccggggggac tttgccaaca tgctgcacct taaggagctg      1750
ggactgaaca acatggagga gctggtctcc atcgacaagt tgccctggt       1800
gaacctcccc gagctgacca agctggacat caccaataac ccacggctgt      1850
ccttcatcca ccccgcgcc ttccaccacc tgccccagat ggagaccctc       1900
atgctcaaca acaacgctct cagtgccttg caccagcaga cggtggagtc      1950
cctgcccaac ctgcaggagg taggtctcca cggcaacccc atccgctgtg      2000
actgtgtcat ccgctgggcc aatgccacgg gcacccgtgt ccgcttcatc      2050
gagccgcaat ccaccctgtg tgcggagcct ccggacctcc agcgcctccc      2100
ggtccgtgag gtgcccttcc gggagatgac ggaccactgt ttgcccctca      2150
tctccccacg aagcttcccc ccaagcctcc aggtagccag tggagagagc      2200
atggtgctgc attgccgggc actggccgaa cccgaacccg agatctactg      2250
ggtcactcca gctgggcttc gactgacacc tgcccatgca ggcaggaggt      2300
accgggtgta ccccgagggg accctggagc tgcggagggt gacagcagaa      2350
gaggcagggc tatacacctg tgtgcccag aacctggtgg gggctgacac        2400
taagacggtt agtgtggttg tgggccgtgc tctcctccag ccaggcaggg      2450
acgaaggaca ggggctggag ctccgggtgc aggagaccca ccctatcac       2500
atcctgctat cttgggtcac cccacccaac acagtgtcca ccaacctcac      2550
ctggtccagt gcctcctccc tccggggcca gggggccaca gctctggccc     2600
gcctgcctcg gggaacccac agctacaaca ttacccgcct ccttcaggcc      2650
acggagtact gggcctgcct gcaagtggcc tttgctgatg cccacaccca     2700
gttggcttgt gtatgggcca ggaccaaaga ggccacttct tgccacagag      2750
ccttagggga tcgtcctggg ctcattgcca tcctggctct cgctgtcctt     2800
ctcctggcag ctgggctagc ggcccacctt ggcacaggcc aacccaggaa      2850
gggtgtgggt gggaggcggc ctctcctcc agcctgggct ttctggggct       2900
ggagtgcccc ttctgtccgg gttgtgtctg ctcccctcgt cctgccctgg     2950
aatccaggga ggaagctgcc cagatcctca gaagggagaa cactgttgcc      3000
accattgtct caaaattctt gaagctcagc ctgttctcag cagtagagaa      3050
atcactagga ctacttttta ccaaaagaga agcagtctgg gccagatgcc      3100
ctgccaggaa agggacatgg acccacgtgc ttgaggcctg gcagctgggc      3150
caagacagat ggggctttgt ggccctgggg gtgcttctgc agccttgaaa      3200
aagttgccct tacctcctag ggtcacctct gctgccattc tgaggaacat      3250
```

| | |
|---|---:|
| ctccaaggaa caggagggac tttggctaga gcctcctgcc tccccatctt | 3300 |
| ctctctgccc agaggctcct gggcctggct tggctgtccc ctacctgtgt | 3350 |
| ccccgggctg cacccottcc tcttctcttt tctgtacag tctcagttgc | 3400 |
| ttgctcttgt gcctcctggg caagggctga aggaggccac tccatctcac | 3450 |
| ctcgggggc tgccctcaat gtgggagtga ccccagccag atctgaagga | 3500 |
| catttgggag agggatgccc aggaacgcct catctcagca gcctgggctc | 3550 |
| ggcattccga agctgacttt ctataggcaa ttttgtacct ttgtggagaa | 3600 |
| atgtgtcacc tccccaacc cgattcactc ttttctcctg ttttgtaaaa | 3650 |
| aataaaaata aataataaca ataaaaaaa | 3679 |

<210> SEQ ID NO 61
<211> LENGTH: 713
<212> TYPE: PRT
<213> ORGANISM: Homo sapiens

<400> SEQUENCE: 61

Met Arg Leu Leu Val Ala Pro Leu Leu Ala Trp Val Ala Gly
1               5                   10                  15

Ala Thr Ala Thr Val Pro Val Pro Trp His Val Pro Cys Pro
            20                  25                  30

Pro Gln Cys Ala Cys Gln Ile Arg Pro Trp Tyr Thr Pro Arg Ser
        35                  40                  45

Ser Tyr Arg Glu Ala Thr Thr Val Asp Cys Asn Asp Leu Phe Leu
        50                  55                  60

Thr Ala Val Pro Pro Ala Leu Pro Ala Gly Thr Gln Thr Leu Leu
        65                  70                  75

Leu Gln Ser Asn Ser Ile Val Arg Val Asp Gln Ser Glu Leu Gly
        80                  85                  90

Tyr Leu Ala Asn Leu Thr Glu Leu Asp Leu Ser Gln Asn Ser Phe
        95                  100                 105

Ser Asp Ala Arg Asp Cys Asp Phe His Ala Leu Pro Gln Leu Leu
        110                 115                 120

Ser Leu His Leu Glu Glu Asn Gln Leu Thr Arg Leu Glu Asp His
        125                 130                 135

Ser Phe Ala Gly Leu Ala Ser Leu Gln Glu Leu Tyr Leu Asn His
        140                 145                 150

Asn Gln Leu Tyr Arg Ile Ala Pro Arg Ala Phe Ser Gly Leu Ser
        155                 160                 165

Asn Leu Leu Arg Leu His Leu Asn Ser Asn Leu Leu Arg Ala Ile
        170                 175                 180

Asp Ser Arg Trp Phe Glu Met Leu Pro Asn Leu Glu Ile Leu Met
        185                 190                 195

Ile Gly Gly Asn Lys Val Asp Ala Ile Leu Asp Met Asn Phe Arg
        200                 205                 210

Pro Leu Ala Asn Leu Arg Ser Leu Val Leu Ala Gly Met Asn Leu
        215                 220                 225

Arg Glu Ile Ser Asp Tyr Ala Leu Glu Gly Leu Gln Ser Leu Glu
        230                 235                 240

Ser Leu Ser Phe Tyr Asp Asn Gln Leu Ala Arg Val Pro Arg Arg
        245                 250                 255

Ala Leu Glu Gln Val Pro Gly Leu Lys Phe Leu Asp Leu Asn Lys
        260                 265                 270

```
Asn Pro Leu Gln Arg Val Gly Pro Gly Asp Phe Ala Asn Met Leu
            275                 280                 285

His Leu Lys Glu Leu Gly Leu Asn Asn Met Glu Glu Leu Val Ser
            290                 295                 300

Ile Asp Lys Phe Ala Leu Val Asn Leu Pro Glu Leu Thr Lys Leu
            305                 310                 315

Asp Ile Thr Asn Asn Pro Arg Leu Ser Phe Ile His Pro Arg Ala
            320                 325                 330

Phe His His Leu Pro Gln Met Glu Thr Leu Met Leu Asn Asn Asn
            335                 340                 345

Ala Leu Ser Ala Leu His Gln Gln Thr Val Glu Ser Leu Pro Asn
            350                 355                 360

Leu Gln Glu Val Gly Leu His Gly Asn Pro Ile Arg Cys Asp Cys
            365                 370                 375

Val Ile Arg Trp Ala Asn Ala Thr Gly Thr Arg Val Arg Phe Ile
            380                 385                 390

Glu Pro Gln Ser Thr Leu Cys Ala Glu Pro Pro Asp Leu Gln Arg
            395                 400                 405

Leu Pro Val Arg Glu Val Pro Phe Arg Glu Met Thr Asp His Cys
            410                 415                 420

Leu Pro Leu Ile Ser Pro Arg Ser Phe Pro Pro Ser Leu Gln Val
            425                 430                 435

Ala Ser Gly Glu Ser Met Val Leu His Cys Arg Ala Leu Ala Glu
            440                 445                 450

Pro Glu Pro Glu Ile Tyr Trp Val Thr Pro Ala Gly Leu Arg Leu
            455                 460                 465

Thr Pro Ala His Ala Gly Arg Arg Tyr Arg Val Tyr Pro Glu Gly
            470                 475                 480

Thr Leu Glu Leu Arg Arg Val Thr Ala Glu Glu Ala Gly Leu Tyr
            485                 490                 495

Thr Cys Val Ala Gln Asn Leu Val Gly Ala Asp Thr Lys Thr Val
            500                 505                 510

Ser Val Val Val Gly Arg Ala Leu Leu Gln Pro Gly Arg Asp Glu
            515                 520                 525

Gly Gln Gly Leu Glu Leu Arg Val Gln Glu Thr His Pro Tyr His
            530                 535                 540

Ile Leu Leu Ser Trp Val Thr Pro Pro Asn Thr Val Ser Thr Asn
            545                 550                 555

Leu Thr Trp Ser Ser Ala Ser Ser Leu Arg Gly Gln Gly Ala Thr
            560                 565                 570

Ala Leu Ala Arg Leu Pro Arg Gly Thr His Ser Tyr Asn Ile Thr
            575                 580                 585

Arg Leu Leu Gln Ala Thr Glu Tyr Trp Ala Cys Leu Gln Val Ala
            590                 595                 600

Phe Ala Asp Ala His Thr Gln Leu Ala Cys Val Trp Ala Arg Thr
            605                 610                 615

Lys Glu Ala Thr Ser Cys His Arg Ala Leu Gly Asp Arg Pro Gly
            620                 625                 630

Leu Ile Ala Ile Leu Ala Leu Ala Val Leu Leu Leu Ala Ala Gly
            635                 640                 645

Leu Ala Ala His Leu Gly Thr Gly Gln Pro Arg Lys Gly Val Gly
            650                 655                 660
```

```
Gly Arg Arg Pro Leu Pro Pro Ala Trp Ala Phe Trp Gly Trp Ser
            665                 670                 675

Ala Pro Ser Val Arg Val Val Ser Ala Pro Leu Val Leu Pro Trp
            680                 685                 690

Asn Pro Gly Arg Lys Leu Pro Arg Ser Ser Glu Gly Glu Thr Leu
            695                 700                 705

Leu Pro Pro Leu Ser Gln Asn Ser
            710

<210> SEQ ID NO 62
<211> LENGTH: 1186
<212> TYPE: DNA
<213> ORGANISM: Homo sapiens
<220> FEATURE:
<221> NAME/KEY: Unsure
<222> LOCATION: 54-55
<223> OTHER INFORMATION: Unknown base

<400> SEQUENCE: 62
ggcacgagcc ggcaagccga gctagggtga aaactggggg cgcaccagga        50
tgtnngacag aaaagcagaa gatgagactc tgttcattca cttttcctag       100
gcccatcctg tggtcatctt tccccctccc atcataccte ctccttcctg       150 gagcctctgc cggcttggct gtaatggtgg cacttacctg gatatttcag       200
tgggaggatg aaaggcgaga ctcaccctac gcggtgggac agatggggag       250
aggaaaaagg cagagatggc caggagaggg gtgcaggaca aaccagagag       300
gttgggtcag ggggaaaggg tggggagaaa gaggggtgca ggccctgcag       350
gccggttagc cagcagctgc ggcctccccg ggcccttggc atccaacttc       400
gcagacaggt taccagcctc ctggtgtgta tcataggatt tgttcacata       450
gtgttatgca tgatcttcgt aaggttaaga agccgtggtg gtgcaccatg       500
acatccaacc cgtatatata aagataaata tatatatata tgtatgtaaa       550
ttatggcacg agaaattata gcactgaggg ccctgctgcc ctgctggacc       600
aagcaaaact aagccttttg gtttgggtat tatgtttcgt tttgttattt       650
gtttgttttt gtggcttgtc ttatgtcgtg atagcacaag tgccagtcgg       700
attgctctgt attacagaat agtgttttta attcatcaat gttctagtta       750
atgtctacct cagcacctcc tcttagccta attttaggag gttgcccaat       800
tttgtttctt caattttact ggttactttt ttgtacaaat caatctcttt       850
ctctctttct ctcctcccca cctctcaccc ttgccctctc catctccctc       900
tcccgccctc ccctcctccc tctggctccc cgtctcattt ctgtccactc       950
cattctctct ccctctctcc tgcctcctgc tgcccctcc ccagcccact      1000 tccccgagtt gtgcttgccg ctccttatct gttctagttc cgaagcagtt      1050
tcactcgaag ttgtgcagtc ctggttgcag ctttccgcat ctgccttcgt      1100
ttcgtgtaga ttgacgcgtt tctttgtaat ttcagtgttt ctgacaagat      1150
ttaaaaaaaa aaaaggaaa aaaaaaaaaa aaaaaa                      1186

<210> SEQ ID NO 63
<211> LENGTH: 145
<212> TYPE: PRT
<213> ORGANISM: Homo sapiens

<400> SEQUENCE: 63
```

```
Met Ser Thr Ser Ala Pro Pro Leu Ser Leu Ile Leu Gly Gly Cys
 1               5                  10                  15

Pro Ile Leu Phe Leu Gln Phe Tyr Trp Leu Leu Phe Cys Thr Asn
                20                  25                  30

Gln Ser Leu Ser Leu Phe Leu Ser Ser Pro Leu Thr Leu Ala
                35                  40                  45

Leu Ser Ile Ser Leu Ser Arg Pro Pro Leu Leu Pro Leu Ala Pro
                50                  55                  60

Arg Leu Ile Ser Val His Ser Ile Leu Ser Pro Ser Leu Leu Pro
                65                  70                  75

Pro Ala Ala Pro Ser Pro Ala His Phe Pro Glu Leu Cys Leu Pro
                80                  85                  90

Leu Leu Ile Cys Ser Ser Ser Glu Ala Val Ser Leu Glu Val Val
                95                 100                 105

Gln Ser Trp Leu Gln Leu Ser Ala Ser Ala Phe Val Ser Cys Arg
               110                 115                 120

Leu Thr Arg Phe Phe Val Ile Ser Val Phe Leu Thr Arg Phe Lys
               125                 130                 135

Lys Lys Lys Arg Lys Lys Lys Lys Lys
               140                 145

<210> SEQ ID NO 64
<211> LENGTH: 1685
<212> TYPE: DNA
<213> ORGANISM: Homo sapiens

<400> SEQUENCE: 64
cccacgcgtc cgcacctcgg ccccgggctc cgaagcggct cggggggcgcc         50 ctttcggtca acatcgtagt ccaccccctc cccatcccca gccccgggg          100 attcaggctc gccagcgccc agccagggag ccggccggga agcgcgatgg         150 gggcccccagc cgcctcgctc ctgctcctgc tcctgctgtt cgcctgctgc        200
tgggcgcccg gcggggccaa cctctcccag gacgacagcc agccctggac         250
atctgatgaa acagtggtgg ctggtggcac cgtggtgctc aagtgccaag         300
tgaaagatca cgaggactca tccctgcaat ggtctaaccc tgctcagcag         350
actctctact ttggggagaa gagagccctt cgagataatc gaattcagct         400
ggttacctct acgccccacg agctcagcat cagcatcagc aatgtggccc         450
tggcagacga gggcgagtac acctgctcaa tcttcactat gcctgtgcga         500
actgccaagt ccctcgtcac tgtgctagga attccacaga agcccatcat         550
cactggttat aaatcttcat tacgggaaaa agacacagcc accctaaact         600
gtcagtcttc tgggagcaag cctgcagccc ggctcacctg agaaagggt          650 gaccaagaac tccacggaga accaacccgc atacaggaag atcccaatgg         700
taaaaccttc actgtcagca gctcggtgac attccaggtt acccgggagg         750
atgatggggc gagcatcgtg tgctctgtga accatgaatc tctaaaggga         800
gctgacagat ccacctctca acgcattgaa gttttataca caccaactgc         850
gatgattagg ccagaccctc cccatcctcg tgagggccag aagctgttgc         900
tacactgtga gggtcgcggc aatccagtcc ccagcagta cctatgggag          950 aaggagggca gtgtgccacc cctgaagatg acccaggaga gtgccctgat        1000
```

```
cttcccttc ctcaacaaga gtgacagtgg cacctacggc tgcacagcca    1050
ccagcaacat gggcagctac aaggcctact acaccctcaa tgttaatgac    1100
cccagtccgg tgcctcctc ctccagcacc taccacgcca tcatcggtgg    1150
gatcgtggct ttcattgtct tcctgctgct catcatgctc atcttccttg    1200
gccactactt gatccggcac aaaggaacct acctgacaca tgaggcaaaa    1250
ggctccgacg atgctccaga cgcggacacg gccatcatca atgcagaagg    1300
cgggcagtca ggaggggacg acaagaagga atatttcatc tagaggcgcc    1350
tgcccacttc ctgcgccccc caggggccct gtggggactg ctggggccgt    1400
caccaacccg gacttgtaca gagcaaccgc agggccgccc ctcccgcttg    1450
ctccccagcc cacccacccc cctgtacaga atgtctgctt tgggtgcggt    1500
tttgtactcg gtttggaatg gggagggagg agggcggggg gaggggaggg    1550
ttgccctcag ccctttccgt ggcttctctg catttgggtt attattattt    1600
ttgtaacaat cccaaatcaa atctgtctcc aggctggaga ggcaggagcc    1650
ctggggtgag aaaagcaaaa aacaaacaaa aaaca                    1685
```

<210> SEQ ID NO 65
<211> LENGTH: 398
<212> TYPE: PRT
<213> ORGANISM: Homo sapiens

<400> SEQUENCE: 65

```
Met Gly Ala Pro Ala Ser Leu Leu Leu Leu Leu Leu Leu Leu Phe
 1               5                  10                  15

Ala Cys Cys Trp Ala Pro Gly Gly Ala Asn Leu Ser Gln Asp Asp
                20                  25                  30

Ser Gln Pro Trp Thr Ser Asp Glu Thr Val Val Ala Gly Gly Thr
                35                  40                  45

Val Val Leu Lys Cys Gln Val Lys Asp His Glu Asp Ser Ser Leu
                50                  55                  60

Gln Trp Ser Asn Pro Ala Gln Gln Thr Leu Tyr Phe Gly Glu Lys
                65                  70                  75

Arg Ala Leu Arg Asp Asn Arg Ile Gln Leu Val Thr Ser Thr Pro
                80                  85                  90

His Glu Leu Ser Ile Ser Ile Ser Asn Val Ala Leu Ala Asp Glu
                95                 100                 105

Gly Glu Tyr Thr Cys Ser Ile Phe Thr Met Pro Val Arg Thr Ala
               110                 115                 120

Lys Ser Leu Val Thr Val Leu Gly Ile Pro Gln Lys Pro Ile Ile
               125                 130                 135

Thr Gly Tyr Lys Ser Ser Leu Arg Glu Lys Asp Thr Ala Thr Leu
               140                 145                 150

Asn Cys Gln Ser Ser Gly Ser Lys Pro Ala Ala Arg Leu Thr Trp
               155                 160                 165

Arg Lys Gly Asp Gln Glu Leu His Gly Glu Pro Thr Arg Ile Gln
               170                 175                 180

Glu Asp Pro Asn Gly Lys Thr Phe Thr Val Ser Ser Val Thr
               185                 190                 195

Phe Gln Val Thr Arg Glu Asp Asp Gly Ala Ser Ile Val Cys Ser
               200                 205                 210

Val Asn His Glu Ser Leu Lys Gly Ala Asp Arg Ser Thr Ser Gln
```

```
                        215                 220                 225
Arg Ile Glu Val Leu Tyr Thr Pro Thr Ala Met Ile Arg Pro Asp
                230                 235                 240

Pro Pro His Pro Arg Glu Gly Gln Lys Leu Leu His Cys Glu
            245                 250                 255

Gly Arg Gly Asn Pro Val Pro Gln Gln Tyr Leu Trp Glu Lys Glu
            260                 265                 270

Gly Ser Val Pro Pro Leu Lys Met Thr Gln Glu Ser Ala Leu Ile
            275                 280                 285

Phe Pro Phe Leu Asn Lys Ser Asp Ser Gly Thr Tyr Gly Cys Thr
            290                 295                 300

Ala Thr Ser Asn Met Gly Ser Tyr Lys Ala Tyr Tyr Thr Leu Asn
            305                 310                 315

Val Asn Asp Pro Ser Pro Val Pro Ser Ser Ser Thr Tyr His
            320                 325                 330

Ala Ile Ile Gly Gly Ile Val Ala Phe Ile Val Phe Leu Leu Leu
            335                 340                 345

Ile Met Leu Ile Phe Leu Gly His Tyr Leu Ile Arg His Lys Gly
            350                 355                 360

Thr Tyr Leu Thr His Glu Ala Lys Gly Ser Asp Asp Ala Pro Asp
            365                 370                 375

Ala Asp Thr Ala Ile Ile Asn Ala Glu Gly Gly Gln Ser Gly Gly
            380                 385                 390

Asp Asp Lys Lys Glu Tyr Phe Ile
            395

<210> SEQ ID NO 66
<211> LENGTH: 681
<212> TYPE: DNA
<213> ORGANISM: Homo sapiens

<400> SEQUENCE: 66
cttggatctg cctgccaggc catcctgggc gctgcaggaa gcaacatgac          50
ttaggtaact gcccagaggt gcaccagaca tgatgcagca gccgcgagtg         100
gagacagata ccatcggggc tggcgagggg ccacagcagg cagtgcctgg         150
tcagcctggg tcacgaggca tggctgggtg cgctggtggg tgagccacat         200
gcccccgagc tggatccagt ggtggagcac ctcgaactgg cggcaaccgc         250
tgcagcgcct gctgtggggt ctggagggga tactctacct gctgctggca         300
ctgatgttgt gccatgcact cttcaccact ggctcccacc tgctgagctc         350
cttgtggcct gtcgtggccg cggtgtggcg ccacctgcta ccggctctcc         400
tgctgctggt gctcagtgct ctgcctgccc tcctcttcac ggcctccttc         450
ctgctgctct tctccacact gctgagcctt gtgggcctcc tcacctccat         500
gactcaccca ggcgacactc aggatttgga tcaatagaag ggcaaccca          550 tcccactgcc tgtgtttgtt gagccctggc ctagggcctg agaccccacg         600
gggagaggga gggcaatggg atcagggctc cctgccttgg cagggcccag         650 accccctagtc cctaacaggt aggctggcct g                            681

<210> SEQ ID NO 67
<211> LENGTH: 112
<212> TYPE: PRT
<213> ORGANISM: Homo sapiens
```

<400> SEQUENCE: 67

Met Pro Pro Ser Trp Ile Gln Trp Trp Ser Thr Ser Asn Trp Arg
1               5                   10                  15

Gln Pro Leu Gln Arg Leu Leu Trp Gly Leu Glu Gly Ile Leu Tyr
                20                  25                  30

Leu Leu Leu Ala Leu Met Leu Cys His Ala Leu Phe Thr Thr Gly
                35                  40                  45

Ser His Leu Leu Ser Ser Leu Trp Pro Val Val Ala Ala Val Trp
                50                  55                  60

Arg His Leu Leu Pro Ala Leu Leu Leu Val Leu Ser Ala Leu
                65                  70                  75

Pro Ala Leu Leu Phe Thr Ala Ser Phe Leu Leu Leu Phe Ser Thr
                80                  85                  90

Leu Leu Ser Leu Val Gly Leu Leu Thr Ser Met Thr His Pro Gly
                95                  100                 105

Asp Thr Gln Asp Leu Asp Gln
                110

<210> SEQ ID NO 68
<211> LENGTH: 2600
<212> TYPE: DNA
<213> ORGANISM: Homo sapiens

<400> SEQUENCE: 68

| | |
|---|---:|
| acatgcgccc tgacagccca acaatggcgg cgcccgcgga gtcgctgagg | 50 |
| aggcggaaga ctgggtactc ggatccggag cctgagtcgc cgcccgcgcc | 100 |
| ggggcgtggc cccgcaggct ctccggccca tcttcacacg ggcaccttct | 150 |
| ggctgacccg gatcgtgctc ctgaaggccc tagccttcgt gtacttcgtg | 200 |
| gcattcctgg tggctttcca tcagaacaag cagctcatcg gtgacagggg | 250 |
| gctgcttccc tgcagagtgt tcctgaagga cttccagcag tacttccagg | 300 |
| acaggacaag ctgggaagtc ttcagctaca tgcccaccat cctctggctg | 350 |
| atggactggt cagacatgaa ctccaacctg gacttgctgg ctcttctcgg | 400 |
| actgggcatc tcgtctttcg tactgatcac gggttgcgcc aacatgcttc | 450 |
| tcatggctgc cctgtggggc tctacatgt ccctggttaa tgtgggccat | 500 |
| gtctggtact ctttcggatg ggagtcccag cttctggaga cgggattcct | 550 |
| ggggatcttc ctgtgccctc tgtggacgct gtcaaggctg ccccagcata | 600 |
| cccccacatc ccggattgtc ctgtggggct tccggtggct gatcttcagg | 650 |
| atcatgcttg gagcaggcct gatcaagatc cggggggacc ggtgctggcg | 700 |
| agacctcacc tgcatggact ccactatga cccagccg atgcccaatc | 750 |
| ctgtggcata ctacctgcac cactcaccct ggtggttcca tcgcttcgag | 800 |
| acgctcagca accacttcat cgagctcctg gtgcccttct tcctcttcct | 850 |
| cggccggcgg gcgtgcatca tccacggggt gctgcagatc ctgttccagg | 900 |
| ccgtcctcat cgtcagcggg aacctcagct tcctgaactg gctgactatg | 950 |
| gtgcccagcc tggcctgctt tgatgacgcc accctgggat tcttgttccc | 1000 |
| ctctgggcca gcagcctga aggaccgagt tctgcagatg cagagggaca | 1050 |
| tccgaggggc ccggcccgag cccagattcg gctccgtggt gcggcgtgca | 1100 |

-continued

| | |
|---|---|
| gccaacgtct cgctgggcgt cctgctggcc tggctcagcg tgcccgtggt | 1150 |
| cctcaacttg ctgagctcca ggcaggtcat gaacacccac ttcaactctc | 1200 |
| ttcacatcgt caacacttac ggggccttcg gaagcatcac caaggagcgg | 1250 |
| gcggaggtga tcctgcaggg cacagccagc tccaacgcca gcgcccccga | 1300 |
| tgccatgtgg gaggactacg agttcaagtg caagccaggt gaccccagca | 1350 |
| gacggccctg cctcatctcc ccgtaccact accgcctgga ctggctgatg | 1400 |
| tggttcgcgg ccttccagac ctacgagcac aacgactgga tcatccacct | 1450 |
| ggctggcaag ctcctggcca gcgacgccga ggccttgtcc ctgctggcac | 1500 |
| acaacccctt cgcgggcagg ccccgccca gtgggtccg aggagagcac | 1550 |
| tacaggtaca agttcagccg tcctggggc aggcacgccg ccgagggcaa | 1600 |
| gtggtgggtg cggaagagga tcggagccta cttccctccg ctcagcctgg | 1650 |
| aggagctgag gccctacttc agggaccgtg ggtggcctct gcccgggccc | 1700 |
| ctctagacgt gcaccagaaa taaaggcgaa gacccagccc ctcggcggct | 1750 |
| cagcaacgtt tgcccttccc tgcgcccagc ccaagctggg catcgccaag | 1800 |
| agagacgtgg agaggagagc ggtgggaccc agccccagc acgggggtcc | 1850 |
| agggtggggt ctgttgtcac atactgtggc ggctcccagg ccctgcccac | 1900 |
| ctggggcccc acatccaggc caaccttgt cccaggcgcc aggggctctg | 1950 |
| atctcccatc catcccaccc tcctcccaga ggcccagcct ggggctgtgc | 2000 |
| cgcccacagg agttgagaca atggcaatcc tgacaccttc ctccactaca | 2050 |
| gccctgacca tagacccagc caggtagctc ttggggtctc tagcgtccca | 2100 |
| gggcctggtt tctgttccct cttcaatggt gtgttcccag ccaggtcctg | 2150 |
| accctcagag ccaagtccct gtcacgtctg gggcagccaa accctcgccc | 2200 |
| cacagggacc tggacacgcc cggccaggat gtggggttgg atgggccatt | 2250 |
| ttctgtccta tccctcatct ccaccccgc cacagcctac acgcatccca | 2300 |
| cacatgcagg cacacacagc ctgtgcacac atgtgttctt ggcccggttt | 2350 |
| catcccccca tgactggtgt ctgtgaggtg cagatggaca cagcgcacac | 2400 |
| ccagaccctc caccaggctg tgacctcgct gcctctgagg ccttgacaag | 2450 |
| gcccctcaat cggaggacag ccggccgtgc acactttcat catcgtcgga | 2500 |
| caaacagcgt ctactgcaca tttttcttat tcctattctt gagccatagc | 2550 |
| tatggcatat tcttctacta ttcctattat accacttacc agcttactcg | 2600 |

<210> SEQ ID NO 69
<211> LENGTH: 567
<212> TYPE: PRT
<213> ORGANISM: Homo sapiens

<400> SEQUENCE: 69

Met Arg Pro Asp Ser Pro Thr Met Ala Ala Pro Ala Glu Ser Leu
1               5                   10                  15

Arg Arg Arg Lys Thr Gly Tyr Ser Asp Pro Glu Pro Glu Ser Pro
                20                  25                  30

Pro Ala Pro Gly Arg Gly Pro Ala Gly Ser Pro Ala His Leu His
                35                  40                  45

Thr Gly Thr Phe Trp Leu Thr Arg Ile Val Leu Leu Lys Ala Leu
                50                  55                  60

```
Ala Phe Val Tyr Phe Val Ala Phe Leu Val Ala Phe His Gln Asn
                 65                  70                  75

Lys Gln Leu Ile Gly Asp Arg Gly Leu Leu Pro Cys Arg Val Phe
                 80                  85                  90

Leu Lys Asp Phe Gln Gln Tyr Phe Gln Asp Arg Thr Ser Trp Glu
                 95                 100                 105

Val Phe Ser Tyr Met Pro Thr Ile Leu Trp Leu Met Asp Trp Ser
                110                 115                 120

Asp Met Asn Ser Asn Leu Asp Leu Leu Ala Leu Leu Gly Leu Gly
                125                 130                 135

Ile Ser Ser Phe Val Leu Ile Thr Gly Cys Ala Asn Met Leu Leu
                140                 145                 150

Met Ala Ala Leu Trp Gly Leu Tyr Met Ser Leu Val Asn Val Gly
                155                 160                 165

His Val Trp Tyr Ser Phe Gly Trp Glu Ser Gln Leu Leu Glu Thr
                170                 175                 180

Gly Phe Leu Gly Ile Phe Leu Cys Pro Leu Trp Thr Leu Ser Arg
                185                 190                 195

Leu Pro Gln His Thr Pro Thr Ser Arg Ile Val Leu Trp Gly Phe
                200                 205                 210

Arg Trp Leu Ile Phe Arg Ile Met Leu Gly Ala Gly Leu Ile Lys
                215                 220                 225

Ile Arg Gly Asp Arg Cys Trp Arg Asp Leu Thr Cys Met Asp Phe
                230                 235                 240

His Tyr Glu Thr Gln Pro Met Pro Asn Pro Val Ala Tyr Tyr Leu
                245                 250                 255

His His Ser Pro Trp Trp Phe His Arg Phe Glu Thr Leu Ser Asn
                260                 265                 270

His Phe Ile Glu Leu Leu Val Pro Phe Phe Leu Phe Leu Gly Arg
                275                 280                 285

Arg Ala Cys Ile Ile His Gly Val Leu Gln Ile Leu Phe Gln Ala
                290                 295                 300

Val Leu Ile Val Ser Gly Asn Leu Ser Phe Leu Asn Trp Leu Thr
                305                 310                 315

Met Val Pro Ser Leu Ala Cys Phe Asp Asp Ala Thr Leu Gly Phe
                320                 325                 330

Leu Phe Pro Ser Gly Pro Gly Ser Leu Lys Asp Arg Val Leu Gln
                335                 340                 345

Met Gln Arg Asp Ile Arg Gly Ala Arg Pro Glu Pro Arg Phe Gly
                350                 355                 360

Ser Val Val Arg Arg Ala Ala Asn Val Ser Leu Gly Val Leu Leu
                365                 370                 375

Ala Trp Leu Ser Val Pro Val Val Leu Asn Leu Leu Ser Ser Arg
                380                 385                 390

Gln Val Met Asn Thr His Phe Asn Ser Leu His Ile Val Asn Thr
                395                 400                 405

Tyr Gly Ala Phe Gly Ser Ile Thr Lys Glu Arg Ala Glu Val Ile
                410                 415                 420

Leu Gln Gly Thr Ala Ser Ser Asn Ala Ser Pro Asp Ala Met
                425                 430                 435

Trp Glu Asp Tyr Glu Phe Lys Cys Lys Pro Gly Asp Pro Ser Arg
                440                 445                 450
```

```
Arg Pro Cys Leu Ile Ser Pro Tyr His Tyr Arg Leu Asp Trp Leu
            455                 460                 465

Met Trp Phe Ala Ala Phe Gln Thr Tyr Glu His Asn Asp Trp Ile
            470                 475                 480

Ile His Leu Ala Gly Lys Leu Leu Ala Ser Asp Ala Glu Ala Leu
            485                 490                 495

Ser Leu Leu Ala His Asn Pro Phe Ala Gly Arg Pro Pro Pro Arg
            500                 505                 510

Trp Val Arg Gly Glu His Tyr Arg Tyr Lys Phe Ser Arg Pro Gly
            515                 520                 525

Gly Arg His Ala Ala Glu Gly Lys Trp Trp Val Arg Lys Arg Ile
            530                 535                 540

Gly Ala Tyr Phe Pro Pro Leu Ser Leu Glu Glu Leu Arg Pro Tyr
            545                 550                 555

Phe Arg Asp Arg Gly Trp Pro Leu Pro Gly Pro Leu
            560                 565

<210> SEQ ID NO 70
<211> LENGTH: 1900
<212> TYPE: DNA
<213> ORGANISM: Homo sapiens

<400> SEQUENCE: 70
```

| | | | | |
|---|---|---|---|---|
| ggcacgagga | gaagactttg | gtggggtagt | ctcggggcag | ctcagcggcc | 50 |
| cgctgtgccc | gtttctggcc | tcgctcgcag | cttgcacgtc | gagactcgta | 100 |
| ggccgcaccg | tagggcgagc | gtgcgggtcg | ccgccgcggc | cgcctcgggg | 150 |
| tctgggccca | gccgcagcct | cttctaccgc | ggccggttgg | gagtcgccgc | 200 |
| gagatgcagc | ctccgggccc | gcccccggcc | tatgccccca | ctaacgggga | 250 |
| cttcaccttt | gtctcctcag | cagacgcgga | agatctcagt | ggttcaatag | 300 |
| catccccaga | tgtcaaatta | aatcttggtg | gagattttat | caaagaatct | 350 |
| acagctacta | catttctgag | acaaagaggt | tatggctggc | ttctggaagt | 400 |
| tgaagatgat | gatcctgaag | ataacaagcc | actcttggaa | gaattggaca | 450 |
| ttgatctaaa | ggatatttac | tacaaaatcc | gatgtgtttt | gatgccaatg | 500 |
| ccatcacttg | gttttaatag | acaagtggtg | agagacaatc | ctgacttttg | 550 |
| gggtcctctg | gctgttgttc | ttttcttttc | catgatatca | ttatatggac | 600 |
| agtttagggt | ggtctcatgg | attataacca | tttggatatt | tggttcacta | 650 |
| acaattttct | tactggccag | agttcttggt | ggagaagttg | catatggcca | 700 |
| agtccttgga | gttataggat | attcattact | tcctctcatt | gtaatagccc | 750 |
| ctgtactttt | ggtggttgga | tcatttgaag | tggtgtctac | acttataaaa | 800 |
| ctgtttggtg | tgttttgggc | tgcctacagt | gctgcttcat | tgttagtggg | 850 |
| tgaagaattc | aagaccaaaa | agcctcttct | gatttatcca | atcttttat | 900 |
| tatacattta | ttttttgtcg | ttatatactg | gtgtgtgatc | caagttatac | 950 |
| atgaatagaa | aaagatggtg | ttaaatttgt | gtgtaggctg | ggaattcttg | 1000 |
| ctgaaggaat | tggagaaaac | tgttgctgc | aaaatttac | atgttccaga | 1050 |
| tggaaaggga | agtctaagcg | cttttttaaaa | caatttttt | ttgtatttaa | 1100 |
| ttaagcaatt | gcagttatct | gggatttttg | ggtcagaatt | ttaaattctg | 1150 |
| tttgattctc | catattccag | tgaataaaat | acaaaagcat | tgtgttttta | 1200 |

```
agattgtgtc gatattcacc taaaaacttg tgccaaaagc acctggattg      1250
gtaattatat ttcacttaaa gggtaaattt gacaatatct tgataatcaa      1300
aagtgcaatt ttttcttca aaatgttttc tccagcatca cagatcctgc       1350
agatatatat ttatatttat acatatatat ttatgaaata attcttactc      1400
acaaaatata tttctgataa acattaagat attaaatctg atgcacaaac      1450
tttaatttgg ccattaatct ttttattta aaaatttaaa tttgttttta       1500
aaattgtata tagttttaa aatctcacac atgcttcgat acttccttgt       1550
taagaattct taataactac taaaactgat ttttaatagt tgctgatata      1600
tatttggttt gtttgggtat acttttcaaa accatttttg aatgtccaaa      1650
catctgattt aaagtttctg tttatctttc tgaccaaagg agcaagaggt      1700
ataatggata tggcattcat taaaatcttt actatgtaca aaaacagtaa      1750
tatttacagc atcagtaaat atttttaagt ggtacttcta aatcataaaa      1800 gttgggaaa gagacccttta aaatcttgtg gtgttgaaca atgttatatg      1850
aagtagaaaa aataaaatac ttcccagttg tgaaaaaaaa aaaaaaaaaa      1900
```

<210> SEQ ID NO 71
<211> LENGTH: 240
<212> TYPE: PRT
<213> ORGANISM: Homo sapiens

<400> SEQUENCE: 71

```
Met Gln Pro Pro Gly Pro Pro Ala Tyr Ala Pro Thr Asn Gly
  1               5                  10                  15

Asp Phe Thr Phe Val Ser Ser Ala Asp Ala Glu Asp Leu Ser Gly
                 20                  25                  30

Ser Ile Ala Ser Pro Asp Val Lys Leu Asn Leu Gly Gly Asp Phe
             35                  40                  45

Ile Lys Glu Ser Thr Ala Thr Thr Phe Leu Arg Gln Arg Gly Tyr
         50                  55                  60

Gly Trp Leu Leu Glu Val Glu Asp Asp Pro Glu Asp Asn Lys
     65                  70                  75

Pro Leu Leu Glu Glu Leu Asp Ile Asp Leu Lys Asp Ile Tyr Tyr
             80                  85                  90

Lys Ile Arg Cys Val Leu Met Pro Met Pro Ser Leu Gly Phe Asn
         95                 100                 105

Arg Gln Val Val Arg Asp Asn Pro Asp Phe Trp Gly Pro Leu Ala
            110                 115                 120

Val Val Leu Phe Phe Ser Met Ile Ser Leu Tyr Gly Gln Phe Arg
            125                 130                 135

Val Val Ser Trp Ile Ile Thr Ile Trp Ile Phe Gly Ser Leu Thr
            140                 145                 150

Ile Phe Leu Leu Ala Arg Val Leu Gly Gly Glu Val Ala Tyr Gly
            155                 160                 165

Gln Val Leu Gly Val Ile Gly Tyr Ser Leu Leu Pro Leu Ile Val
            170                 175                 180

Ile Ala Pro Val Leu Leu Val Gly Ser Phe Glu Val Val Ser
            185                 190                 195

Thr Leu Ile Lys Leu Phe Gly Val Phe Trp Ala Ala Tyr Ser Ala
            200                 205                 210
```

```
Ala Ser Leu Leu Val Gly Glu Glu Phe Lys Thr Lys Lys Pro Leu
            215                 220                 225

Leu Ile Tyr Pro Ile Phe Leu Leu Tyr Ile Tyr Phe Leu Ser Leu
            230                 235                 240

<210> SEQ ID NO 72
<211> LENGTH: 21
<212> TYPE: DNA
<213> ORGANISM: Homo sapiens

<400> SEQUENCE: 72
gggcaccaag aaccgaatca t                                      21

<210> SEQ ID NO 73
<211> LENGTH: 21
<212> TYPE: DNA
<213> ORGANISM: Homo sapiens

<400> SEQUENCE: 73
cctagaggca gcgattaagg g                                      21

<210> SEQ ID NO 74
<211> LENGTH: 21
<212> TYPE: DNA
<213> ORGANISM: Homo sapiens

<400> SEQUENCE: 74
tcagcacgtg gattcgagtc a                                      21

<210> SEQ ID NO 75
<211> LENGTH: 18
<212> TYPE: DNA
<213> ORGANISM: Homo sapiens

<400> SEQUENCE: 75
gtgaggacgg ggcgagac                                          18
```

COMPOSITIONS AND METHODS FOR THE TREATMENT OF TUMOR OF HEMATOPOIETIC ORIGIN

RELATED APPLICATIONS

The present application is a continuation of, and claims priority under 35 USC §120 to U.S. application Ser. No. 12/756,149, filed Apr. 7, 2010, now abandoned which is a continuation of, and claims priority under 35 USC §120 to U.S. application Ser. No. 12/079,893, filed Mar. 27, 2008, which is a continuation of, and claims priority under 35 U.S.C. §120 to U.S. application Ser. No. 10/989,826, filed Nov. 16, 2004, now abandoned which is a continuation-in-part of, and claims priority under 35 USC §120 to both, PCT Application PCT/US03/36298, filed Nov. 13, 2003 and also to U.S. application Ser. No. 10/712,892, filed Nov. 12, 2003, now abandoned both of which claim priority under 35 USC §119 to U.S. Provisional Application 60/405,645, filed Aug. 21, 2002 and also to 60/426,847, filed Nov. 15, 2002, and wherein PCT Application PCT US03/36298, filed Nov. 13, 2003 and U.S. application Ser. No. 10/712,892, filed Nov. 13, 2003 are also both continuations-in-part of, and claim priority under 35 USC §120 to both, PCT Application PCT/US03/25892, filed Aug. 19, 2003 and also to U.S. application Ser. No. 10/643,795, filed Aug. 19, 2003, both of which claim priority under 35 USC §119 to U.S. Provisional Application 60/404,809, filed Aug. 19, 2002, and also to 60/405,645, filed Aug. 21, 2002, and wherein PCT Application PCT/US03/25892, filed Aug. 19, 2003 and U.S. application Ser. No. 10/643,795, filed Aug. 19, 2003, both of which are also continuations-in-part of, and claim priority under 35 USC §120 to both PCT Application PCT/US03/11148, filed Apr. 10, 2003 and also to U.S. application Ser. No. 10/411,010, filed Apr. 10, 2003, both of which claim priority under 35 USC §119 to U.S. Provisional Applications, 60/378,885, filed May 8, 2002, and also to 60/404,809, filed Aug. 19, 2002, and wherein PCT Application PCT/US03/11148, filed Apr. 10, 2003 and U.S. application Ser. No. 10/411,010, filed Apr. 10, 2003, both of which are also continuations-in-part of, and claim priority under 35 USC §120 to both, PCT Application PCT/US02/28859, filed Sep. 11, 2002 and also to U.S. application Ser. No. 10/241,220, filed Sep. 11, 2002, both of which claim priority under 35 USC §119 to U.S. Provisional Application 60/339,227, filed Oct. 19, 2001, and wherein PCT Application PCT/US02/28859, filed Sep. 11, 2002 and U.S. application Ser. No. 10/241,220, filed Sep. 11, 2002, both of which are also continuations-in-part of, and claim priority under 35 USC §120 to both, PCT/US02/12206, filed Apr. 17, 2002 and also to U.S. application Ser. No. 10/125,166, filed Apr. 17, 2002, and wherein the present application also claims priority under 35 USC §119 to U.S. Provisional Application 60/520,842, filed Nov. 17, 2003, and also to U.S. Provisional Application 60/532,426, filed Dec. 24, 2003, and also to U.S. Provisional Application 60/576,517, filed Jun. 1, 2004, and also to U.S. Provisional Application 60/616,098, filed Oct. 5, 2004.

FIELD OF THE INVENTION

The present invention is directed to compositions of matter useful for the treatment of hematopoietic tumor in mammals and to methods of using those compositions of matter for the same.

BACKGROUND OF THE INVENTION

Malignant tumors (cancers) are the second leading cause of death in the United States, after heart disease (Boring et al., CA Cancel J. Clin. 43:7 (1993)). Cancer is characterized by the increase in the number of abnormal, or neoplastic, cells derived from a normal tissue which proliferate to form a tumor mass, the invasion of adjacent tissues by these neoplastic tumor cells, and the generation of malignant cells which eventually spread via the blood or lymphatic system to regional lymph nodes and to distant sites via a process called metastasis. In a cancerous state, a cell proliferates under conditions in which normal cells would not grow. Cancer manifests itself in a wide variety of forms, characterized by different degrees of invasiveness and aggressiveness.

Cancers which involve cells generated during hematopoiesis, a process by which cellular elements of blood, such as lymphocytes, leukocytes, platelets, erythrocytes and natural killer cells are generated are referred to as hematopoietic cancers. Lymphocytes which can be found in blood and lymphatic tissue and are critical for immune response are categorized into two main classes of lymphocytes: B lymphocytes (B cells) and T lymphocytes (T cells), which mediate humoral and cell mediated immunity, respectively.

B cells mature within the bone marrow and leave the marrow expressing an antigen-binding antibody on their cell surface. When a naive B cell first encounters the antigen for which its membrane-bound antibody is specific, the cell begins to divide rapidly and its progeny differentiate into memory B cells and effector cells called "plasma cells". Memory B cells have a longer life span and continue to express membrane-bound antibody with the same specificity as the original parent cell. Plasma cells do not produce membrane-bound antibody but instead produce the antibody in a form that can be secreted. Secreted antibodies are the major effector molecule of humoral immunity.

T cells mature within the thymus which provides an environment for the proliferation and differentiation of immature T cells. During T cell maturation, the T cells undergo the gene rearrangements that produce the T-cell receptor and the positive and negative selection which helps determine the cell-surface phenotype of the mature T cell. Characteristic cell surface markers of mature T cells are the CD3:T-cell receptor complex and one of the coreceptors, CD4 or CD8.

In attempts to discover effective cellular targets for cancer therapy, researchers have sought to identify transmembrane or otherwise membrane-associated polypeptides that are specifically expressed on the surface of one or more particular type(s) of cancer cell as compared to on one or more normal non-cancerous cell(s). Often, such membrane-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies. In this regard, it is noted that antibody-based therapy has proved very effective in the treatment of certain cancers. For example, HERCEPTIN® and RITUXAN® (both from Genentech Inc., South San Francisco, Calif.) are antibodies that have been used successfully to treat breast cancer and non-Hodgkin's lymphoma, respectively. More specifically, HERCEPTIN® is a recombinant DNA-derived humanized monoclonal antibody that selectively binds to the extracellular domain of the human epidermal growth factor receptor 2 (HER2) proto-oncogene. HER2 protein overexpression is observed in 25-30% of primary breast cancers. RITUXAN® is a genetically engineered chimeric murine/human monoclonal antibody directed against the CD20 antigen found on the surface of normal and malignant B lymphocytes. Both these antibodies are recombinantly produced in CHO cells.

In other attempts to discover effective cellular targets for cancer therapy, researchers have sought to identify (1) non-membrane-associated polypeptides that are specifically produced by one or more particular type(s) of cancer cell(s) as compared to by one or more particular type(s) of non-cancerous normal cell(s), (2) polypeptides that are produced by cancer cells at an expression level that is significantly higher than that of one or more normal non-cancerous cell(s), or (3) polypeptides whose expression is specifically limited to only a single (or very limited number of different) tissue type(s) in both the cancerous and non-cancerous state (e.g., normal prostate and prostate tumor tissue). Such polypeptides may remain intracellularly located or may be secreted by the cancer cell. Moreover, such polypeptides may be expressed not by the cancer cell itself, but rather by cells which produce and/or secrete polypeptides having a potentiating or growth-enhancing effect on cancer cells. Such secreted polypeptides are often proteins that provide cancer cells with a growth advantage over normal cells and include such things as, for example, angiogenic factors, cellular adhesion factors, growth factors, and the like. Identification of antagonists of such non-membrane associated polypeptides would be expected to serve as effective therapeutic agents for the treatment of such cancers. Furthermore, identification of the expression pattern of such polypeptides would be useful for the diagnosis of particular cancers in mammals.

Despite the above identified advances in mammalian cancer therapy, there is a great need for additional therapeutic agents capable of detecting the presence of tumor in a mammal and for effectively inhibiting neoplastic cell growth, respectively. Accordingly, it is an objective of the present invention to identify polypeptides, cell membrane-associated, secreted or intracellular polypeptides whose expression is specifically limited to only a single (or very limited number of different) tissue type(s), hematopoietic tissues, in both a cancerous and non-cancerous state, and to use those polypeptides, and their encoding nucleic acids, to produce compositions of matter useful in the therapeutic treatment detection of hematopoietic cancer in mammals.

SUMMARY OF THE INVENTION

A. Embodiments

In the present specification, Applicants describe for the first time the identification of various cellular polypeptides (and their encoding nucleic acids or fragments thereof) which are specifically expressed by both tumor and normal cells of a specific cell type, for example cells generated during hematopoiesis, i.e. lymphocytes, leukocytes, erythrocytes and platelets. All of the above polypeptides are herein referred to as Tumor Antigens of Hematopoietic Origin polypeptides ("TAHO" polypeptides) and are expected to serve as effective targets for cancer therapy in mammals.

Accordingly, in one embodiment of the present invention, the invention provides an isolated nucleic acid molecule having a nucleotide sequence that encodes a tumor antigen of hematopoietic origin polypeptide (a "TAHO" polypeptide) or fragment thereof.

In certain aspects, the isolated nucleic acid molecule comprises a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% nucleic acid sequence identity, to (a) a DNA molecule encoding a full-length TAHO polypeptide having an amino acid sequence as disclosed herein, a TAHO polypeptide amino acid sequence lacking the signal peptide as disclosed herein, an extracellular domain of a transmembrane TAHO polypeptide, with or without the signal peptide, as disclosed herein or any other specifically defined fragment of a full-length TAHO polypeptide amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% nucleic acid sequence identity, to (a) a DNA molecule comprising the coding sequence of a full-length TAHO polypeptide cDNA as disclosed herein, the coding sequence of a TAHO polypeptide lacking the signal peptide as disclosed herein, the coding sequence of an extracellular domain of a transmembrane TAHO polypeptide, with or without the signal peptide, as disclosed herein or the coding sequence of any other specifically defined fragment of the full-length TAHO polypeptide amino acid sequence as disclosed herein, or (b) the complement of the DNA molecule of (a).

In further aspects, the invention concerns an isolated nucleic acid molecule comprising a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% nucleic acid sequence identity, to (a) a DNA molecule that encodes the same mature polypeptide encoded by the full-length coding region of any of the human protein cDNAs deposited with the ATCC as disclosed herein, or (b) the complement of the DNA molecule of (a).

Another aspect of the invention provides an isolated nucleic acid molecule comprising a nucleotide sequence encoding a TAHO polypeptide which is either transmembrane domain-deleted or transmembrane domain-inactivated, or is complementary to such encoding nucleotide sequence, wherein the transmembrane domain(s) of such polypeptide(s) are disclosed herein. Therefore, soluble extracellular domains of the herein described TAHO polypeptides are contemplated.

In other aspects, the present invention is directed to isolated nucleic acid molecules which hybridize to (a) a nucleotide sequence encoding a TAHO polypeptide having a full-length amino acid sequence as disclosed herein, a TAHO polypeptide amino acid sequence lacking the signal peptide as disclosed herein, an extracellular domain of a transmembrane TAHO polypeptide, with or without the signal peptide, as disclosed herein or any other specifically defined fragment of a full-length TAHO polypeptide amino acid sequence as disclosed herein, or (b) the complement of the nucleotide sequence of (a). In this regard, an embodiment of the present invention is directed to fragments of a full-length TAHO polypeptide coding sequence, or the complement thereof, as disclosed herein, that may find use as, for example, hybridization probes useful as, for example, detection probes, antisense oligonucleotide probes, or for encoding fragments of a full-length TAHO polypeptide that may optionally encode a polypeptide comprising a binding site for an anti-TAHO polypeptide antibody, a TAHO binding oligopeptide or other small organic molecule that binds to a TAHO polypeptide. Such nucleic acid fragments are usually at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length. It is noted that novel fragments of a TAHO polypeptide-encoding nucleotide sequence may be determined in a routine manner by aligning the TAHO polypeptide-encoding nucleotide sequence with other known nucleotide sequences using any of a number of well known sequence alignment programs and determining which TAHO polypeptide-encoding nucleotide sequence fragment(s) are novel. All of such novel fragments of TAHO polypeptide-encoding nucleotide sequences are contemplated herein. Also contemplated are the TAHO polypeptide fragments encoded by these nucleotide molecule fragments, preferably those TAHO polypeptide fragments that comprise a binding site for an anti-TAHO antibody, a TAHO binding oligopeptide or other small organic molecule that binds to a TAHO polypeptide.

In another embodiment, the invention provides isolated TAHO polypeptides encoded by any of the isolated nucleic acid sequences hereinabove identified.

In a certain aspect, the invention concerns an isolated TAHO polypeptide, comprising an amino acid sequence having at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% amino acid sequence identity, to a TAHO polypeptide having a full-length amino acid sequence as disclosed herein, a TAHO polypeptide amino acid sequence lacking the signal peptide as disclosed herein, an extracellular domain of a transmembrane TAHO polypeptide protein, with or without the signal peptide, as disclosed herein, an amino acid sequence encoded by any of the nucleic acid sequences disclosed herein or any other specifically defined fragment of a full-length TAHO polypeptide amino acid sequence as disclosed herein.

In a further aspect, the invention concerns an isolated TAHO polypeptide comprising an amino acid sequence having at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to an amino acid sequence encoded by any of the human protein cDNAs deposited with the ATCC as disclosed herein.

In a specific aspect, the invention provides an isolated TAHO polypeptide without the N-terminal signal sequence and/or without the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the TAHO polypeptide and recovering the TAHO polypeptide from the cell culture.

Another aspect of the invention provides an isolated TAHO polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the TAHO polypeptide and recovering the TAHO polypeptide from the cell culture.

In other embodiments of the present invention, the invention provides vectors comprising DNA encoding any of the herein described polypeptides. Host cells comprising any such vector are also provided. By way of example, the host cells may be CHO cells, *E. coli* cells, or yeast cells. A process for producing any of the herein described polypeptides is further provided and comprises culturing host cells under conditions suitable for expression of the desired polypeptide and recovering the desired polypeptide from the cell culture.

In other embodiments, the invention provides isolated chimeric polypeptides comprising any of the herein described TAHO polypeptides fused to a heterologous (non-TAHO) polypeptide. Example of such chimeric molecules comprise any of the herein described TAHO polypeptides fused to a heterologous polypeptide such as, for example, an epitope tag sequence or a Fc region of an immunoglobulin.

In another embodiment, the invention provides an antibody which binds, preferably specifically, to any of the above or below described polypeptides. Optionally, the antibody is a monoclonal antibody, antibody fragment, chimeric antibody, humanized antibody, single-chain antibody or antibody that competitively inhibits the binding of an anti-TAHO polypeptide antibody to its respective antigenic epitope. Antibodies of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies of the present invention may optionally be produced in CHO cells or bacterial cells and preferably induce death of a cell to which they bind. For detection purposes, the antibodies of the present invention may be detectably labeled, attached to a solid support, or the like.

In other embodiments of the present invention, the invention provides vectors comprising DNA encoding any of the herein described antibodies. Host cell comprising any such vector are also provided. By way of example, the host cells may be CHO cells, *E. coli* cells, or yeast cells. A process for producing any of the herein described antibodies is further provided and comprises culturing host cells under conditions suitable for expression of the desired antibody and recovering the desired antibody from the cell culture.

In another embodiment, the invention provides oligopeptides ("TAHO binding oligopeptides") which bind, preferably specifically, to any of the above or below described TAHO polypeptides. Optionally, the TAHO binding oligopeptides of the present invention may be conjugated to a growth inhibitory agent or cytotoxic agent such as a toxin, including, for example, a maytansinoid or calicheamicin, an antibiotic, a radioactive isotope, a nucleolytic enzyme, or the like. The TAHO binding oligopeptides of the present invention may optionally be produced in CHO cells or bacterial cells and preferably induce death of a cell to which they bind. For detection purposes, the TAHO binding oligopeptides of the present invention may be detectably labeled, attached to a solid support, or the like.

In other embodiments of the present invention, the invention provides vectors comprising DNA encoding any of the herein described TAHO binding oligopeptides. Host cell comprising any such vector are also provided. By way of example, the host cells may be CHO cells, *E. coli* cells, or yeast cells. A process for producing any of the herein described TAHO binding oligopeptides is further provided and comprises culturing host cells under conditions suitable for expression of the desired oligopeptide and recovering the desired oligopeptide from the cell culture.

In another embodiment, the invention provides small organic molecules ("TAHO binding organic molecules") which bind, preferably specifically, to any of the above or below described TAHO polypeptides. Optionally, the TAHO binding organic molecules of the present invention may be conjugated to a growth inhibitory agent or cytotoxic agent such as a toxin, including, for example, a maytansinoid or calicheamicin, an antibiotic, a radioactive isotope, a nucleolytic enzyme, or the like. The TAHO binding organic molecules of the present invention preferably induce death of a cell to which they bind. For detection purposes, the TAHO binding organic molecules of the present invention may be detectably labeled, attached to a solid support, or the like.

In a still further embodiment, the invention concerns a composition of matter comprising a TAHO polypeptide as described herein, a chimeric TAHO polypeptide as described herein, an anti-TAHO antibody as described herein, a TAHO binding oligopeptide as described herein, or a TAHO binding organic molecule as described herein, in combination with a carrier. Optionally, the carrier is a pharmaceutically acceptable carrier.

In yet another embodiment, the invention concerns an article of manufacture comprising a container and a composition of matter contained within the container, wherein the composition of matter may comprise a TAHO polypeptide as described herein, a chimeric TAHO polypeptide as described herein, an anti-TAHO antibody as described herein, a TAHO binding oligopeptide as described herein, or a TAHO binding organic molecule as described herein. The article may further optionally comprise a label affixed to the container, or a package insert included with the container, that refers to the use of the composition of matter for the therapeutic treatment.

Another embodiment of the present invention is directed to the use of a TAHO polypeptide as described herein, a chimeric TAHO polypeptide as described herein, an anti-TAHO polypeptide antibody as described herein, a TAHO binding oligopeptide as described herein, or a TAHO binding organic molecule as described herein, for the preparation of a medicament useful in the treatment of a condition which is responsive to the TAHO polypeptide, chimeric TAHO polypeptide, anti-TAHO polypeptide antibody, TAHO binding oligopeptide, or TAHO binding organic molecule.

B. Further Additional Embodiments

In yet further embodiments, the invention is directed to the following set of potential claims for this application:
1. Isolated nucleic acid having a nucleotide sequence that has at least 80% nucleic acid sequence identity to:
(a) a DNA molecule encoding the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71);

(b) a DNA molecule encoding the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26); FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(c) a DNA molecule encoding an extracellular domain of the polypeptide having the amino acid selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), with its associated signal peptide;

(d) a DNA molecule encoding an extracellular domain of the polypeptide having the amino acid selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(e) the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70);

(f) the full-length coding region of the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70); or (g) the complement of (a), (b), (c), (d), (e) or (f).

2. Isolated nucleic acid having:

(a) a nucleotide sequence that encodes the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71);

(b) a nucleotide sequence that encodes the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(c) a nucleotide sequence that encodes an extracellular domain of the polypeptide having the amino acid selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), with its associated signal peptide;

(d) a nucleotide sequence that encodes an extracellular domain of the polypeptide having the amino acid selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(e) the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70);

(f) the full-length coding region of the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41

(SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70); or (g) the complement of (a), (b), (c), (d), (e) or (f).

3. Isolated nucleic acid that hybridizes to:

(a) a nucleic acid that encodes the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71);

(b) a nucleic acid that encodes the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(c) a nucleic acid that encodes an extracellular domain of the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), with its associated signal peptide;

(d) a nucleic acid that encodes an extracellular domain of the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(e) the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70);

(f) the full-length coding region of the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70); or (g) the complement of (a), (b), (c), (d), (e) or (f).

4. The nucleic acid of Claim 3, wherein the hybridization occurs under stringent conditions.

5. The nucleic acid of Claim 3 which is at least about 5 nucleotides in length.

6. An expression vector comprising the nucleic acid of Claim 1, 2 or 3.

7. The expression vector of Claim 6, wherein said nucleic acid is operably linked to control sequences recognized by a host cell transformed with the vector.

8. A host cell comprising the expression vector of Claim 7.

9. The host cell of Claim 8 which is a CHO cell, an *E. coli* cell or a yeast cell.

10. A process for producing a polypeptide comprising culturing the host cell of Claim 8 under conditions suitable for expression of said polypeptide and recovering said polypeptide from the cell culture.

11. An isolated polypeptide having at least 80% amino acid sequence identity to:

(a) the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 5), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71);

(b) the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(c) an extracellular domain of the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), with its associated signal peptide;

(d) an extracellular domain of the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44) and FIG. 46 (SEQ ID NO: 46), lacking its associated signal peptide;

(e) a polypeptide encoded by the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70); or (f) a polypeptide encoded by the full-length coding region of the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70).

12. An isolated polypeptide having:

(a) the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71);

(b) the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide sequence;

(c) an amino acid sequence of an extracellular domain of the polypeptide selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44, FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), with its associated signal peptide sequence;

(d) an amino acid sequence of an extracellular domain of the polypeptide selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44, FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide sequence;

(e) an amino acid sequence encoded by the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70); or (f) an amino acid sequence encoded by the full-length coding region of the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70).

13. A chimeric polypeptide comprising the polypeptide of Claim 11 or 12 fused to a heterologous polypeptide.

14. The chimeric polypeptide of Claim 13, wherein said heterologous polypeptide is an epitope tag sequence or an Fc region of an immunoglobulin.

15. An isolated antibody that binds to a polypeptide having at least 80% amino acid sequence identity to:

(a) the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71);

(b) the polypeptide selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(c) an extracellular domain of the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), with its associated signal peptide;

(d) an extracellular domain of the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44, FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(e) a polypeptide encoded by the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70); or (f) a polypeptide encoded by the full-length coding region of the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45). FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70).

16. An isolated antibody that binds to a polypeptide having:

(a) the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71);

(b) the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide sequence;

(c) an amino acid sequence of an extracellular domain of the polypeptide selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), with its associated signal peptide sequence;

(d) an amino acid sequence of an extracellular domain of the polypeptide selected from the group consisting of the amino acid sequence shown in FIG. 2 (SEQ ID NO: 2), FIG.

4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53). FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide sequence;

(e) an amino acid sequence encoded by the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 1 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70); or (f) an amino acid sequence encoded by the full-length coding region of the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70).

17. The antibody of Claim 15 or 16 which is a monoclonal antibody.

18. The antibody of Claim 15 or 16 which is an antibody fragment.

19. The antibody of Claim 15 or 16 which is a chimeric or a humanized antibody.

20. The antibody of Claim 15 or 16 which is conjugated to a growth inhibitory agent.

21. The antibody of Claim 15 or 16 which is conjugated to a cytotoxic agent.

22. The antibody of Claim 21, wherein the cytotoxic agent is selected from the group consisting of toxins, antibiotics, radioactive isotopes and nucleolytic enzymes.

23. The antibody of Claim 21, wherein the cytotoxic agent is a toxin.

24. The antibody of Claim 23, wherein the toxin is selected from the group consisting of maytansinoid and calicheamicin.

25. The antibody of Claim 23, wherein the toxin is a maytansinoid.

26. The antibody of Claim 15 or 16 which is produced in bacteria.

27. The antibody of Claim 15 or 16 which is produced in CHO cells.

28. The antibody of Claim 15 or 16 which induces death of a cell to which it binds.

29. The antibody of Claim 15 or 16 which is detectably labeled.

30. An isolated nucleic acid having a nucleotide sequence that encodes the antibody of Claim 15 or 16.

31. An expression vector comprising the nucleic acid of Claim 30 operably linked to control sequences recognized by a host cell transformed with the vector.

32. A host cell comprising the expression vector of Claim 31.

33. The host cell of Claim 32 which is a CHO cell, an *E. coli* cell or a yeast cell.

34. A process for producing an antibody comprising culturing the host cell of Claim 32 under conditions suitable for expression of said antibody and recovering said antibody from the cell culture.

35. An isolated oligopeptide that binds to a polypeptide having at least 80% amino acid sequence identity to:

(a) the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71);

(b) the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(c) an extracellular domain of the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), with its associated signal peptide;

(d) an extracellular domain of the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44, FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(e) a polypeptide encoded by the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70); or (f) a polypeptide encoded by the full-length coding region of the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70).

36. An isolated oligopeptide that binds to a polypeptide having:

(a) the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71);

(b) the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide sequence;

(c) an amino acid sequence of an extracellular domain of the polypeptide selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), with its associated signal peptide sequence;

(d) an amino acid sequence of an extracellular domain of the polypeptide selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide sequence;

(e) an amino acid sequence encoded by the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70); or (f) an amino acid sequence encoded by the full-length coding region of the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70).

37. The oligopeptide of Claim 35 or 36 which is conjugated to a growth inhibitory agent.

38. The oligopeptide of Claim 35 or 36 which is conjugated to a cytotoxic agent.

39. The oligopeptide of Claim 38, wherein the cytotoxic agent is selected from the group consisting of toxins, antibiotics, radioactive isotopes and nucleolytic enzymes.

40. The oligopeptide of Claim 38, wherein the cytotoxic agent is a toxin.

41. The oligopeptide of Claim 40, wherein the toxin is selected from the group consisting of maytansinoid and calicheamicin.

42. The oligopeptide of Claim 40, wherein the toxin is a maytansinoid.

43. The oligopeptide of Claim 35 or 36 which induces death of a cell to which it binds.

44. The oligopeptide of Claim 35 or 36 which is detectably labeled.

45. A TAHO binding organic molecule that binds to a polypeptide having at least 80% amino acid sequence identity to:

(a) the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71);

(b) the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(c) an extracellular domain of the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), with its associated signal peptide;

(d) an extracellular domain of the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO:

12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(e) a polypeptide encoded by the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70); or (f) a polypeptide encoded by the full-length coding region of the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70).

46. The organic molecule of Claim 45 that binds to a polypeptide having:

(a) the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71);

(b) the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide sequence;

(c) an amino acid sequence of an extracellular domain of the polypeptide selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), with its associated signal peptide sequence;

(d) an amino acid sequence of an extracellular domain of the polypeptide selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44, FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide sequence;

(e) an amino acid sequence encoded by the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70); or (f) an amino acid sequence encoded by the full-length coding region of the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70).

47. The organic molecule of Claim 45 or 46 which is conjugated to a growth inhibitory agent.

48. The organic molecule of Claim 45 or 46 which is conjugated to a cytotoxic agent.

49. The organic molecule of Claim 48, wherein the cytotoxic agent is selected from the group consisting of toxins, antibiotics, radioactive isotopes and nucleolytic enzymes.

50. The organic molecule of Claim 48, wherein the cytotoxic agent is a toxin.

51. The organic molecule of Claim 50, wherein the toxin is selected from the group consisting of maytansinoid and calicheamicin.

52. The organic molecule of Claim 50, wherein the toxin is a maytansinoid.

53. The organic molecule of Claim 45 or 46 which induces death of a cell to which it binds.

54. The organic molecule of Claim 45 or 4 which is detectably labeled.

55. A composition of matter comprising:
    (a) the polypeptide of Claim 11;
    (b) the polypeptide of Claim 12;
    (c) the antibody of Claim 15;
    (d) the antibody of Claim 16;
    (e) the oligopeptide of Claim 35;
    (f) the oligopeptide of Claim 36;
    (g) the TAHO binding organic molecule of Claim 45; or
    (h) the TAHO binding organic molecule of Claim 46; in combination with a carrier.

56. The composition of matter of Claim 55, wherein said carrier is a pharmaceutically acceptable carrier.

57. An article of manufacture comprising:
    (a) a container; and
    (b) the composition of matter of Claim 55 contained within said container.

58. The article of manufacture of Claim 57 further comprising a label affixed to said container, or a package insert included with said container, referring to the use of said composition of matter for the therapeutic treatment of or the diagnostic detection of a cancer.

59. A method of inhibiting the growth of a cell that expresses a protein having at least 80% amino acid sequence identity to:
    (a) the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71);

(b) the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(c) an extracellular domain of the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), with its associated signal peptide;

(d) an extracellular domain of the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22

(SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(e) a polypeptide encoded by the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70); or (f) a polypeptide encoded by the full-length coding region of the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70), said method comprising contacting said cell with an antibody, oligopeptide or organic molecule that binds to said protein, the binding of said antibody, oligopeptide or organic molecule to said protein thereby causing an inhibition of growth of said cell.

60. The method of Claim 59, wherein said antibody is a monoclonal antibody.

61. The method of Claim 59, wherein said antibody is an antibody fragment.

62. The method of Claim 59, wherein said antibody is a chimeric or a humanized antibody.

63. The method of Claim 59, wherein said antibody, oligopeptide or organic molecule is conjugated to a growth inhibitory agent.

64. The method of Claim 59, wherein said antibody, oligopeptide or organic molecule is conjugated to a cytotoxic agent.

65. The method of Claim 64, wherein said cytotoxic agent is selected from the group consisting of toxins, antibiotics, radioactive isotopes and nucleolytic enzymes.

66. The method of Claim 64, wherein the cytotoxic agent is a toxin.

67. The method of Claim 66, wherein the toxin is selected from the group consisting of maytansinoid and calicheamicin.

68. The method of Claim 66, wherein the toxin is a maytansinoid.

69. The method of Claim 59, wherein said antibody is produced in bacteria.

70. The method of Claim 59, wherein said antibody is produced in CHO cells.

71. The method of Claim 59, wherein said cell is a hematopoietic cell.

72. The method of Claim 71, wherein said hematopoietic cell is selected from the group consisting of a lymphocyte, leukocyte, platelet, erythrocyte and natural killer cell.

73. The method of Claim 72, wherein said lymphocyte is a B cell or T cell.

74. The method of claim 73 wherein said lymphocyte is a cancer cell.

75. The method of claim 74 wherein said cancer cell is further exposed to radiation treatment or a chemotherapeutic agent.

76. The method of claim 75, wherein said cancer cell is selected from the group consisting of a lymphoma cell, a myeloma cell and a leukemia cell.

77. The method of Claim 71, wherein said protein is more abundantly expressed by said hematopoietic cell as compared to a non-hematopoietic cell.

78. The method of Claim 59 which causes the death of said cell.

79. The method of Claim 59, wherein said protein has:

(a) the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71);

(b) the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide sequence;

(c) an amino acid sequence of an extracellular domain of the polypeptide selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), with its associated signal peptide sequence;

(d) an amino acid sequence of an extracellular domain of the polypeptide selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide sequence;

(e) an amino acid sequence encoded by the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70); or (f) an amino acid sequence encoded by the full-length coding region of the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70).

80. A method of therapeutically treating a mammal having a cancerous tumor comprising cells that express a protein having at least 80% amino acid sequence identity to:

(a) the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71);

(b) the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(c) an extracellular domain of the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), with its associated signal peptide;

(d) an extracellular domain of the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(e) a polypeptide encoded by the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70); or (f) a polypeptide encoded by the full-length coding region of the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35); FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70), said method comprising administering to said mammal a therapeutically effective amount of an antibody, oligopeptide or organic molecule that binds to said protein, thereby effectively treating said mammal.

81. The method of Claim 80, wherein said antibody is a monoclonal antibody.

82. The method of Claim 80, wherein said antibody is an antibody fragment.

83. The method of Claim 80, wherein said antibody is a chimeric or a humanized antibody.

84. The method of Claim 80, wherein said antibody, oligopeptide or organic molecule is conjugated to a growth inhibitory agent.

85. The method of Claim 80, wherein said antibody, oligopeptide or organic molecule is conjugated to a cytotoxic agent.

86. The method of Claim 85, wherein said cytotoxic agent is selected from the group consisting of toxins, antibiotics, radioactive isotopes and nucleolytic enzymes.

87. The method of Claim 85, wherein the cytotoxic agent is a toxin.

88. The method of Claim 87, wherein the toxin is selected from the group consisting of maytansinoid and calicheamicin.

89. The method of Claim 87, wherein the toxin is a maytansinoid.

90. The method of Claim 80, wherein said antibody is produced in bacteria.

91. The method of Claim 80, wherein said antibody is produced in CHO cells.

92. The method of Claim 80, wherein said tumor is further exposed to radiation treatment or a chemotherapeutic agent.

93. The method of Claim 80, wherein said tumor is a lymphoma, leukemia or myeloma tumor.

94. The method of Claim 80, wherein said protein is more abundantly expressed by a hematopoietic cell as compared to a non-hematopoietic cell of said tumor.

95. The method of Claim 94, wherein said protein is more abundantly expressed by cancerous hematopoietic cells of said tumor as compared to normal hematopoietic cells of said tumor.

96. The method of Claim 80, wherein said protein has:

(a) the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71);

(b) the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide sequence;

(c) an amino acid sequence of an extracellular domain of the polypeptide selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44, FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), with its associated signal peptide sequence;

(d) an amino acid sequence of an extracellular domain of the polypeptide selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide sequence;

(e) an amino acid sequence encoded by the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70); or (f) an amino acid sequence encoded by the full-length coding region of the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70).

97. A method of determining the presence of a protein in a sample suspected of containing said protein, wherein said protein has at least 80% amino acid sequence identity to:

(a) the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71);

(b) the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(c) an extracellular domain of the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44, FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), with its associated signal peptide;

(d) an extracellular domain of the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(e) a polypeptide encoded by the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70); or (f) a polypeptide encoded by the full-length coding region of the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70), said method comprising exposing said sample to an antibody, oligopeptide or organic molecule that binds to said protein and determining binding of said antibody, oligopeptide or organic molecule to said protein in said sample, wherein binding of the antibody, oligopeptide or organic molecule to said protein is indicative of the presence of said protein in said sample.

98. The method of Claim 97, wherein said sample comprises a cell suspected of expressing said protein.

99. The method of Claim 98, wherein said cell is a cancer cell.

100. The method of Claim 97, wherein said antibody, oligopeptide or organic molecule is detectably labeled.

101. The method of Claim 97, wherein said protein has:

(a) the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID 37 NO: 63), FIG. 65 (SEQ ID NO: 65), FIG. 67 (SEQ ID NO: 67), FIG. 69 (SEQ ID NO: 69) and FIG. 71 (SEQ ID NO: 71);

(b) the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide sequence;

(c) an amino acid sequence of an extracellular domain of the polypeptide selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44, FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), with its associated signal peptide sequence;

(d) an amino acid sequence of an extracellular domain of the polypeptide selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44, FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide sequence;

(e) an amino acid sequence encoded by the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70); or (f) an amino acid sequence encoded by the full-length coding region of the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70).

102. A method for treating or preventing a cell proliferative disorder associated with increased expression or activity of a protein having at least 80% amino acid sequence identity to:

(a) the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71);

(b) the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(c) an extracellular domain of the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), with its associated signal peptide;

(d) an extracellular domain of the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(e) a polypeptide encoded by the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23

(SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70); or (f) a polypeptide encoded by the full-length coding region of the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70), said method comprising administering to a subject in need of such treatment an effective amount of an antagonist of said protein, thereby effectively treating or preventing said cell proliferative disorder.

103. The method of Claim 102, wherein said cell proliferative disorder is cancer.

104. The method of Claim 102, wherein said antagonist is an anti-TAHO polypeptide antibody, TAHO binding oligopeptide, TAHO binding organic molecule or antisense oligonucleotide.

105. A method of binding an antibody, oligopeptide or organic molecule to a cell that expresses a protein having at least 80% amino acid sequence identity to:

(a) the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71);

(b) the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(c) an extracellular domain of the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), with its associated signal peptide;

(d) an extracellular domain of the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(e) a polypeptide encoded by the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70); or (f) a polypeptide encoded by the full-length coding region of the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70), said method comprising contacting said cell with an antibody, oligopeptide or organic molecule that binds to said protein and allowing the binding of the antibody, oligopeptide or organic molecule to said protein to occur, thereby binding said antibody, oligopeptide or organic molecule to said cell.

106. The method of Claim 105, wherein said antibody is a monoclonal antibody.

107. The method of Claim 105, wherein said antibody is an antibody fragment.

108. The method of Claim 105, wherein said antibody is a chimeric or a humanized antibody.

109. The method of Claim 105, wherein said antibody, oligopeptide or organic molecule is conjugated to a growth inhibitory agent.

110. The method of Claim 105, wherein said antibody, oligopeptide or organic molecule is conjugated to a cytotoxic agent.

111. The method of Claim 110, wherein said cytotoxic agent is selected from the group consisting of toxins, antibiotics, radioactive isotopes and nucleolytic enzymes.

112. The method of Claim 110, wherein the cytotoxic agent is a toxin.

113. The method of Claim 112, wherein the toxin is selected from the group consisting of maytansinoid and calicheamicin.

114. The method of Claim 112, wherein the toxin is a maytansinoid.

115. The method of Claim 105, wherein said antibody is produced in bacteria.

116. The method of Claim 105, wherein said antibody is produced in CHO cells.

117. The method of Claim 105, wherein said cell is a hematopoietic cell.

118. The method of Claim 117, wherein said hematopoietic cell is a selected from the group consisting of a lymphocyte, leukocyte, platelet, erythrocyte and natural killer cell.

119. The method of claim 118, wherein said lymphocyte is a B cell or a T cell.

120. The method of Claim 119, wherein said lymphocyte is a cancer cell.

121. The method of Claim 120 wherein said cancer cell is further exposed to radiation treatment or a chemotherapeutic agent.

122. The method of Claim 120, wherein said cancer cell is selected from the group consisting of a leukemia cell, a lymphoma cell and a myeloma cell.

123. The method of Claim 120, wherein said protein is more abundantly expressed by said hematopoietic cell as compared to a non-hematopoietic cell.

124. The method of Claim 105 which causes the death of said cell.

125. Use of a nucleic acid as claimed in any of Claims 1 to 5 or 30 in the preparation of a medicament for the therapeutic treatment or diagnostic detection of a cancer.

126. Use of a nucleic acid as claimed in any of Claims 1 to 5 or 30 in the preparation of a medicament for treating a tumor.

127. Use of a nucleic acid as claimed in any of Claims 1 to 5 in the preparation of a medicament for treatment or prevention of a cell proliferative disorder.

128. Use of an expression vector as claimed in Claim 6 in the preparation of a medicament for the therapeutic treatment or diagnostic detection of a cancer.

129. Use of an expression vector as claimed in Claim 6 in the preparation of medicament for treating a tumor.

130. Use of an expression vector as claimed in Claim 6 in the preparation of a medicament for treatment or prevention of a cell proliferative disorder.

131. Use of a host cell as claimed in Claim 8 in the preparation of a medicament for the therapeutic treatment or diagnostic detection of a cancer.

132. Use of a host cell as claimed in Claim 8 in the preparation of a medicament for treating a tumor.

133. Use of a host cell as claimed in Claim 8 in the preparation of a medicament for treatment or prevention of a cell proliferative disorder.

134. Use of a polypeptide as claimed in Claim 11 or 12 in the preparation of a medicament for the therapeutic treatment or diagnostic detection of a cancer.

135. Use of a polypeptide as claimed in Claim 11 or 12 in the preparation of a medicament for treating a tumor.

136. Use of a polypeptide as claimed in Claim 11 or 12 in the preparation of a medicament for treatment or prevention of a cell proliferative disorder.

137. Use of an antibody as claimed in Claim 15 or 16 in the preparation of a medicament for the therapeutic treatment or diagnostic detection of a cancer.

138. Use of an antibody as claimed in Claim 15 or 16 in the preparation of a medicament for treating a tumor.

139. Use of an antibody as claimed in Claim 15 or 16 in the preparation of a medicament for treatment or prevention of a cell proliferative disorder.

140. Use of an oligopeptide as claimed in Claim 35 or 36 in the preparation of a medicament for the therapeutic treatment or diagnostic detection of a cancer.

141. Use of an oligopeptide as claimed in Claim 35 or 36 in the preparation of a medicament for treating a tumor.

142. Use of an oligopeptide as claimed in Claim 35 or 36 in the preparation of a medicament for treatment or prevention of a cell proliferative disorder.

143. Use of a TAHO binding organic molecule as claimed in Claim 45 or 46 in the preparation of a medicament for the therapeutic treatment or diagnostic detection of a cancer.

144. Use of a TAHO binding organic molecule as claimed in Claim 45 or 46 in the preparation of a medicament for treating a tumor.

145. Use of a TAHO binding organic molecule as claimed in Claims 45 or 46 in the preparation of a medicament for treatment or prevention of a cell proliferative disorder.

146. Use of a composition of matter as claimed in Claim 55 in the preparation of a medicament for the therapeutic treatment or diagnostic detection of a cancer.

147. Use of a composition of matter as claimed in Claim 55 in the preparation of a medicament for treating a tumor.

148. Use of a composition of matter as claimed in Claim 55 in the preparation of a medicament for treatment or prevention of a cell proliferative disorder.

149. Use of an article of manufacture as claimed in Claim 57 in the preparation of a medicament for the therapeutic treatment or diagnostic detection of a cancer.

150. Use of an article of manufacture as claimed in Claim 58 in the preparation of a medicament for treating a tumor.

151. Use of an article of manufacture as claimed in Claim 58 in the preparation of a medicament for treatment or prevention of a cell proliferative disorder.

152. A method for inhibiting the growth of a cell, wherein the growth of said cell is at least in part dependent upon a growth potentiating effect of a protein having at least 80% amino acid sequence identity to:

(a) the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), (b) the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(c) an extracellular domain of the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44, FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), with its associated signal peptide;

(d) an extracellular domain of the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(e) a polypeptide encoded by the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70); or (f) a polypeptide encoded by the full-length coding region of the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70), said method comprising contacting said protein with an antibody, oligopeptide or organic molecule that binds to said protein, there by inhibiting the growth of said cell.

153. The method of Claim 152, wherein said cell is a hematopoietic cell.

154. The method of Claim 152, wherein said protein is expressed by said cell.

155. The method of Claim 152, wherein the binding of said antibody, oligopeptide or organic molecule to said protein antagonizes a cell growth-potentiating activity of said protein.

156. The method of Claim 152, wherein the binding of said antibody, oligopeptide or organic molecule to said protein induces the death of said cell.

157. The method of Claim 152, wherein said antibody is a monoclonal antibody.

158. The method of Claim 152, wherein said antibody is an antibody fragment.

159. The method of Claim 152, wherein said antibody is a chimeric or a humanized antibody.

160. The method of Claim 152, wherein said antibody, oligopeptide or organic molecule is conjugated to a growth inhibitory agent.

161. The method of Claim 152, wherein said antibody, oligopeptide or organic molecule is conjugated to a cytotoxic agent.

162. The method of Claim 161, wherein said cytotoxic agent is selected from the group consisting of toxins, antibiotics, radioactive isotopes and nucleolytic enzymes.

163. The method of Claim 161, wherein the cytotoxic agent is a toxin.

164. The method of Claim 163, wherein the toxin is selected from the group consisting of maytansinoid and calicheamicin.

165. The method of Claim 163, wherein the toxin is a maytansinoid.

166. The method of Claim 152, wherein said antibody is produced in bacteria.

167. The method of Claim 152, wherein said antibody is produced in CHO cells.

168. The method of Claim 152, wherein said protein has:

(a) the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71);

(b) the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide sequence;

(c) an amino acid sequence of an extracellular domain of the polypeptide selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), with its associated signal peptide sequence;

(d) an amino acid sequence of an extracellular domain of the polypeptide selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44, FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide sequence;

(e) an amino acid sequence encoded by the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70); or (f) an amino acid sequence encoded by the full-length coding region of the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29). FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70).

169. A method of therapeutically treating a tumor in a mammal, wherein the growth of said tumor is at least in part dependent upon a growth potentiating effect of a protein having at least 80% amino acid sequence identity to:

(a) the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71);

(b) the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44, FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(c) an extracellular domain of the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44, FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), with its associated signal peptide;

(d) an extracellular domain of the polypeptide having the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide;

(e) a polypeptide encoded by the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70); or (f) a polypeptide encoded by the full-length coding region of the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58); FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG.

70 (SEQ ID NO: 70), said method comprising contacting said protein with an antibody, oligopeptide or organic molecule that binds to said protein, thereby effectively treating said tumor.

170. The method of Claim 169, wherein said protein is expressed by cells of said tumor.

171. The method of Claim 169, wherein the binding of said antibody, oligopeptide or organic molecule to said protein antagonizes a cell growth-potentiating activity of said protein.

172. The method of Claim 169, wherein said antibody is a monoclonal antibody.

173. The method of Claim 169, wherein said antibody is an antibody fragment.

174. The method of Claim 169, wherein said antibody is a chimeric or a humanized antibody.

175. The method of Claim 169, wherein said antibody, oligopeptide or organic molecule is conjugated to a growth inhibitory agent.

176. The method of Claim 169, wherein said antibody, oligopeptide or organic molecule is conjugated to a cytotoxic agent.

177. The method of Claim 176, wherein said cytotoxic agent is selected from the group consisting of toxins, antibiotics, radioactive isotopes and nucleolytic enzymes.

178. The method of Claim 176, wherein the cytotoxic agent is a toxin.

179. The method of Claim 178, wherein the toxin is selected from the group consisting of maytansinoid and calicheamicin.

180. The method of Claim 178, wherein the toxin is a maytansinoid.

181. The method of Claim 169, wherein said antibody is produced in bacteria.

182. The method of Claim 169, wherein said antibody is produced in CHO cells.

183. The method of Claim 169, wherein said protein has:

(a) the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71);

(b) the amino acid sequence selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide sequence;

(c) an amino acid sequence of an extracellular domain of the polypeptide selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), with its associated signal peptide sequence;

(d) an amino acid sequence of an extracellular domain of the polypeptide selected from the group consisting of the amino acid sequence shown in FIG. 2 (SEQ ID NO: 2), FIG. 4 (SEQ ID NO: 4), FIG. 6 (SEQ ID NO: 6), FIG. 8 (SEQ ID NO: 8), FIG. 10 (SEQ ID NO: 10), FIG. 12 (SEQ ID NO: 12), FIG. 14 (SEQ ID NO: 14), FIG. 16 (SEQ ID NO: 16), FIG. 18 (SEQ ID NO: 18), FIG. 20 (SEQ ID NO: 20), FIG. 22 (SEQ ID NO: 22), FIG. 24 (SEQ ID NO: 24), FIG. 26 (SEQ ID NO: 26), FIG. 28 (SEQ ID NO: 28), FIG. 30 (SEQ ID NO: 30), FIG. 32 (SEQ ID NO: 32), FIG. 34 (SEQ ID NO: 34), FIG. 36 (SEQ ID NO: 36), FIG. 40 (SEQ ID NO: 40), FIG. 42 (SEQ ID NO: 42), FIG. 44 (SEQ ID NO: 44), FIG. 46 (SEQ ID NO: 46), FIG. 49 (SEQ ID NO: 49), FIG. 51 (SEQ ID NO: 51), FIG. 53 (SEQ ID NO: 53), FIG. 55 (SEQ ID NO: 55), FIG. 57 (SEQ ID NO: 57), FIG. 59 (SEQ ID NO: 59), FIG. 61 (SEQ ID NO: 61), FIG. 63 (SEQ ID NO: 63), FIG. 65 (SEQ ID NO: 65), FIG. 67 (SEQ ID NO: 67), FIG. 69 (SEQ ID NO: 69) and FIG. 71 (SEQ ID NO: 71), lacking its associated signal peptide sequence;

(e) an amino acid sequence encoded by the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11 (SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70); or (f) an amino acid sequence encoded by the full-length coding region of the nucleotide sequence selected from the group consisting of the nucleotide sequence shown in FIG. 1 (SEQ ID NO: 1), FIG. 3 (SEQ ID NO:3), FIG. 5 (SEQ ID NO: 5), FIG. 7 (SEQ ID NO: 7), FIG. 9 (SEQ ID NO: 9), FIG. 11

(SEQ ID NO: 11), FIG. 13 (SEQ ID NO: 13), FIG. 15 (SEQ ID NO: 15), FIG. 17 (SEQ ID NO: 17), FIG. 19 (SEQ ID NO: 19), FIG. 21 (SEQ ID NO: 21), FIG. 23 (SEQ ID NO: 23), FIG. 25 (SEQ ID NO: 25), FIG. 27 (SEQ ID NO: 27), FIG. 29 (SEQ ID NO: 29), FIG. 31 (SEQ ID NO: 31), FIG. 33 (SEQ ID NO: 33), FIG. 35 (SEQ ID NO: 35), FIG. 37 (SEQ ID NO: 37), FIG. 39 (SEQ ID NO: 39), FIG. 41 (SEQ ID NO: 41), FIG. 43 (SEQ ID NO: 43), FIG. 45 (SEQ ID NO: 45), FIG. 47 (SEQ ID NO: 47), FIG. 48 (SEQ ID NO: 48), FIG. 50 (SEQ ID NO: 50), FIG. 52 (SEQ ID NO: 52), FIG. 54 (SEQ ID NO: 54), FIG. 56 (SEQ ID NO: 56), FIG. 58 (SEQ ID NO: 58), FIG. 60 (SEQ ID NO: 60), FIG. 62 (SEQ ID NO: 62), FIG. 64 (SEQ ID NO: 64), FIG. 66 (SEQ ID NO: 66), FIG. 68 (SEQ ID NO: 68) and FIG. 70 (SEQ ID NO: 70).

184. A composition of matter comprising the chimeric polypeptide of Claim 13.

185. Use of a nucleic acid as claimed in Claim 30 in the preparation of a medicament for treatment or prevention of a cell proliferative disorder.

186. Use of an expression vector as claimed in Claim 7 in the preparation of a medicament for the therapeutic treatment or diagnostic detection of a cancer.

187. Use of an expression vector as claimed in Claim 31 in the preparation of a medicament for the therapeutic treatment or diagnostic detection of a cancer.

188. Use of an expression vector as claimed in Claim 7 in the preparation of medicament for treating a tumor.

189. Use of an expression vector as claimed in Claim 31 in the preparation of medicament for treating a tumor.

190. Use of an expression vector as claimed in Claim 7 in the preparation of a medicament for treatment or prevention of a cell proliferative disorder.

191. Use of an expression vector as claimed in Claim 31 in the preparation of a medicament for treatment or prevention of a cell proliferative disorder.

192. Use of a host cell as claimed in Claim 9 in the preparation of a medicament for the therapeutic treatment or diagnostic detection of a cancer.

193. Use of a host cell as claimed in Claim 32 in the preparation of a medicament for the therapeutic treatment or diagnostic detection of a cancer.

194. Use of a host cell as claimed in Claim 33 in the preparation of a medicament for the therapeutic treatment or diagnostic detection of a cancer.

195. Use of a host cell as claimed in Claim 9 in the preparation of a medicament for treating a tumor.

196. Use of a host-cell as claimed in Claim 32 in the preparation of a medicament for treating a tumor.

197. Use of a host cell as claimed in Claim 33 in the preparation of a medicament for treating a tumor.

198. Use of a host cell as claimed in Claim 9 in the preparation of a medicament for treatment or prevention of a cell proliferative disorder.

199. Use of a host cell as claimed in Claim 32 in the preparation of a medicament for treatment or prevention of a cell proliferative disorder.

200. Use of a host cell as claimed in Claim 33 in the preparation of a medicament for treatment or prevention of a cell proliferative disorder.

201. Use of a polypeptide as claimed in Claim 13 in the preparation of a medicament for the therapeutic treatment or diagnostic detection of a cancer.

202. Use of a polypeptide as claimed in Claim 14 in the preparation of a medicament for the therapeutic treatment or diagnostic detection of a cancer.

203. Use of a polypeptide as claimed in Claim 13 in the preparation of a medicament for treating a tumor.

204. Use of a polypeptide as claimed in Claim 14 in the preparation of a medicament for treating at tumor.

205. Use of a polypeptide as claimed in Claim 13 in the preparation of a medicament for treatment or prevention of a cell proliferative disorder.

206. Use of a polypeptide as claimed in Claim 14 in the preparation of a medicament for treatment or prevention of a cell proliferative disorder.

207. Use of an antibody as claimed in Claim 17 in the preparation of a medicament for the therapeutic treatment or diagnostic detection of a cancer.

208. Use of an antibody as claimed in Claim 18 in the preparation of a medicament for the therapeutic treatment or diagnostic detection of a cancer.

209. Use of an antibody as claimed in Claim 19 in the preparation of a medicament for the therapeutic treatment or diagnostic detection of a cancer.

210. Use of an antibody as claimed in Claim 20 in the preparation of a medicament for the therapeutic treatment or diagnostic detection of a cancer.

211. Use of an antibody as claimed in Claim 21 in the preparation of a medicament for the therapeutic treatment or diagnostic detection of a cancer.

212. Use of an antibody as claimed in Claim 22 in the preparation of a medicament for the therapeutic treatment or diagnostic detection of a cancer.

213. Use of an antibody as claimed in Claim 23 in the preparation of a medicament for the therapeutic treatment or diagnostic detection of a cancer.

214. Use of an antibody as claimed in Claim 24 in the preparation of a medicament for the therapeutic treatment or diagnostic detection of a cancer.

215. Use of an antibody as claimed in Claim 25 in the preparation of a medicament for the therapeutic treatment or diagnostic detection of a cancer.

216. Use of an antibody as claimed in Claim 26 in the preparation of a medicament for the therapeutic treatment or diagnostic detection of a cancer.

217. Use of an antibody as claimed in Claim 27 in the preparation of a medicament for the therapeutic treatment or diagnostic detection of a cancer.

218. Use of an antibody as claimed in Claim 28 in the preparation of a medicament for the therapeutic treatment or diagnostic detection of a cancer.

219. Use of an antibody as claimed in Claim 29 in the preparation of a medicament for the therapeutic treatment or diagnostic detection of a cancer.

220. Use of an antibody as claimed in Claim 17 in the preparation of a medicament for treating a tumor.

221. Use of an antibody as claimed in Claim 18 in the preparation of a medicament for treating a tumor.

222. Use of an antibody as claimed in Claim 19 in the preparation of a medicament for treating a tumor.

223. Use of an antibody as claimed in Claim 20 in the preparation of a medicament for treating a tumor.

224. Use of an antibody as claimed in Claim 21 in the preparation of a medicament for treating a tumor.

225. Use of an antibody as claimed in Claim 22 in the preparation of a medicament for treating a tumor.

226. Use of an antibody as claimed in Claim 23 in the preparation of a medicament for treating a tumor.

227. Use of an antibody as claimed in Claim 24 in the preparation of a medicament for treating a tumor.

228. Use of an antibody as claimed in Claim 25 in the preparation of a medicament for treating a tumor.

229. Use of an antibody as claimed in Claim 26 in the preparation of a medicament for treating a tumor.

230. Use of an antibody as claimed in Claim 27 in the preparation of a medicament for treating a tumor.
231. Use of an antibody as claimed in Claim 28 in the preparation of a medicament for treating a tumor.
232. Use of an antibody as claimed in Claim 29 in the preparation of a medicament for treating a tumor.
233. Use of an antibody as claimed in Claim 17 in the preparation of a medicament for treatment or prevention of a cell proliferative disorder.
234. Use of an antibody as claimed in Claim 18 in the preparation of a medicament for treatment or prevention of a cell proliferative disorder.
235. Use of an antibody as claimed in Claim 17 in the preparation of a medicament for treatment or prevention of a cell proliferative disorder.
235. Use of an antibody as claimed in Claim 18 in the preparation of a medicament for treatment or prevention of a cell proliferative disorder.
237. Use of an antibody as claimed in Claim 19 in the preparation of a medicament for treatment or prevention of a cell proliferative disorder.
238. Use of an antibody as claimed in Claim 20 in the preparation of a medicament for treatment or prevention of a cell proliferative disorder.
239. Use of an antibody as claimed in Claim 21 in the preparation of a medicament for treatment or prevention of a cell proliferative disorder.
240. Use of an antibody as claimed in Claim 22 in the preparation of a medicament for treatment or prevention of a cell proliferative disorder.
241. Use of an antibody as claimed in Claim 23 in the preparation of a medicament for treatment or prevention of a cell proliferative disorder.
242. Use of an antibody as claimed in Claim 24 in the preparation of a medicament for treatment or prevention of a cell proliferative disorder.
243. Use of an antibody as claimed in Claim 25 in the preparation of a medicament for treatment or prevention of a cell proliferative disorder.
244. Use of an antibody as claimed in Claim 26 in the preparation of a medicament for treatment or prevention of a cell proliferative disorder.
245. Use of an antibody as claimed in Claim 27 in the preparation of a medicament for treatment or prevention of a cell proliferative disorder.
246. Use of an antibody as claimed in Claim 28 in the preparation of a medicament for treatment or prevention of a cell proliferative disorder.
247. Use of an antibody as claimed in Claim 29 in the preparation of a medicament for treatment or prevention of a cell proliferative disorder.
248. Use of an oligopeptide as claimed in Claim 37 in the preparation of a medicament for the therapeutic treatment or diagnostic detection of a cancer.
249. Use of an oligopeptide as claimed in Claim 38 in the preparation of a medicament for the therapeutic treatment or diagnostic detection of a cancer.
250. Use of an oligopeptide as claimed in Claim 39 in the preparation of a medicament for the therapeutic treatment or diagnostic detection of a cancer.
251. Use of an oligopeptide as claimed in Claim 40 in the preparation of a medicament for the therapeutic treatment or diagnostic detection of a cancer.
252. Use of an oligopeptide as claimed in Claim 41 in the preparation of a medicament for the therapeutic treatment or diagnostic detection of a cancer.
253. Use of an oligopeptide as claimed in Claim 42 in the preparation of a medicament for the therapeutic treatment or diagnostic detection of a cancer.
254. Use of an oligopeptide as claimed in Claim 43 in the preparation of a medicament for the therapeutic treatment or diagnostic detection of a cancer.
255. Use of an oligopeptide as claimed in Claim 44 in the preparation of a medicament for the therapeutic treatment or diagnostic detection of a cancer.
256. Use of an oligopeptide as claimed in Claim 37 in the preparation of a medicament for treating a tumor.
257. Use of an oligopeptide as claimed in Claim 38 in the preparation of a medicament for treating a tumor.
258. Use of an oligopeptide as claimed in Claim 39 in the preparation of a medicament for treating a tumor.
259. Use of an oligopeptide as claimed in Claim 40 in the preparation of a medicament for treating a tumor.
260. Use of an oligopeptide as claimed in Claim 41 in the preparation of a medicament for treating a tumor.
261. Use of an oligopeptide as claimed in Claim 42 in the preparation of a medicament for treating a tumor.
262. Use of an oligopeptide as claimed in Claim 43 in the preparation of a medicament for treating a tumor.
263. Use of an oligopeptide as claimed in Claim 44 in the preparation of a medicament for treating a tumor.
264. Use of an oligopeptide as claimed in Claim 37 in the preparation of a medicament for treatment or prevention of a cell proliferative disorder.
265. Use of an oligopeptide as claimed in Claim 38 in the preparation of a medicament for treatment or prevention of a cell proliferative disorder.
266. Use of an oligopeptide as claimed in Claim 39 in the preparation of a medicament for treatment or prevention of a cell proliferative disorder.
267. Use of an oligopeptide as claimed in Claim 40 in the preparation of a medicament for treatment or prevention of a cell proliferative disorder.
268. Use of an oligopeptide as claimed in Claim 41 in the preparation of a medicament for treatment or prevention of a cell proliferative disorder.
269. Use of an oligopeptide as claimed in Claim 42 in the preparation of a medicament for treatment or prevention of a cell proliferative disorder.
270. Use of an oligopeptide as claimed in Claim 43 in the preparation of a medicament for treatment or prevention of a cell proliferative disorder.
271. Use of an oligopeptide as claimed in Claim 44 in the preparation of a medicament for treatment or prevention of a cell proliferative disorder.
272. Use of a TAHO binding organic molecule as claimed in Claim 47 in the preparation of a medicament for the therapeutic treatment or diagnostic detection of a cancer.
273. Use of a TAHO binding organic molecule as claimed in Claim 48 in the preparation of a medicament for the therapeutic treatment or diagnostic detection of a cancer.
274. Use of a TAHO binding organic molecule as claimed in Claim 49 in the preparation of a medicament for the therapeutic treatment or diagnostic detection of a cancer.
275. Use of a TAHO binding organic molecule as claimed in Claim 50 in the preparation of a medicament for the therapeutic treatment or diagnostic detection of a cancer.
276. Use of a TAHO binding organic molecule as claimed in Claim 51 in the preparation of a medicament for the therapeutic treatment or diagnostic detection of a cancer.
277. Use of a TAHO binding organic molecule as claimed in Claim 52 in the preparation of a medicament for the therapeutic treatment or diagnostic detection of a cancer.

278. Use of a TAHO binding organic molecule as claimed in Claim 53 in the preparation of a medicament for the therapeutic treatment or diagnostic detection of a cancer.
279. Use of a TAHO binding organic molecule as claimed in Claim 54 in the preparation of a medicament for the therapeutic treatment or diagnostic detection of a cancer.
280. Use of a TAHO binding organic molecule as claimed in Claim 47 in the preparation of a medicament for treating a tumor.
281. Use of a TAHO binding organic molecule as claimed in Claim 48 in the preparation of a medicament for treating a tumor.
282. Use of a TAHO binding organic molecule as claimed in Claim 49 in the preparation of a medicament for treating a tumor.
283. Use of a TAHO binding organic molecule as claimed in Claim 50 in the preparation of a medicament for treating a tumor.
284. Use of a TAHO binding organic molecule as claimed in Claim 51 in the preparation of a medicament for treating a tumor.
285. Use of a TAHO binding organic molecule as claimed in Claim 52 in the preparation of a medicament for treating a tumor.
286. Use of a TAHO binding organic molecule as claimed in Claim 53 in the preparation of a medicament for treating a tumor.
287. Use of a TAHO binding organic molecule as claimed in Claim 54 in the preparation of a medicament for treating a tumor.
288. Use of a TAHO binding organic molecule as claimed in Claim 47 in the preparation of a medicament for treatment or prevention of a cell proliferative disorder.
289. Use of a TAHO binding organic molecule as claimed in Claim 48 in the preparation of a medicament for treatment or prevention of a cell proliferative disorder.
290. Use of a TAHO binding organic molecule as claimed in Claim 49 in the preparation of a medicament for treatment or prevention of a cell proliferative disorder.
291. Use of a TAHO binding organic molecule as claimed in Claim 50 in the preparation of a medicament for treatment or prevention of a cell proliferative disorder.
292. Use of a TAHO binding organic molecule as claimed in Claim 51 in the preparation of a medicament for treatment or prevention of a cell proliferative disorder.
293. Use of a TAHO binding organic molecule as claimed in Claim 52 in the preparation of a medicament for treatment or prevention of a cell proliferative disorder.
294. Use of a TAHO binding organic molecule as claimed in Claim 53 in the preparation of a medicament for treatment or prevention of a cell proliferative disorder.
295. Use of a TAHO binding organic molecule as claimed in Claim 54 in the preparation of a medicament for treatment or prevention of a cell proliferative disorder.
296. Use of a composition of matter as claimed in Claim 56 in the preparation of a medicament for the therapeutic treatment or diagnostic detection of a cancer.
297. Use of a composition of matter as claimed in Claim 56 in the preparation of a medicament for treating a tumor.
298. Use of a composition of matter as claimed in Claim 56 in the preparation of a medicament for treatment or prevention of a cell proliferative disorder.
299. Use of an article of manufacture as claimed in Claim 58 in the preparation of a medicament for the therapeutic treatment or diagnostic detection of a cancer.
300. Use of an article of manufacture as claimed in Claim 58 in the preparation of a medicament for treating a tumor.
301. Use of an article of manufacture as claimed in Claim 58 in the preparation of a medicament for treatment or prevention of a cell proliferative disorder.

BRIEF DESCRIPTION OF THE DRAWINGS

FIG. 1 shows a nucleotide sequence (SEQ ID NO: 1) of a TAHO1 (PRO7201) cDNA, wherein SEQ ID NO: 1 is a clone designated herein as "DNA105250" (also referred here in as "CD180" or "LY64").

FIG. 2 shows the amino acid sequence (SEQ ID NO:2) derived from the coding sequence of SEQ ID NO:1 shown in FIG. 1.

FIG. 3 shows a nucleotide sequence (SEQ ID NO:3) of a TAHO2 (PRO4644) cDNA, wherein SEQ ID NO:3 is a clone designated herein as "DNA150004" (also referred here in as "CD20" or "MSA41").

FIG. 4 shows the amino acid sequence (SEQ ID NO:4) derived from the coding sequence of SEQ ID NO:3 shown in FIG. 3.

FIG. 5 shows a nucleotide sequence (SEQ ID NO:5) of a TAHO3 (PRO31998) cDNA, wherein SEQ ID NO:5 is a clone designated herein as "DNA182432" (also referred here in as "FcRH2" or "SPAP1").

FIG. 6 shows the amino acid sequence (SEQ ID NO:6) derived from the coding sequence of SEQ ID NO:5 shown in FIG. 5.

FIG. 7 shows a nucleotide sequence (SEQ ID NO:7) of a TAHO4 (PRO36248) cDNA, wherein SEQ ID NO:7 is a clone designated herein as "DNA225785" (also referred here in as "CD79A").

FIG. 8 shows the amino acid sequence (SEQ ID NO:8) derived from the coding sequence of SEQ ID NO:7 shown in FIG. 7.

FIG. 9 shows a nucleotide sequence (SEQ ID NO:9) of a TAHO5 (PRO36249) cDNA, wherein SEQ ID NO:9 is a clone designated herein as "DNA225786" (also referred here in as "CD79B").

FIG. 10 shows the amino acid sequence (SEQ ID NO:10) derived from the coding sequence of SEQ ID NO:9 shown in FIG. 9.

FIG. 11 shows a nucleotide sequence (SEQ ID NO:11) of a TAHO6 (PRO36338) wherein SEQ ID NO:11 is a clone designated herein as "DNA225875" (also referred here in as "CD21" or "CR2").

FIG. 12 shows the amino acid sequence (SEQ ID NO: 12) derived from the coding sequence of SEQ ID NO:11 shown in FIG. 11.

FIG. 13 shows a nucleotide sequence (SEQ ID NO:13) of a TAHO7 (PRO36642) wherein SEQ ID NO: 13 is a clone designated herein as "DNA226179" (also referred here in as "CCR6").

FIG. 14 shows the amino acid sequence (SEQ ID NO:14) derived from the coding sequence of SEQ ID NO: 13 shown in FIG. 13.

FIG. 15 shows a nucleotide sequence (SEQ ID NO: 15) of a TAHO8 (PRO36702) cDNA, wherein SEQ ID NO:15 is a clone designated herein as "DNA226239" (also referred herein as "CD72").

FIG. 16 shows the amino acid sequence (SEQ ID NO:16) derived from the coding sequence of SEQ ID NO:15 shown in FIG. 15.

FIG. 17 shows a nucleotide sequence (SEQ ID NO: 17) of a TAHO9 (PRO36857) cDNA, wherein SEQ ID NO:17 is a clone designated herein as "DNA226394" (also referred herein as "P2RX5").

FIG. 18 shows the amino acid sequence (SEQ ID NO: 18) derived from the coding sequence of SEQ ID NO:17 shown in FIG. 17.

FIG. 19 shows a nucleotide sequence (SEQ ID NO: 19) of a TAHO10 (PRO36886) cDNA, wherein SEQ ID NO: 19 is a clone designated herein as "DNA226423" (also referred herein as "HLA-DOB").

FIG. 20 shows the amino acid sequence (SEQ ID NO:20) derived from the coding sequence of SEQ ID NO:19 shown in FIG. 19.

FIG. 21 shows a nucleotide sequence (SEQ ID NO:21) of a TAHO1 (PRO38244) cDNA, wherein SEQ ID NO:21 is a clone designated herein as "DNA227781" (also referred herein as "CXCR5").

FIG. 22 shows the amino acid sequence (SEQ ID NO:22) derived from the coding sequence of SEQ ID NO:21 shown in FIG. 21.

FIG. 23 shows a nucleotide sequence (SEQ ID NO:23) of a TAHO12 (PRO38342) cDNA, wherein SEQ ID NO:23 is a clone designated herein as "DNA227879" (also referred herein as "CD23" or "FCER2").

FIG. 24 shows the amino acid sequence (SEQ ID NO:24) derived from the coding sequence of SEQ ID NO:23 shown in FIG. 23.

FIG. 25 shows a nucleotide sequence (SEQ ID NO:25) of a TAHO13 (PRO51405) cDNA, wherein SEQ ID NO:25 is a clone designated herein as "DNA256363" (also referred herein as "GPR2").

FIG. 26 shows the amino acid sequence (SEQ ID NO:26) derived from the coding sequence of SEQ ID NO:25 shown in FIG. 25.

FIG. 27 shows a nucleotide sequence (SEQ ID NO:27) of a TAHO14 (PRO87299) cDNA, wherein SEQ ID NO:27 is a clone designated herein as "DNA332467" (also referred herein as "Btig").

FIG. 28 shows the amino acid sequence (SEQ ID NO:28) derived from the coding sequence of SEQ ID NO:27 shown in FIG. 27.

FIG. 29 shows a nucleotide sequence (SEQ ID NO:29) of a TAHO15 PRO1111cDNA, wherein SEQ ID NO:29 is a clone designated herein as "DNA58721" (also referred herein as "NAG14").

FIG. 30 shows the amino acid sequence (SEQ ID NO:30) derived from the coding sequence of SEQ ID NO:29 shown in FIG. 29.

FIG. 31 shows a nucleotide sequence (SEQ ID NO:31) of a TAHO16 (PRO90213) cDNA, wherein SEQ ID NO:31 is a clone designated herein as "DNA335924" (also referred herein as "SLGC16270").

FIG. 32 shows the amino acid sequence (SEQ ID NO:32) derived from the coding sequence of SEQ ID NO:31 shown in FIG. 31.

FIG. 33 shows a nucleotide sequence (SEQ ID NO:33) of a TAHO17 PRO85143 cDNA, wherein SEQ ID NO:33 is a clone designated herein as "DNA340394" (also referred herein as "FcRH1" or "IRTA5").

FIG. 34 shows the amino acid sequence (SEQ ID NO:34) derived from the coding sequence of SEQ ID NO:33 shown in FIG. 33.

FIG. 35 shows a nucleotide sequence (SEQ ID NO:35) of a TAHO18 PRO820 cDNA, wherein SEQ ID NO:35 is a clone designated herein as "DNA56041" (also referred herein as "FcRH5" or "IRTA2").

FIG. 36 shows the amino acid sequence (SEQ ID NO:36) derived from the coding sequence of SEQ ID NO:35 shown in FIG. 35.

FIG. 37 shows a nucleotide sequence (SEQ ID NO:37) of a TAHO19 (PRO1140) cDNA, wherein SEQ ID NO:37 is a clone designated herein as "DNA59607" (also referred herein as "ATWD578").

FIG. 38 shows the amino acid sequence (SEQ ID NO:38) derived from the coding sequence of SEQ ID NO:37 shown in FIG. 37.

FIG. 39 shows a nucleotide sequence (SEQ ID NO:39) of a TAHO20 PRO52483 cDNA, wherein SEQ ID NO:39 is a clone designated herein as "DNA257955" (also referred herein as "FcRH3" or "IRTA3").

FIG. 40 shows the amino acid sequence (SEQ ID NO:40) derived from the coding sequence of SEQ ID NO:39 shown in FIG. 39.

FIG. 41 shows a nucleotide sequence (SEQ ID NO:41) of a TAHO21 PRO85193 cDNA, wherein SEQ ID NO:41 is a clone designated herein as "DNA329863" (also referred herein as "FcRH4" or "IRTA1").

FIG. 42 shows the amino acid sequence (SEQ ID NO:42) derived from the coding sequence of SEQ ID NO:41 shown in FIG. 41.

FIG. 43 shows a nucleotide sequence (SEQ ID NO:43) of a TAHO22 PRO96849 cDNA, wherein SEQ ID NO:43 is a clone designated herein as "DNA346528" (also referred herein as "FcRH6" or "FAIL").

FIG. 44 shows the amino acid sequence (SEQ ID NO:44) derived from the coding sequence of SEQ ID NO:43 shown in FIG. 43.

FIG. 45 shows a nucleotide sequence (SEQ ID NO:45) of a TAHO23 (PRO34414) cDNA, wherein SEQ ID NO:45 is a clone designated herein as "DNA212930" (also referred herein as "BCMA").

FIG. 46 shows the amino acid sequence (SEQ ID NO:46) derived from the coding sequence of SEQ ID NO:45 shown in FIG. 45.

FIG. 47 shows a nucleotide sequence (SEQ ID NO:47) of a TAHO24 (PRO90207) cDNA, wherein SEQ ID NO:47 is a clone designated herein as "DNA335918" (also referred herein as "239287_at").

FIG. 48 shows a nucleotide sequence (SEQ ID NO: 48) of a TAHO25 (PRO36283) cDNA, wherein SEQ ID NO: 48 is a cloned designated herein as "DNA225820" (also referred here in as "CD19").

FIG. 49 shows the amino acid sequence (SEQ ID NO: 49) derived from the coding sequence of SEQ ID NO: 48 shown in FIG. 48.

FIG. 50 shows a nucleotide sequence (SEQ ID NO: 50) of a TAHO26 (PRO2177) cDNA, wherein SEQ ID NO: 50 is a cloned designated herein as "DNA88116" (also referred here in as "CD22").

FIG. 51 shows the amino acid sequence (SEQ ID NO: 51) derived from the coding sequence of SEQ ID NO: 50 shown in FIG. 50.

FIG. 52 shows a nucleotide sequence (SEQ ID NO: 52) of a TAHO27 (PRO38215) cDNA, wherein SEQ ID NO: 52 is a cloned designated herein as "DNA227752" (also referred here in as "CXCR3").

FIG. 53 shows the amino acid sequence (SEQ ID NO: 53) derived from the coding sequence of SEQ ID NO: 52 shown in FIG. 52.

FIG. 54 shows a nucleotide sequence (SEQ ID NO: 54) of a TAHO28 (PRO9993) cDNA, wherein SEQ ID NO: 54 is a cloned designated herein as "DNA119476" (also referred here in as "SILV").

FIG. 55 shows the amino acid sequence (SEQ ID NO: 55) derived from the coding sequence of SEQ ID NO: 54 shown in FIG. 54.

FIG. 56 shows a nucleotide sequence (SEQ ID NO: 56) of a TAHO29 (PRO49980) cDNA, wherein SEQ ID NO: 56 is a cloned designated herein as "DNA254890" (also referred here in as "KCNK4").

FIG. 57 shows the amino acid sequence (SEQ ID NO: 57) derived from the coding sequence of SEQ ID NO: 56 shown in FIG. 56.

FIG. 58 shows a nucleotide sequence (SEQ ID NO: 58) of a TAHO30 (PRO34756) cDNA, wherein SEQ ID NO: 58 is a cloned designated herein as "DNA254890" (also referred here in as "CXorf1").

FIG. 59 shows the amino acid sequence (SEQ ID NO: 59) derived from the coding sequence of SEQ ID NO: 58 shown in FIG. 58.

FIG. 60 shows a nucleotide sequence (SEQ ID NO: 60) of a TAHO31 (PRO293) cDNA, wherein SEQ ID NO: 60 is a cloned designated herein as "DNA254890" (also referred here in as "LRRN5").

FIG. 61 shows the amino acid sequence (SEQ ID NO: 61) derived from the coding sequence of SEQ ID NO: 60 shown in FIG. 60.

FIG. 62 shows a nucleotide sequence (SEQ ID NO: 62) of a TAHO32 (PRO33767) cDNA, wherein SEQ ID NO: 62 is a cloned designated herein as "DNA210233".

FIG. 63 shows the amino acid sequence (SEQ ID NO: 63) derived from the coding sequence of SEQ ID NO: 62 shown in FIG. 62.

FIG. 64 shows a nucleotide sequence (SEQ ID NO: 64) of a TAHO33 (PRO258) cDNA, wherein SEQ ID NO: 64 is a cloned designated herein as "DNA35918" (also referred herein as "IGSF4B").

FIG. 65 shows the amino acid sequence (SEQ ID NO: 65) derived from the coding sequence of SEQ ID NO: 64 shown in FIG. 64.

FIG. 66 shows a nucleotide sequence (SEQ ID NO: 66) of a TAHO34 (PRO53968) cDNA, wherein SEQ ID NO: 66 is a cloned designated herein as "DNA260038".

FIG. 67 shows the amino acid sequence (SEQ ID NO: 67) derived from the coding sequence of SEQ ID NO: 66 shown in FIG. 66.

FIG. 68 shows a nucleotide sequence (SEQ ID NO: 68) of a TAHO35 (PRO89267) cDNA, wherein SEQ ID NO: 68 is a cloned designated herein as "DNA334818" (also referred herein as "FLJ12681").

FIG. 69 shows the amino acid sequence (SEQ ID NO: 69) derived from the coding sequence of SEQ ID NO: 68 shown in FIG. 68.

FIG. 70 shows a nucleotide sequence (SEQ ID NO: 70) of a TAHO36 (PRO51405) cDNA, wherein SEQ ID NO: 70 is a cloned designated herein as "DNA257501".

FIG. 71 shows the amino acid sequence (SEQ ID NO: 71) derived from the coding sequence of SEQ ID NO: 70 shown in FIG. 70.

FIG. 80 is shown as two panels. The panel in FIG. 80A represents normal tissue from left to right as follows: salivary gland (1), bone marrow (2), tonsil (3), fetal liver (4), blood (5), bladder (6), thymus (7), spleen (8), adrenal gland (9), fetal brain (10), small intestine (11), testes (12), heart (13), colon (14), lung (15), prostate (16), brain cerebellum (17), skeletal muscle (18), kidney (19), pancrease (20), placenta (21), uterus (22) and mammary gland (23). The panel in FIG. 80B represents the samples tested from left to right as follows: NK cells (1), neutrophils (2), CD4+ cells (3), CD8+ cells (4), CD34+ cells (5), normal B cells (6), monocytes (7), dendritic cells (8), multiple myeloma cells (9-11), memory B cells (12), naive B cells (13), centrocytes (14), centroblasts (15-16), centrocytes (17), memory B cells (18), naive B cells (19), normal B cells (20-38), multiple myeloma cells (39), CD138+ cells (40), multiple myeloma cells (41-46), tonsil plasma cells (47), bone marrow plasma cells (48), multiple myeloma cells (49-60), centrocytes (61), plasma bone marrow cells (62-70), plasma cell CD19+ (71), plasma cell CD19− (72), multiple myeloma cells (73-75).

FIGS. 84A-84B are shown as two panels. The panel in FIG. 84A represents normal tissue from left to right as follows: brain cerebellum (1), pancreas (2), fetal liver (3), placenta (4), adrenal gland (5), kidney (6), small intestine (7), colon (8), prostate (9), lung (10), uterus (11), bladder (12), bone marrow (13), tonsil (14), spleen (15), thymus (16), blood (17), fetal brain (18), salivary gland (19), testes (20), heart (21), skeletal muscle (22) and mammary gland (23). The panel in FIG. 84B represents the samples tested from left to right as follows: NK cells (1), neutrophils (2), CD4+ cells (3), CD8+ cells (4), CD34+ cells (5), normal B cells (6), monocytes (7), dendritic cells (8), multiple myeloma cells (9-11), memory B cells (12), naive B cells (13), centrocytes (14), centroblasts (15-16), centrocytes (17), memory B cells (18), naive B cells (19), normal B cells (20-38), multiple myeloma cells (39), CD138+ cells (40), multiple myeloma cells (41-46), tonsil plasma cells (47), bone marrow plasma cells (48), multiple myeloma cells (49-60), centrocytes (61), plasma bone marrow cells (62-70), plasma cell CD19+ (71), plasma cell CD19− (72), multiple myeloma cells (73-75).

FIGS. 92A-92D are shown as two panels. The panel in FIG. 92A represents normal tissue from left to right as follows: brain cerebellum (1), pancreas (2), fetal liver (3), placenta (4), adrenal gland (5), kidney (6), small intestine (7), colon (8), prostate (9), lung (10), uterus (1), bladder (12), bone marrow (13), tonsil (14), spleen (15), thymus (16), blood (17), fetal brain (18), salivary gland (19), testes (20), heart (21), skeletal muscle (22) and mammary gland (23). The panel in FIG. 92B represents the samples tested from left to right as follows: NK cells (1), neutrophils (2), CD4+ cells (3), CD8+ cells (4), CD34+ cells (5), normal B cells (6), monocytes (7), dendritic cells (8), multiple myeloma cells (9-11), memory B cells (12), naive B cells (13), centrocytes (14), centroblasts (15-16), centrocytes (17), memory B cells (18), naive B cells (19), normal B cells (20-38), multiple myeloma cells (39), CD138+ cells (40), multiple myeloma cells (41-46), tonsil plasma cells (47), bone marrow plasma cells (48), multiple myeloma cells (49-60), centrocytes (61), plasma bone marrow cells (62-70), plasma cell CD19+ (71), plasma cell CD19− (72), multiple myeloma cells (73-75).

FIGS. 93A-93B are shown as two panels. The panel in FIG. 93A represents normal tissue from left to right as follows: brain cerebellum (1), pancreas (2), fetal liver (3), placenta (4), adrenal gland (5), kidney (6), small intestine (7), colon (8), prostate (9), lung (10), uterus (11), bladder (12), bone marrow (13), tonsil (14), spleen (15), thymus (16), blood (17), fetal brain (18), salivary gland (19), testes (20), heart (21), skeletal muscle (22) and mammary gland (23). The panel in FIG. 93B represents the samples tested from left to right as follows: NK cells (1), neutrophils (2), CD4+ cells (3), CD8+ cells (4), CD34+ cells (5), normal B cells (6), monocytes (7), dendritic cells (8), multiple myeloma cells (9-11), memory B cells (12), naive B cells (13), centrocytes (14), centroblasts (15-16), centrocytes (17), memory B cells (18), naive B cells (19), normal B cells (20-38), multiple myeloma cells (39), CD138+ cells (40), multiple myeloma cells (41-46), tonsil plasma cells (47), bone marrow plasma cells (48), multiple myeloma cells (49-60), centrocytes (61), plasma bone marrow cells (62-70), plasma cell CD19+ (71), plasma cell CD19− (72), multiple myeloma cells (73-75).

FIGS. 94A-94B are shown as two panels. The panel in FIG. 94A represents normal tissue from left to right as follows: brain cerebellum (1), pancreas (2), fetal liver (3), placenta (4), adrenal gland (5), kidney (6), small intestine (7), colon (8), prostate (9), lung (10), uterus (1), bladder (12), bone marrow (13), tonsil (14), spleen (15), thymus (16), blood (17), fetal brain (18), salivary gland (19), testes (20), heart (21), skeletal muscle (22) and mammary gland (23). The panel in FIG. 94B represents the samples tested from left to right as follows: NK cells (1), neutrophils (2), CD4+ cells (3), CD8+ cells (4), CD34+ cells (5), normal B cells (6), monocytes (7), dendritic cells (8), multiple myeloma cells (9-11), memory B cells (12), naive B cells (13), centrocytes (14), centroblasts (15-16), centrocytes (17), memory B cells (18), naive B cells (19), normal B cells (20-38), multiple myeloma cells (39), CD138+ cells (40), multiple myeloma cells (41-46), tonsil plasma cells (47), bone marrow plasma cells (48), multiple myeloma cells (49-60), centrocytes (61), plasma bone marrow cells (62-70), plasma cell CD19+ (71), plasma cell CD19− (72), multiple myeloma cells (73-75).

FIGS. 95A-95B are shown as two panels. The panel in FIG. 95A represents normal tissue from left to right as follows: brain cerebellum (1), pancreas (2), fetal liver (3), placenta (4), adrenal gland (5), kidney (6), small intestine (7), colon (8), prostate (9), lung (10), uterus (11), bladder (12), bone marrow (13), tonsil (14), spleen (15), thymus (16), blood (17), fetal brain (18), salivary gland (19), testes (20), heart (21), skeletal muscle (22) and mammary gland (23). The panel in FIG. 95B represents the samples tested from left to right as follows: NK cells (1), neutrophils (2), CD4+ cells (3), CD8+ cells (4), CD34+ cells (5), normal B cells (6), monocytes (7), dendritic cells (8), multiple myeloma cells (9-11), memory B cells (12), naive B cells (13), centrocytes (14), centroblasts (15-16), centrocytes (17), memory B cells (18), naive B cells (19), normal B cells (20-38), multiple myeloma cells (39), CD138+ cells (40), multiple myeloma cells (41-46), tonsil plasma cells (47), bone marrow plasma cells (48), multiple myeloma cells (49-60), centrocytes (61), plasma bone marrow cells (62-70), plasma cell CD19+ (71), plasma cell CD19− (72), multiple myeloma cells (73-75).

FIGS. 96A-96B are shown as two panels. The panel in FIG. 96A represents normal tissue from left to right as follows: brain cerebellum (1), pancreas (2), fetal liver (3), placenta (4), adrenal gland (5), kidney (6), small intestine (7), colon (8), prostate (9), lung (10), uterus (11), bladder (12), bone marrow (13), tonsil (14), spleen (15), thymus (16), blood (17), fetal brain (18), salivary gland (19), testes (20), heart (21), skeletal muscle (22) and mammary gland (23). The panel in FIG. 96B represents the samples tested from left to right as follows: NK cells (1), neutrophils (2), CD4+ cells (3), CD8+ cells (4), CD34+ cells (5), normal B cells (6), monocytes (7), dendritic cells (8), multiple myeloma cells (9-11), memory B cells (12), naive B cells (13), centrocytes (14), centroblasts (15-16), centrocytes (17), memory B cells (18), naive B cells (19), normal B cells (20-38), multiple myeloma cells (39), CD138+ cells (40), multiple myeloma cells (41-46), tonsil plasma cells (47), bone marrow plasma cells (48), multiple myeloma cells (49-60), centrocytes (61), plasma bone marrow cells (62-70), plasma cell CD19+ (71), plasma cell CD19− (72), multiple myeloma cells (73-75).

FIGS. 97A-97B are shown as two panels. The panel in FIG. 97A represents normal tissue from left to right as follows: brain cerebellum (1), pancreas (2), fetal liver (3), placenta (4), adrenal gland (5), kidney (6), small intestine (7), colon (8), prostate (9), lung (10), uterus (11), bladder (12), bone marrow (13), tonsil (14), spleen (15), thymus (16), blood (17), fetal brain (18), salivary gland (19), testes (20), heart (21), skeletal muscle (22) and mammary gland (23). The panel in FIG. 97B represents the samples tested from left to right as follows: NK cells (1), neutrophils (2), CD4+ cells (3), CD8+ cells (4), CD34+ cells (5), normal B cells (6), monocytes (7), dendritic cells (8), multiple myeloma cells (9-11), memory B cells (12), naive B cells (13), centrocytes (14), centroblasts (15-16), centrocytes (17), memory B cells (18), naive B cells (19), normal B cells (20-38), multiple myeloma cells (39), CD138+ cells (40), multiple myeloma cells (41-46), tonsil plasma cells (47), bone marrow plasma cells (48), multiple myeloma cells (49-60), centrocytes (61), plasma bone marrow cells (62-70), plasma cell CD19+ (71), plasma cell CD19− (72), multiple myeloma cells (73-75).

FIGS. 98A-98B are shown as two panels. The panel in FIG. 98A represents normal tissue from left to right as follows: brain cerebellum (1), pancreas (2), fetal liver (3), placenta (4), adrenal gland (5), kidney (6), small intestine (7), colon (8), prostate (9), lung (10), uterus (11), bladder (12), bone marrow (13), tonsil (14), spleen (15), thymus (16), blood (17), fetal brain (18), salivary gland (19), testes (20), heart (21), skeletal muscle (22) and mammary gland (23). The panel in FIG. 98B represents the samples tested from left to right as follows: NK cells (1), neutrophils (2), CD4+ cells (3), CD8+ cells (4), CD34+ cells (5), normal B cells (6), monocytes (7), dendritic cells (8), multiple myeloma cells (9-11), memory B cells (12), naive B cells (13), centrocytes (14), centroblasts (15-16), centrocytes (17), memory B cells (18), naive B cells (19), normal B cells (20-38), multiple myeloma cells (39), CD138+ cells (40), multiple myeloma cells (41-46), tonsil plasma cells (47), bone marrow plasma cells (48), multiple myeloma cells (49-60), centrocytes (61), plasma bone marrow cells (62-70), plasma cell CD19+ (71), plasma cell CD19− (72), multiple myeloma cells (73-75).

FIGS. 98A-98B are shown as two panels. The panel in FIG. 94A represents normal tissue from left to right as follows: brain cerebellum (1), pancreas (2), fetal liver (3), placenta (4), adrenal gland (5), kidney (6), small intestine (7), colon (8), prostate (9), lung (10), uterus (11), bladder (12), bone marrow (13), tonsil (14), spleen (15), thymus (16), blood (17), fetal brain (18), salivary gland (19), testes (20), heart (21), skeletal muscle (22) and mammary gland (23). The panel in FIG. 94B represents the samples tested from left to right as follows: NK cells (1), neutrophils (2), CD4+ cells (3), CD8+ cells (4), CD34+ cells (5), normal B cells (6), monocytes (7), dendritic cells (8), multiple myeloma cells (9-11), memory B cells (12), naive B cells (13), centrocytes (14), centroblasts (15-16), centrocytes (17), memory B cells (18), naive B cells (19), normal B cells (20-38), multiple myeloma cells (39), CD138+ cells (40), multiple myeloma cells (41-46), tonsil plasma cells (47), bone marrow plasma cells (48), multiple myeloma cells (49-60), centrocytes (61), plasma bone marrow cells (62-70), plasma cell CD19+ (71), plasma cell CD19− (72), multiple myeloma cells (73-75).

FIGS. 100A-100B are shown as two panels. The panel in FIG. 100A represents normal tissue from left to right as follows: brain cerebellum (1), pancreas (2), fetal liver (3), placenta (4), adrenal gland (5), kidney (6), small intestine (7), colon (8), prostate (9), lung (10), uterus (11), bladder (12), bone marrow (13), tonsil (14), spleen (15), thymus (16), blood (17), fetal brain (18), salivary gland (19), testes (20), heart (21), skeletal muscle (22) and mammary gland (23). The panel in FIG. 100B represents the samples tested from left to right as follows: NK cells (1), neutrophils (2), CD4+ cells (3), CD8+ cells (4), CD34+ cells (5), normal B cells (6), monocytes (7), dendritic cells (8), multiple myeloma cells (9-11), memory B cells (12), naive B cells (13), centrocytes (14), centroblasts (15-16), centrocytes (17), memory B cells (18), naive B cells (19), normal B cells (20-38), multiple myeloma cells (39), CD138+ cells (40), multiple myeloma cells (41-46), tonsil plasma cells (47), bone marrow plasma cells (48), multiple myeloma cells (49-60), centrocytes (61), plasma bone marrow cells (62-70), plasma cell CD19+ (71), plasma cell CD19− (72), multiple myeloma cells (73-75).

FIG. 101 show microarray data showing the expression of TAHO36 in normal samples and in diseased samples, such as significant expression in in multiple myeloma.

DETAILED DESCRIPTION OF THE PREFERRED EMBODIMENTS

I. Definitions

Figure 72:
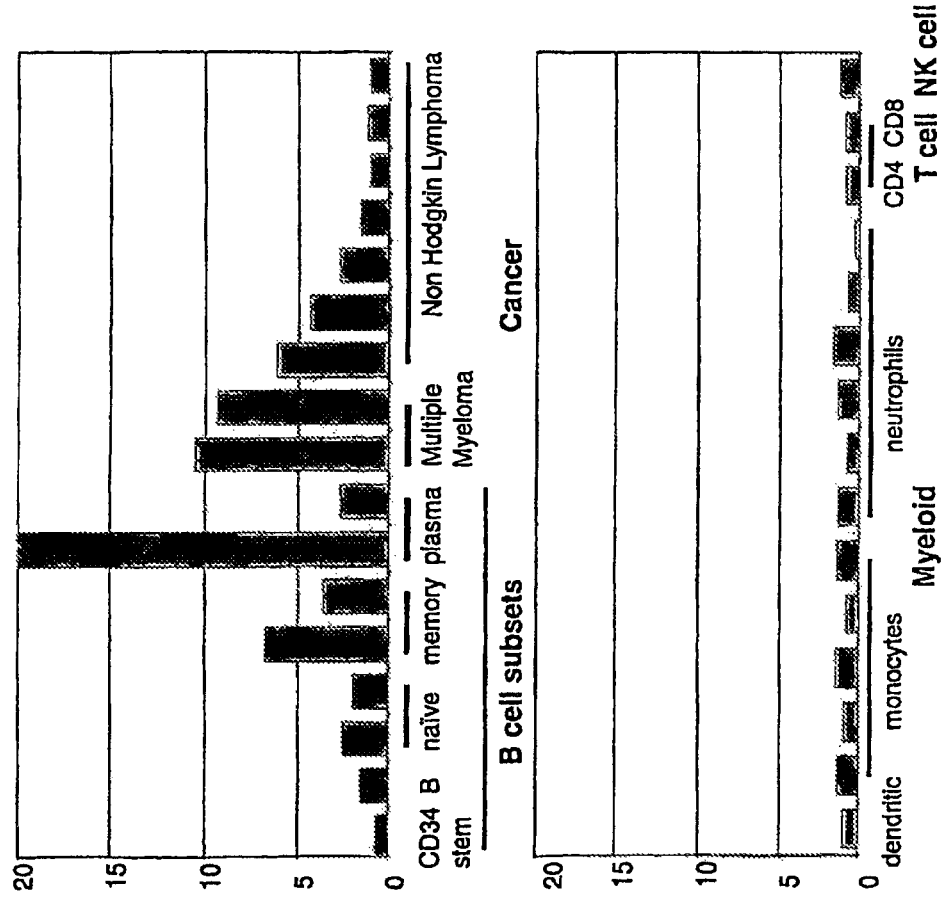
FIG. 72 summarizes the Agilent human microarrays that demonstrate significant expression of TAHO15 in bone marrow plasma cells and multiple myeloma cells as compared to low expression in non-B cells, such as neutrophils, T cells and natural killer (NK) cells. TAHO15 is also significantly expressed in some non-hodgkin lymphoma cells.
Figure 73A:
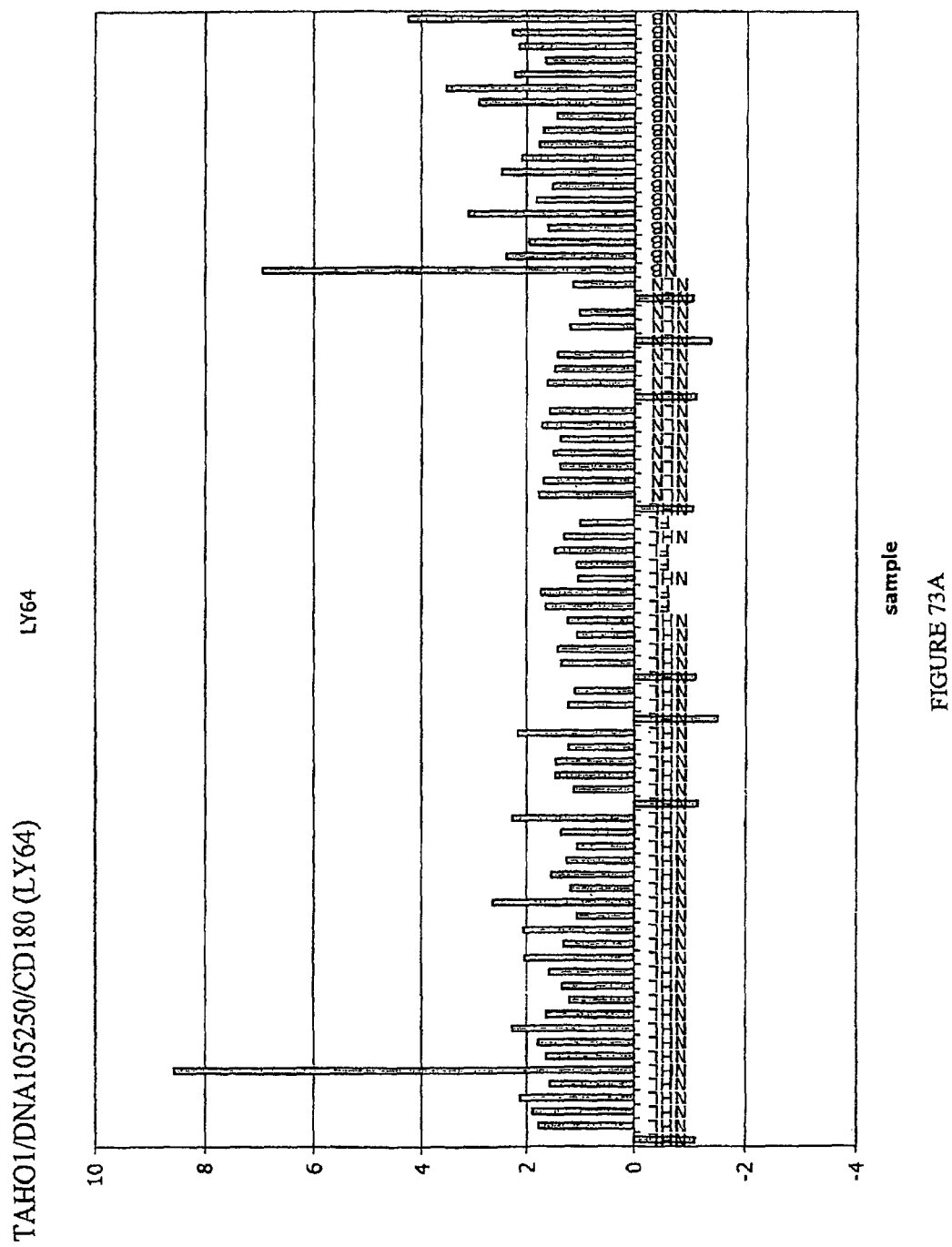
FIGS. 73A-73D show microarray data showing the expression of TAHO1 in normal samples and in diseased samples, such as significant expression in Non-Hodgkin's Lyphoma (NHL) samples and normal B cells (NB). Abbreviations used in the Figures are designated as follows: Non-Hodgkin's Lymphoma (NHL), follicular lymphoma (FL), normal lymph node (NLN), normal B cells (NB), multiple myeloma cells (MM), small intestine (s. intestine), fetal liver (f. liver), smooth muscle (s. muscle), fetal brain (f. brain), natural killer cells (NK), neutrophils (N'phil), dendrocytes (DC), memory B cells (mem B), plasma cells (PC), bone marrow plasma cells (BM PC).
Figure 73B:
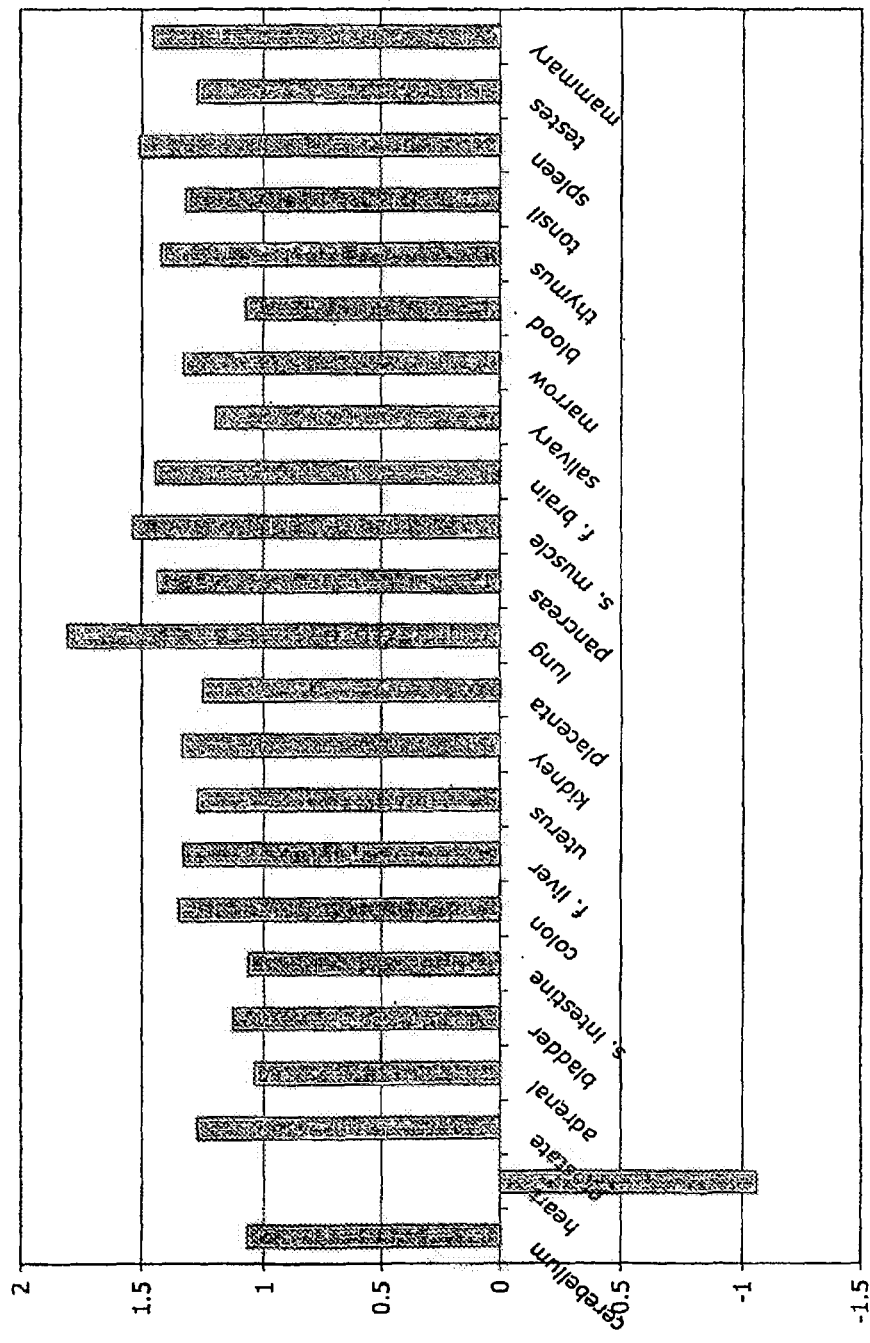
Figure 73C:
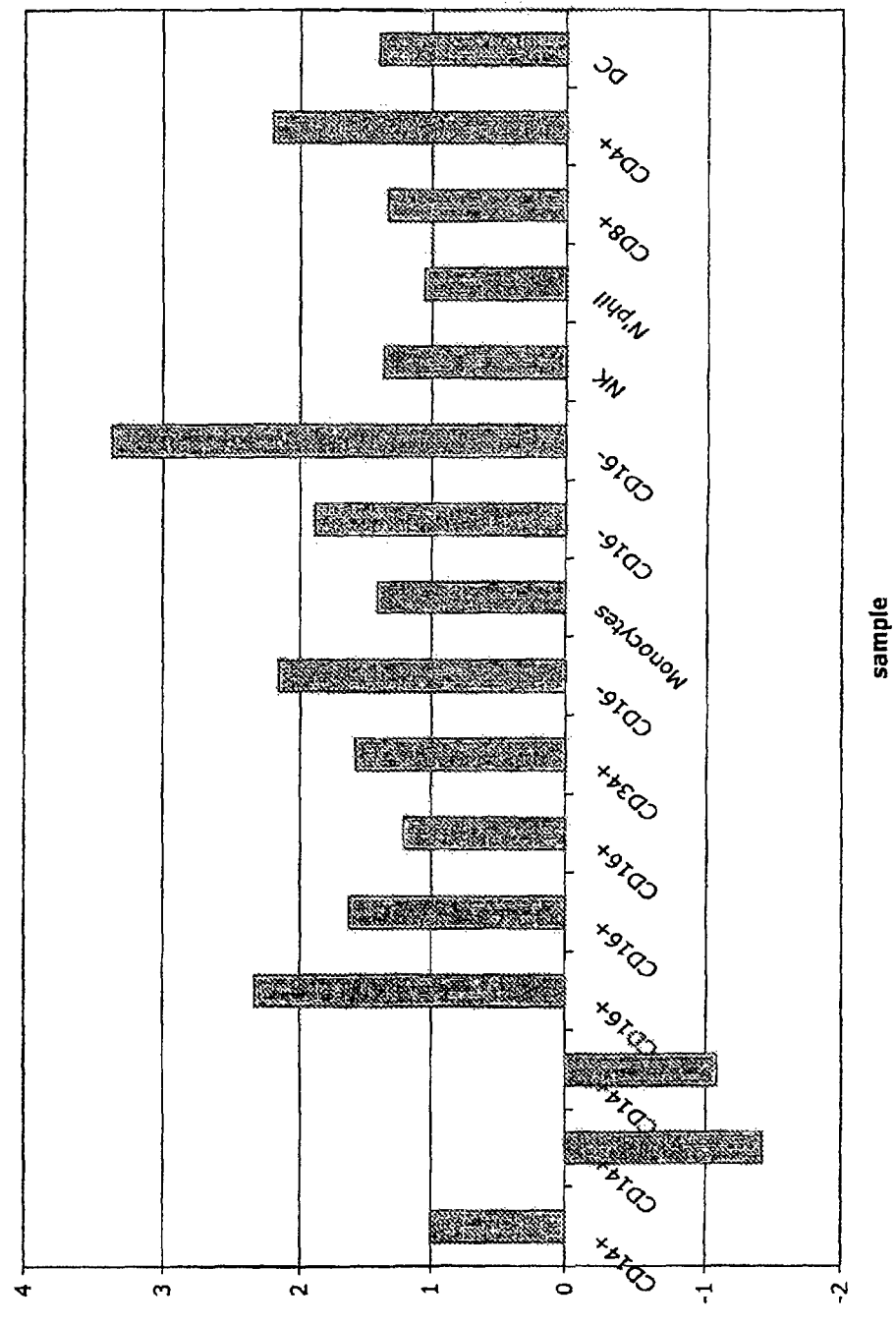
Figure 73D:
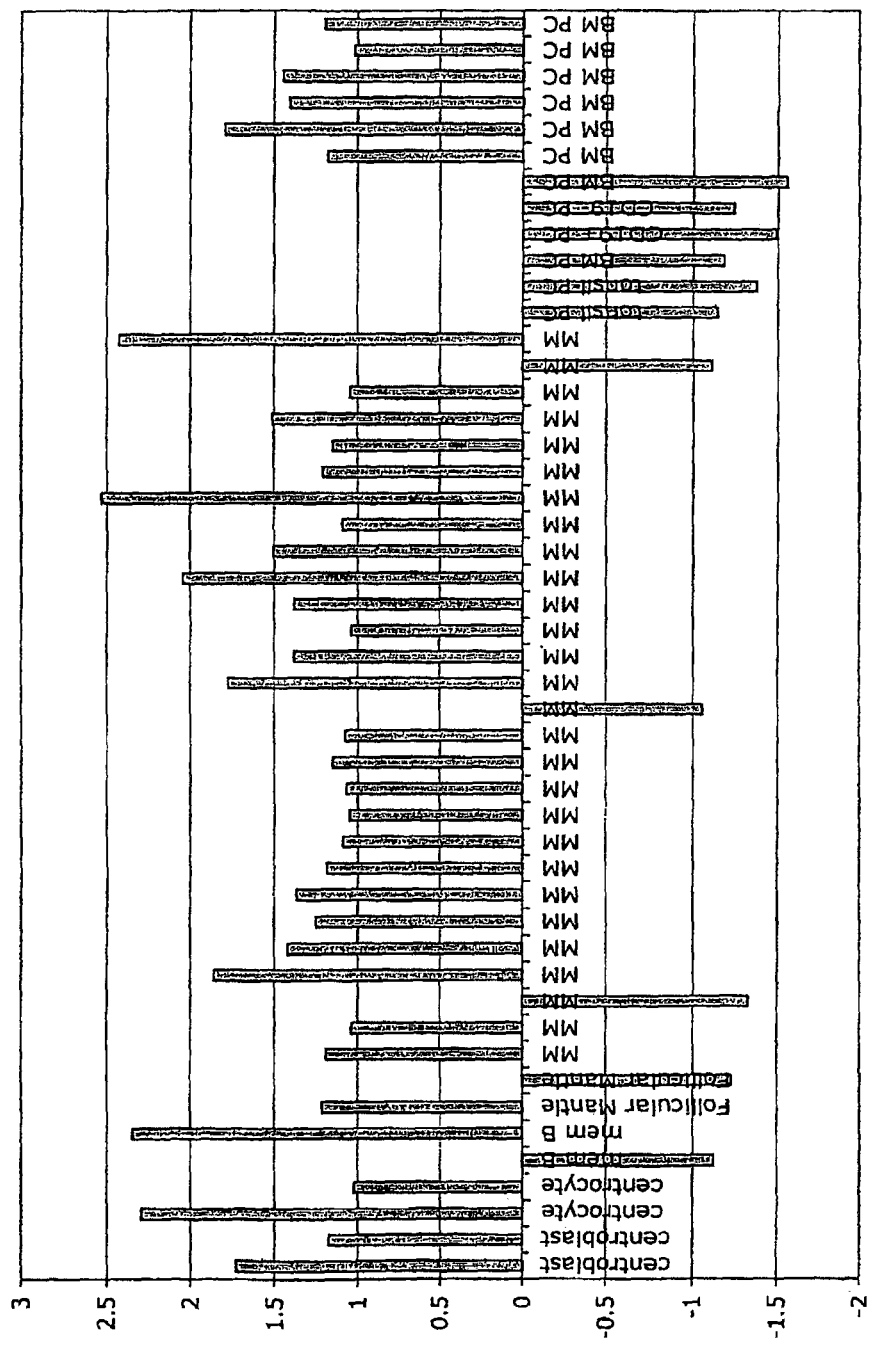
Figure 74A:
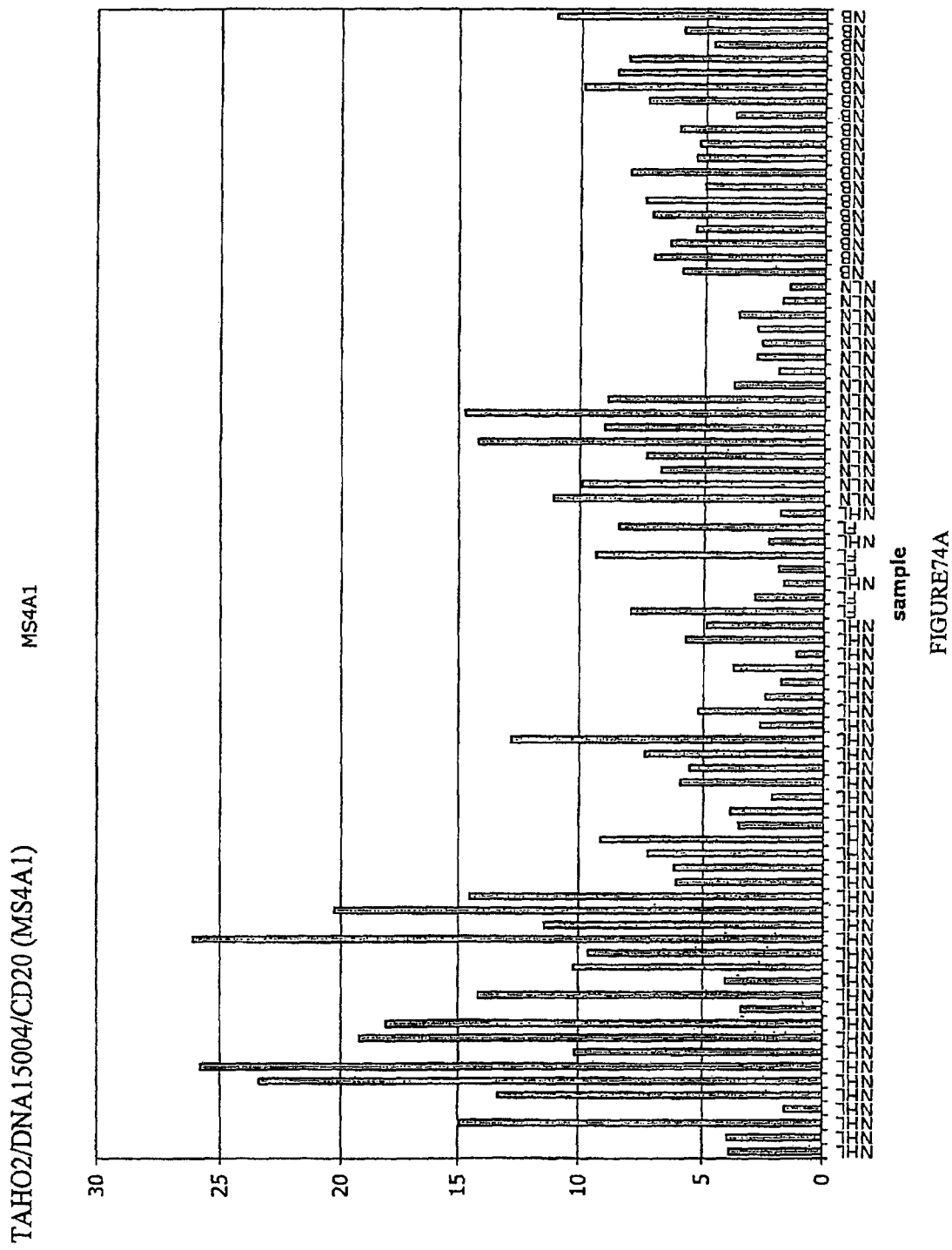
FIGS. 74A-74D show microarray data showing the expression of TAHO2 in normal samples and in diseased samples, such as significant expression in NHL samples, follicular lymphoma (FL), normal lymph node (NLN), normal B cells (NB). Abbreviations used in the Figures are designated as follows: Non-Hodgkin's Lymphoma (NHL), follicular lymphoma (FL), normal lymph node (NLN), normal B cells (NB), multiple myeloma cells (MM), small intestine (s. intestine), fetal liver (f. liver), smooth muscle (s. muscle), fetal brain (f. brain), natural killer cells (NK), neutrophils (N'phil), dendrocytes (DC), memory B cells (mem B), plasma cells (PC), bone marrow plasma cells (BM PC).
Figure 74B:
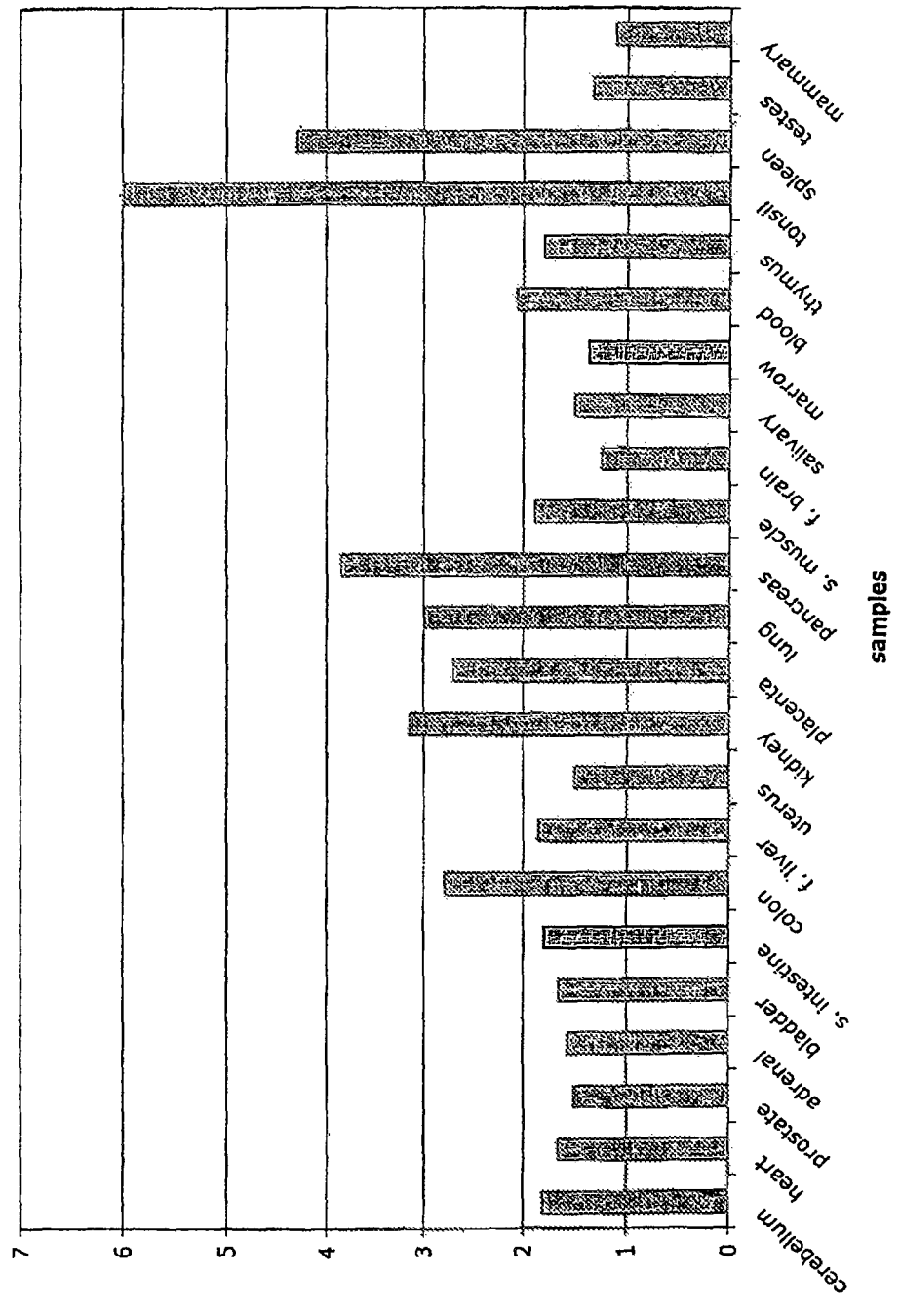
Figure 74C:
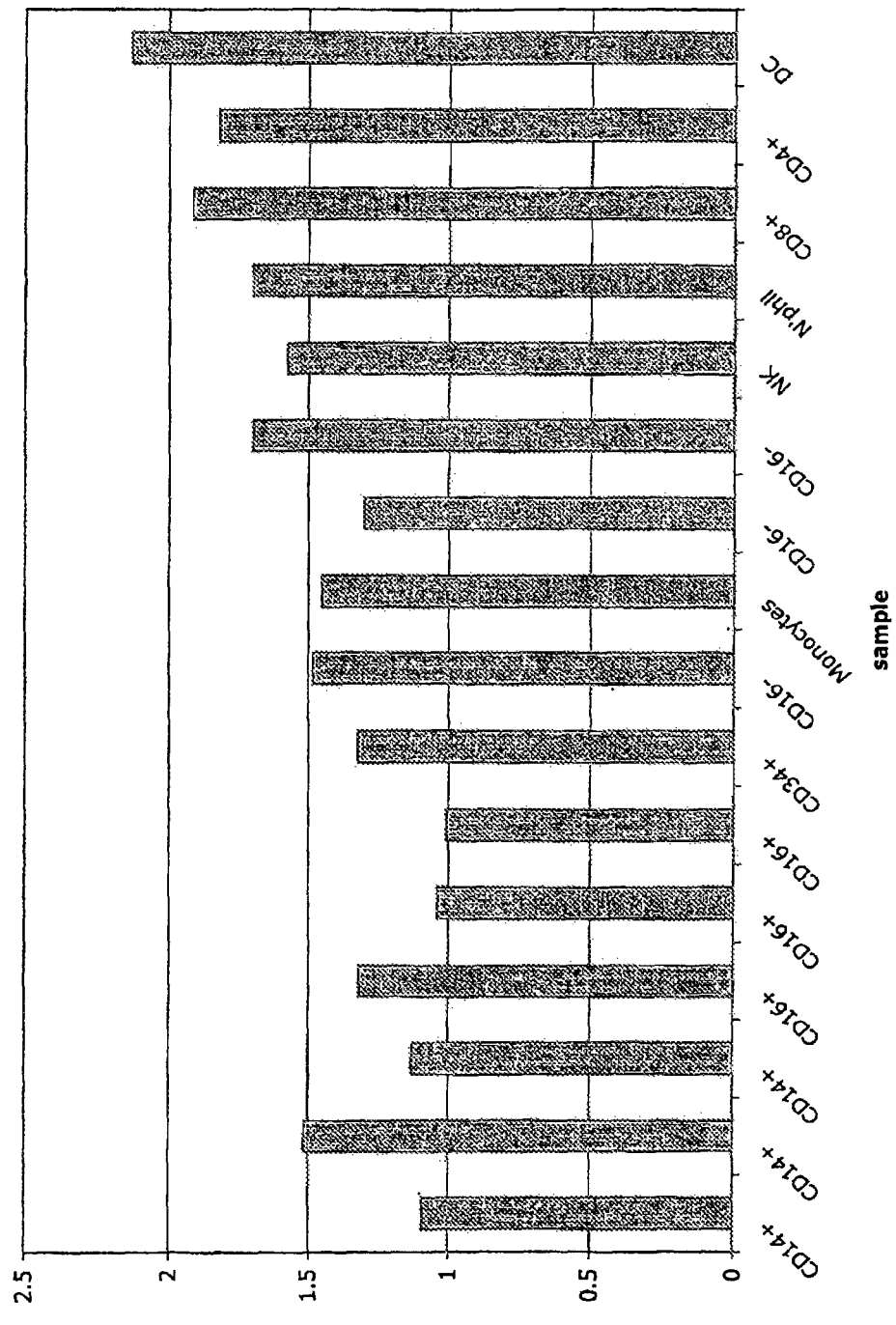
Figure 74D:
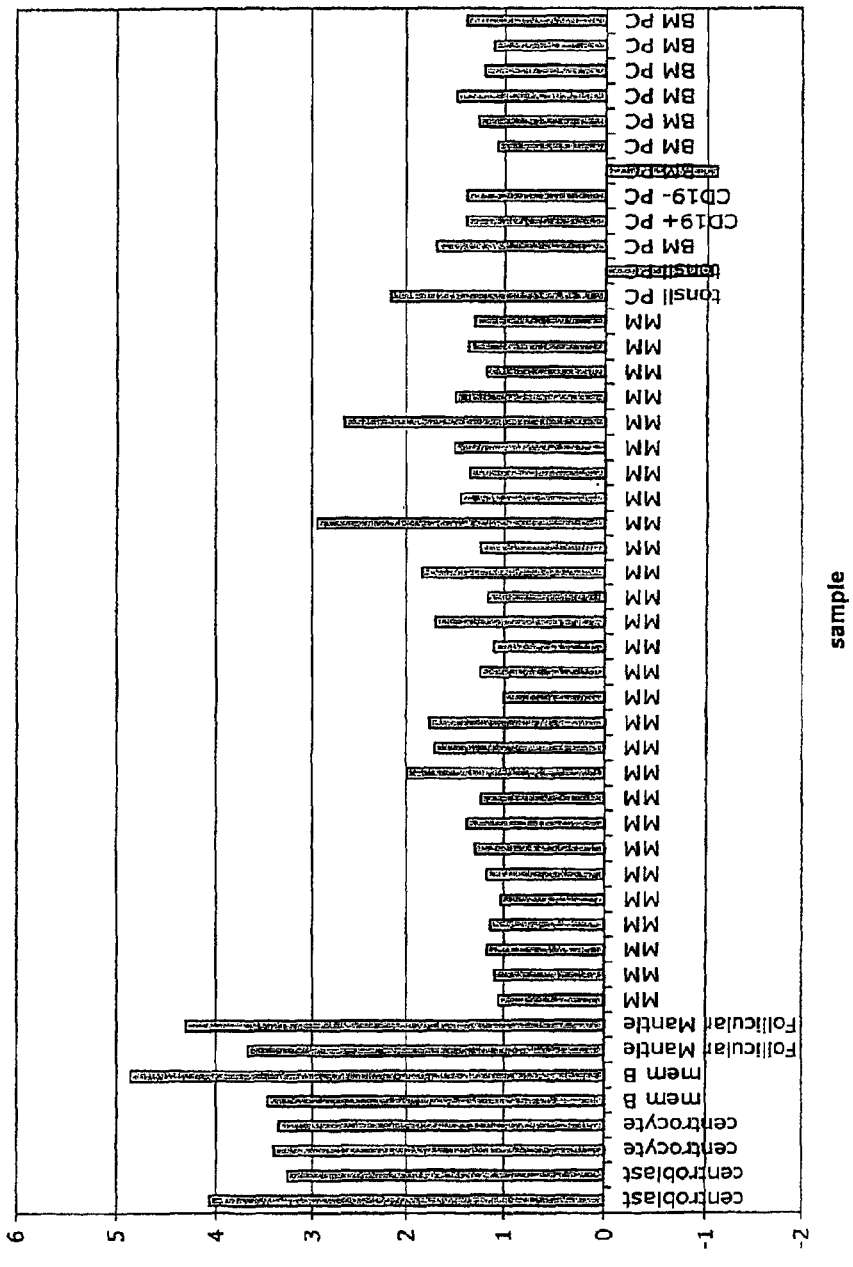
Figure 75A:
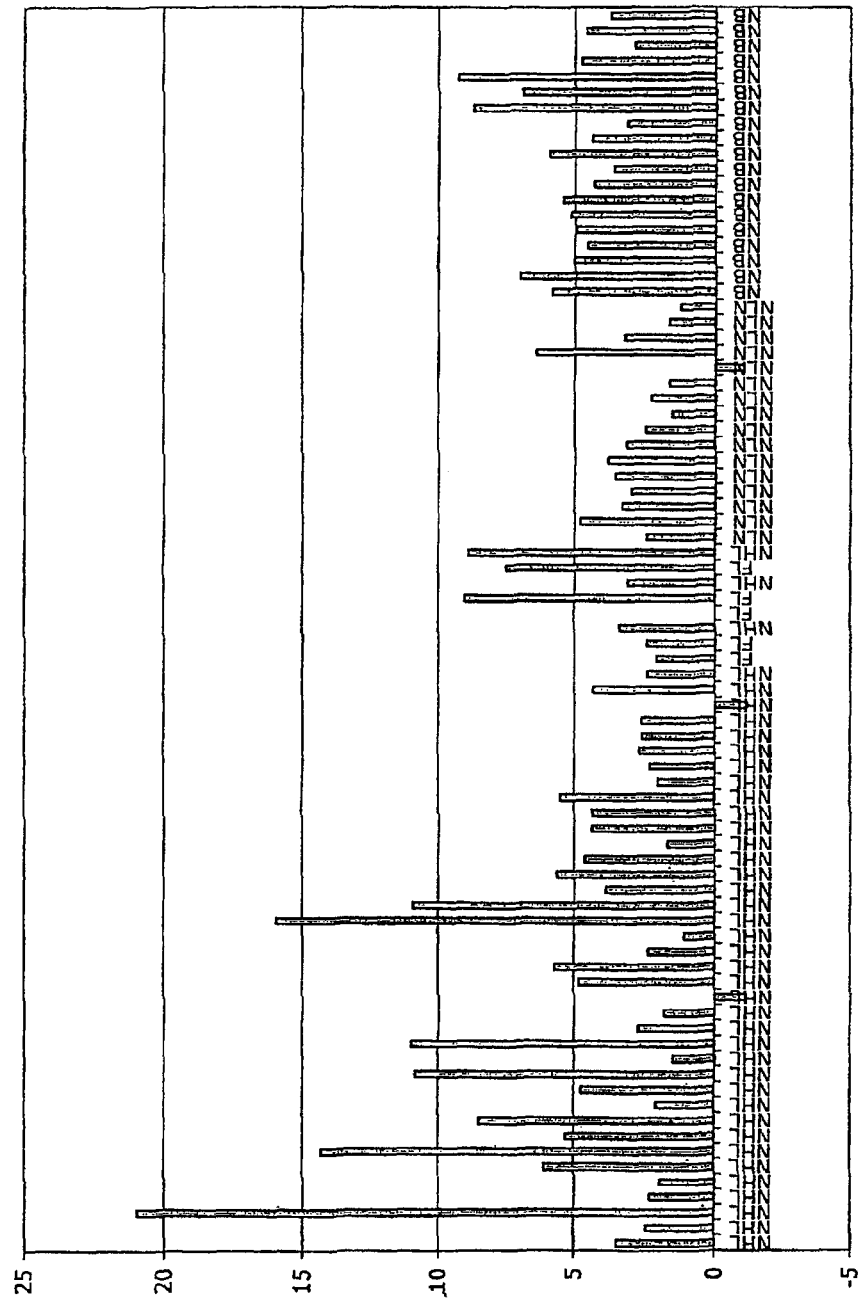
FIGS. 75A-75D show microarray data showing the expression of TAHO3 in normal samples and in diseased samples, such as significant expression in NHL samples, follicular lymphoma (FL) and memory B cells (mem B). Abbreviations used in the Figures are designated as follows: Non-Hodgkin's Lymphoma (NHL), follicular lymphoma (FL), normal lymph node (NLN), normal B cells (NB), multiple myeloma cells (MM), small intestine (s. intestine), fetal liver (f. liver), smooth muscle (s. muscle), fetal brain (f. brain), natural killer cells (NK), neutrophils (N'phil), dendrocytes (DC), memory B cells (mem B), plasma cells (PC), bone marrow plasma cells (BM PC).
Figure 75B:
Figure 75C:
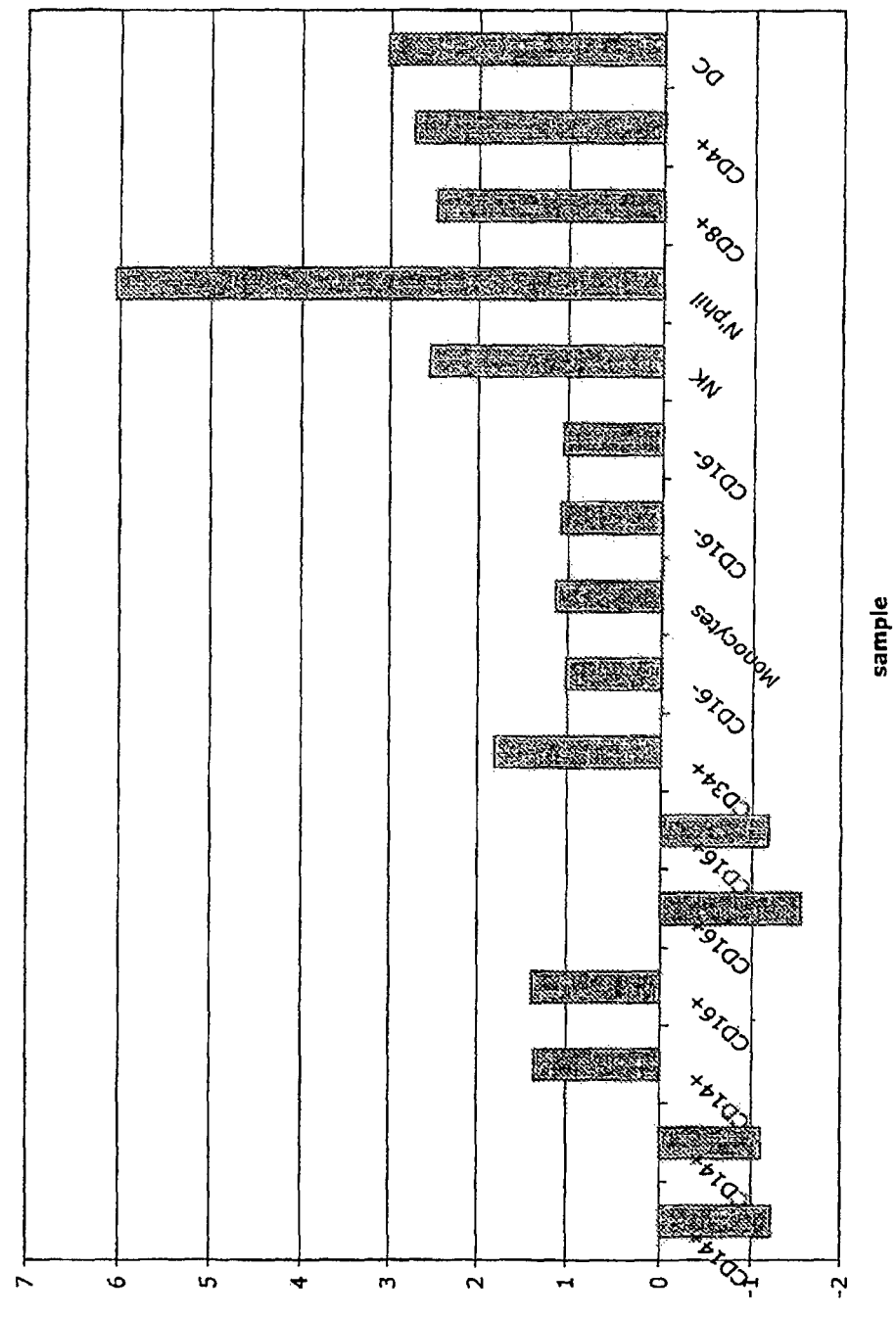
Figure 75D:
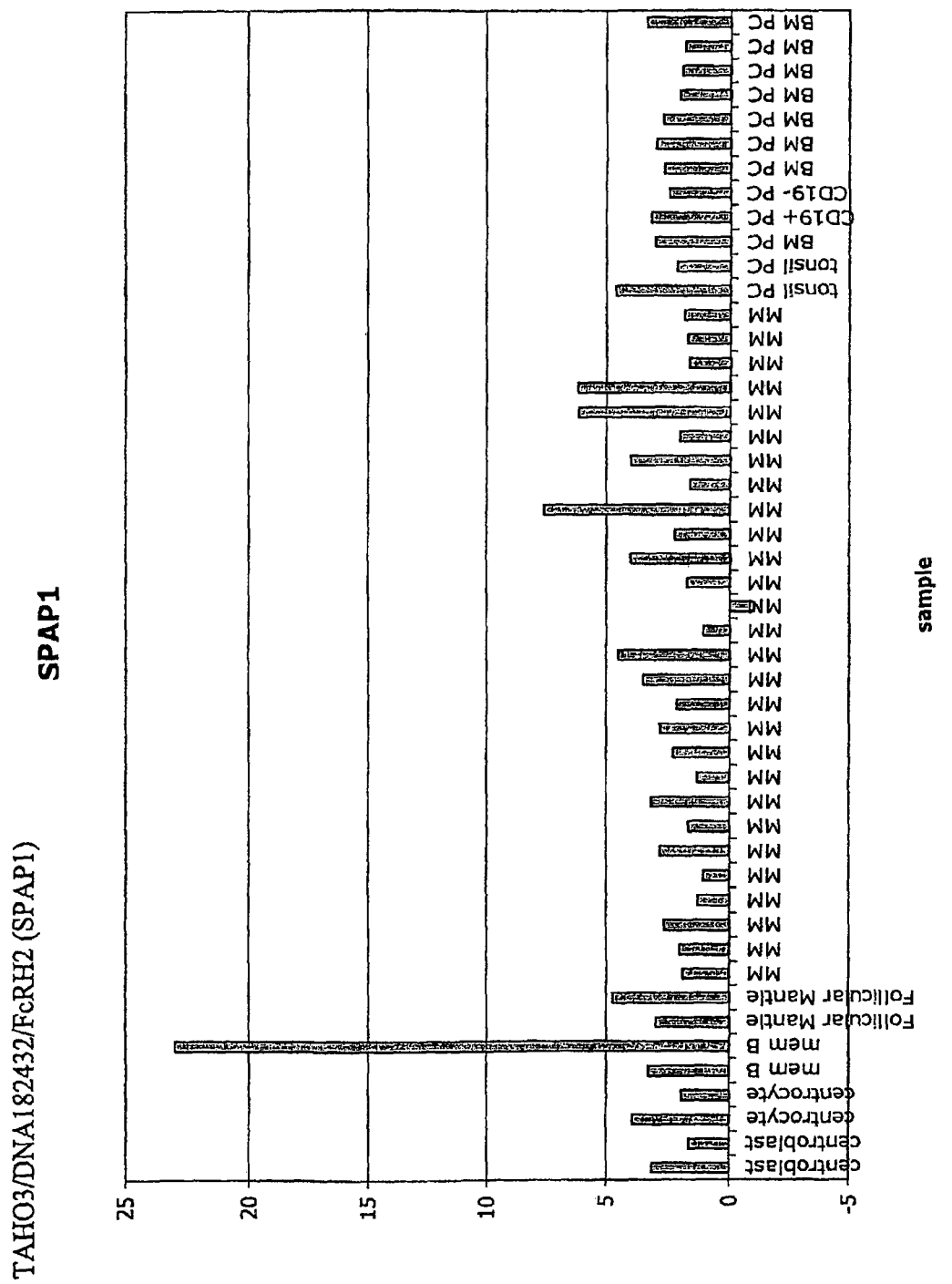
Figure 76A:
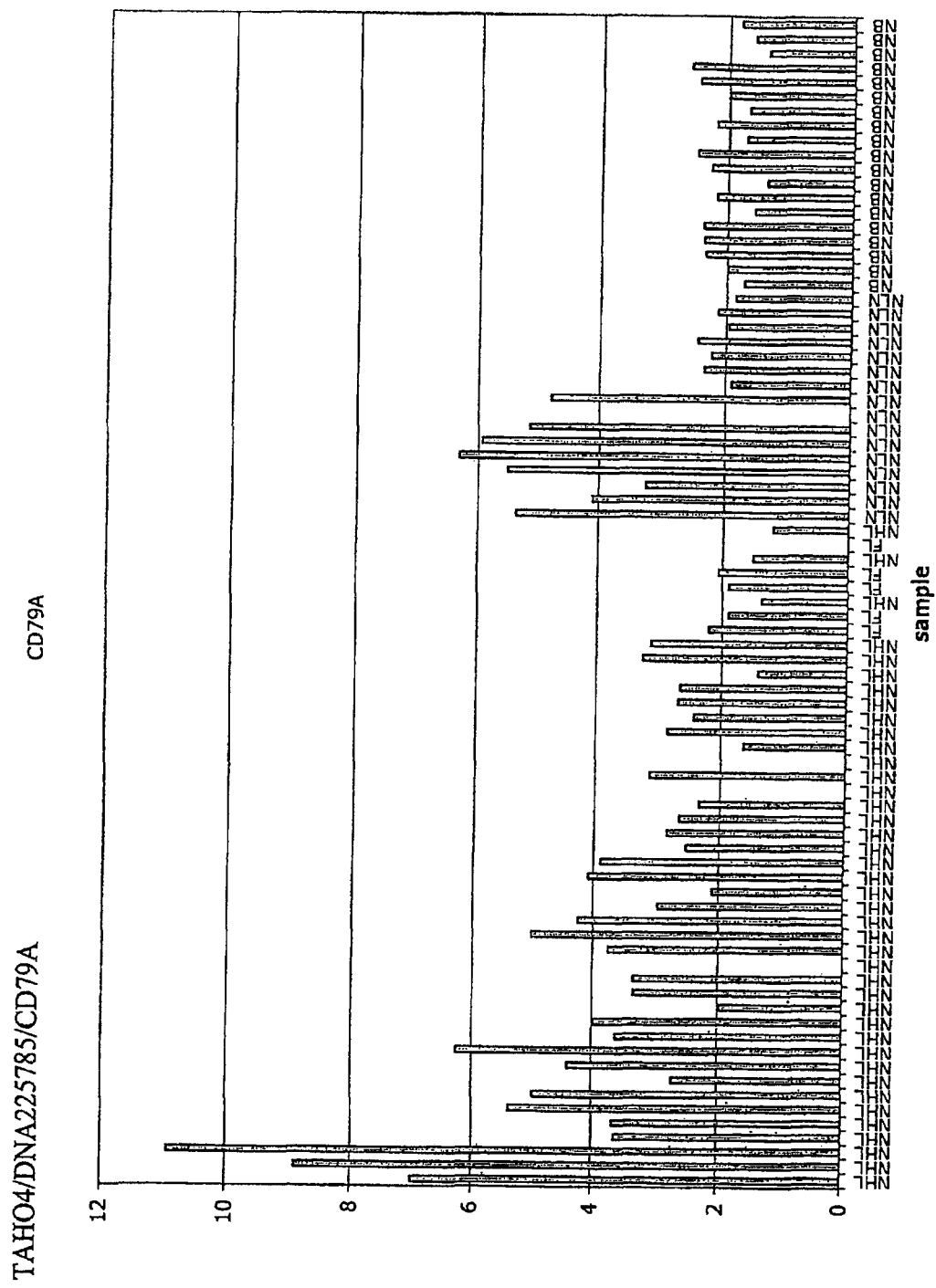
FIGS. 76A-76D show microarray data showing the expression of TAHO4 in normal samples and in diseased samples, such as significant expression in NHL samples and multiple myeloma samples (MM), and normal cerebellum and normal blood. Abbreviations used in the Figures are designated as follows: Non-Hodgkin's Lymphoma (NHL), follicular lymphoma (FL), normal lymph node (NLN), normal B cells (NB), multiple myeloma cells (MM), small intestine (s. intestine), fetal liver (f. liver), smooth muscle (s. muscle), fetal brain (f. brain), natural killer cells (NK), neutrophils (N'phil), dendrocytes (DC), memory B cells (mem B), plasma cells (PC), bone marrow plasma cells (BM PC).
Figure 76B:
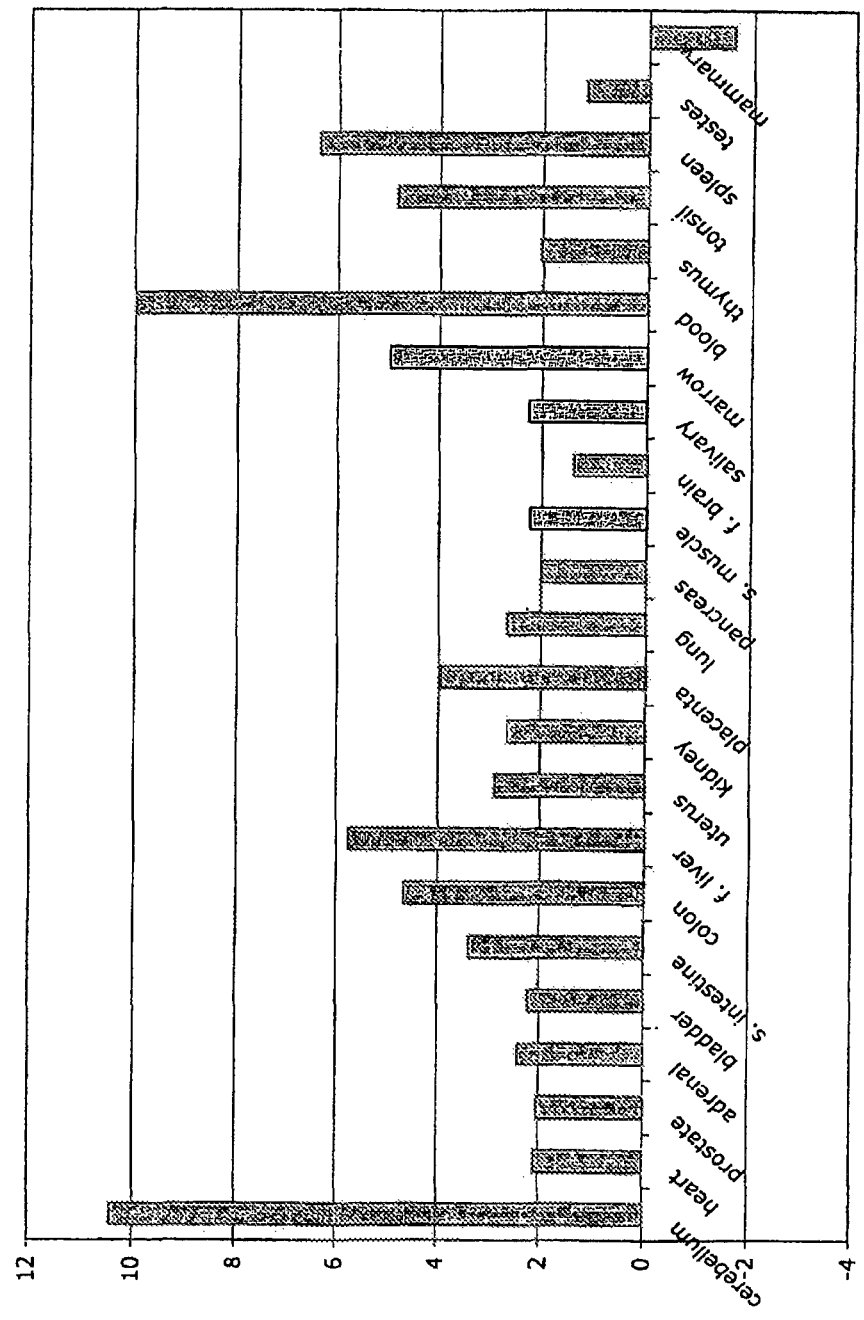
Figure 76C:
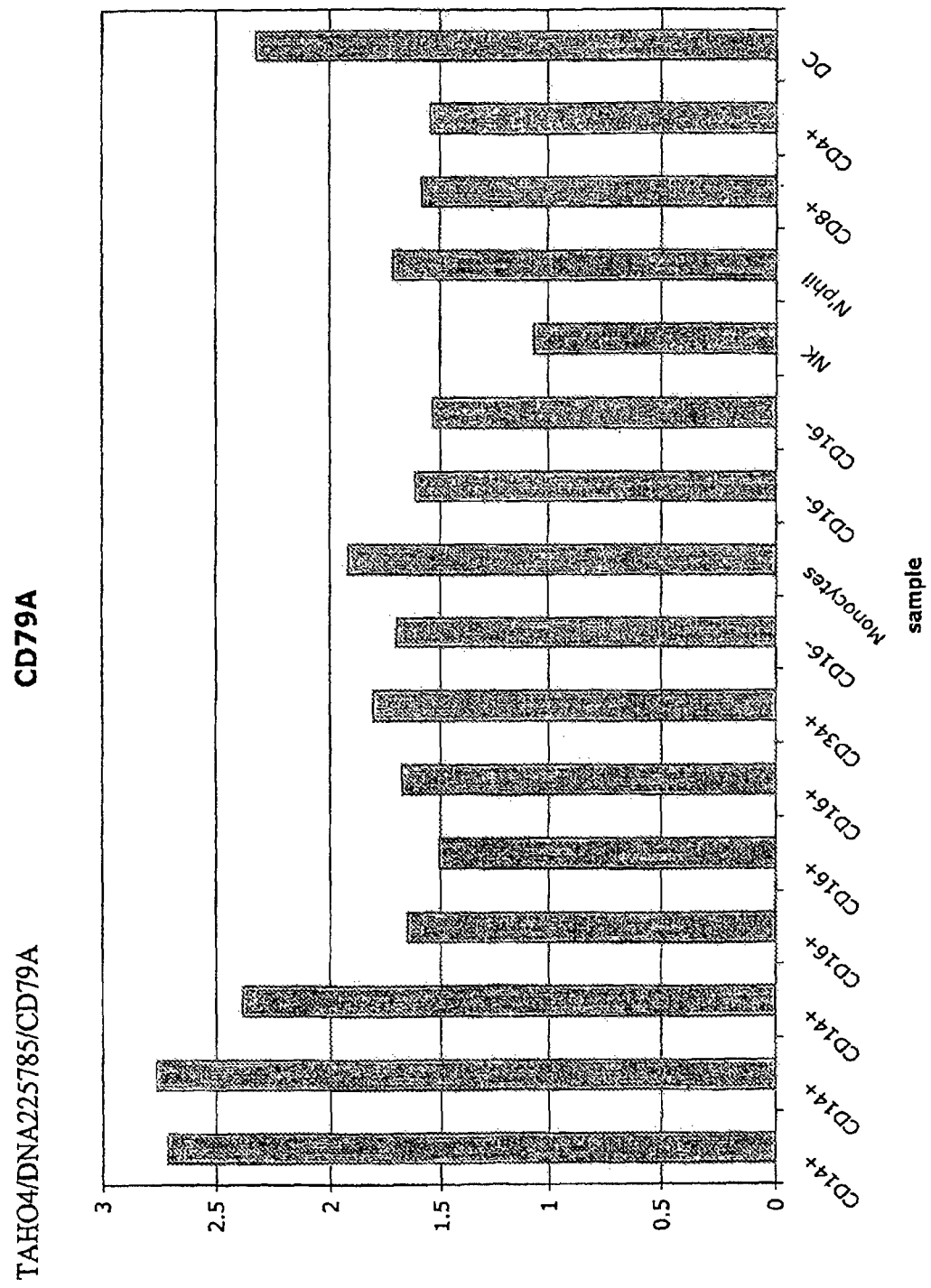
Figure 76D:
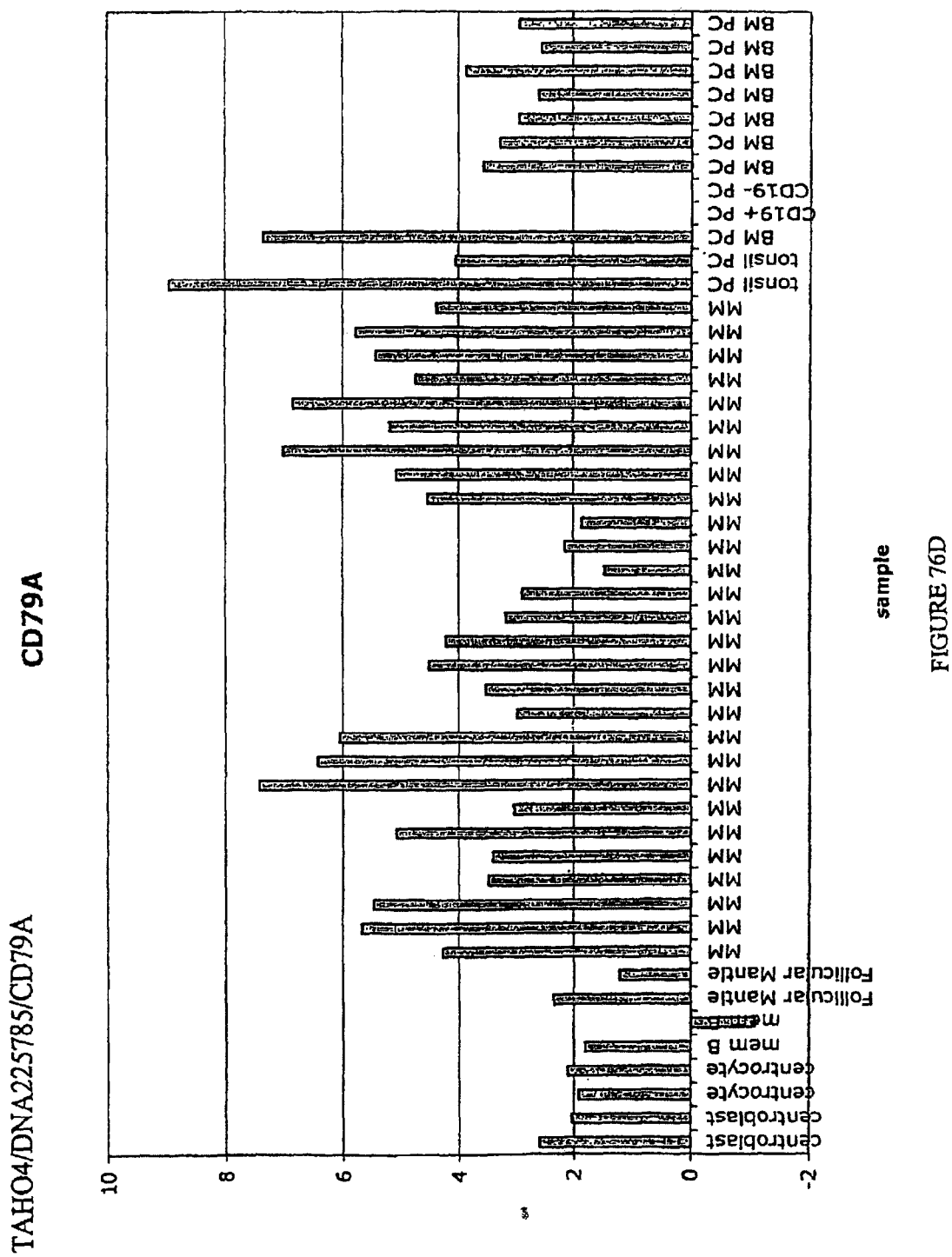
Figure 77A:
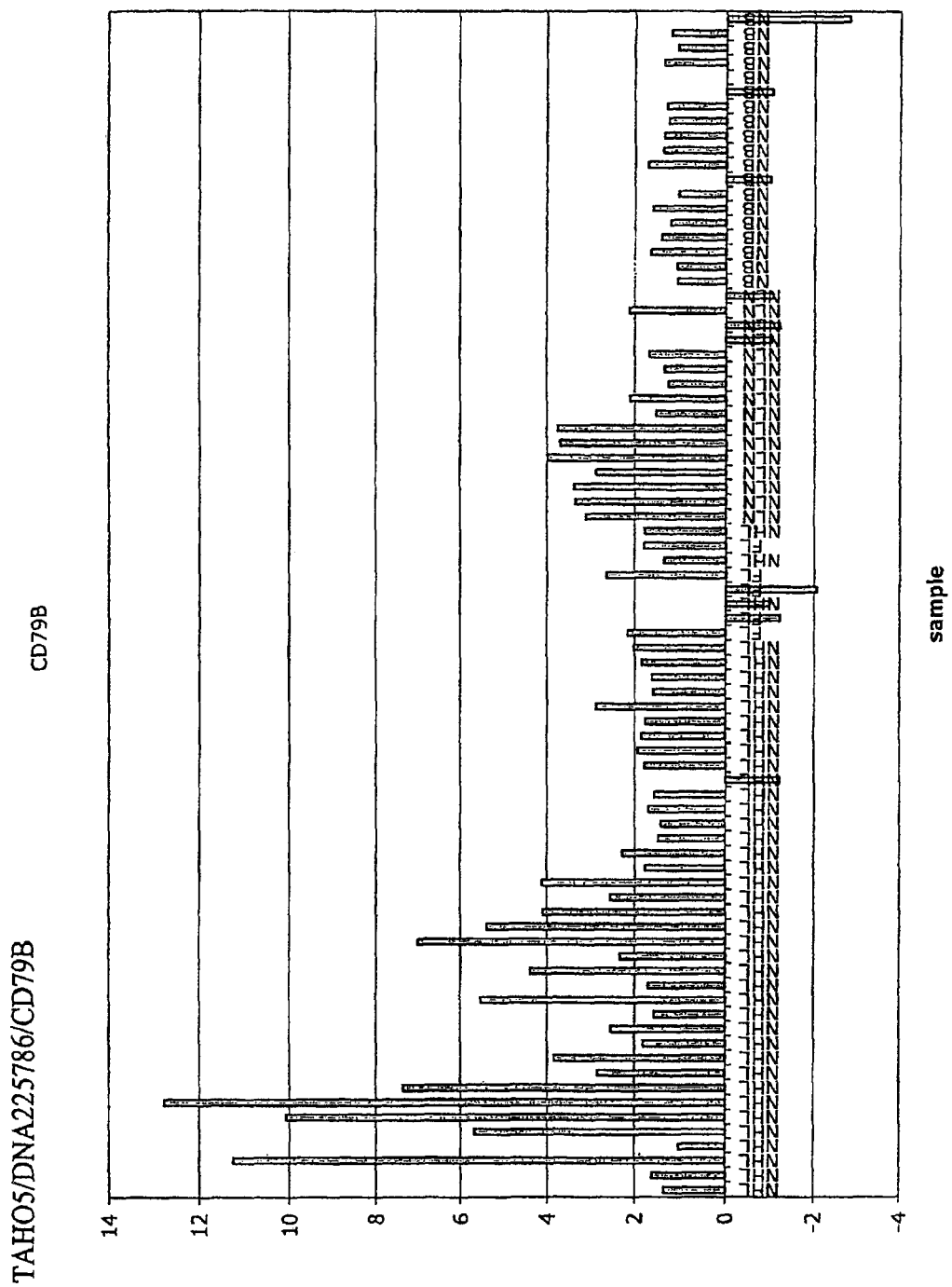
FIGS. 77A-77D show microarray data showing the expression of TAHO5 in normal samples and in diseased samples, such as significant expression in NHL samples. Abbreviations used in the Figures are designated as follows: Non-Hodgkin's Lymphoma (NHL), follicular lymphoma (FL), normal lymph node (NLN), normal B cells (NB), multiple myeloma cells (MM), small intestine (s. intestine), fetal liver (f. liver), smooth muscle (s. muscle), fetal brain (f. brain), natural killer cells (NK), neutrophils (N'phil), dendrocytes (DC), memory B cells (mem B), plasma cells (PC), bone marrow plasma cells (BM PC).
Figure 77B:
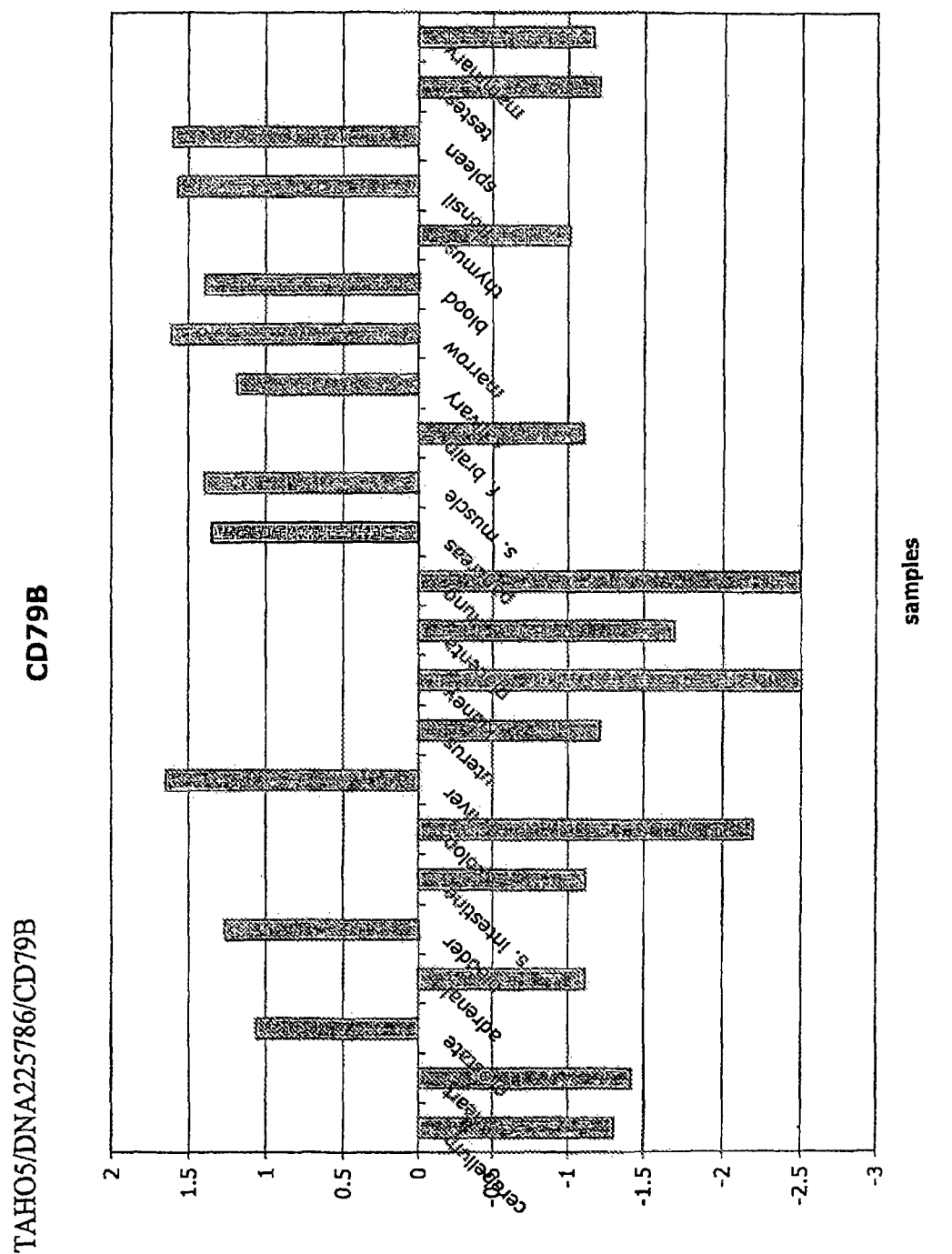
Figure 77C:
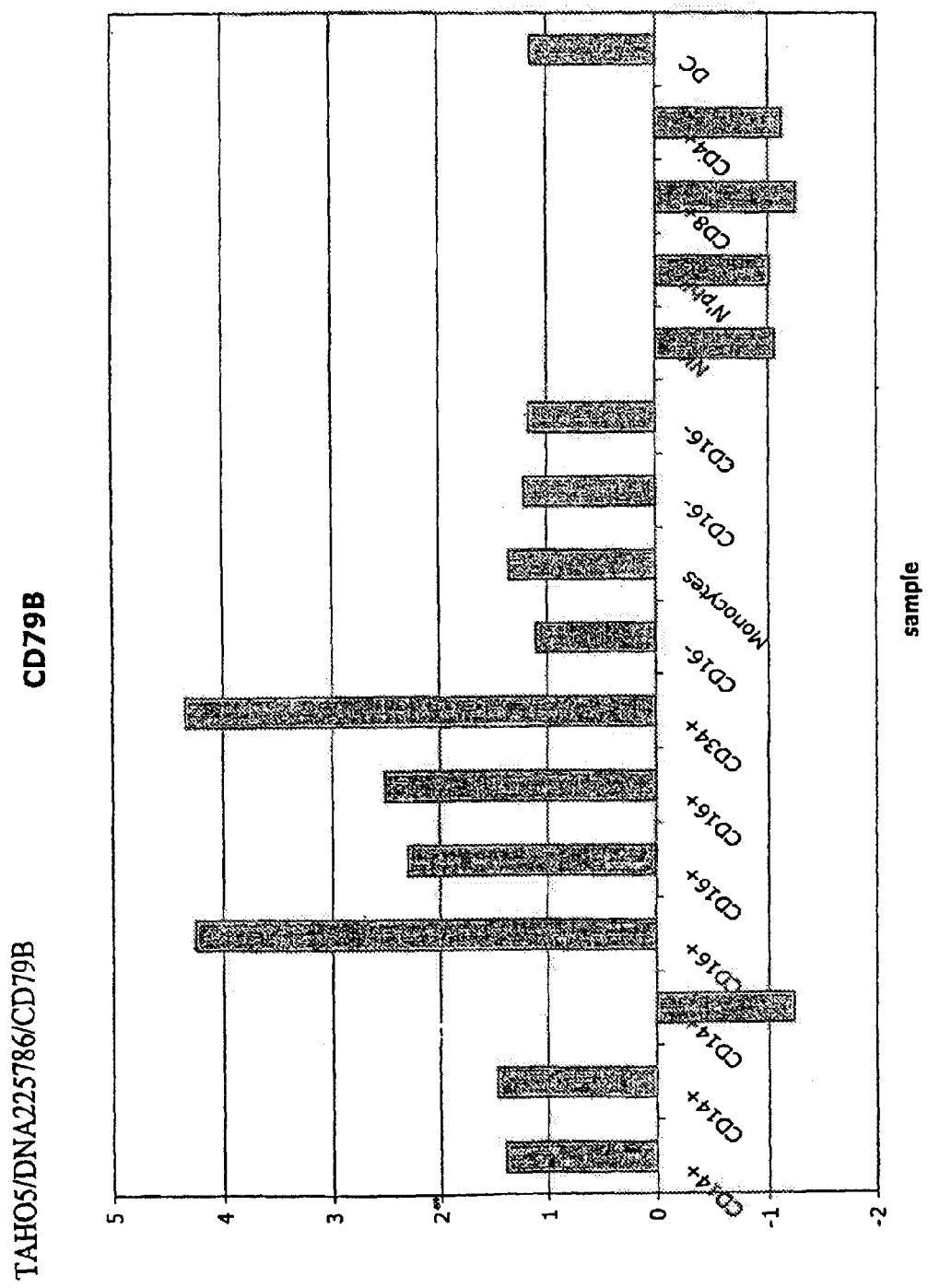
Figure 77D:
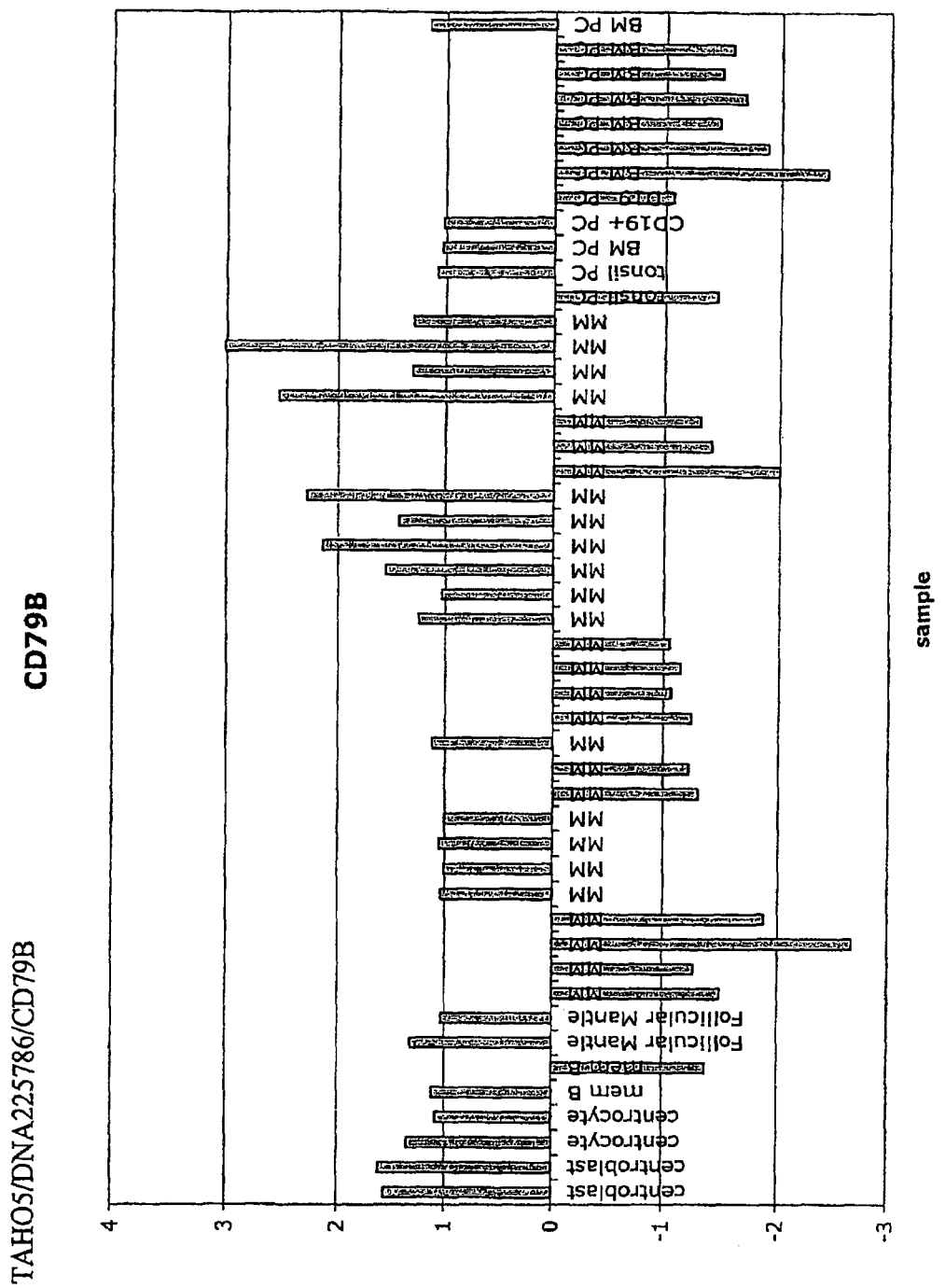
Figure 78A:
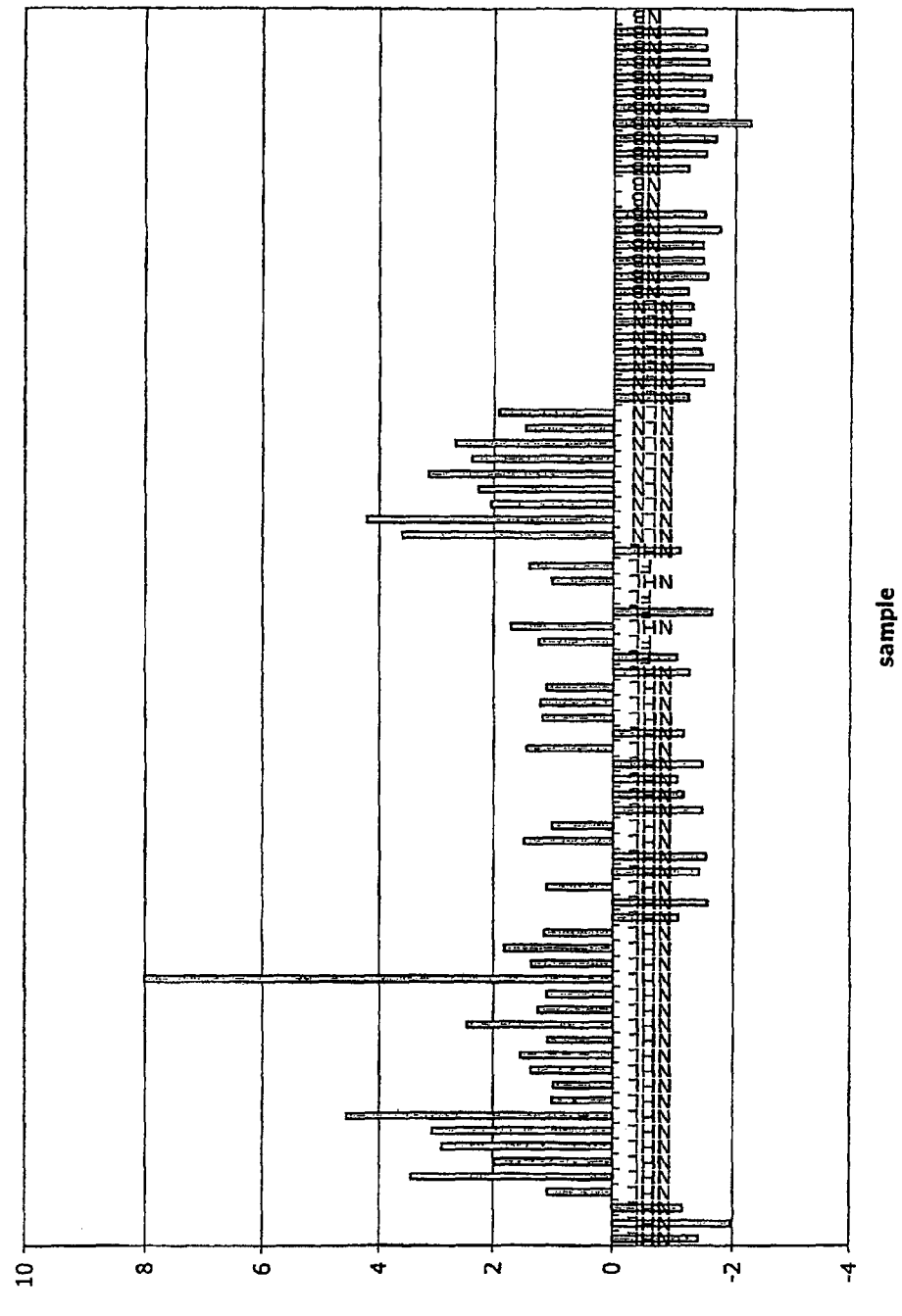
FIGS. 78A-78D show microarray data showing the expression of TAHO6 in normal samples and in diseased samples, such as significant expression in NHL samples and normal lymph node (NLN). Abbreviations used in the Figures are designated as follows: Non-Hodgkin's Lymphoma (NHL), follicular lymphoma (FL), normal lymph node (NLN), normal B cells (NB), multiple myeloma cells (MM), small intestine (s. intestine), fetal liver (f. liver), smooth muscle (s. muscle), fetal brain (f. brain), neutrophils (N'phil), dendrocytes (DC), memory B cells (mem B), plasma cells (PC), bone marrow plasma cells (BM PC).
Figure 78B:
Figure 78C:
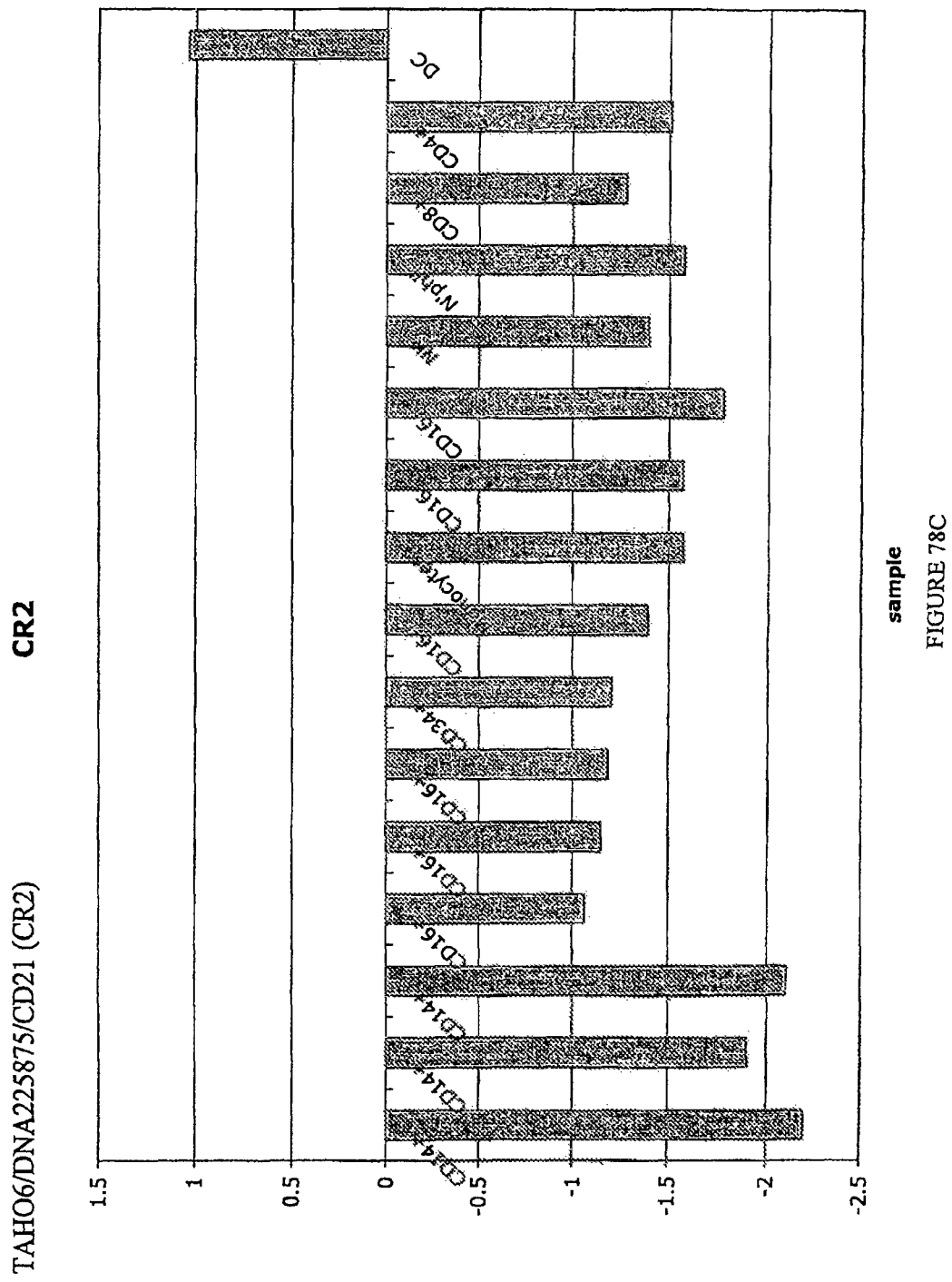
Figure 78D:
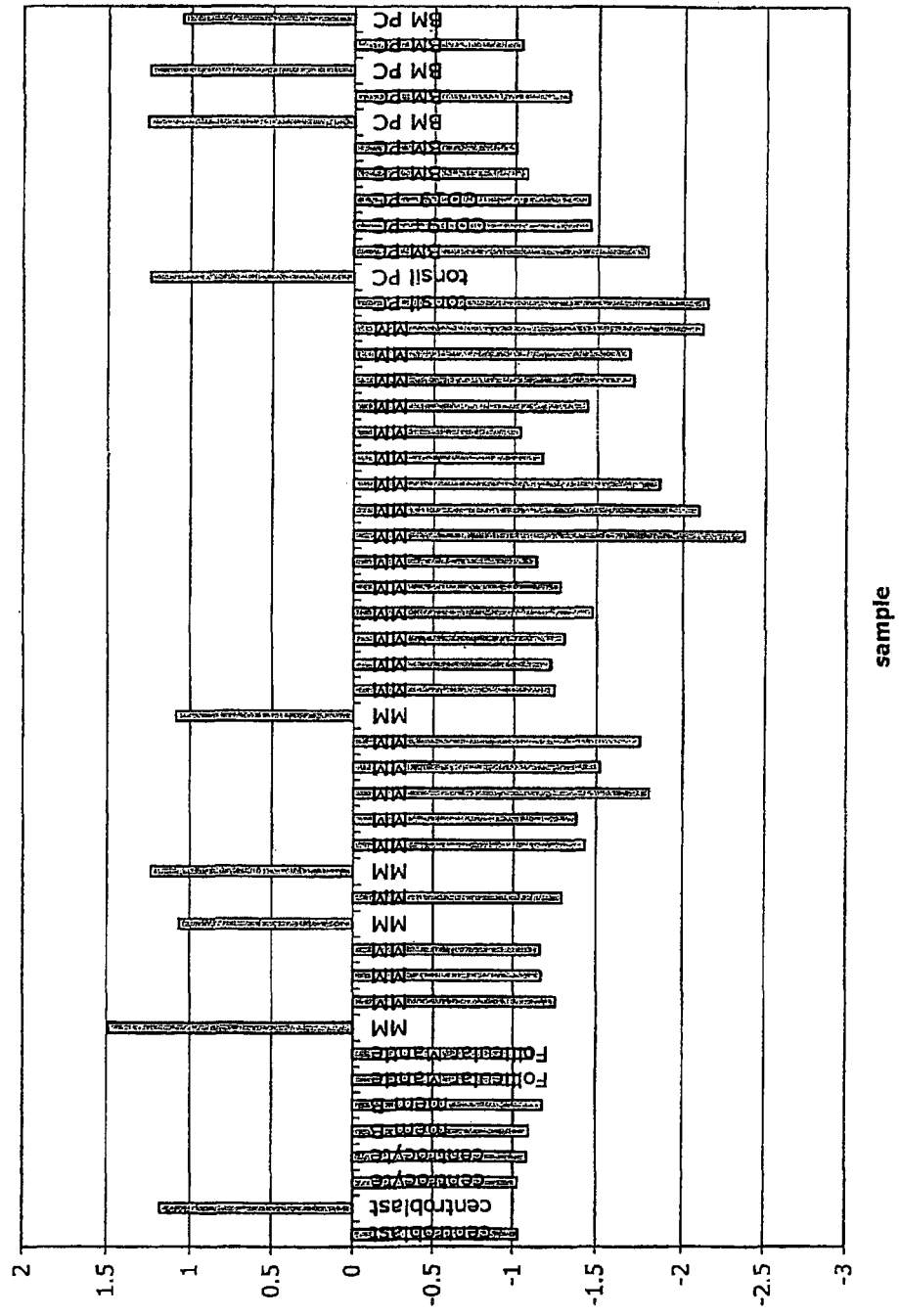
Figure 79A:
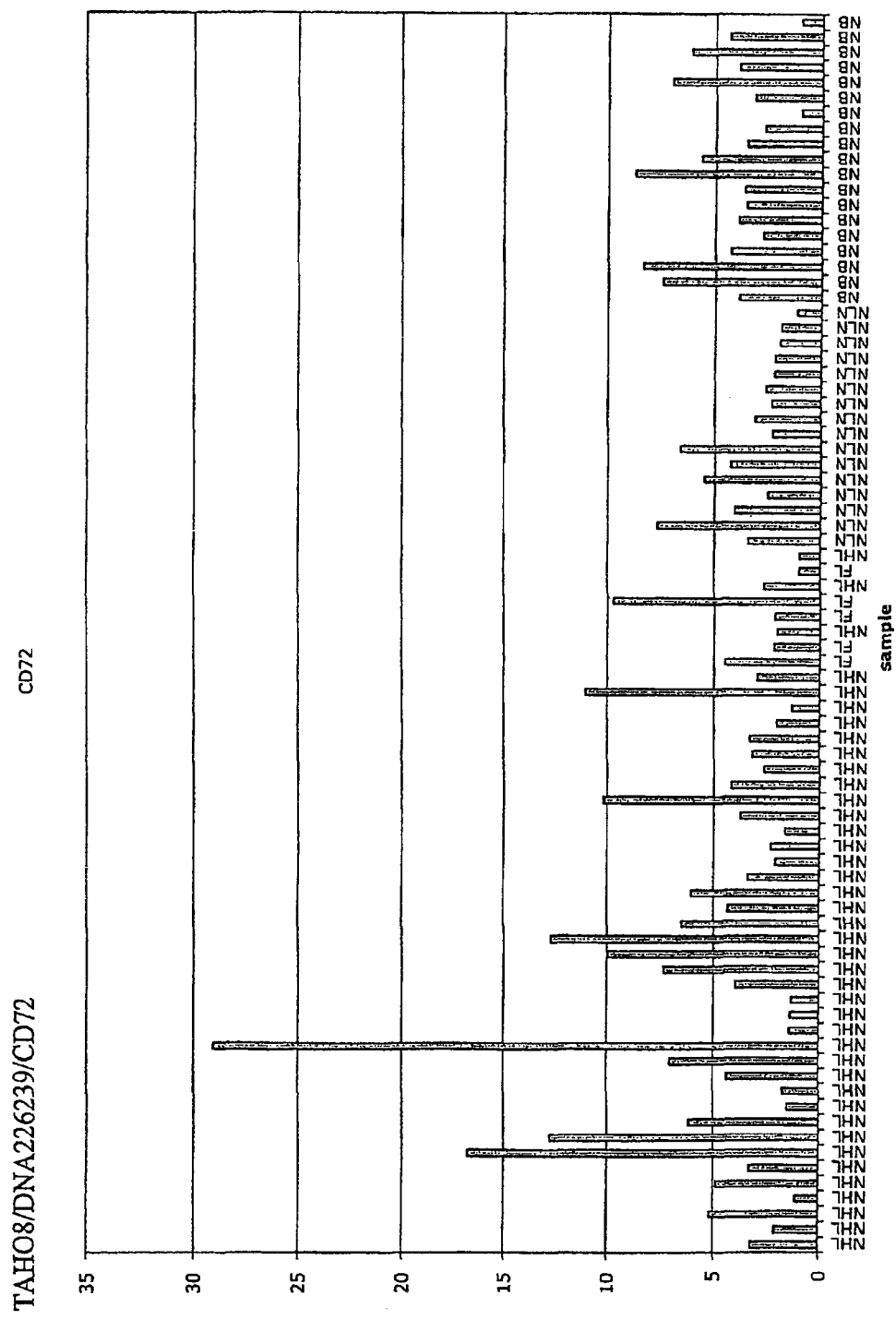
FIGS. 79A-79D show microarray data showing the expression of TAHO8 in normal samples and in diseased samples, such as significant expression in NHL samples, multiple myeloma samples (MM), follicular lymphoma (FL) and normal tonsil. Abbreviations used in the Figures are designated as follows: Non-Hodgkin's Lymphoma (NHL), follicular lymphoma (FL), normal lymph node (NLN), normal B cells (NB), multiple myeloma cells (MM), small intestine (s. intestine), fetal liver (f. liver), smooth muscle (s. muscle), fetal brain (f. brain), natural killer cells (NK), neutrophils (N'phil), dendrocytes (DC), memory B cells (mem B), plasma cells (PC), bone marrow plasma cells (BM PC).
Figure 79B:
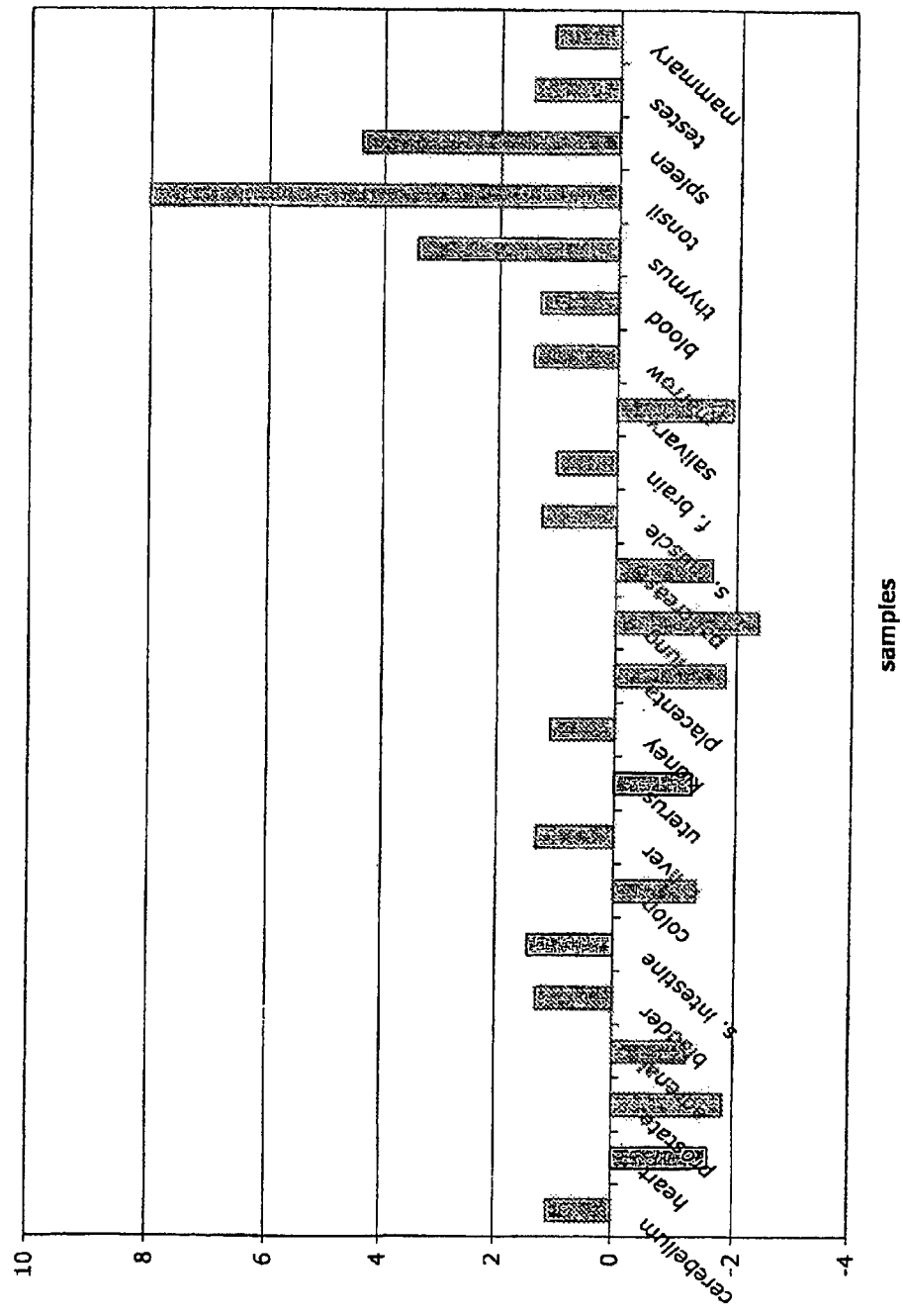
Figure 79C:
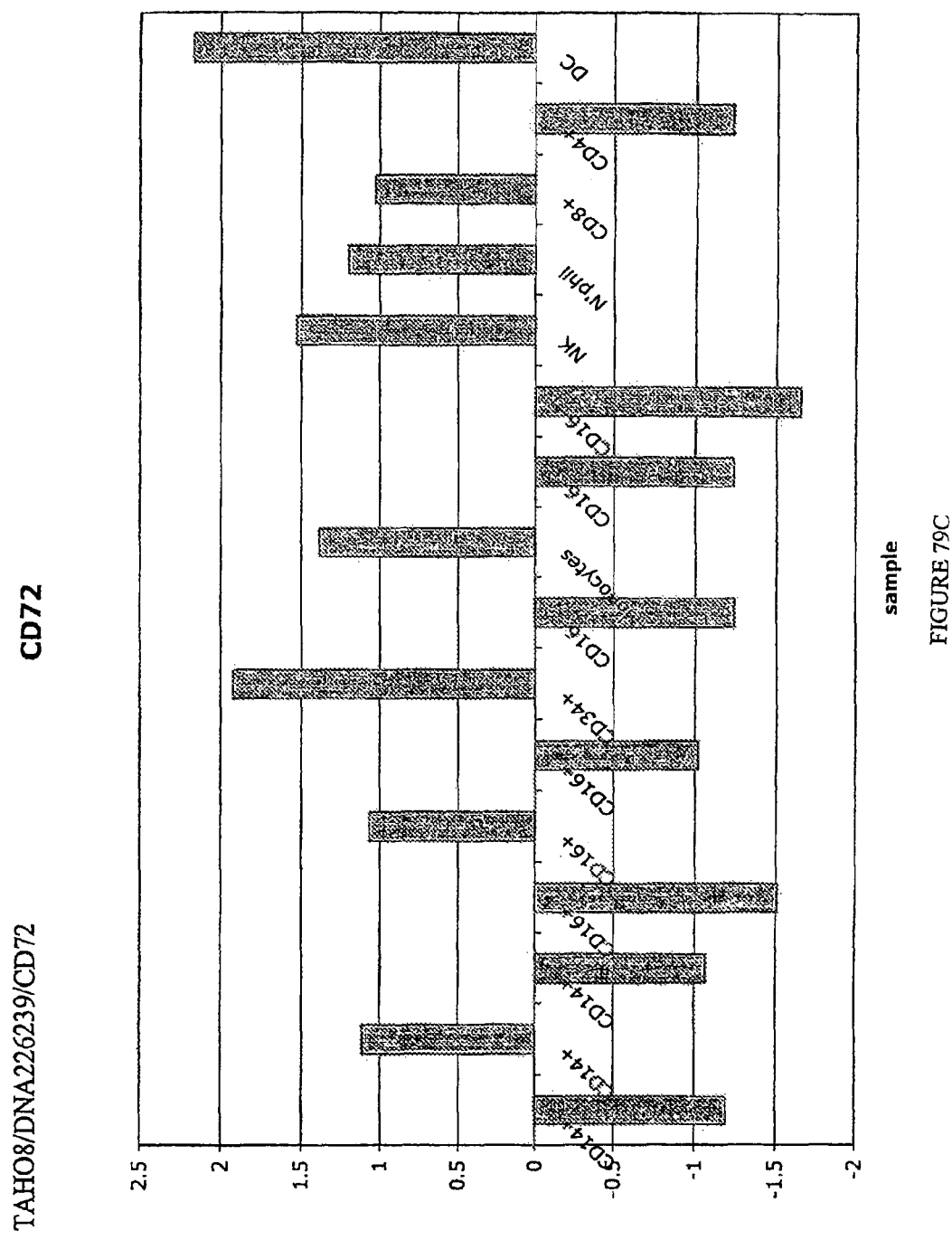
Figure 79D:
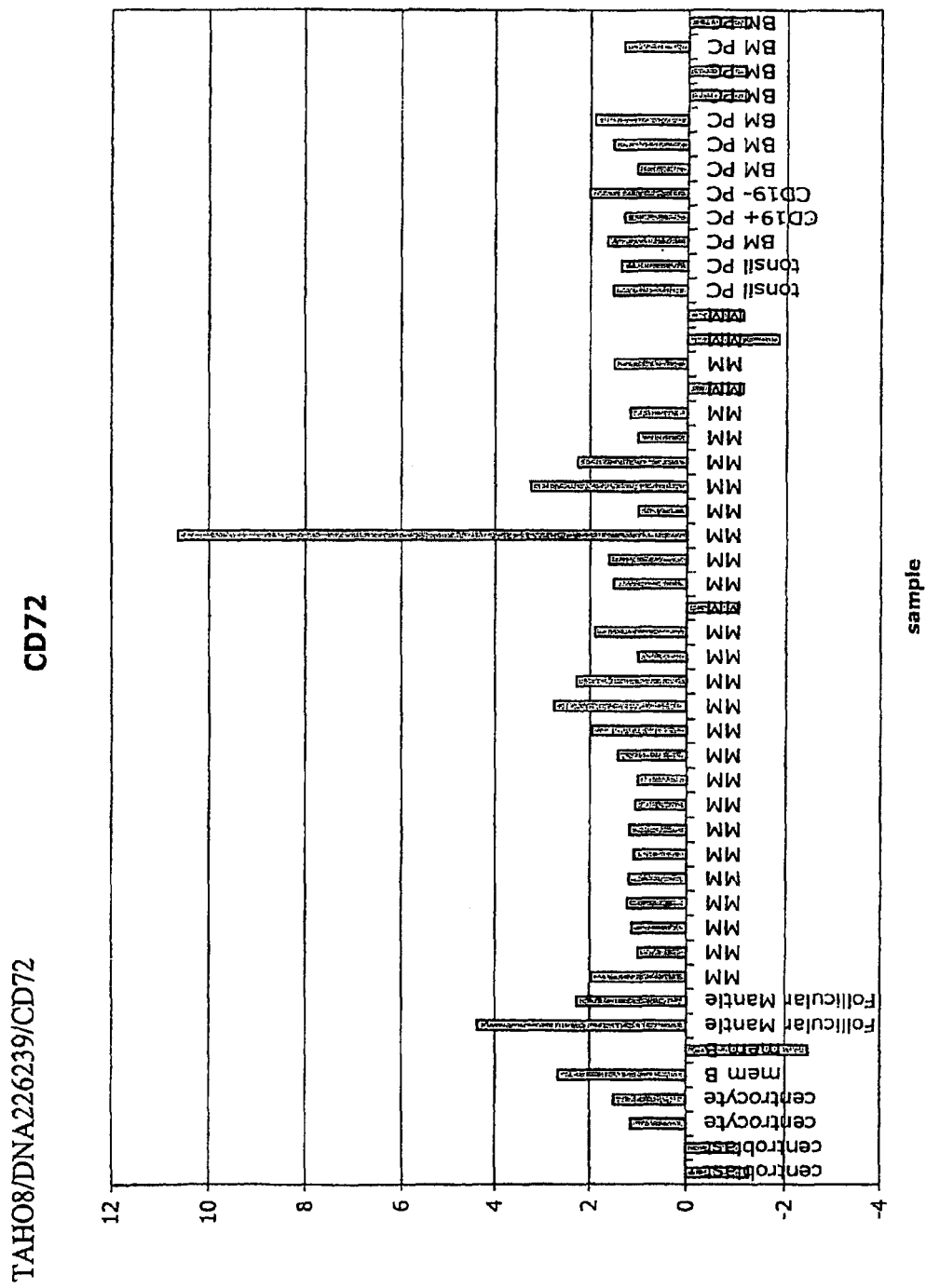

The terms "TAHO polypeptide" and "TAHO" as used herein and when immediately followed by a numerical designation, refer to various polypeptides, wherein the complete designation (i.e., TAHO/number) refers to specific polypeptide sequences as described herein. The terms "TAHO/number polypeptide" and "TAHO/number" wherein the term "number" is provided as an actual numerical designation as used herein encompass native sequence polypeptides, polypeptide variants and fragments of native sequence polypeptides and polypeptide variants (which are further defined herein). The TAHO polypeptides described herein may be isolated from a variety of sources, such as from human tissue types or from another source, or prepared by recombinant or synthetic methods. The term "TAHO polypeptide" refers to each individual TAHO/number polypeptide disclosed herein. All disclosures in this specification which refer to the "TAHO polypeptide" refer to each of the polypeptides individually as well as jointly. For example, descriptions of the preparation of, purification of, derivation of, formation of antibodies to or against, formation of TAHO binding oligopeptides to or against, formation of TAHO binding organic molecules to or against, administration of, compositions containing, treatment of a disease with, etc., pertain to each polypeptide of the invention individually. The term "TAHO polypeptide" also includes variants of the TAHO/number polypeptides disclosed herein.

"TAHO1" is also herein referred to as "RP105", "CD180" or "LY64". "TAHO2" is also herein referred to as "CD20" or "MS4A1". "TAHO3" is also herein referred to as "FcRH2" or "SPAP1". "TAHO4" is also herein referred to as "CD79A". "TAHO5" is also herein referred to as "CD79B". "TAHO6" is also herein referred to as "CR2" or "CD21". "TAHO7" is also herein referred to as "CCR6". "TAHO8" is also herein referred to as "CD72". "TAHO9" is also herein referred to as "P2RX5" or "UNQ2170". "TAHO10" is also herein referred to as "HLA-DOB". "TAHO11" is also herein referred to as "CXCR5" or "BLR1". "TAHO12" is also herein referred to as "FCER2" or "CD23". "TAHO13" is also herein referred to as "GPR2" or "UNQ12100". "TAHO14" is also herein referred to as "BTig". "TAHO15" is also herein referred to as "NAG14" or "LRRC4". "TAHO16" is also herein referred to as "SLGC16270". "TAHO17" is also herein referred to as "FcRH1" or "IRTA5". "TAHO18" is also herein referred to as "IRTA2" or "FcRH5". "TAHO19" is also herein referred to as "ATWD578". "TAHO20" is also herein referred to as "FcRH3" or "IRTA3". "TAHO21" is also herein referred to as "IRTA1" or "FcRH4". "TAHO22" is also herein referred to as "FcRH6" or "FAIL". "TAHO23" is also herein referred to as "BCMA". "TAHO24" is also herein referred to as "239287 at". "TAHO25" is also herein referred to as "CD19". "TAHO26" is also herein referred to as "CD22". "TAHO27" is also herein referred to as "CXCR3" or "UNQ8371". "TAHO28" is also herein referred to as "SILV" or "UNQ1747". "TAHO29" is also herein referred to as "KCNK4" or "UNQ11492". "TAHO30" is also herein referred to as "CXorf1" or "UNQ9197". "TAHO31" is also herein referred to as "LRRN5" or "UNQ256". "TAHO32" is also herein referred to as "UNQ9308". "TAHO33" is also herein referred to as "IGSF4B" or "UNQ225". "TAHO34" is also herein referred to as "BC021178" or "UNQ13267". "TAHO35" is also herein referred to as "FLJ12681" or "UNQ6034". "TAHO36" is also herein referred to as "1_928646" or "UNQ12376".

A "native sequence TAHO polypeptide" comprises a polypeptide having the same amino acid sequence as the corresponding TAHO polypeptide derived from nature. Such native sequence TAHO polypeptides can be isolated from nature or can be produced by recombinant or synthetic means. The term "native sequence TAHO polypeptide" specifically encompasses naturally-occurring truncated or secreted forms of the specific TAHO polypeptide (e.g., an extracellular domain sequence), naturally-occurring variant forms (e.g., alternatively spliced forms) and naturally-occurring allelic variants of the polypeptide. In certain embodiments of the invention, the native sequence TAHO polypeptides disclosed herein are mature or full-length native sequence polypeptides comprising the full-length amino acids sequences shown in the accompanying figures. Start and stop codons (if indicated) are shown in bold font and underlined in the figures. Nucleic acid residues indicated as "N" in the accompanying figures are any nucleic acid residue. However, while the TAHO polypeptides disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the TAHO polypeptides.

The TAHO polypeptide "extracellular domain" or "ECD" refers to a form of the TAHO polypeptide which is essentially free of the transmembrane and cytoplasmic domains. Ordinarily, a TAHO polypeptide ECD will have less than 1% of such transmembrane and/or cytoplasmic domains and preferably, will have less than 0.5% of such domains. It will be understood that any transmembrane domains identified for the TAHO polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a TAHO polypeptide may contain from about 5 or fewer amino acids on either side of the transmembrane domain/extracellular domain boundary as identified in the Examples or specification and such polypeptides, with or without the associated signal peptide, and nucleic acid encoding them, are contemplated by the present invention.

The approximate location of the "signal peptides" of the various TAHO polypeptides disclosed herein may be shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10:1-6 (1997) and von Heinje et al., *Nucl. Acids. Res.* 14:4683-4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"TAHO polypeptide variant" means a TAHO polypeptide, preferably an active TAHO polypeptide, as defined herein having at least about 80% amino acid sequence identity with a full-length native sequence TAHO polypeptide sequence as disclosed herein, a TAHO polypeptide sequence lacking the signal peptide as disclosed herein, an extracellular domain of a TAHO polypeptide, with or without the signal peptide, as disclosed herein or any other fragment of a full-length TAHO polypeptide sequence as disclosed herein (such as those encoded by a nucleic acid that represents only a portion of the complete coding sequence for a full-length TAHO polypeptide). Such TAHO polypeptide variants include, for instance, TAHO polypeptides wherein one or more amino acid residues are added, or deleted, at the N- or C-terminus of the full-length native amino acid sequence. Ordinarily, a TAHO polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence TAHO polypeptide sequence as disclosed herein, a TAHO polypeptide sequence lacking the signal peptide as disclosed herein, an extracellular domain of a TAHO polypeptide, with or without the signal peptide, as disclosed herein or any other specifically defined fragment of a full-length TAHO polypeptide sequence as disclosed herein. Ordinarily, TAHO variant polypeptides are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, TAHO variant polypeptides will have no more than one conservative amino acid substitution as compared to the native TAHO polypeptide sequence, alternatively no more than 2, 3, 4, 5, 6, 7, 8, 9, or 10 conservative amino acid substitution as compared to the native TAHO polypeptide sequence.

"Percent (%) amino acid sequence identity" with respect to the TAHO polypeptide sequences identified herein is defined as the percentage of amino acid residues in a candidate sequence that are identical with the amino acid residues in the specific TAHO polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "TAHO", wherein "TAHO" represents the amino acid sequence of a hypothetical TAHO polypeptide of interest, "Comparison Protein" represents the amino acid sequence of a polypeptide against which the "TAHO" polypeptide of interest is being compared, and "X", "Y" and "Z" each represent different hypothetical amino acid residues. Unless specifically stated otherwise, all % amino acid sequence identity values used herein are obtained as described in the immediately preceding paragraph using the ALIGN-2 computer program.

"TAHO variant polynucleotide" or "TAHO variant nucleic acid sequence" means a nucleic acid molecule which encodes a TAHO polypeptide, preferably an active TAHO polypeptide, as defined herein and which has at least about 80% nucleic acid sequence identity with a nucleotide acid sequence encoding a full-length native sequence TAHO polypeptide sequence as disclosed herein, a full-length native sequence TAHO polypeptide sequence lacking the signal peptide as disclosed herein, an extracellular domain of a TAHO polypeptide, with or without the signal peptide, as disclosed herein or any other fragment of a full-length TAHO polypeptide sequence as disclosed herein (such as those encoded by a nucleic acid that represents only a portion of the complete coding sequence for a full-length TAHO polypeptide). Ordinarily, a TAHO variant polynucleotide will have at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% nucleic acid sequence identity with a nucleic acid sequence encoding a full-length native sequence TAHO polypeptide sequence as disclosed herein, a full-length native sequence TAHO polypeptide sequence lacking the signal peptide as disclosed herein, an extracellular domain of a TAHO polypeptide, with or without the signal sequence, as disclosed herein or any other fragment of a full-length TAHO polypeptide sequence as disclosed herein. Variants do not encompass the native nucleotide sequence.

Ordinarily, TAHO variant polynucleotides are at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 15, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

"Percent (%) nucleic acid sequence identity" with respect to TAHO-encoding nucleic acid sequences identified herein is defined as the percentage of nucleotides in a candidate sequence that are identical with the nucleotides in the TAHO nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction $W/Z$ where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "TAHO-DNA", wherein "TAHO-DNA" represents a hypothetical TAHO-encoding nucleic acid sequence of interest, "Comparison DNA" represents the nucleotide sequence of a nucleic acid molecule against which the "TAHO-DNA" nucleic acid molecule of interest is being compared, and "N", "L" and "V" each represent different hypothetical nucleotides. Unless specifically stated otherwise, all % nucleic acid sequence identity values used herein are obtained as described in the immediately preceding paragraph using the ALIGN-2 computer program.

In other embodiments, TAHO variant polynucleotides are nucleic acid molecules that encode a TAHO polypeptide and which are capable of hybridizing, preferably under stringent hybridization and wash conditions, to nucleotide sequences encoding a full-length TAHO polypeptide as disclosed herein. TAHO variant polypeptides may be those that are encoded by a TAHO variant polynucleotide.

The term "full-length coding region" when used in reference to a nucleic acid encoding a TAHO polypeptide refers to the sequence of nucleotides which encode the full-length TAHO polypeptide of the invention (which is often shown between start and stop codons, inclusive thereof, in the accompanying figures). The term "full-length coding region" when used in reference to an ATCC deposited nucleic acid refers to the TAHO polypeptide-encoding portion of the cDNA that is inserted into the vector deposited with the ATCC (which is often shown between start and stop codons, inclusive thereof, in the accompanying figures (start and stop codons are bolded and underlined in the figures)).

"Isolated," when used to describe the various TAHO polypeptides disclosed herein, means polypeptide that has been identified and separated and/or recovered from a component of its natural environment. Contaminant components of its natural environment are materials that would typically interfere with therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the TAHO polypeptide natural environment will not be present. Ordinarily, however, isolated polypeptide will be prepared by at least one purification step.

An "isolated" TAHO polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence.

For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with a 10 minute wash at 42° C. in 0.2×SSC (sodium chloride/sodium citrate) followed by a 10 minute high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a TAHO polypeptide or anti-TAHO antibody fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" for the purposes herein refers to form(s) of a TAHO polypeptide which retain a biological and/or an immunological activity of native or naturally-occurring TAHO, wherein "biological" activity refers to a biological function (either inhibitory or stimulatory) caused by a native or naturally-occurring TAHO other than the ability to induce the production of an antibody against an antigenic epitope possessed by a native or naturally-occurring TAHO and an "immunological" activity refers to the ability to induce the production of an antibody against an antigenic epitope possessed by a native or naturally-occurring TAHO.

The term "antagonist" is used in the broadest sense, and includes any molecule that partially or fully blocks, inhibits, or neutralizes a biological activity of a native TAHO polypeptide disclosed herein. In a similar manner, the term "agonist" is used in the broadest sense and includes any molecule that mimics a biological activity of a native TAHO polypeptide disclosed herein. Suitable agonist or antagonist molecules specifically include agonist or antagonist antibodies or antibody fragments, fragments or amino acid sequence variants of native TAHO polypeptides, peptides, antisense oligonucleotides, small organic molecules, etc. Methods for identifying agonists or antagonists of a TAHO polypeptide may comprise contacting a TAHO polypeptide with a candidate agonist or antagonist molecule and measuring a detectable change in one or more biological activities normally associated with the TAHO polypeptide.

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for a TAHO polypeptide-expressing cancer if, after receiving a therapeutic amount of an anti-TAHO antibody, TAHO binding oligopeptide or TAHO binding organic molecule according to the methods of the present invention, the patient shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. To the extent the anti-TAHO antibody or TAHO binding oligopeptide may prevent growth and/or kill existing cancer cells, it may be cytostatic and/or cytotoxic. Reduction of these signs or symptoms may also be felt by the patient.

The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR). Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB).

For bladder cancer, which is a more localized cancer, methods to determine progress of disease include urinary cytologic evaluation by cystoscopy, monitoring for presence of blood in the urine, visualization of the urothelial tract by sonography or an intravenous pyelogram, computed tomography (CT) and magnetic resonance imaging (MRI). The presence of distant metastases can be assessed by CT of the abdomen, chest x-rays, or radionuclide imaging of the skeleton.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of the treatment of, alleviating the symptoms of a cancer refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

By "solid phase" or "solid support" is meant a non-aqueous matrix to which an antibody, TAHO binding oligopeptide or TAHO binding organic molecule of the present invention can adhere or attach. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a TAHO polypeptide, an antibody thereto or a TAHO binding oligopeptide) to a mammal. The components of the liposome are commonly arranged in a bilayer formation, similar to the lipid arrangement of biological membranes.

A "small" molecule or "small" organic molecule is defined herein to have a molecular weight below about 500 Daltons.

An "effective amount" of a polypeptide, antibody, TAHO binding oligopeptide, TAHO binding organic molecule or an agonist or antagonist thereof as disclosed herein is an amount sufficient to carry out a specifically stated purpose. An "effective amount" may be determined empirically and in a routine manner, in relation to the stated purpose.

The term "therapeutically effective amount" refers to an amount of an antibody, polypeptide, TAHO binding oligopeptide, TAHO binding organic molecule or other drug effective to "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See the definition herein of "treating". To the extent the drug may prevent growth and/or kill existing cancer cells, it may be cytostatic and/or cytotoxic.

A "growth inhibitory amount" of an anti-TAHO antibody, TAHO polypeptide, TAHO binding oligopeptide or TAHO binding organic molecule is an amount capable of inhibiting the growth of a cell, especially tumor, e.g., cancer cell, either in vitro or in vivo. A "growth inhibitory amount" of an anti-TAHO antibody, TAHO polypeptide, TAHO binding oligopeptide or TAHO binding organic molecule for purposes of inhibiting neoplastic cell growth may be determined empirically and in a routine manner.

A "cytotoxic amount" of an anti-TAHO antibody, TAHO polypeptide, TAHO binding oligopeptide or TAHO binding organic molecule is an amount capable of causing the destruction of a cell, especially tumor, e.g., cancer cell, either in vitro or in vivo. A "cytotoxic amount" of an anti-TAHO antibody, TAHO polypeptide, TAHO binding oligopeptide or TAHO binding organic molecule for purposes of inhibiting neoplastic cell growth may be determined empirically and in a routine manner.

The term "antibody" is used in the broadest sense and specifically covers, for example, single anti-TAHO monoclonal antibodies (including agonist, antagonist, and neutralizing antibodies), anti-TAHO antibody compositions with polyepitopic specificity, polyclonal antibodies, single chain anti-TAHO antibodies, and fragments of anti-TAHO antibodies (see below) as long as they exhibit the desired biological or immunological activity. The term "immunoglobulin" (Ig) is used interchangeable with antibody herein.

An "isolated antibody" is one which has been identified and separated and/or recovered from a component of its natural environment. Contaminant components of its natural environment are materials which would interfere with therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H 1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., *Basic and Clinical Immunology*, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the $V_L$, and around about 1-35 (H1), 50-65 (H2) and 95-102 (H3) in the $V_H$; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 53-55 (H2) and 96-101 (H3) in the $V_H$; Chothia and Lesk *J. Mol. Biol.* 196:901-917 (1987)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., *Nature*, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a $C_L$ and at least heavy chain constant domains, $C_H 1$, $C_H 2$ and $C_H 3$. The constant domains may be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., *Pro-* tein Eng. 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large $F(ab')_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332: 323-329 (1988); and Presta, *Curr. Op. Struct. Biol.* 2:593-596 (1992).

A "species-dependent antibody," e.g., a mammalian anti-human IgE antibody, is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1\times10^{-7}$ M, preferably no more than about $1\times10^{-8}$ and most preferably no more than about $1\times10^{-9}$ M) but has a binding affinity for a homologue of the antigen from a second non-human mammalian species which is at least about 50 fold, or at least about 500 fold, or at least about 1000 fold, weaker than its binding affinity for the human antigen. The species-dependent antibody can be of any of the various types of antibodies as defined above, but preferably is a humanized or human antibody.

A "TAHO binding oligopeptide" is an oligopeptide that binds, preferably specifically, to a TAHO polypeptide as described herein. TAHO binding oligopeptides may be chemically synthesized using known oligopeptide synthesis methodology or may be prepared and purified using recombinant technology. TAHO binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a TAHO polypeptide as described herein. TAHO binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708, 871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998-4002 (1984); Geysen et al., Proc. Natl. Acad. Sci. U.S.A., 82:178-182 (1985); Geysen et al., in Synthetic Peptides as Antigens, 130-149 (1986); Geysen et al., J. Immunol. Meth., 102:259-274 (1987); Schoofs et al., J. Immunol. 140:611-616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

A "TAHO binding organic molecule" is an organic molecule other than an oligopeptide or antibody as defined herein that binds, preferably specifically, to a TAHO polypeptide as described herein. TAHO binding organic molecules may be identified and chemically synthesized using known methodology (see, e.g., PCT Publication Nos. WO00/00823 and WO00/39585). TAHO binding organic molecules are usually less than about 2000 daltons in size, alternatively less than about 1500, 750, 500, 250 or 200 daltons in size, wherein such organic molecules that are capable of binding, preferably specifically, to a TAHO polypeptide as described herein may be identified without undue experimentation using well known techniques. In this regard, it is noted that techniques for screening organic molecule libraries for molecules that are capable of binding to a polypeptide target are well known in the art (see, e.g., PCT Publication Nos. WO00/00823 and WO00/39585).

An antibody, oligopeptide or other organic molecule "which binds" an antigen of interest, e.g. a tumor-associated polypeptide antigen target, is one that binds the antigen with sufficient affinity such that the antibody, oligopeptide or other organic molecule is useful as a therapeutic agent in targeting a cell or tissue expressing the antigen, and does not significantly cross-react with other proteins. In such embodiments, the extent of binding of the antibody, oligopeptide or other organic molecule to a "non-target" protein will be less than about 10% of the binding of the antibody, oligopeptide or other organic molecule to its particular target protein as determined by fluorescence activated cell sorting (FACS) analysis or radioimmunoprecipitation (RIA). With regard to the binding of an antibody, oligopeptide or other organic molecule to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

An antibody, oligopeptide or other organic molecule that "inhibits the growth of tumor cells expressing a TAHO polypeptide" or a "growth inhibitory" antibody, oligopeptide or other organic molecule is one which results in measurable growth inhibition of cancer cells expressing or overexpressing the appropriate TAHO polypeptide. The TAHO polypeptide may be a transmembrane polypeptide expressed on the surface of a cancer cell or may be a polypeptide that is produced and secreted by a cancer cell. Preferred growth inhibitory anti-TAHO antibodies, oligopeptides or organic molecules inhibit growth of TAHO-expressing tumor cells by greater than 20%, preferably from about 20% to about 50%, and even more preferably, by greater than 50% (e.g., from about 50% to about 100%) as compared to the appropriate control, the control typically being tumor cells not treated with the antibody, oligopeptide or other organic molecule being tested. In one embodiment, growth inhibition can be measured at an antibody concentration of about 0.1 to 30 µg/ml or about 0.5 nM to 200 nM in cell culture, where the growth inhibition is determined 1-10 days after exposure of the tumor cells to the antibody. Growth inhibition of tumor cells in vivo can be determined in various ways such as is described in the Experimental Examples section below. The antibody is growth inhibitory in vivo if administration of the anti-TAHO antibody at about 1 µg/kg to about 100 mg/kg body weight results in reduction in tumor size or tumor cell proliferation within about 5 days to 3 months from the first administration of the antibody, preferably within about 5 to 30 days.

An antibody, oligopeptide or other organic molecule which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses a TAHO polypeptide. Preferably the cell is a tumor cell, e.g., a hematopoietic cell, such as a B cell, T cell, basophil, eosinophil, neutrophil, monocyte, platelet or erythrocyte. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody, oligopeptide or other organic molecule which induces apoptosis is one which results in about 2 to 50 fold, preferably about 5 to 50 fold, and most preferably about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express Fc γRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. (USA) 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FγRIIA contains an immunoreceptor tyrosine-based activation motif (ITAM) in its cytoplasmic domain. Inhibiting receptor FγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol.* 9:457-492 (1991); Capel et al., *Immunomethods* 4:25-34 (1994); and de Haas et al., *J. Lab. Clin. Med.* 126: 330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *Immunol. Methods* 202:163 (1996), may be performed.

The terms "cancer" and "cancerous" refer to or describe the physiological condition in mammals that is typically characterized by unregulated cell growth. Examples of cancer include, but are not limited to, hematopoietic cancers or blood-related cancers, such as lymphoma, leukemia, myeloma or lymphoid malignancies, but also cancers of the spleen and cancers of the lymph nodes. More particular examples of such B-cell associated cancers, including for example, high, intermediate and low grade lymphomas (including B cell lymphomas such as, for example, mucosa-associated-lymphoid tissue B cell lymphoma and non-Hodgkin's lymphoma, mantle cell lymphoma, Burkitt's lymphoma, small lymphocytic lymphoma, marginal zone lymphoma, diffuse large cell lymphoma, follicular lymphoma, and Hodgkin's lymphoma and T cell lymphomas) and leukemias (including secondary leukemia, chronic lymphocytic leukemia, such as B cell leukemia (CD5+ B lymphocytes), myeloid leukemia, such as acute myeloid leukemia, chronic myeloid leukemia, lymphoid leukemia, such as acute lymphoblastic leukemia and myelodysplasia), multiple myeloma, such as plasma cell malignancy, and other hematological and/or B cell- or T-cell-associated cancers. Also included are cancers of additional hematopoietic cells, including polymorphonuclear leukocytes, such as basophils, eosinophils, neutrophils and monocytes, dendritic cells, platelets, erythrocytes and natural killer cells. The origins of B-cell cancers are as follows: marginal zone B-cell lymphoma origins in memory B-cells in marginal zone, follicular lymphoma and diffuse large B-cell lymphoma originates in centrocytes in the light zone of germinal centers, multiple myeloma originates in plasma cells, chronic lymphocytic leukemia and small lymphocytic leukemia originates in B1 cells (CD5+), mantle cell lymphoma originates in naive B-cells in the mantle zone and Burkitt's lymphoma originates in centroblasts in the dark zone of germinal centers. Tissues which include hematopoietic cells referred herein to as "hematopoietic cell tissues" include thymus and bone marrow and peripheral lymphoid tissues, such as spleen, lymph nodes, lymphoid tissues associated with mucosa, such as the gut-associated lymphoid tissues, tonsils, Peyer's patches and appendix and lymphoid tissues associated with other mucosa, for example, the bronchial linings.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all pre-cancerous and cancerous cells and tissues.

An antibody, oligopeptide or other organic molecule which "induces cell death" is one which causes a viable cell to become nonviable. The cell is one which expresses a TAHO polypeptide and is of a cell type which specifically expresses or overexpresses a TAHO polypeptide. The cell may be cancerous or normal cells of the particular cell type. The TAHO polypeptide may be a transmembrane polypeptide expressed on the surface of a cancer cell or may be a polypeptide that is produced and secreted by a cancer cell. The cell may be a cancer cell, e.g., a B cell or T cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody, oligopeptide or other organic molecule is able to induce cell death, loss of membrane integrity as evaluated by uptake of propidium iodide (PI), trypan blue (see Moore et al. *Cytotechnology* 17:1-11 (1995)) or 7AAD can be assessed relative to untreated cells. Preferred cell death-inducing antibodies, oligopeptides or other organic molecules are those which induce PI uptake in the PI uptake assay in BT474 cells.

A "TAHO-expressing cell" is a cell which expresses an endogenous or transfected TAHO polypeptide either on the cell surface or in a secreted form. A "TAHO-expressing cancer" is a cancer comprising cells that have a TAHO polypeptide present on the cell surface or that produce and secrete a TAHO polypeptide. A "TAHO-expressing cancer" optionally produces sufficient levels of TAHO polypeptide on the surface of cells thereof, such that an anti-TAHO antibody, oligopeptide to other organic molecule can bind thereto and have a therapeutic effect with respect to the cancer. In another embodiment, a "TAHO-expressing cancer" optionally produces and secretes sufficient levels of TAHO polypeptide, such that an anti-TAHO antibody, oligopeptide to other organic molecule antagonist can bind thereto and have a therapeutic effect with respect to the cancer. With regard to the latter, the antagonist may be an antisense oligonucleotide which reduces, inhibits or prevents production and secretion of the secreted TAHO polypeptide by tumor cells. A cancer which "overexpresses" a TAHO polypeptide is one which has significantly higher levels of TAHO polypeptide at the cell surface thereof, or produces and secretes, compared to a noncancerous cell of the same tissue type. Such overexpression may be caused by gene amplification or by increased transcription or translation. TAHO polypeptide overexpression may be determined in a detection or prognostic assay by evaluating increased levels of the TAHO protein present on the surface of a cell, or secreted by the cell (e.g., via an immunohistochemistry assay using anti-TAHO antibodies prepared against an isolated TAHO polypeptide which may be prepared using recombinant DNA technology from an isolated nucleic acid encoding the TAHO polypeptide; FACS analysis, etc.). Alternatively, or additionally, one may measure levels of TAHO polypeptide-encoding nucleic acid or mRNA in the cell, e.g., via fluorescent in situ hybridization using a nucleic acid based probe corresponding to a TAHO-encoding nucleic acid or the complement thereof; (FISH; see WO98/45479 published October, 1998), Southern blotting, Northern blotting, or polymerase chain reaction (PCR) techniques; such as real time quantitative PCR (RT-PCR). One may also study TAHO polypeptide overexpression by measuring shed antigen in a biological fluid such as serum, e.g, using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al., *J. Immunol. Methods* 132:73-80 (1990)). Aside from the above assays, various in vivo assays are available to the skilled practitioner. For example, one may expose cells within the body of the patient to an antibody which is optionally labeled with a detectable label, e.g., a radioactive isotope, and binding of the antibody to cells in the patient can be evaluated, e.g., by external scanning for radioactivity or by analyzing a biopsy taken from a patient previously exposed to the antibody.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The word "label" when used herein refers to a detectable compound or composition which is conjugated directly or indirectly to the antibody, oligopeptide or other organic molecule so as to generate a "labeled" antibody, oligopeptide or other organic molecule. The label may be detectable by itself (e.g. radioisotope labels or fluorescent labels) or, in the case of an enzymatic label, may catalyze chemical alteration of a substrate compound or composition which is detectable.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "growth inhibitory agent" when used herein refers to a compound or composition which inhibits growth of a cell, especially a TAHO-expressing cancer cell, either in vitro or in vivo. Thus, the growth inhibitory agent may be one which significantly reduces the percentage of TAHO-expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulat ing factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "package insert" is used to refer to instructions customarily included in commercial packages of therapeutic products, that contain information about the indications, usage, dosage, administration, contraindications and/or warnings concerning the use of such therapeutic products.

TABLE 1

```
/*
 *
 * C-C increased from 12 to 15
 * Z is average of EQ
 * B is average of ND
 * match with stop is _M; stop-stop = 0; J (joker) match = 0
 */
#define     _M              -8        /* value of a match with a stop */
int         _day[26][26] = {
/*    A B C D E F G H I J K L M N O P Q R S T U V W X Y Z */
/* A */    { 2, 0,-2, 0, 0,-4, 1,-1,-1, 0,-1,-2,-1, 0,_M, 1, 0,-2, 1, 1, 0, 0,-6, 0,-3, 0},
/* B */    { 0, 3,-4, 3, 2,-5, 0, 1,-2, 0, 0,-3,-2, 2,_M,-1, 1, 0, 0, 0, 0,-2,-5, 0,-3, 1},
/* C */    {-2,-4,15,-5,-5,-4,-3,-3,-2, 0,-5,-6,-5,-4,_M,-3,-5,-4, 0,-2, 0,-2,-8, 0, 0,-5},
/* D */    { 0, 3,-5, 4, 3,-6, 1, 1,-2, 0, 0,-4,-3, 2,_M,-1, 2,-1, 0, 0, 0,-2,-7, 0,-4, 2},
/* E */    { 0, 2,-5, 3, 4,-5, 0, 1,-2, 0, 0,-3,-2, 1,_M,-1, 2,-1, 0, 0, 0,-2,-7, 0,-4, 3},
/* F */    {-4,-5,-4,-6,-5, 9,-5,-2, 1, 0,-5, 2, 0,-4,_M,-5,-5,-4,-3,-3, 0,-1, 0, 0, 7,-5},
/* G */    { 1, 0,-3, 1, 0,-5, 5,-2,-3, 0,-2,-4,-3, 0,_M,-1,-1,-3, 1, 0, 0,-1,-7, 0,-5, 0},
/* H */    {-1, 1,-3, 1, 1,-2,-2, 6,-2, 0, 0,-2,-2, 2,_M, 0, 3, 2,-1,-1, 0,-2,-3, 0, 0, 2},
/* I */    {-1,-2,-2,-2, 2, 1,-3,-2, 5, 0,-2, 2, 2,-2,_M,-2,-2,-2,-1, 0, 0, 4,-5, 0,-1,-2},
/* J */    { 0, 0, 0, 0, 0, 0, 0, 0, 0, 0, 0, 0, 0, 0,_M, 0, 0, 0, 0, 0, 0, 0, 0, 0, 0, 0},
/* K */    {-1, 0,-5, 0, 0,-5,-2, 0,-2, 0, 5,-3, 0, 1,_M,-1, 1, 3, 0, 0, 0,-2,-3, 0,-4, 0},
/* L */    {-2,-3,-6,-4,-3, 2,-4,-2, 2, 0,-3, 6, 4,-3,_M,-3,-2,-3,-3,-1, 0, 2,-2, 0,-1,-2},
/* M */    {-1,-2,-5,-3,-2, 0,-3,-2, 2, 0, 0, 4, 6,-2,_M,-2,-1, 0,-2,-1, 0, 2,-4, 0,-2,-1},
/* N */    { 0, 2,-4, 2, 1,-4, 0, 2,-2, 0, 1,-3,-2, 2,_M,-1, 1, 0, 1, 0, 0,-2,-4, 0,-2, 1},
/* O */    {_M,_M,_M,_M,_M,_M,_M,_M,_M,_M,_M,_M,_M,_M, 0,_M,_M,
            _M,_M,_M,_M,_M,_M,_M,_M,_M},
/* P */    { 1,-1,-3,-1,-1,-5,-1, 0,-2, 0,-1,-3,-2,-1,_M, 6, 0, 0, 1, 0, 0,-1,-6, 0,-5, 0},
/* Q */    { 0, 1,-5, 2, 2,-5,-1, 3,-2, 0, 1,-2,-1, 1,_M, 0, 4, 1,-1,-1, 0,-2,-5, 0,-4, 3},
/* R */    {-2, 0,-4,-1,-1,-4,-3, 2,-2, 0, 3,-3, 0, 0,_M, 0, 1, 6, 0,-1, 0,-2, 2, 0,-4, 0},
/* S */    { 1, 0, 0, 0, 0,-3, 1,-1,-1, 0, 0,-3,-2, 1,_M, 1,-1, 0, 2, 1, 0,-1,-2, 0,-3, 0},
/* T */    { 1, 0,-2, 0, 0,-3, 0,-1, 0, 0, 0,-1,-1, 0,_M, 0,-1,-1, 1, 3, 0, 0,-5, 0,-3, 0},
/* U */    { 0, 0, 0, 0, 0, 0, 0, 0, 0, 0, 0, 0, 0, 0,_M, 0, 0, 0, 0, 0, 0, 0, 0, 0, 0, 0},
/* V */    { 0,-2,-2,-2,-2,-1,-1,-2, 4, 0,-2, 2, 2,-2,_M,-1,-2,-2,-1, 0, 0, 4,-6, 0,-2,-2},
/* W */    {-6,-5,-8,-7,-7, 0,-7,-3,-5, 0,-3,-2,-4,-4,_M,-6,-5, 2,-2,-5, 0,-6,17, 0, 0,-6},
/* X */    { 0, 0, 0, 0, 0, 0, 0, 0, 0, 0, 0, 0, 0, 0,_M, 0, 0, 0, 0, 0, 0, 0, 0, 0, 0, 0},
/* Y */    {-3,-3, 0,-4,-4, 7,-5, 0,-1, 0,-4,-1,-2,-2,_M,-5,-4,-4,-3,-3, 0,-2, 0, 0,10,-4},
/* Z */    { 0, 1,-5, 2, 3,-5, 0, 2,-2, 0, 0,-2,-1, 1,_M, 0, 3, 0, 0, 0, 0,-2,-6, 0,-4, 4}
};
/*
 */
#include    <stdio.h>
#include    <ctype.h>
#define     MAXJMP          16        /* max jumps in a diag */
#define     MAXGAP          24        /* don't continue to penalize gaps larger than this */
#define     JMPS            1024      /* max jmps in an path */
#define     MX              4         /* save if there's at least MX-1 bases since last jmp */
#define     DMAT            3         /* value of matching bases */
#define     DMIS            0         /* penalty for mismatched bases */
#define     DINS0           8         /* penalty for a gap */
#define     DINS1           1         /* penalty per base */
#define     PINS0           8         /* penalty for a gap */
#define     PINS1           4         /* penalty per residue */
struct jmp {
            short           n[MAXJMP];        /* size of jmp (neg for dely) */
            unsigned short  x[MAXJMP];        /* base no. of jmp in seq x */
};                                            /* limits seq to 2^16 -1 */
struct diag {
            int             score;            /* score at last jmp */
            long            offset;           /* offset of prev block */
            short           ijmp;             /* current jmp index */
            struct jmp      jp;               /* list of jmps */
};
struct path {
            int             spc;              /* number of leading spaces */
            short           n[JMPS];          /* size of jmp (gap) */
            int             x[JMPS];          /* loc of jmp (last elem before gap) */
};
char                        *ofile;           /* output file name */
char                        *namex[2];        /* seq names: getseqs( ) */
char                        *prog;            /* prog name for err msgs */
```

TABLE 1-continued

```
char            *seqx[2];                       /* seqs: getseqs( ) */
int             dmax;                           /* best diag: nw( ) */
int             dmax0;                          /* final diag */
int             dna;                            /* set if dna: main( ) */
int             endgaps;                        /* set if penalizing end gaps */
int             gapx, gapy;                     /* total gaps in seqs */
int             len0, len1;                     /* seq lens */
int             ngapx, ngapy;                   /* total size of gaps */
int             smax;                           /* max score: nw( ) */
int             *xbm;                           /* bitmap for matching */
long            offset;                         /* current offset in jmp file */
struct  diag    *dx;                            /* holds diagonals */
struct  path    pp[2];                          /* holds path for seqs */
char            *calloc( ), *malloc( ), *index( ), *strcpy( );
char            *getseq( ), *g_calloc( );
/* Needleman-Wunsch alignment program
*
* usage: progs file1 file2
* where file1 and file2 are two dna or two protein sequences.
* The sequences can be in upper- or lower-case an may contain ambiguity
* Any lines beginning with ';', '>' or '<' are ignored
* Max file length is 65535 (limited by unsigned short x in the jmp struct)
* A sequence with 1/3 or more of its elements ACGTU is assumed to be DNA
* Output is in the file "align.out"
*
* The program may create a tmp file in /tmp to hold info about traceback.
* Original version developed under BSD 4.3 on a vax 8650
*/
#include "nw.h"
#include "day.h"
static    _dbval[26] = {
          1,14,2,13,0,0,4,11,0,0,12,0,3,15,0,0,0,5,6,8,8,7,9,0,10,0
};
static    _pbval[26] = {
          1, 2|(1<<('D'-'A'))|(1<<('N'-'A')), 4, 8, 16, 32, 64,
          128, 256, 0xFFFFFFFF, 1<<10, 1<<11, 1<<12, 1<<13, 1<<14,
          1<<15, 1<<16, 1<<17, 1<<18, 1<<19, 1<<20, 1<<21, 1<<22,
          1<<23, 1<<24, 1<<25|(1<<('E'-'A'))|(1<<('Q'-'A'))
};
main(ac, av)                                                                main
          int     ac;
          char    *av[ ];
{
    prog = av[0];
    if(ac != 3) {
          fprintf(stderr,"usage: %s file1 file2\n", prog);
          fprintf(stderr,"where file1 and file2 are two dna or two protein sequences.\n");
          fprintf(stderr,"The sequences can be in upper- or lower-case\n");
          fprintf(stderr,"Any lines beginning with ';' or '<' are ignored\n");
          fprintf(stderr,"Output is in the file \"align.out\"\n");
          exit(1);
    }
    namex[0] = av[1];
    namex[1] = av[2];
    seqx[0] = getseq(namex[0], &len0);
    seqx[1] = getseq(namex[1], &len1);
    xbm = (dna)? _dbval : _pbval;
    endgaps = 0;                        /* 1 to penalize endgaps */
    ofile = "align.out";                /* output file */
    nw( );                 /* fill in the matrix, get the possible jmps */
    readjmps( );           /* get the actual jmps */
    print( );              /* print stats, alignment */
    cleanup(0);            /* unlink any tmp files */
}
/* do the alignment, return best score: main( )
* dna: values in Fitch and Smith, PNAS, 80, 1382-1386, 1983
* pro: PAM 250 values
* When scores are equal, we prefer mismatches to any gap, prefer
* a new gap to extending an ongoing gap, and prefer a gap in seqx
* to a gap in seq y.
*/
nw( )                                                                       nw
          {
          char      *px, *py;           /* seqs and ptrs */
          int       *ndely, *dely;      /* keep track of dely */
          int       ndelx, delx;        /* keep track of delx */
          int       *tmp;               /* for swapping row0, row1 */
          int       mis;                /* score for each type */
          int       ins0, ins1;         /* insertion penalties */
          register  id;                 /* diagonal index */
```

TABLE 1-continued

```
register     ij;                  /* jmp index*/
register     *col0, *col1;        /* score for curr, last row */
register     xx, yy;              /* index into seqs */
dx = (struct diag *)g_calloc("to get diags", len0+len1+1, sizeof(struct diag));
ndely = (int *)g_calloc("to get ndely", len1+1, sizeof(int));
dely = (int *)g_calloc("to get dely", len1+1, sizeof(int));
col0 = (int *)g_calloc("to get col0", len1+1, sizeof(int));
col1 = (int *)g_calloc("to get col1", len1+1, sizeof(int));
ins0 = (dna)? DINS0 : PINS0;
ins1 = (dna)? DINS1 : PINS1;
smax = -10000;
if (endgaps) {
    for (col0[0] = dely[0] = -ins0, yy = 1 ; yy <= len1 ; yy++) {
        col0[yy] = dely[yy] = col0[yy-1] - ins1;
        ndely[yy] = yy;
    }
    col0[0] = 0;         /* Waterman Bull Math Biol 84 */
}
else
    for (yy = 1 ; yy <= len1; yy++)
        dely[yy] = -ins0;
/* fill in match matrix
 */
for (px = seqx[0], xx = 1; xx <= len0; px++, xx++) {
    /* initialize first entry in col
     */
    if (endgaps) {
        if(xx == 1)
            col1[0] = delx = -(ins0+ins1);
        else
            col1[0] = delx = col0[0] - ins1;
        ndelx = xx;
    }
    else {
        col1[0] = 0;
        delx = -ins0;
        ndelx = 0;
    }
                                                                                    ...nw
    for (py = seqx[1], yy = 1; yy <= len1 ; py++, yy++) {
        mis = col0[yy-1];
        if (dna)
            mis += (xbm[*px-'A']&xbm[*py-'A'])? DMAT : DMIS;
        else
            mis += _day[*px-'A'][*py-'A'];
        /* update penalty for del in x seq;
         * favor new del over ongong del
         * ignore MAXGAP if weighting endgaps
         */
        if (endgaps || ndely[yy] < MAXGAP) {
            if (col0[yy] - ins0 >= dely[yy]) {
                dely[yy] = col0[yy] - (ins0+ins1);
                ndely[yy] = 1;
            } else {
                dely[yy] -= ins1;
                ndely[yy]++;
            }
        } else {
            if (col0[yy] - (ins0+ins1) >= dely[yy]) {
                dely[yy] = col0[yy] - (ins0+ins1);
                ndely[yy] = 1;
            } else
                ndely[yy]++;
        }
        /* update penalty for del in y seq;
         * favor new del over ongong del
         */
        if (endgaps || ndelx < MAXGAP) {
            if (col1[yy-1] - ins0 >= delx) {
                delx = col1[yy-1] - (ins0+ins1);
                ndelx = 1;
            } else {
                delx -= ins1;
                ndelx++;
            }
        } else {
            if (col1[yy-1] - (ins0+ins1) >= delx) {
                delx = col1[yy-1] - (ins0+ins1);
                ndelx = 1;
            } else
```

TABLE 1-continued

```
                ndelx++;
        }
        /* pick the maximum score; we're favoring
         * mis over any del and delx over dely
         */
                                                            ...nw
        id = xx - yy + len1 - 1;
        if (mis >= delx && mis >= dely[yy])
                col1[yy] = mis;
        else if (delx >= dely[yy]) {
                col1[yy] = delx;
                ij = dx[id].ijmp;
                if (dx[id].jp.n[0] && (!dna || (ndelx >= MAXJMP
                 && xx > dx[id].jp.x[ij]+MX) || mis > dx[id].score+DINS0)) {
                        dx[id].ijmp++;
                        if (++ij >= MAXJMP) {
                                writejmps(id);
                                ij = dx[id].ijmp = 0;
                                dx[id].offset = offset;
                                offset += sizeof(struct jmp) + sizeof(offset);
                        }
                }
                dx[id].jp.n[ij] = ndelx;
                dx[id].jp.x[ij] =xx;
                dx[id].score = delx;
        }
        else {
                col1[yy] = dely[yy];
                ij = dx[id].ijmp;
        if (dx[id].jp.n[0] && (!dna || (ndely[yy] >= MAXJMP
                 && xx > dx[id].jp.x[ij]+MX) || mis > dx[id].score+DINS0)) {
                        dx[id].ijmp++;
                        if (++ij >= MAXJMP) {
                                writejmps(id);
                                ij = dx[id].ijmp = 0;
                                dx[id].offset = offset;
                                offset += sizeof(struct jmp) + sizeof(offset);
                        }
                }
                dx[id].jp.n[ij] = -ndely[yy];
                dx[id].jp.x[ij] = xx;
                dx[id].score = dely[yy];
        }
        if (xx == len0 && yy < len1) {
                /* last col
                 */
                if (endgaps)
                        col1[yy] -= ins0+ins1*(len1-yy);
                if (col1[yy] > smax) {
                        smax = col1[yy];
                        dmax = id;
                }
        }
    }
    if (endgaps && xx < len0)
            col1[yy-1] -= ins0+ins1*(len0-xx);
    if (col1[yy-1] > smax) {
            smax = col1[yy-1];
            dmax = id;
    }
    tmp = col0; col0 = col1; col1 = tmp;           }
    (void) free((char *)ndely);
    (void) free((char *)dely);
    (void) free((char *)col0);
    (void) free((char *)col1);                     }
/*
*
* print( ) -- only routine visible outside this module
*
* static:
* getmat( ) -- trace back best path, count matches: print( )
* pr_align( ) -- print alignment of described in array p[ ]: print( )
* dumpblock( ) -- dump a block of lines with numbers, stars: pr_align( )
* nums( ) -- put out a number line: dumpblock( )
* putline( ) -- put out a line (name, [num], seq, [num]): dumpblock( )
* stars( ) - -put a line of stars: dumpblock( )
* stripname( ) -- strip any path and prefix from a seqname
*/
#include "nw.h"
#define SPC          3
```

TABLE 1-continued

```
#define P_LINE      256          /* maximum output line */
#define P_SPC       3            /* space between name or num and seq */
extern      _day[26][26];
int         olen;                /* set output line length */
FILE        *fx;                 /* output file */
print( )                                                                       print
{
    int     lx, ly, firstgap, lastgap;    /* overlap */
    if ((fx = fopen(ofile, "w")) == 0) {
        fprintf(stderr,"%s: can't write %s\n", prog, ofile);
        cleanup(1);
    }
    fprintf(fx, "<first sequence: %s (length = %d)\n", namex[0], len0);
    fprintf(fx, "<second sequence: %s (length = %d)\n", namex[1], len1);
    olen = 60;
    lx = len0;
    ly = len1;
    firstgap = lastgap = 0;
    if (dmax < len1 − 1) {              /* leading gap in x */
        pp[0].spc = firstgap = len1 − dmax − 1;
        ly −= pp[0].spc;
    }
    else if (dmax > len1 − 1) {         /* leading gap in y */
        pp[1].spc = firstgap = dmax − (len1 − 1);
        lx −= pp[1].spc;
    }
    if (dmax0 < len0 − 1) {             /* trailing gap in x */
        lastgap = len0 − dmax0 −1;
        lx −= lastgap;
    }
    else if (dmax0 > len0 − 1) {        /* trailing gap in y */
        lastgap = dmax0 − (len0 − 1);
        ly −= lastgap;
    }
    getmat(lx, ly, firstgap, lastgap);
    pr_align( );                }
/*
* trace back the best path, count matches
*/
static
getmat(lx, ly, firstgap, lastgap)                                              getmat
    int     lx, ly;                      /* "core" (minus endgaps) */
    int     firstgap, lastgap;           /* leading trailing overlap */
{
    int             nm, i0, i1, siz0, siz1;
    char            outx[32];
    double          pct;
    register        n0, n1;
    register char   *p0, *p1;
    /* get total matches, score
    */
    i0 = i1 = siz0 = siz1 = 0;
    p0 = seqx[0] + pp[1].spc;
    p1 = seqx[1] + pp[0].spc;
    n0 = pp[1].spc + 1;
    n1 = pp[0].spc + 1;
    nm = 0;
    while ( *p0 && *p1 ) {
        if (siz0) {
            p1++;
            n1++;
            siz0−−;
        }
        else if (siz1) {
            p0++;
            n0++;
            siz1−−;
        }
        else {
            if (xbm[*p0−'A']&xbm[*p1−'A'])
                nm++;
            if (n0++ == pp[0].x[i0])
                siz0 = pp[0].n[i0++];
            if (n1++ == pp[1].x[i1])
                siz1 = pp[1].n[i1++];
            p0++;
            p1++;
        }
    }
    /* pct homology:
```

TABLE 1-continued

```
    * if penalizing endgaps, base is the shorter seq
    * else, knock off overhangs and take shorter core
    */
    if (endgaps)
         lx = (len0 < len1)? len0 : len1;
    else
         lx = (lx < ly)? lx : ly;
    pct = 100.*(double)nm/(double)lx;
    fprintf(fx, "\n");
    fprintf(fx, "<%d match %s in an overlap of %d: %.2f percent similarity\n",
         nm, (nm == 1)? "" : "es", lx, pct);
    fprintf(fx, "<gaps in first sequence: %d", gapx);                                          ...getmat
    if (gapx) {
         (void) sprintf(outx, " (%d %s%s)",
              ngapx, (dna)? "base":"residue", (ngapx == 1)? "":"s");
         fprintf(fx,"%s", outx);
    }
    fprintf(fx, ", gaps in second sequence: %d", gapy);
    if (gapy) {
         (void) sprintf(outx, " (%d %s%s)",
              ngapy, (dna)? "base":"residue", (ngapy == 1)? "":"s");
         fprintf(fx,"%s", outx);
    }
    if (dna)
         fprintf(fx,
         "\n<score: %d (match = %d, mismatch = %d, gap penalty = %d + %d per base)\n",
         smax, DMAT, DMIS, DINS0, DINS1);
    else
         fprintf(fx,
         "\n<score: %d (Dayhoff PAM 250 matrix, gap penalty = %d + %d per residue)\n",
         smax, PINS0, PINS1);
    if (endgaps)
         fprintf(fx,
         "<endgaps penalized. left endgap: %d %s%s, right endgap: %d %s%s\n",
         firstgap, (dna)? "base" : "residue", (firstgap == 1)? "" : "s",
         lastgap, (dna)? "base" : "residue", (lastgap == 1)? "" : "s");
    else
         fprintf(fx, "<endgaps not penalized\n");
}
static      nm;              /* matches in core -- for checking */
static      lmax;            /* lengths of stripped file names */
static      ij[2];           /* jmp index for a path */
static      nc[2];           /* number at start of current line */
static      ni[2];           /* current elem number -- for gapping */
static      siz[2];
static char *ps[2];          /* ptr to current element */
static char *po[2];          /* ptr to next output char slot */
static char out[2][P_LINE];  /* output line */
static char star[P_LINE];    /* set by stars( ) */
/*
* print alignment of described in struct path pp[ ]
*/
static
pr_align( )                                                                                    pr_align
{
    int       nn;        /* char count */
    int       more;
    register  i;
    for (i = 0, lmax = 0; i < 2; i++) {
         nn = stripname(namex[i]);
         if (nn > lmax)
              lmax = nn;
         nc[i] = 1;
         ni[i] = 1;
         siz[i] = ij[i] = 0;
         ps[i] = seqx[i];
         po[i] = out[i];              }
    for (nn = nm = 0, more = 1; more; ) {                                                      ...pr_align
         for (i = more = 0; i < 2; i++) {
              /*
              * do we have more of this sequence?
              */
              if (!*ps[i])
                   continue;
              more++;
              if (pp[i].spc) {   /* leading space */
                   *po[i]++ = ' ';
                   pp[i].spc--;
              }
              else if (siz[i]) {   /* in a gap */
                   *po[i]++ = '-';
```

TABLE 1-continued

```
                    siz[i]--;
                }
                else {          /* we're putting a seq element
                                */
                    *po[i] = *ps[i];
                    if (islower(*ps[i]))
                        *ps[i] = toupper(*ps[i]);
                    po[i]++;
                    ps[i]++;
                    /*
                     * are we at next gap for this seq?
                     */
                    if (ni[i] == pp[i].x[ij[i]]) {
                        /*
                         * we need to merge all gaps
                         * at this location
                         */
                        siz[i] = pp[i].n[ij[i]++];
                        while (ni[i] == pp[i].x[ij[i]])
                            siz[i] += pp[i].n[ij[i]++];
                    }
                    ni[i]++;
                }
            }
            if (++nn == olen || !more && nn) {
                dumpblock( );
                for (i = 0; i < 2; i++)
                    po[i] = out[i];
                nn = 0;
            }
        }
    }
}
/*
 * dump a block of lines, including numbers, stars: pr_align( )
 */
static
dumpblock( )                                                              dumpblock
{
    register i;
    for (i = 0; i < 2; i++)
        *po[i]-- = '\0';
                                                                          ...dumpblock
    (void) putc('\n', fx);
    for (i = 0; i < 2; i++) {
        if (*out[i] && (*out[i] != ' ' || *(po[i]) != ' ')) {
            if (i == 0)
                nums(i);
            if (i == 0 && *out[1])
                stars( );
            putline(i);
            if (i == 0 && *out[1])
                fprintf(fx, star);
            if (i == 1)
                nums(i);
        }
    }
}
/*
 * put out a number line: dumpblock( )
 */
static
nums(ix)                                                                  nums
    int         ix;        /* index in out[ ] holding seq line */
{
    char            nline[P_LINE];
    register        i, j;
    register char   *pn, *px, *py;
    for (pn = nline, i = 0; i < lmax+P_SPC; i++, pn++)
        *pn = ' ';
    for (i = nc[ix], py = out[ix]; *py; py++, pn++) {
        if (*py == ' ' || *py == '-')
            *pn = ' ';
        else {
            if (i%10 == 0 || (i == 1 && nc[ix] != 1)) {
                j = (i < 0)? -i : i;
                for (px = pn; j; j /= 10, px--)
                    *px = j%10 + '0';
                if (i < 0)
                    *px = '-';
            }
```

TABLE 1-continued

```
                else
                        *pn = ' ';
                i++;
            }
        }
        *pn = '\0';
        nc[ix] = i;
        for (pn = nline; *pn; pn++)
                (void) putc(*pn, fx);
        (void) putc('\n', fx);
}
/*
* put out a line (name, [num], seq, [num]): dumpblock( )
*/
static
putline(ix)                                                                     putline
        int     ix;             {
                                                                                ...putline
        int             i;
        register char       *px;
        for (px = namex[ix], i = 0; *px && *px != ':'; px++, i++)
                (void) putc(*px, fx);
        for (; i < lmax+P_SPC; i++)
                (void) putc(' ', fx);
        /* these count from 1:
         * ni[ ] is current element (from 1)
         * nc[ ] is number at start of current line
         */
        for (px = out[ix]; *px; px++)
                (void) putc(*px&0x7F, fx);
        (void) putc('\n', fx);
}
/*
* put a line of stars (seqs always in out[0], out[1]): dumpblock( )
*/
static                                                                          stars
stars( )
{
        int             i;
        register char       *p0, *p1, cx, *px;
        if (!*out[0] || (*out[0] == ' ' && *(po[0]) == ' ') ||
          !*out[1] || (*out[1] == ' ' && *(po[1]) == ' '))
                return;
        px = star;
        for (i = lmax+P_SPC; i; i--)
                *px++ = ' ';
        for (p0 = out[0], p1 = out[1]; *p0 && *p1; p0++, p1++) {
                if (isalpha(*p0) && isalpha(*p1)) {
                        if (xbm[*p0-'A']&xbm[*p1-'A']) {
                                cx = '*';
                                nm++;
                        }
                        else if (!dna && _day[*p0-'A'][*p1-'A'] > 0)
                                cx = '.';
                        else
                                cx = ' ';
                }
                else
                        cx = ' ';
                *px++ = cx;
        }
        *px++ = '\n';
        *px = '\0';
}
/*
* strip path or prefix from pn, return len: pr_align( )
*/
static                                                                          stripname
stripname(pn)
        char        *pn;        /* file name (may be path) */
{
        register char       *px, *py;
        py = 0;
        for (px = pn; *px; px++)
                if (*px == '/')
                        py = px + 1;
        if (py)
                (void) strcpy(pn, py);
        return(strlen(pn));
}
```

TABLE 1-continued

```
/*
 * cleanup( ) -- cleanup any tmp file
 * getseq( ) -- read in seq, set dna, len, maxlen
 * g_calloc( ) -- calloc( ) with error checkin
 * readjmps( ) -- get the good jmps, from tmp file if necessary
 * writejmps( ) -- write a filled array of jmps to a tmp file: nw( )
 */
#include "nw.h"
#include <sys/file.h>
char        *jname = "/tmp/homgXXXXXX";       /* tmp file for jmps */
FILE        *fj;
int         cleanup( );                        /* cleanup tmp file */
long        lseek( );
/*
 * remove any tmp file if we blow
 */
cleanup(i)                                                                          cleanup
    int   i;
{
    if (fj)
        (void) unlink(jname);
    exit(i);
}
/*
 * read, return ptr to seq, set dna, len, maxlen
 * skip lines starting with ';', '<', or '>'
 * seq in upper or lower case
 */
char       *
getseq(file, len)                                                                   getseq
    char            *file;   /* file name */
    int             *len;    /* seq len */
{
    char            line[1024], *pseq;
    register char   *px, *py;
    int             natgc, tlen;
    FILE            *fp;
    if ((fp = fopen(file,"r")) == 0) {
        fprintf(stderr,"%s: can't read %s\n", prog, file);
        exit(1);
    }
    tlen = natgc = 0;
    while (fgets(line, 1024, fp)) {
        if (*line == ';' || *line == '<' || *line == '>')
            continue;
        for (px = line; *px != '\n'; px++)
            if (isupper(*px) || islower(*px))
                tlen++;
    }
    if ((pseq = malloc((unsigned)(tlen+6))) == 0) {
        fprintf(stderr,"%s: malloc( ) failed to get %d bytes for %s\n", prog, tlen+6, file);
        exit(1);
    }
    pseq[0] = pseq[1] = pseq[2] = pseq[3] = '\0';
                                                                                    ...getseq
    py = pseq + 4;
    *len = tlen;
    rewind(fp);
    while (fgets(line, 1024, fp)) {
        if (*line == ';' || *line == '<' || *line == '>')
            continue;
        for (px = line; *px != '\n'; px++) {
            if (isupper(*px))
                *py++ = *px;
            else if (islower(*px))
                *py++ = toupper(*px);
            if (index("ATGCU",*(py-1)))
                natgc++;
        }
    }
    *py++ = '\0';
    *py = '\0';
    (void) fclose(fp);
    dna = natgc > (tlen/3);
    return(pseq+4);
}
char       *
g_calloc(msg, nx, sz)                                                               g_calloc
    char    *msg;        /* program, calling routine */
    int     nx, sz;      /* number and size of elements */
```

TABLE 1-continued

```
{
    char            *px, *calloc( );
    if ((px = calloc((unsigned)nx, (unsigned)sz)) == 0) {
        if (*msg) {
            fprintf(stderr, "%s: g_calloc( ) failed %s (n=%d, sz=%d)\n", prog, msg, nx, sz);
            exit(1);
        }
    }
    return(px);
}
/*
* get final jmps from dx[ ] or tmp file, set pp[ ], reset dmax: main( )
*/
readjmps( )                                                                                 readjmps
{
    int             fd = -1;
    int             siz, i0, i1;
    register i, j, xx;
    if (fj) {
        (void) fclose(fj);
        if ((fd = open(jname, O_RDONLY, 0)) < 0) {
            fprintf(stderr, "%s: can't open( ) %s\n", prog, jname);
            cleanup(1);
        }
    }
    for (i = i0 = i1 = 0, dmax0 = dmax, xx = len0; ; i++) {
        while (1) {
            for (j = dx[dmax].ijmp; j >= 0 && dx[dmax].jp.x[j] >= xx; j--)
                ;
                                                                                            ...readjmps
            if (j < 0 && dx[dmax].offset && fj) {
                (void) lseek(fd, dx[dmax].offset, 0);
                (void) read(fd, (char *)&dx[dmax].jp, sizeof(struct jmp));
                (void) read(fd, (char *)&dx[dmax].offset, sizeof(dx[dmax].offset));
                dx[dmax].ijmp = MAXJMP-1;        }
            else
                break;                          }
            if (i >= JMPS) {
                fprintf(stderr, "%s: too many gaps in alignment\n", prog);
                cleanup(1);
            }
            if (j >= 0) {
                siz = dx[dmax].jp.n[j];
                xx = dx[dmax].jp.x[j];
                dmax += siz;
                if (siz < 0) {                  /* gap in second seq */
                    pp[1].n[i1] = -siz;
                    xx += siz;
                    /* id = xx - yy + len1 - 1          */
                    pp[1].x[i1] = xx - dmax + len1 - 1;
                    gapy++;
                    ngapy -= siz;
/* ignore MAXGAP when doing endgaps */
                    siz = (-siz < MAXGAP || endgaps)? -siz : MAXGAP;
                    i1++;
                }
                else if (siz > 0) {             /* gap in first seq */
                    pp[0].n[i0] = siz;
                    pp[0].x[i0] = xx;
                    gapx++;
                    ngapx += siz;
/* ignore MAXGAP when doing endgaps */
                    siz = (siz < MAXGAP || endgaps)? siz : MAXGAP;
                    i0++;
                }
            }
            else
                break;
    }
    /* reverse the order of jmps */
    for (j = 0, i0--; j < i0; j++, i0--) {
        i = pp[0].n[j]; pp[0].n[j] = pp[0].n[i0]; pp[0].n[i0] = i;
        i = pp[0].x[j]; pp[0].x[j] = pp[0].x[i0]; pp[0].x[i0] = i;
    }
    for (j = 0, i1--; j < i1; j++, i1--) {
        i = pp[1].n[j]; pp[1].n[j] = pp[1].n[i1]; pp[1].n[i1] = i;
        i = pp[1].x[j]; pp[1].x[j] = pp[1].x[i1]; pp[1].x[i1] = i;
    }
    if (fd >= 0)
        (void) close(fd);
```

TABLE 1-continued

```
        if (fj) {
            (void) unlink(jname);
            fj = 0;
            offset = 0;
        }               }
/*
 * write a filled jmp struct offset of the prev one (if any): nw( )
 */
writejmps(ix)                                                        writejmps
        int     ix;
{
    char        *mktemp( );
    if (!fj) {
        if (mktemp(jname) < 0) {
            fprintf(stderr, "%s: can't mktemp( ) %s\n", prog, jname);
            cleanup(1);
        }
        if ((fj = fopen(jname, "w")) == 0) {
            fprintf(stderr, "%s: can't write %s\n", prog, jname);
            exit(1);
        }
    }
    (void) fwrite((char *)&dx[ix].jp, sizeof(struct jmp), 1, fj);
    (void) fwrite((char *)&dx[ix].offset, sizeof(dx[ix].offset), 1, fj);
}
```

TABLE 2

| TAHO | XXXXXXXXXXXXXXX | (Length = 15 amino acids) |
|---|---|---|
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the TAHO polypeptide) = 5 divided by 15 = 33.3%

TABLE 3

| TAHO | XXXXXXXXXX | (Length = 10 amino acids) |
|---|---|---|
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the TAHO polypeptide) = 5 divided by 10 = 50%

TABLE 4

| TAHO-DNA | NNNNNNNNNNNNNN | (Length = 14 nucleotides) |
|---|---|---|
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the TAHO-DNA nucleic acid sequence) = 6 divided by 14 = 42.9%

TABLE 5

| TAHO-DNA | NNNNNNNNNNNN | (Length = 12 nucleotides) |
|---|---|---|
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the TAHO-DNA nucleic acid sequence) = 4 divided by 12 = 33.3%

II. Compositions and Methods of the Invention

A. Anti-TAHO Antibodies

In one embodiment, the present invention provides anti-TAHO antibodies which may find use herein as therapeutic agents. Exemplary antibodies include polyclonal, monoclonal, humanized, bispecific, and heteroconjugate antibodies.

1. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5.1 µg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, *J. Immunol.*, 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., *Anal. Biochem.*, 107:220 (1980).

Once hybridoma cells that produce antibodies of the desired specificity, affinity, and/or activity are identified, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.* 130: 151-188 (1992).

In a further embodiment, monoclonal antibodies or antibody fragments can be isolated from antibody phage libraries generated using the techniques described in McCafferty et al., *Nature*, 348:552-554 (1990). Clackson et al., *Nature*, 352: 624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567; and Morrison, et al., *Proc. Natl. Acad. Sci. USA*, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

The anti-TAHO antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., *J. Immunol.* 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.* 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-TAHO antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggemann et al., *Year in Immuno.* 7:33 (1993); U.S. Pat. Nos. 5,545,806, 5,569,825, 5,591,669 (all of GenPharm); 5,545,807; and WO 97/17852.

Alternatively, phage display technology (McCafferty et al., *Nature* 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., *Current Opinion in Structural Biology* 3:564-571 (1993). Several sources of V-gene segments can be used for phage display. Clackson et al., *Nature*, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

4. Antibody fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See *Antibody Engineering*, ed. Borrebaeck, supra. The antibody fragment may also be a "linear antibody", e.g., as described in U.S. Pat. No. 5,641, 870 for example. Such linear antibody fragments may be monospecific or bispecific.

5. Bispecific Antibodies

Bispecific antibodies are antibodies that have binding specificities for at least two different epitopes. Exemplary bispecific antibodies may bind to two different epitopes of a TAHO protein as described herein. Other such antibodies may combine a TAHO binding site with a binding site for another protein. Alternatively, an anti-TAHO arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), so as to focus and localize cellular defense mechanisms to the TAHO-expressing cell. Bispecific antibodies may also be used to localize cytotoxic agents to cells which express TAHO. These antibodies possess a TAHO-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')$_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fc α antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., *Nature* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.* 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology* 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of 1.5 HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.* 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets. Various techniques for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al., *J. Immunol.* 147:60 (1991).

6. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

7. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

8. Effector Function Engineering

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

9. Immunoconjugates

The invention also pertains to immunoconjugates comprising an antibody conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, auristatin peptides, such as monomethylauristatin (MMAE) (synthetic analog of dolastatin), maytansinoids, such as DM1, a trichothene, and CC1065, and the derivatives of these toxins that have toxin activity, are also contemplated herein.

Maytansine and Maytansinoids

In one preferred embodiment, an anti-TAHO antibody (full length or fragments) of the invention is conjugated to one or more maytansinoid molecules.

Maytansinoids, such as DM1, are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3\times10^5$ HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

Anti-TAHO Polypeptide Antibody-Maytansinoid Conjugates (Immunoconjugates).

Anti-TAHO antibody-maytansinoid conjugates are prepared by chemically linking an anti-TAHO antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., *Cancer Research* 52:127-131 (1992). The linking groups include disufide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., *Biochem. J.* 173:723-737 [1978]), sulfosuccinimidyl maleimidomethyl cyclohexane carboxylate (SMCC) and N-succinimidyl-4-(2-pyridylthio)pentanoate (SPP) to provide for a disulfide linkage. Other useful linkers includecys-MC-vc-PAB (a valine-citrulline (vc) dipeptide linker reagent having a maleimide component and a para-aminobenzylcarbamoyl (PAB) self-immolative component.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hyrdoxymethyl, the C-15 position modified with a hydroxyl group, and the C-20 position having a hydroxyl group. In a preferred embodiment, the linkage is formed at the C-3 position of maytansinol or a maytansinol analogue.

Calicheamicin

Another immunoconjugate of interest comprises an anti-TAHO antibody conjugated to one or more calicheamicin molecules. The calicheamicin family of antibiotics are capable of producing double-stranded DNA breaks at subpicomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al., *Cancer Research* 53:3336-3342 (1993), Lode et al., *Cancer Research* 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the anti-TAHO antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated anti-TAHO antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208,020) may be used.

Alternatively, a fusion protein comprising the anti-TAHO antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

10. Immunoliposomes

The anti-TAHO antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., *Proc. Natl. Acad. Sci. USA* 82:3688 (1985); Hwang et al., *Proc. Natl. Acad. Sci. USA* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide interchange reaction. A chemotherapeutic agent is optionally contained within the liposome. See Gabizon et al., *J. National Cancer Inst.* 81(19): 1484 (1989).

B. TAHO Binding Oligopeptides

TAHO binding oligopeptides of the present invention are oligopeptides that bind, preferably specifically, to a TAHO polypeptide as described herein. TAHO binding oligopeptides may be chemically synthesized using known oligopeptide synthesis methodology or may be prepared and purified using recombinant technology. TAHO binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a TAHO polypeptide as described herein. TAHO binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.,* 81:3998-4002 (1984); Geysen et al., *Proc. Natl. Acad. Sci. U.S.A.,* 82:178-182 (1985); Geysen et al., in Synthetic Peptides as Antigens, 130-149 (1986); Geysen et al., *J. Immunol. Meth.,* 102:259-274 (1987); Schoofs et al., *J. Immunol.,* 140:611-616 (1988), Cwirla, S. E. et al. (1990) *Proc. Natl. Acad. Sci. USA,* 87:6378; Lowman, H. B. et al. (1991) *Biochemistry,* 30:10832; Clackson, T. et al. (1991) *Nature,* 352: 624; Marks, J. D. et al. (1991), *J. Mol. Biol.,* 222:581; Kang, A. S. et al. (1991) *Proc. Natl. Acad. Sci. USA,* 88:8363, and Smith, G. P. (1991) *Current Opin. Biotechnol.,* 2:668).

In this regard, bacteriophage (phage) display is one well known technique which allows one to screen large oligopeptide libraries to identify member(s) of those libraries which are capable of specifically binding to a polypeptide target. Phage display is a technique by which variant polypeptides are displayed as fusion proteins to the coat protein on the surface of bacteriophage particles (Scott, J. K. and Smith, G. P. (1990) *Science* 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) *Proc. Natl. Acad. Sci. USA,* 87:6378) or protein (Lowman, H. B. et al. (1991) *Biochemistry,* 30:10832; Clackson, T. et al. (1991) *Nature,* 352: 624; Marks, J. D. et al. (1991), *J. Mol. Biol.,* 222:581; Kang, A. S. et al. (1991) *Proc. Natl. Acad. Sci. USA,* 88:8363) libraries on phage have been used for screening millions of polypeptides or oligopeptides for ones with specific binding properties (Smith, G. P. (1991) *Current Opin. Biotechnol.,* 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409, 5,403,484, 5,571,689, and 5,663,143.

Although most phage display methods have used filamentous phage, lambdoid phage display systems (WO 95/34683; U.S. Pat. No. 5,627,024), T4 phage display systems (Ren et al., *Gene,* 215: 439 (1998); Zhu et al., *Cancer Research,* 58(15): 3209-3214 (1998); Jiang et al., *Infection & Immunity,* 65(11): 4770-4777 (1997); Ren et al., *Gene,* 195(2):303-311 (1997); Ren, *Protein Sci.,* 5: 1833 (1996); Efimov et al., *Virus Genes,* 10: 173 (1995)) and T7 phage display systems (Smith and Scott, *Methods in Enzymology,* 217: 228-257 (1993); U.S. Pat. No. 5,766,905) are also known.

Many other improvements and variations of the basic phage display concept have now been developed. These improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of *Staphylococcus aureus* protein A as an affinity tag has also been reported (Li et al. (1998) Mol Biotech., 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432,018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

C. TAHO Binding Organic Molecules

TAHO binding organic molecules are organic molecules other than oligopeptides or antibodies as defined herein that bind, preferably specifically, to a TAHO polypeptide as described herein. TAHO binding organic molecules may be identified and chemically synthesized using known methodology (see, e.g., PCT Publication Nos. WO00/00823 and WO00/39585). TAHO binding organic molecules are usually less than about 2000 daltons in size, alternatively less than about 1500, 750, 500, 250 or 200 daltons in size, wherein such organic molecules that are capable of binding, preferably specifically, to a TAHO polypeptide as described herein may be identified without undue experimentation using well known techniques. In this regard, it is noted that techniques for screening organic molecule libraries for molecules that are capable of binding to a polypeptide target are well known in the art (see, e.g., PCT Publication Nos. WO00/00823 and WO00/39585). TAHO binding organic molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

D. Screening for Anti-TAHO Antibodies, TAHO Binding Oligopeptides and TAHO Binding Organic Molecules with the Desired Properties Techniques for generating antibodies, oligopeptides and organic molecules that bind to TAHO polypeptides have been described above. One may further select antibodies, oligopeptides or other organic molecules with certain biological characteristics, as desired.

The growth inhibitory effects of an anti-TAHO antibody, oligopeptide or other organic molecule of the invention may be assessed by methods known in the art, e.g., using cells which express a TAHO polypeptide either endogenously or following transfection with the TAHO gene. For example, appropriate tumor cell lines and TAHO-transfected cells may be treated with an anti-TAHO monoclonal antibody, oligopeptide or other organic molecule of the invention at various concentrations for a few days (e.g., 2-7) days and stained with crystal violet or MTT or analyzed by some other colorimetric assay. Another method of measuring proliferation would be by comparing $^3$H-thymidine uptake by the cells treated in the presence or absence an anti-TAHO antibody, TAHO binding oligopeptide or TAHO binding organic molecule of the invention. After treatment, the cells are harvested and the amount of radioactivity incorporated into the DNA quantitated in a scintillation counter. Appropriate positive controls include treatment of a selected cell line with a growth inhibitory antibody known to inhibit growth of that cell line. Growth inhibition of tumor cells in vivo can be determined in various ways known in the art. The tumor cell may be one that overexpresses a TAHO polypeptide. The anti-TAHO antibody, TAHO binding oligopeptide or TAHO binding organic molecule will inhibit cell proliferation of a TAHO-expressing tumor cell in vitro or in vivo by about 25-100% compared to the untreated tumor cell, more preferably, by about 30-100%, and even more preferably by about 50-100% or 70-100%, in one embodiment, at an antibody concentration of about 0.5 to 30 µg/ml. Growth inhibition can be measured at an antibody concentration of about 0.5 to 3 µg/ml or about 0.5 nM to 200 nM in cell culture, where the growth inhibition is determined 1-10 days after exposure of the tumor cells to the antibody. The antibody is growth inhibitory in vivo if administration of the anti-TAHO antibody at about 1 µg/kg to about 100 mg/kg body weight results in reduction in tumor size or reduction of tumor cell proliferation within about 5 days to 3 months from the first administration of the antibody, preferably within about 5 to 30 days.

To select for an anti-TAHO antibody, TAHO binding oligopeptide or TAHO binding organic molecule which induces cell death, loss of membrane integrity as indicated by, e.g., propidium iodide (PI), trypan blue or 7AAD uptake may be assessed relative to control. A PI uptake assay can be performed in the absence of complement and immune effector cells. TAHO polypeptide-expressing tumor cells are incubated with medium alone or medium containing the appropriate anti-TAHO antibody (e.g, at about 10 µg/ml), TAHO binding oligopeptide or TAHO binding organic molecule. The cells are incubated for a 3 day time period. Following each treatment, cells are washed and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN® flow cytometer and FACSCONVERT® CellQuest software (Becton Dickinson). Those anti-TAHO antibodies, TAHO binding oligopeptides or TAHO binding organic molecules that induce statistically significant levels of cell death as determined by PI uptake may be selected as cell death-inducing anti-TAHO antibodies, TAHO binding oligopeptides or TAHO binding organic molecules.

To screen for antibodies, oligopeptides or other organic molecules which bind to an epitope on a TAHO polypeptide bound by an antibody of interest, a routine cross-blocking assay such as that described in *Antibodies, A Laboratory Manual*, Cold Spring Harbor Laboratory, Ed Harlow and David Lane (1988), can be performed. This assay can be used to determine if a test antibody, oligopeptide or other organic molecule binds the same site or epitope as a known anti-TAHO antibody. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of a TAHO polypeptide can be used in competition assays with the test antibodies or with a test antibody and an antibody with a characterized or known epitope.

E. Antibody Dependent Enzyme Mediated Prodrug Therapy (ADEPT)

The antibodies of the present invention may also be used in ADEPT by conjugating the antibody to a prodrug-activating enzyme which converts a prodrug (e.g., a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328:457-458 (1987)). Antibody-abzyme conjugates can be prepared as described herein for delivery of the abzyme to a tumor cell population.

The enzymes of this invention can be covalently bound to the anti-TAHO antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature* 312:604-608 (1984).

F. Full-Length TAHO Polypeptides

The present invention also provides newly identified and isolated nucleotide sequences encoding polypeptides referred to in the present application as TAHO polypeptides. In particular, cDNAs (partial and full-length) encoding various TAHO polypeptides have been identified and isolated, as disclosed in further detail in the Examples below.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the TAHO polypeptides and encoding nucleic acids described herein, in some cases, Applicants have identified what is believed to be the reading frame best identifiable with the sequence information available at the time.

G. Anti-TAHO Antibody and TAHO Polypeptide Variants

In addition to the anti-TAHO antibodies and full-length native sequence TAHO polypeptides described herein, it is contemplated that anti-TAHO antibody and TAHO polypeptide variants can be prepared. Anti-TAHO antibody and TAHO polypeptide variants can be prepared by introducing appropriate nucleotide changes into the encoding DNA, and/ or by synthesis of the desired antibody or polypeptide. Those skilled in the art will appreciate that amino acid changes may alter post-translational processes of the anti-TAHO antibody or TAHO polypeptide, such as changing the number or position of glycosylation sites or altering the membrane anchoring characteristics.

Variations in the anti-TAHO antibodies and TAHO polypeptides described herein, can be made, for example, using any of the techniques and guidelines for conservative and non-conservative mutations set forth, for instance, in U.S. Pat. No. 5,364,934. Variations may be a substitution, deletion or insertion of one or more codons encoding the antibody or polypeptide that results in a change in the amino acid sequence as compared with the native sequence antibody or polypeptide. Optionally the variation is by substitution of at least one amino acid with any other amino acid in one or more of the domains of the anti-TAHO antibody or TAHO polypeptide. Guidance in determining which amino acid residue may be inserted, substituted or deleted without adversely affecting the desired activity may be found by comparing the sequence of the anti-TAHO antibody or TAHO polypeptide with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

Anti-TAHO antibody and TAHO polypeptide fragments are provided herein. Such fragments may be truncated at the N-terminus or C-terminus, or may lack internal residues, for example, when compared with a full length native antibody or protein. Certain fragments lack amino acid residues that are not essential for a desired biological activity of the anti-TAHO antibody or TAHO polypeptide.

Anti-TAHO antibody and TAHO polypeptide fragments may be prepared by any of a number of conventional techniques. Desired peptide fragments may be chemically synthesized. An alternative approach involves generating antibody or polypeptide fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired antibody or polypeptide fragment, by polymerase chain reaction (PCR). Oligonucleotides that define the desired termini of the DNA fragment are employed at the 5' and 3' primers in the PCR. Preferably, anti-TAHO antibody and TAHO polypeptide fragments share at least one biological and/or immunological activity with the native anti-TAHO antibody or TAHO polypeptide disclosed herein.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the anti-TAHO antibody or TAHO polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., Nucl. Acids Res., 13:4331 (1986); Zoller et al., Nucl. Acids Res., 10:6487 (1987)], cassette mutagenesis [Wells et al., Gene, 34:315 (1985)], restriction selection mutagenesis [Wells et al., Philos. Trans. R. Soc. London SerA, 317:415 (1986)] or other known techniques can be performed on the cloned DNA to produce the anti-TAHO antibody or TAHO polypeptide variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, Science, 244:1081-1085 (1989)]. Alanine is also typically preferred because it is the most common amino acid. Further, it is frequently found in both buried and exposed positions [Creighton, The Proteins, (W.H. Freeman & Co., N.Y.); Chothia, *J. Mol. Biol.*, 150:1 (1976)]. If alanine substitution does not yield adequate amounts of variant, an isoteric amino acid can be used.

Any cysteine residue not involved in maintaining the proper conformation of the anti-TAHO antibody or TAHO polypeptide also may be substituted, generally with serine, to improve the oxidative stability of the molecule and prevent aberrant crosslinking. Conversely, cysteine bond(s) may be added to the anti-TAHO antibody or TAHO polypeptide to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human TAHO polypeptide. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the anti-TAHO antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-TAHO antibody.

H. Modifications of Anti-TAHO Antibodies and TAHO Polypeptides

Covalent modifications of anti-TAHO antibodies and TAHO polypeptides are included within the scope of this invention. One type of covalent modification includes reacting targeted amino acid residues of an anti-TAHO antibody or TAHO polypeptide with an organic derivatizing agent that is capable of reacting with selected side chains or the N- or C-terminal residues of the anti-TAHO antibody or TAHO polypeptide. Derivatization with bifunctional agents is useful, for instance, for crosslinking anti-TAHO antibody or TAHO polypeptide to a water-insoluble support matrix or surface for use in the method for purifying anti-TAHO antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the anti-TAHO antibody or TAHO polypeptide included within the scope of this invention comprises altering the native glycosylation pattern of the antibody or polypeptide. "Altering the native glycosylation pattern" is intended for purposes herein to mean deleting one or more carbohydrate moieties found in native sequence anti-TAHO antibody or TAHO polypeptide (either by removing the underlying glycosylation site or by deleting the glycosylation by chemical and/or enzymatic means), and/or adding one or more glycosylation sites that are not present in the native sequence anti-TAHO antibody or TAHO polypeptide. In addition, the phrase includes qualitative changes in the glycosylation of the native proteins, involving a change in the nature and proportions of the various carbohydrate moieties present.

Glycosylation of antibodies and other polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the anti-TAHO antibody or TAHO polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original anti-TAHO antibody or TAHO polypeptide (for O-linked glycosylation sites). The anti-TAHO antibody or TAHO polypeptide amino acid sequence may optionally be altered through changes at the DNA level, particularly by mutating the DNA encoding the anti-TAHO antibody or TAHO polypeptide at preselected bases such that codons are generated that will translate into the desired amino acids.

Another means of increasing the number of carbohydrate moieties on the anti-TAHO antibody or TAHO polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the anti-TAHO antibody or TAHO polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of anti-TAHO antibody or TAHO polypeptide comprises linking the antibody or polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337. The antibody or polypeptide also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 16th edition, Oslo, A., Ed., (1980).

The anti-TAHO antibody or TAHO polypeptide of the present invention may also be modified in a way to form chimeric molecules comprising an anti-TAHO antibody or TAHO polypeptide fused to another, heterologous polypeptide or amino acid sequence.

In one embodiment, such a chimeric molecule comprises a fusion of the anti-TAHO antibody or TAHO polypeptide with a tag polypeptide which provides an epitope to which an anti-tag antibody can selectively bind. The epitope tag is generally placed at the amino- or carboxyl-terminus of the anti-TAHO antibody or TAHO polypeptide. The presence of such epitope-tagged forms of the anti-TAHO antibody or TAHO polypeptide can be detected using an antibody against the tag polypeptide. Also, provision of the epitope tag enables the anti-TAHO antibody or TAHO polypeptide to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

In an alternative embodiment, the chimeric molecule may comprise a fusion of the anti-TAHO antibody or TAHO polypeptide with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an anti-TAHO antibody or TAHO polypeptide in place of at least one variable region within an Ig molecule. In a particularly preferred embodiment, the immunoglobulin fusion includes the hinge, $CH$ and $CH_3$, or the hinge, $CH_1$, $CH_2$ and $CH_3$ regions of an IgG1 molecule. For the production of immunoglobulin fusions see also U.S. Pat. No. 5,428,130 issued Jun. 27, 1995.

I. Preparation of Anti-TAHO Antibodies and TAHO Polypeptides

The description below relates primarily to production of anti-TAHO antibodies and TAHO polypeptides by culturing cells transformed or transfected with a vector containing anti-TAHO antibody- and TAHO polypeptide-encoding nucleic acid. It is, of course, contemplated that alternative methods, which are well known in the art, may be employed to prepare anti-TAHO antibodies and TAHO polypeptides. For instance, the appropriate amino acid sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the anti-TAHO antibody or TAHO polypeptide may be chemically synthesized separately and combined using chemical or enzymatic methods to produce the desired anti-TAHO antibody or TAHO polypeptide.

1. Isolation of DNA Encoding Anti-TAHO Antibody or TAHO Polypeptide

DNA encoding anti-TAHO antibody or TAHO polypeptide may be obtained from a cDNA library prepared from tissue believed to possess the anti-TAHO antibody or TAHO polypeptide mRNA and to express it at a detectable level. Accordingly, human anti-TAHO antibody or TAHO polypeptide DNA can be conveniently obtained from a cDNA library prepared from human tissue. The anti-TAHO antibody- or TAHO polypeptide-encoding gene may also be obtained from a genomic library or by known synthetic procedures (e.g., automated nucleic acid synthesis).

Libraries can be screened with probes (such as oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding anti-TAHO antibody or TAHO polypeptide is to use PCR methodology [Sambrook et al., supra; Dieffenbach et al., *PCR Primer: A Laboratory Manual* (Cold Spring Harbor Laboratory Press, 1995)].

Techniques for screening a cDNA library are well known in the art. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for anti-TAHO antibody or TAHO polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach* M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene,* 23:315 (1983) and WO 89/05859 published 29 Jun. 1989. For mammalian cells without such cell walls, the calcium phosphate precipitation method of Graham and van der Eb, *Virology,* 52:456-457 (1978) can be employed. General aspects of mammalian cell host system transfections have been described in U.S. Pat. No. 4,399,216. Transformations into yeast are typically carried out according to the method of Van Solingen et al., *J. Bact.,* 130:946 (1977) and Hsiao et al., *Proc. Natl. Acad. Sci. (USA),* 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology,* 185:527-537 (1990) and Mansour et al., *Nature,* 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli, Enterobacter, Erwinia, Klebsiella, Proteus, Salmonella,* e.g., *Salmonella typhimurium, Serratia,* e.g., *Serratia marcescans,* and *Shigella,* as well as Bacilli such as *B. subtilis* and *B. licheniformis* (e.g., *B. licheniformis* 41P disclosed in DD 266,710 published 12 Apr. 1989), *Pseudomonas* such as *P. aeruginosa,* and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3, *E. coli* W3110 strain 27C7 (ATCC 55,244), which has the complete genotype tonA ptr3 phoA E15 (argF-lac)169 degP ompT kah *E. coli* W3110 strain 37D6, which has the complete genotype tonA ptr3 phoA E15 (argF-lac)169 degP ompT rbs7 ilvG kah *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789, 199 (Joly et al.), and U.S. Pat. No. 5,840,523 (Simmons et al.) which describes translation initiation regio (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for anti-TAHO antibody- or TAHO polypeptide-encoding vectors. *Saccharomyces cerevisiae* is a commonly used lower eukaryotic host microorganism. Others include *Schizosaccharomyces pombe* (Beach and Nurse, *Nature,* 290: 140 [1981]; EP 139,383 published 2 May 1985); *Kluyveromyces* hosts (U.S. Pat. No. 4,943,529; Fleer et al., *Bio/Technology,* 9:968-975 (1991)) such as, e.g. lactis (MW98-8C, CBS683, CBS4574; Louvencourt et al., *J. Bacteriol.,* 154(2): 737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology,* 8:135 (1990)), *K. thermotolerans,* and *K. marxianus; yarrowia* (EP 402,226); *Pichia pastoris* (EP 183,070; Sreekrishna et al., *J. Basic Microbiol.,* 28:265-278 [1988]); *Candida; Trichoderma reesia* (EP 244, 234); *Neurospora crassa* (Case et al., *Proc. Natl. Acad. Sci. USA,* 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.,* 112:284-289 [1983]; Tilburn et al., *Gene,* 26:205-221 [1983]; Yelton et al., *Proc. Natl. Acad. Sci. USA,* 81: 1470-1474 [1984]) and *A. niger* (Kelly and Hynes, *EMBO J.,* 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis,* and *Rhodotorula*. A list of specific species that are exemplary of this class of yeasts may be found in C. Anthony, *The Biochemistry of Methylotrophs,* 269 (1982).

Suitable host cells for the expression of glycosylated anti-TAHO antibody or TAHO polypeptide are derived from multicellular organisms. Examples of invertebrate cells include insect cells such as *Drosophila* S2 and *Spodoptera* Sf9, as well as plant cells, such as cell cultures of cotton, corn, potato, soybean, petunia, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC cells; FS4 cells; and a human hepatoma line (Hep G2).

Host cells are transformed with the above-described expression or cloning vectors for anti-TAHO antibody or TAHO polypeptide production and cultured in conventional nutrient media modified as appropriate for inducing promoters, selecting transformants, or amplifying the genes encoding the desired sequences.

3. Selection and Use of a Replicable Vector

The nucleic acid (e.g., cDNA or genomic DNA) encoding anti-TAHO antibody or TAHO polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The TAHO may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the anti-TAHO antibody- or TAHO polypeptide-encoding DNA that is inserted into the vector. The signal sequence may be a prokaryotic signal sequence selected, for example, from the group of the alkaline phosphatase, penicillinase, 1 pp, or heat-stable enterotoxin II leaders. For yeast secretion the signal sequence may be, e.g., the yeast invertase leader, alpha factor leader (includes *Saccharomyces* and *Kluyveromyces* α-factor leaders, the latter described in U.S. Pat. No. 5,010, 182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the anti-TAHO antibody- or TAHO polypeptide-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-[Jones, *Genetics*, 85:12 (1977)].

Expression and cloning vectors usually contain a promoter operably linked to the anti-TAHO antibody- or TAHO polypeptide-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21-25 (1983)]. Promoters for use in bacterial systems also will contain a Shine-Dalgarno (S.D.) sequence operably linked to the DNA encoding anti-TAHO antibody or TAHO polypeptide.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Anti-TAHO antibody or TAHO polypeptide transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the anti-TAHO antibody or TAHO polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the anti-TAHO antibody or TAHO polypeptide coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-TAHO antibody or TAHO polypeptide.

Still other methods, vectors, and host cells suitable for adaptation to the synthesis of anti-TAHO antibody or TAHO polypeptide in recombinant vertebrate cell culture are described in Gething et al., *Nature,* 293:620-625 (1981); Mantei et al., *Nature,* 281:40-46 (1979); EP 117,060; and EP 117,058.

4. Culturing the Host Cells

The host cells used to produce the anti-TAHO antibody or TAHO polypeptide of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Patent Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

5. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA,* 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence TAHO polypeptide or against a synthetic peptide based on the DNA sequences provided herein or against exogenous sequence fused to TAHO DNA and encoding a specific antibody epitope.

6. Purification of Anti-TAHO Antibody and TAHO Polypeptide

Forms of anti-TAHO antibody and TAHO polypeptide may be recovered from culture medium or from host cell lysates. If membrane-bound, it can be released from the membrane using a suitable detergent solution (e.g. Triton-X 100) or by enzymatic cleavage. Cells employed in expression of anti-TAHO antibody and TAHO polypeptide can be disrupted by various physical or chemical means, such as freeze-thaw cycling, sonication, mechanical disruption, or cell lysing agents.

It may be desired to purify anti-TAHO antibody and TAHO polypeptide from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the anti-TAHO antibody and TAHO polypeptide. Various methods of protein purification may be employed and such methods are known in the art and described for example in Deutscher, *Methods in Enzymology* 182 (1990); Scopes *Protein Purification: Principles and Practice,* Springer-Verlag, New York (1982). The purification step(s) selected will depend, for example, on the nature of the production process used and the particular anti-TAHO antibody or TAHO polypeptide produced.

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2 or γ4 heavy chains (Lindmark et al., *J. Immunol. Meth.* 62:1-13 (1983)). Protein G is recommended for all mouse isotypes and for humanγ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

J. Pharmaceutical Formulations

Therapeutic formulations of the anti-TAHO antibodies, TAHO binding oligopeptides, TAHO binding organic molecules and/or TAHO polypeptides used in accordance with the present invention are prepared for storage by mixing the antibody, polypeptide, oligopeptide or organic molecule having the desired degree of purity with optional pharmaceutically acceptable carriers, excipients or stabilizer *Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic-acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN®, PLURONICS® or polyethylene glycol (PEG). The antibody preferably comprises the antibody at a concentration of between 5-200 mg/ml, preferably between 10-100 mg/ml.

The formulations herein may also contain more than one active compound as necessary for the particular indication being treated, preferably those with complementary activities that do not adversely affect each other. For example, in addition to an anti-TAHO antibody, TAHO binding oligopeptide, or TAHO binding organic molecule, it may be desirable to include in the one formulation, an additional antibody, e.g., a second anti-TAHO antibody which binds a different epitope on the TAHO polypeptide, or an antibody to some other target such as a growth factor that affects the growth of the particular cancer. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences*, 16th edition, Osol, A. Ed. (1980).

Sustained-release preparations may be prepared. Suitable examples of sustained-release preparations include semi-permeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

K. Treatment with Anti-TAHO Antibodies, TAHO Binding Oligopeptides and TAHO Binding Organic Molecules To determine TAHO expression in the cancer, various detection assays are available. In one embodiment, TAHO polypeptide overexpression may be analyzed by immunohistochemistry (IHC). Parrafin embedded tissue sections from a tumor biopsy may be subjected to the IHC assay and accorded a TAHO protein staining intensity criteria as follows:

Score 0—no staining is observed or membrane staining is observed in less than 10% of tumor cells.

Score 1+—a faint/barely perceptible membrane staining is detected in more than 10% of the tumor cells. The cells are only stained in part of their membrane.

Score 2+—a weak to moderate complete membrane staining is observed in more than 10% of the tumor cells.

Score 3+—a moderate to strong complete membrane staining is observed in more than 10% of the tumor cells.

Those tumors with 0 or 1+ scores for TAHO polypeptide expression may be characterized as not overexpressing TAHO, whereas those tumors with 2+ or 3+ scores may be characterized as overexpressing TAHO.

Alternatively, or additionally, FISH assays such as the INFORM® (sold by Ventana, Ariz.) or PATHVISION® (Vysis, Ill.) may be carried out on formalin-fixed, paraffin-embedded tumor tissue to determine the extent (if any) of TAHO overexpression in the tumor.

TAHO overexpression or amplification may be evaluated using an in vivo detection assay, e.g., by administering a molecule (such as an antibody, oligopeptide or organic molecule) which binds the molecule to be detected and is tagged with a detectable label (e.g., a radioactive isotope or a fluorescent label) and externally scanning the patient for localization of the label.

As described above, the anti-TAHO antibodies, oligopeptides and organic molecules of the invention have various non-therapeutic applications. The anti-TAHO antibodies, oligopeptides and organic molecules of the present invention can be useful for staging of TAHO polypeptide-expressing cancers (e.g., in radioimaging). The antibodies, oligopeptides and organic molecules are also useful for purification or immunoprecipitation of TAHO polypeptide from cells, for detection and quantitation of TAHO polypeptide in vitro, e.g., in an ELISA or a Western blot, to kill and eliminate TAHO-expressing cells from a population of mixed cells as a step in the purification of other cells.

Currently, depending on the stage of the cancer, cancer treatment involves one or a combination of the following therapies: surgery to remove the cancerous tissue, radiation therapy, and chemotherapy. Anti-TAHO antibody, oligopeptide or organic molecule therapy may be especially desirable in elderly patients who do not tolerate the toxicity and side effects of chemotherapy well and in metastatic disease where radiation therapy has limited usefulness. The tumor targeting anti-TAHO antibodies, oligopeptides and organic molecules of the invention are useful to alleviate TAHO-expressing cancers upon initial diagnosis of the disease or during relapse. For therapeutic applications, the anti-TAHO antibody, oligopeptide or organic molecule can be used alone, or in combination therapy with, e.g., hormones, antiangiogens, or radiolabelled compounds, or with surgery, cryotherapy, and/or radiotherapy. Anti-TAHO antibody, oligopeptide or organic molecule treatment can be administered in conjunction with other forms of conventional therapy, either consecutively with, pre- or post-conventional therapy. Chemotherapeutic drugs such as TAXOTERE® (docetaxel), TAXOL® (palictaxel), estramustine and mitoxantrone are used in treating cancer, in particular, in good risk patients. In the present method of the invention for treating or alleviating cancer, the cancer patient can be administered anti-TAHO antibody, oligopeptide or organic molecule in conjunction with treatment with the one or more of the preceding chemotherapeutic agents. In particular, combination therapy with palictaxel and modified derivatives (see, e.g., EP0600517) is contemplated. The anti-TAHO antibody, oligopeptide or organic molecule will be administered with a therapeutically effective dose of the chemotherapeutic agent. In another embodiment, the anti-TAHO antibody, oligopeptide or organic molecule is administered in conjunction with chemotherapy to enhance the activity and efficacy of the chemotherapeutic agent, e.g., paclitaxel. The Physicians' Desk Reference (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

In one particular embodiment, a conjugate comprising an anti-TAHO antibody, oligopeptide or organic molecule conjugated with a cytotoxic agent is administered to the patient. Preferably, the immunoconjugate bound to the TAHO protein is internalized by the cell, resulting in increased therapeutic efficacy of the immunoconjugate in killing the cancer cell to which it binds. In a preferred embodiment, the cytotoxic agent targets or interferes with the nucleic acid in the cancer cell. Examples of such cytotoxic agents are described above and include maytansinoids, calicheamicins, ribonucleases and DNA endonucleases.

The anti-TAHO antibodies, oligopeptides, organic molecules or toxin conjugates thereof are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody, oligopeptide or organic molecule is preferred.

Other therapeutic regimens may be combined with the administration of the anti-TAHO antibody, oligopeptide or organic molecule. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the anti-TAHO antibody or antibodies, oligopeptides or organic molecules, with administration of an antibody directed against another tumor antigen associated with the particular cancer.

In another embodiment, the therapeutic treatment methods of the present invention involves the combined administration of an anti-TAHO antibody (or antibodies), oligopeptides or organic molecules and one or more chemotherapeutic agents or growth inhibitory agents, including co-administration of cocktails of different chemotherapeutic agents. Chemotherapeutic agents include estramustine phosphate, prednimustine, cisplatin, 5-fluorouracil, melphalan, cyclophosphamide, hydroxyurea and hydroxyureataxanes (such as paclitaxel and doxetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The antibody, oligopeptide or organic molecule may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is androgen independent cancer, the patient may previously have been subjected to anti-androgen therapy and, after the cancer becomes androgen independent, the anti-TAHO antibody, oligopeptide or organic molecule (and optionally other agents as described herein) may be administered to the patient.

Sometimes, it may be beneficial to also co-administer a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy, before, simultaneously with, or post antibody, oligopeptide or organic molecule therapy. Suitable dosages for any of the above co-administered agents are those presently used and may be lowered due to the combined action (synergy) of the agent and anti-TAHO antibody, oligopeptide or organic molecule.

For the prevention or treatment of disease, the dosage and mode of administration will be chosen by the physician according to known criteria. The appropriate dosage of antibody, oligopeptide or organic molecule will depend on the type of disease to be treated, as defined above, the severity and course of the disease, whether the antibody, oligopeptide or organic molecule is administered for preventive or therapeutic purposes, previous therapy, the patient's clinical history and response to the antibody, oligopeptide or organic molecule, and the discretion of the attending physician. The antibody, oligopeptide or organic molecule is suitably administered to the patient at one time or over a series of treatments. Preferably, the antibody, oligopeptide or organic molecule is administered by intravenous infusion or by subcutaneous injections. Depending on the type and severity of the disease, about 1 μg/kg to about 50 mg/kg body weight (e.g., about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the anti-TAHO antibody. However, other dosage regimens may be useful. A typical daily dosage might range from about μg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

Aside from administration of the antibody protein to the patient, the present application contemplates administration of the antibody by gene therapy. Such administration of nucleic acid encoding the antibody is encompassed by the expression "administering a therapeutically effective amount of an antibody". See, for example, WO96/07321 published Mar. 14, 1996 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et al., Science 256:808-813 (1992). See also WO 93/25673 and the references cited therein.

The anti-TAHO antibodies of the invention can be in the different forms encompassed by the definition of "antibody" herein. Thus, the antibodies include full length or intact antibody, antibody fragments, native sequence antibody or amino acid variants, humanized, chimeric or fusion antibodies, immunoconjugates, and functional fragments thereof. In fusion antibodies an antibody sequence is fused to a heterologous polypeptide sequence. The antibodies can be modified in the Fc region to provide desired effector functions. As discussed in more detail in the sections herein, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, so as to minimize side effects or therapeutic complications, certain other Fc regions may be used.

In one embodiment, the antibody competes for binding or bind substantially to, the same epitope as the antibodies of the invention. Antibodies having the biological characteristics of the present anti-TAHO antibodies of the invention are also contemplated, specifically including the in vivo tumor targeting and any cell proliferation inhibition or cytotoxic characteristics.

Methods of producing the above antibodies are described in detail herein.

The present anti-TAHO antibodies, oligopeptides and organic molecules are useful for treating a TAHO-expressing cancer or alleviating one or more symptoms of the cancer in a mammal. Such a cancer includes, but is not limited to, hematopoietic cancers or blood-related cancers, such as lymphoma, leukemia, myeloma or lymphoid malignancies, but also cancers of the spleen and cancers of the lymph nodes. More particular examples of such B-cell associated cancers, including for example, high, intermediate and low grade lymphomas (including B cell lymphomas such as, for example, mucosa-associated-lymphoid tissue B cell lymphoma and non-Hodgkin's lymphoma, mantle cell lymphoma, Burkitt's lymphoma, small lymphocytic lymphoma, marginal zone lymphoma, diffuse large cell lymphoma, follicular lymphoma, and Hodgkin's lymphoma and T cell lymphomas) and leukemias (including secondary leukemia, chronic lymphocytic leukemia, such as B cell leukemia (CD5+ B lymphocytes), myeloid leukemia, such as acute myeloid leukemia, chronic myeloid leukemia, lymphoid leukemia, such as acute lymphoblastic leukemia and myelodysplasia), multiple myeloma, such as plasma cell malignancy, and other hematological and/or B cell- or T-cell-associated cancers. The cancers encompass metastatic cancers of any of the preceding. The antibody, oligopeptide or organic molecule is able to bind to at least a portion of the cancer cells that express TAHO polypeptide in the mammal. In a preferred embodiment, the antibody. oligopeptide or organic molecule is effective to destroy or kill TAHO-expressing tumor cells or inhibit the growth of such tumor cells, in vitro or in vivo, upon binding to TAHO polypeptide on the cell. Such an antibody includes a naked anti-TAHO antibody (not conjugated to any agent). Naked antibodies that have cytotoxic or cell growth inhibition properties can be further harnessed with a cytotoxic agent to render them even more potent in tumor cell destruction. Cytotoxic properties can be conferred to an anti-TAHO antibody by, e.g., conjugating the antibody with a cytotoxic agent, to form an immunoconjugate as described herein. The cytotoxic agent or a growth inhibitory agent is preferably a small molecule. Toxins such as calicheamicin or a maytansinoid and analogs or derivatives thereof, are preferable.

The invention provides a composition comprising an anti-TAHO antibody, oligopeptide or organic molecule of the invention, and a carrier. For the purposes of treating cancer, compositions can be administered to the patient in need of such treatment, wherein the composition can comprise one or more anti-TAHO antibodies present as an immunoconjugate or as the naked antibody. In a further embodiment, the compositions can comprise these antibodies, oligopeptides or organic molecules in combination with other therapeutic agents such as cytotoxic or growth inhibitory agents, including chemotherapeutic agents. The invention also provides formulations comprising an anti-TAHO antibody, oligopeptide or organic molecule of the invention, and a carrier. In one embodiment, the formulation is a therapeutic formulation comprising a pharmaceutically acceptable carrier.

Another aspect of the invention is isolated nucleic acids encoding the anti-TAHO antibodies. Nucleic acids encoding both the H and L chains and especially the hypervariable region residues, chains which encode the native sequence antibody as well as variants, modifications and humanized versions of the antibody, are encompassed.

The invention also provides methods useful for treating a TAHO polypeptide-expressing cancer or alleviating one or more symptoms of the cancer in a mammal, comprising administering a therapeutically effective amount of an anti-TAHO antibody, oligopeptide or organic molecule to the mammal. The antibody, oligopeptide or organic molecule therapeutic compositions can be administered short term (acute) or chronic, or intermittent as directed by physician. Also provided are methods of inhibiting the growth of, and killing a TAHO polypeptide-expressing cell.

The invention also provides kits and articles of manufacture comprising at least one anti-TAHO antibody, oligopeptide or organic molecule. Kits containing anti-TAHO antibodies, oligopeptides or organic molecules find use, e.g., for TAHO cell killing assays, for purification or immunoprecipitation of TAHO polypeptide from cells. For example, for isolation and purification of TAHO, the kit can contain an anti-TAHO antibody, oligopeptide or organic molecule coupled to beads (e.g., sepharose beads). Kits can be provided which contain the antibodies, oligopeptides or organic molecules for detection and quantitation of TAHO in vitro, e.g., in an ELISA or a Western blot. Such antibody, oligopeptide or organic molecule useful for detection may be provided with a label such as a fluorescent or radiolabel.

L. Articles of Manufacture and Kits

Another embodiment of the invention is an article of manufacture containing materials useful for the treatment of anti-TAHO expressing cancer. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the cancer condition and may have a sterile access port (for example the container may be an intravenous solution bag or a vial having a stopper pierceable by a hypodermic injection needle). At least one active agent in the composition is an anti-TAHO antibody, oligopeptide or organic molecule of the invention. The label or package insert indicates that the composition is used for treating cancer. The label or package insert will further comprise instructions for administering the antibody, oligopeptide or organic molecule composition to the cancer patient. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for TAHO-expressing cell killing assays, for purification or immunoprecipitation of TAHO polypeptide from cells. For isolation and purification of TAHO polypeptide, the kit can contain an anti-TAHO antibody, oligopeptide or organic molecule coupled to beads (e.g., sepharose beads). Kits can be provided which contain the antibodies, oligopeptides or organic molecules for detection and quantitation of TAHO polypeptide in vitro, e.g., in an ELISA or a Western blot. As with the article of manufacture, the kit comprises a container and a label or package insert on or associated with the container. The container holds a composition comprising at least one anti-TAHO antibody, oligopeptide or organic molecule of the invention. Additional containers may be included that contain, e.g., diluents and buffers, control antibodies. The label or package insert may provide a description of the composition as well as instructions for the intended in vitro or detection use.

M. Uses for TAHO Polypeptides and TAHO-Polypeptide Encoding Nucleic Acids

Nucleotide sequences (or their complement) encoding TAHO polypeptides have various applications in the art of molecular biology, including uses as hybridization probes, in chromosome and gene mapping and in the generation of anti-sense RNA and DNA probes. TAHO-encoding nucleic acid will also be useful for the preparation of TAHO polypeptides by the recombinant techniques described herein, wherein those TAHO polypeptides may find use, for example, in the preparation of anti-TAHO antibodies as described herein.

The full-length native sequence TAHO gene, or portions thereof, may be used as hybridization probes for a cDNA library to isolate the full-length TAHO cDNA or to isolate still other cDNAs (for instance, those encoding naturally-occurring variants of TAHO or TAHO from other species) which have a desired sequence identity to the native TAHO sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence TAHO. By way of example, a screening method will comprise isolating the coding region of the TAHO gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the TAHO gene of the present invention can be used to screen libraries of human cDNA, genomic DNA or mRNA to determine which members of such libraries the probe hybridizes to. Hybridization techniques are described in further detail in the Examples below. Any EST sequences disclosed in the present application may similarly be employed as probes, using the methods disclosed herein.

Other useful fragments of the TAHO-encoding nucleic acids include antisense or sense oligonucleotides comprising a singe-stranded nucleic acid sequence (either RNA or DNA) capable of binding to target TAHO mRNA (sense) or TAHO DNA (antisense) sequences. Antisense or sense oligonucleotides, according to the present invention, comprise a fragment of the coding region of TAHO DNA: Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. Such methods are encompassed by the present invention. The antisense oligonucleotides thus may be used to block expression of TAHO proteins, wherein those TAHO proteins may play a role in the induction of cancer in mammals. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Preferred intragenic sites for antisense binding include the region incorporating the translation initiation/start codon (5'-AUG/5'-ATG) or termination/stop codon (5'-UAA, 5'-UAG and 5-UGA/5'-TAA, 5'-TAG and 5'-TGA) of the open reading frame (ORF) of the gene. These regions refer to a portion of the mRNA or gene that encompasses from about 25 to about 50 contiguous nucleotides in either direction (i.e., 5' or 3') from a translation initiation or termination codon. Other preferred regions for antisense binding include: introns; exons; intron-exon junctions; the open reading frame (ORF) or "coding region," which is the region between the translation initiation codon and the translation termination codon; the 5' cap of an mRNA which comprises an N7-methylated guanosine residue joined to the 5'-most residue of the mRNA via a 5'-5' triphosphate linkage and includes 5' cap structure itself as well as the first 50 nucleotides adjacent to the cap; the 5' untranslated region (5'UTR), the portion of an mRNA in the 5' direction from the translation initiation codon, and thus including nucleotides between the 5' cap site and the translation initiation codon of an mRNA or corresponding nucleotides on the gene; and the 3' untranslated region (3'UTR), the portion of an mRNA in the 3' direction from the translation termination codon, and thus including nucleotides between the translation termination codon and 3' end of an mRNA or corresponding nucleotides on the gene.

Specific examples of preferred antisense compounds useful for inhibiting expression of TAHO proteins include oligonucleotides containing modified backbones or non-natural internucleoside linkages. Oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides. Preferred modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included. Representative United States patents that teach the preparation of phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH.sub.2 component parts. Representative United States patents that teach the preparation of such oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

In other preferred antisense oligonucleotides, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Preferred antisense oligonucleotides incorporate phosphorothioate backbones and/or heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($C_3$)—$CH_2$—$CH_2$— [wherein the native phosphodiester backbone is represented as —O—P—O—$CH_2$—] described in the above referenced U.S. Pat. No. 5,489,677, and the amide backbones of the above referenced U.S. Pat. No. 5,602,240. Also preferred are antisense oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-alkyl, S-alkyl, or N-alkyl; O-alkenyl, S-alkeynyl, or N-alkenyl; O-alkynyl, S-alkynyl or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. Other preferred antisense oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2$ $CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_3$)$_2$.

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methylene (—$CH_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$ or —$CH_2$—C≡CH) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deaza-guanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi et al, Antisense Research and Applications, CRC Press, Boca Raton, 1993, pp. 276-278) and are preferred base substitutions, even more particularly when combined with 2'-O-methoxyethyl sugar modifications. Representative United States patents that teach the preparation of modified nucleobases include, but are not limited to: U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,681,941 and 5,750,692, each of which is herein incorporated by reference.

Another modification of antisense oligonucleotides chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, cation lipids, phospholipids, cationic phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) and U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Chimeric antisense compounds of the invention may be formed as composite structures of two or more oligonucleotides, modified oligonucleotides, oligonucleosides and/or oligonucleotide mimetics as described above. Preferred chimeric antisense oligonucleotides incorporate at least one 2' modified sugar (preferably 2'-O—($C_2$)$H_2$—O—$CH_5$) at the 3' terminal to confer nuclease resistance and a region with at least 4 contiguous 2'-H sugars to confer RNase H activity. Such compounds have also been referred to in the art as hybrids or gapmers. Preferred gapmers have a region of 2' modified sugars (preferably 2'-O—$(CH_2)_2$—O—$CH_3$) at the 3'-terminal and at the 5' terminal separated by at least one region having at least 4 contiguous 2'-H sugars and preferably incorporate phosphorothioate backbone linkages. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, CaPO$_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

The probes may also be employed in PCR techniques to generate a pool of sequences for identification of closely related TAHO coding sequences.

Nucleotide sequences encoding a TAHO can also be used to construct hybridization probes for mapping the gene which encodes that TAHO and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for TAHO encode a protein which binds to another protein (example, where the TAHO is a receptor), the TAHO can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor TAHO can be used to isolate correlative ligand(s). Screening assays can be designed to find lead compounds that mimic the biological activity of a native TAHO or a receptor for TAHO. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode TAHO or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding TAHO can be used to clone genomic DNA encoding TAHO in accordance with established techniques and the genomic sequences used to generate transgenic animals that contain cells which express DNA encoding TAHO. Methods for generating transgenic animals, particularly animals such as mice or rats, have become conventional in the art and are described, for example, in U.S. Pat. Nos. 4,736,866 and 4,870,009. Typically, particular cells would be targeted for TAHO transgene incorporation with tissue-specific enhancers. Transgenic animals that include a copy of a transgene encoding TAHO introduced into the germ line of the animal at an embryonic stage can be used to examine the effect of increased expression of DNA encoding TAHO. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of TAHO can be used to construct a TAHO "knock out" animal which has a defective or altered gene encoding TAHO as a result of homologous recombination between the endogenous gene encoding TAHO and altered genomic DNA encoding TAHO introduced into an embryonic stem cell of the animal. For example, cDNA encoding TAHO can be used to clone genomic DNA encoding TAHO in accordance with established techniques. A portion of the genomic DNA encoding TAHO can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, Cell, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., Cell, 69:915 (1992)]. The selected cells are then injected into a blastocyst of an animal (e.g., a mouse or rat) to form aggregation chimeras [see e.g., Bradley, in Teratocarcinomas and Embryonic Stem Cells: A Practical Approach, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the TAHO polypeptide.

Nucleic acid encoding the TAHO polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., Proc. Natl. Acad. Sci. USA 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., Trends in Biotechnology 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429-4432 (1987); and Wagner et al., Proc. Natl. Acad. Sci. USA 87, 3410-3414 (1990). For review of gene marking and gene therapy protocols see Anderson et al., Science 256, 808-813 (1992).

The nucleic acid molecules encoding the TAHO polypeptides or fragments thereof described herein are useful for chromosome identification. In this regard, there exists an ongoing need to identify new chromosome markers, since relatively few chromosome marking reagents, based upon actual sequence data are presently available. Each TAHO nucleic acid molecule of the present invention can be used as a chromosome marker.

The TAHO polypeptides and nucleic acid molecules of the present invention may also be used diagnostically for tissue typing, wherein the TAHO polypeptides of the present invention may be differentially expressed in one tissue as compared to another, preferably in a diseased tissue as compared to a normal tissue of the same tissue type. TAHO nucleic acid molecules will find use for generating probes for PCR, Northern analysis, Southern analysis and Western analysis.

This invention encompasses methods of screening compounds to identify those that mimic the TAHO polypeptide (agonists) or prevent the effect of the TAHO polypeptide (antagonists). Screening assays for antagonist drug candidates are designed to identify compounds that bind or complex with the TAHO polypeptides encoded by the genes identified herein, or otherwise interfere with the interaction of the encoded polypeptides with other cellular proteins, including e.g., inhibiting the expression of TAHO polypeptide from cells. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a TAHO polypeptide encoded by a nucleic acid identified herein under conditions and for a time sufficient to allow these two components to interact.

In binding assays, the interaction is binding and the complex formed can be isolated or detected in the reaction mixture. In a particular embodiment, the TAHO polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the TAHO polypeptide and drying. Alternatively, an immobilized antibody, e.g., a monoclonal antibody, specific for the TAHO polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular TAHO polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, Nature (London), 340:245-246 (1989); Chien et al., Proc. Natl. Acad. Sci. USA, 88:9578-9582 (0.1991)) as disclosed by Chevray and Nathans, Proc. Natl. Acad. Sci. USA, 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a TAHO polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the TAHO polypeptide may be added to a cell along with the compound to be screened for a particular activity and the ability of the compound to inhibit the activity of interest in the presence of the TAHO polypeptide indicates that the compound is an antagonist to the TAHO polypeptide. Alternatively, antagonists may be detected by combining the TAHO polypeptide and a potential antagonist with membrane-bound TAHO polypeptide receptors or recombinant receptors under appropriate conditions for a competitive inhibition assay. The TAHO polypeptide can be labeled, such as by radioactivity, such that the number of TAHO polypeptide molecules bound to the receptor can be used to determine the effectiveness of the potential antagonist. The gene encoding the receptor can be identified by numerous methods known to those of skill in the art, for example, ligand panning and FACS sorting. Coligan et al., Current Protocols in Immun., 1(2): Chapter 5 (1991). Preferably, expression cloning is employed wherein polyadenylated RNA is prepared from a cell responsive to the TAHO polypeptide and a cDNA library created from this RNA is divided into pools and used to transfect COS cells or other cells that are not responsive to the TAHO polypeptide. Transfected cells that are grown on glass slides are exposed to labeled TAHO polypeptide. The TAHO polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled TAHO polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled TAHO polypeptide in the presence of the candidate compound. The ability of the compound to enhance or block this interaction could then be measured.

More specific examples of potential antagonists include an oligonucleotide that binds to the fusions of immunoglobulin with TAHO polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the TAHO polypeptide that recognizes the receptor but imparts no effect, thereby competitively inhibiting the action of the TAHO polypeptide.

Another potential TAHO polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature TAHO polypeptides herein, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al., Science, 241: 456 (1988); Dervan et al., Science, 251:1360 (1991)), thereby preventing transcription and the production of the TAHO polypeptide. The antisense RNA oligonucleotide hybridizes to the mRNA in vivo and blocks translation of the mRNA molecule into the TAHO polypeptide (antisense—Okano, Neurochem., 56:560 (1991); Oligodeoxynucleotides as Antisense Inhibitors of Gene Expression (CRC Press: Boca Raton, Fla., 1988). The oligonucleotides described above can also be delivered to cells such that the antisense RNA or DNA may be expressed in vivo to inhibit production of the TAHO polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the TAHO polypeptide, thereby blocking the normal biological activity of the TAHO polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Isolated TAHO polypeptide-encoding nucleic acid can be used herein for recombinantly producing TAHO polypeptide using techniques well known in the art and as described herein. In turn, the produced TAHO polypeptides can be employed for generating anti-TAHO antibodies using techniques well known in the art and as described herein.

Antibodies specifically binding a TAHO polypeptide identified herein, as well as other molecules identified by the screening assays disclosed hereinbefore, can be administered for the treatment of various disorders, including cancer, in the form of pharmaceutical compositions.

If the TAHO polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA*, 90: 7889-7893 (1993).

The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. Antibodies used in the examples are commercially available antibodies and include, but are not limited to, anti-CD180(eBioscience MRH73-11, BD Pharmingen G28-8) and Serotec MHR73), anti-CD20 (Ancell 2H7 and BD Pharmingen 2H7), anti-CD72 (BD Pharmingen J4-117), anti-CXCR5 (R&D Systems 51505), anti-CD22 (Ancell RFB4, DAKO To15, Diatec 157, Sigma HIB-22 and Monosan BL-BC34), anti-CD22 (Leinco RFB-4 and Neo-Markers 22C04), anti-CD21 (ATCC HB-135 and ATCC HB5), anti-HLA-DOB (BD Pharmingen DOB.L1), anti-CD79a (Caltag ZL7-4 and Serotec ZL7-4), anti-CD79b (Biomeda SN8 and BD Pharmingen CB-3), anti-CD19 (Biomeda CB-19), anti-FCER2 (Ancell BU38 and Serotec D3.6 and BD Pharmingen M-L233). The source of those cells identified in the following examples, and throughout the specification, by ATCC accession numbers is the American Type Culture Collection, Manassas, Va.

Example 1

Microarray Data Analysis of TAHO Expression

Microarray data involves the analysis of TAHO expression by the performance of DNA microarray analysis on a wide a variety of RNA samples from tissues and cultured cells. Samples include normal and cancerous human tissue and various kinds of purified immune cells both at rest and following external stimulation. These RNA samples may be analyzed according to regular microarray protocols on Agilent microarrays.

In this experiment, RNA was isolated from cells and cyanine-3 and cyanine-5 labeled cRNA probes were generated by in vitro transcription using the Agilent Low Input RNA Fluorescent Linear Amplification Kit (Agilent). Cyanine-5 was used to label the samples to be tested for expression of the PRO polypeptide, for example, the myeloma and plasma cells, and cyanine-3 was used to label the universal reference (the Stratagene cell line pool) with which the expression of the test samples were compared. 0.1 μg-0.2 mg of cyanine-3 and cyanine-5 labeled cRNA probe was hybridized to Agilent 60-mer oligonucleotide array chips using the In Situ Hybridization Kit Plus (Agilent). These probes were hybridized to microarrays. For multiple myeloma analysis, probes were hybridized to Agilent Whole Human Genome oligonucleotide microarrays using standard Agilent recommended conditions and buffers (Agilent).

The cRNA probes are hybridized to the microarrays at 60° C. for 17 hours on a hybridization rotator set at 4 RPM. After washing, the microarrays are scanned with the Agilent microarray scanner which is capable of exciting and detecting the fluorescence from the cyanine-3 and cyanine-5 fluorescent molecules (532 and 633 nm laser lines). The data for each gene on the 60-mer oligonucleotide array was extracted from the scanned microarray image using Agilent feature extraction software which accounts for feature recognition, background subtraction and normalization and the resulting data was loaded into the software package known as the Rosetta Resolver Gene Expression Data Analysis System (Rosetta Inpharmatics, Inc.). Rosetta Resolver includes a relational database and numerous analytical tools to store, retrieve and analyze large quantities of intensity or ratio gene expression data.

In this example, B cells and T cells (control) were obtained for microarray analysis. For isolation of naive and memory B cells and plasma cells, human peripheral blood mononuclear cells (PBMC) were separated from either leukopack provided by four healthy male donors or from whole blood of several normal donors. CD138+. plasma cells were isolated from PBMC using the MACS (Miltenyi Biotec) magnetic cell sorting system and anti-CD138 beads. Alternatively, total CD19+ B cells were selected with anti-CD19 beads and MACS sorting. After enrichment of CD19+ (purity around 90%), FACS (Moflo) sorting was performed to separate naive and memory B cells. Sorted cells were collected by subjecting the samples to centrifugation. The sorted cells were immediately lysed in LTR buffer and homogenized with QIAshredder (Qiagen) spin column and followed by RNeasy mini kit for RNA purification. RNA yield was variable from 0.4-10 μg and depended on the cell numbers.

As a control, T cells were isolated for microarray analysis. Peripheral blood CD8 cells were isolated from leukopacks by negative selection using the Stem Cell Technologies CD8 cell isolation kit (Rosette Separation) and further purified by the MACS magnetic cell sorting system using CD8 cell isolation kit and CD45RO microbeads were added to remove CD45RO cells (Miltenyi Biotec). CD8 T cells were divided into 3 samples with each sample subjected to the stimulation as follows: (1) anti-CD3 and anti-CD28, plus IL-12 and anti-IL4 antibody, (2) anti-CD3 and anti-CD29 without adding cytokines or neutralizing antibodies and (3) anti-CD3 and anti-CD28, plus IL-4, anti-IL12 antibody and anti-IFN-γ antibody. 48 hours after stimulation, RNA was collected. After 72 hours, cells were expanded by adding diluting 8-fold with fresh media. 7 days after the RNA was collected, CD8 cells were collected, washed and restimulated by anti-CD3 and anti-CD28. 16 hours later, a second collection of RNA was made. 48 hours after restimulation, a third collection of RNA was made. RNA was collected by using Qiagen Midi preps as per the instructions in the manual with the addition of an on-column DNAse I digestion after the first RW1 wash step. RNA was eluted in RNAse free water and subsequently concentrated by ethanol precipitation. Precipitated RNA was taken up in nuclease free water to a final minimum concentration of 0.5 μg/l.

Additional control microrrays were performed on RNA isolated from CD4+ T helper T cells, natural killer (NK) cells, neutrophils (N'phil), CD14+, CD16+ and CD16– monocytes and dendritic cells (DC).

Additional microarrays were performed on RNA isolated from cancerous tissue, such as Non-Hodgkin's Lymphoma (NHL), follicular lymphoma (FL) and multiple myeloma (MM). Additional microarrays were performed on RNA isolated from normal cells, such as normal lymph node (NLN), normal B cells, such as B cells from centroblasts, centrocytes and follicular mantel, memory B cells, and normal plasma cells (PC), which are from the B cell lineage and are normal counterparts of the myeloma cell, such as tonsil plasma cells, bone marrow plasma cells (BM PC), CD19+ plasma cells (CD19+ PC), CD19– plasma cells (CD19– PC). Additional microarrays were performed on normal tissue, such as cerebellum, heart, prostate, adrenal, bladder, small intestine (s. intestine), colon, fetal liver, uterus, kidney, placenta, lung, pancreas, muscle, brain, salivary, bone marrow (marrow), blood, thymus, tonsil, spleen, testes, and mammary gland.

The molecules listed below have been identified as being significantly expressed in B cells as compared to non-B cells. Specifically, the molecules are differentially expressed in naive B cells, memory B cells that are either IgGA+ or IgM+ and plasma cells from either PBMC or bone marrow, in comparison to non-B-cells, for example T cells. Accordingly, these molecules represent excellent targets for therapy of tumors in mammals.

| Molecule | specific expression in: | as compared to: |
| --- | --- | --- |
| DNA105250 (TAHO1) | B cells | non-B cells |
| DNA150004 (TAHO2) | B cells | non-B cells |
| DNA182432 (TAHO3) | B cells | non-B cells |
| DNA225785 (TAHO4) | B cells | non-B cells |
| DNA225786 (TAHO5) | B cells | non-B cells |
| DNA225875 (TAHO6) | B cells | non-B cells |
| DNA226179 (TAHO7) | B cells | non-B cells |
| DNA226239 (TAHO8) | B cells | non-B cells |
| DNA226394 (TAHO9) | B cells | non-B cells |
| DNA226423 (TAHO10) | B cells | non-B cells |
| DNA227781 (TAHO11) | B cells | non-B cells |
| DNA227879 (TAHO12) | B cells | non-B cells |
| DNA256363 (TAHO13) | B cells | non-B cells |
| DNA332467 (TAHO14) | B cells | non-B cells |
| DNA58721 (TAHO15) | B cells | non-B cells |
| DNA335924 (TAHO16) | B cells | non-B cells |
| DNA340394 (TAHO17) | B cells | non-B cells |
| DNA56041 (TAHO18) | B cells | non-B cells |
| DNA59607 (TAHO19) | B cells | non-B cells |
| DNA257955 (TAHO20) | B cells | non-B cells |
| DNA329863 (TAHO21) | B cells | non-B cells |
| DNA346528 (TAHO22) | B cells | non-B cells |
| DNA212930 (TAHO23) | B cells | non-B cells |
| DNA335918 (TAHO24) | B cells | non-B cells |
| DNA225820 (TAHO25) | B cells | non-B cells |
| DNA88116 (TAHO26) | B cells | non-B cells |
| DNA227752 (TAHO27) | B cells | non-B cells |
| DNA119476 (TAHO28) | B cells | non-B cells |
| DNA254890 (TAHO29) | B cells | non-B cells |
| DNA219240 (TAHO30) | B cells | non-B cells |
| DNA37151 (TAHO31) | B cells | non-B cells |
| DNA210233 (TAHO32) | B cells | non-B cells |
| DNA35918 (TAHO33) | B cells | non-B cells |
| DNA260038 (TAHO34) | B cells | non-B cells |
| DNA334818 (TAHO35) | B cells | non-B cells |
| DNA257501 (TAHO36) | B cells | non-B cells |

Summary

In FIGS. 73-101, significant mRNA expression was generally indicated as a ratio value of greater than 2 (vertical axis of FIGS. 73-101). In FIGS. 73-101, any apparent expression in non-B cells, such as in prostate, spleen, etc. may represent an artifact, infiltration of normal tissue by lymphocytes or loss of sample integrity by the vendor.

(1) TAHO1 (also referred herein as LY64 and CD180) was significantly expressed in non-hodgkin's lymphoma (NHL) and normal B (NB) cell samples (FIG. 73).

(2) TAHO2 (also referred herein as MS4A1 and CD20) was significantly expressed in non-hodgkin's lymphoma (NHL), follicular lymphoma (FL), normal lymph node (NLN) and normal B (NB) cells. Further, TAHO2 was significantly expressed in normal tonsil and spleen (FIG. 74).

(3) TAHO3 (also referred herein as SPAP1 and FcRH2) was significantly expressed in non-hodgkin's lymphoma (NHL) and follicular lymphoma (FL) and memory B cells (mem B). Further TAHO3 was significantly expressed in blood and spleen (FIG. 75). However, as indicated above, any apparent expression in non-B cells, such as in prostate, spleen, blood etc. may represent an artifact, infiltration of normal tissue by lymphocytes or loss of sample integrity by the vendor.

(4) TAHO4 (also referred herein as CD79a) was significantly expressed in non-hodgkin's lymphoma (NHL) multiple myeloma (MM) samples and normal cerebellum and normal blood. Further TAHO4 was significantly expressed in cerebellum, blood and spleen (FIG. 76). However, as indicated above, any apparent expression in non-B cells, such as in prostate, spleen, blood etc. may represent an artifact, infiltration of normal tissue by lymphocytes or loss of sample integrity by the vendor.

(5) TAHO5 (also referred herein as CD79b) was significantly expressed in non-hodgkin's lymphoma (NHL) (FIG. 77).

(6) TAHO6 (also referred herein as CR2 and CD21) was significantly expressed in non-hodgkin's lymphoma (NHL) and normal lymph node (NLN). Further TAHO6 was significantly expressed in spleen FIG. 78).

(7) TAHO8 (also referred herein as CD72) was significantly expressed in non-hodgkin's lymphoma (NHL), multiple myeloma (MM) and follicular lymphoma (FL) and normal tonsil (FIG. 79). However, as indicated above, any apparent expression in non-B cells, such as in prostate, spleen, blood, tonsil etc. may represent an artifact, infiltration of normal tissue by lymphocytes or loss of sample integrity by the vendor.

Figure 80A:
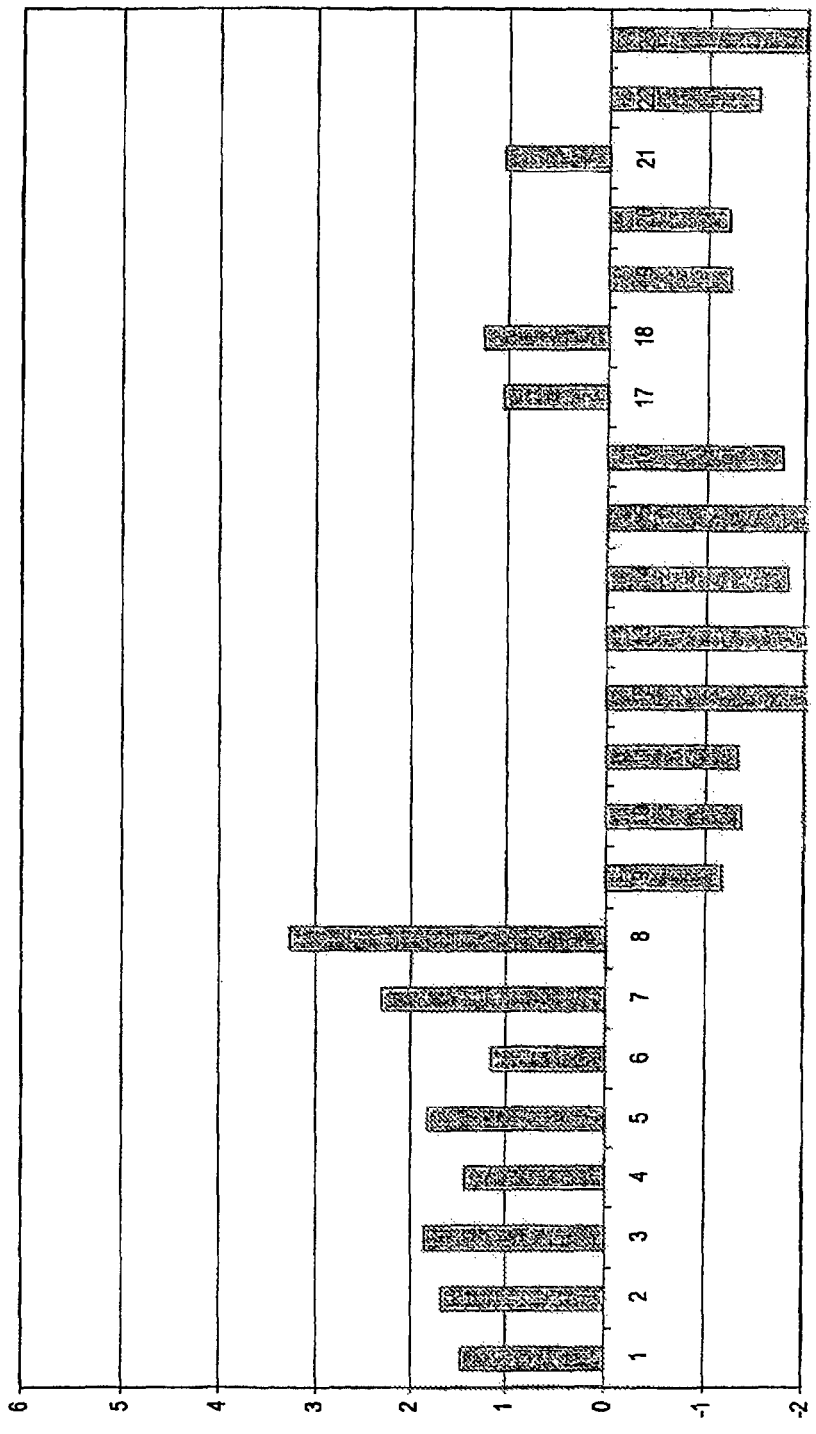
FIGS. 80A-80B show microarray data showing the expression of TAHO9 in normal samples and in diseased samples, such as significant expression in normal B cells (circulating and lymph-node derived B cells) and not significantly expressed in non B cells and significantly expressed in normal plasma cells and multiple myeloma samples and the lymphoid organs, spleen and thymus.
Figure 80B:
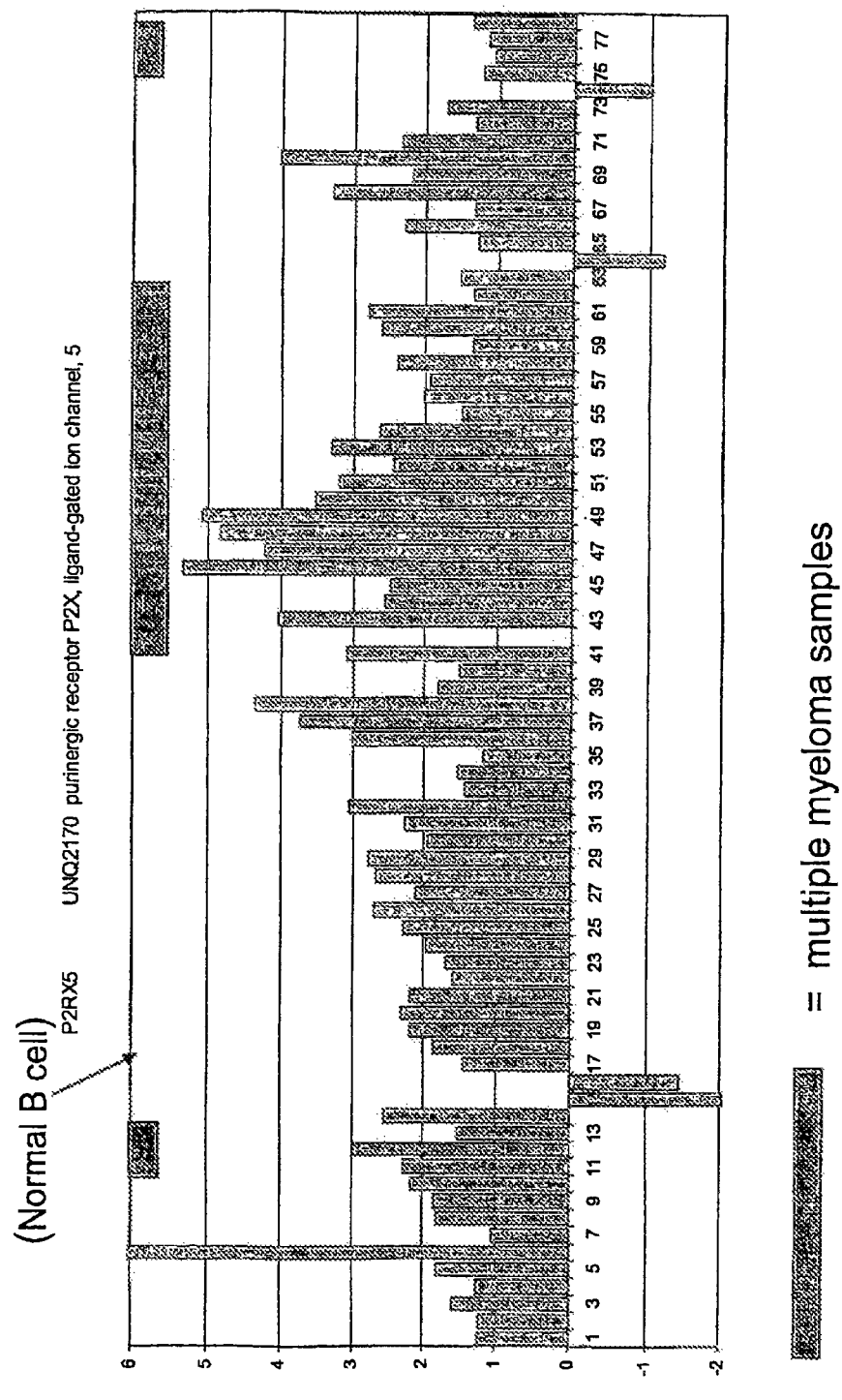
Figure 81A:
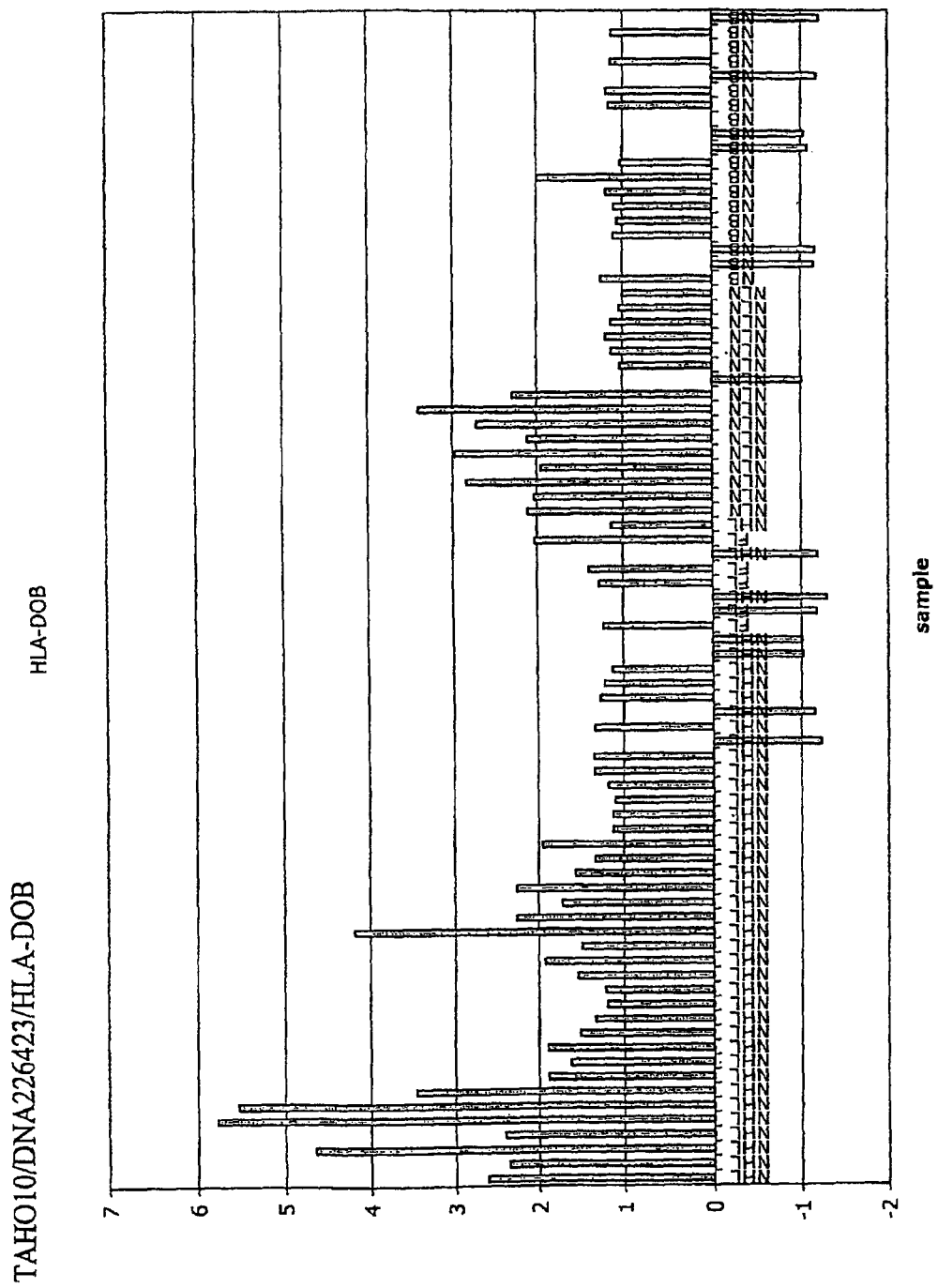
FIGS. 81A-81D show microarray data showing the expression of TAHO10 in normal samples and in diseased samples, such as significant expression in NHL samples and multiple myeloma samples. Abbreviations used in the Figures are designated as follows: Non-Hodgkin's Lymphoma (NHL), follicular lymphoma (FL), normal lymph node (NLN), normal B cells (NB), multiple myeloma cells (MM), small intestine (s. intestine), fetal liver (f. liver), smooth muscle (s. muscle), fetal brain (f. brain), natural killer cells (NK), neutrophils (N'phil), dendrocytes (DC), memory B cells (mem B), plasma cells (PC), bone marrow plasma cells (BM PC).
Figure 81B:
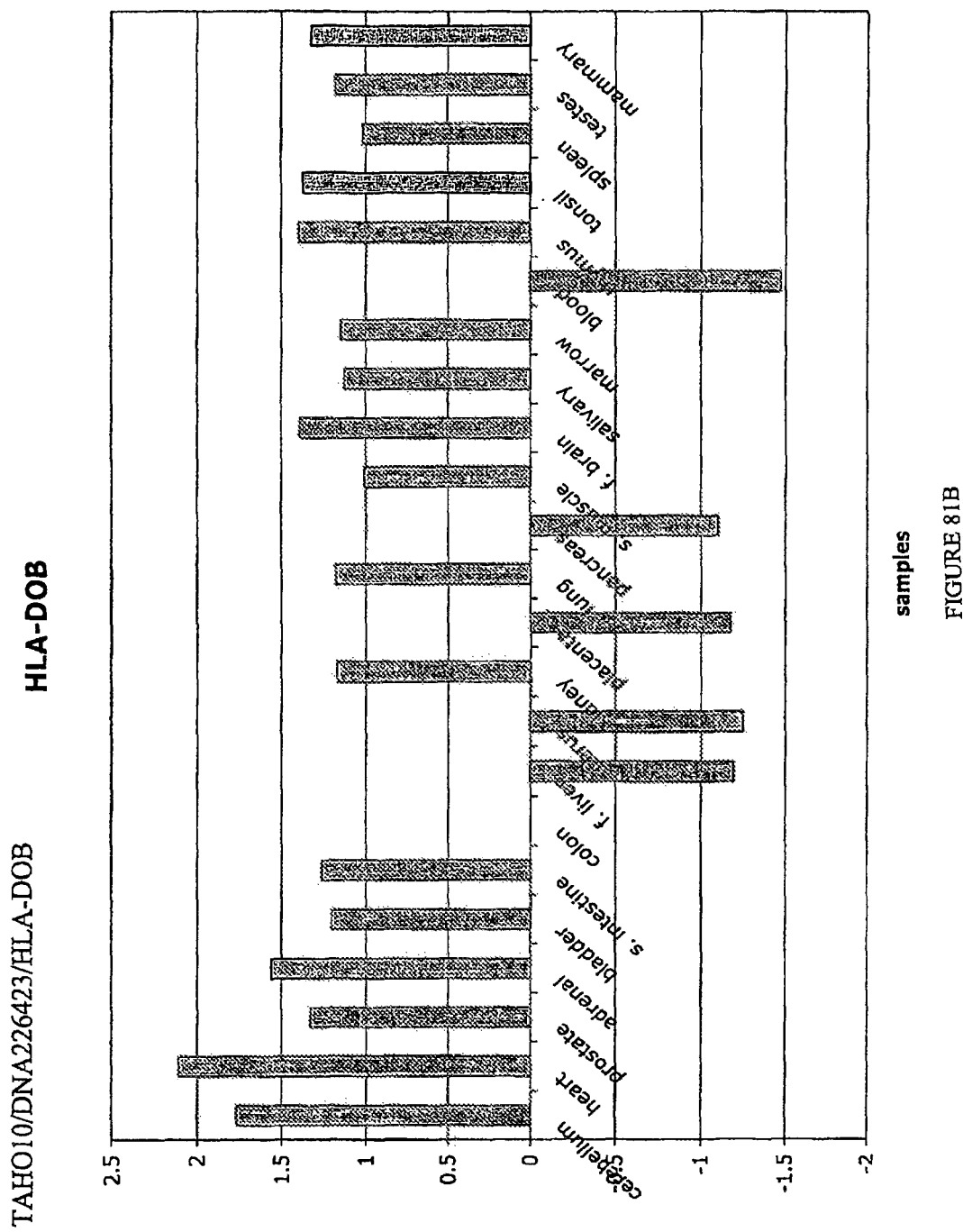
Figure 81C:
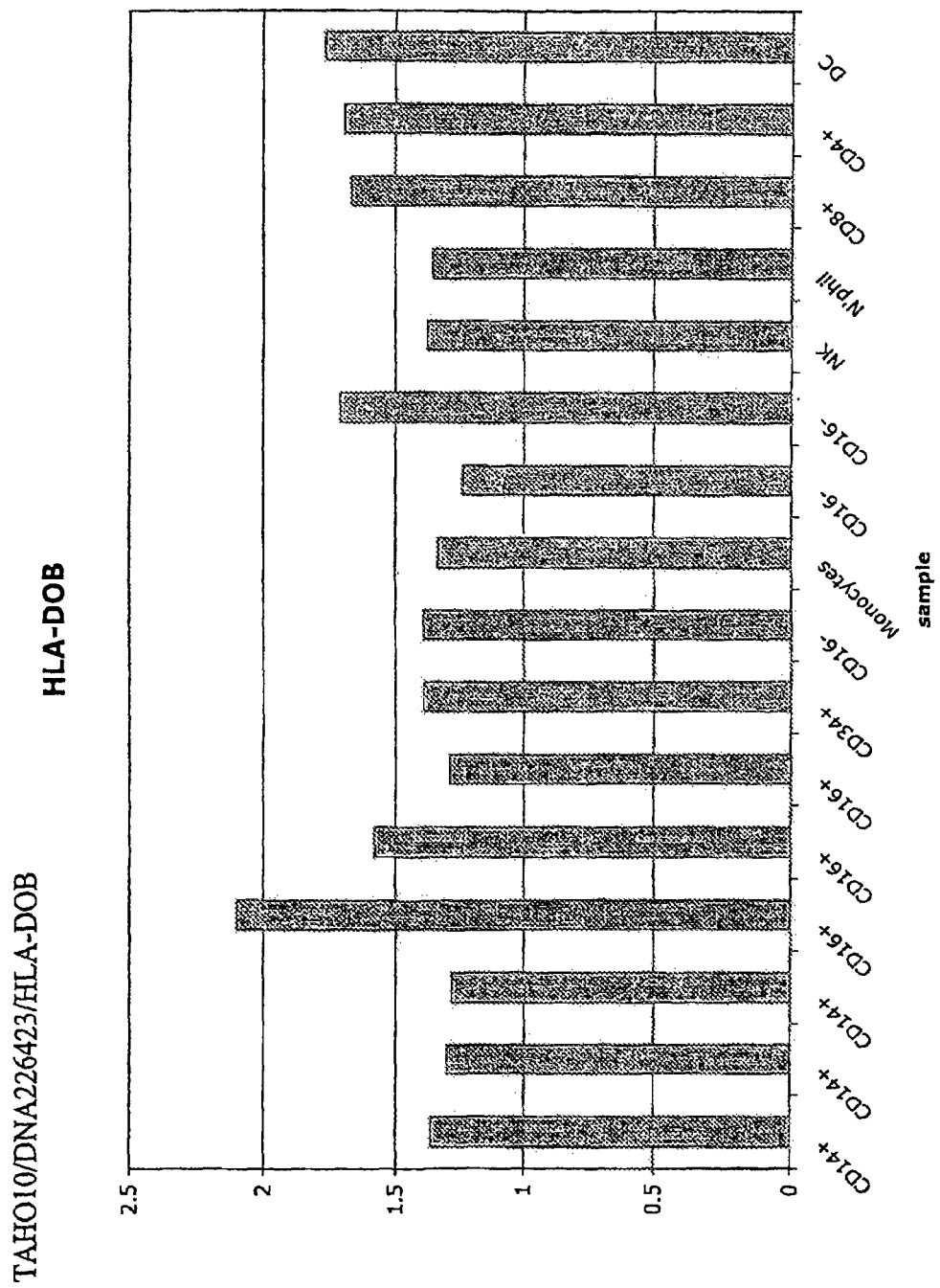
Figure 81D:
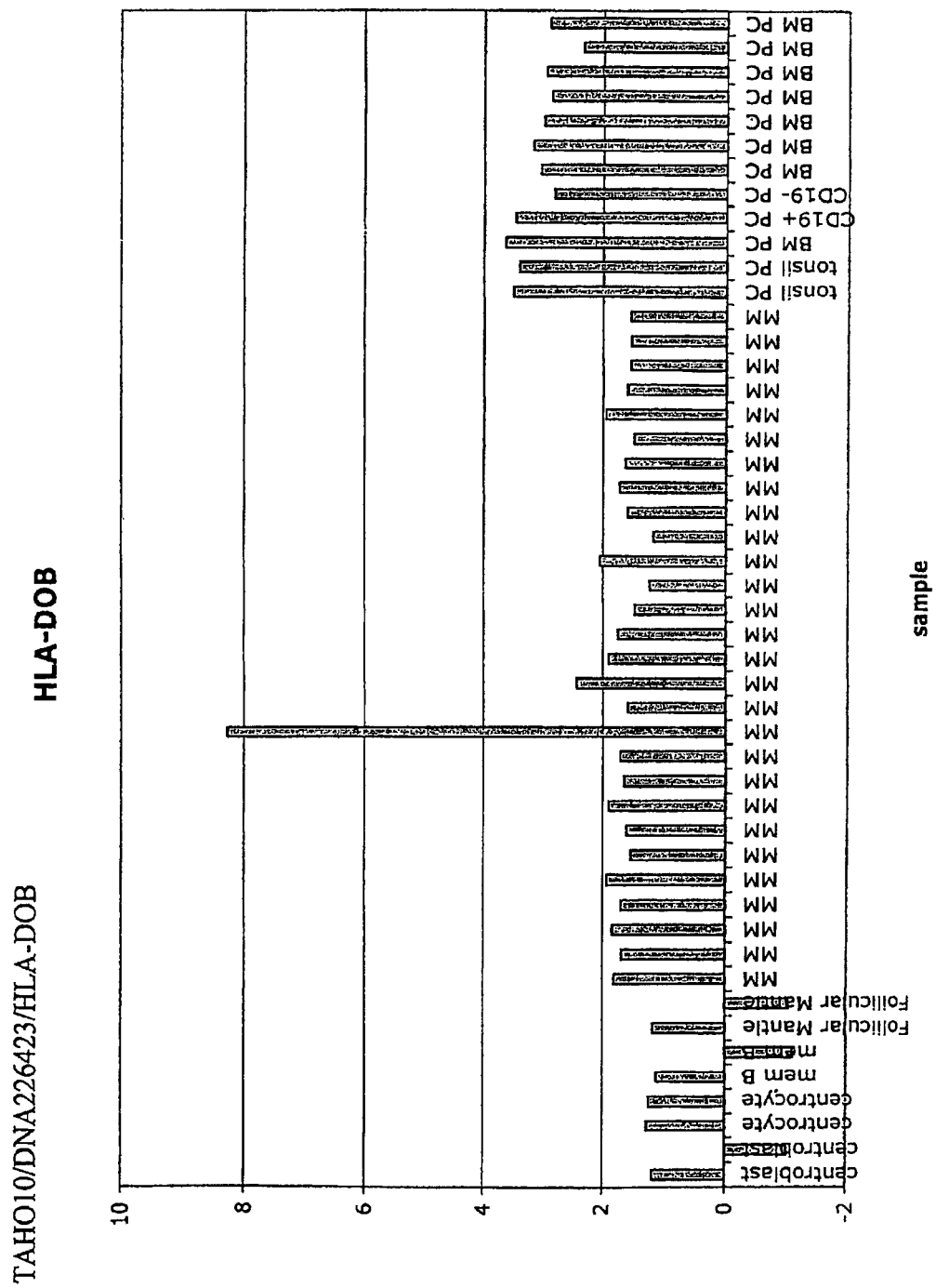
Figure 82A:
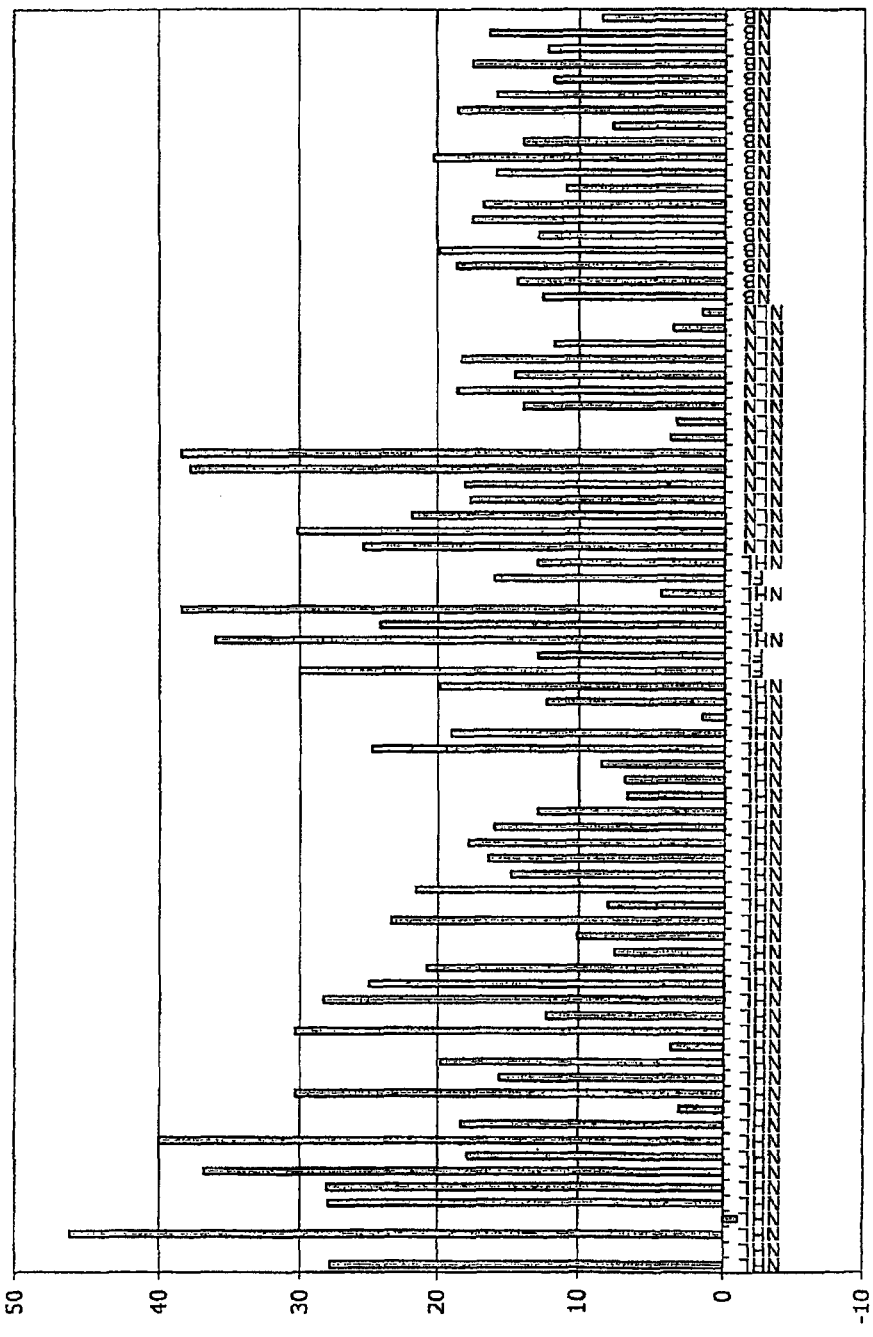
FIGS. 82A-82D show microarray data showing the expression of TAHO11 in normal samples and in diseased samples, such as significant expression in NHL samples, follicular lymphoma (FL), normal lymph node (NLN), normal b cells (NB), centroblasts and follicular mantle cells and normal spleen and normal tonsil. Abbreviations used in the Figures are designated as follows: Non-Hodgkin's Lymphoma (NHL), follicular lymphoma (FL), normal lymph node (NLN), normal B cells (NB), multiple myeloma cells (MM), small intestine (s. intestine), fetal liver (f. liver), smooth muscle (s. muscle), fetal brain (f. brain), natural killer cells (NK), neutrophils (N'phil), dendrocytes (DC), memory B cells (mem B), plasma cells (PC), bone marrow plasma cells (BM PC).
Figure 82B:
Figure 82C:
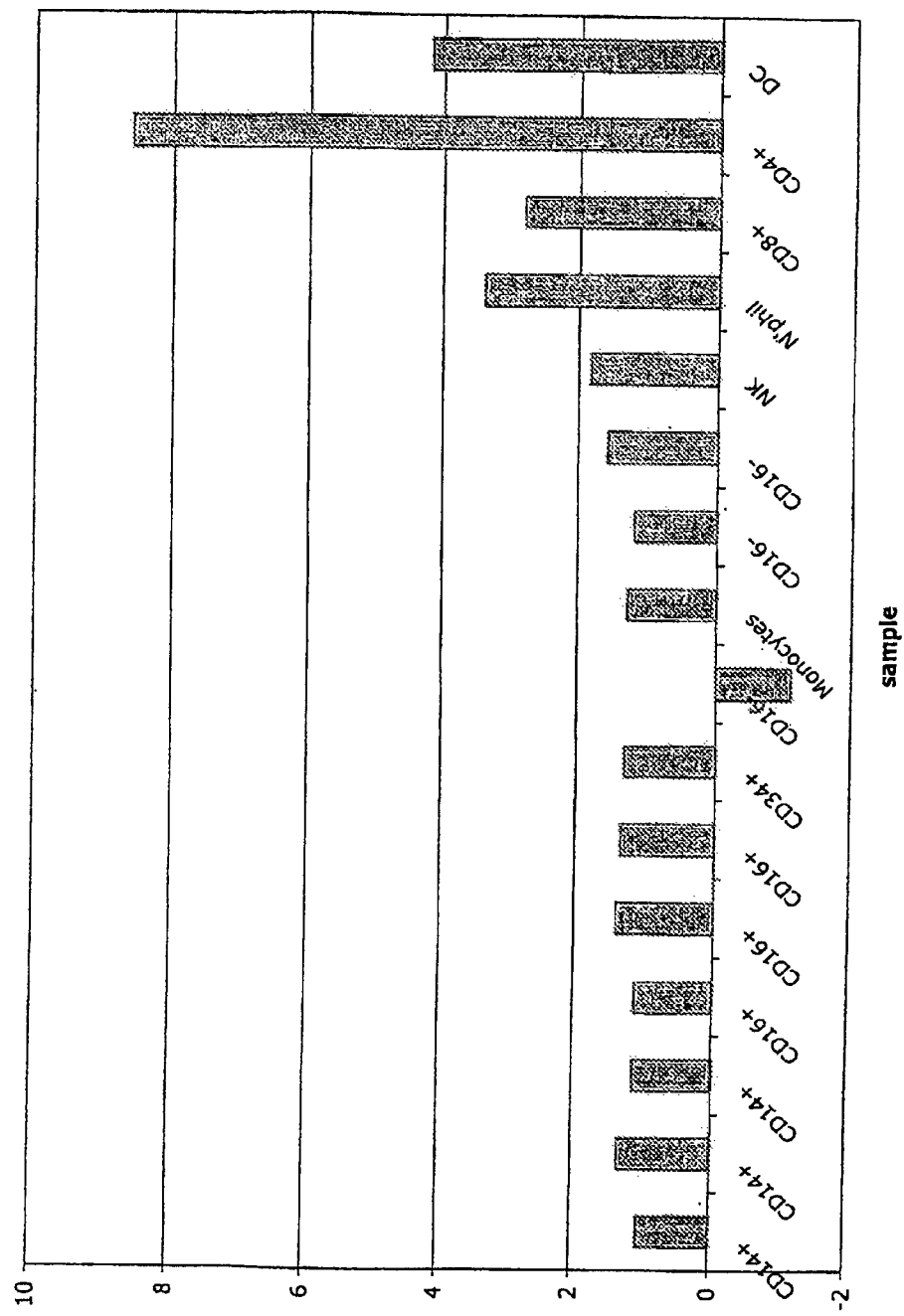
Figure 82D:
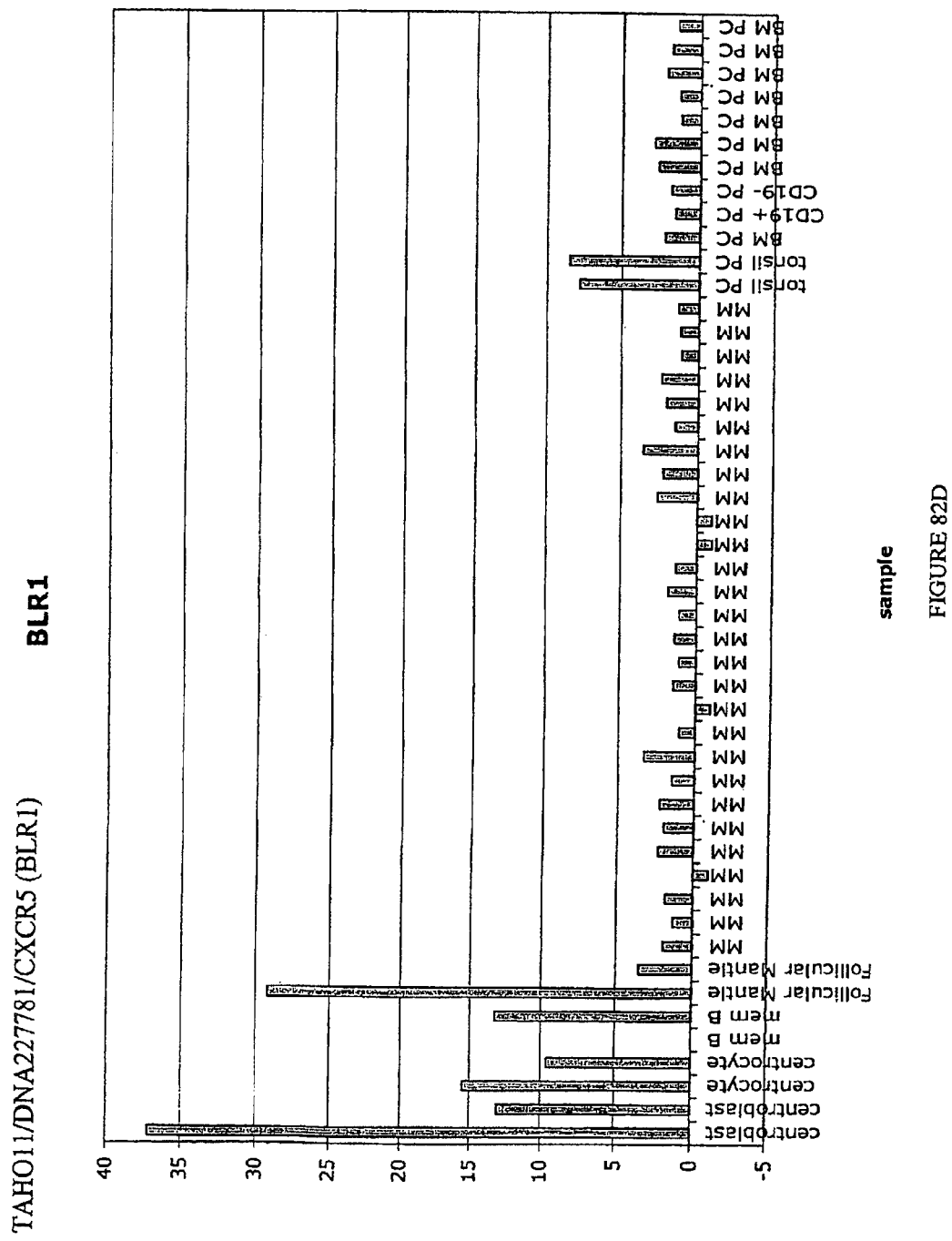
Figure 83A:
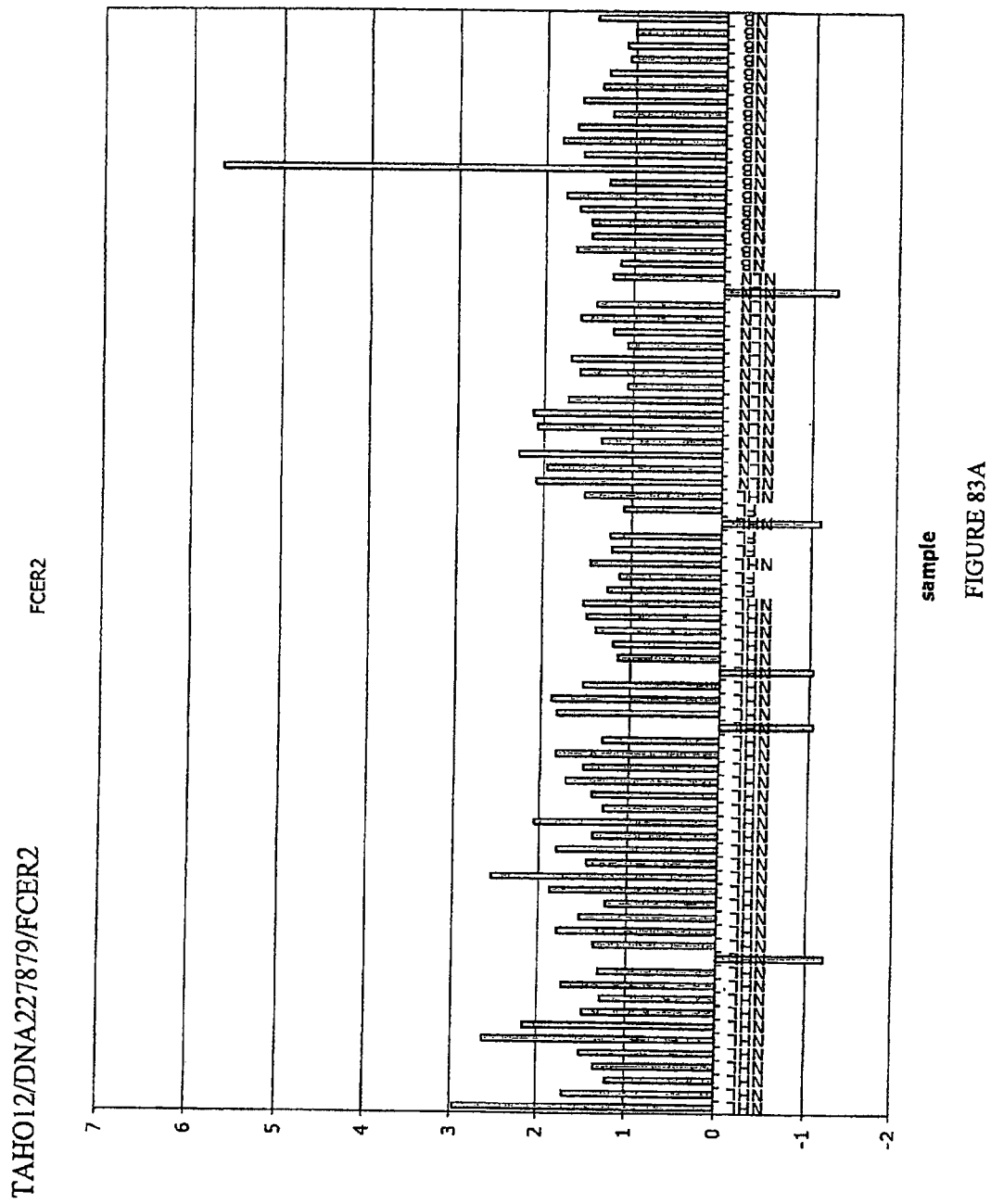
FIGS. 83A-83D show microarray data showing the expression of TAHO12 in normal samples and in diseased samples, such as significant expression in normal B cells, multiple myeloma and normal prostate. Abbreviations used in the Figures are designated as follows: Non-Hodgkin's Lymphoma (NHL), follicular lymphoma (FL), normal lymph node (NLN), normal B cells (NB), multiple myeloma cells (MM), small intestine (s. intestine), fetal liver (f. liver), smooth muscle (s. muscle), fetal brain (f. brain), natural killer cells (NK), neutrophils (N'phil), dendrocytes (DC), memory B cells (mem B), plasma cells (PC), bone marrow plasma cells (BM PC).
Figure 83B:
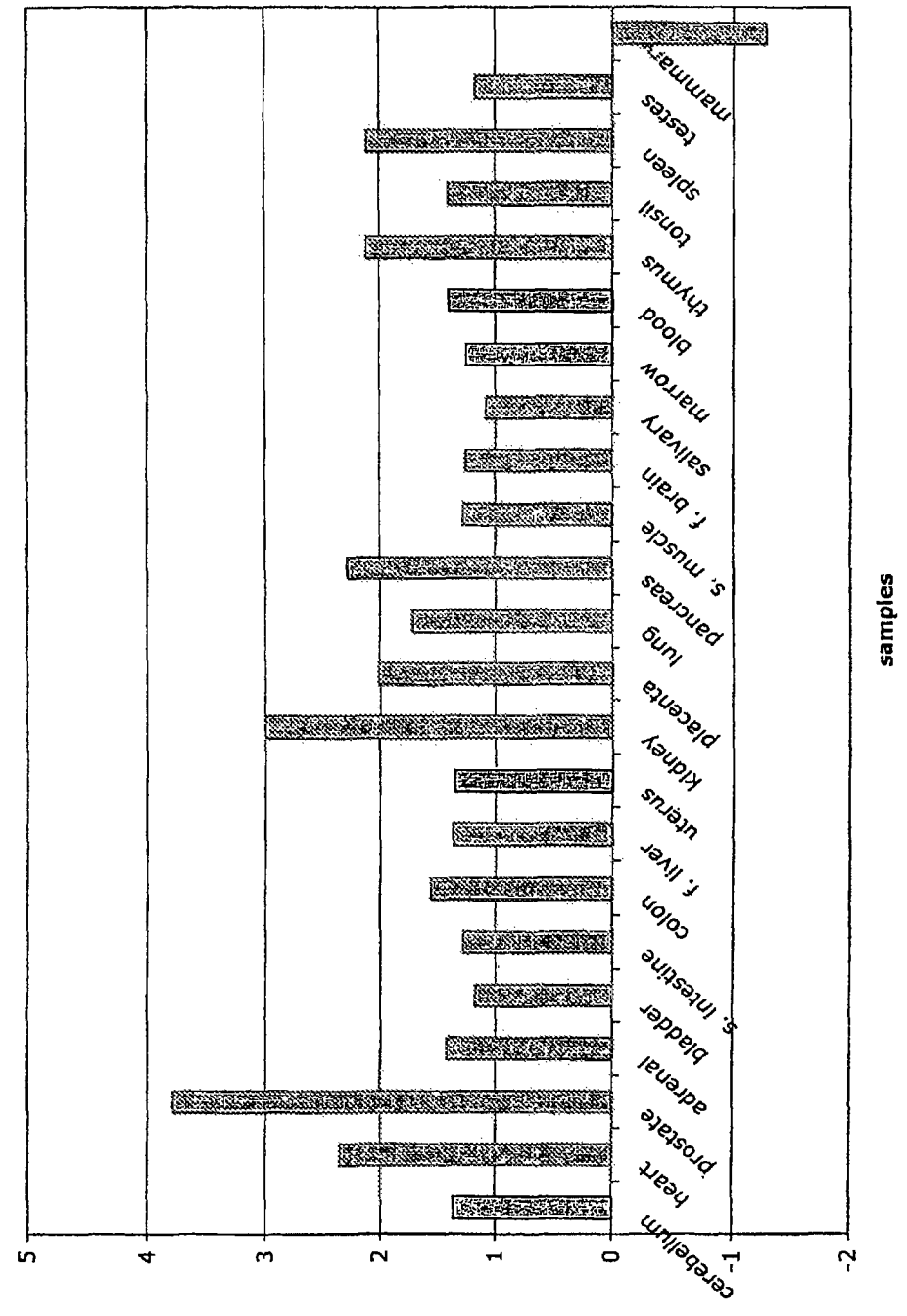
Figure 83C:
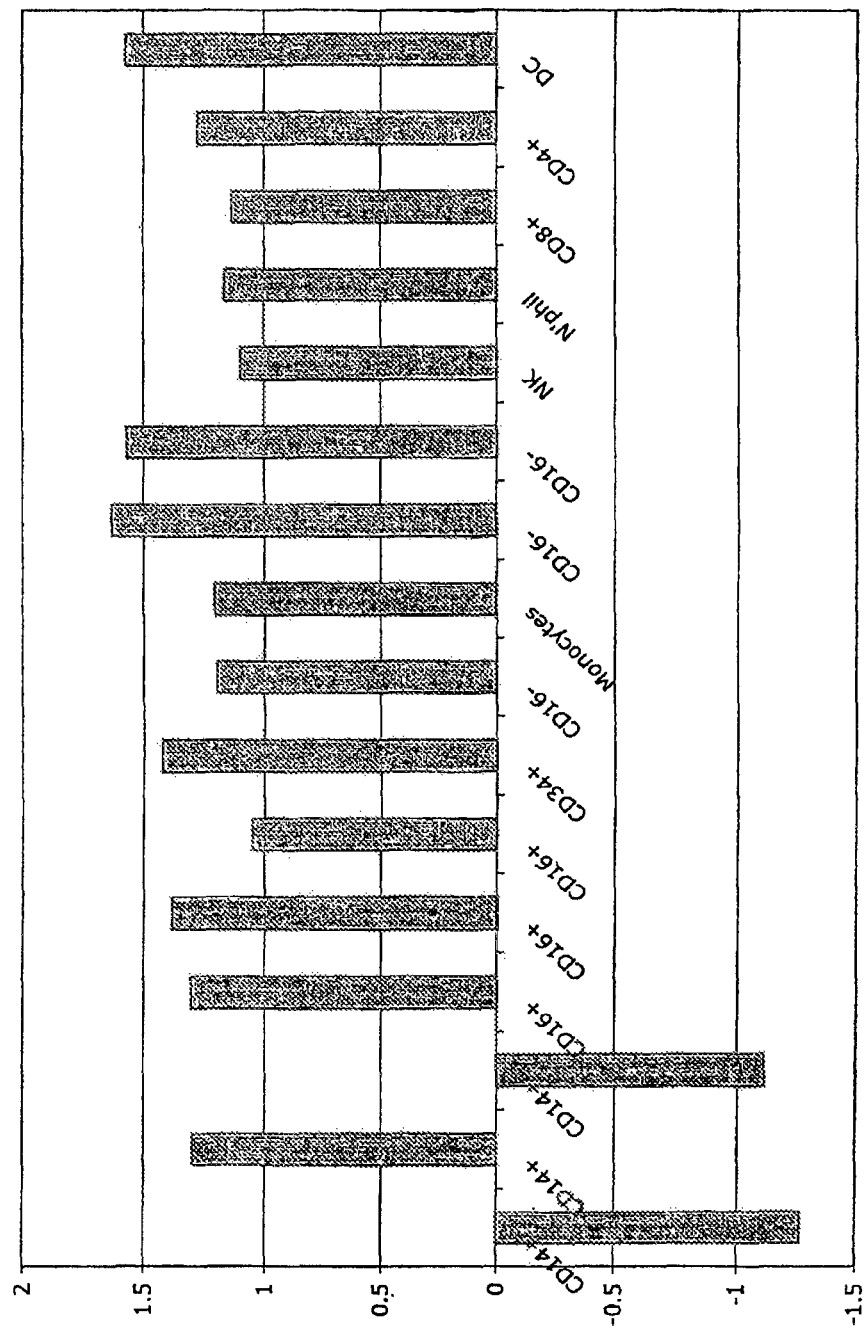
Figure 83D:
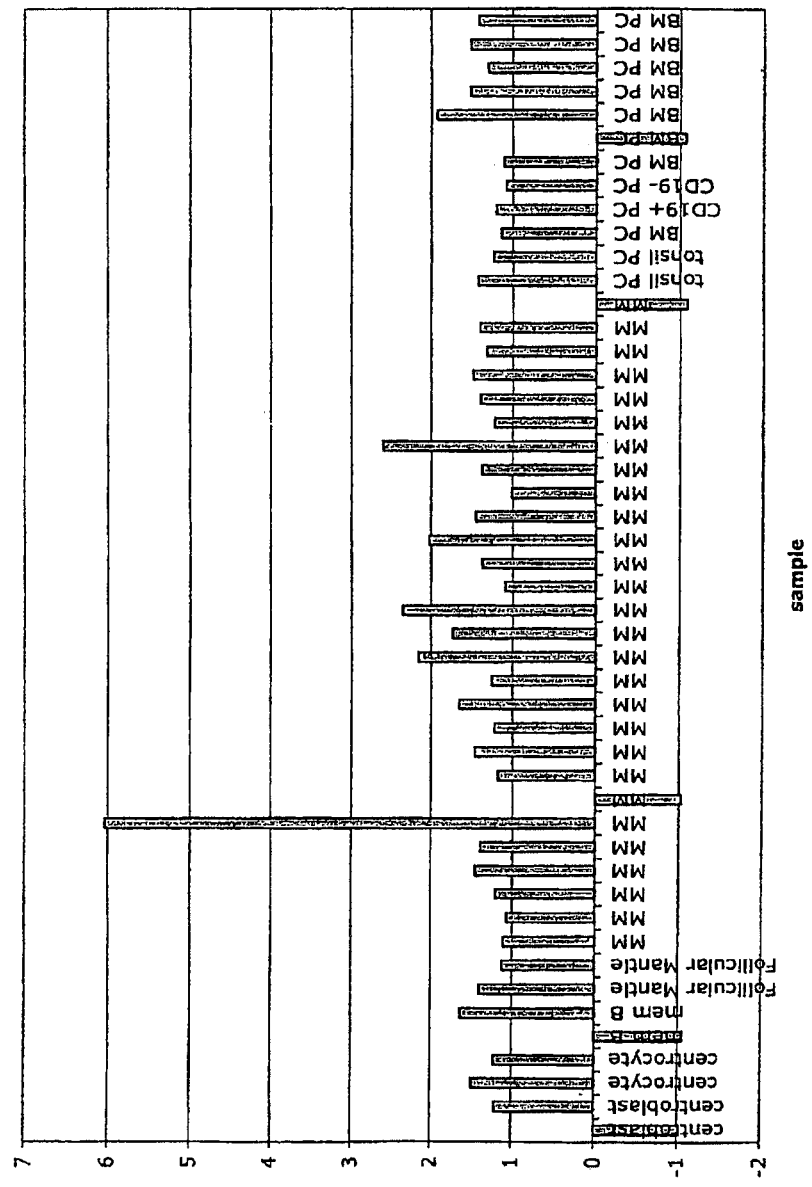

(8) TAHO9 (also referred herein as P2RX5) was significantly expressed in normal B cells (circulating and lymphnode derived B cells) and not significantly expressed in non B cells. Further, TAHO9 was significantly expressed in normal plasma cells and in multiple myeloma (FIGS. 80A-80B). In normal tissues, expression of TAHO9 is relatively low, but with significant expression in lymphoid organs such as spleen and thymus. FIGS. 80A-80B are shown as two panels. The panel in FIG. 80A represents normal tissue from left to right as follows: salivary gland (1), bone marrow (2), tonsil (3), fetal liver (4), blood (5), bladder (6), thymus (7), spleen (8), adrenal gland (9), fetal brain (10), small intestine (11), testes (12), heart (13), colon (14), lung (15), prostate (16), brain cerebellum (17), skeletal muscle (18), kidney (19), pancrease (20), placenta (21), uterus (22) and mammary gland (23). The panel in FIG. 80B represents the samples tested from left to right as follows: NK cells (1), neutrophils (2), CD4+ cells (3), CD8+ cells (4), CD34+ cells (5), normal B cells (6), monocytes (7), dendritic cells (8), multiple myeloma cells (9-11), memory B cells (12), naive B cells (13), centrocytes (14), centroblasts (15-16), centrocytes (17), memory B cells (18), naive B cells (19), normal B cells (20-38), multiple myeloma cells (39), CD138+ cells (40), multiple myeloma cells (41-46), tonsil plasma cells (47), bone marrow plasma cells (48), multiple myeloma cells (49-60), centrocytes (61), plasma bone marrow cells (62-70), plasma cell CD19+ (71), plasma cell CD19− (72), multiple myeloma cells (73-75).

(9) TAHO10 (also referred herein as HLA-DOB) was significantly expressed in multiple myeloma (MM), non-hodgkin's lymphoma (NHL) (FIG. 81).

(10) TAHO11 (also referred herein as CXCR5 and BLR1) was significantly expressed in non-hodgkin's lymphoma (NHL), follicular lymphoma (FL), normal lymph node (NLN), normal B cells (NB), centroblasts and follicular mantle cells, and normal spleen and normal tonsil (FIG. 82). However, as indicated above, any apparent expression in non-B cells, such as in prostate, spleen, blood, tonsil, etc. may represent an artifact, infiltration of normal tissue by lymphocytes or loss of sample integrity by the vendor.

(11) TAHO12 (also referred herein as FCER2) was significantly expressed in normal B cells (NB), multiple myeloma (MM) and prostate (FIG. 83). However, as indicated above, any apparent expression in non-B cells, such as in prostate, spleen, blood, tonsil, etc. may represent an artifact, infiltration of normal tissue by lymphocytes or loss of sample integrity by the vendor.

Figure 84A:
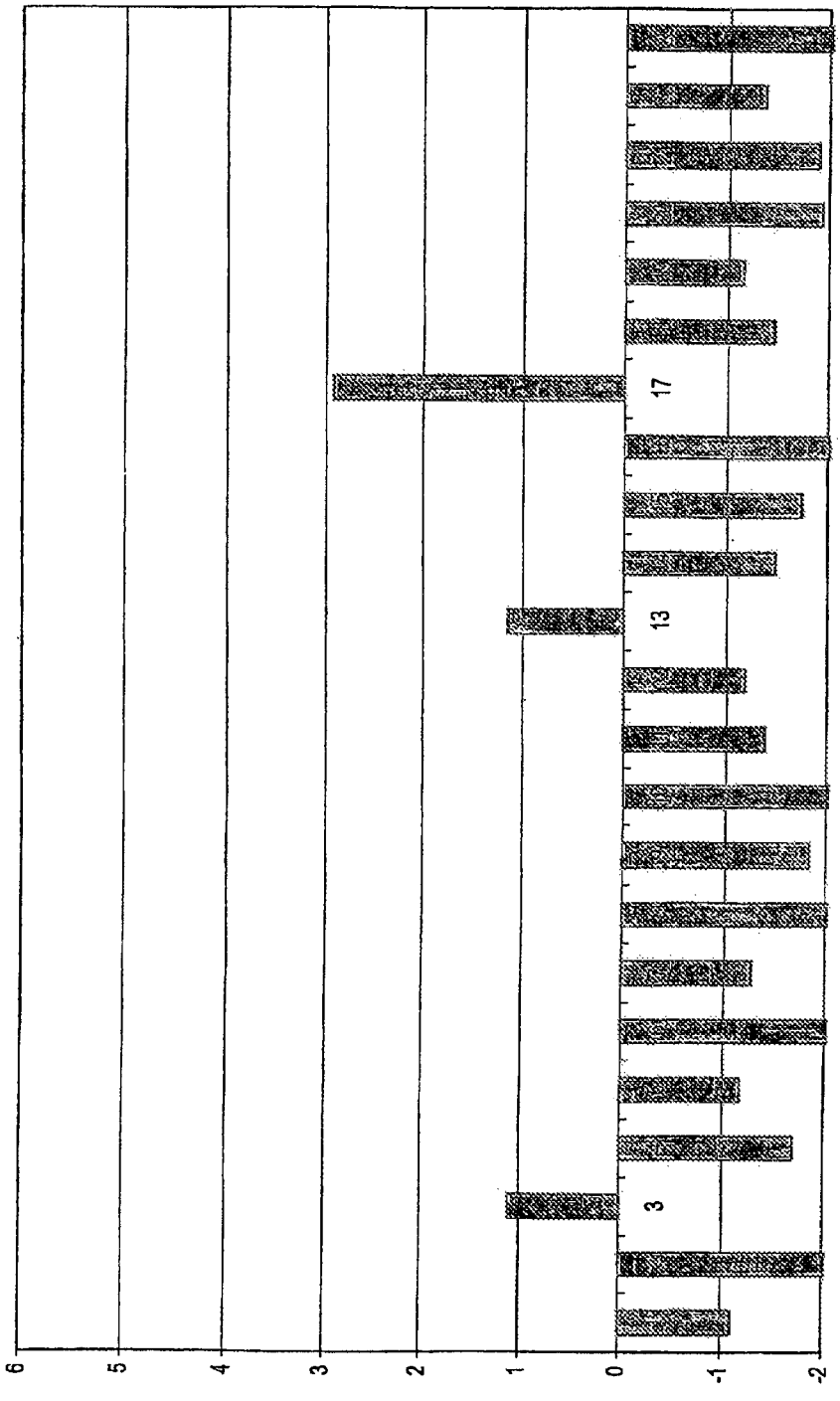
FIGS. 84A-84B show microarray data showing the expression of TAHO13 in normal samples and in diseased samples, such as significant expression in multiple myeloma and normal blood.
Figure 84B:
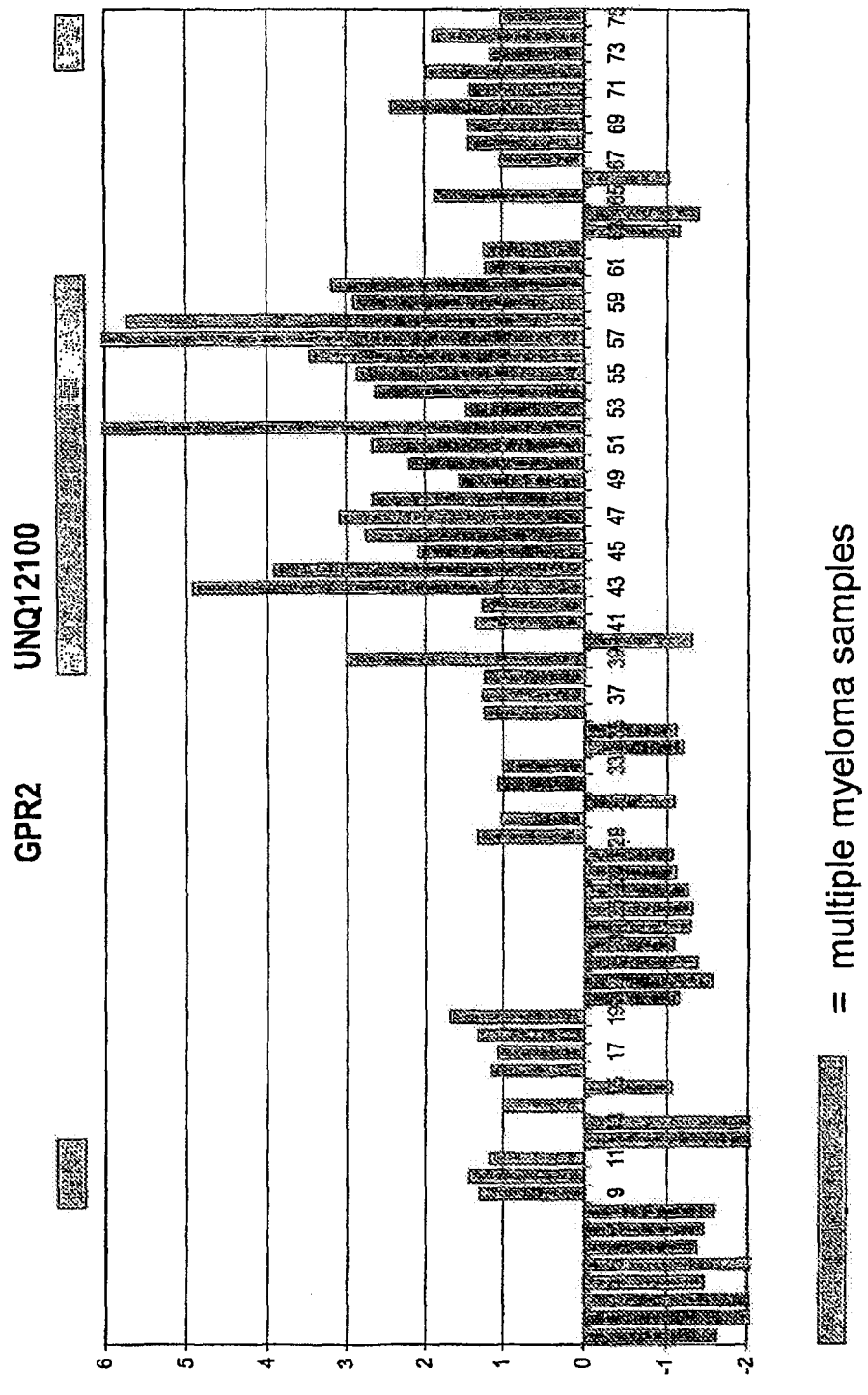
Figure 85A:
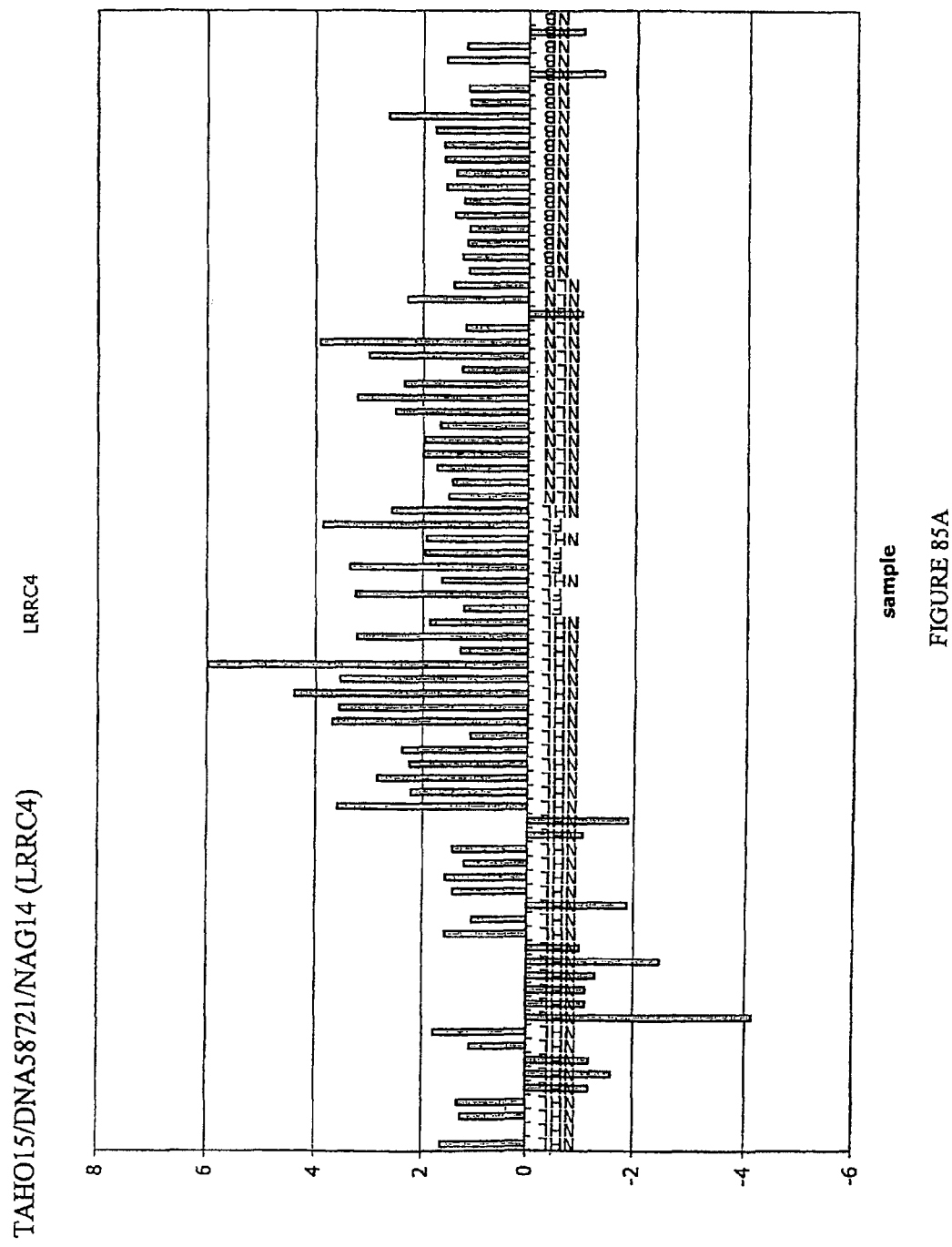
FIGS. 85A-85D show microarray data showing the expression of TAHO15 in normal samples and in diseased samples, such as significant expression in NHL samples. Abbreviations used in the Figures are designated as follows: Non-Hodgkin's Lymphoma (NHL), follicular lymphoma (FL), normal lymph node (NLN), normal B cells (NB), multiple myeloma cells (MM), small intestine (s. intestine), fetal liver (f. liver), smooth muscle (s. muscle), fetal brain (f. brain), natural killer cells (NK), neutrophils (N'phil), dendrocytes (DC), memory B cells (mem B), plasma cells (PC), bone marrow plasma cells (BM PC).
Figure 85B:
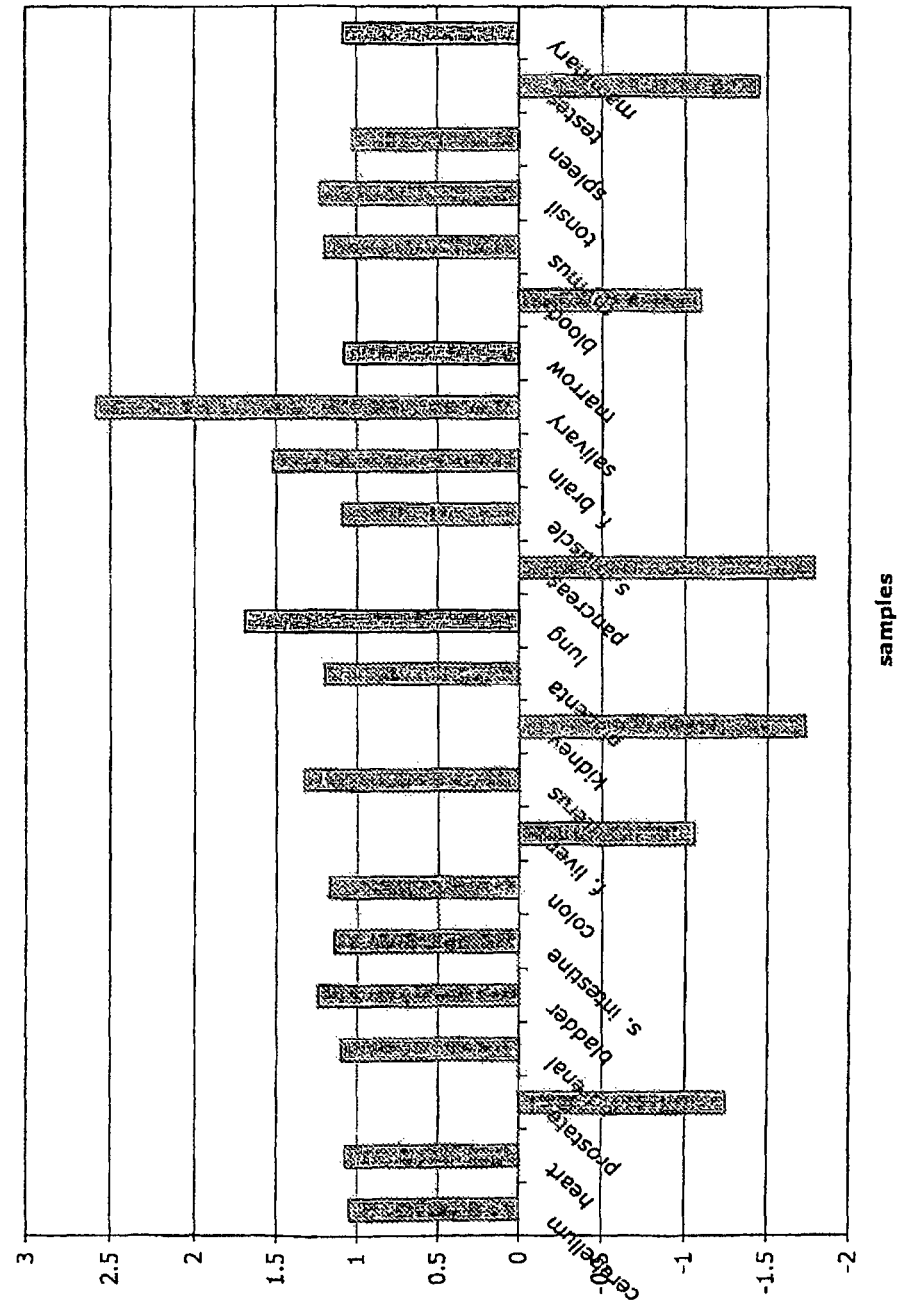
Figure 85C:
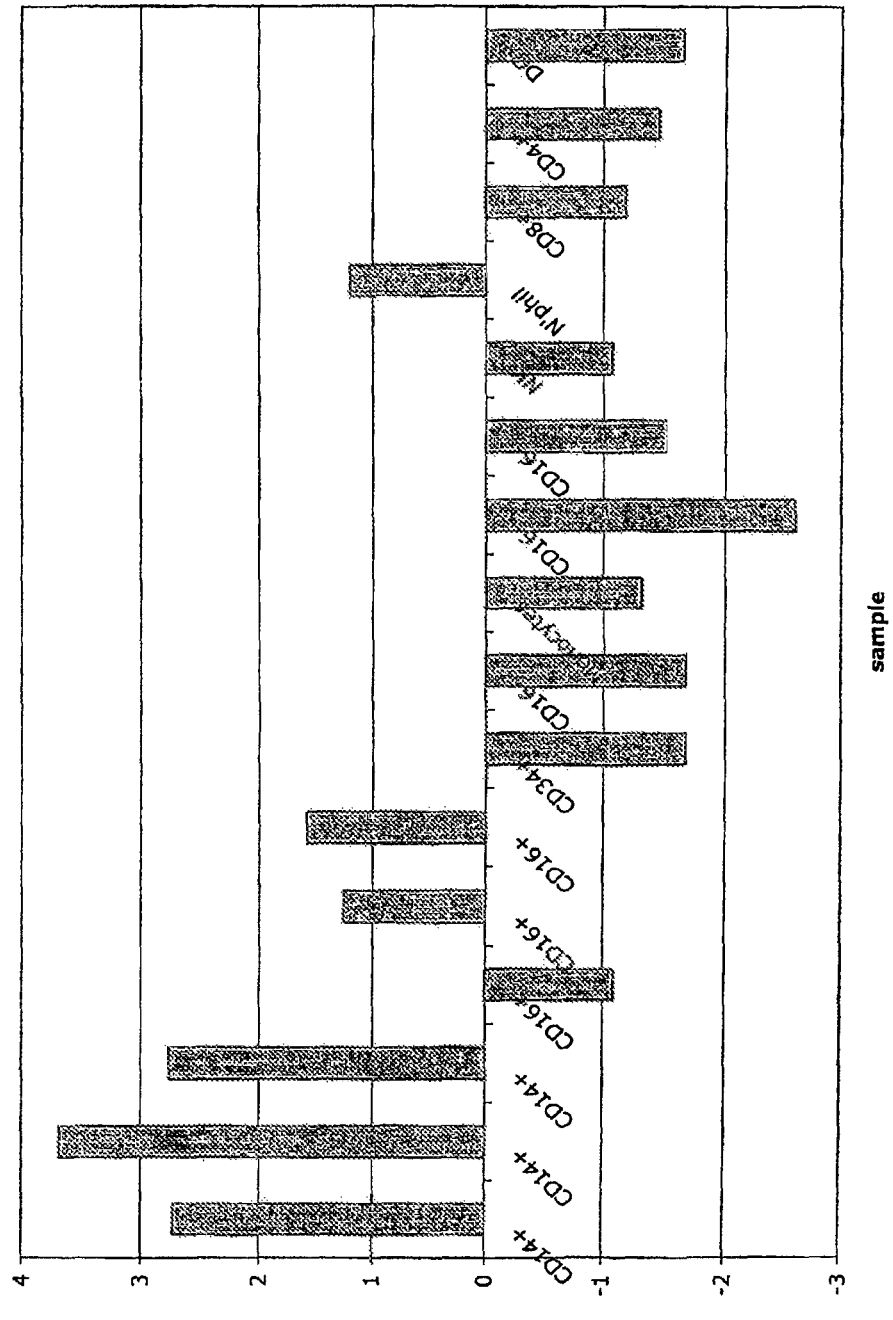
Figure 85D:
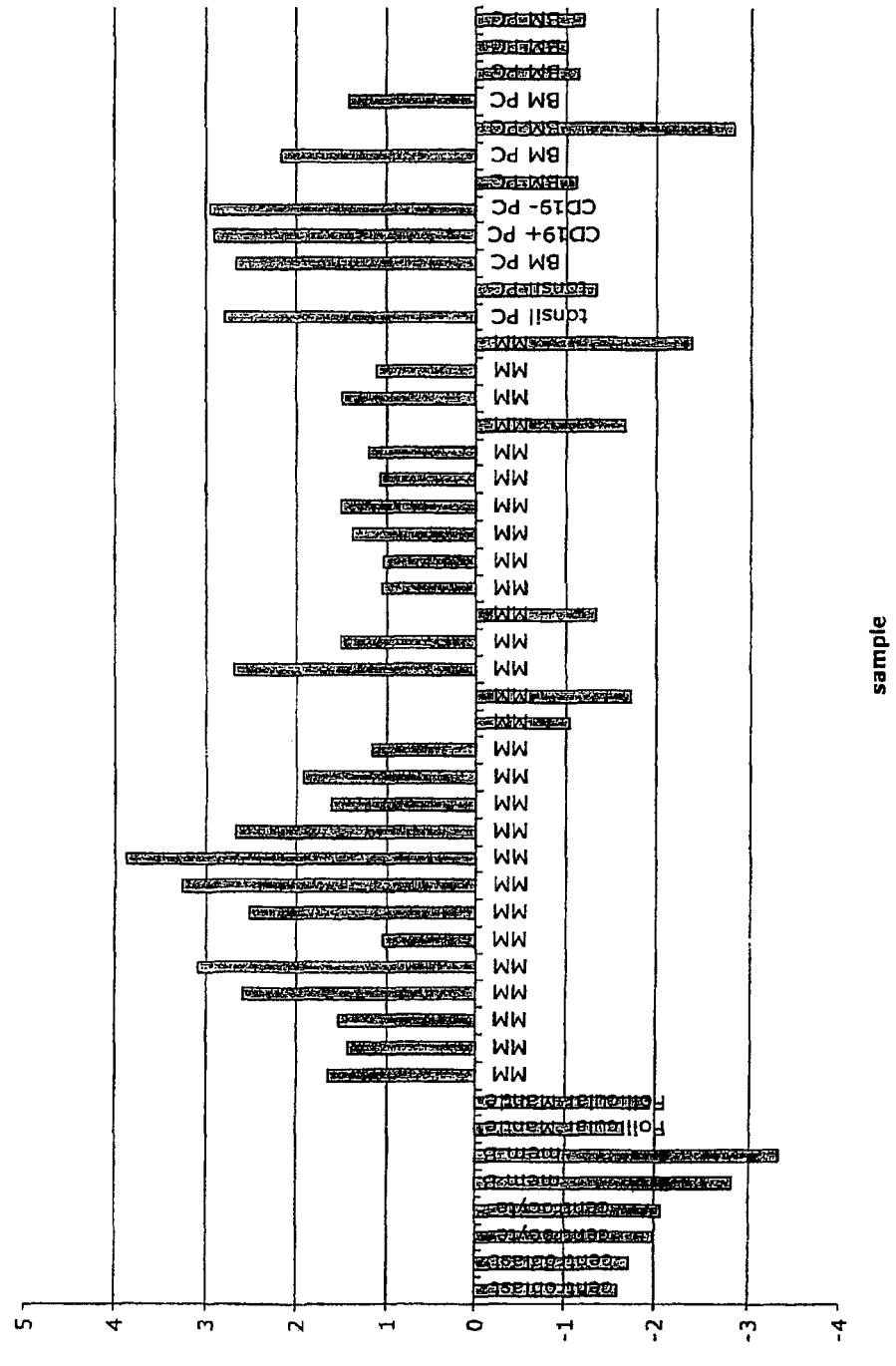
Figure 86A:
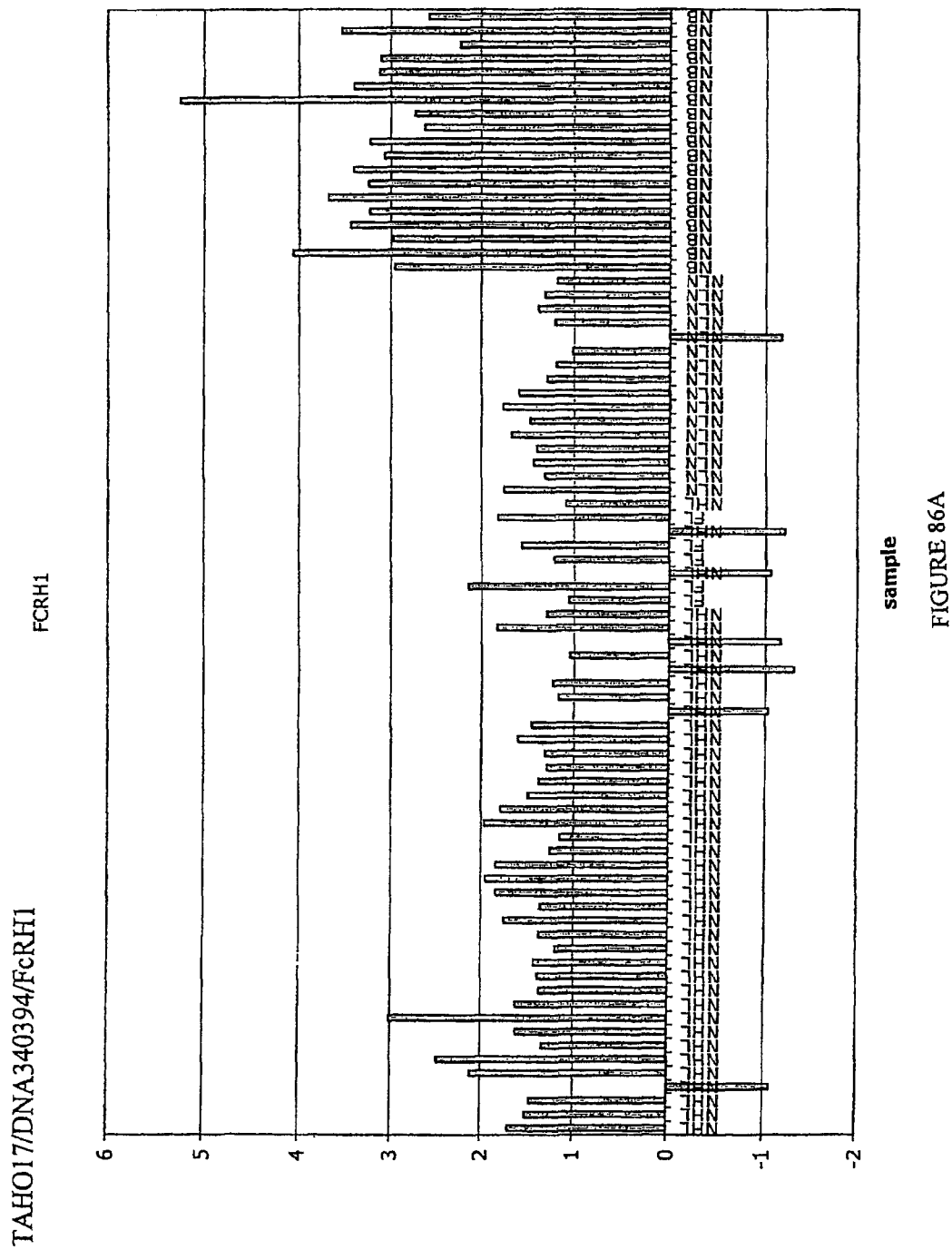
FIGS. 86A-86D show microarray data showing the expression of TAHO17 in normal samples and in diseased samples, such as significant expression in normal B cells (NB) and memory B cells (mem B). Abbreviations used in the Figures are designated as follows: Non-Hodgkin's Lymphoma (NHL), follicular lymphoma (FL), normal lymph node (NLN), normal B cells (NB), multiple myeloma cells (MM), small intestine (s. intestine), fetal liver (f. liver), smooth muscle (s. muscle), fetal brain (f. brain), natural killer cells (NK), neutrophils (N'phil), dendrocytes (DC), memory B cells (mem B), plasma cells (PC), bone marrow plasma cells (BM PC).
Figure 86B:
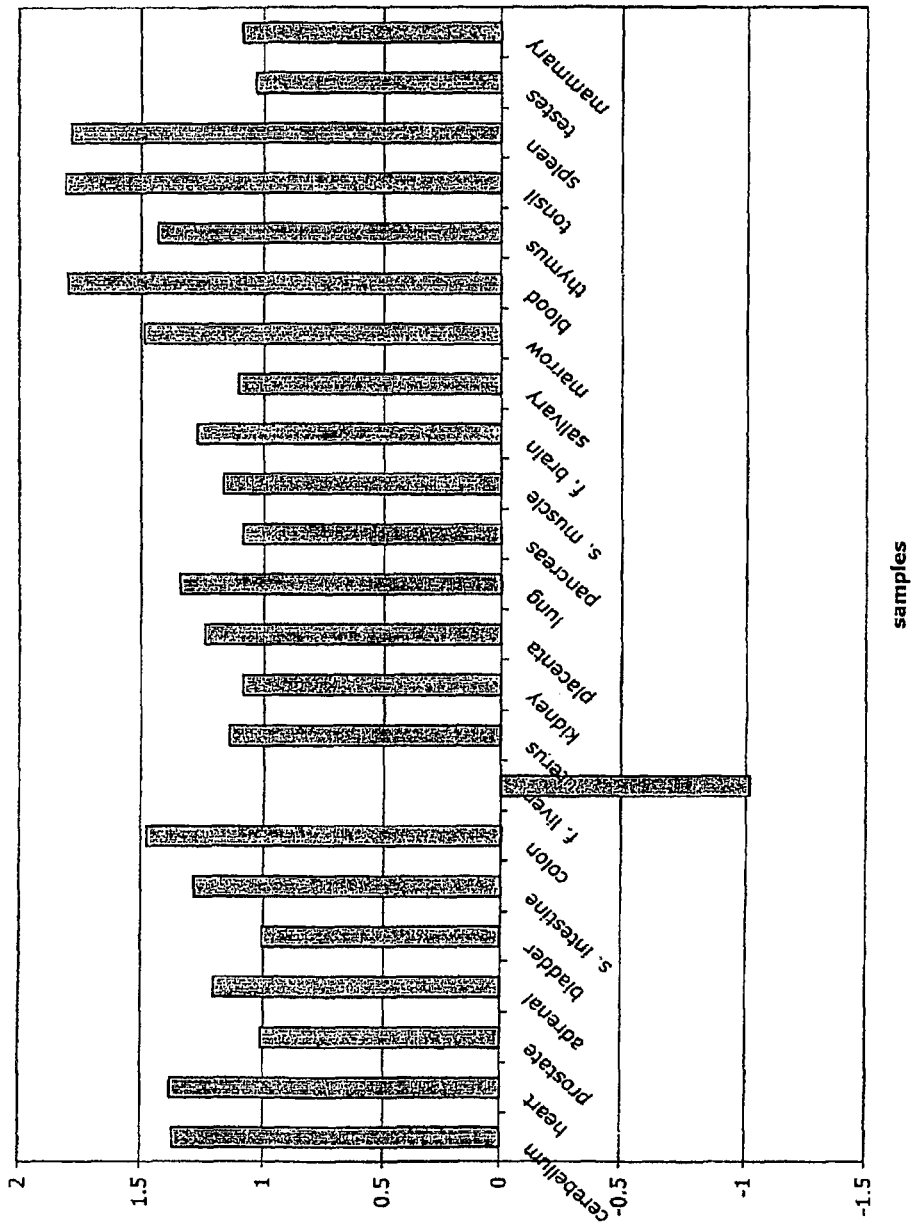
Figure 86C:
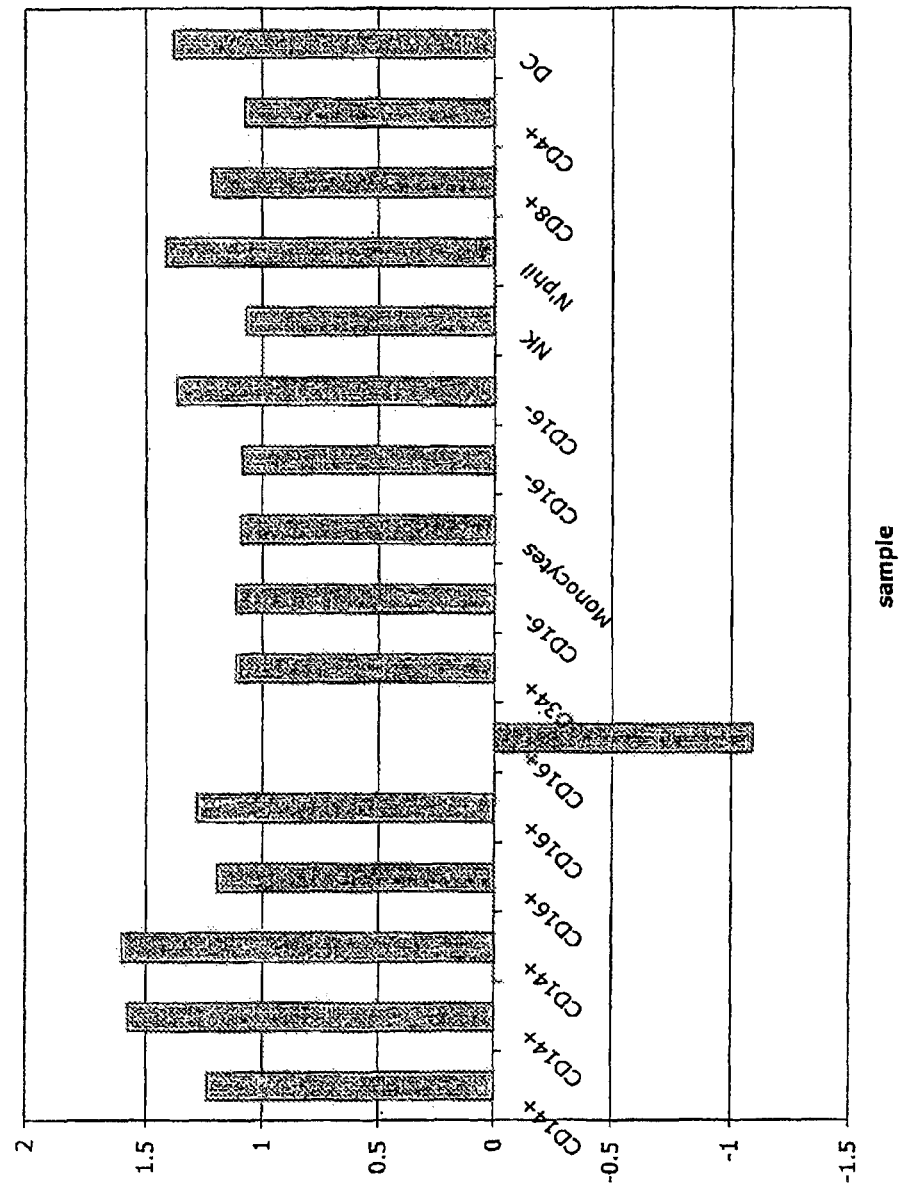
Figure 86D:
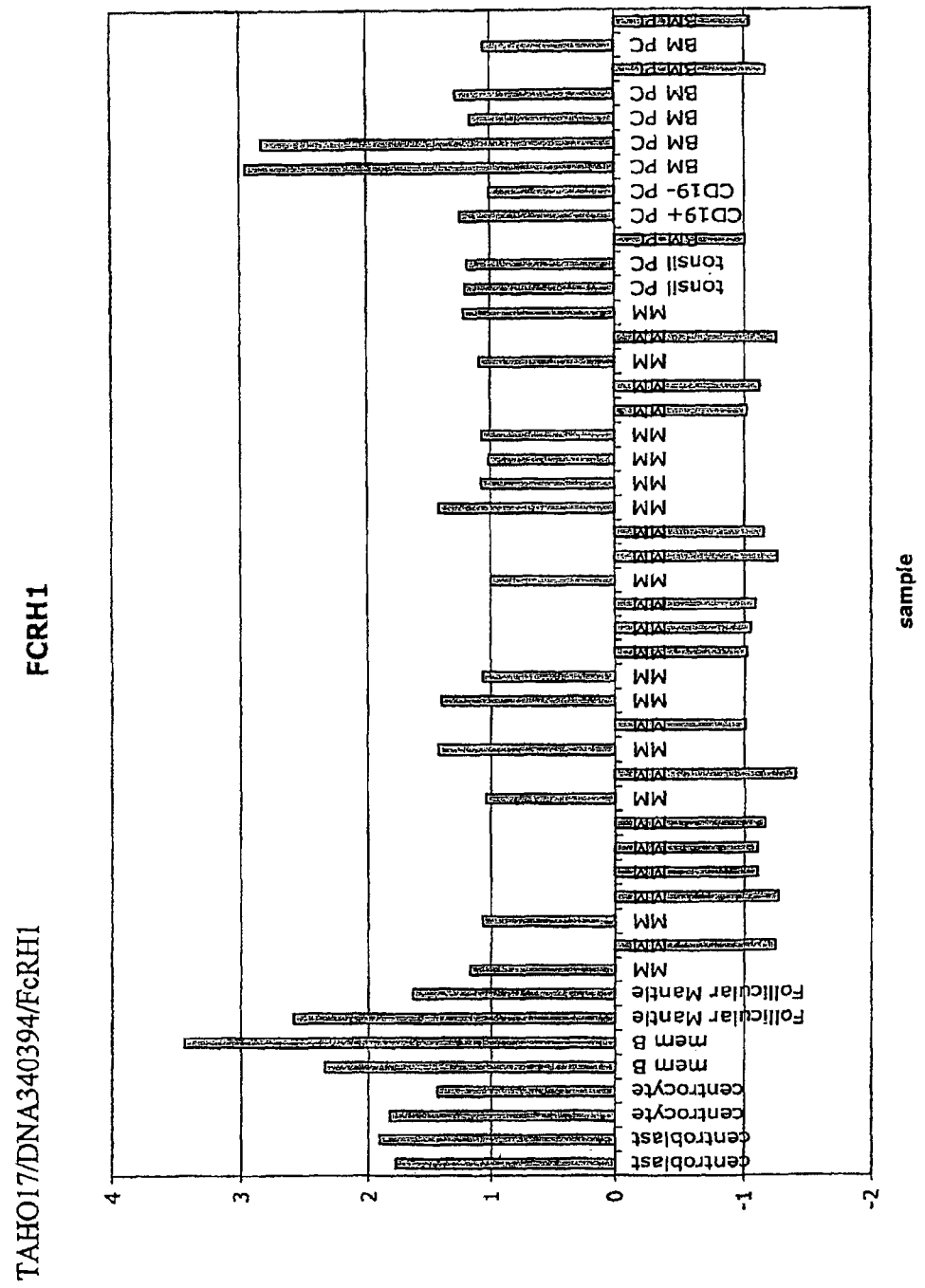
Figure 87A:
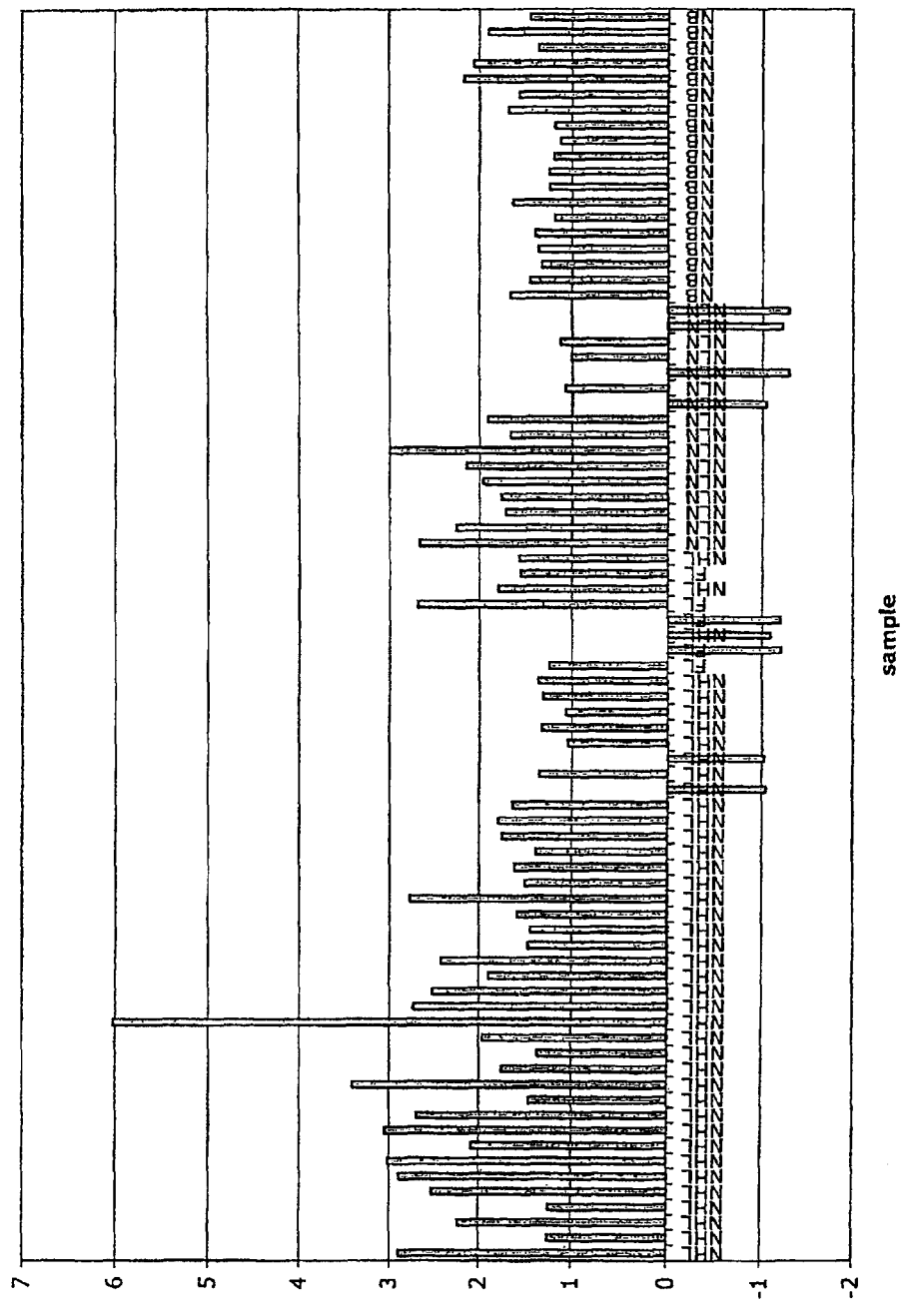
FIGS. 87A-87D show microarray data showing the expression of TAHO18 in normal samples and in diseased samples, such as significant expression in NHL samples. Abbreviations used in the Figures are designated as follows: Non-Hodgkin's Lymphoma (NHL), follicular lymphoma (FL), normal lymph node (NLN), normal B cells (NB), multiple myeloma cells (MM), small intestine (s. intestine), fetal liver (f. liver), smooth muscle (s. muscle), fetal brain (f. brain), natural killer cells (NK), neutrophils (N'phil), dendrocytes (DC), memory B cells (mem B), plasma cells (PC), bone marrow plasma cells (BM PC).
Figure 87B:
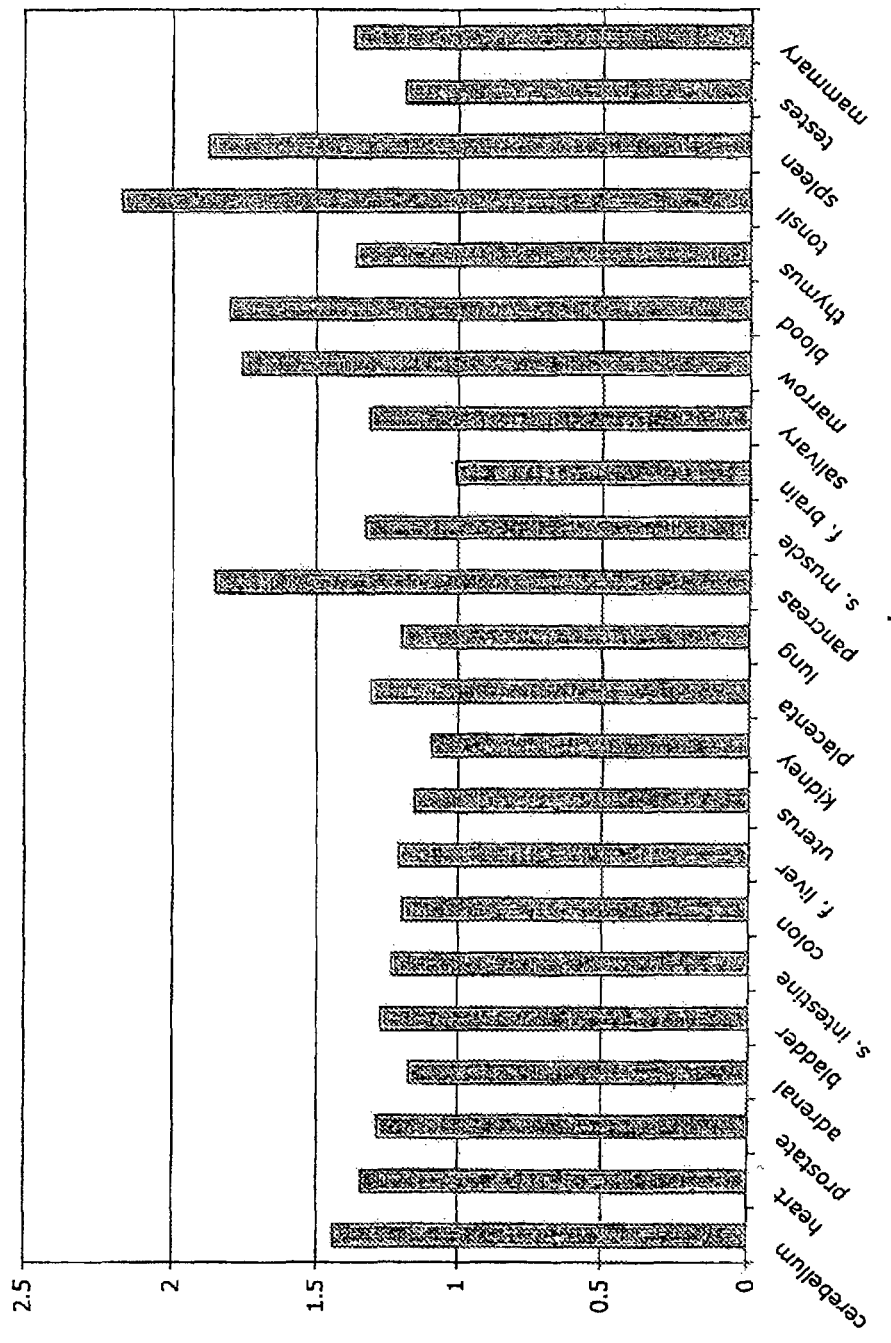
Figure 87C:
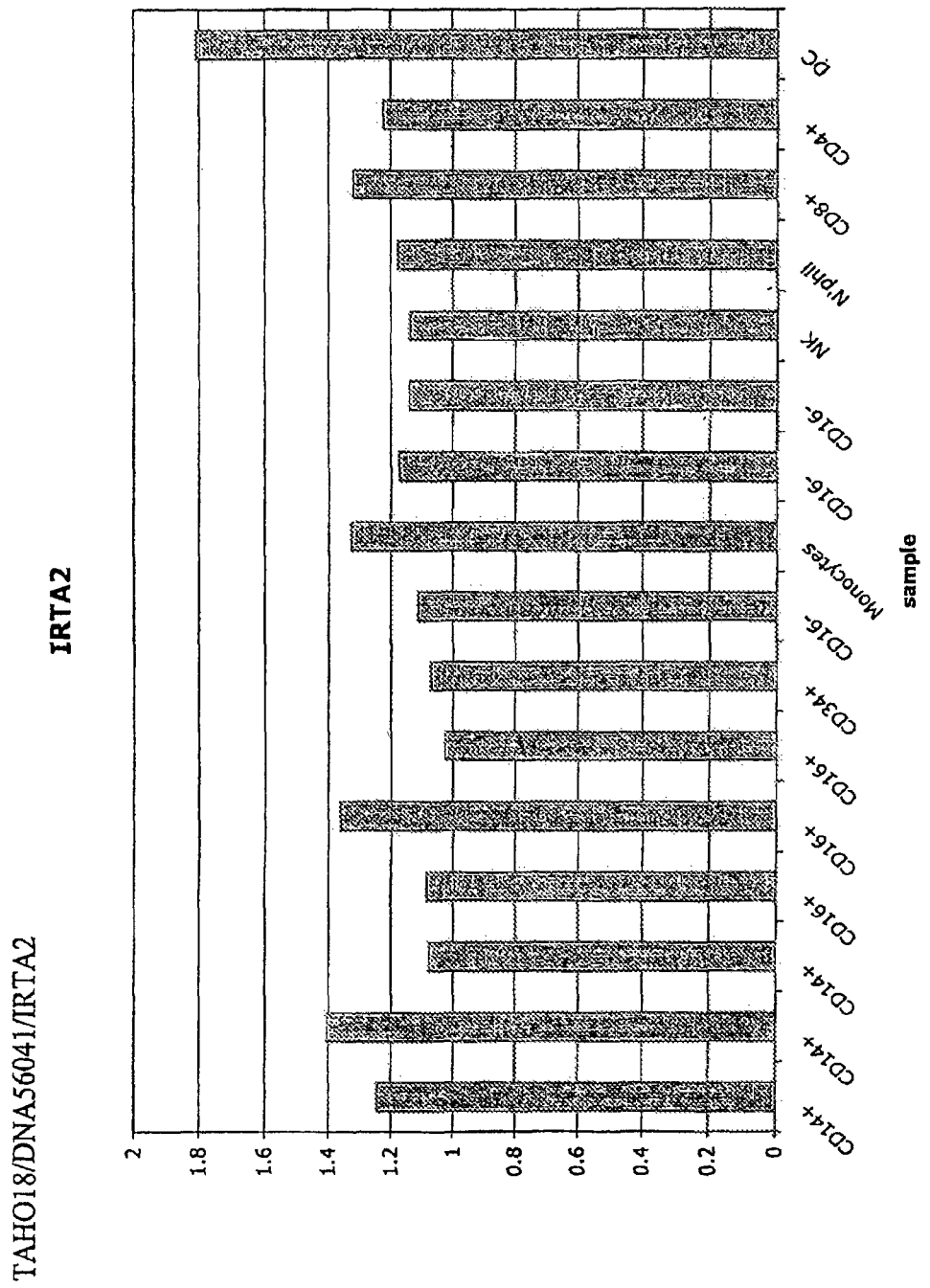
Figure 87D:
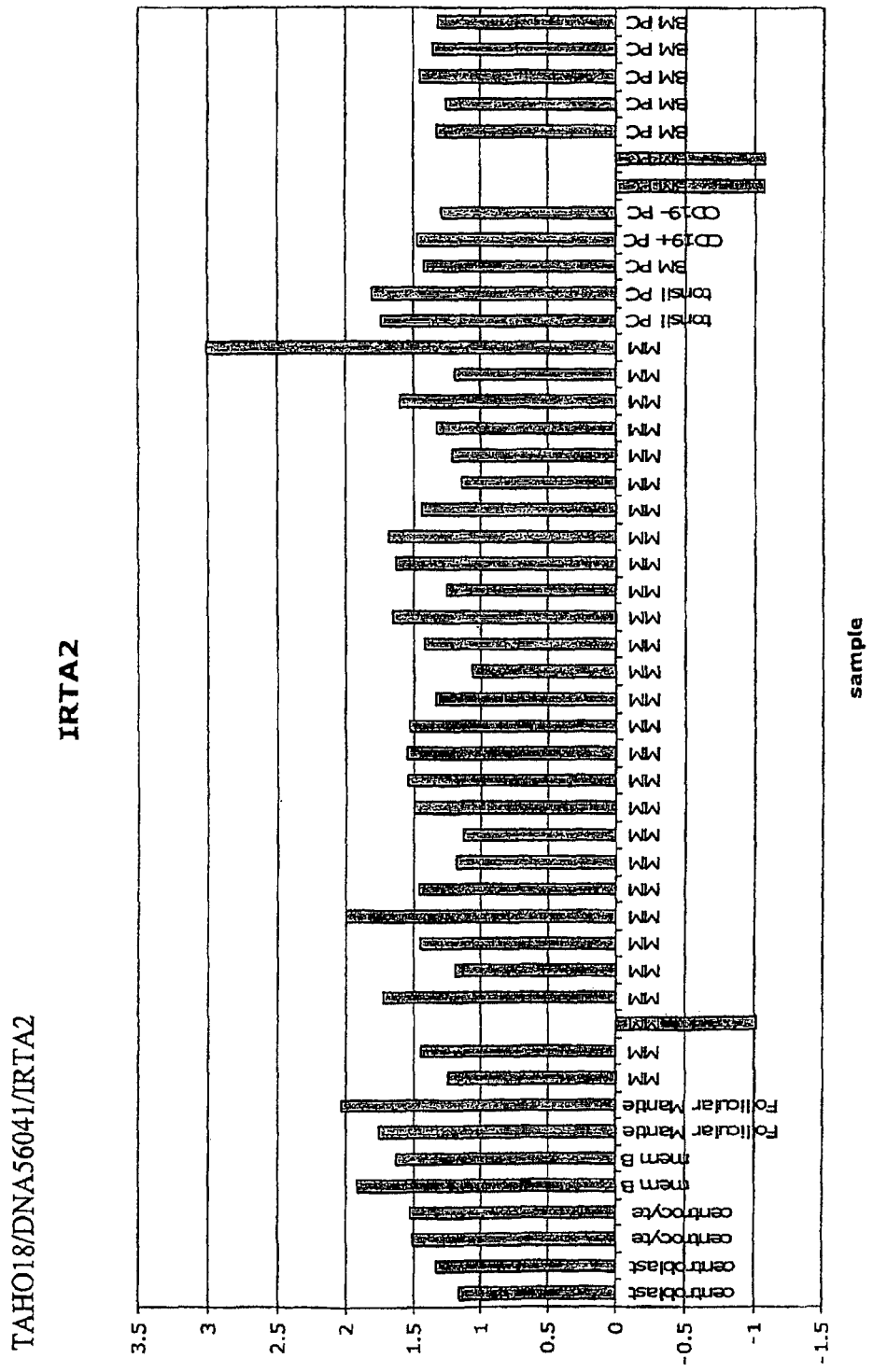
Figure 88A:
FIGS. 88A-88D show microarray data showing the expression of TAHO20 in normal samples and in diseased samples, such as significant expression in multiple myeloma (MM), normal B cells (NB) and normal colon, placenta, lung and spleen and bone marrow plasma cells (BM PC). Abbreviations used in the Figures are designated as follows: Non- Hodgkin's Lymphoma (NHL), follicular lymphoma (FL), normal lymph node (NLN), normal B cells (NB), multiple myeloma cells (MM), small intestine (s. intestine), fetal liver (f. liver), smooth muscle (s. muscle), fetal brain (f. brain), natural killer cells (NK), neutrophils (N'phil), dendrocytes (DC), memory B cells (mem B), plasma cells (PC), bone marrow plasma cells (BM PC).
Figure 88B:
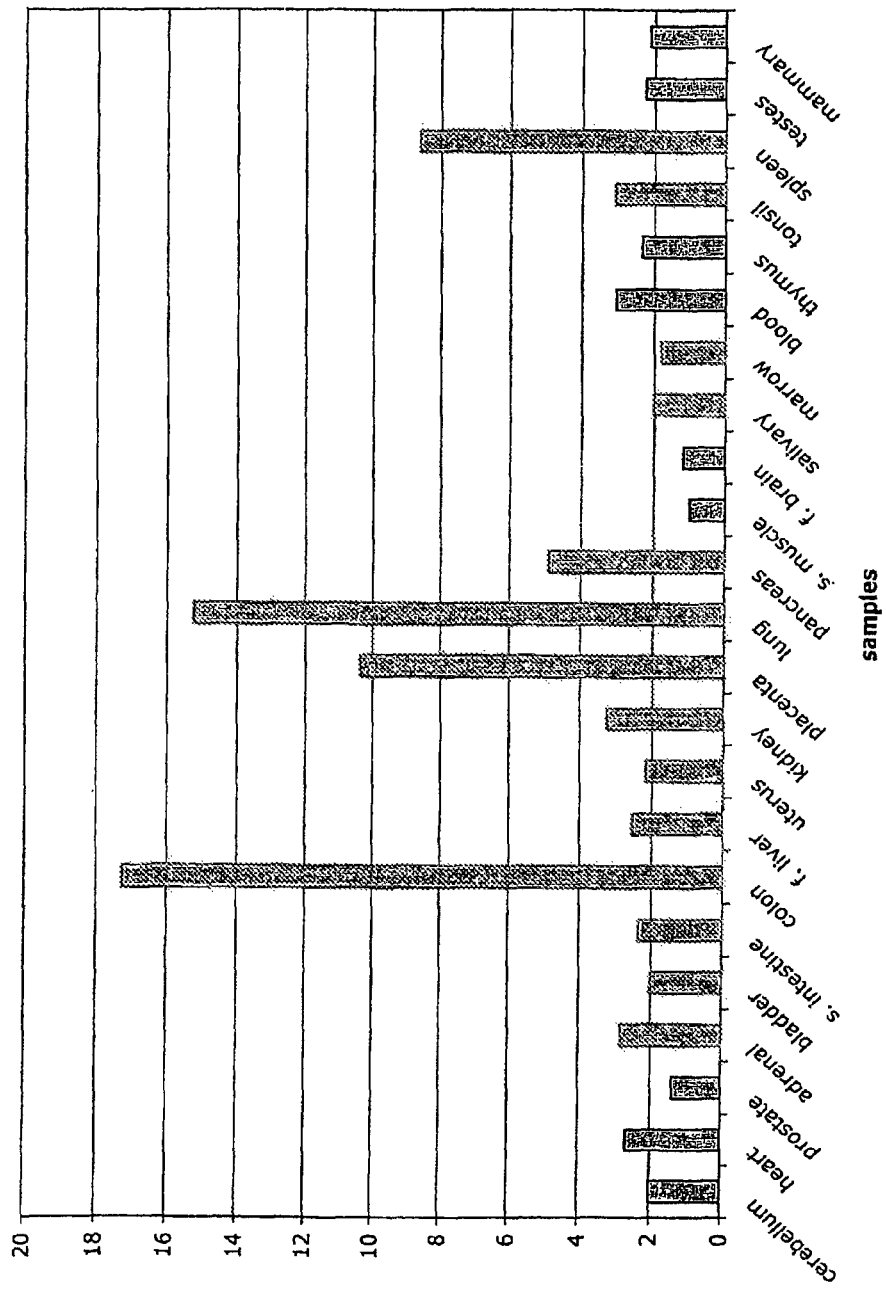
Figure 88C:
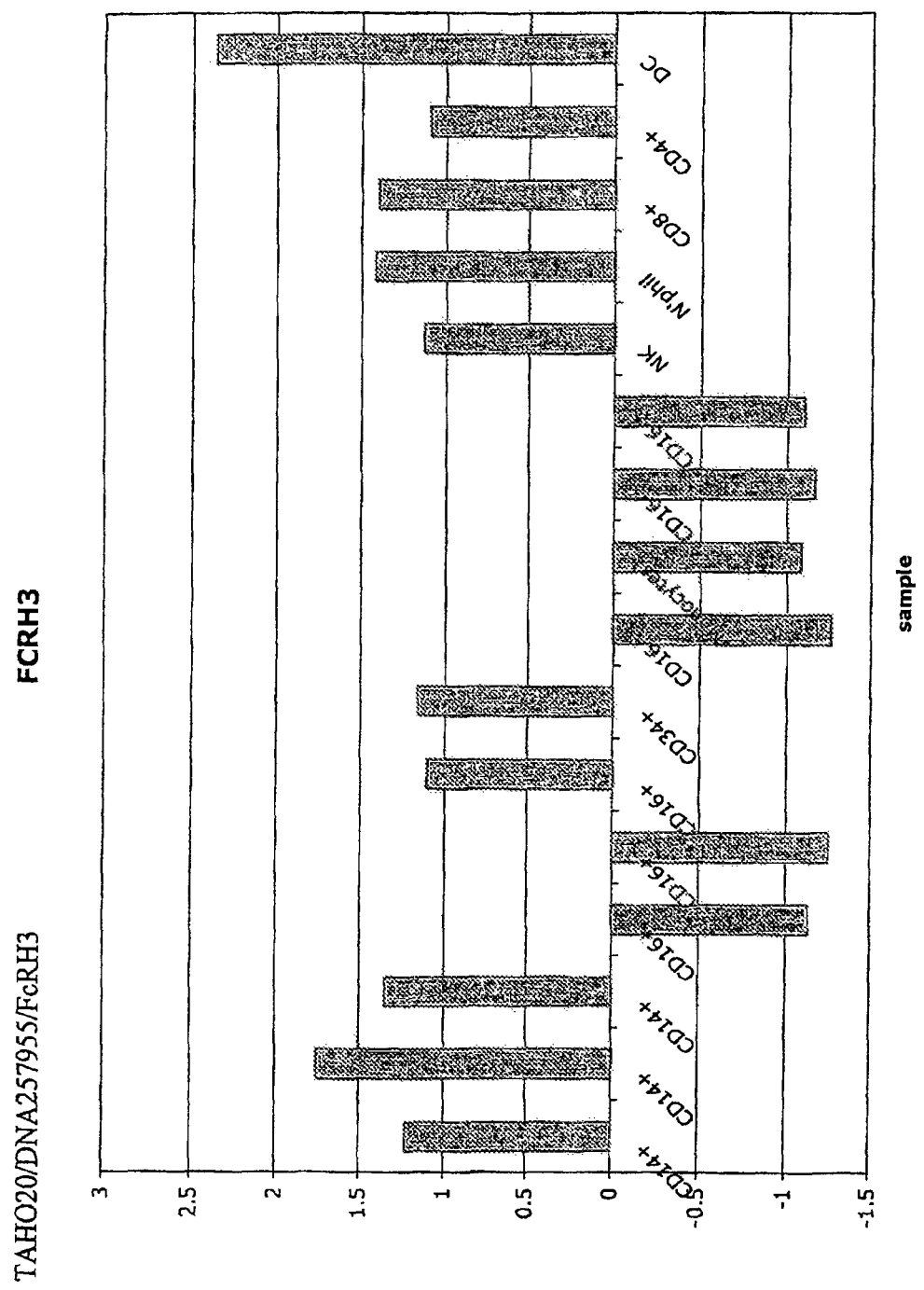
Figure 88D:
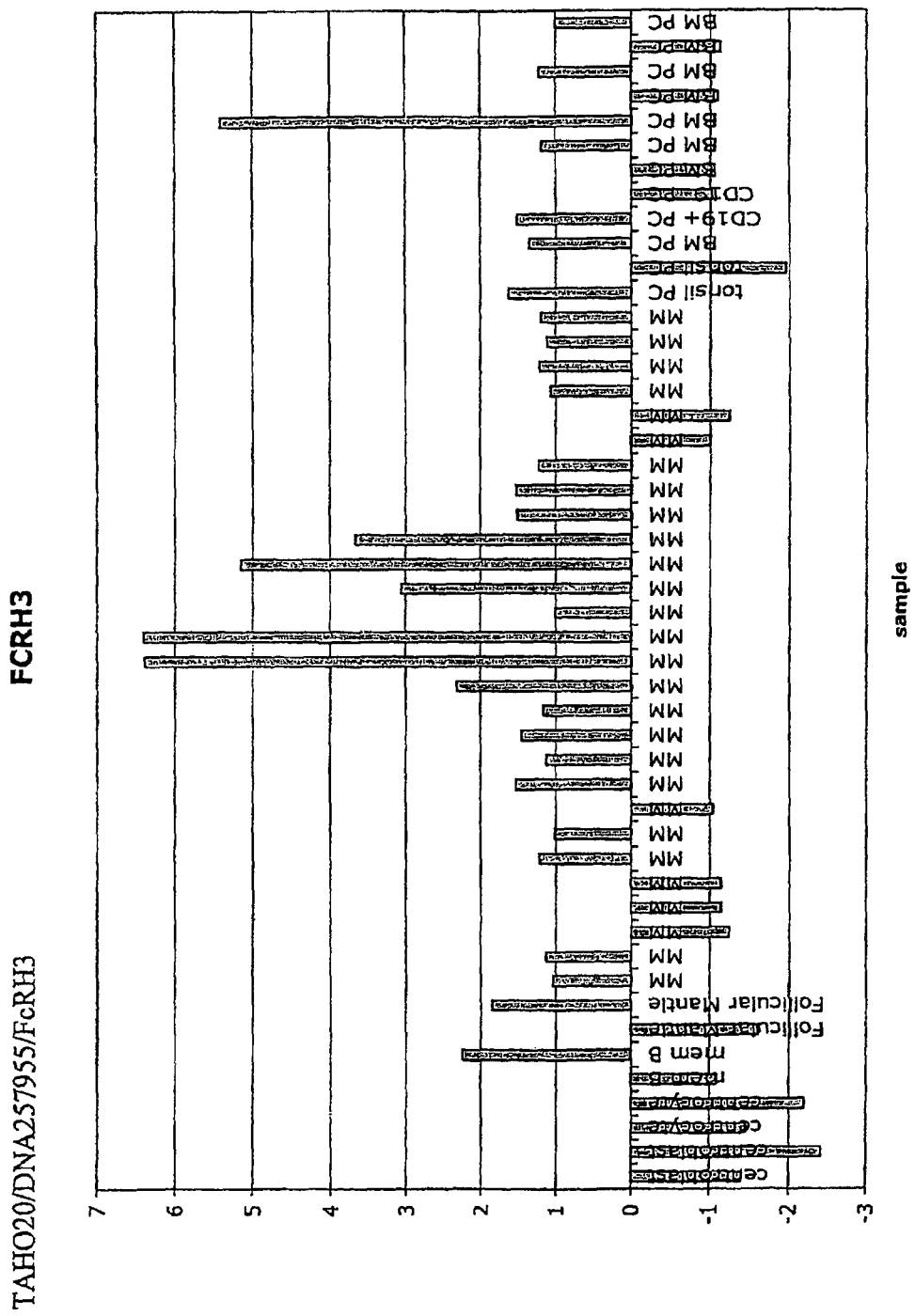
Figure 89A:
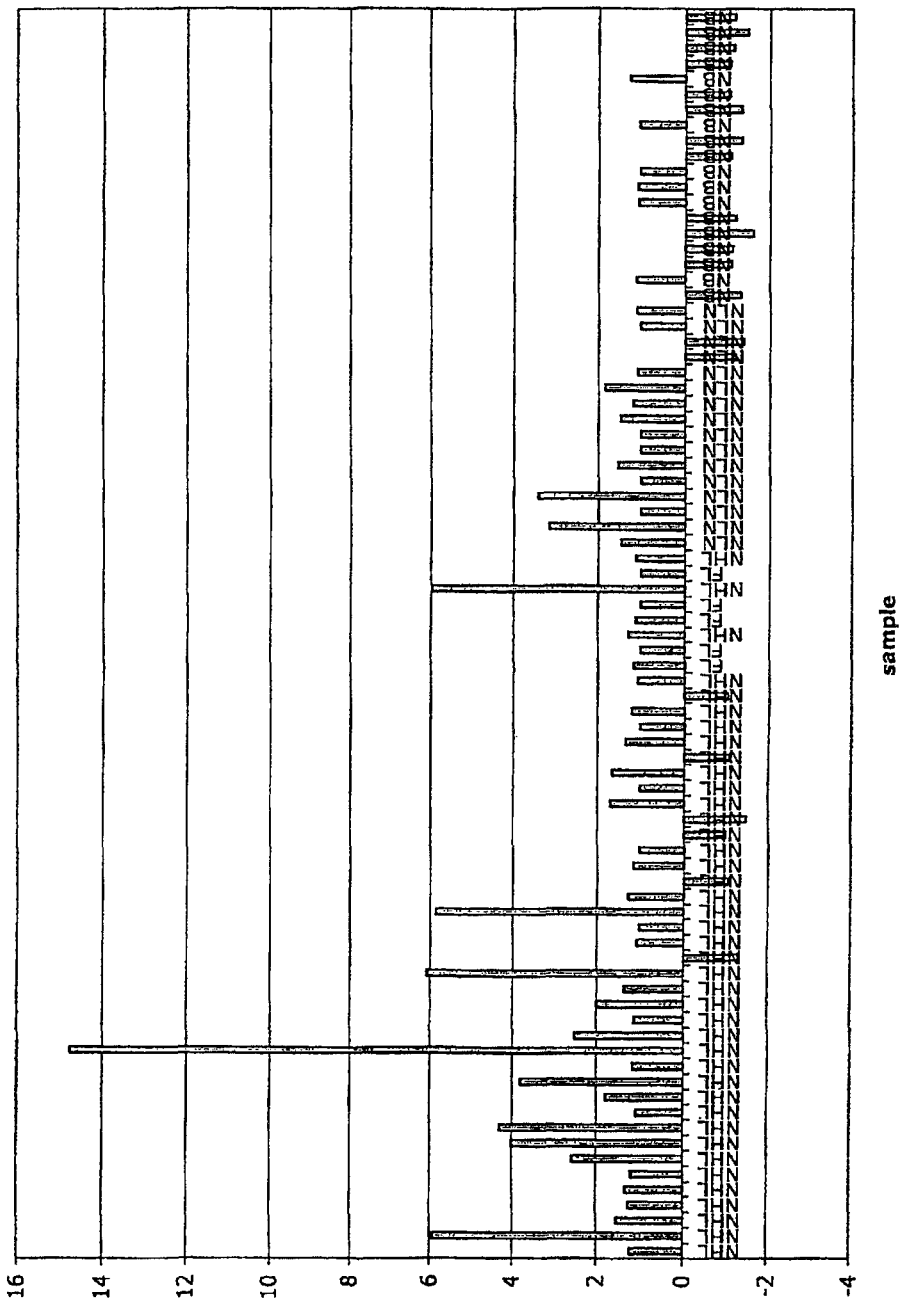
FIGS. 89A-89D show microarray data showing the expression of TAHO21 in normal samples and in diseased samples, such as significant expression in NHL samples, centrocytes and memory B cell abbreviations used in the Figures are designated as follows: Non-Hodgkin's Lymphoma (NHL), follicular lymphoma (FL), normal lymph node (NLN), normal B cells (NB), multiple myeloma cells (MM), small intestine (s. intestine), fetal liver (f. liver), smooth muscle (s. muscle), fetal brain (f. brain), natural killer cells (NK), neutrophils (N'phil), dendrocytes (DC), memory B cells (mem B), plasma cells (PC), bone marrow plasma cells (BM PC).
Figure 89B:
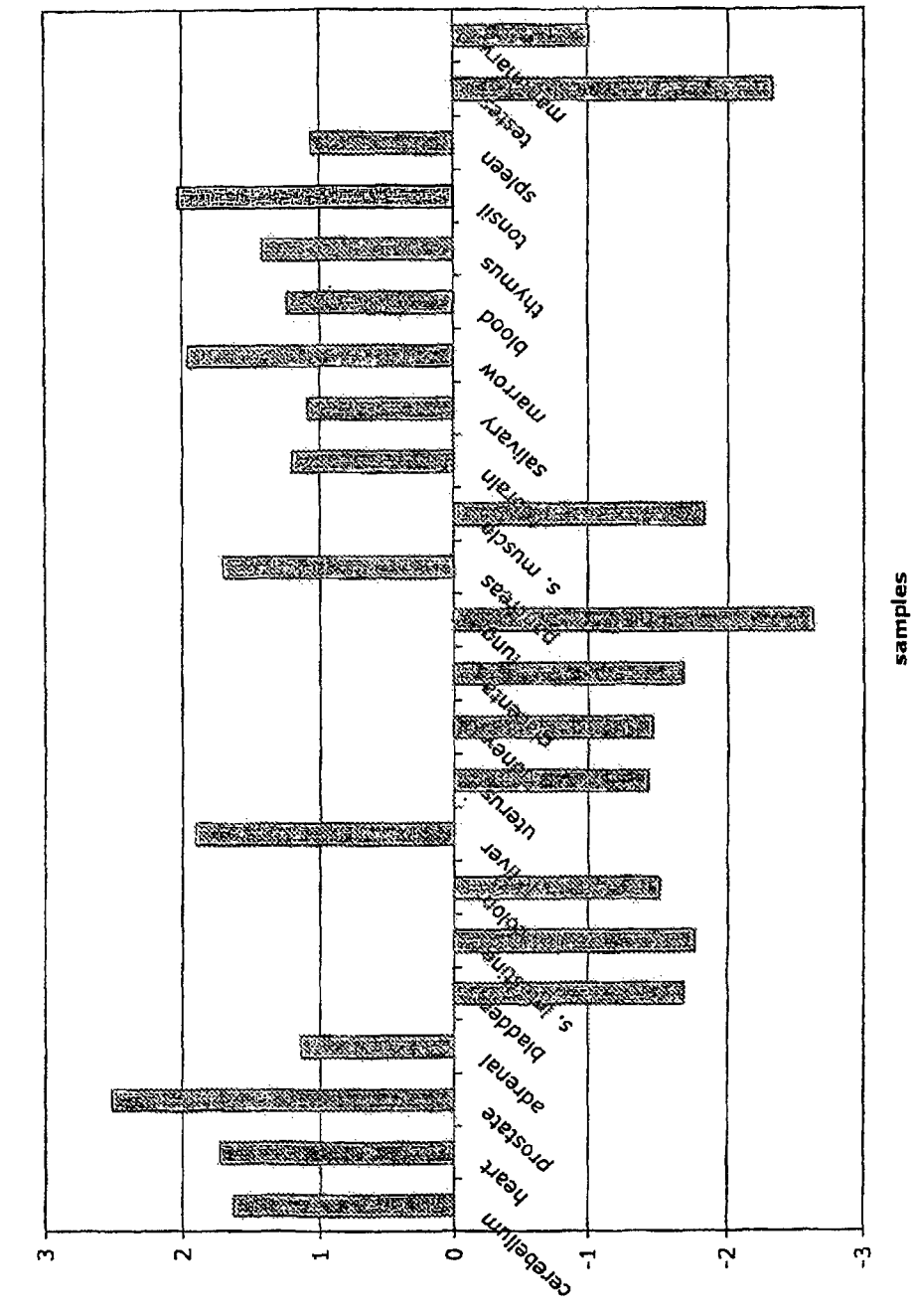
Figure 89C:
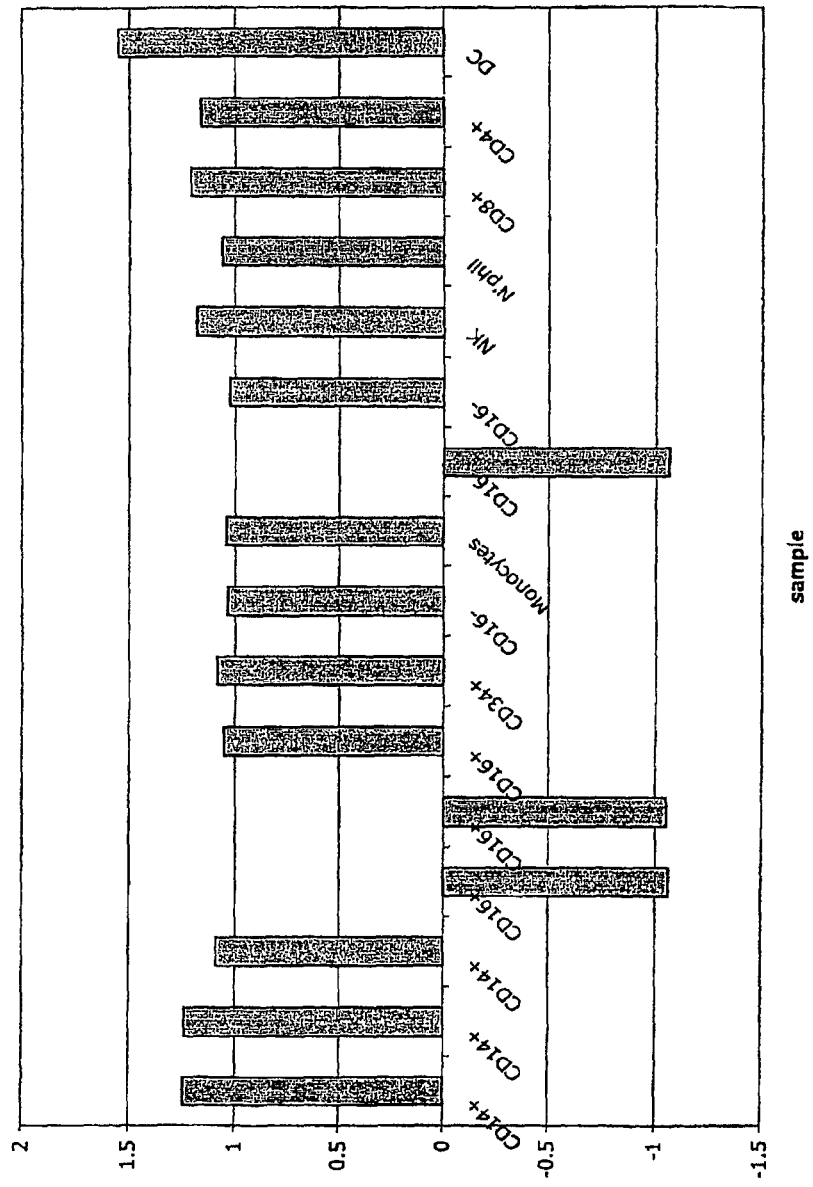
Figure 89D:
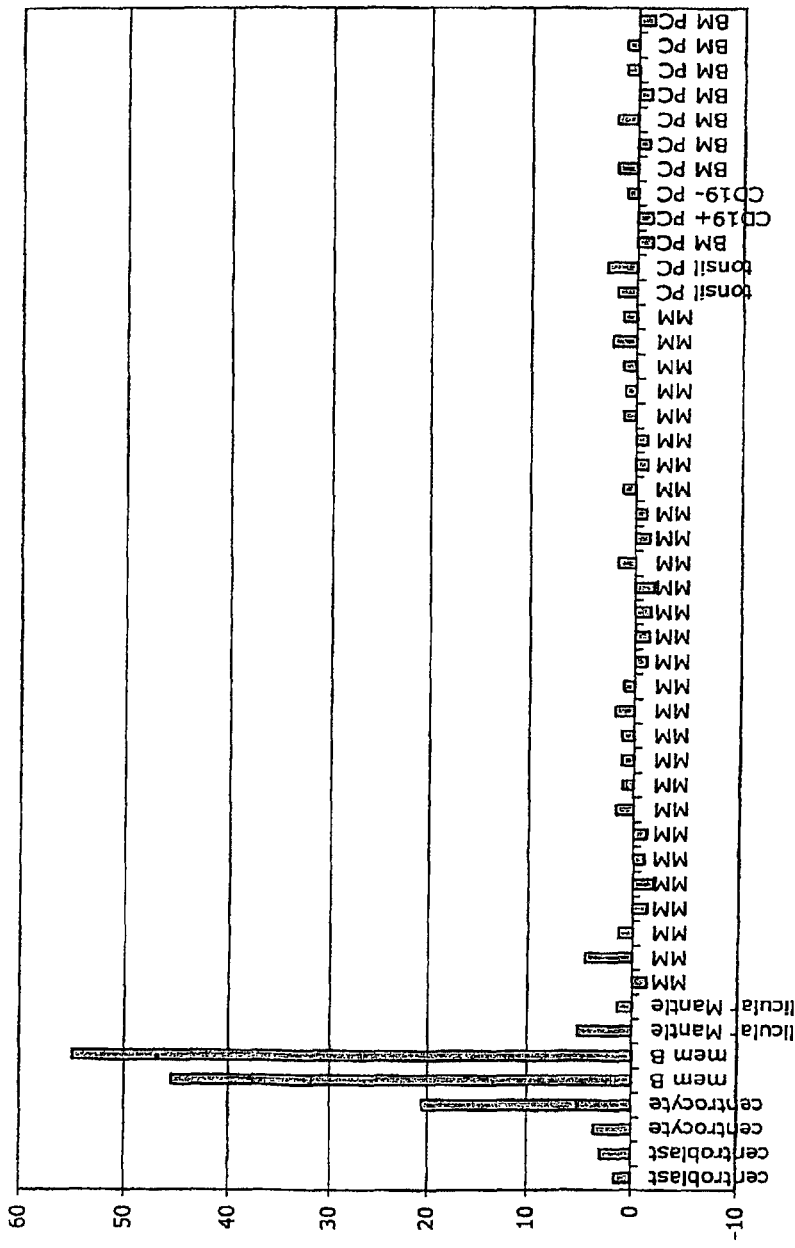
Figure 90A:
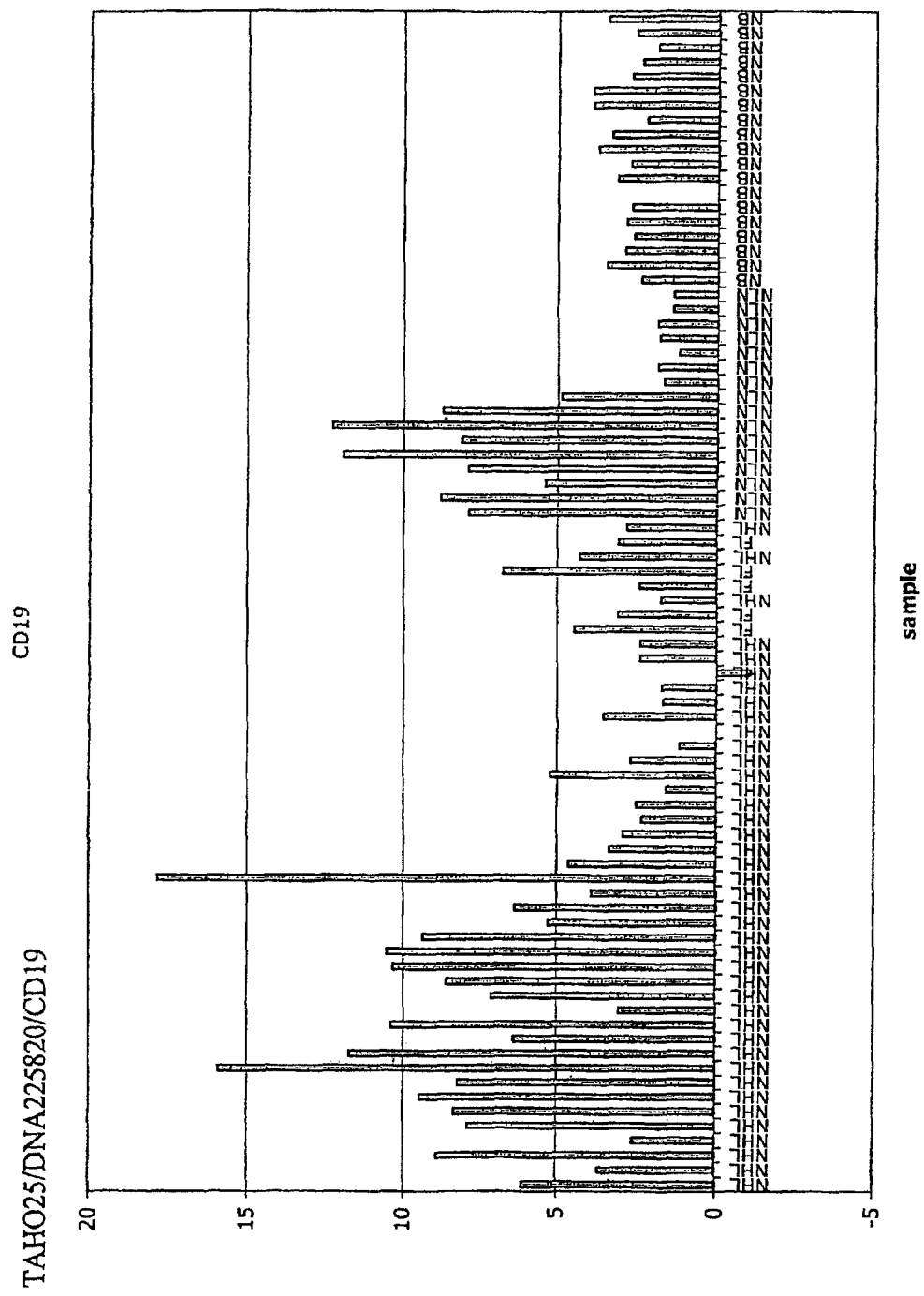
FIGS. 90A-90D show microarray data showing the expression of TAHO25 in normal samples and in diseased samples, such as significant expression in NHL samples, normal lymph node, centroblasts, centrocytes and memory B cells and in normal tonsil and spleen. Abbreviations used in the Figures are designated as follows: Non-Hodgkin's Lymphoma (NHL), follicular lymphoma (FL), normal lymph node (NLN), normal B cells (NB), multiple myeloma cells (MM), small intestine (s. intestine), fetal liver (f. liver), smooth muscle (s. muscle), fetal brain (f. brain), natural killer cells (NK), neutrophils (N'phil), dendrocytes (DC), memory B cells (mem B), plasma cells (PC), bone marrow plasma cells (BM PC).
Figure 90B:
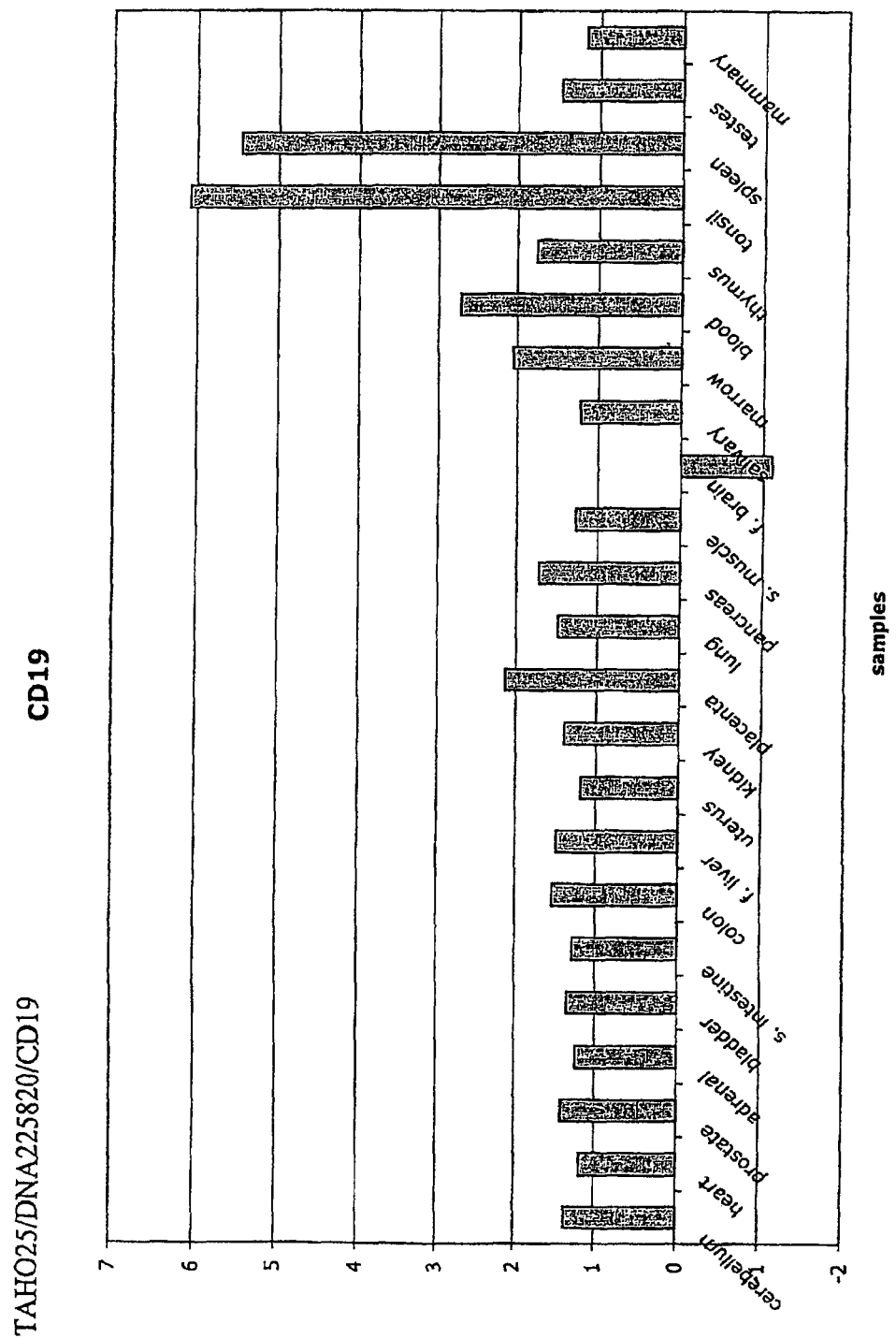
Figure 90C:
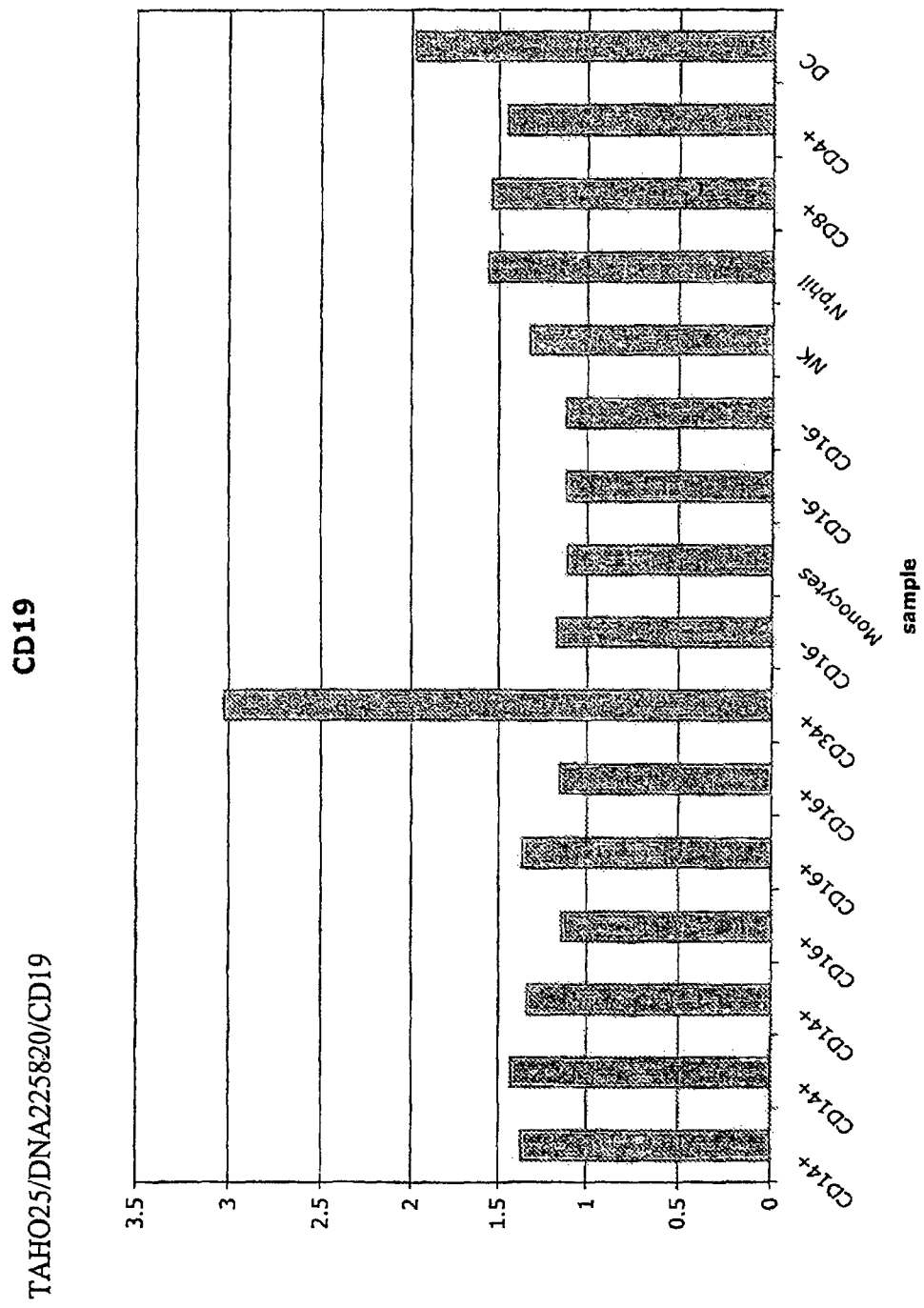
Figure 90D:
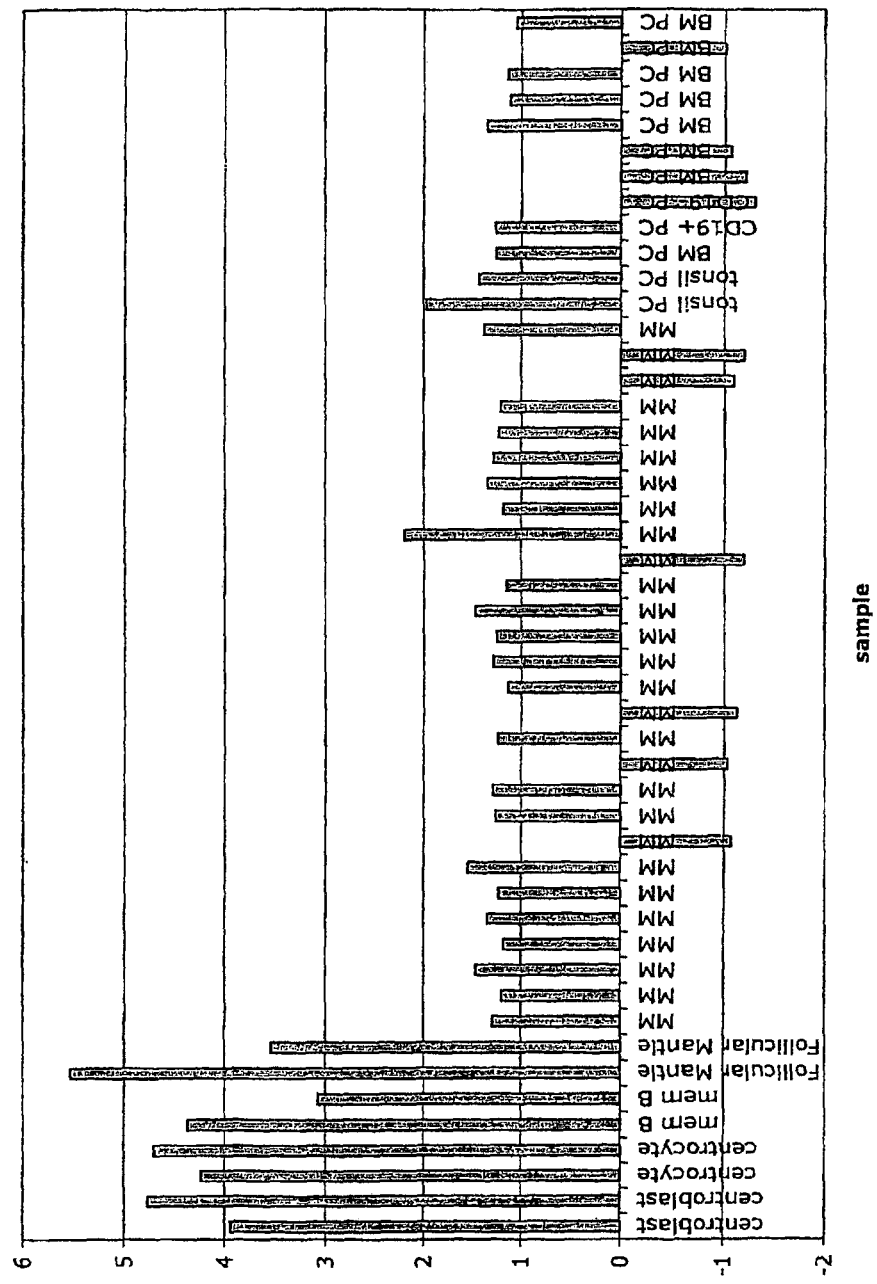
Figure 91A:
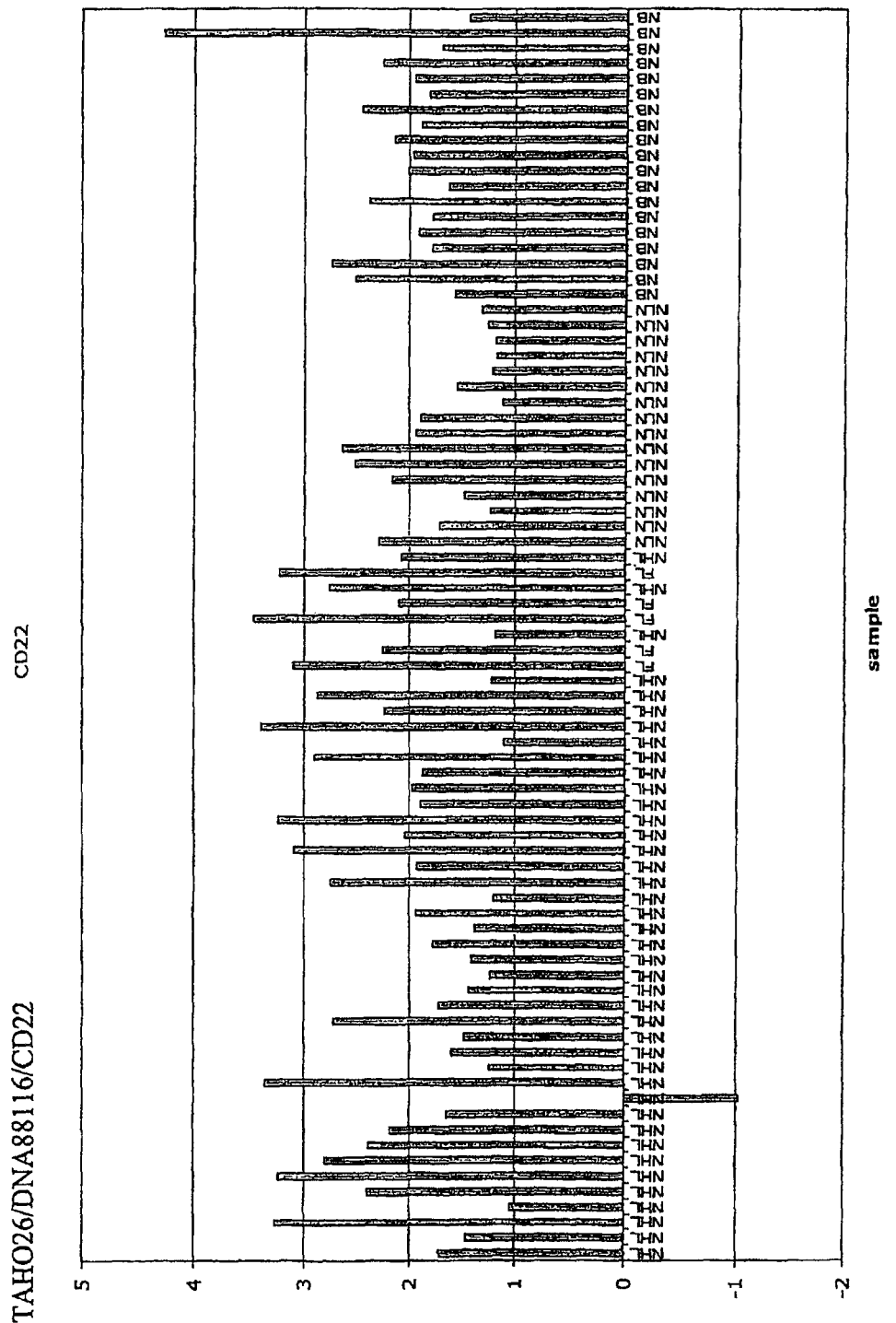
FIGS. 91A-91D show microarray data showing the expression of TAHO26 in normal samples and in diseased samples, such as significant expression in normal B cells. Abbreviations used in the Figures are designated as follows: Non-Hodgkin's Lymphoma (NHL), follicular lymphoma (FL), normal lymph node (NLN), normal B cells (NB), multiple myeloma cells (MM), small intestine (s. intestine), fetal liver (f. liver), smooth muscle (s. muscle), fetal brain (f. brain), natural killer cells (NK), neutrophils (N'phil), dendrocytes (DC), memory B cells (mem B), plasma cells (PC), bone marrow plasma cells (BM PC).
Figure 91B:
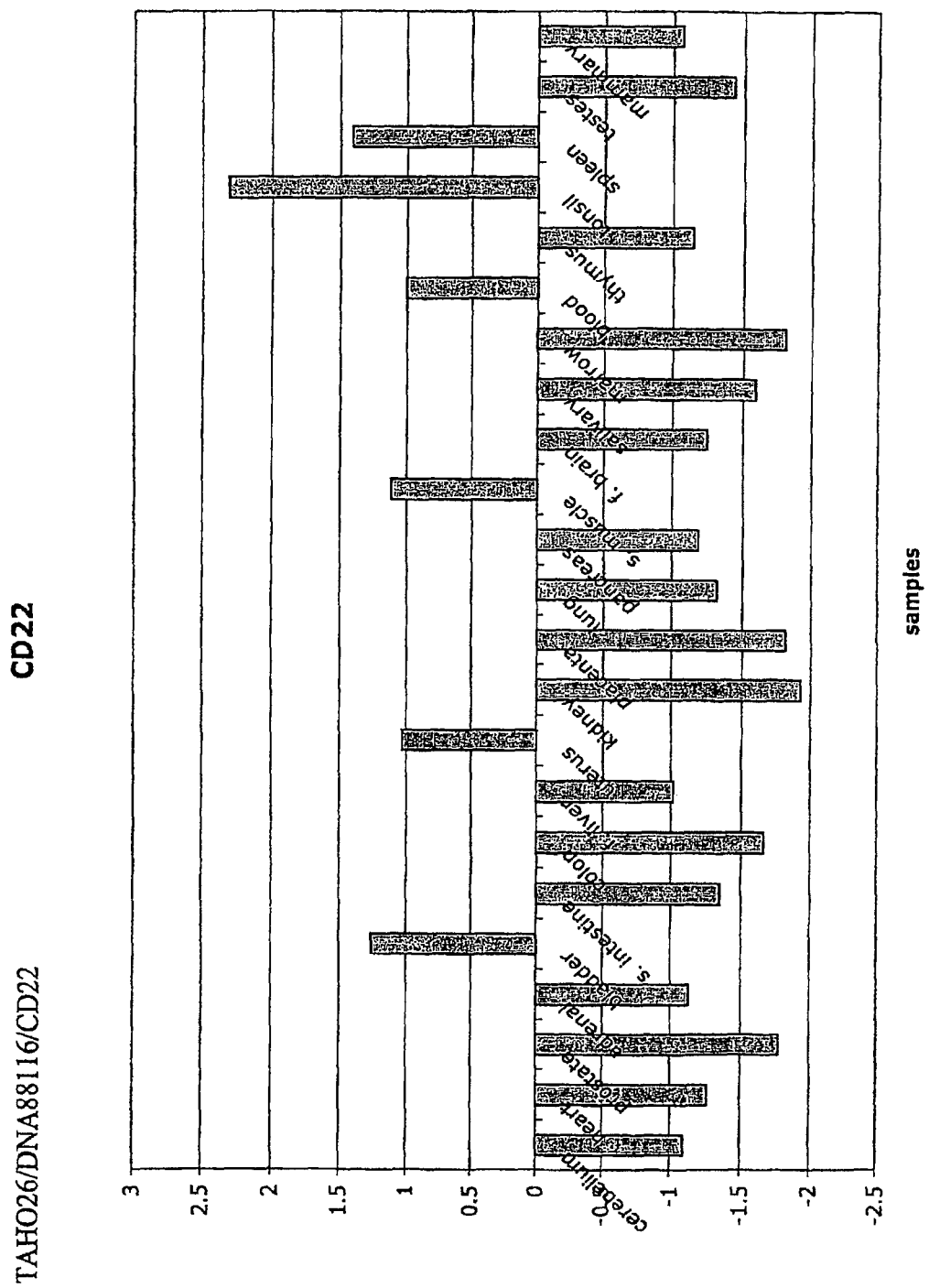
Figure 91C:
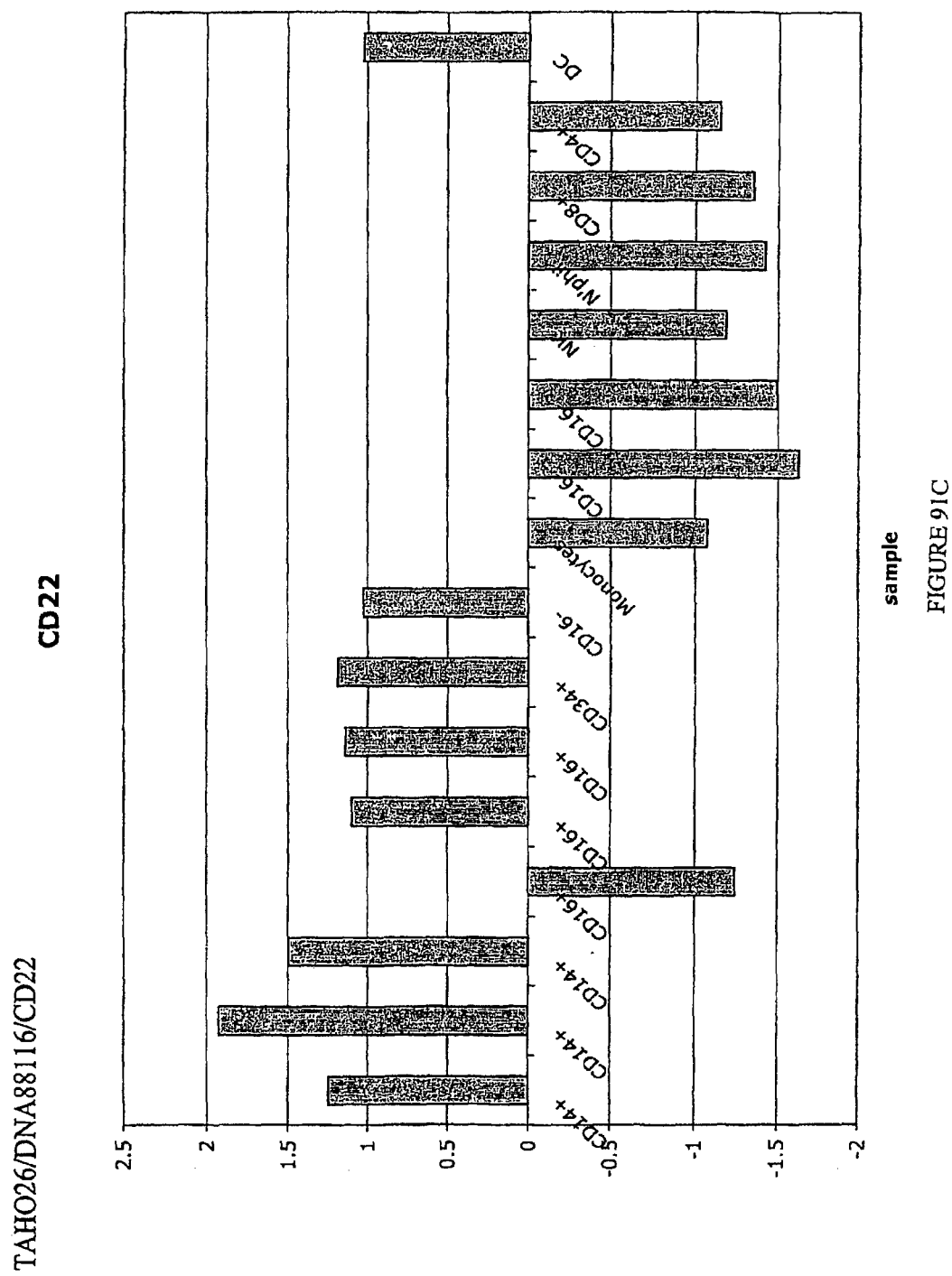
Figure 91D:
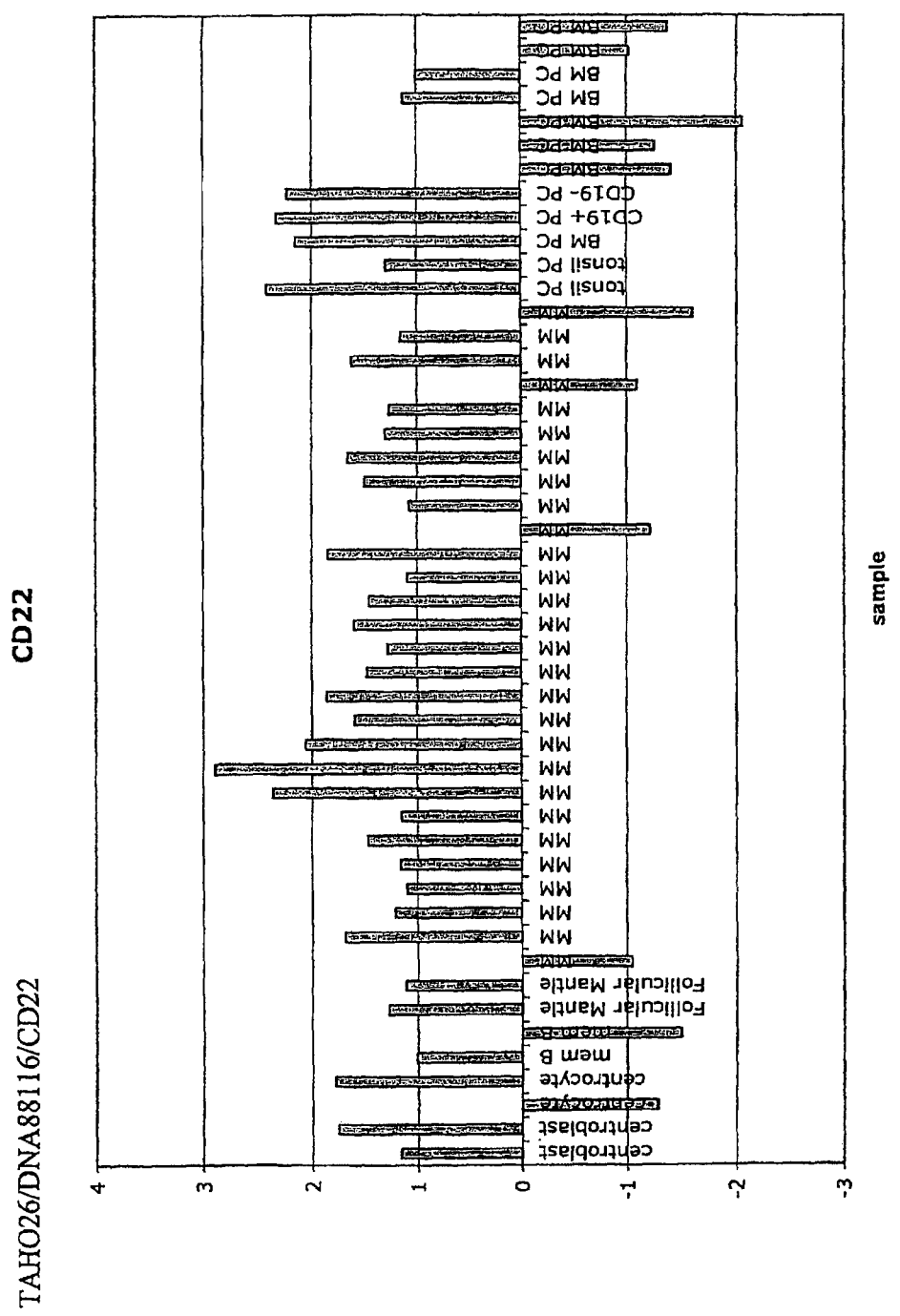

(12) TAHO13 (also referred herein as GPR2) was significantly expressed in multiple myeloma (MM), and normal blood (FIGS. 84A-84B). FIGS. 84A-84B are shown as two panels. The panel in FIG. 84A represents normal tissue from left to right as follows: brain cerebellum (1), pancreas (2), fetal liver (3), placenta (4), adrenal gland (5), kidney (6), small intestine (7), colon (8), prostate (9), lung (10), uterus (11), bladder (12), bone marrow (13), tonsil (14), spleen (15), thymus (16), blood (17), fetal brain (18), salivary gland (19), testes (20), heart (21), skeletal muscle (22) and mammary gland (23). The panel in FIG. 84B represents the samples tested from left to right as follows: NK cells (1), neutrophils (2), CD4+ cells (3), CD8+ cells (4), CD34+ cells (5), normal B cells (6), monocytes (7), dendritic cells (8), multiple myeloma cells (9-11), memory B cells (12), naive B cells (13), centrocytes (14), centroblasts (15-16), centrocytes (17), memory B cells (18), naive B cells (19), normal B cells (20-38), multiple myeloma cells (39), CD138+ cells (40), multiple myeloma cells (41-46), tonsil plasma cells (47), bone marrow plasma cells (48), multiple myeloma cells (49-60), centrocytes (61), plasma bone marrow cells (62-70), plasma cell CD19+ (71), plasma cell CD19− (72), multiple myeloma cells (73-75).

(13) TAHO15 (also referred herein as LRRC4 and NAG14) was significantly expressed in non-hodgkin's lymphoma (NHL) (FIG. 85). As shown in FIG. 72, PRO1111 (TAHO15) was significantly expressed and upregulated in bone marrow plasma cells and multiple myeloma as compared to low expression in non-B cells, including neutrophils, T cells and natural killer (NK) cells. PRO1111 is also significantly expressed in some non-hodgkin lymphoma cells.

(14) TAHO17 (also referred herein as FcRH1) was significantly expressed in normal B cells (NB), and memory B cells (FIG. 86).

(15) TAHO18 (also referred herein as IRTA2) was significantly expressed in non-hodgkin's lymphoma (NHL) (FIG. 87).

(16) TAHO20 (also referred herein as FcRH3) was significantly expressed in normal B cells (NB) and multiple myeloma (MM). Further, TAHO20 was detected in expressed in colon, placenta, lung and spleen (FIG. 88). However, as indicated above, any apparent expression in non-B cells, such as in prostate, spleen, blood, tonsil, etc. may represent an artifact, infiltration of normal tissue by lymphocytes or loss of sample integrity by the vendor.

(17) TAHO21 (also referred herein as IRTA1) was significantly expressed in non-hodgkin's lymphoma (NHL), centrocytes and memory B cells (FIG. 89).

(18) TAHO25 (also referred herein as CD19) was significantly expressed in non-hodgkin's lymphoma (NHL), normal lymph node (NLN), follicular lymphoma (FL), centroblasts, centrocytes, memory B cells and follicular mantle cells. Further TAHO25 was significantly expressed in tonsil and spleen (FIG. 90). However, as indicated above, any apparent expression in non-B cells, such as in prostate, spleen, blood, tonsil, etc. may represent an artifact, infiltration of normal tissue by lymphocytes or loss of sample integrity by the vendor.

(19) TAHO26 (also referred herein as CD22) was significantly expressed in normal B cells (NB) (FIG. 91).

Figure 92A:
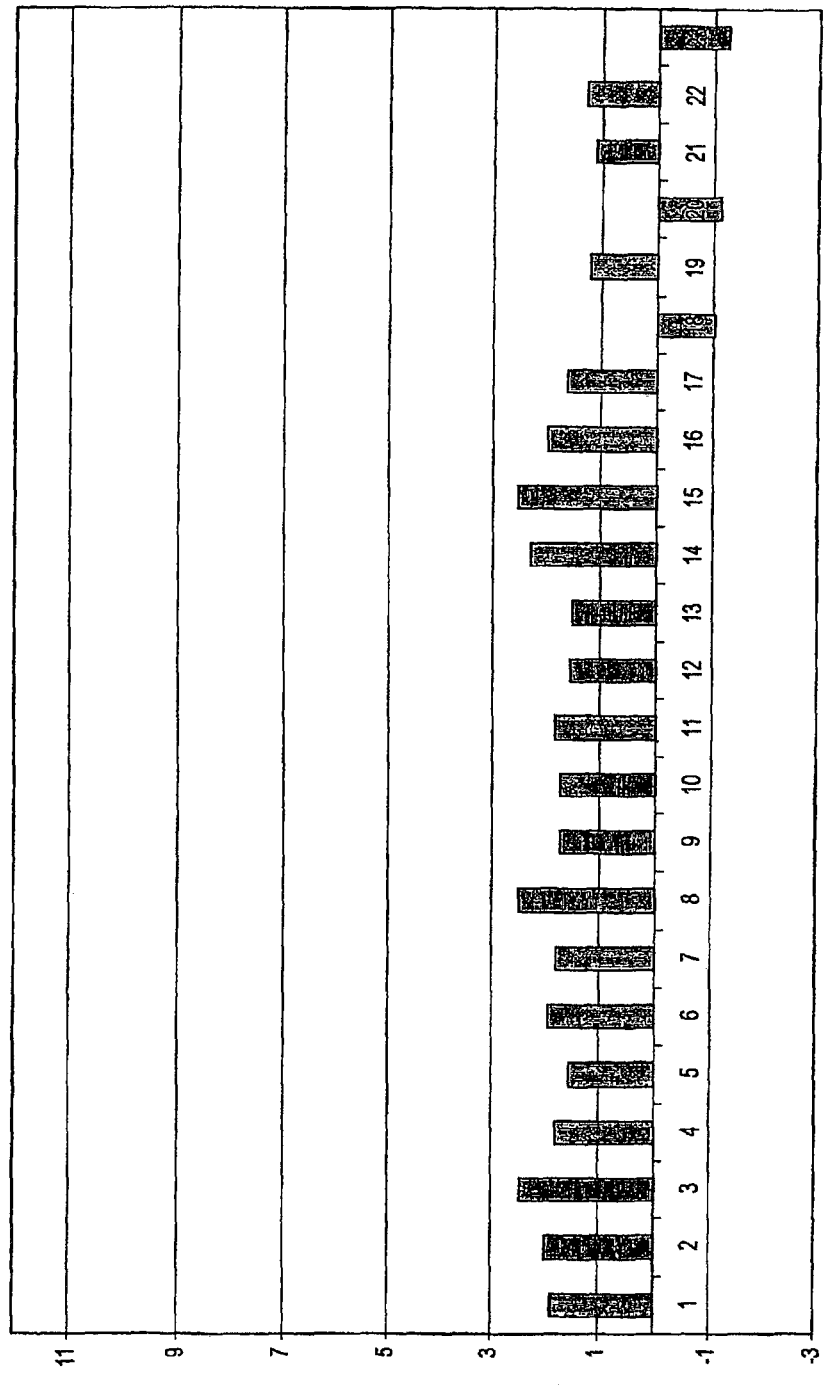
FIGS. 92A-92B show microarray data showing the expression of TAHO27 in normal samples and in diseased samples, such as significant expression in in multiple myeloma.
Figure 92B:
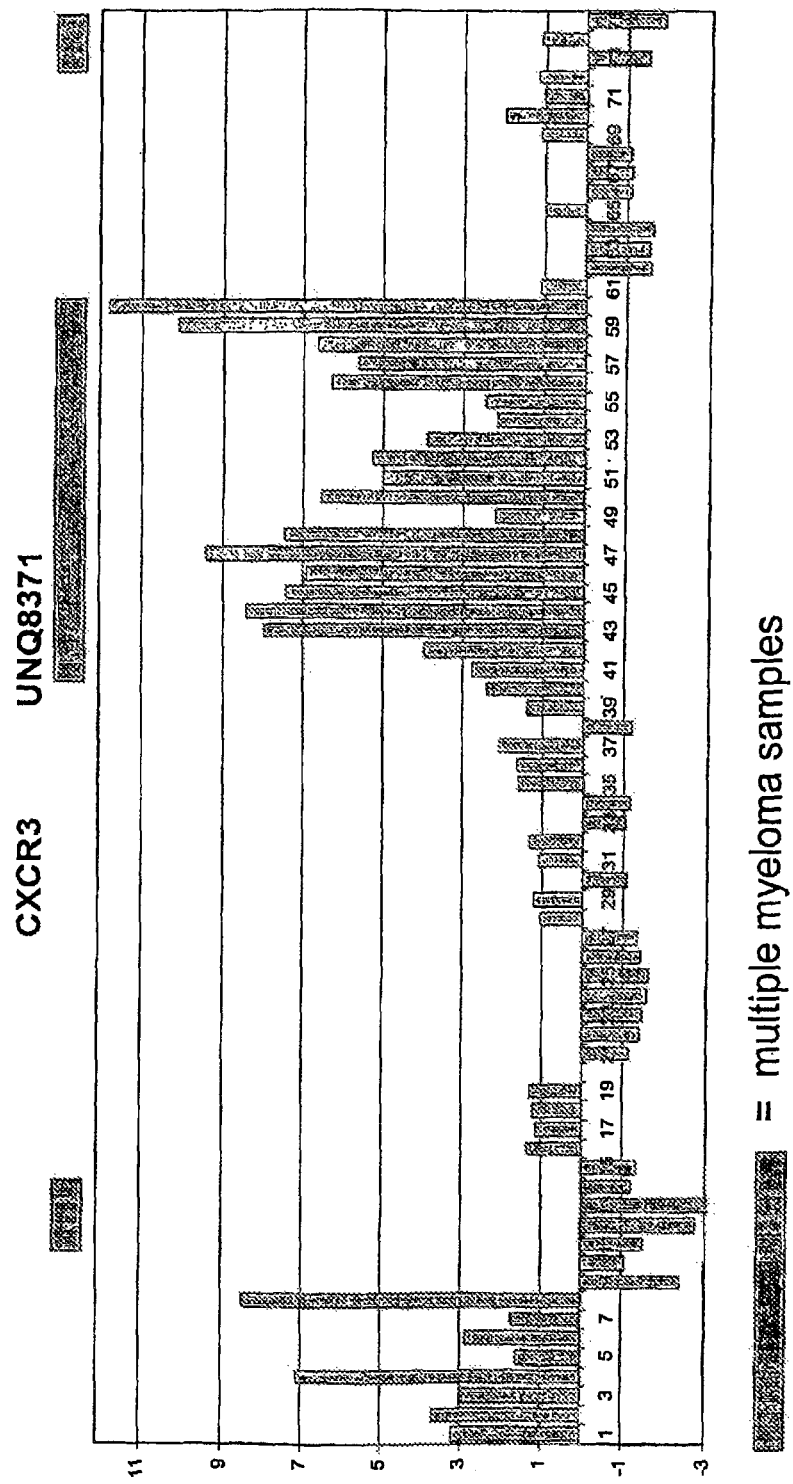

(20) TAHO27 (also referred herein as CXCR3) was significantly expressed in multiple myeloma cells (FIG. 92A-92B). FIGS. 92A-92B are shown as two panels. The panel in FIG. 92A represents normal tissue from left to right as follows: brain cerebellum (1), pancreas (2), fetal liver (3), placenta (4), adrenal gland (5), kidney (6), small intestine (7), colon (8), prostate (9), lung (10), uterus (11), bladder (12), bone marrow (13), tonsil (14), spleen (15), thymus (16), blood (17), fetal brain (18), salivary gland (19), testes (20), heart (21), skeletal muscle (22) and mammary gland (23). The panel in FIG. 92B represents the samples tested from left to right as follows: NK cells (1), neutrophils (2), CD4+ cells (3), CD8+ cells (4), CD34+ cells (5), normal B cells (6), monocytes (7), dendritic cells (8), multiple myeloma cells (9-11), memory B cells (12), naive B cells (13), centrocytes (14), centroblasts (15-16), centrocytes (17), memory B cells (18), naive B cells (19), normal B cells (20-38), multiple myeloma cells (39), CD138+ cells (40), multiple myeloma cells (41-46), tonsil plasma cells (47), bone marrow plasma cells (48), multiple myeloma cells (49-60), centrocytes (61), plasma bone marrow cells (62-70), plasma cell CD19+ (71), plasma cell CD19− (72), multiple myeloma cells (73-75).

Figure 93A:
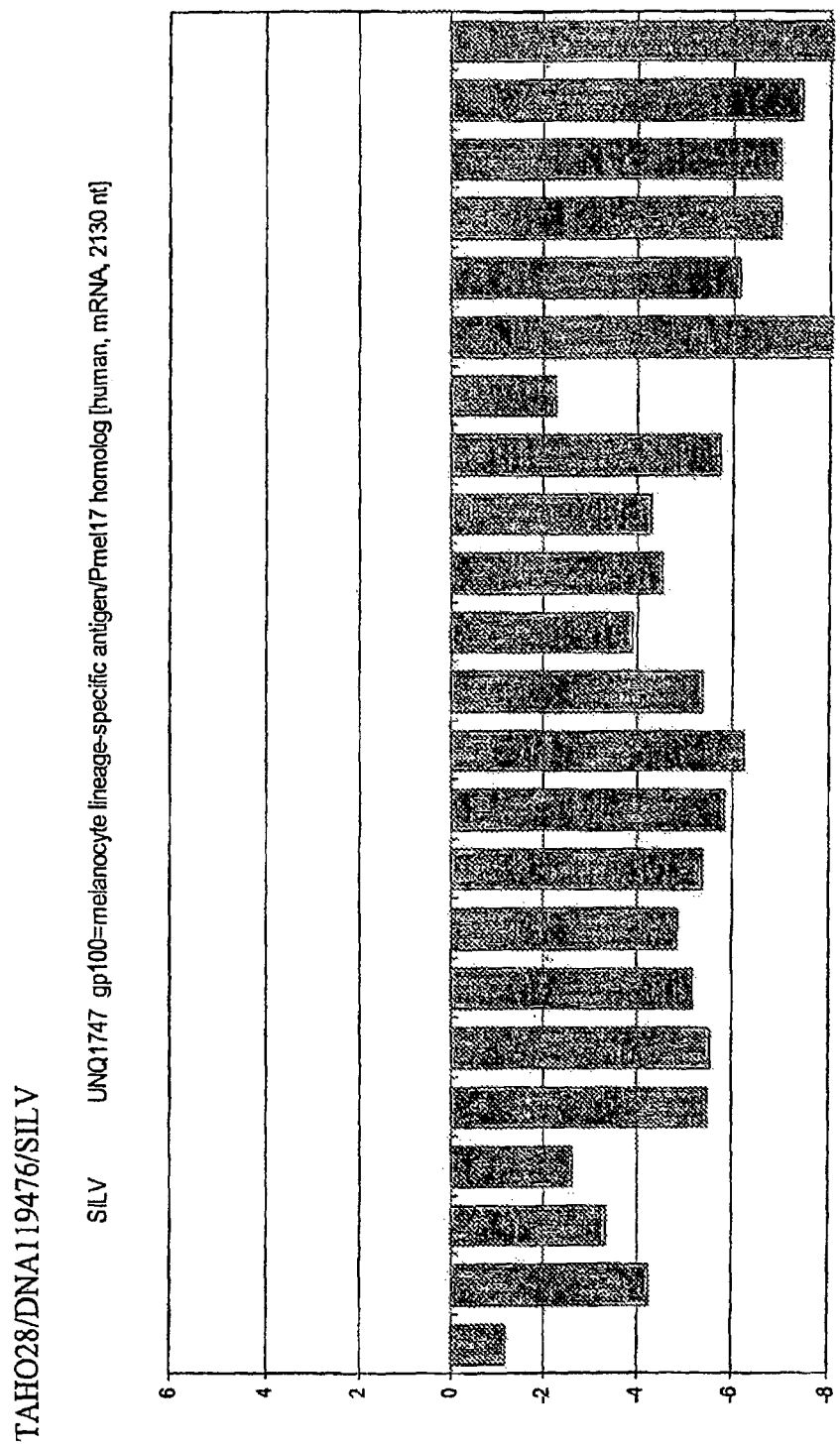
FIGS. 93A-93B show microarray data showing the expression of TAHO28 in normal samples and in diseased samples, such as significant expression in normal plasma cells and in multiple myeloma.
Figure 93B:
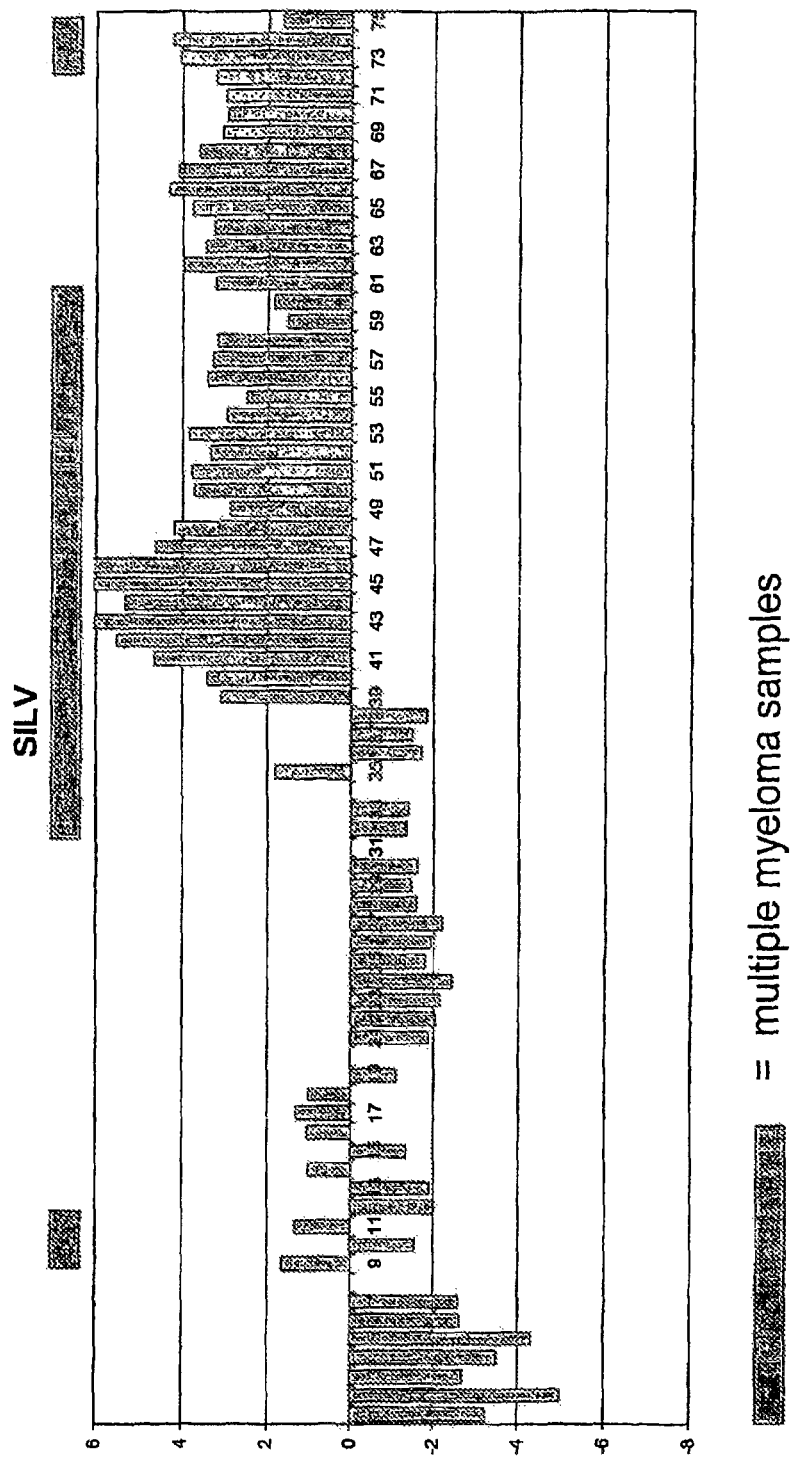

(21) TAHO28 (also referred herein as SILV1) was significantly expressed in normal plasma cells, and more significantly expressed on multiple myeloma cells (FIGS. 93A-93B). FIGS. 93A-93B are shown as two panels. The panel in FIG. 93A represents normal tissue from left to right as follows: brain cerebellum (1), pancreas (2), fetal liver (3), placenta (4), adrenal gland (5), kidney (6), small intestine (7), colon (8), prostate (9), lung (10), uterus (I), bladder (12), bone marrow (13), tonsil (14), spleen (15), thymus (16), blood (17), fetal brain (18), salivary gland (19), testes (20), heart (21), skeletal muscle (22) and mammary gland (23). The panel in FIG. 93B represents the samples tested from left to right as follows: NK cells (1), neutrophils (2), CD4+ cells (3), CD8+ cells (4), CD34+ cells (5), normal B cells (6), monocytes (7), dendritic cells (8), multiple myeloma cells (9-1), memory B cells (12), naive B cells (13), centrocytes (14), centroblasts (15-16), centrocytes (17), memory B cells (18), naive B cells (19), normal B cells (20-38), multiple myeloma cells (39), CD138+ cells (40), multiple myeloma cells (41-46), tonsil plasma cells (47), bone marrow plasma cells (48), multiple myeloma cells (49-60), centrocytes (61), plasma bone marrow cells (62-70), plasma cell CD19+ (71), plasma cell CD19− (72), multiple myeloma cells (73-75).

Figure 94A:
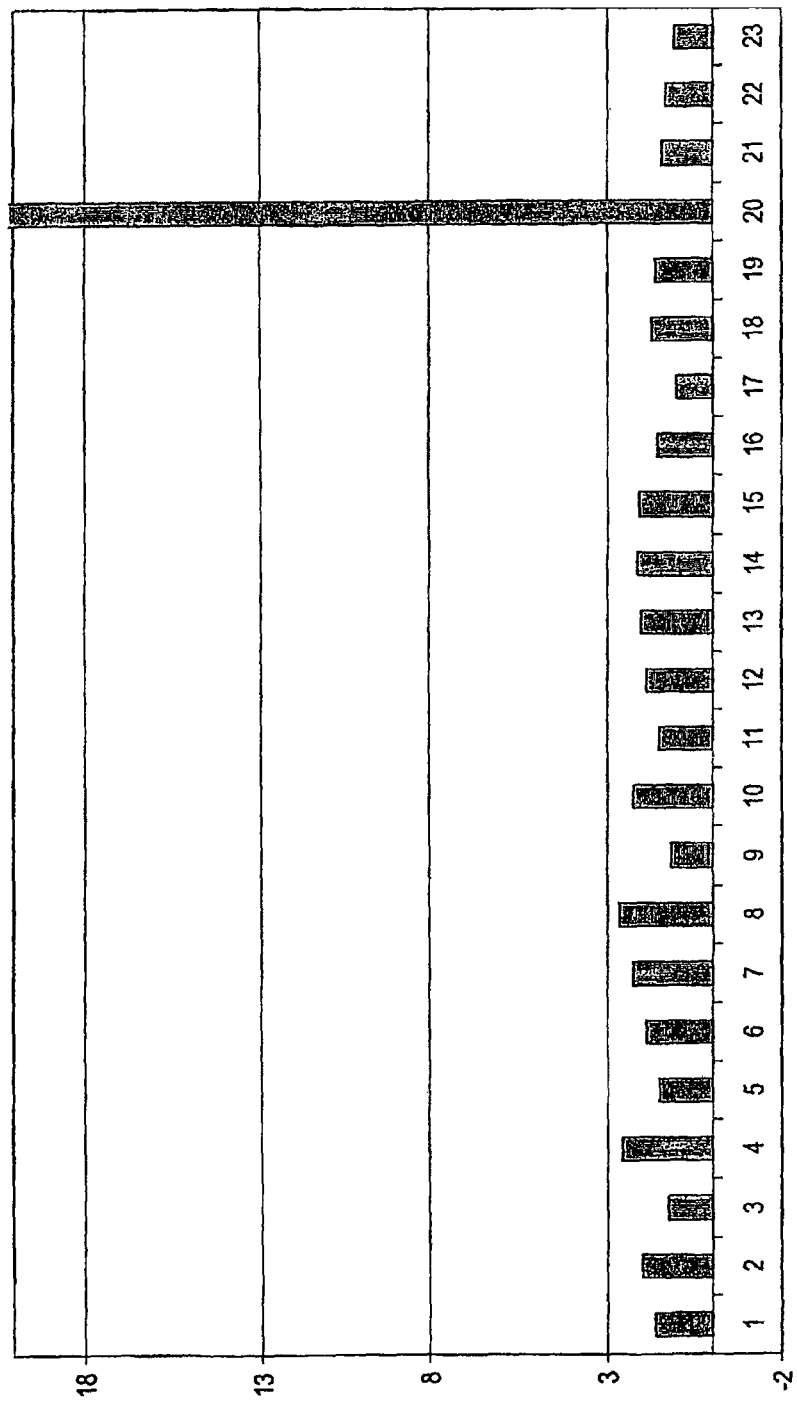
FIGS. 94A-94B show microarray data showing the expression of TAHO29 in normal samples and in diseased samples, such as significant expression in in multiple myeloma, normal plasma cells and normal testes.
Figure 94B:
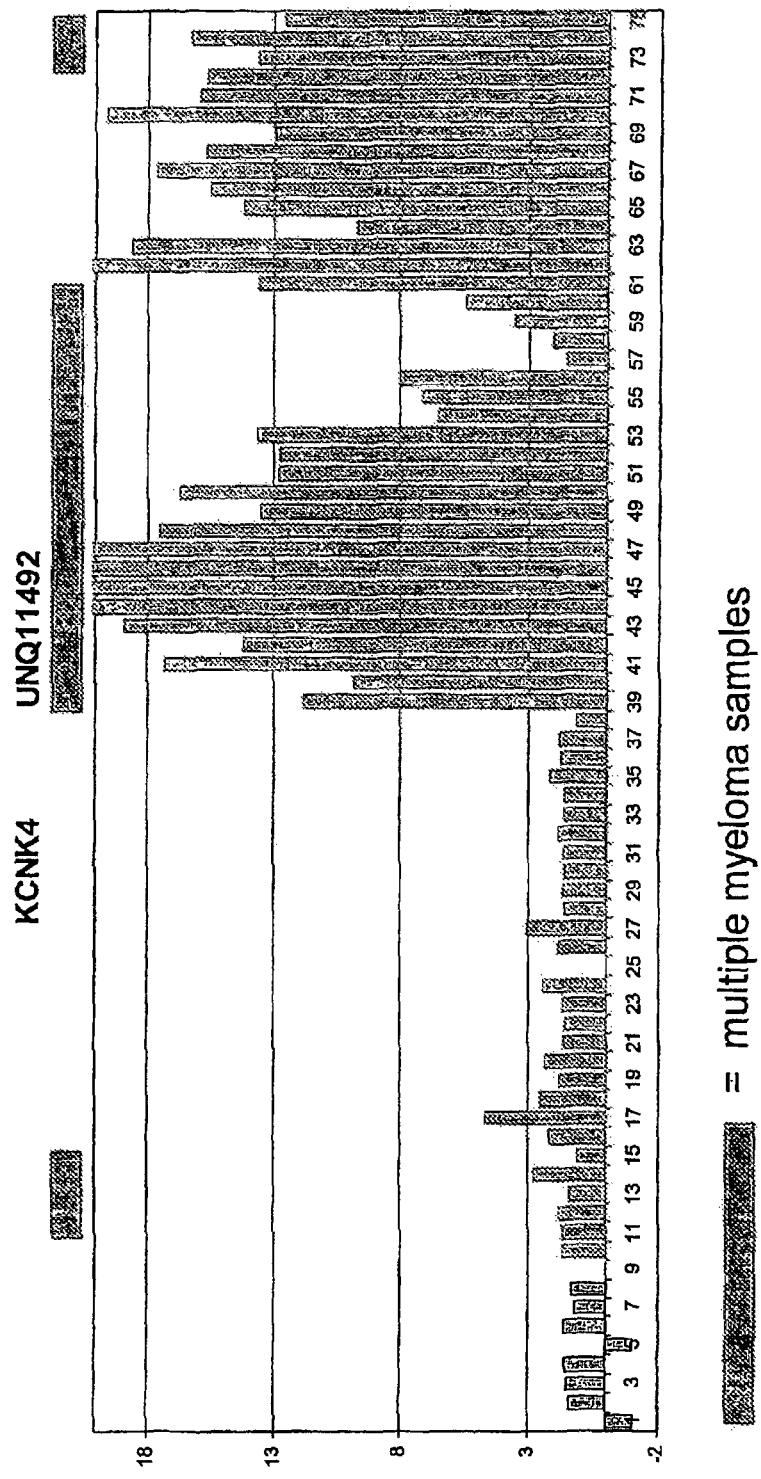

(22) TAHO29 (also referred herein as KCNK4) was significantly expressed in normal plasma cells and in multiple myeloma cells (FIGS. 94A-94B). In normal tissues, expression of TAHO29 is significantly expressed in normal testes. FIGS. 94A-94B are shown as two panels. The panel in FIG. 94A represents normal tissue from left to right as follows: brain cerebellum (1), pancreas (2), fetal liver (3), placenta (4), adrenal gland (5), kidney (6), small intestine (7), colon (8), prostate (9), lung (10), uterus (1), bladder (12), bone marrow (13), tonsil (14), spleen (15), thymus (16), blood (17), fetal brain (18), salivary gland (19), testes (20), heart (21), skeletal muscle (22) and mammary gland (23). The panel in FIG. 94B represents the samples tested from left to right as follows: NK cells (1), neutrophils (2), CD4+ cells (3), CD8+ cells (4), CD34+ cells (5), normal B cells (6), monocytes (7), dendritic cells (8), multiple myeloma cells (9-11), memory B cells (12), naive B cells (13), centrocytes (14), centroblasts (15-16), centrocytes (17), memory B cells (18), naive B cells (19), normal B cells (20-38), multiple myeloma cells (39), CD138+ cells (40), multiple myeloma cells (41-46), tonsil plasma cells (47), bone marrow plasma cells (48), multiple myeloma cells (49-60), centrocytes (61), plasma bone marrow cells (62-70), plasma cell CD19+ (71), plasma cell CD19− (72), multiple myeloma cells (73-75).

Figure 95A:
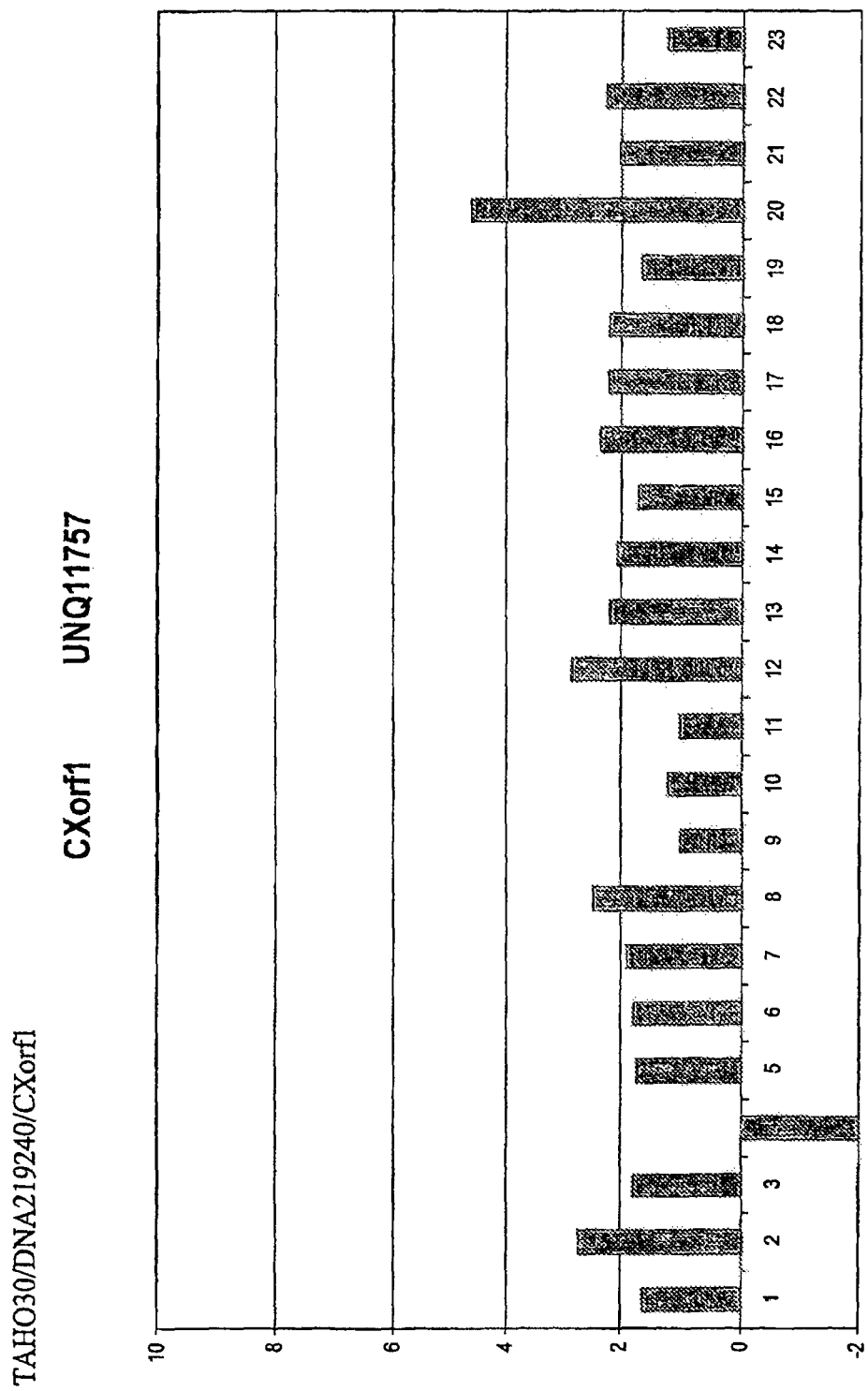
FIGS. 95A-95B show microarray data showing the expression of TAHO30 in normal samples and in diseased samples, such as significant expression in in multiple myeloma and normal testes.
Figure 95B:
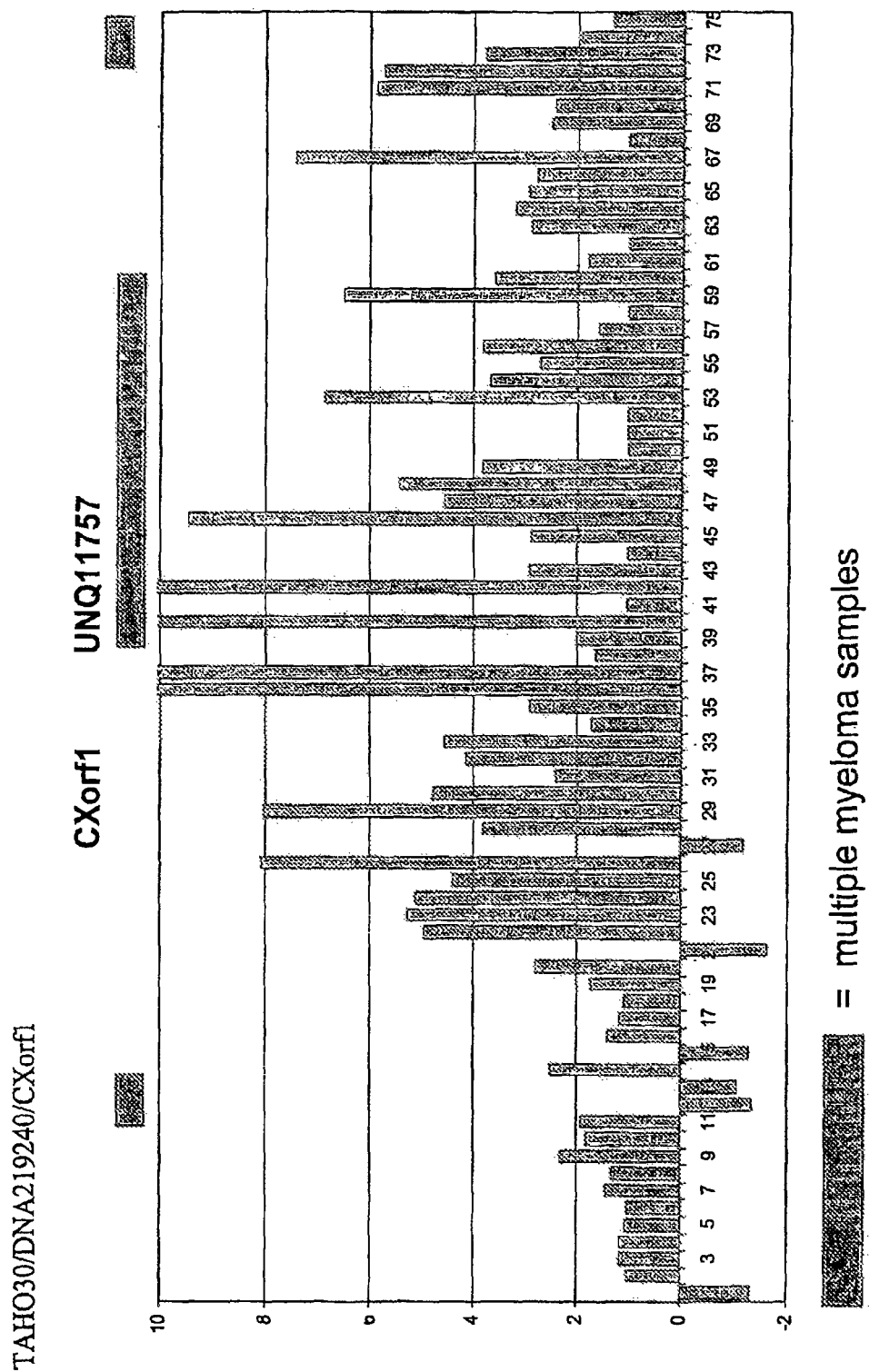

(23) TAHO30 (also referred herein as CXorf1) was significantly expressed in normal plasma cells, and more significantly expressed on multiple myeloma cells (FIGS. 95A-95B). In normal tissues, expression of TAHO30 is significantly expressed in normal testes. FIGS. 95A-95B are shown as two panels. The panel in FIG. 95A represents normal tissue from left to right as follows: brain cerebellum (1), pancreas (2), fetal liver (3), placenta (4), adrenal gland (5), kidney (6), small intestine (7), colon (8), prostate (9), lung (10), uterus (11), bladder (12), bone marrow (13), tonsil (14), spleen (15), thymus (16), blood (17), fetal brain (18), salivary gland (19), testes (20), heart (21), skeletal muscle (22) and mammary gland (23). The panel in FIG. 95B represents the samples tested from left to right as follows: NK cells (1), neutrophils (2), CD4+ cells (3), CD8+ cells (4), CD34+ cells (5), normal B cells (6), monocytes (7), dendritic cells (8), multiple myeloma cells (9-11), memory B cells (12), naive B cells (13), centrocytes (14), centroblasts (15-16), centrocytes (17), memory B cells (18), naive B cells (19), normal B cells (20-38), multiple myeloma cells (39), CD138+ cells (40), multiple myeloma cells (41-46), tonsil plasma cells (47), bone marrow plasma cells (48), multiple myeloma cells (49-60), centrocytes (61), plasma bone marrow cells (62-70), plasma cell CD19+ (71), plasma cell CD19− (72), multiple myeloma cells (73-75).

Figure 96A:
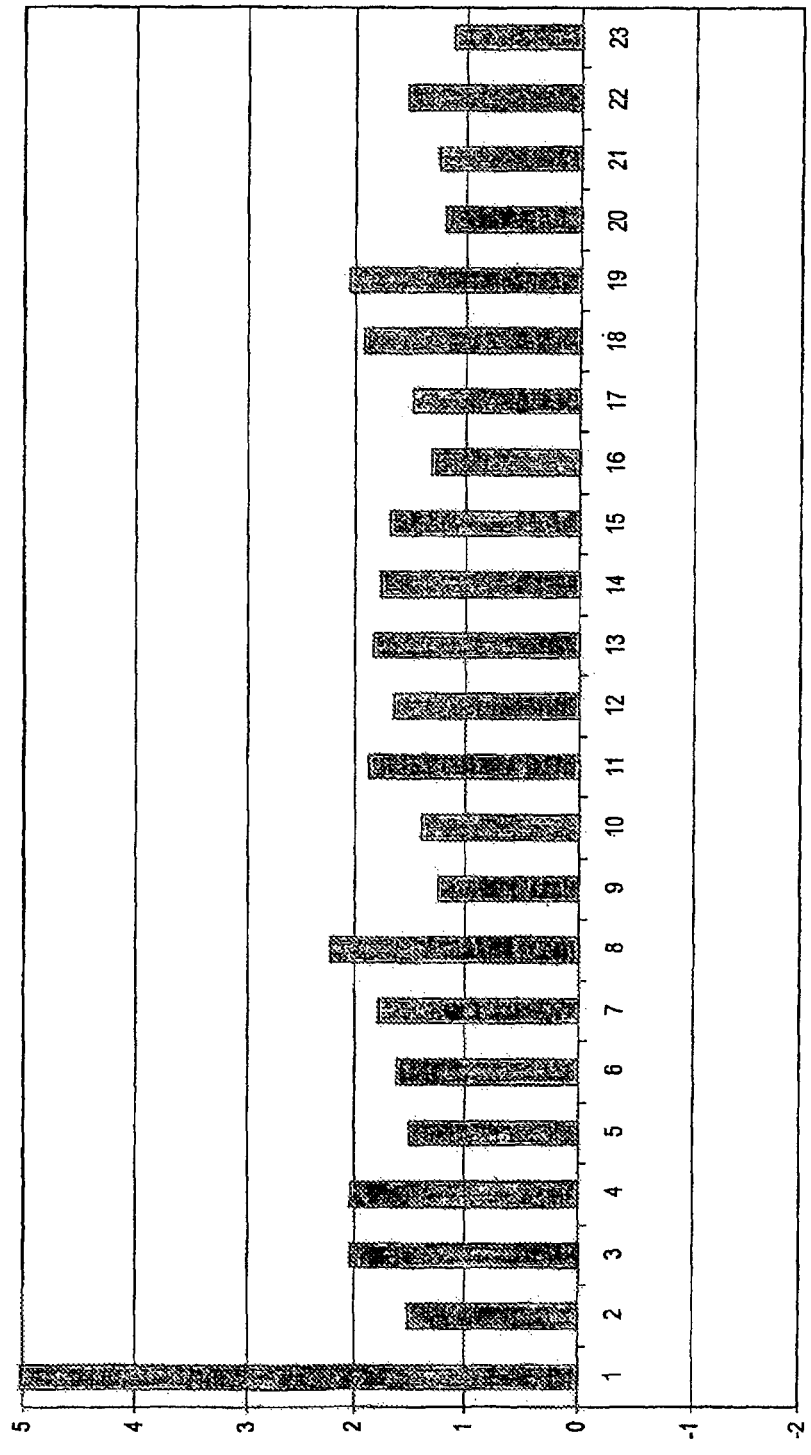
FIGS. 96A-96B show microarray data showing the expression of TAHO31 in normal samples and in diseased samples, such as significant expression in in multiple myeloma, plasma cells and normal brain cerebellum.
Figure 96B:
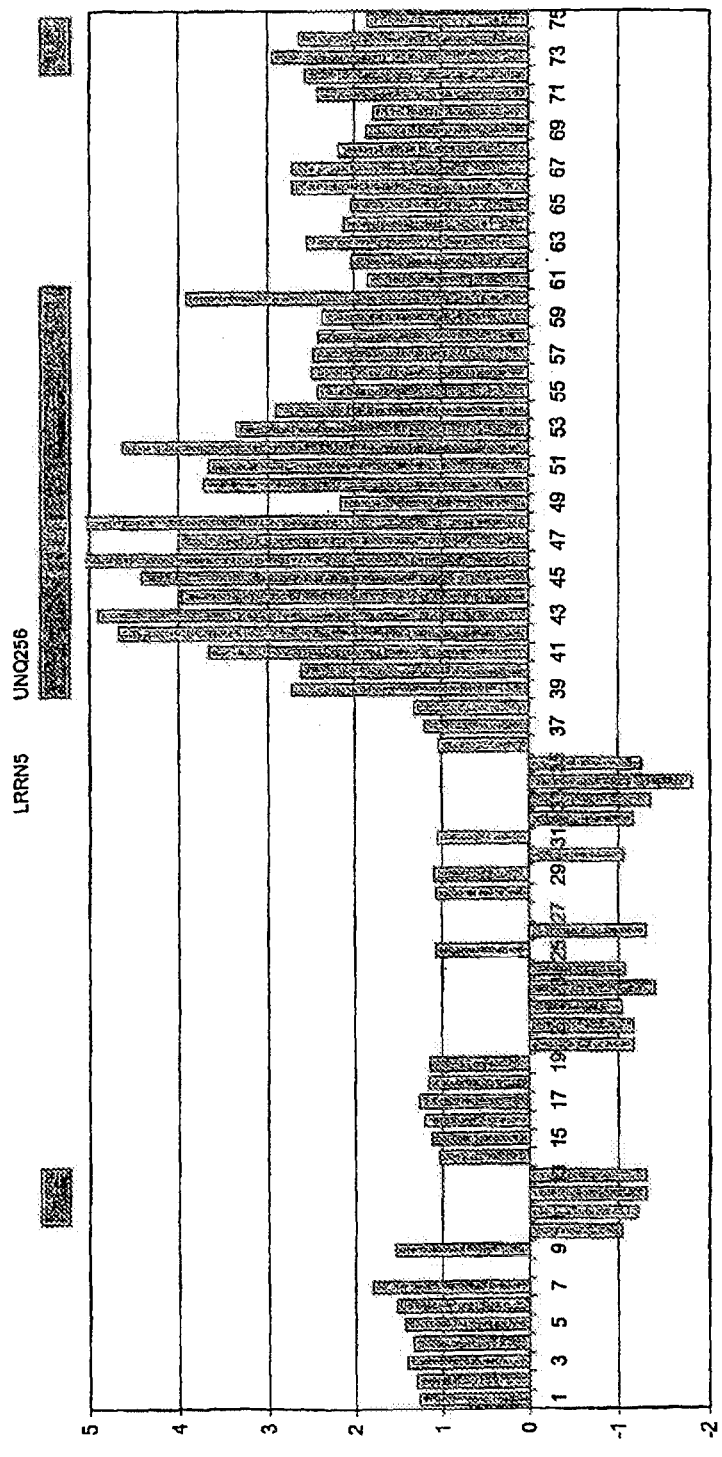

(24) TAHO31 (also referred herein as LRRN5) was significantly expressed in normal plasma cells, and more significantly expressed on multiple myeloma cells (FIGS. 96A-96B). In normal tissues, expression of TAHO31 is significantly expressed in cerebellum. FIGS. 96A-96B are shown as two panels. The panel in FIG. 96A represents normal tissue from left to right as follows: brain cerebellum (1), pancreas (2), fetal liver (3), placenta (4), adrenal gland (5), kidney (6), small intestine (7), colon (8), prostate (9), lung (10), uterus (11), bladder (12), bone marrow (13), tonsil (14), spleen (15), thymus (16), blood (17), fetal brain (18), salivary gland (19), testes (20), heart (21), skeletal muscle (22) and mammary gland (23). The panel in FIG. 96B represents the samples tested from left to right as follows: NK cells (1), neutrophils (2), CD4+ cells (3), CD8+ cells (4), CD34+ cells (5), normal B cells (6), monocytes (7), dendritic cells (8), multiple myeloma cells (9-11), memory B cells (12), naive B cells (13), centrocytes (14), centroblasts (15-16), centrocytes (17), memory B cells (18), naive B cells (19), normal B cells (20-38), multiple myeloma cells (39), CD138+ cells (40), multiple myeloma cells (41-46), tonsil plasma cells (47), bone marrow plasma cells (48), multiple myeloma cells (49-60), centrocytes (61), plasma bone marrow cells (62-70), plasma cell CD19+ (71), plasma cell CD19− (72), multiple myeloma cells (73-75).

Figure 97A:
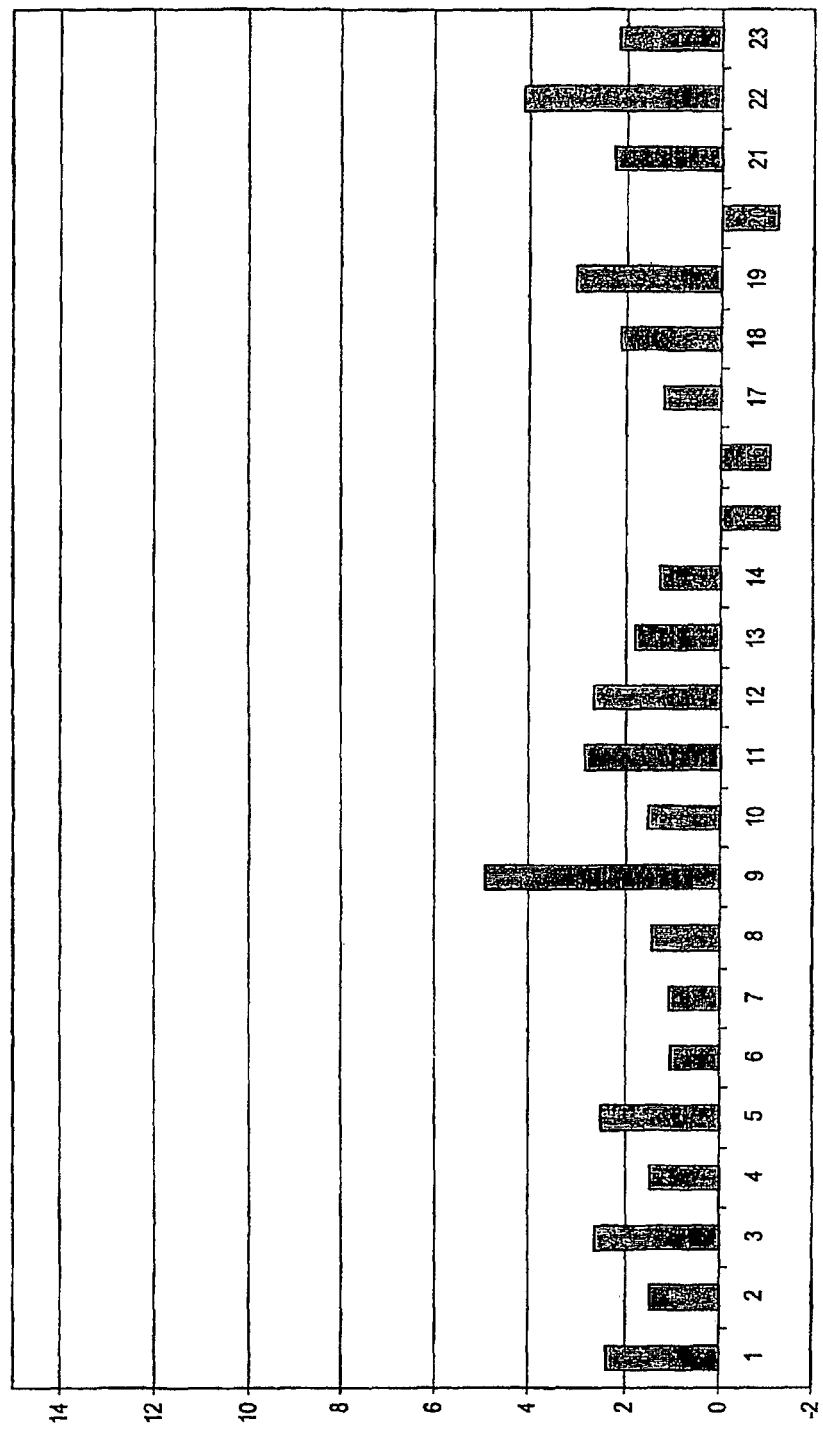
FIGS. 97A-97B show microarray data showing the expression of TAHO32 in normal samples and in diseased samples, such as significant expression in in multiple myeloma and normal prostate.
Figure 97B:
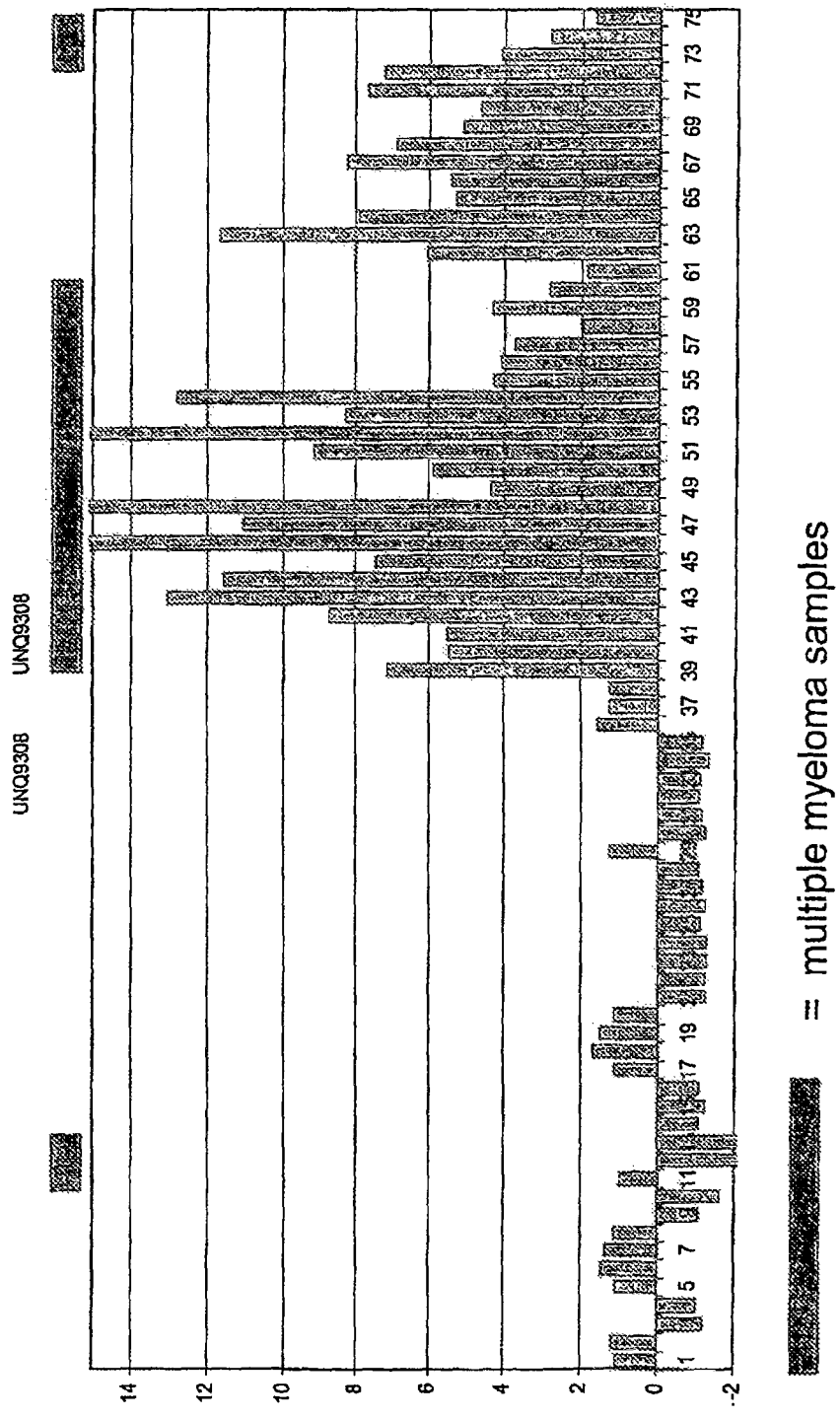

(25) TAHO32 (also referred herein as UNQ9308) was significantly expressed in normal plasma cells, and more significantly expressed on multiple myeloma cells (FIGS. 97A-97B). TAHO32 was also significantly expressed in normal prostate. FIGS. 97A-97B are shown as two panels. The panel in FIG. 97A represents normal tissue from left to right as follows: brain cerebellum (1), pancreas (2), fetal liver (3), placenta (4), adrenal gland (5), kidney (6), small intestine (7), colon (8), prostate (9), lung (10), uterus (11), bladder (12), bone marrow (13), tonsil (14), spleen (15), thymus (16), blood (17), fetal brain (18), salivary gland (19), testes (20), heart (21), skeletal muscle (22) and mammary gland (23). The panel in FIG. 97B represents the samples tested from left to right as follows: NK cells (1), neutrophils (2), CD4+ cells (3), CD8+ cells (4), CD34+ cells (5), normal B cells (6), monocytes (7), dendritic cells (8), multiple myeloma cells (9-11), memory B cells (12), naive B cells (13), centrocytes (14), centroblasts (15-16), centrocytes (17), memory B cells (18), naive B cells (19), normal B cells (20-38), multiple myeloma cells (39), CD138+ cells (40), multiple myeloma cells (41-46), tonsil plasma cells (47), bone marrow plasma cells (48), multiple myeloma cells (49-60), centrocytes (61), plasma bone marrow cells (62-70), plasma cell CD19+ (71), plasma cell CD19− (72), multiple myeloma cells (73-75).

Figure 98A:
FIGS. 98A-98B show microarray data showing the expression of TAHO33 in normal samples and in diseased samples, such as significant expression in in multiple myeloma.
Figure 98B:
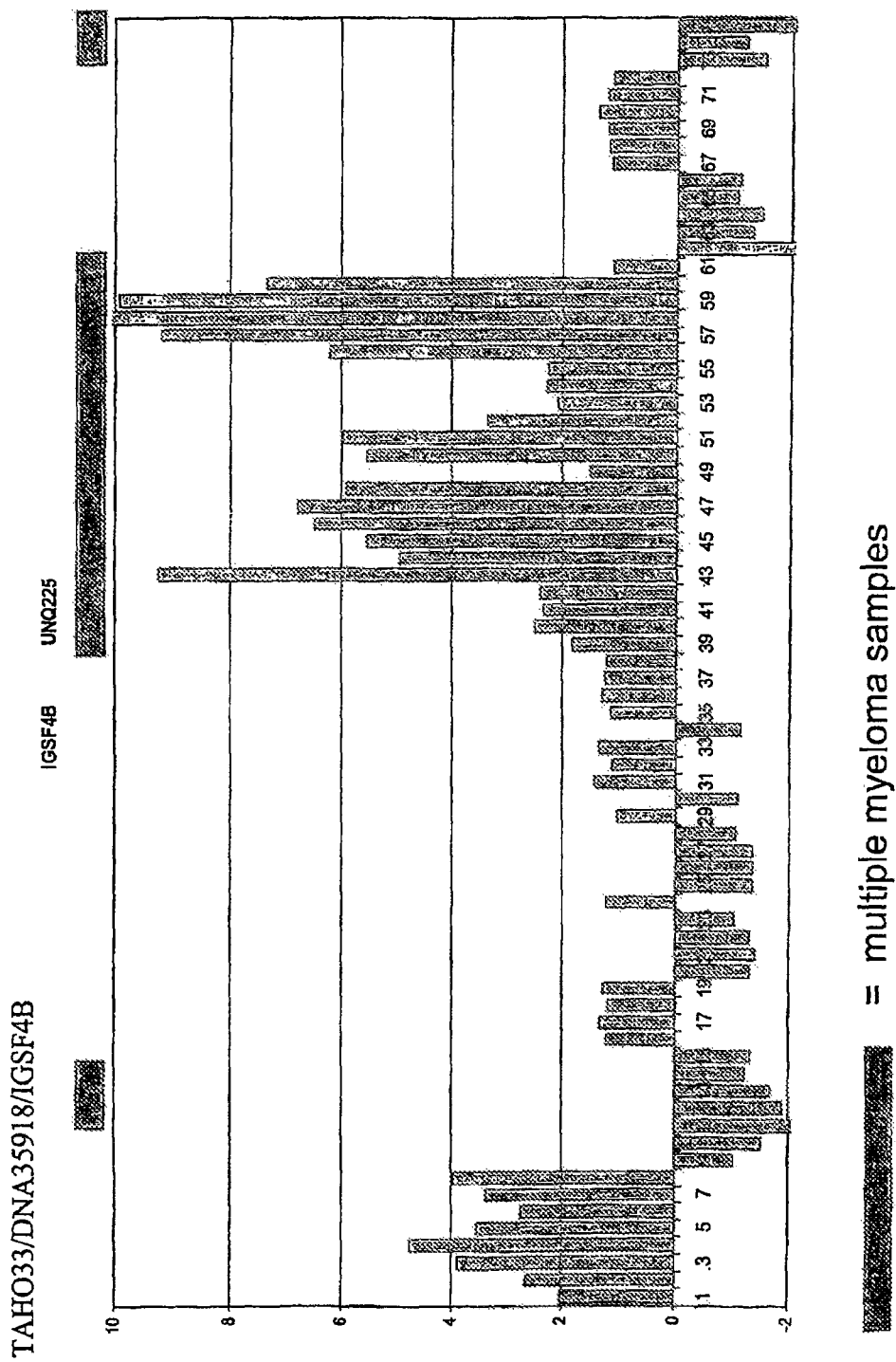

(26) TAHO33 (also referred herein as IGSF4B) was significantly expressed in multiple myeloma cells (FIGS. 98A-98D). FIGS. 98A-98B are shown as two panels. The panel in FIG. 98A represents normal tissue from left to right as follows: brain cerebellum (1), pancreas (2), fetal liver (3), placenta (4), adrenal gland (5), kidney (6), small intestine (7), colon (8), prostate (9), lung (10), uterus (11), bladder (12), bone marrow (13), tonsil (14), spleen (15), thymus (16), blood (17), fetal brain (18), salivary gland (19), testes (20), heart (21), skeletal muscle (22) and mammary gland (23). The panel in FIG. 98B represents the samples tested from left to right as follows: NK cells (1), neutrophils (2), CD4+ cells (3), CD8+ cells (4), CD34+ cells (5), normal B cells (6), monocytes (7), dendritic cells (8), multiple myeloma cells (9-11), memory B cells (12), naive B cells (13), centrocytes (14), centroblasts (15-16), centrocytes (17), memory B cells (18), naive B cells (19), normal B cells (20-38), multiple myeloma cells (39), CD138+ cells (40), multiple myeloma cells (41-46), tonsil plasma cells (47), bone marrow plasma cells (48), multiple myeloma cells (49-60), centrocytes (61), plasma bone marrow cells (62-70), plasma cell CD19+ (71), plasma cell CD19− (72), multiple myeloma cells (73-75).

Figure 99A:
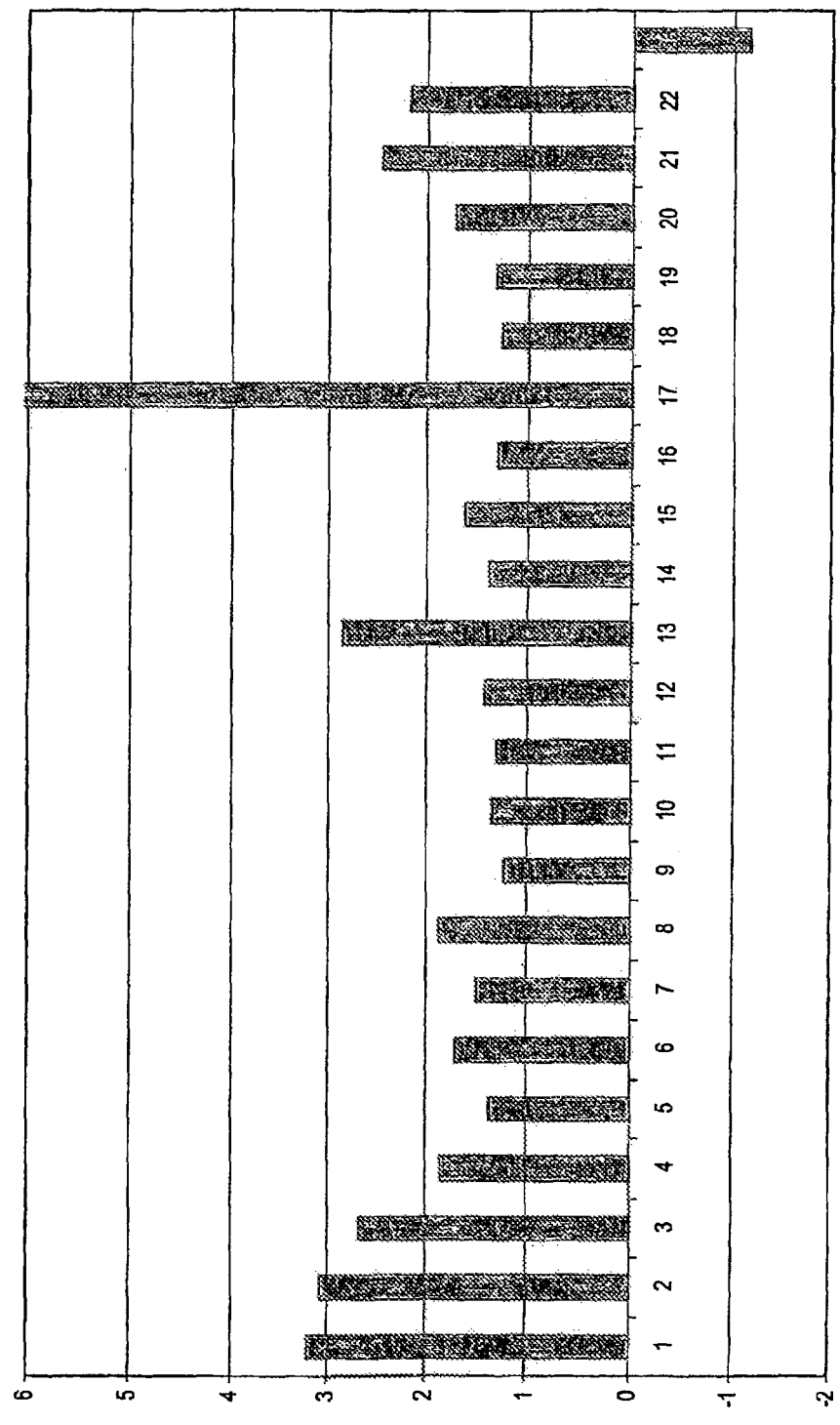
FIGS. 99A-99B show microarray data showing the expression of TAHO34 in normal samples and in diseased samples, such as significant expression in in multiple myeloma, normal plasma cells and normal blood.
Figure 99B:
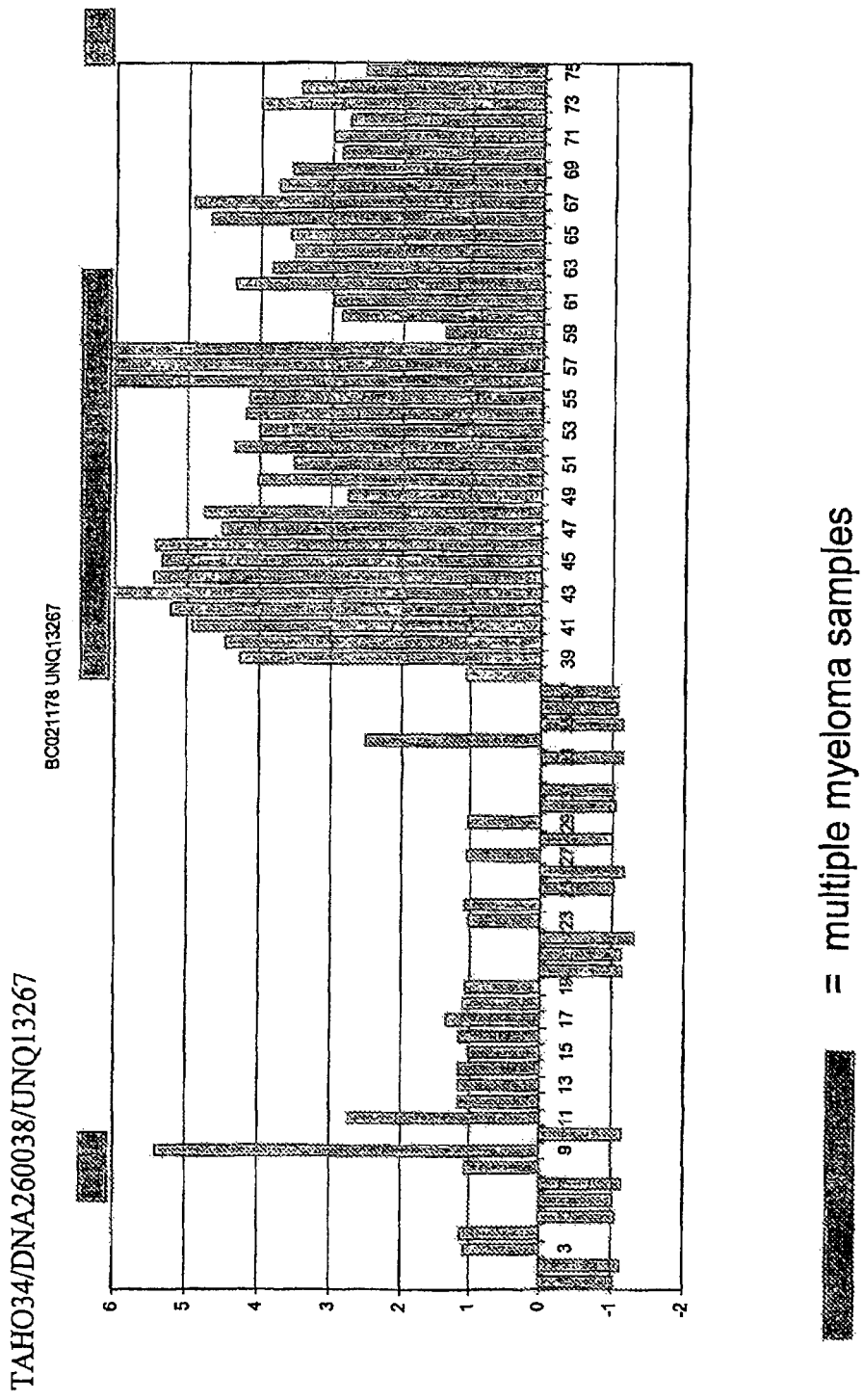

(27) TAHO34 (also referred herein as UNQ13267) was significantly expressed in normal plasma cells, and more significantly expressed on multiple myeloma cells (FIGS. 99A-99D), TAHO34 was also significantly expressed in normal blood. FIGS. 99A-99B are shown as two panels. The panel in FIG. 99A represents normal tissue from left to right as follows: brain cerebellum (1), pancreas (2), fetal liver (3), placenta (4), adrenal gland (5), kidney (6), small intestine (7), colon (8), prostate (9), lung (10), uterus (11), bladder (12), bone marrow (13), tonsil (14), spleen (15), thymus (16), blood (17), fetal brain (18), salivary gland (19), testes (20), heart (21), skeletal muscle (22) and mammary gland (23). The panel in FIG. 99B represents the samples tested from left to right as follows: NK cells (1), neutrophils (2), CD4+ cells (3), CD8+ cells (4), CD34+ cells (5), normal B cells (6), monocytes (7), dendritic cells (8), multiple myeloma cells (9-11), memory B cells (12), naive B cells (13), centrocytes (14), centroblasts (15-16), centrocytes (17), memory B cells (18), naive B cells (19), normal B cells (20-38), multiple myeloma cells (39), CD138+ cells (40), multiple myeloma cells (41-46), tonsil plasma cells (47), bone marrow plasma cells (48), multiple myeloma cells (49-60), centrocytes (61), plasma bone marrow cells (62-70), plasma cell CD19+ (71), plasma cell CD19− (72), multiple myeloma cells (73-75).

Figure 100A:
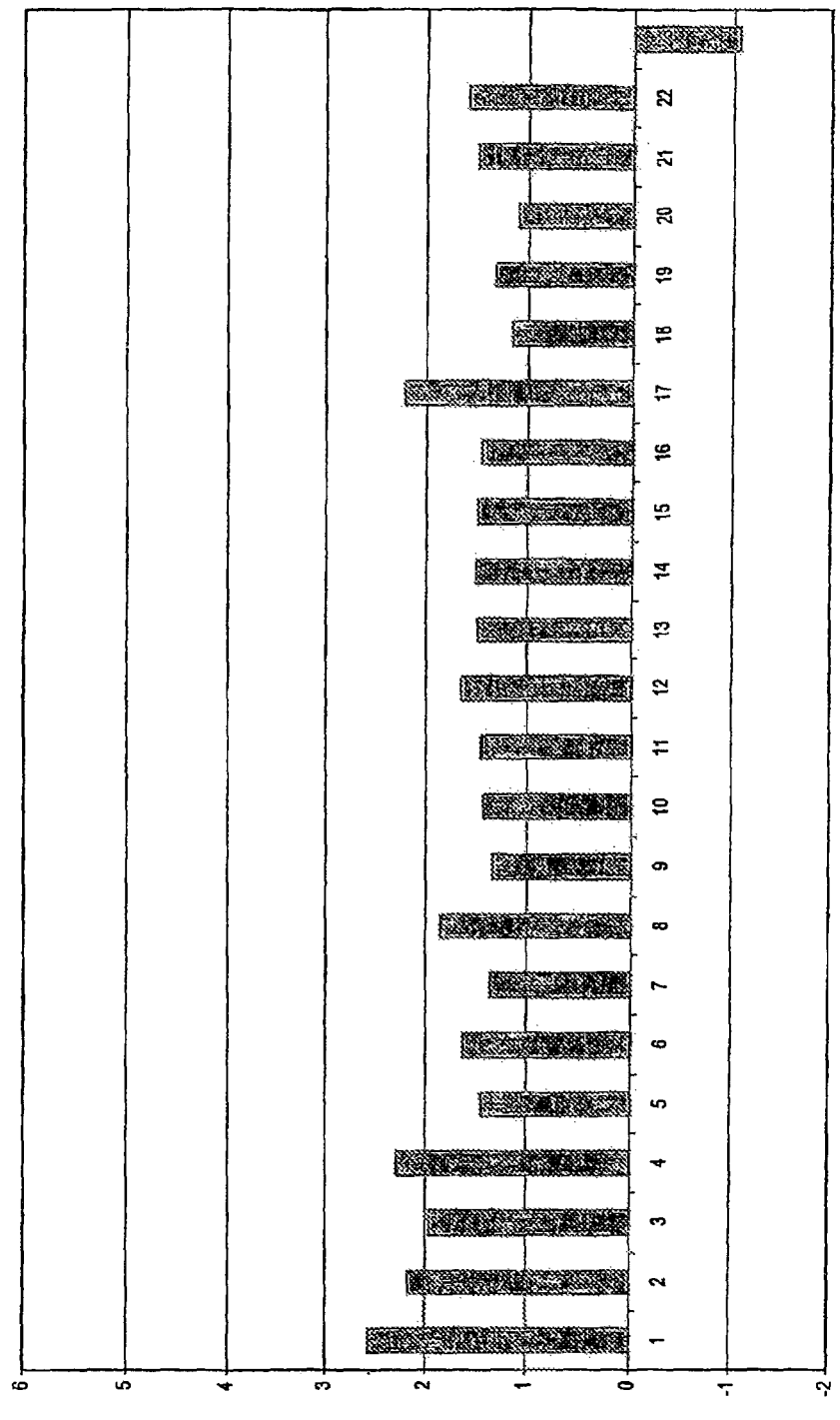
FIGS. 100A-100B show microarray data showing the expression of TAHO35 in normal samples and in diseased samples, such as significant expression in in multiple myeloma.
Figure 100B:
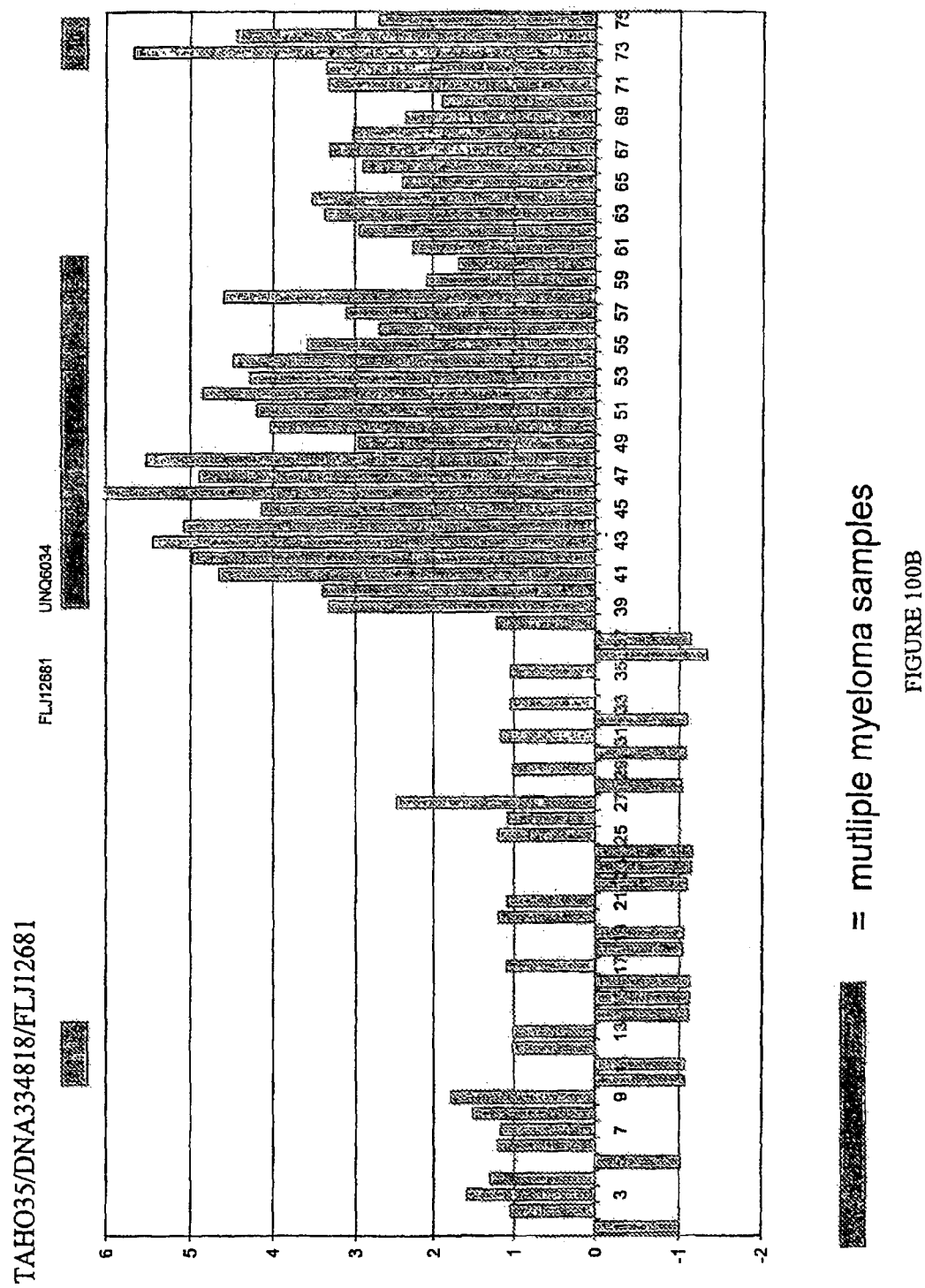

(28) TAHO35 (also referred herein as FLJ12681) was significantly expressed in normal plasma cells, and more significantly expressed on multiple myeloma cells (FIGS. 100A-100B). FIGS. 100A-00B are shown as two panels. The panel in FIG. 100A represents normal tissue from left to right as follows: brain cerebellum (1), pancreas (2), fetal liver (3), placenta (4), adrenal gland (5), kidney (6), small intestine (7), colon (8), prostate (9), lung (10), uterus (11), bladder (12), bone marrow (13), tonsil (14), spleen (15), thymus (16), blood (17), fetal brain (18), salivary gland (19), testes (20), heart (21), skeletal muscle (22) and mammary gland (23). The panel in FIG. 100B represents the samples tested from left to right as follows: NK cells (1), neutrophils (2), CD4+ cells (3), CD8+ cells (4), CD34+ cells (5), normal B cells (6), monocytes (7), dendritic cells (8), multiple myeloma cells (9-11), memory B cells (12), naive B cells (13), centrocytes (14), centroblasts (15-16), centrocytes (17), memory B cells (18), naive B cells (19), normal B cells (20-38), multiple myeloma cells (39), CD138+ cells (40), multiple myeloma cells (41-46), tonsil plasma cells (47), bone marrow plasma cells (48), multiple myeloma cells (49-60), centrocytes (61), plasma bone marrow cells (62-70), plasma cell CD19+ (71), plasma cell CD19− (72), multiple myeloma cells (73-75).

Figure 101A:
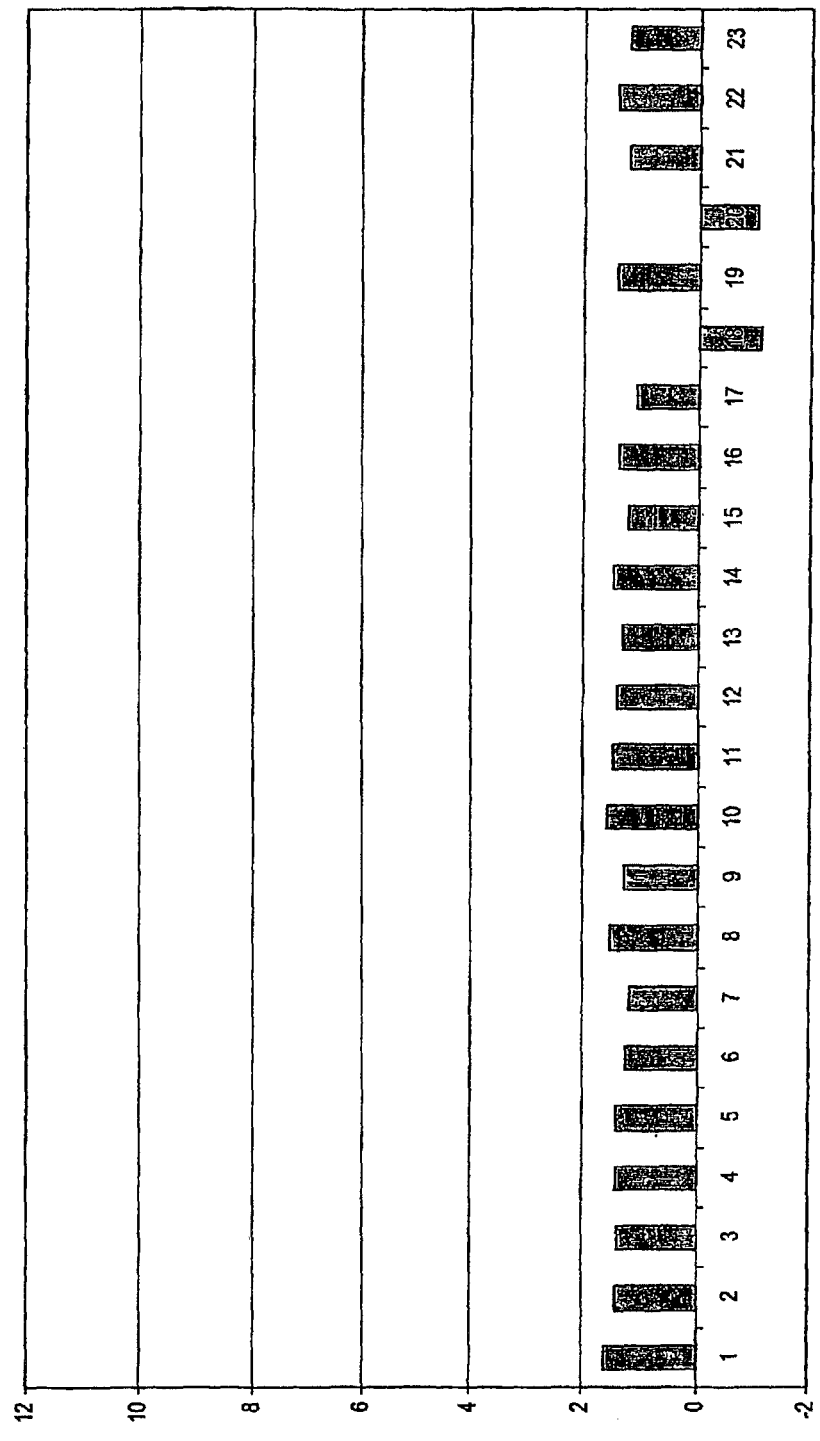
FIGS. 101A-101B are shown as two panels. The panel in FIG. 101A represents normal tissue from left to right as follows: brain cerebellum (1), pancreas (2), fetal liver (3), placenta (4), adrenal gland (5), kidney (6), small intestine (7), colon (8), prostate (9), lung (10), uterus (11), bladder (12), bone marrow (13), tonsil (14), spleen (15), thymus (16), blood (17), fetal brain (18), salivary gland (19), testes (20), heart (21), skeletal muscle (22) and mammary gland (23). The panel in FIG. 101B represents the samples tested from left to right as follows: NK cells (1), neutrophils (2), CD4+ cells (3), CD8+ cells (4), CD34+ cells (5), normal B cells (6), monocytes (7), dendritic cells (8), multiple myeloma cells (9-11), memory B cells (12), naive B cells (13), centrocytes (14), centroblasts (15-16), centrocytes (17), memory B cells (18), naive B cells (19), normal B cells (20-38), multiple myeloma cells (39), CD138+ cells (40), multiple myeloma cells (41-46), tonsil plasma cells (47), bone marrow plasma cells (48), multiple myeloma cells (49-60), centrocytes (61), plasma bone marrow cells (62-70), plasma cell CD19+ (71), plasma cell CD19- (72), multiple myeloma cells (73-75).
Figure 101B:
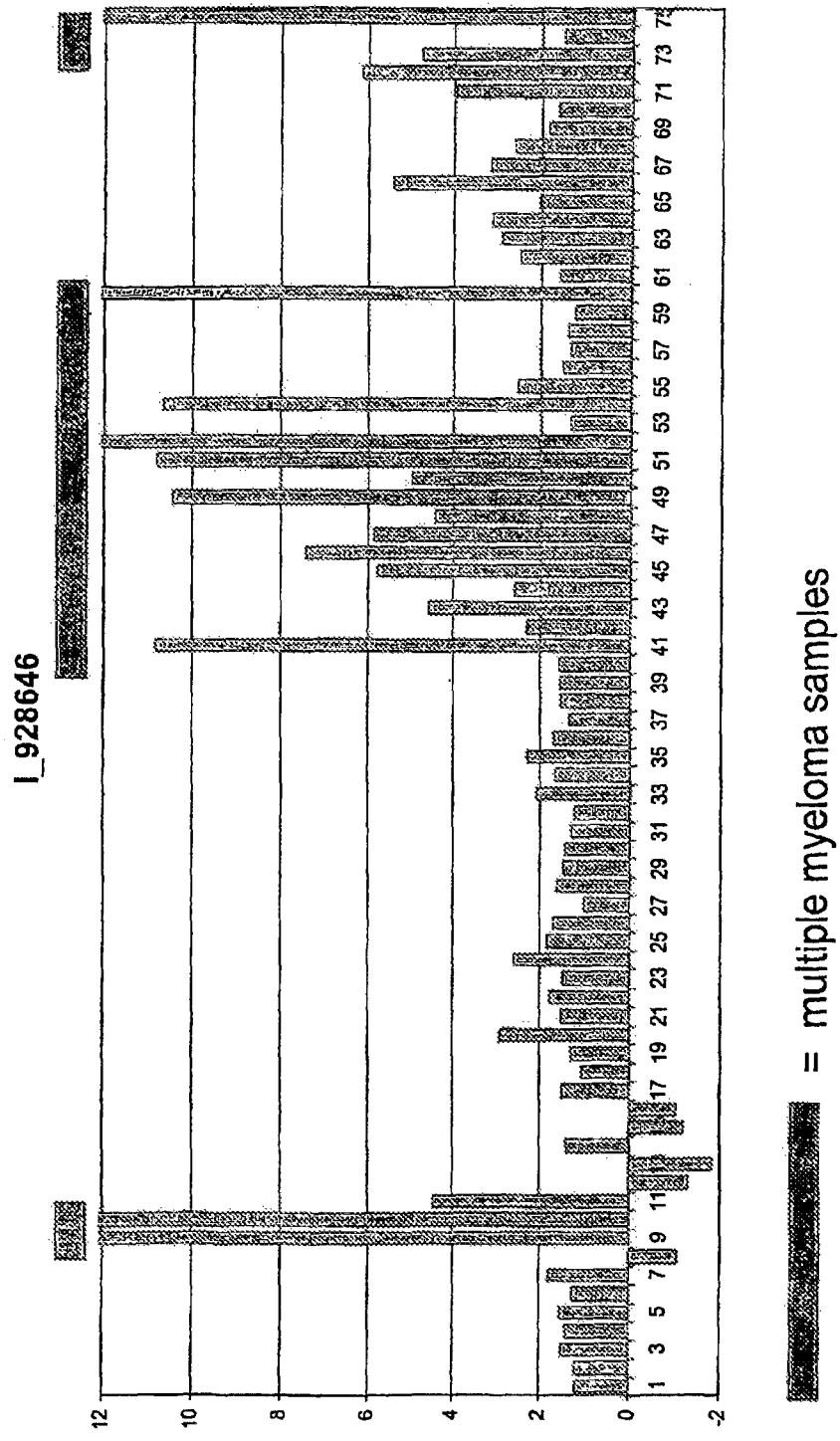

(29) TAHO36 (also referred herein as UNQ12376) was significantly expressed in normal plasma cells, and more significantly expressed on multiple myeloma cells (FIGS. 101A-101B). FIGS. 101A-101B are shown as two panels. The panel in FIG. 101A represents normal tissue from left to right as follows: brain cerebellum (1), pancreas (2), fetal liver (3), placenta (4), adrenal gland (5), kidney (6), small intestine (7), colon (8), prostate (9), lung (10), uterus (1), bladder (12), bone marrow (13), tonsil (14), spleen (15), thymus (16), blood (17), fetal brain (18), salivary gland (19), testes (20), heart (21), skeletal muscle (22) and mammary gland (23). The panel in FIG. 101B represents the samples tested from left to right as follows: NK cells (1), neutrophils (2), CD4+ cells (3), CD8+ cells (4), CD34+ cells (5), normal B cells (6), monocytes (7), dendritic cells (8), multiple myeloma cells (9-11), memory B cells (12), naive B cells (13), centrocytes (14), centroblasts (15-16), centrocytes (17), memory B cells (18), naive B cells (19), normal B cells (20-38), multiple myeloma cells (39), CD138+ cells (40), multiple myeloma cells (41-46), tonsil plasma cells (47), bone marrow plasma cells (48), multiple myeloma cells (49-60), centrocytes (61), plasma bone marrow cells (62-70), plasma cell CD19+ (71), plasma cell CD19− (72), multiple myeloma cells (73-75).

As TAHO1-36 have been identified as being significantly expressed in B cells and in samples from B-cell associated diseases, such as Non-Hodgkin's lymphoma, follicular lymphoma and multiple myeloma as compared to non-B cells as detected by microarray analysis, the molecules are excellent targets for therapy of tumors in mammals, including B-cell associated cancers, such as lymphomas, leukemias, myelomas and other cancers of hematopoietic cells.

Example 2

Quantitative Analysis of TAHO mRNA Expression

In this assay, a 5' nuclease assay (for example, TaqMan®) and real-time quantitative PCR (for example, Mx3000P™ Real-Time PCR System (Stratagene, La Jolla, Calif.)), were used to find genes that are significantly overexpressed in a specific tissue type, such as B cells, as compared to a different cell type, such as other primary white blood cell types, and which further may be overexpressed in cancerous cells of the specific tissue type as compared to non-cancerous cells of the specific tissue type. The 5' nuclease assay reaction is a fluorescent PCR-based technique which makes use of the 5' exonuclease activity of Taq DNA polymerase enzyme to monitor gene expression in real time. Two oligonucleotide primers (whose sequences are based upon the gene or EST sequence of interest) are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the PCR amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

The 5' nuclease procedure is run on a real-time quantitative PCR device such as the Mx3000™ Real-Time PCR System. The system consists of a thermocycler, a quartz-tungsten lamp, a photomultiplier tube (PMT) for detection and a computer. The system amplifies samples in a 96-well format on a thermocycler. During amplification, laser-induced fluorescent signal is collected in real-time through fiber optics cables for all 96 wells, and detected at the PMT. The system includes software for running the instrument and for analyzing the data. The starting material for the screen was mRNA (50 ng/well run in duplicate) isolated from a variety of different white blood cell types (Neturophil (Neutr), Natural Killer cells (NK), Dendritic cells (Dend.), Monocytes (Mono), T cells (CD4+ and CD8+ subsets), stem cells (CD34+) as well as 20 separate B cell donors (donor Ids 310, 330, 357, 362, 597, 635, 816, 1012, 1013, 1020, 1072, 1074, 1075, 1076, 1077, 1086, 1096, 1098, 1109, 1112) to test for donor variability. All RNA was purchased commercially (AllCells, LLC, Berkeley, Calif.) and the concentration of each was measured precisely upon receipt. The mRNA is quantitated precisely, e.g., fluorometrically.

5' nuclease assay data are initially expressed as Ct, or the threshold cycle. This is defined as the cycle at which the reporter signal accumulates above the background level of fluorescence. The ΔCt values are used as quantitative measurement of the relative number of starting copies of a particular target sequence in a nucleic acid sample. As one Ct unit corresponds to 1 PCR cycle or approximately a 2-fold relative increase relative to normal, two units corresponds to a 4-fold relative increase, 3 units corresponds to an 8-fold relative increase and so on, one can quantitatively measure the relative fold increase in mRNA expression between two or more different tissues. The lower the Ct value in a sample, the higher the starting copy number of that particular gene. If a standard curve is included in the assay, the relative amount of each target can be extrapolated and facilitates viewing of the data as higher copy numbers also have relative quantities (as opposed to higher copy numbers have lower Ct values) and also corrects for any variation of the generalized 1 Ct equals a 2 fold increase rule. Using this technique, the molecules listed below have been identified as being significantly overexpressed (i.e., at least 2 fold) in a single (or limited number) of specific tissue or cell types as compared to a different tissue or cell type (from both the same and different tissue donors) with some also being identified as being significantly overexpressed (i.e., at least 2 fold) in cancerous cells when compared to normal cells of the particular tissue or cell type, and thus, represent excellent polypeptide targets for therapy of cancer in mammals.

| Molecule | specific expression in: | as compared to: |
| --- | --- | --- |
| DNA105250 (TAHO1) | B cells | non-B cells |
| DNA150004 (TAHO2) | B cells | non-B cells |
| DNA182432 (TAHO3) | B cells | non-B cells |
| DNA225785 (TAHO4) | B cells | non-B cells |
| DNA225786 (TAHO5) | B cells/CD34+ cells | non-B cells |
| DNA225875 (TAHO6) | B cells | non-B cells |
| DNA226239 (TAHO8) | B cells | non-B cells |
| DNA226394 (TAHO9) | B cells | non-B cells |
| DNA226423 (TAHO10) | B cells | non-B cells |
| DNA227781 (TAHO11) | B cells | non-B cells |
| DNA227879 (TAHO12) | B cells | non-B cells |
| DNA260953 (TAHO13) | B cells | non-B cells |
| DNA335924 (TAHO16) | B cells | non-B cells |
| DNA340394 (TAHO17) | B cells | non-B cells |
| DNA225820 (TAHO25) | B cells | non-B cells |
| DNA88116 (TAHO26) | B cells | non-B cells |

Summary

TAHO1-TAHO6, TAHO8-TAHO13, TAHO16-TAHO17 and TAHO25-TAHO26 expression levels in total RNA isolated from purified B cells or from B cells from 20 B cell donors (310-1112) (AlllCells) and averaged (Avg. B) was significantly higher than respective TAHO1-TAHO6, TAHO8-TAHO13, TAHO16-17 and TAHO25-TAHO26 expression levels in total RNA isolated from several white blood cell types, neutrophils (Neutr), natural killer cells (NK) (a T cell subset), dendritic cells (Dend), monocytes (Mono), CD4+ T cells, CD8+ T cells, CD34+ stem cells (data not shown).

Accordingly, as TAHO1-TAHO6, TAHO8-TAHO13, TAHO16-TAHO17 and TAHO25-TAHO26 are significantly expressed on B cells as compared to non-B cells as detected by TaqMan analysis, the molecules are excellent targets for therapy of tumors in mammals, including B-cell associated cancers, such as lymphomas (i.e. Non-Hodgkin's Lyphoma), leukemias (i.e. chronic lymphocytic leukemia), myelomas (i.e. multiple myeloma) and other cancers of hematopoietic cells.

Example 3

In Situ Hybridization

In situ hybridization is a powerful and versatile technique for the detection and localization of nucleic acid sequences within cell or tissue preparations. It may be useful, for example, to identify sites of gene expression, analyze the tissue distribution of transcription, identify and localize viral infection, follow changes in specific mRNA synthesis and aid in chromosome mapping.

In situ hybridization was performed following an optimized version of the protocol by Lu and Gillett, *Cell Vision* 1:169-176 (1994), using PCR-generated $^{33}$P-labeled riboprobes. Briefly, formalin-fixed, paraffin-embedded human tissues were sectioned, deparaffinized, deproteinated in proteinase K (20 g/ml) for 15 minutes at 37° C., and further processed for in situ hybridization as described by Lu and Gillett, supra. A [$^{33}$-P] UTP-labeled antisense riboprobe was generated from a PCR product and hybridized at 55° C. overnight. The slides were dipped in Kodak NTB2 nuclear track emulsion and exposed for 4 weeks.

$^{33}$P-Riboprobe Synthesis 6.0 μl (125 mCi) of $^{33}$P-UTP (Amersham BF 1002, SA<2000 Ci/mmol) were speed vac dried. To each tube containing dried $^{33}$P-UTP, the following ingredients were added:

2.0 μl 5× transcription buffer
1.0 μl DTT (100 mM)
2.0 μl NTP mix (2.5 mM:10μ; each of 10 mM GTP, CTP & ATP+10 μl H$_2$O)

1.0 µl UTP (50 µM)
1.0 µl Rnasin
1.0 µl DNA template (1 µg)
1.0 µl H$_2$O
1.0 µl RNA polymerase (for PCR products T3=AS, T7=S, usually)

The tubes were incubated at 37° C. for one hour. 1.0 µl RQ1 DNase were added, followed by incubation at 37° C. for 15 minutes. 90 µl TE (10 mM Tris pH 7.6/1 mM EDTA pH 8.0) were added, and the mixture was pipetted onto DE81 paper. The remaining solution was loaded in a Microcon-50 ultra-filtration unit, and spun using program 10 (6 minutes). The filtration unit was inverted over a second tube and spun using program 2 (3 minutes). After the final recovery spin, 100 µl TE were added. 1 µl of the final product was pipetted on DE81 paper and counted in 6 ml of Biofluor II.

The probe was run on a TBE/urea gel. 1-3 µl of the probe or 5 µl of RNA Mrk III were added to 3 µl of loading buffer. After heating on a 95° C. heat block for three minutes, the probe was immediately placed on ice. The wells of gel were flushed, the sample loaded, and run at 180-250 volts for 45 minutes. The gel was wrapped in saran wrap and exposed to XAR film with an intensifying screen in −70° C. freezer one hour to overnight.

$^{33}$P-Hybridization

A. Pretreatment of Frozen Sections

The slides were removed from the freezer, placed on aluminium trays and thawed at room temperature for 5 minutes. The trays were placed in 55° C. incubator for five minutes to reduce condensation. The slides were fixed for 10 minutes in 4% paraformaldehyde on ice in the fume hood, and washed in 0.5×SSC for 5 minutes, at room temperature (25 ml 20×SSC+ 975 ml SQ H$_2$O). After deproteination in 0.5 µg/ml proteinase K for 10 minutes at 37° C. (12.5 µl of 10 mg/ml stock in 250 ml prewarmed RNase-free RNAse buffer), the sections were washed in 0.5×SSC for 10 minutes at room temperature. The sections were dehydrated in 70%, 95%, 100% ethanol, 2 minutes each.

B. Pretreatment of Paraffin-Embedded Sections

The slides were deparaffinized, placed in SQ H$_2$O, and rinsed twice in 2×SSC at room temperature, for minutes each time. The sections were deproteinated in 20 µg/ml proteinase K (500 µl of 10 mg/ml in 250 ml RNase-free RNase buffer; 37° C., 15 minutes)—human embryo, or 8× proteinase K (100 µl in 250 ml Rnase buffer, 37° C., 30 minutes)—formalin tissues. Subsequent rinsing in 0.5×SSC and dehydration were performed as described above.

C. Prehybridization

The slides were laid out in a plastic box lined with Box buffer (4×SSC, 50% formamide)—saturated filter paper.

D. Hybridization 1.0×10$^6$ cpm probe and 1.0 µl tRNA (50 mg/ml stock) per slide were heated at 95° C. for 3 minutes. The slides were cooled on ice, and 48 µl hybridization buffer were added per slide. After vortexing, 50 µl $^{33}$P mix were added to 50 µl prehybridization on slide. The slides were incubated overnight at 55° C.

E. Washes

Washing was done 2×10 minutes with 2×SSC, EDTA at room temperature (400 ml 20×SSC+16 ml 0.25M EDTA, V$_f$=4 L), followed by RNaseA treatment at 37° C. for 30 minutes (500 µl of 10 mg/ml in 250 ml Rnase buffer=20 µg/ml). The slides were washed 2×10 minutes with 2×SSC, EDTA at room temperature. The stringency wash conditions were as follows: 2 hours at 55° C., 0.1×SSC, EDTA (20 ml 20×SSC+16 ml EDTA, V$_f$=4 L).

F. Oligonucleotides

In situ analysis was performed on a variety of DNA sequences disclosed herein. The oligonucleotides employed for these analyses were obtained so as to be complementary to the nucleic acids (or the complements thereof) as shown in the accompanying figures.

(1) DNA225785 (TAHO4)
p1  5'-GGGCACCAAGAACCGAATCAT-3'  (SEQ ID NO: 72)

p2  5'-CCTAGAGGCAGCGATTAAGGG-3'  (SEQ ID NO: 73)

(2) DNA257955 (TAHO20)
p1  5'-TCAGCACGTGGATTCGAGTCA-3'  (SEQ ID NO: 74)

p2  5'-GTGAGGACGGGGCGAGAC-3'  (SEQ ID NO: 75)

G. Results

In situ analysis was performed on a variety of DNA sequences disclosed herein. The results from these analyses are as follows.

(1) DNA225785 (TAHO4)

Expression was observed in lymphoid cells. Specifically, in normal tissues, expression was observed in spleen and lymph nodes and coincides with B cell areas, such as germinal centers, mantle, and marginal zones. Significant expression was also observed in tissue sections of a variety of malignant lymphomas, including Hodgkin's lymphoma, follicular lymphoma, diffuse large cell lymphoma, small lymphocytic lymphoma and non-Hodgkin's lymphoma. This data is consistent with the potential role of this molecule in hematopoietic tumors, specifically B-cell tumors.

(2) DNA257955 (TAHO20)

Expression was observed in benign and neoplastic lymphoid cells. Specifically, in normal tissues, expression was observed in B cell areas, such as germinal centers, mantle and marginal zones, and in white pulp tissue of the spleen. This data is consistent with the potential role of this molecule in hematopoietic tumors, specifically B-cell tumors.

Example 4

Use of TAHO as a Hybridization Probe

The following method describes use of a nucleotide sequence encoding TAHO as a hybridization probe for, i.e., detection of the presence of TAHO in a mammal.

DNA comprising the coding sequence of full-length or mature TAHO as disclosed herein can also be employed as a probe to screen for homologous DNAs (such as those encoding naturally-occurring variants of TAHO) in human tissue cDNA libraries or human tissue genomic libraries.

Hybridization and washing of filters containing either library DNAs is performed under the following high stringency conditions. Hybridization of radiolabeled TAHO-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence TAHO can then be identified using standard techniques known in the art.

Example 5

Expression of TAHO in *E. coli*

This example illustrates preparation of an unglycosylated form of TAHO by recombinant expression in *E. coli*.

The DNA sequence encoding TAHO is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the TAHO coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized TAHO protein can then be purified using a metal chelating column under conditions that allow tight binding of the protein.

TAHO may be expressed in *E. coli* in a poly-His tagged form, using the following procedure. The DNA encoding TAHO is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA(tonA) lon galE rpoHts(htpRts) clpP(lacIq). Transformants are first grown in LB containing 50 mg/ml carbenicillin at 30° C. with shaking until an O.D. 600 of 3-5 is reached. Cultures are then diluted 50-100 fold into CRAP media (prepared by mixing 3.57 g $(NH_4)_2SO_4$, 0.71 g sodium citrate.$2H_2O$, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

*E. coli* paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1 M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded TAHO polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Certain of the TAHO polypeptides disclosed herein have been successfully expressed and purified using this technique(s).

Example 6

Expression of TAHO in Mammalian Cells

This example illustrates preparation of a potentially glycosylated form of TAHO by recombinant expression in mammalian cells.

The vector, pRK5 (see EP 307,247, published Mar. 15, 1989), is employed as the expression vector. Optionally, the TAHO DNA is ligated into pRK5 with selected restriction enzymes to allow insertion of the TAHO DNA using ligation methods such as described in Sambrook et al., supra. The resulting vector is called pRK5-TAHO.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-TAHO DNA is mixed with about 1 μg DNA encoding the VA RNA gene [Thimmappaya et al., *Cell*, 31:543 (1982)] and dissolved in 500 μl of 1 mM Tris-HCl, 0.1 mM EDTA, 0.227 M CaCl$_2$. To this mixture is added, dropwise, 500 μl of 50 mM HEPES (pH 7.35), 280 mM NaCl, 1.5 mM NaPO$_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of TAHO polypeptide. The cultures containing transfected cells may undergo further incubation (in serum free medium) and the medium is tested in selected bioassays.

In an alternative technique, TAHO may be introduced into 293 cells transiently using the dextran sulfate method described by Somparyrac et al., *Proc. Natl. Acad. Sci.*, 12:7575 (1981). 293 cells are grown to maximal density in a spinner flask and 700 μg pRK5-TAHO DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed TAHO can then be concentrated and purified by any selected method, such as dialysis and/or column chromatography.

In another embodiment, TAHO can be expressed in CHO cells. The pRK5-TAHO can be transfected into CHO cells using known reagents such as CaPO$_4$ or DEAE-dextran. As described above, the cell cultures can be incubated, and the medium replaced with culture medium (alone) or medium containing a radiolabel such as $^{35}$S-methionine. After determining the presence of TAHO polypeptide, the culture medium may be replaced with serum free medium. Preferably, the cultures are incubated for about 6 days, and then the conditioned medium is harvested. The medium containing the expressed TAHO can then be concentrated and purified by any selected method.

Epitope-tagged TAHO may also be expressed in host CHO cells. The TAHO may be subcloned out of the pRK5 vector. The subclone insert can undergo PCR to fuse in frame with a selected epitope tag such as a poly-his tag into a Baculovirus expression vector. The poly-his tagged TAHO insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged TAHO can then be concentrated and purified by any selected method, such as by Ni$^{2+}$-chelate affinity chromatography.

TAHO may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Quiagen), Dosper® or Fugene® (Boehringer Mannheim). The cells are grown as described in Lucas et al., supra. Approximately 3×10' cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 μm filtered PS20 with 5% 0.2 μm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with 3×10$^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at 1.2×10$^6$ cells/mL. On day 0, the cell number pH ie determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 μm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 µL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Certain of the TAHO polypeptides disclosed herein have been successfully expressed and purified using this technique(s).

Example 7

Expression of TAHO in Yeast

The following method describes recombinant expression of TAHO in yeast.

First, yeast expression vectors are constructed for intracellular production or secretion of TAHO from the ADH2/GAPDH promoter. DNA encoding TAHO and the promoter is inserted into suitable restriction enzyme sites in the selected plasmid to direct intracellular expression of TAHO. For secretion, DNA encoding TAHO can be cloned into the selected plasmid, together with DNA encoding the ADH2/GAPDH promoter, a native TAHO signal peptide or other mammalian signal peptide, or, for example, a yeast alpha-factor or invertase secretory signal/leader sequence, and linker sequences (if needed) for expression of TAHO.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant TAHO can subsequently be isolated and purified by removing the yeast cells from the fermentation medium by centrifugation and then concentrating the medium using selected cartridge filters. The concentrate containing TAHO may further be purified using selected column chromatography resins.

Certain of the TAHO polypeptides disclosed herein have been successfully expressed and purified using this technique(s).

Example 8

Expression of TAHO in Baculovirus-Infected Insect Cells

The following method describes recombinant expression of TAHO in Baculovirus-infected insect cells.

The sequence coding for TAHO is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids-such as pVL1393 (Novagen). Briefly, the sequence encoding TAHO or the desired portion of the coding sequence of TAHO such as the sequence encoding an extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged TAHO can then be purified, for example, by $Ni^{2+}$-chelate affinity chromatography as follows. Extracts are prepared from recombinant virus-infected Sf9 cells as described by Rupert et al., *Nature*, 362:175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 µm filter. A $Ni^{2+}$-NTA agarose column (commercially available from Qiagen) is prepared with a bed volume of 5 mL, washed with mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged TAHO are pooled and dialyzed against loading buffer.

Alternatively, purification of the IgG tagged (or Fc tagged) TAHO can be performed using known chromatography techniques, including for instance, Protein A or protein G column chromatography.

Certain of the TAHO polypeptides disclosed herein have been successfully expressed and purified using this technique(s).

Example 9

Preparation of Antibodies that Bind TAHO

This example illustrates preparation of monoclonal antibodies which can specifically bind TAHO.

Techniques for producing the monoclonal antibodies are known in the art and are described, for instance, in Goding, supra. Immunogens that may be employed include purified TAHO, fusion proteins containing TAHO, and cells expressing recombinant TAHO on the cell surface. Selection of the immunogen can be made by the skilled artisan without undue experimentation.

Mice, such as Balb/c, are immunized with the TAHO immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-TAHO antibodies.

After a suitable antibody titer has been detected, the animals "positive" for antibodies can be injected with a final intravenous injection of immunogen. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against immunogen. Determination of "positive" hybridoma cells secreting the desired monoclonal antibodies against immunogen is within the skill in the art.

The positive hybridoma cells can be injected intraperitoneally into syngeneic Balb/c mice to produce ascites containing the anti-immunogen monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Antibodies directed against certain of the TAHO polypeptides disclosed herein can be successfully produced using this technique(s). More specifically, functional monoclonal antibodies that are capable of recognizing and binding to TAHO protein (as measured by standard ELISA, FACS sorting analysis and/or immunohistochemistry analysis) can be successfully generated against the following TAHO proteins as disclosed herein: TAHO1 (DNA105250), TAHO2 (DNA150004), TAHO3 (DNA182432), TAHO4 (DNA225785), TAHO5 (DNA225786), TAHO6 (DNA225875), TAHO7 (DNA226179), TAHO8 (DNA226239), TAHO9 (DNA226239), TAHO10 (DNA226423), TAHO11 (DNA227781), TAHO12 (DNA227879), TAHO13 (DNA256363), TAHO14 (DNA332467), TAHO15 (DNA58721), TAHO16 (DNA335924), TAHO17 (DNA340394), TAHO18 (DNA56041), TAHO19 (DNA59607), TAHO20 (DNA257955), TAHO21 (DNA329863), TAHO22 (DNA346528), TAHO23 (DNA212930) and TAHO24 (DNA335918), TAHO 25 (DNA225820), TAHO26 (DNA88116), and TAHO27 (DNA227752), TAHO28 (DNA119476), TAHO29 (DNA254890), TAHO30 (DNA219240), TAHO31 (DNA37151), TAHO32 (DNA210233), TAHO33 (DNA35918), TAHO34 (DNA260038), TAHO35 (DNA334818) and TAHO36 (DNA257501).

In addition to the preparation of monoclonal antibodies directed against the TAHO polypeptides as described herein, many of the monoclonal antibodies can be successfully conjugated to a cell toxin for use in directing the cellular toxin to a cell (or tissue) that expresses a TAHO polypeptide of interested (both in vitro and in vivo). For example, toxin (e.g., DM1) derivitized monoclonal antibodies can be successfully generated to the following TAHO polypeptides as described herein: TAHO1 (DNA105250), TAHO2 (DNA150004), TAHO3 (DNA182432), TAHO4 (DNA225785), TAHO5 (DNA225786), TAHO6 (DNA225875), TAHO7 (DNA226179), TAHO8 (DNA226239), TAHO9 (DNA226239), TAHO10 (DNA226423), TAHO11 (DNA227781), TAHO12 (DNA227879), TAHO13 (DNA256363), TAHO14 (DNA332467), TAHO15 (DNA58721), TAHO16 (DNA335924), TAHO17 (DNA340394), TAHO18 (DNA56041), TAHO19 (DNA59607), TAHO20 (DNA257955), TAHO21 (DNA329863), TAHO22 (DNA346528), TAHO23 (DNA212930) and TAHO24 (DNA335918), TAHO 25 (DNA225820), TAHO26 (DNA88116), TAHO27 (DNA227752), TAHO28 (DNA119476), TAHO29 (DNA254890), TAHO30 (DNA219240), TAHO31 (DNA37151), TAHO32 (DNA210233), TAHO33 (DNA35918), TAHO34 (DNA260038), TAHO35 (DNA334818) and TAHO36 (DNA257501).

Example 10

Purification of TAHO Polypeptides Using Specific Antibodies

Native or recombinant TAHO polypeptides may be purified by a variety of standard techniques in the art of protein purification. For example, pro-TAHO polypeptide, mature TAHO polypeptide, or pre-TAHO polypeptide is purified by immunoaffinity chromatography using antibodies specific for the TAHO polypeptide of interest. In general, an immunoaffinity column is constructed by covalently coupling the anti-TAHO polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of TAHO polypeptide by preparing a fraction from cells containing TAHO polypeptide in a soluble form. This preparation is derived by solubilization of the whole cell or of a subcellular fraction obtained via differential centrifugation by the addition of detergent or by other methods well known in the art. Alternatively, soluble TAHO polypeptide containing a signal sequence may be secreted in useful quantity into the medium in which the cells are grown.

A soluble TAHO polypeptide-containing preparation is passed over the immunoaffinity column, and the column is washed under conditions that allow the preferential absorbance of TAHO polypeptide (e.g., high ionic strength buffers in the presence of detergent). Then, the column is eluted under conditions that disrupt antibody/TAHO polypeptide binding (e.g., a low pH buffer such as approximately pH 2-3, or a high concentration of a chaotrope such as urea or thiocyanate ion), and TAHO polypeptide is collected.

Example 11

In Vitro Tumor Cell Killing Assay

Mammalian cells expressing the TAHO polypeptide of interest may be obtained using standard expression vector and cloning techniques. Alternatively, many tumor cell lines expressing TAHO polypeptides of interest are publicly available, for example, through the ATCC and can be routinely identified using standard ELISA or FACS analysis. Anti-TAHO polypeptide monoclonal antibodies (commercially available and toxin conjugated derivatives thereof) may then be employed in assays to determine the ability of the antibody to kill TAHO polypeptide expressing cells in vitro.

For example, cells expressing the TAHO polypeptide of interest are obtained as described above and plated into 96 well dishes. In one analysis, the antibody/toxin conjugate (or naked antibody) is included throughout the cell incubation for a period of 4 days. In a second independent analysis, the cells are incubated for 1 hour with the antibody/toxin conjugate (or naked antibody) and then washed and incubated in the absence of antibody/toxin conjugate for a period of 4 days. Cell viability is then measured using the CellTiter-Glo Luminescent Cell Viability Assay from Promega (Cat#G7571). Untreated cells serve as a negative control.

B cell lines (ARH-77, BJAB, Daudi, DOHH-2, Su-DHL-4, Raji and Ramos) were prepared at 5000 cells/well in separate sterile round bottom 96 well tissue culture treated plates (Cellstar 650 185). Cells were assay media (RPMI 1460, 1% L-Glutamine, 10% fetal bovine serum (FBS; from Hyclone) and 10 mM HEPES). Cells were immediately placed in a 37° C. incubator overnight. Antibody drug conjugates (using commercially available anti-CD19, anti-CD20, anti-CD21, anti-CD79A, anti-CD79B) were diluted at 2×10 µg/ml in assay medium. Conjugates were linked with crosslinkers SMCC or disulfide linker SPP to DM1 toxin. Further, conjugates may be linked with Vc-PAB to MMAE toxin. Herceptin based conjugates (SMCC-DM1 or SPP-DM1) were used as negative controls. Free L-DM1 equivalent to the conjugate loading dose was used as a positive control. Samples were vortexed to ensure homogeneous mixture prior to dilution. The antibody drug conjugates were further diluted serially 1:3. The cell lines were loaded 50 µl of each sample per row using a Rapidplate® 96/384 Zymark automation system. When the entire plate was loaded, the plates were reincubated for 3 days to permit the toxins to take effect. The reactions were stopped by applying 10 µl/well of Cell Glo (Promega, Cat. #G7571/2/3) to all the wells for 10 minutes. The 100 µl of the stopped well were transferred into 96 well white tissue culture treated plates, clear bottom (Costar 3610) and the luminescence was read and reported as relative light units (RLU). TAHO antibodies for this experiment included commercially available antibodies, including anti-TAHO4/CD79a (Caltag ZL7-4), anti-TAHO5/CD79b (Biomeda SN8), anti-TAHO6/CD21 (ATCC HB5), anti-TAHO26/CD22 (Leinco RFB-4) and anti-TAHO25/CD19 (Biomeda CB-19).

Summary (1) Anti-TAHO26/CD22 antibody conjugated to DM1 toxin (CD22-SPP-DM1 and CD22-SMCC-DM1) showed significant tumor cell killing when compared to anti-TAHO26/CD22 antibody alone or negative control anti-HER2 conjugated to DM1 toxin (anti-HER2-SMCC-DM1) in RAJI or RAMOS cells. Further, greater tumor cell killing was observed with CD22-SPP-DM1 compared to CD22-SMCC-DM1.

(2) Anti-TAHO25/CD19 antibody conjugated to DM1 toxin (CD19-SPP-DM1 and CD19-SMCC-DM1) showed significant tumor cell killing when compared to anti-TAHO25/CD19 antibody alone or negative control anti-HER2 conjugated to DM1 toxin (anti-HER2-SMCC-DM1) in RAJI or RAMOS cells. Further, greater tumor cell killing was observed with CD19-SMCC-DM1 compared to CD19-SPP-DM1.

(3) Anti-TAHO6/CD21 antibody conjugated to DM1 toxin (CD21-SPP-DM1 and CD2-SMCC-DM1) showed weak tumor cell killing when compared to anti-TAHO6/CD21 antibody alone or negative control anti-HER2 conjugated to DM1 toxin (anti-HER2-SMCC-DM1) in RAJI or RAMOS cells. Further, greater tumor cell killing was observed with CD21-SPP-DM1 compared to CD21-SMCC-DM1.

(4) Anti-TAHO4/CD79A antibody conjugated to DM1 toxin (CD79A-SMCC-DM1) showed significant tumor cell killing when compared to anti-TAHO4/CD79A antibody alone or negative control anti-HER2 conjugated to DM1 toxin (anti-HER2-SMCC-DM1) in RAMOS cells.

(5) Anti-TAHO5/CD79B antibody conjugated to DM1 toxin (CD79BSMCC-DM1) showed significant tumor cell killing when compared to anti-TAHO5/CD79B antibody alone or negative control anti-HER2 conjugated to DM1 toxin (anti-HER2-SMCC-DM1) in RAJI or RAMOS cells.

Anti-TAHO polypeptide monoclonal antibodies are useful for reducing in vitro tumor growth of tumors, including B-cell associated cancers, such as lymphomas (i.e. Non-Hodgkin's Lyphoma), leukemias (i.e. chronic lymphocytic leukemia), myelomas (i.e. multiple myeloma) and other cancers of hematopoietic cells.

Example 12

In Vivo Tumor Cell Killing Assay

To test the efficacy of conjugated or unconjugated anti-TAHO polypeptide monoclonal antibodies, the effect of anti-TAHO antibody on tumors in mice were analyzed. Female CB17 ICR SCID mice (6-8 weeks of age from Charles Rivers Laboratories; Hollister, Calif.) were inoculated subcutaneously with $5\times10^6$ RAJI cells or $2\times10^7$ BJAB-luciferase cells. Tumor volume was calculated based on two dimensions, measured using calipers, and was expressed in $mm^3$ according to the formula: $V=0.5a\times b^2$, where a and b are the long and the short diameters of the tumor, respectively. Data collected from each experimental group were expressed as mean±SE. Mice were separated into groups of 8-10 mice with a mean tumor volume between 100-200 $mm^3$, at which point intravenous (i.v.) treatment began at the antibody dose of 5 mg/kg weekly for two to three weeks. Tumors were measured either once or twice a week throughout the experiment. Mice were euthanized before tumor volumes reached 3000 $mm^3$ or when tumors showed signs of impending ulceration. All animal protocols were approved by an Institutional Animal Care and Use Committee (IACUC). Linkers between the antibody and the toxin that were used were SPP, SMCC or cys-MC-vc-PAB (a valine-citrulline (vc) dipeptide linker reagent having a maleimide component and a para-aminobenzylcarbamoyl (PAB) self-immolative component. Toxins used were DM1 or MMAE. TAHO antibodies for this experiment included commercially available antibodies, including anti-TAHO4/CD79a (Caltag ZL7-4), anti-TAHO5/CD79b (Biomeda SN8), anti-TAHO6/CD21 (ATCC HB135) and anti-TAHO25/CD19 (Biomeda CB-19).

Summary (1) Anti-TAHO6/CD21 antibody conjugated with DM1 toxin (anti-CD21-SPP-DM1) showed inhibition of tumor growth in SCID mice with RAJI tumors when treated weekly with 5 mg/kg of antibody compared to anti-CD21 antibodies and herceptin antibodies conjugated to DM1 toxin (anti-Herceptin-SMCC-DM1 and anti-Herceptin-SPP-DM1). Specifically, at day 19, 8 out of 8 mice treated with anti-CD21-SPP-DM1 showed complete regression of tumors. At day 19, 8 out of 8 mice treated with anti-CD21, anti-herceptin-SPP-DM1, anti-herceptin-SMCC-DM1 or anti-CD21-SMCC-DM1 showed tumor incidence. At day 19, 7 out of 8 mice treated with anti-CD20-SMCC-DM1 antibody showed tumor incidence.

(2) Anti-TAHO6/CD21 antibody conjugated with MMAE toxin (anti-CD21-cys-Mc-vc-PAB-MMAE) showed inhibition of tumor growth in SCID mice with RAJI tumors when treated with 5 mg/kg of antibody compared to negative control anti-CD1 antibody or anti-herceptin antibody. Specifically at day 14, 5 out of 9 mice treated with anti-CD21-cys-MC-vc-PAB-MMAE showed partical regression of tumors and 4 out of 9 mice treated with anti-CD21-cys-MC-vc-PAB-MMAE showed complete regression of tumors. At day 14, 10 out of 10 mice treated with anti-herceptin or anti-CD21 antibody showed tumor incidence.

(3) Anti-TAHO25/CD19 antibody conjugated with DM1 toxin (anti-CD19-SPP-DM1) showed inhibition of tumor growth in SCID mice with RAJI tumors when treated with 5 mg/kg of antibody compared to negative control anti-CD19 antibody conjugated to DM1 (anti-CD19-SMCC-DM1), anti-CD22 antibody conjugated to DM1 (anti-CD22-SMCC-DM1) and anti-herceptin antibody conjugated to DM1 (anti-herceptin-smcc-DM1 or anti-herceptin-spp-DM1). Specifically at day 14, 2 out of 6 mice treated with anti-CD19-SPP-DM1 showed partical regression of tumors and 3 out of 6 mice treated with anti-CD19-SPP-DM1 showed complete regression of tumors. At day 14, 8 out of 8 mice treated with anti-herceptin-SPP-DM1, anti-herceptin-SMCC-DM1, anti-CD19-SMCC-DM1 or anti-CD22-SMCC-DM1 showed tumor incidence.

(4) Anti-TAHO4/CD79A antibody conjugated with DM1 (anti-CD79A-SMCC-DM1) showed inhibition of tumor growth in SCID mice with RAMOS tumors compared to negative control, anti-herceptin-SMCC-DM1.

(5) Anti-TAHO5/CD79B antibody conjugated with DM1 (anti-CD79B-SMCC-DM1) showed inhibition of tumor growth in SCID mice with RAMOS tumors compared to negative control, anti-herceptin-SMCC-DMA. Anti-TAHO5/CD79B antibody conjugated with DM1 (anti-CD79B-SMCC-DM1) showed inhibition of tumor growth in SCID mice with BJAB-luciferase tumors compared to negative control, anti-herceptin-SMCC-DM1 or anti-herceptin antibody. The level of inhibition by anti-CD79B-SMCC-DM1 antibodies was similar to the level of inhibition by anti-CD20 antibodies. Specifically at day 15, 1 out of 10 mice treated with anti-CD79B-SMCC-DM1 showed partical regression of tumors and 9 out of 10 mice treated with anti-CD79B-SMCC-DM1 showed complete regression of tumors. At day 15, 10 out of 10 mice treated with anti-herceptin-SMCC-DM1, anti-herceptin antibody showed tumor incidence. At day 15, 5 out of 10 mice treated with anti-CD20 antibodies showed partial regression of tumors.

Anti-TAHO polypeptide monoclonal antibodies are useful for reducing in vivo tumor growth of tumors in mammals, including B-cell associated cancers, such as lymphomas (i.e. Non-Hodgkin's Lyphoma), leukemias (i.e. chronic lymphocytic leukemia), myelomas (i.e. multiple myeloma) and other cancers of hematopoietic cells.

Example 13

Immunohistochemistry

To determine tissue expression of TAHO polypeptide and to confirm the microarray results from Example 1, immunohistochemical detection of TAHO polypeptide expression was examined in snap-frozen and formalin-fixed paraffin-embedded (FFPE) lymphoid tissues, including palatine tonsil, spleen, lymph node and Peyer's patches from the Genentech Human Tissue Bank.

Prevalence of TAHO target expression was evaluated on FFPE lymphoma tissue microarrays (Cybrdi) and a panel of 24 frozen human lymphoma specimens. Frozen tissue specimens were sectioned at 5 µm, air-dried and fixed in acetone for 5 minutes prior to immunostaining. Paraffin-embedded tissues were sectioned at 5 µm and mounted on SuperFrost Plus microscope slides (VWR).

For frozen sections, slides were placed in TBST, 1% BSA and 10% normal horse serum containing 0.05% sodium azide for 30 minutes, then incubated with Avidin/Biotin blocking kit (Vector) reagents before addition of primary antibody. Mouse monoclonal primary antibodies (commercially available) were detected with biotinylated horse anti-mouse IgG (Vector), followed by incubation in Avidin-Biotin peroxidase complex (ABC Elite, Vector) and metal-enhanced diaminobenzidine tetrahydrochloride (DAB, Pierce). Control sections were incubated with isotype-matched irrelevant mouse monoclonal antibody (Pharmingen) at equivalent concentration. Following application of the ABC-HRP reagent, sections were incubated with biotinyl-tyramide (Perkin Elmer) in amplification diluent for 5-10 minutes, washed, and again incubated with ABC-HRP reagent. Detection was using DAB as described above.

FFPE human tissue sections were dewaxed into distilled water, treated with Target Retrieval solution (Dako) in a boiling water bath for 20 minutes, followed by a 20 minute cooling period. Residual endogenous peroxidase activity was blocked using 1× Blocking Solution (KPL) for 4 minutes. Sections were incubated with Avidin/Biotin blocking reagents and Blocking Buffer containing 10% normal horse serum before addition of the monoclonal antibodies, diluted to 0.5-5.0 µg/ml in Blocking Buffer. Sections were then incubated sequentially with biotinylated anti-mouse secondary antibody, followed by ABC-HRP and chromogenic detection with DAB. Tyramide Signal Amplification, described above, was used to increase sensitivity of staining for a number of TAHO targets (CD21, CD22, HLA-DOB).

Summary (1) TAHO26 (CD22) showed strong labeling of mantle zone B cells and weaker, but significant labeling of germinal centers as detected with primary antibody clone RFB-4 (Leinco) in frozen human tonsil tissue and clone 22C04 (Neomarkers) in FFPE human tonsil tissue (data not shown).

(2) TAHO10 (HLA-DOB) showed punctuate labeling pattern, possibly due to labeling of TAHO10 on intracellular vesicles as detected with clone DOB.L1 (BD/Pharmingen) in FFPE human tonsil tissue (data not shown).

(3) TAHO8 (CD72) showed punctuate labeling pattern, possibly due to labeling of TAHO8 on intracellular vesicles as detected with clone J4-117 (BD/Pharmingen) in frozen human tonsil tissue (data not shown).

(4) TAHO1 (CD180) showed punctuate labeling pattern, possibly due to labeling of TAHO1 on intracellular vesicles as detected with clone MHR73 (Serotec) in frozen human tonsil tissue (data not shown).

(5) TAHO6 (CD21) showed strong labeling of follicular dendritic cells in germinal centers and mature B cells within mantle zone as detected with clone HB-135 (ATCC) in FFPE human tonsil tissue and using tyramide signal amplification (TSA) (data not shown).

(6) TAHO11(CXCR5) showed significant labeling in both mantle zone and germinal centers as detected with clone 51505 (R&D Systems) and using a Cy3-conjugated anti-mouse antibody (R&D Systems) in frozen human tonsil.

Accordingly, in light of TAHO1, TAHO6, TAHO8, TAHO10, TAHO11 and TAHO26 expression pattern as assessed by immunohistochemistry in tonsil samples, a lymphoid organ where B cells develop, the molecules are excellent targets for therapy of tumors in mammals, including B-cell associated cancers, such as lymphomas (i.e. Non-Hodgkin's Lyphoma), leukemias (i.e. chronic lymphocytic leukemia), myelomas (i.e. multiple myeloma) and other cancers of hematopoietic cells.

Example 14

Flow Cytometry

To determine the expression of TAHO molecules, FACS analysis was performed using a variety of cells, including normal cells and diseased cells, such as chronic lymphocytic leukemia (CLL) cells.

A. Normal Cells: TAHO2 (CD20), TAHO1 (CD180), TAHO26 (CD22), TAHO4 (CD79A), TAHO5 (CD79B), TAHO8 (CD72), TAHO11 (CXCR5)

For tonsil B cell subtypes, the fresh tonsil was minced in cold HBSS and passed through a 70 um cell strainer. Cells were washed once and counted. CD19+ B cells were enriched using the AutoMACS (Miltenyi). Briefly, tonsil cells were blocked with human IgG, incubated with anti-CD19 microbeads, and washed prior to positive selection over the AutoMACS. A fraction of CD19+ B cells were saved for flow cytometric analysis of plasma cells. Remaining CD19+ cells were stained with FITC-CD77, PE-IgD, and APC-CD38 for sorting of B-cell subpopulations. CD19+ enrichment was analyzed using PE-Cy5-CD19, and purity ranged from 94-98% CD19+. Tonsil B subpopulations were sorted on the MoFlo by Michael Hamilton at flow rate 18,000-20,000 cells/second. Follicular mantle cells were collected as the IgD+/CD38– fraction, memory B cells were IgD–/CD38–, centrocytes were IgD–/CD38+/CD77–, and centroblasts were IgD–/CD38+/CD77+. Cells were either stored in 50% serum overnight, or stained and fixed with 2% paraformaldehyde. For plasma cell analysis, total tonsil B cells were stained with CD138-PE, CD20-FITC, and biotinylated antibody to the target of interest detected with streptavidin-PE-Cy5. Tonsil B subpopulations were stained with biotinylated antibody to the target of interest, detected with streptavidin-PE-Cy5. Flow analysis was done on the BD FACSCaliber, and data was further analyzed using FlowJo software v 4.5.2 (TreeStar). Biotin-conjugated antibodies which were commercially available such as TAHO2/CD20 (2H7 from Ancell), TAHO1/CD180 (MHR73-11 from eBioscience), TAHO8/CD72 (JF-117 from BD Pharmingen), TAHO26/CD22 (RFB4 from Ancell), TAHO11/CXCR5 (51505 from R&D Systems), TAHO4/CD79A (ZL7-4 from Serotec) and TAHO5/CD79B (CB-3 from BD Pharmingen) were used in the flow cytometry.

Summary of TAHO2 (CD20), TAHO1 (CD180), TAHO26 (CD22), TAHO4 (CD79A), TAHO5 (CD79B), TAHO8 (CD72), TAHO11 (CXCR5) on Normal Cells The expression pattern on sorted tonsil-B subtypes was performed using monoclonal antibody specific to the TAHO polypeptide of interest. TAHO2 (CD20) (using anti-CD20, 2H7 from BD Pharmingen), TAHO26 (CD22) (using anti-CD22, RFB4 from Ancell), TAHO4 (CD79A) (using anti-CD79A), TAHO5 (CD79B) (using anti-CD79B), TAHO8 (CD72) (using anti-CD72), TAHO1 (CD180) (using anti-CD180, MHR73-11 from eBioscience) and TAHO11 (using anti-CXCR5, 51505 from R&D Systems) showed significant expression in memory B cells, follicular mantle cells, centroblasts and centrocytes (data not shown).

The expression pattern on tonsil plasma cells was performed using monoclonal antibody specific to the TAHO polypeptide of interest. TAHO26 (CD22) (using anti-CD22, RFB4 from Ancell), TAHO4 (CD79A) (using anti-CD79A), TAHO5 (CD79B) (using anti-CD79B), TAHO1 (CD180) (using anti-CD180, MHR73-11 from eBioscience) and TAHO8 (CD72) (using anti-CD72) showed significant expression in plasma cells (data not shown).

Accordingly, in light of TAHO2, TAHO11, TAHO26, TAHO04, TAHO5, TAHO8 and TAHO11 expression pattern on tonsil-B subtypes as assessed by FACS, the molecules are excellent targets for therapy of tumors in mammals, including B-cell associated cancers, such as lymphomas (i.e. Non-Hodgkin's Lyphoma), leukemias (i.e. chronic lymphocytic leukemia), myelomas (i.e. multiple myeloma) and other cancers of hematopoietic cells.

B. CLL Cells: TAHO11 (CXCR5), TAHO4 (CD79A), TAHO5 (CD79B), TAHO26 (CD22), TAHO12 (CD23/FCER2), TAHO1 (CD180)

The following purified or fluorochrome-conjugated mAbs were used for flow cytometry of CLL samples: CD5-PE, CD19-PerCP Cy5.5, CD20-FITC, CD20-APC (commercially available from BD Pharmingen). Further, commercially available biotinylated antibodies against CD22 (RFB4 from Ancell), CD23 (M-L233 from BD Pharmingen), CD79A (ZL7-4 from Serotec), CD79B (CB-3 from BD Pharmingen), CD180 (MHR73-11 from eBioscience), CXCR5 (51505 from R&D Systems) were used for the flow cytometry. The CD5, CD19 and CD20 antibodies were used to gate on CLL cells and P1 staining was performed to check the cell viability.

Cells ($10^6$ cells in 100 ml volume) were first incubated with 1 mg of each CD5, CD19 and CD20 antibodies and 10 mg each of human and mouse gamma globulin (Jackson ImmunoResearch Laboratories, West Grove, Pa.) to block the non-specific binding, then incubated with optimal concentrations of mAbs for 30 minutes in the dark at 4° C. When biotinylated antibodies were used, streptavidin-PE or streptavidin-APC (Jackson ImmunoResearch Laboratories) were then added according to manufacture's instructions. Flow cytometry was performed on a FACS calibur (BD Biosciences, San Jose, Calif.). Forward scatter (FSC) and side scatter (SSC) signals were recorded in linear mode, fluorescence signals in logarithmic mode. Dead cells and debris were gated out using scatter properties of the cells. Data were analysed using CellQuest Pro software (BD Biosciences) and FlowJo (Tree Star Inc.).

Summary of TAHO11 (CXCR5), TAHO4 (CD79A), TAHO5 (CD79B), TAHO26 (CD22), TAHO12 (CD23/FCER2), TAHO1 (CD180) on CLL Samples The expression pattern on CLL samples was performed using monoclonal antibody specific to the TAHO polypeptide of interest. TAHO11 (CXCR5), TAHO4 (CD79A), TAHO5

(CD79B), TAHO26 (CD22), TAHO12 (CD23/FCER2), TAHO1 (CD180) showed significant expression in CLL samples (data not shown).

Accordingly, in light of TAHO11, TAHO4, TAHO5, TAHO26, TAHO12 and TAHO1 expression pattern on chronic lymphocytic leukemia (CLL) samples as assessed by FACS, the molecules are excellent targets for therapy of tumors in mammals, including B-cell associated cancers, such as lymphomas (i.e. Non-Hodgkin's Lyphoma), leukemias (i.e. chronic lymphocytic leukemia), myelomas (i.e. multiple myeloma) and other cancers of hematopoietic cells.

Example 15

TAHO Internalization

Internalization of the TAHO antibodies into B-cell lines was assessed in Raji, Ramos, Daudi and other B cell lines, including ARH77, SuDHL4, U698M, huB and BJAB cell lines.

One ready-to-split 15 cm dish of B-cells (~50×10$^6$ cells) with cells for use in up to 20 reactions was used. The cells were below passage 25 (less than 8 weeks old) and growing healthily without any mycoplasma.

In a loosely-capped 15 ml Falcon tube add 1 µg/ml mouse anti-TAHO antibody to 2.5×10$^6$ cells in 2 ml normal growth medium (e.g. RPMI/10% FBS/1% glutamine) containing 1:10 FcR block (MACS kit, dialyzed to remove azide), 1% pen/strep, 5 µM pepstatin A, 10 µg/ml leupeptin (lysosomal protease inhibitors) and 25 µg/ml Alexa488-transferrin (which labeled the recycling pathway and indicated which cells were alive; alternatively Ax488 dextran fluid phase marker may be used to mark all pathways) for 24 hours in a 37° C. 5% $CO_2$ incubator. For quickly-internalizing antibodies, time-points every 5 minutes were taken. For time-points taken less than 1 hour, 1 ml complete carbonate-free medium (Gibco 18045-088+10% FBS, 1% glutamine, 1% pen/strep, 10 mM Hepes pH 7.4) was used and the reactions were performed in a 37° C. waterbath instead of the $CO_2$ incubator.

After completion of the time course, the cells were collected by centrifugation (1500 rpm 4° C. for 5 minutes in G6-SR or 2500 rpm 3 minutes in 4° C. benchtop eppendorf centrifuge), washed once in 1.5 ml carbonate free medium (in Eppendorfs) or 10 ml medium for 15 ml Falcon tubes. The cells were subjected to a second centrifugation and resuspended in 0.5 ml 3% paraformaldehyde (EMS) in PBS for 20 minutes at room temp to allow fixation of the cells.

All following steps are followed by a collection of the cells via centrifugation. Cells were washed in PBS and then quenched for 10 minutes in 0.5 ml 50 mM $NH_4Cl$ (Sigma) in PBS and permeablized with 0.5 ml 0.1% Triton-X-100 in PBS for 4 minutes during a 4 minute centrifugation spin. Cells were washed in PBS and subjected to centrifugation. 1 µg/ml Cy3-anti mouse (or anti-species 1° antibody was) was added to detect uptake of the antibody in 200 µl complete carbonate free medium for 20 minutes at room temperature. Cells were washed twice in carbonate free medium and resuspend in 25 µl carbonate free medium and the cells were allowed to settle as a drop onto one well of a polylysine-coated 8-well LabtekII slide for at least one hour (or overnight in fridge). Any non-bound cells were aspirated and the slides were mounted with one drop per well of DAPI-containing Vectashield under a 50×24 mm coverslip. The cells were examined under 100× objective for internalization of the antibodies.

Summary (1) TAHO25/CD19 (as detected using anti-CD19 antibody Biomeda CB-19) was internalized within 20 minutes in Ramos and Daudi cells, arriving in lysosomes by 1 hour. In Raji and ARH77 cells, TAHO25/CD19 internalization was not detectable in 20 hours.

(2) Significant TAHO6/CR2 (as detected using anti-CR2 antibody ATCC HB-135) internalization was not detectable in Raji cells and in Daudi cells in 20 hours.

(3) TAHO26/CD22 (as detected using anti-CD22 antibody Leinco RFB4) was internalized in 5 minutes in Raji cells, in 5 minutes in Ramos cells, in 5 minutes in Daudi cells, and in 5 minutes in ARH77 cells and was delivered to lysosomes by 1 hour. TAHO26/CD22 (as detected using anti-CD22 antibodies, DAKO To15, Diatec 157, Sigma HIB-22 or Monosan BL-BC34) was internalized in 5 minutes in Raji cells and was delivered to lysosomes by 1 hour.

(4) Significant TAHO12/FCER2 (as detected using anti-FCER2 antibody Ancell BU38 or Serotec D3.6) internalization was not detectable in ARH77 cells in 20 hours.

(5) Significant TAHO8/CD72 (as detected using anti-CD72 antibody BD Pharmingen J4-117) internalization was not detectable in 20 hours in SuDHL4 cells.

(6) TAHO4/CD79a (as detected using anti-CD79a antibody Serotec ZL7-4) was internalized in 1 hour in Ramos cells, in 1 hour in Daudi cells and in 1 hour in SuDHL4 cells, and was delivered to lysosomes in 3 hours.

(7) TAHO1/CD180 (as detected using anti-CD180 antibody BD Pharmingen G28-8) was internalized in minutes in SuDHL4 cells and was delivered to lysosomes in 20 hours.

(8) Significant TAHO11/CXCR5 (as detected using anti-CXCR5 antibody R&D Systems 51505) internalization was not detectable in 20 hours in U698M cells.

(9) TAHO5/CD79b (as detected using anti-CD79b antibody Ancell SN8) internalizes in 20 minutes in Ramos, Daudi and Su-DHL4 cells and is delivered to the lysosomes in 1 hour.

Accordingly, in light of TAHO25, TAHO26, TAHO4, TAHO1 and TAHO5 internalization on B-cell lines as assessed by immunofluorescence using respective anti-TAHO antibodies, the molecules are excellent targets for therapy of tumors in mammals, including B-cell associated cancers, such as lymphomas (i.e. Non-Hodgkin's Lyphoma), leukemias (i.e. chronic lymphocytic leukemia), myelomas (i.e. multiple myeloma) and other cancers of hematopoietic cells.

What is claimed is:

1. A method of inhibiting the growth of a cell that expresses a protein having:
   (a) the amino acid sequence shown in FIG. 10 (SEQ ID NO: 10), with or without its associated signal peptide;
   (b) an extracellular domain of the polypeptide having the amino acid sequence shown in FIG. 10 (SEQ ID NO: 10), with or without its associated signal peptide;
   (c) a polypeptide encoded by the nucleotide sequence shown in FIG. 9 (SEQ ID NO: 9); or
   (d) a polypeptide encoded by the full-length coding region of the nucleotide sequence shown in FIG. 9 (SEQ ID NO: 9),
   said method comprising contacting said cell with an antibody that binds to said protein, wherein said antibody is conjugated to a growth inhibitory agent or cytotoxic agent and is internalized by and inhibits the growth of a cell expressing said polypeptide, wherein said cell is a cancer cell selected from the group consisting of a leukemia cell, a lymphoma cell and a myeloma cell.

2. The method of claim 1, wherein said antibody is a monoclonal antibody.

3. The method of claim 1, wherein said antibody is an antibody fragment.

4. The method of claim 1, wherein said antibody is a chimeric or a humanized antibody.

5. The method of claim 1, wherein said antibody is conjugated to the growth inhibitory agent or cytotoxic agent via a linker.

6. The method of claim 5, wherein the linker is a peptidase-sensitive linker.

7. The method of claim 6, wherein said cytotoxic agent is selected from the group consisting of toxins, antibiotics, radioactive isotopes and nucleolytic enzymes.

8. The method of claim 6, wherein the cytotoxic agent is a toxin.

9. The method of claim 8, wherein the toxin is selected from the group consisting of monomethylauristatin (MMAE), maytansinoid and calicheamicin.

10. The method of claim 8, wherein the toxin is a maytansinoid.

11. The method of claim 1, wherein said antibody is produced in bacteria.

12. The method of claim 1, wherein said antibody is produced in CHO cells.

13. The method of claim 1 wherein said cancer cell is further exposed to radiation treatment or a chemotherapeutic agent.

14. The method of claim 1, wherein said protein is more abundantly expressed by said cancer cell compared to a non-cancer cell.

15. The method of claim 1 which causes the death of said cell.

16. The method of claim 1, wherein said lymphoma cell is selected from the group consisting of a follicular lymphoma cell, mantle cell lymphoma cell or diffuse large cell lymphoma cell.

17. A method for treating a cell proliferative disorder associated with increased expression or activity of a protein having:
(a) the amino acid sequence shown in FIG. 10 (SEQ ID NO: 10), with or without its associated signal peptide;
(b) an extracellular domain of the polypeptide having the amino acid sequence shown in FIG. 10 (SEQ ID NO: 10), with or without its associated signal peptide;
(c) a polypeptide encoded by the nucleotide sequence shown in FIG. 9 (SEQ ID NO: 9); or
(d) a polypeptide encoded by the full-length coding region of the nucleotide sequence shown in FIG. 9 (SEQ ID NO: 9),
said method comprising administering to a subject in need of such treatment an effective amount of an antibody of said protein, wherein said antibody is conjugated to a growth inhibitory agent or cytotoxic agent and is internalized by and thereby effectively treating said cell proliferative disorder, wherein said cell proliferative disorder is a cancer selected from the group consisting of leukemia, lymphoma and myeloma.

18. The method of claim 17, wherein said antibody is an anti-TAHO polypeptide antibody.

19. A method for inhibiting the growth of a cell, wherein the growth of said cell is at least in part dependent upon a growth potentiating effect of a protein having:
(a) the amino acid sequence shown in FIG. 10 (SEQ ID NO: 10), with or without its associated signal peptide;
(b) an extracellular domain of the polypeptide having the amino acid sequence shown in FIG. 10 (SEQ ID NO: 10), with or without its associated signal peptide;
(c) a polypeptide encoded by the nucleotide sequence shown in FIG. 9 (SEQ ID NO: 9); or
(d) a polypeptide encoded by the full-length coding region of the nucleotide sequence shown in FIG. 9 (SEQ ID NO: 9),
said method comprising contacting said protein with an antibody, that binds to said protein, wherein said antibody is conjugated to a growth inhibitory agent or cytotoxic agent and is internalized by and inhibits the growth of a cell expressing said polypeptide, wherein said cell is a cancer cell selected from the group consisting of a leukemia cell, a lymphoma cell and a myeloma cell.

20. The method of claim 19, wherein said protein is expressed by said cell.

21. The method of claim 19, wherein the binding of said antibody to said protein antagonizes a cell growth-potentiating activity of said protein.

22. The method of claim 19, wherein the binding of said antibody to said protein induces the death of said cell.

23. The method of claim 19, wherein said antibody is a monoclonal antibody.

24. The method of claim 19, wherein said antibody is an antibody fragment.

25. The method of claim 19, wherein said antibody is a chimeric or a humanized antibody.

26. The method of claim 19, wherein said antibody is conjugated to the growth inhibitory agent or cytotoxic agent via a linker.

27. The method of claim 26, wherein said linker is a peptidase-sensitive linker.

28. The method of claim 27, wherein said cytotoxic agent is selected from the group consisting of toxins, antibiotics, radioactive isotopes and nucleolytic enzymes.

29. The method of claim 27, wherein the cytotoxic agent is a toxin.

30. The method of claim 29, wherein the toxin is selected from the group consisting of monomethylauristatin (MMAE), maytansinoid and calicheamicin.

31. The method of claim 29, wherein the toxin is a maytansinoid.

32. The method of claim 19, wherein said antibody is produced in bacteria.

33. The method of claim 19, wherein said antibody is produced in CHO cells.

34. The method of claim 19, wherein said lymphoma cell is selected from the group consisting of a follicular lymphoma cell, mantle cell lymphoma cell or diffuse large cell lymphoma cell.

35. The method of claim 5, wherein the antibody is conjugated to a maytansinoid and wherein the linker is selected from the group consisting of sulfosuccinimidyl maleimidomethyl cyclohexane carboxylate (SMCC) and N-succinimidyl-4-(2-pyridylthio)pentanoate (SPP).

36. The method of claim 35, wherein the linker is SMCC.

37. The method of claim 35, wherein the linker is SPP.

38. The method of claim 6, wherein the antibody is conjugated to a maytansinoid and wherein the peptidase-sensitive linker comprises a valine-citrulline (vc) dipeptide linker reagent having a maleimide component and a paraaminobenzylcarbamoyl (PAB) self-immolative component (MC-vc-PAB).

39. The method of claim 5, wherein the antibody is conjugated to monomethylauristatin (MMAE) via vc-PAB.

* * * * *